(12) United States Patent
Di Francesco et al.

(10) Patent No.: US 11,958,849 B2
(45) Date of Patent: *Apr. 16, 2024

(54) GLS1 INHIBITORS FOR TREATING DISEASE

(71) Applicant: Board of Regents, The University of Texas System, Austin, TX (US)

(72) Inventors: Maria Emilia Di Francesco, Houston, TX (US); Philip Jones, Houston, TX (US); Timothy Heffernan, Sugar Land, TX (US); Matthew M. Hamilton, Missouri City, TX (US); Zhijun Kang, Richmond, TX (US); Michael J. Soth, Sugar Land, TX (US); Jason P. Burke, Houston, TX (US); Kang Le, Sugar Land, TX (US); Christopher Lawrence Carroll, Houston, TX (US); Wylie S. Palmer, Houston, TX (US); Richard Lewis, Missouri City, TX (US); Timothy McAfoos, Pearland, TX (US); Barbara Czako, Bellaire, TX (US); Gang Liu, Sugar Land, TX (US); Jay Theroff, Manvel, TX (US); Zachary Herrera, El Cerrito, CA (US); Anne Yau, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/660,541

(22) Filed: Apr. 25, 2022

(65) Prior Publication Data

US 2023/0124815 A1 Apr. 20, 2023

Related U.S. Application Data

(60) Continuation of application No. 16/925,974, filed on Jul. 10, 2020, now Pat. No. 11,370,786, which is a
(Continued)

(51) Int. Cl.
| | |
|---|---|
| *C07D 417/14* | (2006.01) |
| *A61K 31/4192* | (2006.01) |
| *A61K 31/433* | (2006.01) |
| *A61K 31/4439* | (2006.01) |
| *A61K 31/444* | (2006.01) |
| *A61K 31/454* | (2006.01) |
| *A61K 31/497* | (2006.01) |
| *A61K 31/501* | (2006.01) |
| *A61K 45/06* | (2006.01) |
| *C07D 401/14* | (2006.01) |
| *C07D 403/06* | (2006.01) |
| *C07D 403/14* | (2006.01) |

(Continued)

(52) U.S. Cl.
CPC ........ *C07D 417/14* (2013.01); *A61K 31/4192* (2013.01); *A61K 31/433* (2013.01); *A61K 31/4439* (2013.01); *A61K 31/444* (2013.01); *A61K 31/454* (2013.01); *A61K 31/497* (2013.01); *A61K 31/501* (2013.01); *A61K 45/06* (2013.01); *C07D 401/14* (2013.01); *C07D 403/06* (2013.01); *C07D 403/14* (2013.01); *C07D 405/14* (2013.01); *C07D 417/06* (2013.01); *C07D 493/08* (2013.01)

(58) Field of Classification Search
CPC .. C07D 417/14; C07D 401/14; C07D 403/06; C07D 403/14; C07D 405/14; C07D 417/06; C07D 493/08; A61K 31/4192; A61K 31/433; A61K 31/4439; A61K 31/444; A61K 31/454; A61K 31/497; A61K 31/501; A61K 45/06; A61P 3/00; A61P 25/00; A61P 35/00
See application file for complete search history.

(56) References Cited

U.S. PATENT DOCUMENTS

| | | |
|---|---|---|
| 4,399,140 A | 8/1983 | Gacek |
| 4,720,447 A | 1/1988 | De Keyzer |

(Continued)

FOREIGN PATENT DOCUMENTS

| | | |
|---|---|---|
| WO | 1991009848 | 7/1991 |
| WO | 1996037492 | 11/1996 |

(Continued)

OTHER PUBLICATIONS

Golub, T. R., "Molecular classification of cancer: class discovery and class prediction by gene expression monitoring." science 286. 5439 (1999): 531-537.*
Lala, P.K., "Role of nitric oxide in tumor progression: lessons from experimental tumors." Cancer and Metastasis Reviews 17.1 (1998): 91-106.*
Wise, D.R., "Glutamine addiction: a new therapeutic target in cancer." Trends in biochemical sciences 35.8 (2010): 427-433.*
Aurora Fine Chemicals, 1-[3-(3-aminopyrazol-1-yl)propyl]pyrazole-4-carboxamide, Cat. No. A04.256.259 http://online.aurorafinechemicals.com/StrSearch.asp, Jul. 1, 2015.
(Continued)

*Primary Examiner* — John M Mauro
(74) *Attorney, Agent, or Firm* — Cynthia Hathaway; Lauren L. Stevens; Erik M. Larsen

(57) ABSTRACT

Disclosed herein are compounds and compositions useful in the treatment of GLS1 mediated diseases, such as cancer, having the structure of Formula I:

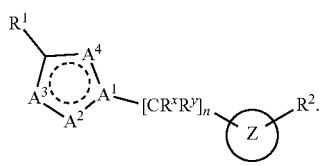

Methods of inhibition GLS1 activity in a human or animal subject are also provided.

12 Claims, No Drawings

Related U.S. Application Data continuation of application No. 16/412,050, filed on May 14, 2019, now Pat. No. 10,766,892, which is a division of application No. 15/624,168, filed on Jun. 15, 2017, now Pat. No. 10,344,025, which is a continuation of application No. 14/791,186, filed on Jul. 2, 2015, now Pat. No. 9,809,588.

(60) Provisional application No. 62/020,539, filed on Jul. 3, 2014.

(51) Int. Cl.
  C07D 405/14 (2006.01)
  C07D 417/06 (2006.01)
  C07D 493/08 (2006.01)

(56) References Cited

U.S. PATENT DOCUMENTS

| | | | |
|---|---|---|---|
| 6,153,628 | A | 11/2000 | Jin |
| 6,239,137 | B1 | 5/2001 | Karmali |
| 7,956,070 | B2 | 6/2011 | Alcaraz |
| 7,985,548 | B2 | 7/2011 | Lorenzi |
| 9,809,588 | B2 | 11/2017 | Di Francesco |
| 10,125,128 | B2 | 11/2018 | Lewis |
| 10,150,753 | B2 | 12/2018 | Jones |
| 10,344,025 | B2 | 7/2019 | Di Francesco |
| 10,722,487 | B2 | 7/2020 | Heffernan |
| 10,738,043 | B2 | 8/2020 | Lewis |
| 10,766,892 | B2 | 9/2020 | Di Francesco |
| 10,899,740 | B2 | 1/2021 | Jones |
| 11,045,443 | B2 | 6/2021 | Heffernan |
| 11,370,786 | B2 | 6/2022 | Di Francesco |
| 11,603,365 | B2 | 3/2023 | Jones |
| 11,713,313 | B2 | 8/2023 | Lewis |
| 2002/0115698 | A1 | 8/2002 | Newcomb |
| 2009/0215750 | A1 | 8/2009 | Bamberg |
| 2010/0255117 | A1 | 10/2010 | Biswal |
| 2011/0229984 | A1 | 9/2011 | Lorenzi |
| 2012/0202776 | A1 | 8/2012 | Wang |
| 2013/0157998 | A1 | 6/2013 | Li |
| 2014/0050699 | A1 | 2/2014 | Li |
| 2014/0142081 | A1 | 5/2014 | Lemieux |
| 2015/0344466 | A1 | 12/2015 | Mitsudera |
| 2015/0368240 | A1 | 12/2015 | Bleisch |
| 2016/0002204 | A1 | 1/2016 | Di Francesco |
| 2016/0002248 | A1 | 1/2016 | Di Francesco |
| 2016/0009704 | A1 | 1/2016 | Di Francesco |
| 2016/0058759 | A1 | 3/2016 | Heffernan |
| 2016/0097040 | A1 | 4/2016 | Gao |
| 2017/0001996 | A1 | 1/2017 | Lewis |
| 2017/0174661 | A1 | 6/2017 | Jones |
| 2017/0291895 | A1 | 10/2017 | Di Francesco |
| 2019/0031651 | A1 | 1/2019 | Lewis |
| 2019/0134032 | A1 | 5/2019 | Heffernan |
| 2019/0144425 | A1 | 5/2019 | Jones |
| 2019/0270736 | A1 | 9/2019 | Di Francesco |
| 2019/0274993 | A1 | 9/2019 | Heffernan |
| 2020/0368196 | A1 | 11/2020 | Heffernan |
| 2021/0122744 | A1 | 4/2021 | Lewis |
| 2021/0206745 | A1 | 7/2021 | Jones |
| 2022/0016069 | A1 | 1/2022 | Heffernan |
| 2023/0250081 | A1 | 8/2023 | Jones |

FOREIGN PATENT DOCUMENTS

| | | |
|---|---|---|
| WO | 1998043962 | 10/1998 |
| WO | 1999026945 | 6/1999 |
| WO | 2008083238 | 7/2008 |
| WO | 2010023946 | 3/2010 |
| WO | 2010099527 | 9/2010 |
| WO | 2010111504 | 9/2010 |
| WO | 2011089995 | 7/2011 |
| WO | 2011143160 | 11/2011 |
| WO | 2013078123 | 5/2013 |
| WO | 2014078645 | 5/2014 |
| WO | 2014079150 | 5/2014 |
| WO | 2014081925 | 5/2014 |
| WO | 2014089048 | 6/2014 |
| WO | 2014119696 | 8/2014 |
| WO | 2015101957 | 7/2015 |
| WO | 2015101958 | 7/2015 |
| WO | 2016004404 | 1/2016 |
| WO | 2016004413 | 1/2016 |
| WO | 2016004417 | 1/2016 |
| WO | 2016004418 | 1/2016 |
| WO | 2017004359 | 1/2017 |
| WO | 2017112831 | 6/2017 |
| WO | 2019079632 | 4/2019 |

OTHER PUBLICATIONS

Balasubramanian, M. et al., "Asparagine Synthetase: Regulation by Cell Stress and Involvement in Tumor Biology", Am J Physiol Endocrinol Metab., 304(8):E789-99, (2013).
Bernstein, J. "Nauka", Polymorphism in Molecular Crystals, pp. 324-330, (2007).
Blair, S. et al., "Glutathione Metabolism in Patients with Non-Small Cell Lung Cancers", Cancer Res., 57(1):152-5, (1997).
Brunton, L. et al., "Chemotherapy of Neoplastic Disease", Goodman and Gilman's, The Pharmacological Basis for Therapeutics, eds., 11:853-903, (2008).
CAPLUS Accession No. 2011:590393; 2 pages, (2011).
CAS Indexed Compounds, 2(1H)-Pyridinone, 1-[3-(1-phenyl-1H-tetrazol-5-yl)propyl]-5(trifluoromethyl), Registry No. 1311902-55-2, Jul. 7, 2011.
CAS Indexed Compounds, 2(1H)-Pyridinone, 1-[3-(3-amino-1H-pyrazol-1-yl)propyl]-4-methyl, Registry No. 1284137-43-4, Apr. 22, 2011.
CAS Indexed Compounds, 2(1H)-Pyridinone, 1-[3-(3-amino-1H-pyrazol-1-yl)propyl]-5-bromo, Registry No. 1272932-30-5, Mar. 31, 2011.
CAS Indexed Compounds, 2(1H)-Pyridinone, 1-[3-(3-amino-1H-pyrazol-1-yl)propyl]-5(trifluoromethyl), Registry No. 1406035-29-7, Nov. 25, 2012.
CAS Indexed Compounds, 2(1H)-Pyridinone, 1-[3-(3-amino-1H-pyrazol-1-yl)propyl], Registry No. 1341730-05-9, Nov. 6, 2011.
CAS Indexed Compounds, 2(1H)-Pyridinone, 1-[3-[3-(3-fluoro-4-methylphenyl)-1,2,4-oxadiazol-5yl]propyl]-5-(trifluoromethyl), Registry No. 1387392-92-8, Aug. 7, 2012.
CAS Indexed Compounds, 2(1H)-Pyridinone, 1-[3-[4-(chloromethyl)-2-thiazolyl]propyl]-4-methyl, Registry No. 1408458-49-0, Nov. 30, 2012.
CAS Indexed Compounds, 2(1H)-Pyridinone, 1-[3-[4-(chloromethyl)-2-thiazolyl]propyl]-5(trifluoromethyl), Registry No. 1484369-40-5, Dec. 1, 2013.
CAS Indexed Compounds, 2(1H)-Pyridinone, 1-[3-[4-(chloromethyl)-2-thiazolyl]propyl], Registry No. 1094436-44-8, Jan. 20, 2009.
CAS Indexed Compounds, 2(1H)-Pyridinone, 1-[4-[4-(chloromethyl)-2-thiazolyl]butyl]-4-methyl, Registry No. 1284050-00-5, Apr. 22, 2011.
CAS Indexed Compounds, 2(1H)-Pyridinone, 1-[4-[4-(chloromethyl)-2-thiazolyl]butyl], Registry No. 1272826-97-7, Mar. 31, 2011.
CAS Indexed Compounds, 2(1H)-Pyridinone, 1-[4-oxo-4-(2-thienyl)butyl]-5-(trifluoromethyl), Registry No. 1456227-69-2, Oct. 6, 2013.
CAS Indexed Compounds, 2(1H)-Pyridinone, 1-[4-oxo-4-(2-thienyl)butyl], Registry No. 1456935-71-9, Oct. 11, 2013.
CAS Indexed Compounds, 2(1H)-Pyridinone, 5-(trifluoromethyl)-1-[3-[3-[3-(trifluoromethyl)phenyl], Registry No. 1100005-80-8, Feb. 3, 2009.
CAS Indexed Compounds, 2(1H)-Pyridinone, 5-bromo-1-[3-(1H-imidazol-1-yl)propyl], Registry No. 1482686-39-4, Nov. 28, 2013.
CAS Indexed Compounds, 2(1H)-Pyridinone, 5-bromo-1-[4-oxo-4-(2-thienyl)butyl], Registry No. 1458260-86-0, Oct. 15, 2013.
CAS Indexed Compounds, 4-Pyridinecarboxylic acid, 1,2-dihydro-1-[3-(1H-imidazol-1-yl)propyl]-2-Oxo, Registry No. 1548114-27-7, Feb. 18, 2014.

(56) References Cited

OTHER PUBLICATIONS

CAS Indexed Compounds, Registry No. 1480499-78-2, Nov. 25, 2013.
CAS Registry No. 1355653-66-5 [Database Registry Chemical Abstracts Service, Columbus, Ohio, entry date Nov. 25, 2013]; p. 1.
Dang, C., "Links Between Metabolism and Cancer", Genes Dev., 26(9):877-90, (2012).
Daye, D. et al., "Metabolic Reprogramming in Cancer: Unraveling the Role of Glutamine in Tumorigenesis", Semin Cell Dev Biol., 23(4):362-9, (2012).
Fung, M. et al., "Drug-Induced Amino Acid Deprivation as Strategy for Cancer Therapy", J Hematol Oncol., 10(1):144 pp. 1-18, (2017).
Golub, T. et al., "Molecular Classification of Cancer: Class Discovery and Class Prediction by Gene Expression Monitoring", Science, 286(5439):531-7, (1999).
Gorrini, C. et al., "Modulation of Oxidative Stress as an Anticancer Strategy", Nat Rev Drug Discov., 12(12):931-47, (2013).
Gross, M. et al., "Antitumor Activity of the Glutaminase Inhibitor CB-839 in Triple-Negative Breast Cancer", Mol Cancer Ther., 13(4):890-901, (2014).
Hays, J. et al., "A phase II Clinical Trial of Polyethylene Glycol-Conjugated L-Asparaginase in Patients with Advanced Ovarian Cancer: Early Closure for Safety", Mol Clin Oncol., 1(3):565-9, (2013).
Hensley, C. et al., "Glutamine and Cancer: Cell Biology, Physiology, and Clinical Opportunities", J Clin Invest., 123(9):3678-84, (2013).
Huang, Q. et al., "Characterization of the Interactions of Potent Allosteric Inhibitors with Glutaminase C, a Key Enzyme in Cancer Cell Glutamine Metabolism", J Biol Chem., 293(10):3535-45, (2018).
Inami, Y. et al., "Persistent Activation of Nrf2 Through p62 in Hepatocellular Carcinoma Cells", J Cell Biol., 193(2):275-84, (2011).
International Application No. PCT/US2015/039134; International Preliminary Report on Patentability, dated Jan. 3, 2017; 06 pages.
International Application No. PCT/US2015/039134; International Search Report and Written Opinion of the International Searching Authority, dated Feb. 9, 2016; 10 pages.
International Application No. PCT/US2015/039143; International Preliminary Report on Patentability, dated Jan. 3, 2017; 06 pages.
International Application No. PCT/US2015/039143; International Search Report and Written Opinion of the International Searching Authority, dated Jan. 11, 2016; 10 pages.
International Application No. PCT/US2015/039150; International Preliminary Report on Patentability dated Jan. 3, 2017; 6 pages.
International Application No. PCT/US2015/039150; International Search Report and Written Opinion of the International Searching Authority, dated Dec. 4, 2015; 9 pages.
International Application No. PCT/US2015/039153; International Preliminary Report on Patentability, dated Jan. 3, 2017; 10 pages.
International Application No. PCT/US2015/039153; International Search Report and Written Opinion of the International Searching Authority, dated Jan. 7, 2016; 12 pages.
International Application No. PCT/US2016/040364; International Preliminary Report on Patentability, dated Jan. 2, 2018; 7 pages.
International Application No. PCT/US2016/040364; International Search Report and Written Opinion of the International Searching Authority, dated Jan. 5, 2017; 8 pages.
International Application No. PCT/US2016/068149; International Preliminary Report on Patentability, dated Jul. 6, 2018; 4 pages.
International Application No. PCT/US2016/068149; International Search Report and Written Opinion of the International Searching Authority, dated Mar. 27, 2017; 5 pages.
International Application No. PCT/US2018/056567; International Search Report and Written Opinion of the International Searching Authority, dated Apr. 30, 2020; 17 pages.
International Application No. PCT/US2018/056567; International Search Report and Written Opinion of the International Searching Authority, dated Dec. 31, 2018; 20 pages.
Ivanisevic, I. et al., "Uses of X-Ray Powder Diffraction in the Pharmaceutical Industry", Pharm Sci Encyclopedia, 42 pages, (2010).
Katt, W. et al., "Glutaminase Regulation in Cancer Cells: A Druggable Chain of Events," Drug Discov Today, 19(4)450-7, (2014).
Kroemer, G. et al., "Tumor Cell Metabolism: Cancer's Achilles' Heel", Cancer Cell., 13(6):472-82, (2008).
Lala, P. et al., "Role of Nitric Oxide in Tumor Progression: Lessons From Experimental Tumors", Cancer Metastasis Rev., 17(1):91-106, (1998).
Li, Y. et al., "Sulforaphane Potentiates the Efficacy of 17-Allylamino 17-Demethoxygeldanamycin Against Pancreatic Cancer Through Enhanced Abrogation of Hsp90 Chaperone Function", Nutrition and Cancer, 63(7):1151-9, (2011).
Lin, C. et al., "Deficiency in Asparagine Synthetase Expression in Rectal Cancers Receiving Concurrent Chemoradiotherapy: Negative Prognostic Impact and Therapeutic Relevance", Tumour Biol., 35(7):6823-30, (2014).
Lorenzi, P. et al., "Asparagine Synthetase as a Causal, Predictive Biomarker for L-Asparaginase Activity in Ovarian Cancer Cells", Mol Cancer Ther., 5(11):2613-23, (2006).
Lorenzi, P. et al., "Asparagine Synthetase is a Predictive Biomarker of L-Asparaginase Activity in Ovarian Cancer Cell Lines", Mol Cancer Ther., 7(10):3123-8, (2008).
McMahon, G., "VEGF Receptor Signaling in Tumor Angiogenesis", The Oncologist, 5(Suppl 1):3-10, (2000).
Neidle, S. et al., "Failure Modes in Clinical Development", Cancer Drug Design & Discovery, pp. 427-431, (2008).
Ni, M. et al., "Novel RGD Peptidomimetics Embedding 1, 2, 3-Triazole as Central Scaffold; Synthesis and $\alpha v\beta 3$ Integrin Affinity", Lett Drug Design and Discov., 8(5):401-5, (2011).
Nikonorova, I. et al., "Obesity Challenges the Hepatoprotective Function of the Integrated Stress Response to Asparaginase Exposure in Mice", J Biol Chem., 292(16):6786-98, (2017).
Pinedo, H. et al., "Translational Research: The Role of VEGF in Tumor Angiogenesis", The Oncologist, 5(Suppl 1):1-2, (2000).
Robinson, M. et al., "Novel Mechanism of Inhibition of Rat Kidney-Type Glutaminase by Bis-2-(5-Phenylacetamido-1,2,4-Thiadiazol-2-yl)Ethyl Sulfide (BPTES)", Biochem J., 406(3):407-14, (2007).
Rotblat, B. et al., "NRF2 and p53: Januses in Cancer?", Oncotarget, 3(11):1272-83, (2012).
Shanware, N. et al., "Glutamine: Pleiotropic Roles in Tumor Growth and Stress Resistance", J Mol Med (Berl)., 89(3):229-36, (2011).
Shukla, K. et al., "Design, Synthesis, and Pharmacological Evaluation of Bis-2-(5-Phenylacetamido-1,2,4-Thiadiazol-2-yl)Ethyl Sulfide 3 (BPTES) Analogs as Glutaminase Inhibitors", J Med Chem., 55(23):10551-63, (2012).
Singh, A. et al., "Dysfunctional KEAP1-NRF2 Interaction in Non-Small-Cell Lung Cancer", PLoS Med., 3(10):e420, pp. 1-10, (2006).
Stanovnik, B. et al., "The Tautomerism of Heterocycles: Substituent Tautomerism of Six-Membered Ring Heterocycles", Advances in Heterocyclic Chemistry, 91:1-134, (2006).
Thangavelu, K. et al., "Structural Basis for the Allosteric Inhibitory Mechanism of Human Kidney-Type Glutaminase (KGA) and its Regulation by Raf-Mek-Erk Signaling in Cancer Cell Metabolism", Proc Natl Acad Sci USA, 109(20):7705-10, (2012).
U.S. Appl. No. 14/791,186; Examiner-Initiated Interview Summary, dated Dec. 6, 2016; 1 page.
U.S. Appl. No. 14/791,186; Final Office Action, dated Dec. 6, 2016; 31 pages.
U.S. Appl. No. 14/791,186; Non-Final Office Action, dated May 31, 2016; 13 pages.
U.S. Appl. No. 14/791,186; Notice of Allowability, dated May 11, 2017; 5 pages.
U.S. Appl. No. 14/791,186; Notice of Allowance, dated Mar. 15, 2017; 8 pages.
U.S. Appl. No. 14/791,284; Non-Final Office Action, dated Apr. 11, 2016; 9 pages.
U.S. Appl. No. 14/791,284; Notice of Allowability, dated Nov. 18, 2016; 4 pages.
U.S. Appl. No. 14/791,284; Notice of Allowance, dated Oct. 14, 2016; 9 pages.
U.S. Appl. No. 14/791,307; Non-Final Office Action, dated Jun. 21, 2017; 12 pages.

(56) References Cited

OTHER PUBLICATIONS

U.S. Appl. No. 15/199,100; Corrected Notice of Allowability, dated Jul. 30, 2018; 8 pages.
U.S. Appl. No. 15/199,100; Examiner-Initiated Interview Summary, dated Jul. 6, 2018; 1 page.
U.S. Appl. No. 15/199,100; Non-Final Office Action, for dated Sep. 13, 2017; 11 pages.
U.S. Appl. No. 15/199,100; Notice of Allowance, dated Jul. 6, 2018; 11 pages.
U.S. Appl. No. 15/387,560; Non-Final Office Action, dated Jan. 5, 2018; 10 pages.
U.S. Appl. No. 15/387,560; Notice of Allowance, dated Jul. 27, 2018; 5 pages.
U.S. Appl. No. 15/624,168; Non-Final Office Action, dated Jul. 13, 2018; 9 pages.
U.S. Appl. No. 15/624,168; Notice of Allowance, dated Feb. 14, 2019; 20 pages.
U.S. Appl. No. 15/851,407; Non-Final Office Action, dated Jan. 27, 2020; 39 pages.
U.S. Appl. No. 16/152,901; Corrected Notice of Allowability, dated Jun. 19, 2020; 6 pages.
U.S. Appl. No. 16/152,901; Non-Final Office Action, dated Sep. 16, 2019; 15 pages.
U.S. Appl. No. 16/152,901; Notice of Allowance, dated Apr. 1, 2020; 10 pages.
U.S. Appl. No. 16/164,581; Non-Final Office Action, dated Aug. 26, 2019; 13 pages.
U.S. Appl. No. 16/164,581; Notice of Allowance, dated Jan. 30, 2020; 5 pages.
U.S. Appl. No. 16/164,581; Notice of Allowance, dated Mar. 4, 2020; 9 pages.
U.S. Appl. No. 16/241,596; Final Office Action, dated Mar. 5, 2020; 102 pages.
U.S. Appl. No. 16/241,596; Non-Final Office Action, dated Jul. 23, 2019; 21 pages.
U.S. Appl. No. 16/241,596; Notice of Allowance, dated Sep. 21, 2020; 14 pages.
U.S. Appl. No. 16/412,050; Non-Final Office Action, dated Dec. 9, 2019; 30 pages.
U.S. Appl. No. 16/412,050; Notice of Allowance, dated Apr. 10, 2020; 16 pages.
U.S. Appl. No. 16/891,791; Non-Final Office Action, dated Nov. 17, 2020; 6 pages.
U.S. Appl. No. 16/925,974; Corrected Notice of Allowance, dated Feb. 4, 2022; 11 pages.
U.S. Appl. No. 16/925,974; Examiner-Initiated Interview Summary, dated Jan. 31, 2022; 1 page.
U.S. Appl. No. 16/925,974; Notice of Allowance, dated Jan. 26, 2022; 11 pages.
U.S. Appl. No. 17/124,051; Non-Final Office Action, dated Jul. 28, 2022; 16 pages.
Van Den Heuvel, A. et al., "Analysis of Glutamine Dependency in Non-Small Cell Lung Cancer", Cancer Biol Ther., 13(12):1185-94, (2012).
Vander Heiden, M. et al., "Targeting Cancer Metabolism: A Therapeutic Window Opens", Nat Rev Drug Discov., 10(9):671-84, (2011).
Vander Heiden, M. et al., "Understanding the Warburg Effect: The Metabolic Requirements of Cell Proliferation", Science, 324(5930):1029-33, (2009).
Vippagunta, S. et al., "Crystalline Solids", Adv Drug Deliv Rev., 48(1):3-26, (2001).
Wang, J. et al., "Targeting Mitochondrial Glutaminase Activity Inhibits Oncogenic Transformation", Cancer Cell, 18(3):207-19, (2010).
Wise, D. et al., "Glutamine Addiction: A New Therapeutic Target in Cancer", Trends Biochem Sci., 35(8):427-33, (2010).
Zhang, D. et al., "Distinct Cysteine Residues in Keap1 Are Required for Keap1-Dependent Ubiquitination of Nrf2 and for Stabilization of Nrf2 by Chemopreventive Agents and Oxidative Stress", Mol Cell Biol., 23(22):8137-51, (2003).
Zhang, P. et al., "Loss of Kelch-Like ECH-Associated Protein 1 Function in Prostate Cancer Cells Causes Chemoresistance and Radioresistance and Promotes Tumor Growth", Mol Cancer Ther., 9(2):336-47, (2010).
Bernstein, J., "Polymorphism in Molecular Crystals, Moscow, Nauka" Publishing House, pp. 324-330, (2007).
Mironov, A. et al., Guidelines for conducting preclinical trials of medicaments. Methodological recommendations for preclinical study of antitumor activity of medicaments. Moscow: Grif and K Publishing House, Chapter 39, pp. 640-654, (2012).
U.S. Appl. No. 16/918,897; Non-Final Office Action, dated Nov. 15, 2022; 18 pages.
U.S. Appl. No. 16/918,897; Notice of Allowance, dated Mar. 9, 2023; 10 pages.
U.S. Appl. No. 17/124,051; Notice of Allowance, dated Nov. 3, 2022; 11 pages.
U.S. Appl. No. 17/327,225; Notice of Allowance, dated Jun. 7, 2023; 11 pages.
U.S. Appl. No. 18/163,151; Application as filed. dated Feb. 1, 2023; 103 pages.

\* cited by examiner

GLS1 INHIBITORS FOR TREATING DISEASE

This application is a continuation of U.S. application Ser. No. 16/925,974, filed Jul. 10, 2020, which is a continuation of U.S. application Ser. No. 16/412,050, filed May 14, 2019, which application issued on Sep. 8, 2020, as U.S. Pat. No. 10,766,892, which is a divisional application of U.S. application Ser. No. 15/624,168, filed Jun. 15, 2017, which application issued on Jul. 9, 2019, as U.S. Pat. No. 10,344,025, which is a continuation of U.S. application Ser. No. 14/791,186, filed Jul. 2, 2015, which application issued on Nov. 7, 2017, as U.S. Pat. No. 9,809,588, which claims the benefit of priority of U.S. provisional Application No. 62/020,539, filed Jul. 3, 2014, the disclosures of each are hereby incorporated by reference as if written herein in their entireties.

The present disclosure relates to new heterocyclic compounds and compositions, and their application as pharmaceuticals for the treatment of disease. Methods of inhibition of GLS1 activity in a human or animal subject are also provided for the treatment of diseases such as cancer.

Metabolic deregulation is a hallmark of cancer as tumors exhibit an increased demand for nutrients and macromolecules to fuel their rapid proliferation. Glutamine (Gln), the most abundant amino acid in circulation, plays an essential role in providing cancer cells with biosynthetic intermediates required to support proliferation and survival. Specifically, glutaminolysis, or the enzymatic conversion of glutamine to glutamate, provides proliferating cancer cells with a source of nitrogen for amino acid and nucleotide synthesis, and a carbon skeleton to fuel ATP and NADPH synthesis through the TCA cycle. In addition to supporting cell growth, glutamine metabolism plays a critical role in maintaining cellular redox homeostasis as glutamate can be converted into glutathione, the major intracellular antioxidant.

Glutaminolysis is regulated by mitochondrial glutaminase (GLS), the rate limiting enzyme that catalyzes the conversion of Gln to glutamate and ammonia. Mammalian cells contain 2 genes that encode glutaminase: the kidney-type (GLS1) and liver-type (GLS2) enzymes. Each has been detected in multiple tissue types, with GLS1 being widely distributed throughout the body. GLS1 is a phosphate-activated enzyme that exists in humans as two major splice variants, a long form (referred to as KGA) and a short form (GAC), which differ only in their C-terminal sequences. Both forms of GLS1 are thought to bind to the inner membrane of the mitochondrion in mammalian cells, although at least one report suggests that glutaminase may exist in the intramembrane space, dissociated from the membrane. GLS is frequently overexpressed in human tumors and has been shown to be positively regulated by oncogenes such as Myc. Consistent with the observed dependence of cancer cell lines on glutamine metabolism, pharmacological inhibition of GLS offers the potential to target Gln addicted tumors.

Thus, there is a need for glutaminase inhibitors that are specific and capable of being formulated for in vivo use.

SUMMARY

Accordingly, the inventors herein disclose new compositions and methods for inhibiting glutaminase activity.

Provided is a compound of structural Formula I

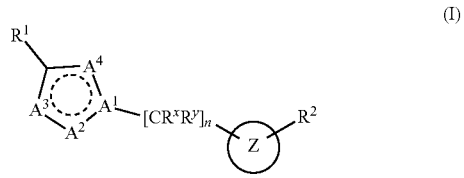

or a salt thereof, wherein: n is chosen from 3, 4, and 5; each $R^X$ and $R^Y$ is independently chosen from alkyl, cyano, H, and halo, or two $R^X$ groups together with the atoms to which they are attached optionally form a cycloalkyl ring; $A^1$ is chosen from C and N; $A^2$, $A^3$, and $A^4$ are independently chosen from N, O, S, and CH, wherein at least one of $A^1$, $A^2$, $A^3$, and $A^4$ is chosen from N, O, and S; $R^1$ and $R^2$ are each independently chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ and $R^2$ each may be optionally substituted with one to three $R^Z$ groups, wherein $R^1$ and $R^2$ together with the atoms to which they are attached optionally form an heteroaryl, or heterocycloalkyl ring, which may be optionally substituted with one to three $R^Z$ groups; $R^3$ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $C(R^4)_2C(O)R^4$, $C(R^4)_2C(O)N(R^4)_2$, $C(R^4)_2N(R^4)_2$, $C(R^4)_2NR^4C(O)R^4$, $C(R^4)_2NR^4C(O)OR^4$, $C(R^4)_2NR^4C(O)N(R^4)_2$, $C(R^4)_2NR^4S(O)R^4$, $C(R^4)_2NR^4S(O)_2R^4$, $N(R^4)_2$, $NR^4C(O)R^4$, $NR^4C(O)OR^4$, $NR^4C(O)N(R^4)_2$, $NR^4S(O)R^4$, $NR^4S(O)_2R^4$, $C(O)N(R^4)_2$, $S(O)N(R^4)_2$, $S(O)_2N(R^4)_2$, $C(O)R^4$, $SR^4$, $S(O)R^4$, and $S(O)_2R^4$; wherein each $R^3$ may be optionally substituted with one to three $R^Z$ groups; each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^4$ may be optionally substituted with one to three $R^Z$ groups, wherein two $R^4$ groups together with the atoms to which they are attached optionally form an heteroaryl, or heterocycloalkyl ring, which may be optionally substituted with one to three $R^Z$ groups; each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$; each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^x$ groups; and Z is a monocyclic heteroaryl, which may be optionally substituted.

Provided is a composition comprising a compound of Formula I and a pharmaceutically acceptable carrier, adjuvant, or vehicle.

Provided is a method of inhibiting GLS1 activity in a biological sample comprising contacting the biological sample with a compound of Formula I.

Provided is a method of treating a GLS1-mediated disorder in a subject in need thereof, comprising the step of administering to the subject a compound of Formula I.

Provided is a method of treating a GLS1-mediated disorder in a subject in need thereof, comprising the sequential or co-administration of a compound of Formula I or a pharmaceutically acceptable salt thereof, and another therapeutic agent.

Provided is a compound of any of Formula I for use in human therapy.

Provided is a compound of any of Formula I for use in treating a GLS1-mediated disease.

Provided is a use of a compound of Formula I for the manufacture of a medicament to treat a GLS1-mediated disease.

DETAILED DESCRIPTION

Abbreviations and Definitions

To facilitate understanding of the disclosure, a number of terms and abbreviations as used herein are defined below as follows:

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

When ranges of values are disclosed, and the notation "from $n_1$ . . . to $n_2$" or "between $n_1$ . . . and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values that it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a $-C(O)CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, the alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, the alkyl will comprise from 1 to 10 carbon atoms. In further embodiments, the alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, the alkynyl comprises from 2 to 6 carbon atoms. In further embodiments, the alkynyl comprises from 2 to 4 carbon atoms. The term "alkynylene" refers to a carbon-carbon triple bond attached at two positions such as ethynylene (—C:::C—, —C—C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl" as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH₃C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl(hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, the cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, the heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzindolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each the heteroatom may be independently selected from the group consisting of nitrogen, oxygen, and sulfur In certain embodiments, the heterocycloalkyl will comprise from 1 to 4 heteroatoms as ring members. In further embodiments, the heterocycloalkyl will comprise from 1 to 2 heteroatoms as ring members. In certain embodiments, the heterocycloalkyl will comprise from 3 to 8 ring members in each ring. In further embodiments, the heterocycloalkyl will comprise from 3 to 7 ring members in each ring. In yet further embodiments, the heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four the members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethylsilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that the group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and Rn where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

GLS1 inhibitor is used herein to refer to a compound that exhibits an IC50 with respect to GLS1 activity of no more than about 100 μM and more typically not more than about 50 μM, as measured in the GLS1 enzyme assay described generally herein below. IC50 is that concentration of inhibitor that reduces the activity of an enzyme (e.g., GLS1) to half-maximal level. Certain compounds disclosed herein have been discovered to exhibit inhibition against GLS1. In certain embodiments, compounds will exhibit an IC50 with respect to GLS1 of no more than about 10 μM; in further embodiments, compounds will exhibit an IC50 with respect to GLS1 of no more than about 5 μM; in yet further embodiments, compounds will exhibit an IC50 with respect to GLS1 of not more than about 1 μM; in yet further embodiments, compounds will exhibit an IC50 with respect to GLS1 of not more than about 200 nM, as measured in the GLS1 binding assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock (farm animals) such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethanesulfonate (isethionate), lactate, maleate, malonate, DL-mandelate, mesitylenesulfonate, methanesulfonate, naphthalenesulfonate, nicotinate, 2-naphthalenesulfonate, oxalate, pamoate, pectinate, persulfate, 3-phenylpropionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

A salt of a compound can be made by reacting the appropriate compound in the form of the free base with the appropriate acid.

Compounds

The present disclosure provides a compound of structural Formula I

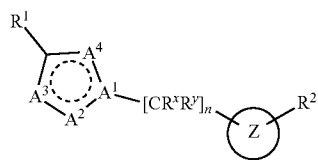

(I)

or a salt thereof, wherein: n is chosen from 3, 4, and 5; each $R^x$ and R' is independently chosen from alkyl, cyano, H, and halo, or two $R^x$ groups together with the atoms to which they are attached optionally form a cycloalkyl ring; $A^1$ is chosen from C and N; $A^2$, $A^3$, and $A^4$ are independently chosen from N, O, S, and CH, wherein at least one of $A^1$, $A^2$, $A^3$, and $A^4$ is chosen from N, O, and S; $R^1$ and $R^2$ are each independently chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ and $R^2$ each may be optionally substituted with one to three $R^Z$ groups, wherein $R^1$ and $R^2$ together with the atoms to which they are attached optionally form an heteroaryl, or heterocycloalkyl ring, which may be optionally substituted with one to three $R^Z$ groups; $R^3$ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $C(R^4)_2C(O)R^4$, $C(R^4)_2C(O)N(R^4)_2$, $C(R^4)_2N(R^4)_2$, $C(R^4)_2NR^4C(O)R^4$, $C(R^4)_2NR^4C(O)OR^4$, $C(R^4)_2NR^4C(O)N(R^4)_2$, $C(R^4)_2NR^4S(O)R^4$, $C(R^4)_2NR^4S(O)_2R^4$, $N(R^4)_2$, $NR^4C(O)R^4$, $NR^4C(O)OR^4$, $NR^4C(O)N(R^4)_2$, $NR^4S(O)R^4$, $NR^4S(O)_2R^4$, $C(O)N(R^4)_2$, $S(O)N(R^4)_2$, $S(O)_2N(R^4)_2$, $C(O)R^4$, $SR^4$, $S(O)R^4$, and $S(O)_2R^4$; wherein each $R^3$ may be optionally substituted with one to three $R^Z$ groups; each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^4$ may be optionally substituted with one to three $R^Z$ groups, wherein two $R^4$ groups together with the atoms to which they are attached optionally form an heteroaryl, or heterocycloalkyl ring, which may be optionally substituted with one to three $R^Z$ groups; each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$; each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^x$ groups; and Z is a monocyclic heteroaryl, which may be optionally substituted.

In some embodiments, the compound, or a pharmaceutically acceptable salt thereof, has Formula II

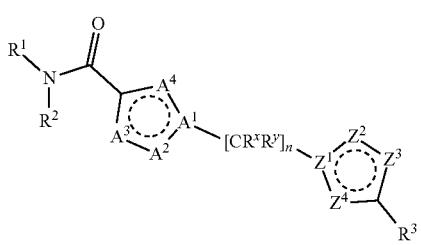
(II)

or a salt thereof, wherein: n is chosen from 3, 4, and 5; each $R^X$ and $R^Y$ is independently chosen from alkyl, cyano, H, and halo, or two $R^X$ groups together with the atoms to which they are attached optionally form a cycloalkyl ring; $A^1$ and $Z^1$ are independently chosen from C and N; $A^2$, $A^3$, $A^4$, $Z^2$, $Z^3$, and $Z^4$ are independently chosen from N, O, S, and CH, wherein at least one of $A^1$, $A^2$, $A^3$, and $A^4$ and at least one of $Z^1$, $Z^2$, $Z^3$, and $Z^4$ is chosen from N, O, and S; $R^1$ and $R^2$ are each independently chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ and $R^2$ each may be optionally substituted with one to three $R^Z$ groups, wherein $R^1$ and $R^2$ together with the atoms to which they are attached optionally form an heteroaryl, or heterocycloalkyl ring, which may be optionally substituted with one to three $R^Z$ groups; $R^3$ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, $C(R^4)_2C(O)R^4$, $C(R^4)_2C(O)N(R^4)_2$, $C(R^4)_2N(R^4)_2$, $C(R^4)_2NR^4C(O)R^4$, $C(R^4)_2NR^4C(O)OR^4$, $C(R^4)_2NR^4C(O)N(R^4)_2$, $C(R^4)_2NR^4S(O)R^4$, $C(R^4)_2NR^4S(O)_2R^4$, $N(R^4)_2$, $NR^4C(O)R^4$, $NR^4C(O)OR^4$, $NR^4C(O)N(R^4)_2$, $NR^4S(O)R^4$, $NR^4S(O)_2R^4$, $C(O)N(R^4)_2$, $S(O)N(R^4)_2$, $S(O)_2N(R^4)_2$, $C(O)R^4$, $SR^4$, $S(O)R^4$, and $S(O)_2R^4$; wherein each $R^3$ may be optionally substituted with one to three $R^Z$ groups; each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each $R^4$ may be optionally substituted with one to three $R^Z$ groups, wherein two $R^4$ groups together with the atoms to which they are attached optionally form an heteroaryl, or heterocycloalkyl ring, which may be optionally substituted with one to three $R^Z$ groups; each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$; each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^X$ groups.

In certain embodiments $A^1$, $A^2$, and $A^3$ are N; and $A^4$ is CH.

In certain embodiments $A^1$ is C; $A^2$ and $A^3$ are N; and $A^4$ is S.

In certain embodiments $Z^1$, $Z^2$, and $Z^3$ are N; $Z^4$ is CH; and $R^3$ is chosen from $N(R^4)_2$, $NR^4C(O)R^4$, $NR^4C(O)R^4$, and $NR^4C(O)N(R^4)_2$.

In certain embodiments $Z^1$, $Z^2$, and $Z^3$ are N; $Z^4$ is CH; and $R^3$ is chosen from $C(O)N(R^4)_2$, $S(O)N(R^4)_2$, $S(O)_2N(R^4)_2$, $C(O)R^4$, $C(O)OR^4$.

In certain embodiments $Z^1$ is C; $Z^2$ and $Z^3$ are N; $Z^4$ is S; and $R^3$ is chosen from $N(R^4)_2$, $NR^4C(O)R^4$, $NR^4C(O)OR^4$, and $NR^4C(O)N(R^4)_2$.

In certain embodiments n is 4.

In certain embodiments each $R^X$ and $R^Y$ is independently chosen from H and fluoro.

In certain embodiments one of $R^X$ is independently fluoro.

In certain embodiments $A^1$, $A^2$, and $A^3$ are N; $A^4$ is CH; n is 4; $Z^1$ is C; $Z^2$ and $Z^3$ are N; $Z^4$ is S; and $R^3$ is chosen from $N(R^4)_2$, $NR^4C(O)R^4$, $NR^4C(O)OR^4$, and $NR^4C(O)N(R^4)_2$.

In certain embodiments $A^1$ is C; $A^2$ and $A^3$ are N; $A^4$ is S; n is 4; $Z^1$, $Z^2$, and $Z^3$ are N; $Z^4$ is CH; and $R^3$ is chosen from $C(O)N(R^4)_2$, $S(O)N(R^4)_2$, $S(O)_2N(R^4)_2$, $C(O)R^4$, $C(O)OR^4$.

In certain embodiments $A^1$, $A^2$, and $A^3$ are N; $A^4$ is CH; n is 4; $Z^1$, $Z^2$, and $Z^3$ are N; $Z^4$ is CH; and $R^3$ is chosen from $N(R^4)_2$, $NR^4C(O)R^4$, $NR^4C(O)OR^4$, and $NR^4C(O)N(R^4)_2$.

In some embodiments, the compound, or a pharmaceutically acceptable salt thereof, has structural Formula III:

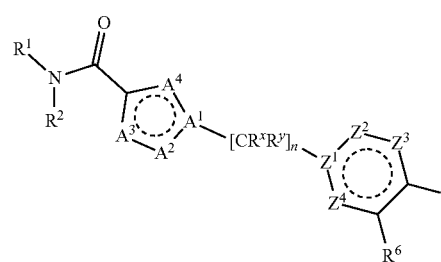
(III)

or a salt thereof, wherein: n is chosen from 3, 4, and 5; each $R^X$ and $R^Y$ is independently chosen from alkyl, cyano, H, and halo, or two $R^X$ groups together with the atoms to which they are attached optionally form a cycloalkyl ring; $A^1$ is chosen from C and N; $A^2$, $A^3$, and $A^4$, are independently chosen from N, O, S, and CH, wherein at least one of $A^1$, $A^2$, $A^3$, and A⁴ is chosen from N, O, and S; Z¹ is C; Z², Z³ and Z⁴ are independently chosen from N and CH, wherein at least one of Z¹, Z², Z³, and Z⁴ is N; R¹ and R² are each independently chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein R¹ and R² each may be optionally substituted with one to three R$^Z$ groups, wherein R¹ and R² together with the atoms to which they are attached optionally form an heteroaryl, or heterocycloalkyl ring, which may be optionally substituted with one to three R$^Z$ groups; R³ is chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, hydroxyl, C(R⁴)₂C(O)R⁴, C(R⁴)₂C(O)N(R⁴)₂, C(R⁴)₂N(R⁴)₂, C(R⁴)₂NR⁴C(O)R⁴, C(R⁴)₂NR⁴C(O)OR⁴, C(R⁴)₂NR⁴C(O)N(R⁴)₂, C(R⁴)₂NR⁴S(O)R⁴, C(R⁴)₂NR⁴S(O)₂R⁴, N(R⁴)₂, NR⁴C(O)R⁴, NR⁴C(O)OR⁴, NR⁴C(O)N(R⁴)₂, NR⁴S(O)R⁴, NR⁴S(O)₂R⁴, C(O)N(R⁴)₂, S(O)N(R⁴)₂, S(O)₂N(R⁴)₂, C(O)R⁴, SR⁴, S(O)R⁴, and S(O)₂R⁴; wherein each R³ may be optionally substituted with one to three R$^Z$ groups; each R⁴ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein each R⁴ may be optionally substituted with one to three R$^Z$ groups, wherein two R⁴ groups together with the atoms to which they are attached optionally form an heteroaryl, or heterocycloalkyl ring, which may be optionally substituted with one to three R$^Z$ groups; each R$^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, N(R⁵)₂, NR⁵C(O)R⁵, NR⁵C(O)OR⁵, NR⁵C(O)N(R⁵)₂, NR⁵S(O)R⁵, NR⁵S(O)₂R⁵, C(O)N(R⁵)₂, S(O)N(R⁵)₂, S(O)₂N(R⁵)₂, C(O)R⁵, C(O)OR⁵, SR⁵, S(O)R⁵, and S(O)₂R⁵; each R⁵ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two R⁵ groups together with the atoms to which they are attached optionally form an aryl, cycloalkyl, heteroaryl, or heterocycloalkyl ring, which may be optionally substituted with one to three R$^X$ groups; and R⁶ is chosen from, alkyl, cyano, cycloalkyl, H, halo, haloalkyl, and heterocycloalkyl, wherein R³ and R⁶ groups together with the atoms to which they are attached optionally form an aryl, cycloalkyl, heteroaryl, or heterocycloalkyl ring, which may be optionally substituted with one to three R$^Z$ groups.

The In certain embodiments A¹ is C; A² and A³ are N; and A⁴ is S.

In certain embodiments A¹, A², and A³ are N; and A⁴ is CH.

In certain embodiments n is 4.

In certain embodiments each R$^X$ and R$^Y$ is independently chosen from H and fluoro.

In certain embodiments one of R$^X$ is independently fluoro.

In certain embodiments R¹ is methyl; and R² is H.

In certain embodiments R¹ is methyl; R² is H; and one of R$^X$ is independently fluoro.

In certain embodiments; Z² and Z³ are N; Z⁴ is CH; R³ is chosen from N(R⁴)₂, NR⁴C(O)R⁴, NR⁴C(O)OR⁴, and NR⁴C(O)N(R⁴)₂; and R⁶ is H.

In certain embodiments A¹ is C; A² and A³ are N; A⁴ is S; n is 4; Z² and Z³ are N; Z⁴ is CH; R³ is chosen from N(R⁴)₂, NR⁴C(O)R⁴, NR⁴C(O)OR⁴, and NR⁴C(O)N(R⁴)₂; and R⁶ is H.

In certain embodiments A¹, A², and A³ are N; A⁴ is CH; n is 4; Z² and Z³ are N; Z⁴ is CH; R³ is chosen from N(R⁴)₂, NR⁴C(O)R⁴, NR⁴C(O)OR⁴, and NR⁴C(O)N(R⁴)₂; and R⁶ is H.

In some embodiments, the compound, or a pharmaceutically acceptable salt thereof, has structural Formula IV:

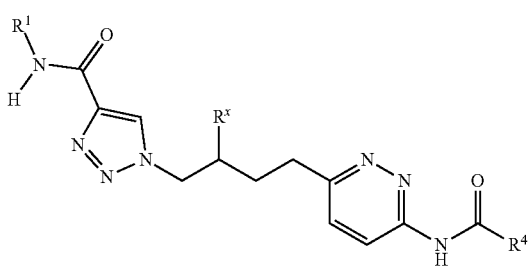

(IV)

or a salt thereof, wherein: R$^X$ is chosen from fluoro and H; R¹ is chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein R¹ may be optionally substituted with one to three R$^Z$ groups; each R⁴ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein R⁴ may be optionally substituted with one to three R$^Z$ groups; each R$^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$; and each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^X$ groups.

In particular embodiments, $R^1$ is methyl.

In some embodiments, the compound, or a pharmaceutically acceptable salt thereof, has structural Formula V:

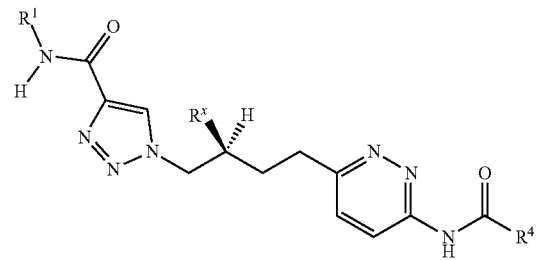

(IV)

or a salt thereof, wherein: $R^X$ is chosen from fluoro and H; $R^1$ is chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ may be optionally substituted with one to three $R^Z$ groups; each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein $R^4$ may be optionally substituted with one to three $R^Z$ groups; each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$; and each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^X$ groups.

In some embodiments, the compound, or a pharmaceutically acceptable salt thereof, has structural Formula VI:

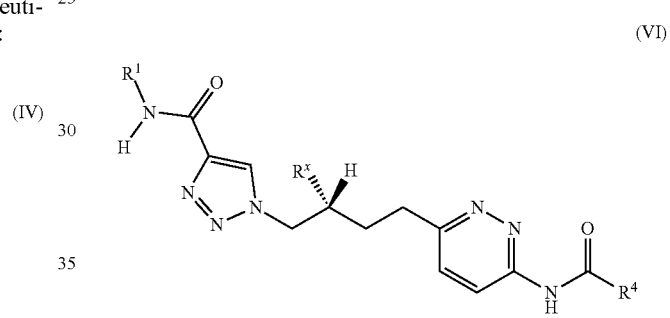

(VI)

or a salt thereof, wherein: $R^X$ is chosen from fluoro and H; $R^1$ is chosen from alkenyl, alkyl, aryl, arylalkyl, cycloalkyl, cycloalkylalkyl, H, halo, haloalkyl, heteroaryl, heteroarylalkyl, heterocycloalkyl, and heterocycloalkylalkyl, wherein $R^1$ may be optionally substituted with one to three $R^Z$ groups; each $R^4$ is independently chosen from alkenyl, alkoxy, alkyl, aryl, arylalkyl, cyano, cycloalkyl, cycloalkylalkyl, H, halo, haloalkyl, heteroaryl, heteroarylalkyl, heterocycloalkyl, heterocycloalkylalkyl, and hydroxyl, wherein $R^4$ may be optionally substituted with one to three $R^Z$ groups; each $R^Z$ group is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, oxo, $N(R^5)_2$, $NR^5C(O)R^5$, $NR^5C(O)OR^5$, $NR^5C(O)N(R^5)_2$, $NR^5S(O)R^5$, $NR^5S(O)_2R^5$, $C(O)N(R^5)_2$, $S(O)N(R^5)_2$, $S(O)_2N(R^5)_2$, $C(O)R^5$, $C(O)OR^5$, $SR^5$, $S(O)R^5$, and $S(O)_2R^5$; and each $R^5$ is independently chosen from alkenyl, alkoxy, alkyl, aryl, arylalkyl, cyano, cycloalkyl, cycloalkylalkyl, H, haloalkyl, heteroaryl, heteroarylalkyl, heterocycloalkyl, and heterocycloalkylalkyl, wherein two $R^5$ groups together with the atoms to which they are attached optionally form an aryl, cycloalkyl, heteroaryl, or heterocycloalkyl ring, which may be optionally substituted with one to three $R^X$ groups.

In some embodiments, the compound, or a pharmaceutically acceptable salt thereof, has structural Formula VII:

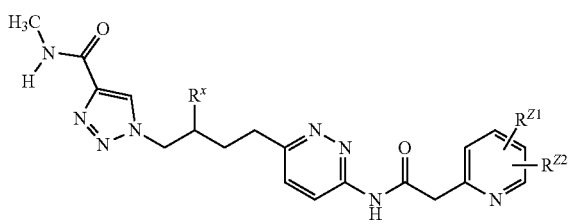

(VII)

or a salt thereof, wherein: $R^X$ is chosen from fluoro and H; each of $R^{Z1}$ and $R^{Z2}$ is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, and oxo.

In some embodiments, the compound, or a pharmaceutically acceptable salt thereof, is chosen from structural Formula VIIa or VIIb:

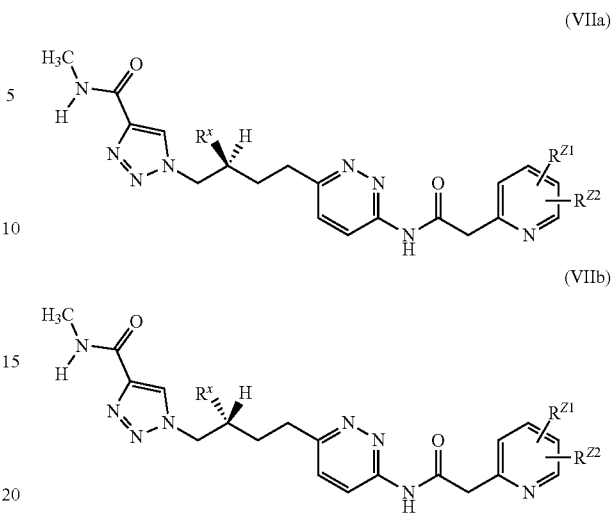

or a salt thereof, wherein: $R^X$ is chosen from fluoro and H; each of $R^{Z1}$ and $R^{Z2}$ is independently chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, and oxo.

In certain embodiments $R^X$ is chosen from fluoro and H; and each of $R^{Z1}$ and $R^{Z2}$ is independently chosen from alkyl, cycloalkyl, cycloalkylhaloalkyl, cycloalkyloxy, H, haloalkoxy, haloalkoxyaryl, haloalkyl, halocycloalkyloxy, heterocycloalkyl, and heterocycloalkyloxy.

In certain embodiments $R^X$ is chosen from fluoro and H; each of $R^{Z1}$ and $R^{Z2}$ is independently chosen from H,

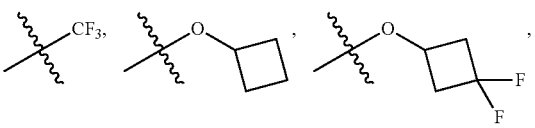

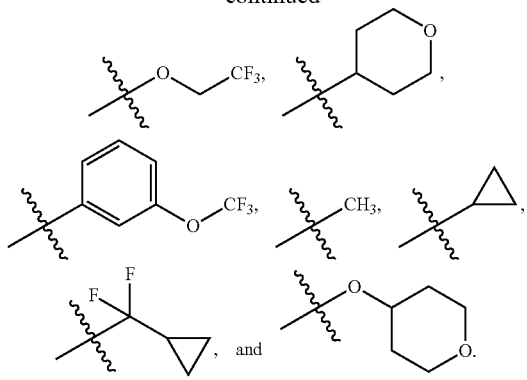

In some embodiments, the compound, or a pharmaceutically acceptable salt thereof, has structural Formula VIII:

(VIII)

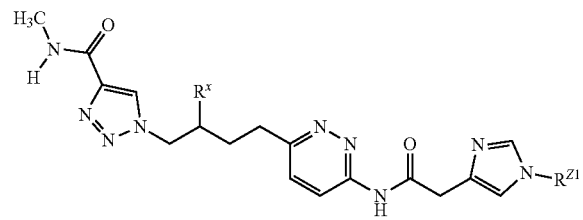

or a salt thereof, wherein: $R^X$ is chosen from fluoro and H; $R^{Z1}$ is chosen from alkenyl, alkoxy, alkoxyalkyl, alkoxyaryl, alkoxyarylalkyl, alkoxycycloalkyl, alkoxycycloalkylalkyl, alkoxyhaloalkyl, alkoxyheteroaryl, alkoxyheteroarylalkyl, alkoxyheterocycloalkyl, alkoxyheterocycloalkylalkyl, alkyl, alkylaryl, alkylarylalkyl, alkylcycloalkyl, alkylcycloalkylalkyl, alkylheteroaryl, alkylheteroarylalkyl, alkylheterocycloalkyl, alkylheterocycloalkylalkyl, aryl, arylalkyl, arylalkyloxy, arylhaloalkyl, aryloxy, cyano, cycloalkyl, cycloalkylalkyl, cycloalkylalkyloxy, cycloalkylhaloalkyl, cycloalkyloxy, H, halo, haloalkoxy, haloalkoxyalkyl, haloalkoxyaryl, haloalkoxyarylalkyl, haloalkoxycycloalkyl, haloalkoxycycloalkylalkyl, haloalkoxyheteroaryl, haloalkoxyheteroarylalkyl, haloalkoxyheterocycloalkyl, haloalkoxyheterocycloalkylalkyl, haloalkyl, haloalkylaryl, haloalkylarylalkyl, haloalkylcycloalkyl, haloalkylcycloalkylalkyl, haloalkylheteroaryl, haloalkylheteroarylalkyl, haloalkylheterocycloalkyl, haloalkylheterocycloalkylalkyl, haloaryl, haloarylalkyl, haloarylalkyloxy, haloaryloxy, halocycloalkyl, halocycloalkylalkyl, halocycloalkylalkyloxy, halocycloalkyloxy, haloheteroaryl, haloheteroarylalkyl, haloheteroarylalkyloxy, haloheteroaryloxy, haloheterocycloalkyl, haloheterocycloalkylalkyl, haloheterocycloalkylalkyloxy, haloheterocycloalkyloxy, heteroaryl, heteroarylalkyl, heteroarylalkyloxy, heteroarylhaloalkyl, heteroaryloxy, heterocycloalkyl, heterocycloalkylalkyl, heterocycloalkylalkyloxy, heterocycloalkylhaloalkyl, heterocycloalkyloxy, hydroxyl, and oxo.

In particular embodiments the compound is chosen from Examples 1-609 and Prophetic Examples 1-2 as disclosed herein.

Pharmaceutical Compositions

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Compounds described herein can be administered as follows:

Oral Administration

The compounds of the present invention may be administered orally, including swallowing, so the compound enters the gastrointestinal tract, or is absorbed into the blood stream directly from the mouth, including sublingual or buccal administration.

Suitable compositions for oral administration include solid formulations such as tablets, pills, cachets, lozenges and hard or soft capsules, which can contain liquids, gels, powders, or granules.

In a tablet or capsule dosage form the amount of drug present may be from about 0.05% to about 95% by weight, more typically from about 2% to about 50% by weight of the dosage form.

In addition, tablets or capsules may contain a disintegrant, comprising from about 0.5% to about 35% by weight, more typically from about 2% to about 25% of the dosage form. Examples of disintegrants include methyl cellulose, sodium or calcium carboxymethyl cellulose, croscarmellose sodium, polyvinylpyrrolidone, hydroxypropyl cellulose, starch and the like.

Suitable binders, for use in a tablet, include gelatin, polyethylene glycol, sugars, gums, starch, hydroxypropyl cellulose and the like. Suitable diluents, for use in a tablet, include mannitol, xylitol, lactose, dextrose, sucrose, sorbitol and starch.

Suitable surface active agents and glidants, for use in a tablet or capsule, may be present in amounts from about 0.1% to about 3% by weight, and include polysorbate 80, sodium dodecyl sulfate, talc and silicon dioxide.

Suitable lubricants, for use in a tablet or capsule, may be present in amounts from about 0.1% to about 5% by weight, and include calcium, zinc or magnesium stearate, sodium stearyl fumarate and the like.

Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with a liquid diluent. Dyes or pigments may be added to tablets for identification or to characterize different combinations of active compound doses.

Liquid formulations can include emulsions, solutions, syrups, elixirs and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

Compositions for oral administration may be formulated as immediate or modified release, including delayed or sustained release, optionally with enteric coating.

In another embodiment, a pharmaceutical composition comprises a therapeutically effective amount of a compound of Formula (I) or a pharmaceutically acceptable salt thereof, and a pharmaceutically acceptable carrier.

Parenteral Administration

Compounds of the present invention may be administered directly into the blood stream, muscle, or internal organs by injection, e.g., by bolus injection or continuous infusion. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods. The formulations may be presented in unit-dose or multi-dose containers, for example sealed ampoules and vials.

Most parenteral formulations are aqueous solutions containing excipients, including salts, buffering, suspending, stabilizing and/or dispersing agents, antioxidants, bacteriostats, preservatives, and solutes which render the formulation isotonic with the blood of the intended recipient, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Compositions for parenteral administration may be formulated as immediate or modified release, including delayed or sustained release. Compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Topical Administration

Compounds of the present invention may be administered topically (for example to the skin, mucous membranes, ear, nose, or eye) or transdermally. Formulations for topical administration can include, but are not limited to, lotions, solutions, creams, gels, hydrogels, ointments, foams, implants, patches and the like. Carriers that are pharmaceutically acceptable for topical administration formulations can include water, alcohol, mineral oil, glycerin, polyethylene glycol and the like. Topical administration can also be performed by, for example, electroporation, iontophoresis, phonophoresis and the like.

Typically, the active ingredient for topical administration may comprise from 0.001% to 10% w/w (by weight) of the formulation. In certain embodiments, the active ingredient may comprise as much as 10% w/w; less than 5% w/w; from 2% w/w to 5% w/w; or from 0.1% to 1% w/w of the formulation.

Compositions for topical administration may be formulated as immediate or modified release, including delayed or sustained release.

Rectal, Buccal, and Sublingual Administration

Suppositories for rectal administration of the compounds of the present invention can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Administration by Inhalation

For administration by inhalation, compounds may be conveniently delivered from an insufflator, nebulizer pressurized packs or other convenient means of delivering an aerosol spray or powder. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Other carrier materials and modes of administration known in the pharmaceutical art may also be used. Pharmaceutical compositions of the invention may be prepared by any of the well-known techniques of pharmacy, such as effective formulation and administration procedures. Preferred unit dosage formulations are those containing an effective dose, as herein recited, or an appropriate fraction thereof, of the active ingredient. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. In addition, the route of administration may vary depending on the condition and its severity. The above considerations concerning effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

Methods of Treatment

The present disclosure provides compounds and pharmaceutical compositions that inhibit glutaminase activity, particularly GLS1 activity and are thus useful in the treatment or prevention of disorders associated with GLS1. Compounds and pharmaceutical compositions of the present disclosure selectively modulate GLS1 and are thus useful in the treatment or prevention of a range of disorders associated with GLS1 and include, but are not limited to, cancer, immunological or neurological diseases associated with GLS1.

Neurological Disorders

In some embodiments, the compounds and pharmaceutical compositions of the present disclosure may be useful in the treatment or prevention of neurological diseases.

The most common neurotransmitter is glutamate, derived from the enzymatic conversion of glutamine via glutaminase. High levels of glutamate have been shown to be neurotoxic. Following traumatic insult to neuronal cells, there occurs a rise in neurotransmitter release, particularly glutamate. Accordingly, inhibition of glutaminase has been hypothesized as a means of treatment following an ischemic insult, such as stroke.

Huntington's disease is a progressive, fatal neurological condition. In genetic mouse models of Huntington's disease, it was observed that the early manifestation of the disease correlated with dysregulated glutamate release (Raymond et al., Neuroscience, 2011). In HIV-associated dementia, HIV infected macrophages exhibit upregulated glutaminase activity and increased glutamate release, leading to neuronal damage (Huang et al., J. Neurosci., 2011). Similarly, in another neurological disease, the activated microglia in Rett Syndrome release glutamate causing neuronal damage. The release of excess glutamate has been associated with the up-regulation of glutaminase (Maezawa et al., J. Neurosci, 2010). In mice bred to have reduced glutaminase levels, sensitivity to psychotic-stimulating drugs, such as amphetamines, was dramatically reduced, thus suggesting that glutaminase inhibition may be beneficial in the treatment of schizophrenia (Gaisler-Salomon et al., Neuropsychopharmacology, 2009). Bipolar disorder is a devastating illness that is marked by recurrent episodes of mania and depression. This disease is treated with mood stabilizers such as lithium and valproate; however, chronic use of these drugs appear to increase the abundance of glutamate receptors (Nanavati et al., J. Neurochem., 2011), which may lead to a decrease in the drug's effectiveness over time. Thus, an alternative treatment may be to reduce the amount of glutamate by inhibiting glutaminase. This may or may not be in conjunction with the mood stabilizers. Memantine, a partial antagonist of N-methyl-D-aspartate receptor (NMDAR), is an approved therapeutic in the treatment of Alzheimer's disease. Currently, research is being conducted looking at memantine as a means of treating vascular dementia and Parkinson's disease (Oliverares et al., Curr. Alzheimer Res., 2011). Since memantine has been shown to partially block the NMDA glutamate receptor also, it is not unreasonable to speculate that decreasing glutamate levels by inhibiting glutaminase could also treat Alzheimer's disease, vascular dementia and Parkinson's disease. Alzheimer's disease, bipolar disorder, HIV-associated dementia, Huntington's disease, ischemic insult, Parkinson's disease, schizophrenia, stroke, traumatic insult and vascular dementia are but a few of the neurological diseases that have been correlated to increased levels of glutamate. Thus, inhibiting glutaminase with a compound described herein can reduce or prevent neurological diseases. Therefore, in certain embodiments, the compounds may be used for the treatment or prevention of neurological diseases.

Immunological Disorders

In some embodiments, the compounds and pharmaceutical compositions of the present disclosure may be useful in the treatment or prevention of immunological diseases.

Activation of T lymphocytes induces cell growth, proliferation, and cytokine production, thereby placing energetic and biosynthetic demands on the cell. Glutamine serves as an amine group donor for nucleotide synthesis, and glutamate, the first component in glutamine metabolism, plays a direct role in amino acid and glutathione synthesis, as well as being able to enter the Krebs cycle for energy production (Carr et al., J. Immunol., 2010). Mitogen-induced T cell proliferation and cytokine production require high levels of glutamine metabolism, thus inhibiting glutaminase may serve as a means of immune modulation. In multiple sclerosis, an inflammatory autoimmune disease, the activated microglia exhibit up-regulated glutaminase and release increased levels of extracellular glutamate. Glutamine levels are lowered by sepsis, injury, burns, surgery and endurance exercise (Calder et al., Amino Acids, 1999). These situations put the individual at risk of immunosuppression. In fact, in general, glutaminase gene expression and enzyme activity are both increased during T cell activity. Patients given glutamine following bone marrow transplantation resulted in a lower level of infection and reduced graft v. host disease (Crowther, Proc. Nutr. Soc., 2009). T cell proliferation and activation is involved in many immunological diseases, such as inflammatory bowel disease, Crohn's disease, sepsis, psoriasis, arthritis (including rheumatoid arthritis), multiple sclerosis, graft v. host disease, infections, lupus and diabetes. In an embodiment of the invention, the compounds described herein can be used to treat or prevent immunological diseases.

Cancer

In some embodiments, the compounds and pharmaceutical compositions of the present disclosure may be useful in the treatment or prevention of cancer.

In addition to serving as the basic building blocks of protein synthesis, amino acids have been shown to contribute to many processes critical for growing and dividing cells, and this is particularly true for cancer cells. Nearly all definitions of cancer include reference to dysregulated proliferation. Numerous studies on glutamine metabolism in cancer indicate that many tumors are avid glutamine consumers (Souba, Ann. Surg., 1993; Collins et al., J. Cell. Physiol., 1998; Medina, J. Nutr., 2001; Shanware et al., J. Mol. Med., 2011). An embodiment of the invention is the use of the compounds described herein for the treatment of cancer.

In some embodiments, the compounds of the present disclosure may be used to prevent or treat cancer, wherein the cancer is one or a variant of Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Basal Cell Carcinoma, Bile Duct Cancer (including Extrahepatic), Bladder Cancer, Bone Cancer (including Osteosarcoma and Malignant Fibrous Histiocytoma), Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sézary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma) Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sézary Syndrome), Hodgkin, Non-Hodgkin, Primary Central Nervous System (CNS), Macroglobulinemia, Waldenström, Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer (such as Epithelial, Germ Cell Tumor, and Low Malignant Potential Tumor), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (like Ewing Sarcoma Family of Tumors, Kaposi, Soft Tissue, Uterine), Sézary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, Supratentorial Primitive Neuroectodermal Tumors, T-Cell Lymphoma (Cutaneous, Mycosis Fungoides and Sézary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenström Macroglobulinemia or Wilms Tumor.

In certain embodiments, the cancer to be treated is one specific to T-cells such as T-cell lymphomia and lymphoblastic T-cell leukemia.

In some embodiments, methods described herein are used to treat a disease condition comprising administering to a subject in need thereof a therapeutically effective amount of a compound of Formula I or pharmaceutically acceptable salt thereof, wherein the condition is cancer which has developed resistance to chemotherapeutic drugs and/or ionizing radiation.

Combinations and Combination Therapy

The compounds of the present invention can be used, alone or in combination with other pharmaceutically active compounds, to treat conditions such as those previously described hereinabove. The compound(s) of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention and one or more additional pharmaceutically active compounds.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-cancer drugs, anti-proliferative drugs, and anti-inflammatory drugs.

GLS1 inhibitor compositions described herein are also optionally used in combination with other therapeutic reagents that are selected for their therapeutic value for the condition to be treated. In general, the compounds described herein and, in embodiments where combination therapy is employed, other agents do not have to be administered in the same pharmaceutical composition and, because of different physical and chemical characteristics, are optionally administered by different routes. The initial administration is generally made according to established protocols and then, based upon the observed effects, the dosage, modes of administration and times of administration subsequently modified. In certain instances, it is appropriate to administer a GLS1 inhibitor compound, as described herein, in combination with another therapeutic agent. By way of example only, the therapeutic effectiveness of a GLS1 inhibitor is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced (i.e., synergistic) benefit. Alternatively, if a compound disclosed herein has a side effect, it may be appropriate to administer an agent to reduce the side effect; or the therapeutic effectiveness of a compound described herein may be enhanced by administration of an adjuvant.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is a GLS1 inhibitor as described herein) may be administered in any order, or simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time between the multiple administration steps ranges from a few minutes to several hours, depending upon the properties of each pharmaceutical agent, such as potency, solubility, bioavailability, plasma half-life and kinetic profile of the pharmaceutical agent.

In another embodiment, a GLS1 inhibitor is optionally used in combination with procedures that provide additional benefit to the patient. A GLS1 inhibitor and any additional therapies are optionally administered before, during or after the occurrence of a disease or condition, and the timing of administering the composition containing a GLS1 inhibitor varies in some embodiments. Thus, for example, a GLS1 inhibitor is used as a prophylactic and is administered continuously to subjects with a propensity to develop conditions or diseases in order to prevent the occurrence of the disease or condition. A GLS1 inhibitor and compositions are optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A GLS1 inhibitor can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors and tyrosine kinase inhibitors.

For use in cancer and neoplastic diseases a GLS1 inhibitor may be optimally used together with one or more of the following non-limiting examples of anti-cancer agents: (1) alkylating agents, including but not limited to cisplatin (PLATIN), carboplatin (PARAPLATIN), oxaliplatin (ELOXATIN), streptozocin (ZANOSAR), busulfan (MYLERAN) and cyclophosphamide (ENDOXAN); (2) anti-metabolites, including but not limited to mercaptopurine (PURINETHOL), thioguanine, pentostatin (NIPENT), cytosine arabinoside (ARA-C), gemcitabine (GEMZAR), fluorouracil (CARAC), leucovorin (FUSILEV) and methotrexate (RHEUMATREX); (3) plant alkaloids and terpenoids, including but not limited to vincristine (ONCOVIN), vinblastine and paclitaxel (TAXOL); (4) topoisomerase inhibitors, including but not limited to irinotecan (CAMPTOSAR), topotecan (HYCAMTIN) and etoposide (EPOSIN); (5) cytotoxic antibiotics, including but not limited to actinomycin D (COSMEGEN), doxorubicin (ADRIAMYCIN), bleomycin (BLENOXANE) and mitomycin (MITOSOL); (6) angiogenesis inhibitors, including but not limited to sunitinib (SUTENT) and bevacizumab (AVASTIN); and (7) tyrosine kinase inhibitors, including but not limited to imatinib (GLEEVEC), erlotinib (TARCEVA), lapatinib (TYKERB) and axitinib (INLYTA).

Where a subject is suffering from or at risk of suffering from an inflammatory condition, a GLS1 inhibitor compound described herein is optionally used together with one or more agents or methods for treating an inflammatory condition in any combination. Therapeutic agents/treatments for treating an autoimmune and/or inflammatory condition include, but are not limited to any of the following examples: (1) corticosteroids, including but not limited to cortisone, dexamethasone, and methylprednisolone; (2) non-steroidal anti-inflammatory drugs (NSAIDs), including but not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONSTEL), nabumetone (RELAFEN) and piroxicam (FELDENE); (3) immunosuppressants, including but not limited to methotrexate (RHEUMATREX), leflunomide (ARAVA), azathioprine (IMURAN), cyclosporine (NEORAL, SANDIMMUNE), tacrolimus and cyclophosphamide (CYTOXAN); (4) CD20 blockers, including but not limited to rituximab (RITUXAN); (5) Tumor Necrosis Factor (TNF) blockers, including but not limited to etanercept (ENBREL), infliximab (REMICADE) and adalimumab (HUMIRA); (6) interleukin-1 receptor antagonists, including but not limited to anakinra (KINERET); (7) interleukin-6 inhibitors, including but not limited to tocilizumab (ACTEMRA); (8) interleukin-17 inhibitors, including but not limited to AIN457; (9) Janus kinase inhibitors, including but not limited to tasocitinib; and (10) syk inhibitors, including but not limited to fostamatinib.

Compound Synthesis

Compounds of the present invention can be prepared using methods illustrated in general synthetic schemes and experimental procedures detailed below. General synthetic schemes and experimental procedures are presented for purposes of illustration and are not intended to be limiting. Starting materials used to prepare compounds of the present invention are commercially available or can be prepared using routine methods known in the art.

List of Abbreviations $Ac_2O$=acetic anhydride; AcCl=acetyl chloride; AcOH=acetic acid; AIBN=azobisisobutyronitrile; aq.=aqueous; BAST=bis(2-methoxyethyl)aminosulfur trifluoride; $Bu_3SnH$=tributyltin hydride; $CD_3OD$=deuterated methanol; $CDCl_3$=deuterated chloroform; CDI=1,1'-Carbonyldiimidazole; DAST=(diethylamino)sulfur trifluoride; DBU=1,8-diazabicyclo[5.4.0]undec-7-ene; DCM=dichloromethane; DEAD=diethyl azodicarboxylate; DIBAL-H=di-iso-butyl aluminium hydride; DIEA=DIPEA=N,N-diisopropylethylamine; DMAP=4-dimethylaminopyridine; DMF=N,N-dimethylformamide; DMSO-$d_6$=deuterated dimethyl sulfoxide; DMSO=dimethyl sulfoxide; DPPA=diphenylphosphoryl azide; EDC·HCl=EDCI·HCl=1-ethyl-3-(3-dimethylaminopropyl) carbodiimide hydrochloride; $Et_2O$=diethyl ether; EtOAc=ethyl acetate; EtOH=ethanol; h=hour; HATU=2-(1H-7-azabenzotriazol-1-yl)-1,1,3,3-tetramethyl uronium hexafluorophosphate methanaminium; HMDS=hexamethyldisilazane; HOBT=1-hydroxybenzotriazole; i-PrOH=isopropanol; LAH=lithium aluminumhydride; LDA=lithium diisopropyl amide; LiHMDS=Lithium bis(trimethylsilyl)amide; MeCN=acetonitrile; MeOH=methanol; MP-carbonate resin=macroporous triethylammonium methylpolystyrene carbonate resin; MsCl=mesyl chloride; MTBE=methyl tertiary butyl ether; n-BuLi=n-butyllithium; NaHMDS=Sodium bis(trimethylsilyl)amide; NaOMe=sodium methoxide; NaOtBu=sodium t-butoxide; NBS=N-bromosuccinimide; NCS=N-chlorosuccinimide; NMP=N-Methyl-2-pyrrolidone; Pd$(Ph_3)_4$=tetrakis(triphenylphosphine)palladium(0); $Pd_2$(dba)$_3$=tris(dibenzylideneacetone)dipalladium(0); $PdCl_2(PPh_3)_2$=bis(triphenylphosphine)palladium(II) dichloride; PG=protecting group; prep-HPLC=preparative high-performance liquid chromatography; PMBCl=para-methoxybenzyl chloride; PyBop=(benzotriazol-1-yloxy)tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; t-BuOH=tert-butanol; T3P=Propylphosphonic Anhydride; TEA=$Et_3N$=triethylamine; TFA=trifluoroacetic acid; TFAA=trifluoroacetic anhydride; THF=tetrahydrofuran; Tol=toluene; TsCl=tosyl chloride; Xantphos=4,5-Bis(diphenylphosphino)-9,9-dimethylxanthene; X-Phos=2-dicyclohexylphosphino-2',4',6'-triisopropylbiphenyl.

General Methods for Preparing Compounds

The following schemes can be used to practice the present invention. Additional structural groups, including but not limited to those defined elsewhere in the specification and not shown in the compounds described in the schemes can be incorporated to give various compounds disclosed herein, or intermediate compounds which can, after further manipulations using techniques known to those skilled in the art, be converted to compounds of the present invention. For example in certain embodiments the A-ring in the structures described in the schemes—wherein A is a heteroaromatic ring—can be substituted with various groups as defined herein.

One route for preparation of compounds of the present invention is described in Scheme 1. A substituted functionalized halo-heteroaromatic amine is reacted with a suitable acyl chloride in the presence of a base such as DIEA or TEA in a solvent such as DMF, DCM or NMP. The resulting carboxamide can be further functionalized, for example by Sonogashira cross-coupling reaction with a suitably functionalized hydroxy alkyne (Tetrahedron Lett. 16: 4467-4470). Typically the above transformation is performed in the presence of a suitable Pd catalyst such as $PdCl_2(PPh_3)_2$ or $Pd(PPh_3)_4$, a copper co-catalyst, typically a halide salt of copper (I), such as CuI or CuBr, and a base such as DIEA or TEA. The transformation can typically be run at RT or with mild heating in a variety of solvents, including DMF, toluene and EtOAc. Further functional group manipulations include hydrogenation of the resulting heteroaromatic alkyne derivative in the presence of a suitable Pd catalyst (such as Pd/C or Pd(OH$_2$)) in a solvent such as EtOH, and conversion of the hydroxyl moiety into an azide, for example by treatment with DPPA and a base such as TEA heating in a solvent such as toluene, according to the procedure published in Bose et al., Tetrahedron Lett. 1977, 18, 1977-1980. Alternatively, the hydroxyl group could be converted into the corresponding mesylate or tosylate and then displaced with NaN$_3$ in a suitable polar solvent such as DMF. The obtained azide derivative can then be progressed to the corresponding triazole-4-carboxylic ester by copper-mediated azide-alkyne cycloaddition with a suitable alkyl propiolate in the presence of a base (e.g. TEA or DIEA), and a copper (I) salt such as CuI, or a copper (II) salt such as CuSO$_4$ in the presence of a reducing agent such as sodium ascorbate, in a solvent such as THF, DMSO, tBuOH or H$_2$O (H. C. Kolb, M. G. Finn and K. B. Sharpless, Angewandte Chemie International Edition, 2001, 40 (11): 2004-2021). Finally, the desired amide in the 4-position of the triazole ring can be installed by direct displacement of the carboxylic ester with a suitable amine heating in a polar solvent such as DMF or MeOH. Alternatively, the same transformation could be achieved with a two-step sequence involving the base-mediated hydrolysis of the carboxylic ester followed by coupling of the resulting carboxylic acid with amine, using standard coupling reagents such as HATU, PyBOP or EDCI·HCl, in the presence of a suitable base such as TEA or DIEA, in a polar solvent such as DMF.

SCHEME 1

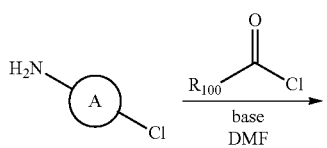

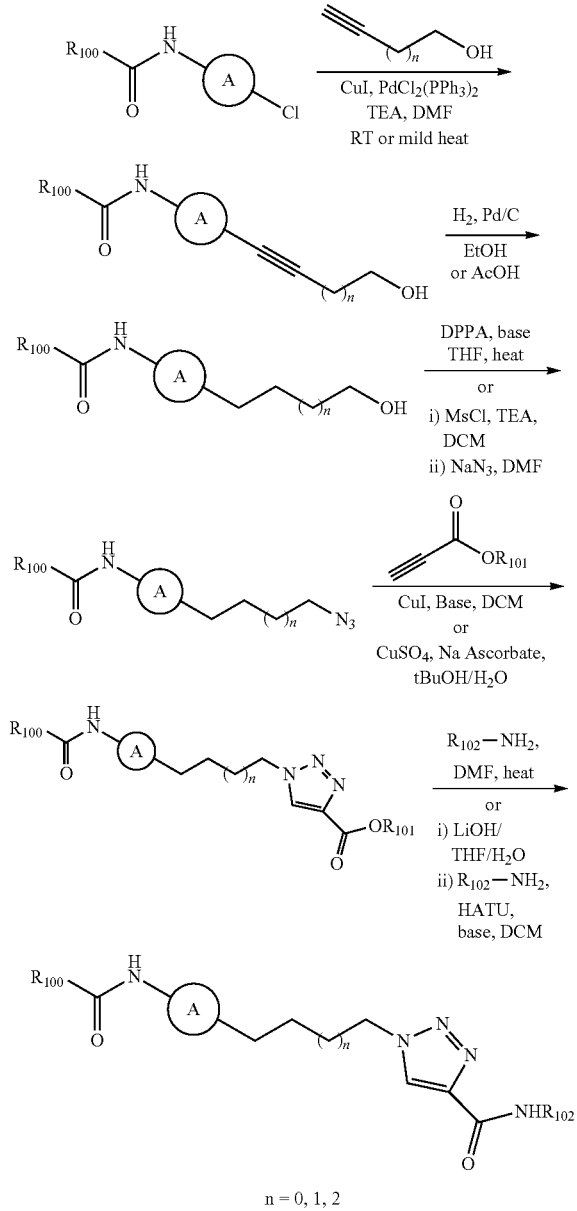

n = 0, 1, 2

Another route for the preparation of compounds of the present invention is described in Scheme 2. A suitably functionalized alkyne hydrazide could be converted in the corresponding 1,3,4-thiadiazole 2-carboxylate derivative by acylation with ethyl chlorooxoacetate followed by heating in a solvent such as toluene in the presence of $P_2S_5$. The resulting alkyne thiadiazole could be further functionalized by Sonogashira cross-coupling with a suitably substituted heteroaryl chloride, in similar conditions to those described in Scheme 1 for such transformation. The resulting heteroaromatic alkyne can then be reduced by hydrogenation in the presence of a suitable Pd catalyst (such as Pd/C or $Pd(OH_2)$) in a solvent such as EtOH. Finally, functional group manipulations similar to those described for Scheme 1 could be employed to progress the 2-carboxy ester thiadiazoles into the desired 2-carboxylic amides derivatives.

SCHEME 2

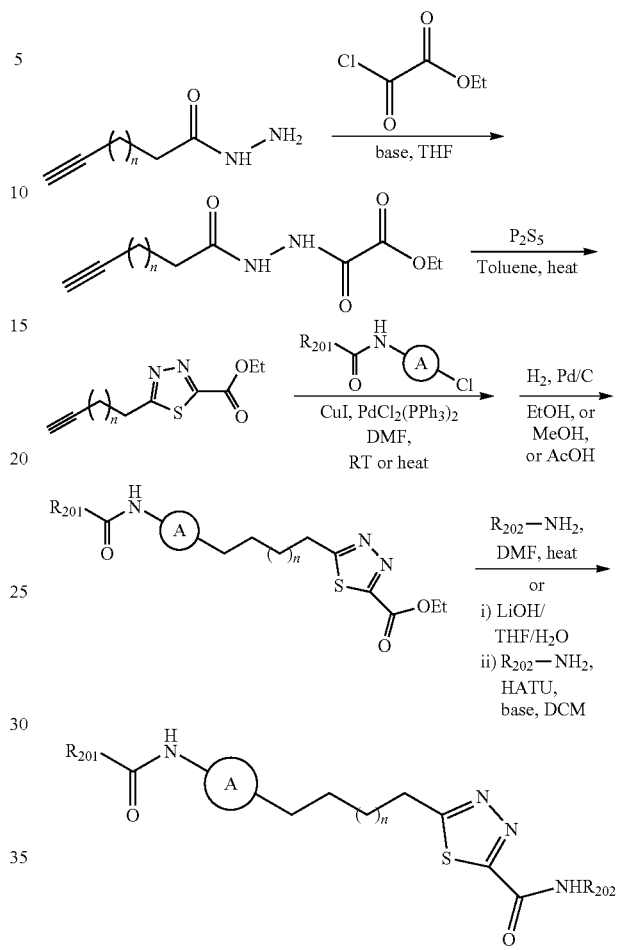

n = 0, 1, 2

A further route of preparation of the compounds described in this invention is depicted in Scheme 3. A suitably functionalized alkyl nitrile bearing a protected hydroxyl moiety can be converted to a 5-alkyl-2-amino thiadiazole by heating in the presence of TFA and hydrazinecarbothioamide. Suitable protecting groups for the hydroxyl moiety can be chosen amongst substituted ethers (e.g. benzyl ether, 3,4-dimethoxy-benzylether, t-butyl ether, t-butyldimethylsilyl ether), esters or other suitable functional groups known to those skilled in the art (see also: P. G. M. Wutz, T. W. Greene, "Greene's protective Groups in Organic Synthesis", Fourth Edition, John Wiley & Sons). The obtained thiadiazole can then be progressed to the corresponding 2-carboxamide derivative by acylation with a suitable acyl chloride in the presence of a base such as TEA or DIEA in a solvent such as DCM. Removal of the hydroxyl protecting group with techniques known to those skilled in the art (for example: reductive removal of a benzyl ether group; see also P. G. M. Wutz, T. W. Greene in reference cited above) can then enable the conversion of the liberated hydroxyl moiety into an azide group, with conditions similar to those described in Scheme 1, i.e. treatment with DPPA heating in the presence of a base such as TEA, or conversion to the corresponding mesylate or tosylate followed by displacement with $NaN_3$ in a polar solvent like DMF. The obtained azide can then be progressed to the corresponding triazole by copper-mediated azide-alkyne cycloaddition in the presence of a suitable alkylpropriolate in the presence of a base such as DIEA, and a copper compound like CuI, or CuSO$_4$ in the presence of sodium ascorbate, similarly to the conditions described for Scheme 1 and 2. Finally, the triazole-2-carboxy ester derivatives can be converted to the corresponding triazole-2-carboxy amides, employing procedures and conditions similar to those described in detail for Scheme 1.

removal of the selected protecting group, the hydroxyl moiety can then be converted into an azide group employing the transformations described in Schemes 1 and 3. The obtained functionalized amide can then be progressed to the desired triazole derivatives by employing a copper-mediated azide-alkyne cycloaddition in the presence of a suitable alkylpropriolate to obtain the 2-carboxy ester triazoles,

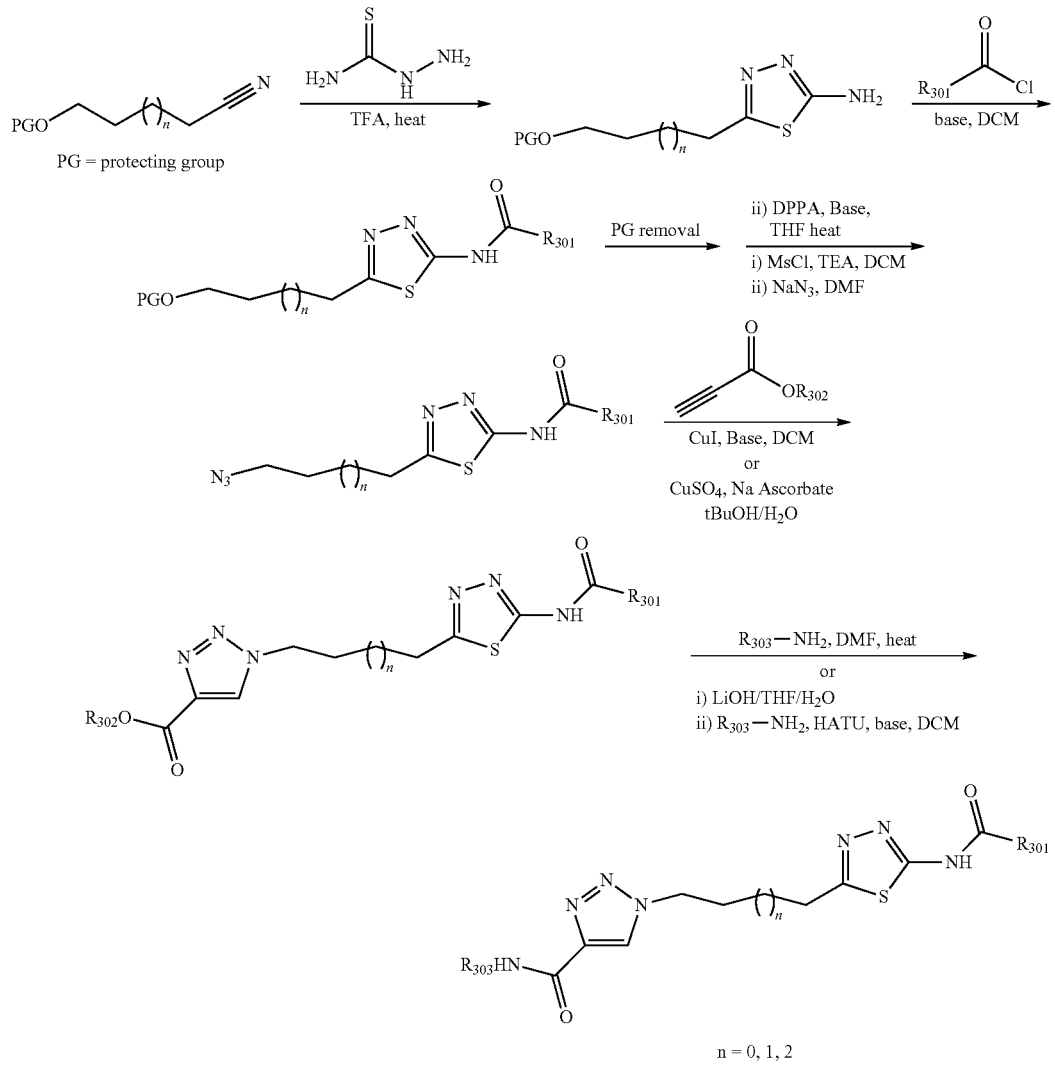

An additional synthetic route to prepare compounds of this invention is described in Scheme 4.

A suitably functionalized alkyl hydrazide bearing a protected hydroxyl moiety can be converted to a 5-alkyl-2-amino thiadiazole by heating in a solvent such as toluene in the presence of P$_2$S$_5$, similarly to the transformation described in Scheme 2. Suitable protecting groups for the hydroxyl moiety can be chosen amongst substituted ethers and others suitable functional groups known to those skilled in the art, as detailed in G. M. Wutz, T. W. Greene, "Greene's protective Groups in Organic Synthesis", Fourth Edition, John Wiley & Sons, and can be removed following the transformations and procedures reported therein. Following followed by functional group manipulation to install the 2-carboxy amide, as already described in detail for Schemes 1-3.

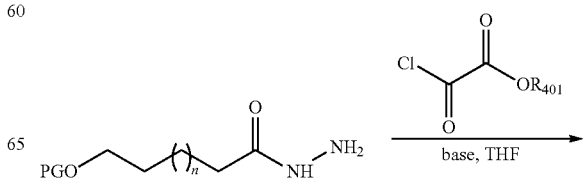

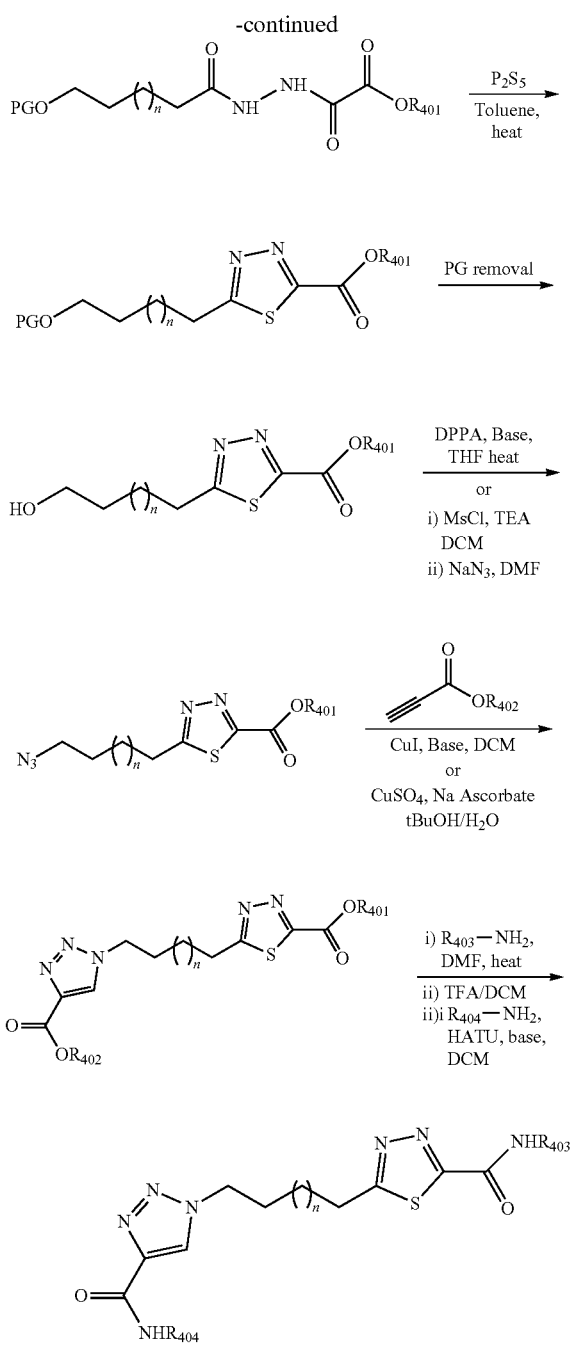

sponding azide by a two-step sequence involving mesylation or tosylation with the required sulfonyl chloride in the presence of a base such as TEA or DIEA in a solvent like DCM, followed by displacement with an inorganic azide such as $NaN_3$ in a polar solvent like DMF. Copper-mediated azide-alkyne cycloaddition in the presence of a suitable alkyl propiolate can then afford the N-alkyne-2-carboxyester triazole derivatives, in conditions similar to those already detailed for Schemes 1-4. The 2-carboxyester triazole derivatives can in turn be progressed to the corresponding 2-carboxyamides, employing similar transformations and conditions to those described for Schemes 1-4. A further copper-mediated azide-alkyne cycloaddion step employing a suitably functionalized azide and in analogous conditions to those detailed in Schemes 1-4 can then afford the desired bis-triazolo derivatives.

SCHEME 5

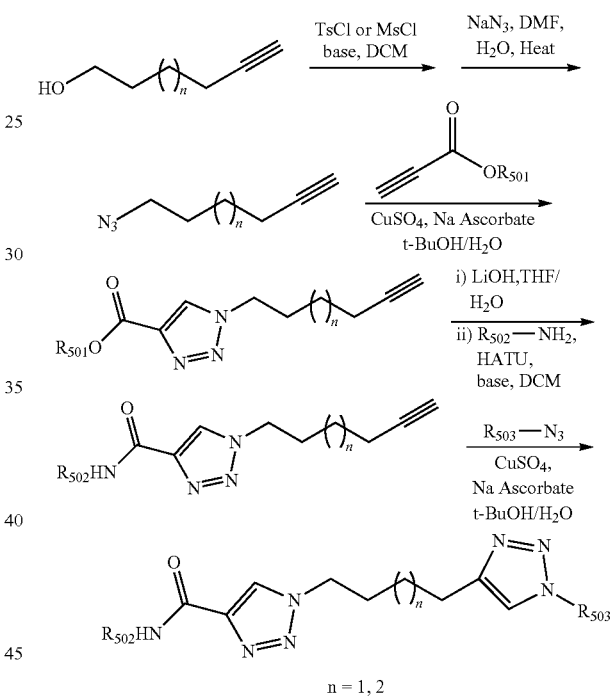

n = 1, 2

Non-limiting examples include the following compounds and pharmaceutically acceptable salts thereof.

An additional synthetic route for the compounds described in this invention is described in Scheme 5. A suitable hydroxy alkyne can be progressed into the corre- Example 1: N-(pyridin-3-ylmethyl)-1-[4-(5-{2-[3-(trifluoromethoxy)phenyl]acetamido}-1,3,4-thiadiazol-2-yl)butyl]-1H-1,2,3-triazole-4-carboxamide

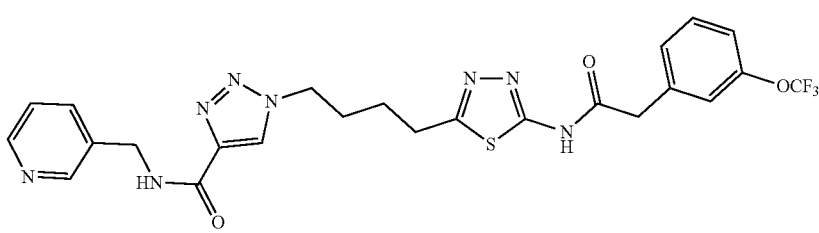 [SMILES: O=C(Cc1cccc(OC(F)(F)F)c1)Nc1nnc(CCCCn2cc(C(=O)NCc3cccnc3)nn2)s1]

Steps 1 to 4

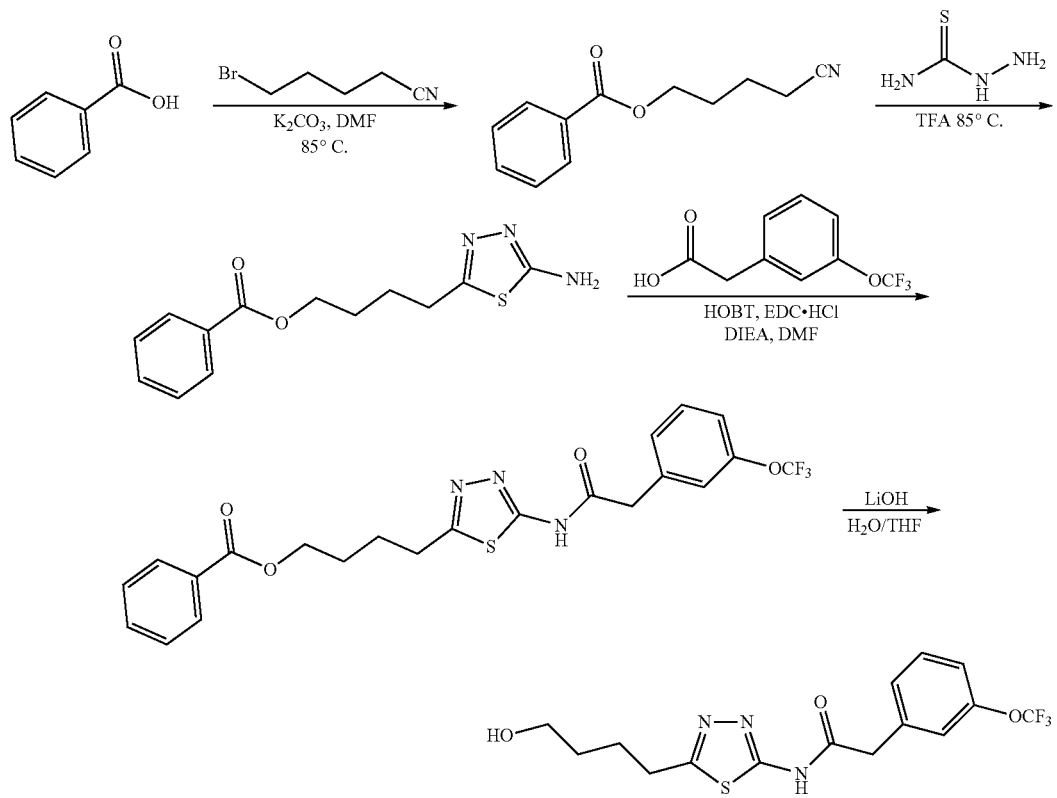

Step 1: 4-cyanobutyl Benzoate

To a solution of benzoic acid (0.543 g, 4.44 mmol) in DMF (5 mL) was added $K_2CO_3$ (1.02 g, 7.41 mmol) and the mixture was stirred at RT for 10 minutes. 5-Bromopentanenitrile (0.60 g, 3.7 mmol) was added dropwise and the reaction was heated in a sealed vial at 85° C. for 2.5 h, then at 60° C. for 17 h. The mixture was concentrated under reduced pressure, diluted with water (75 mL), and extracted with EtOAc (2×50 mL). The combined organic layers were washed with brine, dried ($MgSO_4$), filtered, and concentrated under reduced pressure to give the title compound as a clear oil (765 mg, 3.58 mmol, 97%). MS ($ES^+$) $C_{12}H_{13}NO_2$ requires: 203.1, found: 204 $[M+H]^+$.

Step 2: 4-(5-amino-1,3,4-thiadiazol-2-yl)butyl Benzoate

To a solution of 4-cyanobutyl benzoate (760 mg, 3.74 mmol) in TFA (10 mL) was added hydrazinecarbothioamide (409 mg, 4.49 mmol) and the resulting mixture was stirred at 85° C. for 3 h. The reaction mixture was allowed to cool to RT and the volatiles were removed under reduced pressure. The residue was dissolved in DCM/MeOH (5 mL, 1/1 v/v), MP-carbonate resin (6 g, 6.06 mmol/g) was added, and the mixture was stirred for 3 h at RT. The mixture was filtered and concentrated under reduced pressure to give the title compound as a white solid (822 mg, 2.96 mmol, 79%). MS ($ES^+$) $C_{13}H_{15}N_3O_2S$ requires: 277.1, found: 278 $[M+H]^+$.

Step 3: 4-(5-(2-(3-(trifluoromethoxy)phenyl)acetamido)-1,3,4-thiadiazol-2-yl)butyl Benzoate To a solution of 4-(5-amino-1,3,4-thiadiazol-2-yl)butyl benzoate (571 mg, 2.06 mmol) in DMF (15 mL) were added 2-(3-(trifluoromethoxy)phenyl)acetic acid (544 mg, 2.47 mmol), HOBT (378 mg, 2.47 mmol), DIEA (0.45 mL, 2.6 mmol), and EDC·HCl (474 mg, 2.47 mmol) and the resulting mixture was stirred at RT for 18 h. The reaction was slowly poured onto ice water (250 mL) and stirred for 1 h. The mixture was filtered and the white solid was washed with water, saturated $NaHCO_3$, water, and hexanes to give the title compound as a white solid (530 mg, 1.10 mmol, 54%). MS ($ES^+$) $C_{22}H_{20}F_3N_3O_4S$ requires: 479.1, found: 480 $[M+H]^+$.

Step 4: N-(5-(4-hydroxybutyl)-1,3,4-thiadiazol-2-yl)-2-(3-(trifluoromethoxy)phenyl)acetamide To a solution of 4-(5-(2-(3-(trifluoromethoxy)phenyl)acetamido)-1,3,4-thiadiazol-2-yl)butyl benzoate (527 mg, 1.10 mmol) in THF (7 mL) and water (7 mL) was added LiOH (2 M aq., 5.50 mL, 11.0 mmol) and the resulting mixture was stirred at RT for 5 h. The volatiles were removed under reduced pressure. The residue was partitioned between DCM (200 mL) and $H_2O$ (200 mL), and the layers were separated. The aqueous phase was extracted with DCM (3×100 mL) and the organic layers were combined, washed with brine, dried ($MgSO_4$), filtered, and concentrated under reduced pressure to give the title compound as an off white solid (300 mg, 0.799 mmol, 73%). MS (ES⁺) C₁₅H₁₆F₃N₃O₃S requires: 375.1, found: 376 [M+H]⁺.

Steps 5 to 8

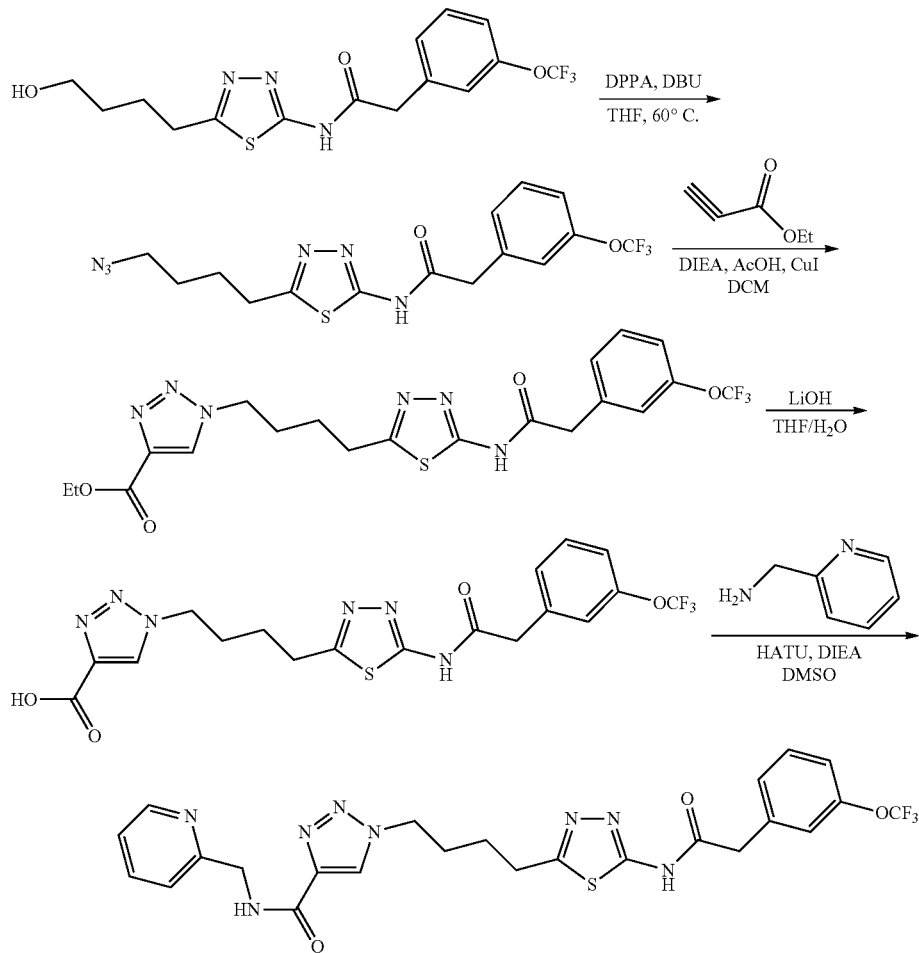

Step 5: N-(5-(4-azidobutyl)-1,3,4-thiadiazol-2-yl)-2-(3-(trifluoromethoxy)phenyl)acetamide To a solution of N-(5-(4-hydroxybutyl)-1,3,4-thiadiazol-2-yl)-2-(3-(trifluoromethoxy)phenyl)acetamide (297 mg, 0.790 mmol) and DBU (0.179 mL, 1.19 mmol) in THF (5 mL) was added DPPA (0.26 mL, 1.2 mmol) dropwise and the resulting mixture was stirred at 60° C. for 3 h. The volatiles were removed under reduced pressure and the residue was purified via SiO₂ gel chromatography (0-100% EtOAc in hexanes) to give the title compound as a white solid (217 mg, 0.542 mmol, 69%). MS (ES⁺) C₁₅H₁₅F₃N₆O₂S requires: 400.1, found: 401 [M+H]⁺.

Step 6: ethyl 1-(4-(5-(2-(3-(trifluoromethoxy)phenyl)acetamido)-1,3,4-thiadiazol-2-yl)butyl)-1H-1,2,3-triazole-4-carboxylate To a solution of N-(5-(4-azidobutyl)-1,3,4-thiadiazol-2-yl)-2-(3-(trifluoromethoxy)phenyl)acetamide (214 mg, 0.534 mmol) in DCM (5 mL) were added DIEA (9.3 µl, 0.053 mmol), AcOH (3.06 µl, 0.053 mmol), ethyl propiolate (0.065 mL, 0.641 mmol), and copper(I) iodide (5.1 mg, 0.027 mmol) and the resulting mixture was stirred at RT for 16 h. The reaction was concentrated under reduced pressure, the residue was taken up in MeOH, and the product was precipitated by addition of saturated aq. NH₄Cl. The precipitate was washed with water, hexanes, and dried under reduced pressure to give the title compound as a white solid (217 mg, 0.430 mmol, 81%). MS (ES⁺) C₂₀H₂₁F₃N₆O₄S requires: 498.1, found: 499 [M+H]⁺.

Step 7: 1-(4-(5-(2-(3-(trifluoromethoxy)phenyl)acetamido)-1,3,4-thiadiazol-2-yl)butyl)-1H-1,2,3-triazole-4-carboxylic Acid To a suspension of ethyl 1-(4-(5-(2-(3-(trifluoromethoxy)phenyl)acetamido)-1,3,4-thiadiazol-2-yl)butyl)-1H-1,2,3-triazole-4-carboxylate (211 mg, 0.423 mmol) in THF/H₂O (10 mL, 1/1 v/v) was added LiOH (2 M aq., 1.06 mL, 2.12 mmol) and the resulting mixture was stirred at RT for 16 h. The volatiles were removed under reduced pressure, the aqueous phase was brought to pH 2 by the addition of 1N aq. HCl, and the resulting solid product was collected by filtration and dried under reduced pressure to give the title compound as a white solid (193 mg, 0.411 mmol, 97%). MS (ES⁺) C₁₈H₁₇F₃N₆O₄S requires: 470.1, found: 471 [M+H]⁺.

Step 8: N-(pyridin-3-ylmethyl)-1-(4-(5-(2-(3-(trifluoromethoxy)phenyl)acetamido)-1,3,4-thiadiazol-2-yl)butyl)-1H-1,2,3-triazole-4-carboxamide To a solution of 1-(4-(5-(2-(3-(trifluoromethoxy)phenyl)acetamido)-1,3,4-thiadiazol-2-yl)butyl)-1H-1,2,3-triazole-4-carboxylic acid (10 mg, 0.021 mmol) in DMSO (0.1 mL) were added DIEA (8.17 µl, 0.0470 mmol), pyridin-3-ylmethanamine (2.3 mg, 0.021 mmol), and HATU (12.1 mg, 0.032 mmol). The resulting mixture was stirred at RT for 16 h and diluted with water. The resulting precipitate was filtered, washed with water, and dried under reduced pressure. The residue was purified by mass-triggered preparative HPLC (Mobile phase: A=0.1% TFA/H$_2$O, B=0.1% TFA/MeCN; Gradient: B=30-70%; 12 min; Column: C18) to give the title compound as a white solid (3.3 mg, 5.9 µmol, 28%). MS (ES$^+$) C$_{24}$H$_{23}$F$_3$N$_8$O$_3$S requires: 560.2, found: 561 [M+H]$^+$. $^1$H NMR (DMSO-d$_6$) δ: 12.70 (br s, 1H), 9.25 (m, 1H), 8.79-8.56 (m, 3H), 8.09 (d, J=7.9 Hz, 1H), 7.67 (m, 1H), 7.47 (m, 1H), 7.38-7.31 (m, 2H), 7.28 (d, J=8.7 Hz, 1H), 4.54 (d, J=6.0 Hz, 2H), 4.45 (t, J=7.0 Hz, 2H), 3.89 (s, 2H), 3.00 (t, J=7.4 Hz, 2H), 1.94-1.87 (m, 2H), 1.68-1.59 (m, 2H).

Example 2: N-Methyl-1-(4-(5-(2-(3-(trifluoromethoxy)phenyl)acetamido)-1,3,4-thiadiazol-2-yl)butyl)-1H-1,2,3-triazole-4-carboxamide

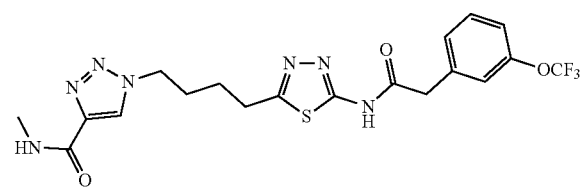 [SMILES: CNC(=O)c1cn(CCCCc2nnc(NC(=O)Cc3cccc(OC(F)(F)F)c3)s2)nn1]

Prepared as described for Example 1. MS (ES$^+$) C$_{19}$H$_{20}$F$_3$N$_7$O$_3$S requires: 483.1, found: 484 [M+H]$^+$. $^1$H NMR (600 MHz, DMSO-d$_6$) δ: 12.69 (s, 1H), 8.54 (s, 1H), 8.44 (q, J=4.5 Hz, 1H), 7.47 (m, 1H), 7.38-7.32 (m, 2H), 7.28 (d, J=8.7 Hz, 1H), 4.48-4.40 (m, 2H), 3.89 (s, 2H), 3.00 (t, J=7.6 Hz, 2H), 2.75 (d, J=4.9 Hz, 3H), 1.95-1.86 (m, 2H), 1.69-1.58 (m, 2H).

Example 3: 1-(4-(5-(2-(3-(Trifluoromethoxy)phenyl)acetamido)-1,3,4-thiadiazol-2-yl)butyl)-1H-1,2,3-triazole-4-carboxamide

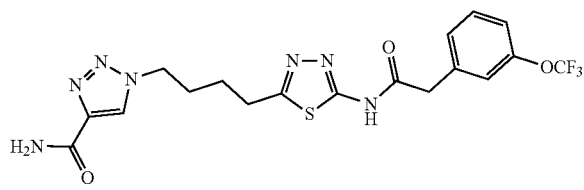 [SMILES: NC(=O)c1cn(CCCCc2nnc(NC(=O)Cc3cccc(OC(F)(F)F)c3)s2)nn1]

To a suspension of N-(2,4-dimethoxybenzyl)-1-(4-(5-(2-(3-(trifluoromethoxy)phenyl)acetamido)-1,3,4-thiadiazol-2-yl)butyl)-1H-1,2,3-triazole-4-carboxamide (prepared as described for Example 1; 14 mg, 0.023 mmol) in DCM (1 mL) was added TFA (0.106 mL, 1.375 mmol) and the resulting mixture was stirred at RT for 7 h. The reaction was concentrated under reduced pressure and the residue was triturated with aq. NaHCO$_3$ (10/1 v/v water/saturated aq. NaHCO$_3$). The resulting solid was filtered and washed with water to give the title compound as an off white solid (7.4 mg, 0.016 mmol, 69%). MS (ES$^+$) C$_{18}$H$_{18}$F$_3$N$_7$O$_3$S requires: 469.1, found: 470 [M+H]$^+$. $^1$H NMR (600 MHz, DMSO-d$_6$) δ: 8.53 (s, 1H), 7.83 (s, 1H), 7.49 (m, 1H), 7.38-7.32 (m, 2H), 7.27 (d, J=8.7 Hz, 1H), 4.44 (t, J=6.8 Hz, 2H), 3.88 (s, 2H), 3.00 (t, J=7.4 Hz, 2H), 1.95-1.86 (m, 2H), 1.69-1.60 (m, 2H).

Example 4: N-Benzyl-1-(5-(5-(2-phenylacetamido)-1,3,4-thiadiazol-2-yl)pentyl)-1H-1,2,3-triazole-4-carboxamide

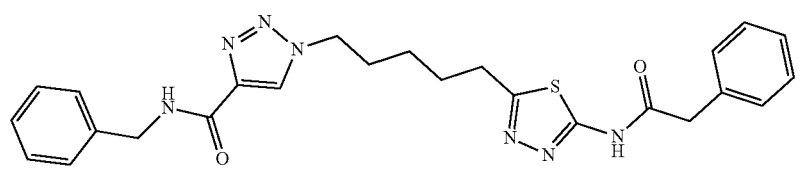 [SMILES: O=C(Cc1ccccc1)Nc1nnc(CCCCCn2cc(C(=O)NCc3ccccc3)nn2)s1]

Prepared as Example 1, using 5-cyanopentyl benzoate instead of 4-cyanobutyl benzoate. MS (ES$^+$) C$_{25}$H$_{27}$N$_7$O$_2$S requires: 489.2, found: 490 [M+H]$^+$. $^1$H NMR (600 MHz, CDCl$_3$) δ: 8.08 (s, 1H), 7.49 (br s, 1H), 7.42-7.37 (m, 2H), 7.37-7.27 (m, 8H), 4.68-4.59 (m, 2H), 4.37 (t, J=7.0 Hz, 2H), 3.98 (s, 2H), 3.02 (t, J=7.4 Hz, 2H), 1.97 (m, 2H), 1.85 (m, 2H), 1.44 (m, 2H).

Example 5: N-Benzyl-1-(4-(6-(2-phenylacetamido)pyridazin-3-yl)butyl)-1H-1,2,3-triazole-4-carboxamide

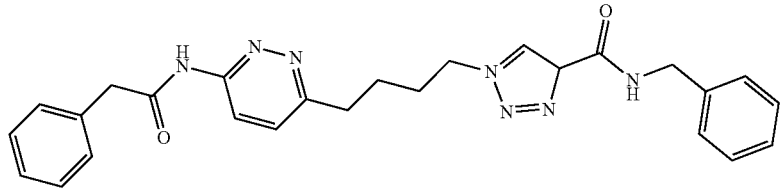

Steps 1 to 5

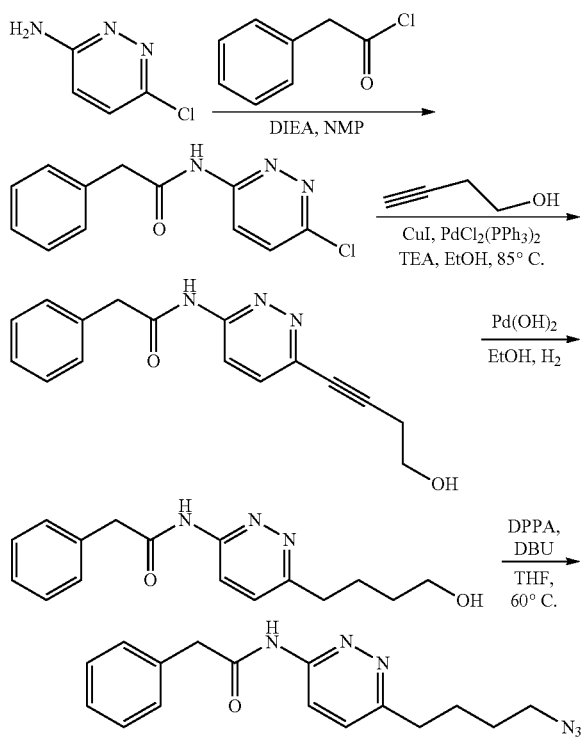

Step 1:
N-(6-chloropyridazin-3-yl)-2-phenylacetamide

To a mixture of 6-chloropyridazin-3-amine (4.0 g, 31 mmol) and DIEA (6.5 mL, 37 mmol) in NMP (40 mL) at 0° C. was added 2-phenylacetyl chloride (4.49 mL, 34.0 mmol) dropwise. The reaction was stirred at 0° C. for 30 minutes, allowed to warm to RT over 19 h, and poured onto ice water (500 mL). The resulting precipitate was filtered, washed with water and Et$_2$O (3×20 mL), and dried under reduced pressure to give the title compound as an off-white solid (3.4 g, 13 mmol, 42%). MS (ES$^+$) C$_{12}$H$_{10}$ClN$_3$O requires: 247.1, found: 248 [M+H]$^+$.

Step 2: N-(6-(4-hydroxybut-1-yn-1-yl)pyridazin-3-yl)-2-phenylacetamide

To a solution of N-(6-chloropyridazin-3-yl)-2-phenylacetamide in DMF (4 mL) were added TEA (2.0 mL, 14 mmol) and but-3-yn-1-ol (0.306 mL, 4.04 mmol), and the mixture was degassed with a stream of N$_2$ for 5 minutes. Copper(I) iodide (0.038 g, 0.20 mmol) and PdCl$_2$(PPh$_3$)$_2$ (0.071 g, 0.101 mmol) were added and the mixture was heated in a sealed vial at 85° C. 16 h. The mixture was cooled to RT, the volatiles were removed under reduced pressure, and the residue was purified via silica gel chromatography (0-5% MeOH in DCM) to give the title compound as a yellow solid (238 mg, 0.846 mmol, 42%). MS (ES$^+$) C$_{16}$H$_{15}$N$_3$O$_2$ requires: 281.1, found: 282 [M+H]$^+$.

Step 3: N-(6-(4-hydroxybutyl)pyridazin-3-yl)-2-phenylacetamide

To a flask containing Pd(OH)$_2$ (20% wt on carbon, 353 mg, 0.252 mmol) under N$_2$ was added EtOH (10 mL) followed by N-(6-(4-hydroxybut-1-yn-1-yl)pyridazin-3-yl)-2-phenylacetamide (236 mg, 0.839 mmol). The flask was evacuated, filled with H$_2$, and the mixture stirred at RT under a hydrogen atmosphere for 3.5 h. The flask was evacuated and filled with N$_2$. The suspension was filtered through a pad of Celite®, rinsed with MeOH and DCM, and the filtrate was concentrated under reduced pressure to give the title compound as a yellow solid (210 mg, 0.735 mmol, 88%). MS (ES$^+$) C$_{16}$H$_{19}$N$_3$O$_2$ requires: 285.2, found: 286 [M+H]$^+$.

Step 4: N-(6-(4-azidobutyl)pyridazin-3-yl)-2-phenylacetamide

Prepared as described for Example 1, step 5. MS (ES$^+$) C$_{16}$H$_{18}$N$_6$O requires: 310.1, found: 311[M+H]$^+$.

Steps 5 to 7

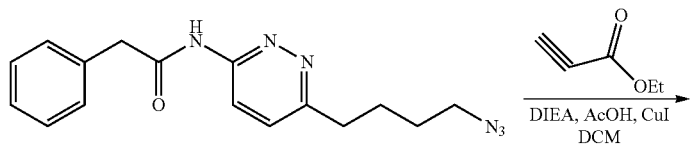

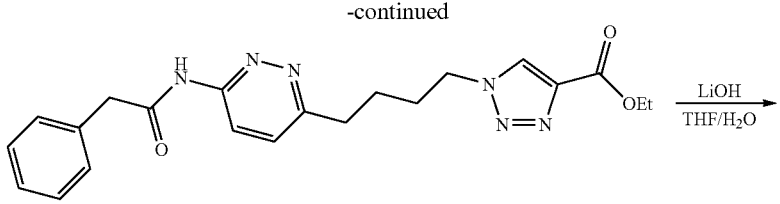

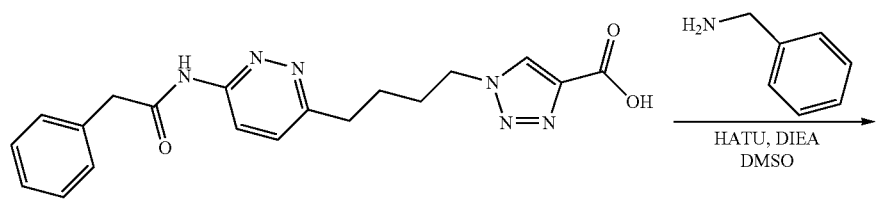

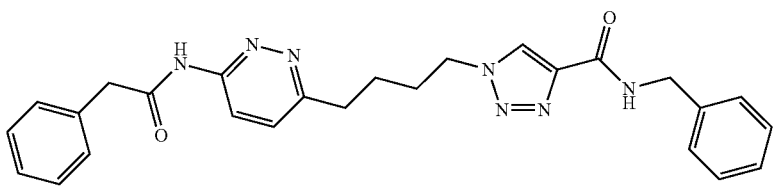

Prepared as described for Example 1, steps 5-to 7;

Step 5: ethyl 1-(4-(6-(2-phenylacetamido)pyridazin-3-yl)butyl)-1H-1,2,3-triazole-4-carboxylate MS (ES⁺) $C_{21}H_{24}N_6O_3$ requires: 408.2, found: 409 [M+H]⁺.

Step 6: 1-(4-(6-(2-phenylacetamido)pyridazin-3-yl)butyl)-1H-1,2,3-triazole-4-carboxylic Acid MS (ES⁺) $C_{19}H_{20}N_6O_3$ requires: 380.2, found: 381 [M+H]⁺.

Step 7: N-benzyl-1-(4-(6-(2-phenylacetamido)pyridazin-3-yl)butyl)-1H-1,2,3-triazole-4-carboxamide MS (ES⁺) $C_{26}H_{27}N_7O_2$ requires: 469.2, found: 470 [M+H]⁺. ¹H NMR (600 MHz, DMSO-d₆) δ: 11.23 (br s, 1H), 9.02 (d, J=5.3 Hz, 1H), 8.57 (s, 1H), 8.19 (d, J=9.1 Hz, 1H), 7.53 (d, J=9.1 Hz, 1H), 7.37-7.28 (m, 8H), 7.27-7.18 (m, 2H), 4.49-4.40 (m, 4H), 3.76 (s, 2H), 2.88 (t, J=7.6 Hz, 2H), 1.94-1.83 (m, 2H), 1.69-1.59 (m, 2H).

Example 6: N-(2-methoxyethyl)-5-(4-(6-(2-(3-(trifluoromethoxy)phenyl)acetamido)pyridazin-3-yl)butyl)-1,3,4-thiadiazole-2-carboxamide

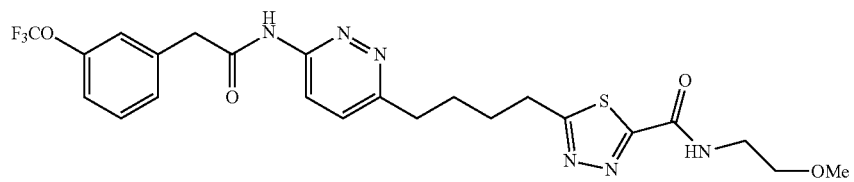 [SMILES: COCCNC(=O)c1nnc(CCCCc2ccc(NC(=O)Cc3cccc(OC(F)(F)F)c3)nn2)s1]

Steps 1 to 3

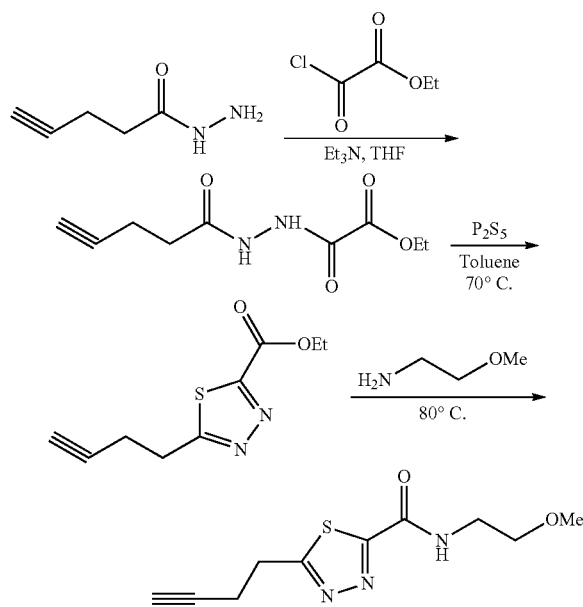

Step 1: Ethyl 2-oxo-2-(2-pent-4-ynoylhydrazinyl)acetate

To a solution of pent-4-ynehydrazide (560 mg, 5.00 mmol) and TEA (530 mg, 5.25 mmol) in DCM/THF (25 mL/5 mL) at 0° C. was slowly added ethyl 2-chloro-2-oxoacetate (717 mg, 5.25 mmol). The resulting mixture was stirred for 30 minutes while warming to RT, then concentrated under reduced pressure. The residue was triturated with EtOAc (20 mL), filtered, and the filtrate was concentrated under reduced pressure to give the title compound. MS (ES$^+$) C$_9$H$_{12}$N$_2$O$_4$, requires: 212.08, found: 213 [M+H]$^+$.

Step 2: Ethyl 5-(but-3-yn-1-yl)-1,3,4-thiadiazole-2-carboxylate

To a solution of ethyl 2-oxo-2-(2-pent-4-ynoylhydrazinyl) acetate (1.0 g, 5.0 mmol) in toluene (50 mL) heated at 70° C. was added P$_2$S$_5$ (1.11 g, 5.0 mmol) portionwise, and the resulting mixture was stirred for 30 minutes at 70° C. The mixture was cooled to RT, filtered, and the filter cake was washed with DCM (20 mL). The filtrate was concentrated under reduced pressure and the residue was purified by SiO$_2$ gel chromatography (20% EtOAc in hexanes) to give the title compound as a yellow solid (532 mg, 50%). MS (ES$^+$) C$_9$H$_{10}$N$_2$O$_2$S, requires: 210.05, found: 211[M+H]$^+$. $^1$H NMR (500 MHz, CDCl3) δ 4.54 (m, 2H), 3.44 (t, J=6.9 Hz, 2H), 2.75 (td, J=7.0, 2.7 Hz, 2H), 2.13 (t, J=2.6 Hz, 1H), 1.49 (m, 3H).

Step 3: 5-(but-3-ynyl)-N-(2-methoxyethyl)-1,3,4-thiadiazole-2-carboxamide

A mixture of ethyl 5-(but-3-ynyl)-1,3,4-thiadiazole-2-carboxylate (300 mg, 1.43 mmol) and 2-methoxyethanamine (2 mL) was heated at 80° C. in a sealed tube for 2 h. The mixture was then cooled to RT, diluted with water (10 mL), and extracted with EtOAc (2×20 mL). The combined organic layers were washed with brine (50 mL), dried (Na$_2$SO$_4$), and concentrated under reduced pressure to give the title compound as a yellow solid (310 mg, 91%). MS (ES$^+$) C$_{10}$H$_{13}$N$_3$O$_2$S requires: 239, found: 240[M+H]$^+$.

Step 4: N-(6-iodopyridazin-3-yl)-2-(3-(trifluoromethoxy)phenyl)acetamide

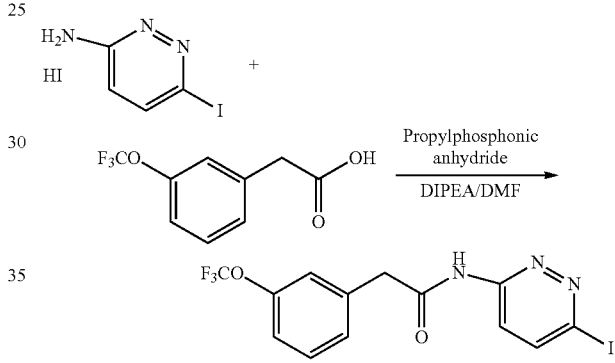

A mixture of 6-iodopyridazin-3-amine hydrogen iodide salt (1.05 g, 3.00 mmol), 2-(3-(trifluoromethoxy)phenyl) acetic acid (792 mg, 3.6 mmol), propylphosphonic anhydride (2.86 g, 4.5 mmol, 50% wt in EtOAc), and DIPEA (1.16 g, 9 mmol) in DMF (10 mL) was stirred at RT for 16 h. The mixture was then poured onto H$_2$O (30 mL) and extracted with EtOAc (2×30 mL). The combined organic layers were washed with brine (50 mL), dried (Na$_2$SO$_4$), and concentrated under reduced pressure. The residue was purified by SiO$_2$ gel chromatography (30% EtOAc in hexanes) to give the title compound as a white solid (1.1 g, 87%). MS (ES$^+$) C$_{13}$H$_9$F$_3$IN$_3$O$_2$ requires: 423, found: 424 [M+H]$^+$.

Steps 5 to 6

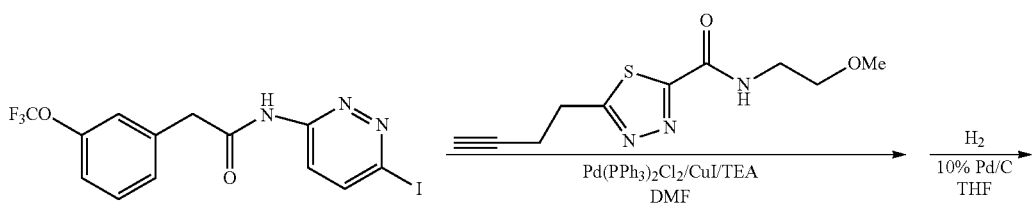

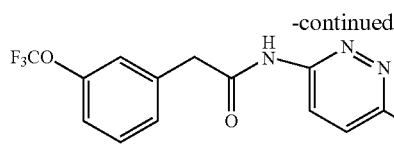

Step 6: N-(2-methoxyethyl)-5-(4-(6-(2-(3-(trifluoromethoxy)phenyl)acetamido)pyridazin-3-yl)butyl)-1,3,4-thiadiazole-2-carboxamide To a flask containing 10% Pd—C (10 mg) under N$_2$ was added THF (1 mL) followed by N-(2-methoxyethyl)-5-(4-(6-(2-(3-(trifluoromethoxy)phenyl)acetamido)pyridazin-3-yl)but-3-ynyl)-1,3,4-thiadiazole-2-carboxamide (30 mg, 0.056 mmol). The flask was evacuated and filled with H$_2$, and the mixture stirred at 30° C. under a H$_2$ atmosphere for 3 h. The flask was evacuated and filled with N$_2$, the suspension was filtered through a pad of Celite®, and the filtrate concentrated under reduced pressure. The residue was purified by preparative HPLC (Mobile phase: A=0.1% TFA/H$_2$O, B=0.1% TFA/MeCN; Gradient: B=30-70%; 12 min; Column: C18) to afford the title compound as a white solid (25 mg, 78%). MS (ES$^+$) C$_{23}$H$_{25}$F$_3$N$_6$O$_4$S requires: 538, found: 539[M+H]$^+$; $^1$H NMR (400 MHz, DMSO) δ 11.32 (s, 1H), 9.11 (t, J=5.4 Hz, 1H), 8.19 (d, J=9.2 Hz, 1H), 7.57 (d, J=9.1 Hz, 1H), 7.47 (m, 1H), 7.40-7.33 (m, 2H), 7.26 (d, J=7.8 Hz, 1H), 3.85 (s, 2H), 3.51-3.39 (m, 4H), 3.25 (s, 3H), 3.18 (t, J=6.1 Hz, 2H), 2.90 (t, J=6.8 Hz, 2H), 1.83-1.71 (m, 4H).

Example 7: N-(2-methoxyethyl)-5-(4-(4-(3-(trifluoromethyl)benzylcarbamoyl)-1H-1,2,3-triazol-1-yl)butyl)-1,3,4-thiadiazole-2-carboxamide

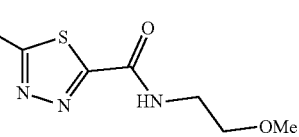

Steps 1 to 6

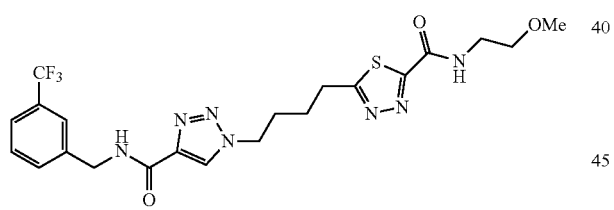

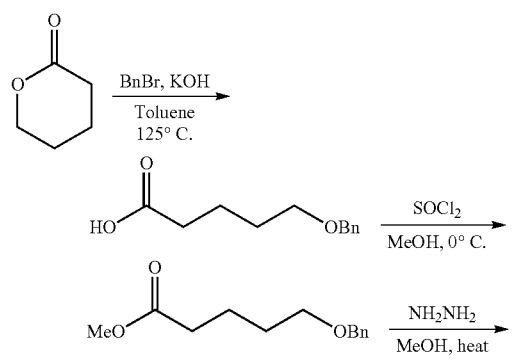

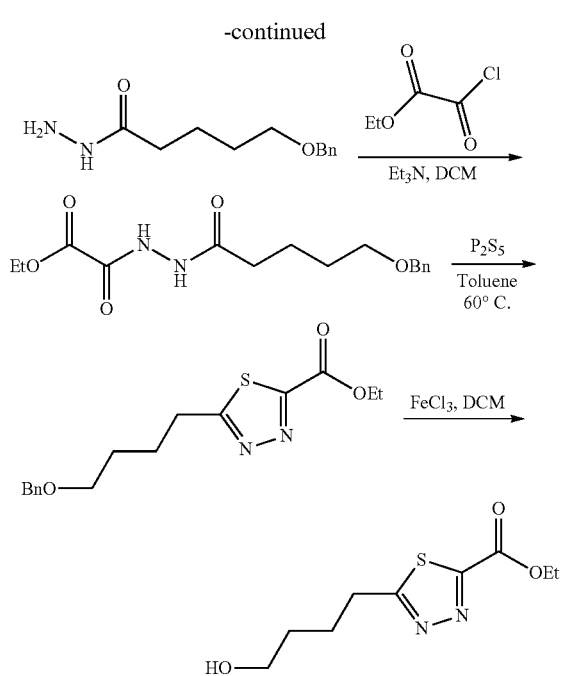

Step 1: 5-(benzyloxy)pentanoic Acid

To a solution of tetrahydro-2H-pyran-2-one (5.0 g, 50 mmol) in toluene (50 mL) were added KOH (15.8 g, 28.2 mmol) and benzylbromide (17.8 mL, 150 mmol), and the mixture was stirred at 125° C. for 16 h. The solution was cooled to RT and diluted with ice/H$_2$O (70 mL). The organic layer was separated and the aqueous layer was washed with MTBE (3×30 mL). The aqueous layer was then cooled to 0° C. and the pH was adjusted to 3-4 by the addition of concentrated aq. HCl (15 mL) and 6N aq. HCl (8 mL). The mixture was extracted with EtOAc (4×50 mL) and the combined organic layers were washed with brine (20 mL), dried (Na$_2$SO$_4$), and concentrated under reduced pressure to give 5-(benzyloxy)pentanoic acid as a light yellow oil (10 g, 96%). MS (ES$^+$) C$_{12}$H$_{16}$O$_3$ requires: 208, found: 209[M+H]$^+$.

Step 2: methyl 5-(benzyloxy)pentanoate

To a solution of 5-(benzyloxy)pentanoic acid (1.0 g, 4.8 mmol) in MeOH (40 mL) at 0° C. was slowly added SOCl$_2$ (0.39 mL, 5.3 mmol) and the mixture was stirred at RT for 1 h. The mixture was then treated with saturated aq. NaHCO$_3$ (5 mL), the volatiles were removed under reduced pressure, and the aqueous layer was extracted with DCM (3×10 mL). The combined organic layers were washed with brine (5 mL), dried (Na$_2$SO$_4$), and concentrated under reduced pressure to afford methyl 5-(benzyloxy) pentanoate as a light yellow oil (1.0 g, 94%). MS (ES⁺) C₁₃H₁₈O₃ requires: 222, found: 223[M+H]⁺.

Step 3: 5-(benzyloxy)pentanehydrazide

A mixture of methyl 5-(benzyloxy)pentanoate (1.0 g, 4.5 mmol) and NH₂NH₂ (35% wt. solution in H₂O, 1.3 mL, 14 mmol) in MeOH (15 mL) was heated at reflux in a pressure safe vial for 18 h. The mixture was cooled to RT and the volatiles were removed under reduced pressure. The residue was taken up in toluene (2×5 mL) and concentrated again. The resulting solid was triturated with hexanes (2×5 mL) and filtered to give 5-(benzyloxy)pentanehydrazide as a white solid (840 mg, 84%). MS (ES⁺) C₁₂H₁₈N₂O₂ requires: 222, found: 223[M+H]⁺.

Step 4: ethyl 2-(2-(5-(benzyloxy)pentanoyl)hydrazinyl)-2-oxoacetate

To a solution of 5-(benzyloxy)pentanehydrazide (500 mg, 2.25 mmol) and TEA (0.627 mL, 4.50 mmol) in DCM (5.0 mL) at 0° C. was added ethyl 2-chloro-2-oxoacetate (0.448 mL, 4.00 mmol), and the resulting mixture was stirred at RT for 30 minutes. The volatiles were removed under reduced pressure to give the title compound as a white solid (800 mg, 100%). MS (ES⁺) C₁₆H₂₂N₂O₅ requires: 322, found: 323 [M+H]⁺.

Step 5: ethyl 5-(4-(benzyloxy)butyl)-1,3,4-thiadiazole-2-carboxylate

To a mixture of ethyl 2-(2-(5-(benzyloxy)pentanoyl)hydrazinyl)-2-oxoacetate (400 mg, 2.30 mmol) in toluene (5 mL) at 60° C. was added P₂O₅ (500 mg, 2.3 mmol). The reaction mixture was stirred at 60° C. for 15 minutes, cooled to RT, and partitioned between saturated aq. NaHCO₃ (30 mL) and EtOAc (50 mL). The organic layer was collected, washed with brine (5 mL), dried (Na₂SO₄), and concentrated under reduced pressure. The residue was purified by SiO₂ gel chromatography (5% to 20% EtOAc in hexanes) to give the title compound as a yellow oil (1.3 g, 48%). MS (ES⁺) C₁₆H₂₀N₂O₃S requires: 320, found: 321 [M+H]⁺.

Step 6: ethyl 5-(4-hydroxybutyl)-1,3,4-thiadiazole-2-carboxylate

To a solution of ethyl 5-(4-(benzyloxy)butyl)-1,3,4-thiadiazole-2-carboxylate (1.0 g, 3.1 mmol) in DCM (30 mL) was added anhydrous FeCl₃ (2.0 g, 13 mmol) portionwise. The reaction mixture was stirred at RT for 25 minutes, a further aliquot of anhydrous FeCl₃ (1.0 g, 6.3 mmol) was added, and the mixture was stirred for an additional 10 minutes. The mixture was then treated with saturated aq. NH₄Cl (10 mL), the layers were separated, and the aqueous phase was extracted with DCM/MeOH=10/1 v/v (3×50 mL). The combined organic layers were washed with brine (10 mL), dried (Na₂SO₄), and concentrated under reduced pressure. The residue was purified by SiO₂ gel chromatography (0% to 2% MeOH in DCM) to give the title compound as a brown oil (730 mg, 100%). MS (ES⁺) C₉H₁₄N₂O₃S requires: 230, found: 231 [M+H]⁺.

Steps 7 to 10

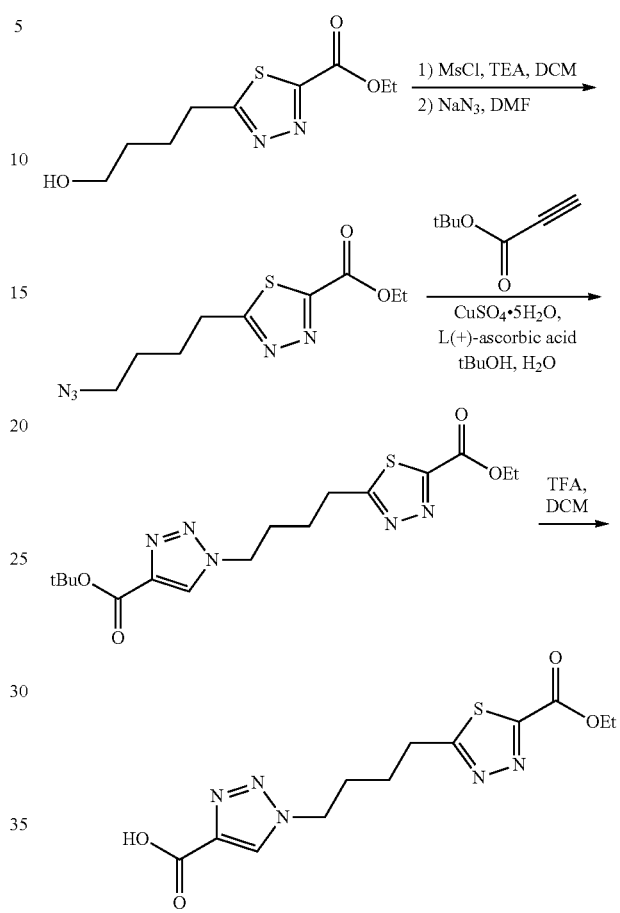

Step 7: 5-(4-(Methylsulfonyloxy)butyl)-1,3,4-thiadiazole-2-carboxylate

To a solution of ethyl 5-(4-hydroxybutyl)-1,3,4-thiadiazole-2-carboxylate (2.30 g, 10.0 mmol; prepared as described for Example 6, step 3) and Et₃N (3.0 g, 30 mmol) in DCM (25 mL) at 0° C. was added MsCl (1.2 mL, 15.0 mmol) in DCM (5 mL) dropwise. The reaction mixture was stirred at 0° C. for 10 minutes, then at RT for 20 minutes. The mixture was then diluted with H₂O (50 mL) and extracted with DCM (100 mL). The organic layer was dried (Na₂SO₄), filtered, and concentrated under reduced pressure to give the title compound as an oil (3.0 g, 97%). MS (ES⁺) C₁₀H₁₆N₂O₅S₂ requires: 308, found: 309 [M+H]⁺.

Step 8: Ethyl 5-(4-azidobutyl)-1,3,4-thiadiazole-2-carboxylate

To a solution of ethyl 5-(4-(methylsulfonyloxy)butyl)-1,3,4-thiadiazole-2-carboxylate (3.0 g, 9.7 mmol) in DMF (15 mL) was added NaN₃ (1.26 g, 19.4 mmol) and the reaction mixture was stirred at 80° C. for 2 h. The mixture was then cooled to RT, poured onto ice water (100 mL) and extracted with DCM (2×100 mL). The combined organic layers were washed with brine (100 mL), dried (Na₂SO₄), and concentrated under reduced pressure to give the title compound as an oil (2.45 g, 96%). MS (ES+) $C_9H_{13}N_5O_2S$ requires: 255, found: 256 [M+H]+.

Step 9: Ethyl 5-(4-(4-(tert-butoxycarbonyl)-1H-1,2,3-triazol-1-yl)butyl)-1,3,4-thiadiazole-2-carboxylate To a solution of ethyl 5-(4-azidobutyl)-1,3,4-thiadiazole-2-carboxylate (2.45 g, 9.60 mmol) in t-BuOH (15 mL) and H₂O (15 mL) were added CuSO₄·0.5H₂O (490 mg, 2.65 mmol) and L-(+)-ascorbic acid (980 mg, 5.57 mmol). The reaction mixture was stirred at RT for 3 h, diluted with water (100 mL), and extracted with EtOAc (2×100 mL). The combined organic layers were washed with brine (100 mL), dried (Na₂SO₄), and concentrated under reduced pressure to give the title compound as a light yellow solid (2.2 g, 5.8 mmol, 60%). MS (ES+) $C_{16}H_{23}N_5O_4S$ requires: 381, found: 382 [M+H]+.

Step 10: 1-(4-(5-(Ethoxycarbonyl)-1,3,4-thiadiazol-2-yl)butyl)-1H-1,2,3-triazole-4-carboxylic Acid To a solution of ethyl 5-(4-(4-(tert-butoxycarbonyl)-1H-1,2,3-triazol-1-yl)butyl)-1,3,4-thiadiazole-2-carboxylate (3.2 g, 5.8 mmol) in DCM (10 mL) was added TFA (5.0 mL). The reaction mixture was stirred at RT for 16 h then concentrated under reduced pressure. CH₃CN (10 mL) was added resulting in the formation of a precipitate, which was filtered off to give the title compound as a light yellow solid (1.30 g, 70%). MS (ES+) $C_{12}H_{15}N_5O_4S$ requires: 325, found: 326 [M+H]+.

Steps 11 to 12

Step 11: Ethyl 5-(4-(4-(3-(trifluoromethyl)benzylcarbamoyl)-1H-1,2,3-triazol-1-yl)butyl)-1,3,4-thiadiazole-2-carboxylate To a solution of 1-(4-(5-(ethoxycarbonyl)-1,3,4-thiadiazol-2-yl)butyl)-1H-1,2,3-triazole-4-carboxylic acid (1.0 g, 3.1 mmol) and (3-(trifluoromethyl)phenyl)methanamine (592 mg, 3.38 mmol) in DMF (6.0 mL) were added HATU (1.75 g, 4.61 mmol) and DIEA (990 mg, 7.70 mmol). The reaction mixture was stirred at RT for 2 h then diluted with H₂O (20 mL). The solid was collected by filtration to give the title compound as a light yellow solid (1.35 g, 91%). MS (ES+) $C_{20}H_{21}F_3N_6O_3S$ requires: 482, found: 483 [M+H]+.

Step 12: N-(2-Methoxyethyl)-5-(4-(4-(3-(trifluoromethyl)benzylcarbamoyl)-1H-1,2,3-triazol-1-yl)butyl)-1,3,4-thiadiazole-2-carboxamide To a suspension of ethyl 5-(4-(4-(3-(trifluoromethyl)benzylcarbamoyl)-1H-1,2,3-triazol-1-yl)butyl)-1,3,4-thiadiazole-2-carboxylate (96 mg, 0.20 mmol) in MeOH (1.0 mL) was added 2-methoxyethanamine (0.05 mL, 0.7 mmol) and the reaction mixture was heated in a sealed tube at 80° C. for 2 h. The mixture was cooled to RT, the solid was filtered off and washed with MeOH (5.0 mL) to give the title compound as a white solid (82 mg, 77%). MS (ES+) $C_{21}H_{24}F_3N_7O_3S$ requires: 511, found: 512 [M+H]+; ¹H NMR (400 MHz, DMSO) δ 9.22 (t, J=6.1 Hz, 1H), 9.13 (t, J=5.2 Hz, 1H), 8.63 (s, 1H), 7.46 (m, 1H), 7.34 (d, J=7.7 Hz, 1H), 7.29 (s, 1H), 7.24 (d, J=7.9 Hz, 1H), 4.61-4.35 (m, 4H), 3.54-3.41 (m, 4H), 3.25 (s, 3H), 2.01-1.87 (m, 2H), 1.79-1.65 (m, 2H).

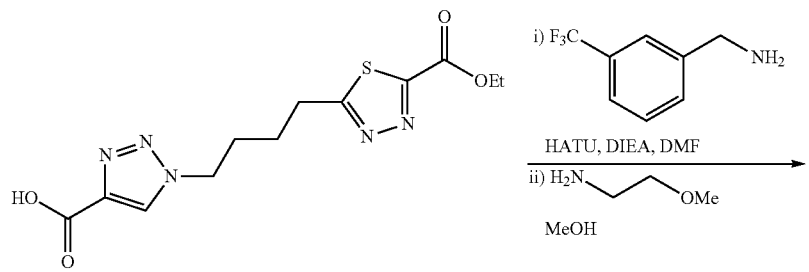

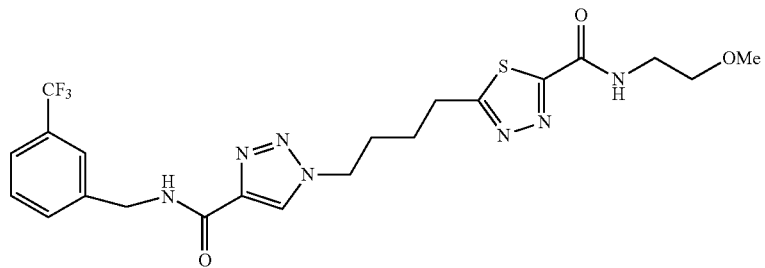

Example 8: Tert-butyl 4-((4-(4-(4-(3-(trifluoromethoxy)benzylcarbamoyl)-1H-1,2,3-triazol-1-yl)butyl)-1H-1,2,3-triazol-1-yl)methyl)piperidine-1-carboxylate

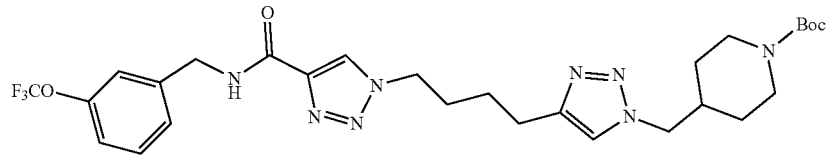 [SMILES: CC(C)(C)OC(=O)N1CCC(Cn2cc(CCCCn3cc(C(=O)NCc4cccc(OC(F)(F)F)c4)nn3)nn2)CC1]

Steps 1 to 5

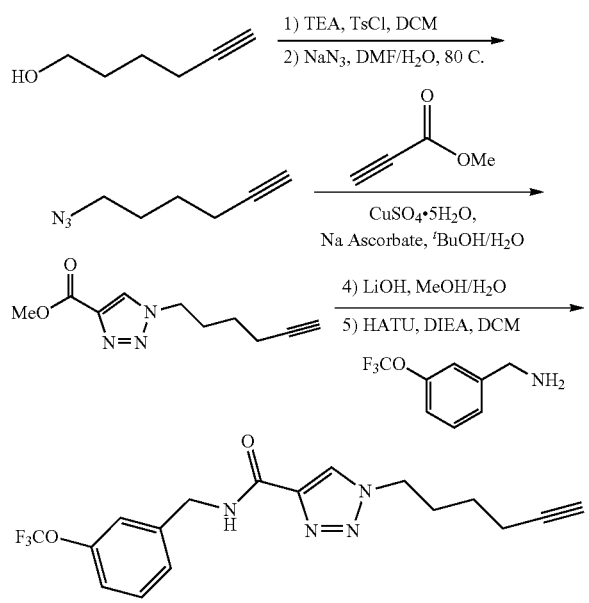

Step 1: Hex-5-ynyl 4-methylbenzenesulfonate

To a solution of hex-5-yn-1-ol (1 g, 10 mmol) in DCM (20 ml) were added TEA (1.24 g, 12.2 mmol) and 4-methylbenzene-1-sulfonyl chloride (1.9 g, 10 mmol). The resulting mixture was stirred at RT for 1 h and concentrated under reduced pressure to give the title compound as yellow oil (2.5 g, 97%). MS (ES$^+$) $C_{13}H_{16}O_3S$ required: 252, found: 253 [M+H]$^+$.

Step 2: 6-Azidohex-1-yne

To a solution of hex-5-ynyl 4-methylbenzenesulfonate (1.0 g, 3.9 mmol) in DMF (10 mL) and water (10 mL) was added NaN$_3$ (525 mg, 7.90 mmol). The resulting mixture was stirred at 80° C. for 12 h, then cooled to RT and partitioned between Et$_2$O (20 mL) and water (20 mL). The organic layer was collected, washed with water (30 mL), brine (30 mL), dried (Na$_2$SO$_4$), filtered, and concentrated under reduced pressure at 0° C. to give the title compound as a yellow oil (460 mg, 94%). MS (ES$^+$) $C_6H_9N_3$ requires: 123, found: 124 [M+H]$^+$.

Step 3: Methyl 1-(hex-5-ynyl)-1H-1,2,3-triazole-4-carboxylate

To a solution of 6-azidohex-1-yne (488 mg, 3.90 mmol) in $^t$BuOH (10 mL) and water (10 mL) were added methyl propiolate (499 mg, 5.90 mmol), CuSO$_4$·0.5H$_2$O (100 mg, 0.400 mmol) and sodium ascorbate (200 mg, 1.00 mmol). The resulting mixture was stirred at RT for 1 h, then partitioned between EtOAc (20 mL) and water (20 mL). The organic layer was collected, washed with water (30 mL), sat. NH$_4$Cl (3×30 mL), brine (30 mL), dried (Na$_2$SO$_4$), filtered, and concentrated under reduced pressure to give the title compound as yellow solid (500 mg, 61%). MS (ES$^+$) $C_{10}H_{13}N_3O_2$ requires: 207, found: 208 [M+H]$^+$.

Step 4: 1-(hex-5-ynyl)-1H-1,2,3-triazole-4-carboxylic Acid

To a solution of methyl 1-(hex-5-ynyl)-1H-1,2,3-triazole-4-carboxylate (500 mg, 2.40 mmol) in MeOH (10 mL) and water (10 mL) was added LiOH·H$_2$O (250 mg, 6.00 mmol) and the resulting mixture was stirred at RT for 2 h. The reaction was partitioned between EtOAc (20 mL) and water (20 mL), the organic layer was collected, washed with water (30 mL), brine (30 mL), dried (Na$_2$SO$_4$), filtered, and concentrated under reduced pressure to give the title compound as yellow solid (450 mg, 96%). MS (ES$^+$) $C_9H_{11}N_3O_2$ requires: 193, found: 194 [M+H]$^+$.

Step 5: 1-(Hex-5-ynyl)-N-(3-(trifluoromethoxy)benzyl)-1H-1,2,3-triazole-4-carboxamide To a solution of 1-(hex-5-ynyl)-1H-1,2,3-triazole-4-carboxylic acid (235 mg, 1.22 mmol) in DCM (15 mL) were added 3-(trifluoromethoxy)phenyl)methanamine (255 mg, 1.34 mmol), HATU (695 mg, 1.83 mmol), and DIEA (472 mg, 3.66 mmol), and the resulting mixture was stirred at RT for 12 h. The mixture was partitioned between DCM (20 mL) and water (20 mL), the organic layer was collected, washed with water (3×30 mL), brine (30 mL), dried (Na$_2$SO$_4$), filtered, and concentrated under reduced pressure. The residue was purified by SiO$_2$ gel chromatography (0 to 20% MeOH in DCM) to give the title compound as yellow solid (300 mg, 67%). MS (ES$^+$) $C_{17}H_{17}F_3N_4O_2$ requires: 366, found: 367 [M+H]$^+$.

Steps 6 to 7

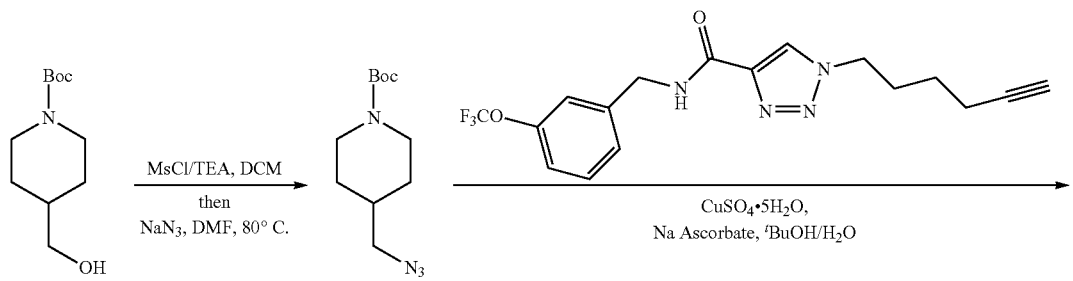

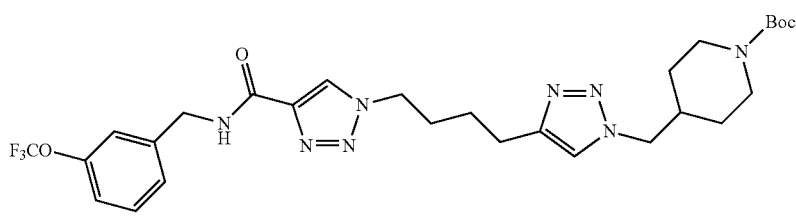

Step 6: Tert-butyl 4-(azidomethyl)piperidine-1-carboxylate

To a solution of tert-butyl 4-(hydroxymethyl)piperidine-1-carboxylate (1.0 g, 4.6 mmol) in DCM (20 mL) at 0° C., were added TEA (0.67 g, 6.9 mmol) and methylsulfonyl chloride (0.57 g, 5.0 mmol). The mixture was stirred at 0° C. for 0.5 h, then diluted with water (20 mL). The organic layer was collected and concentrated under reduced pressure. The residue was immediately taken up in DMF (10 mL) and NaN₃ (330 mg, 5.0 mmol) was added. The mixture was stirred at 80° C. for 2 h, cooled to RT, and extracted with EtOAc (3×20 mL). The combined organic layers were washed with brine, dried (Na₂SO₄), filtered, and concentrated under reduce pressure to afford the title compound as a colorless oil (0.9 g, 80%). $^1$H NMR (500 MHz, CDCl₃) δ 4.15-4.11 (m, 2H), 3.20-3.18 (d, J=6 Hz, 2H), 2.72-2.66 (m, 2H), 1.74-1.70 (m, 3H), 1.46 (s, 9H), 1.18-1.14 (m, 2H).

Step 7: Tert-butyl 4-((4-(4-(4-(3-(trifluoromethoxy)benzylcarbamoyl)-1H-1,2,3-triazol-1-yl)butyl)-1H-1,2,3-triazol-1-yl)methyl)piperidine-1-carboxylate To a solution of 1-(hex-5-ynyl)-N-(3-(trifluoromethoxy)benzyl)-1H-1,2,3-triazole-4-carboxamide (50 mg, 0.14 mmol) in $^t$BuOH (1.5 ml) and water (1.5 ml) were added CuSO₄ (10 mg, 0.06 mmol), sodium ascorbate (20 mg) and tert-butyl 4-(azidomethyl)piperidine-1-carboxylate (49 mg, 0.21 mmol) and the mixture was stirred at RT for 1 h. The volatiles were removed under reduced pressure and the residue was purified by preparative HPLC (Mobile phase: A=0.1% TFA/H₂O, B=0.1% TFA/MeCN; Gradient: B=30-70%; 12 min; Column: C18) to give the title compound as a white solid (25 mg, 30%). $^1$H NMR (500 MHz, CDCl₃) δ 8.07 (s, 1H), 7.55 (m, 1H), 7.39-7.20 (m, 3H), (bd, J=8.0 Hz, 1H), 4.61 (d, J=6.0 Hz, 2H), 4.45 (t, J=6.8 Hz, 2H), 4.19 (d, J=7.2 Hz, 2H), 4.13-4.08 (m, 2H), 2.78-2.75 (t, J=7.6 Hz, 2H), 2.70-2.64 (m, 2H), 2.08-1.98 (m, 3H), 1.80-1.76 (m, 1H), 1.60-1.55 (m, 2H), 1.45 (s, 9H), 1.28-1.15 (m, 3H). MS (ES⁺) C₂₈H₃₇F₃N₈O₄ requires: 606, found: 607 [M+H]⁺.

Example 9: 1-(4-(4-(Methylsulfonamidomethyl)-1H-1,2,3-triazol-1-yl)butyl)-N-(3-(trifluoromethoxy)benzyl)-1H-1,2,3-triazole-4-carboxamide

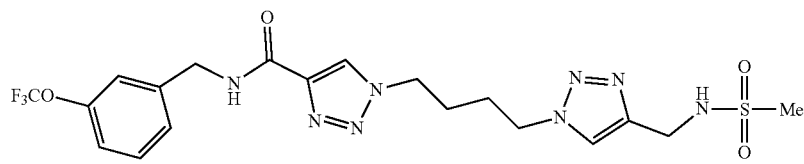 [SMILES: CS(=O)(=O)NCc1cn(CCCCn2cc(C(=O)NCc3cccc(OC(F)(F)F)c3)nn2)nn1]

Steps 1 to 5

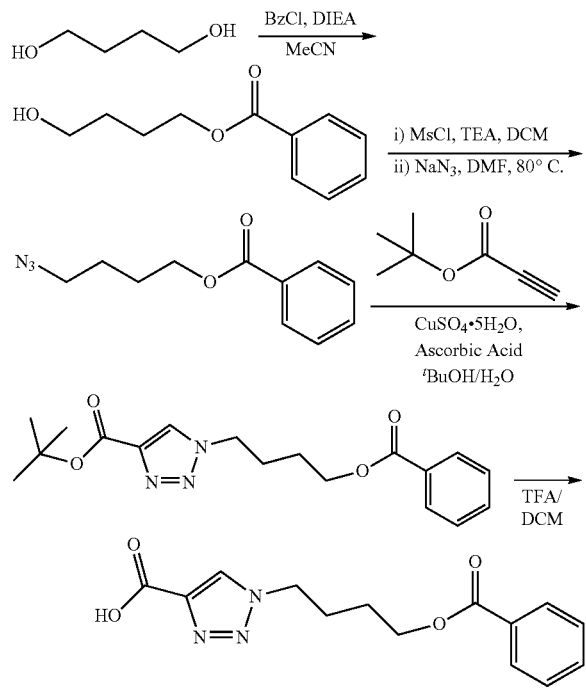

Step 1: 4-Hydroxybutyl Benzoate

To a solution of butane-1,4-diol (7.44 ml, 84.0 mmol) and DIEA (4.70 ml, 27.0 mmol) in MeCN (180 ml) at 0° C. was added dropwise a solution of benzoyl chloride (3.13 ml, 27.0 mmol) in MeCN (10 ml), at such a rate to keep the reaction mixture between 0-5° C. The mixture was stirred for an additional 15 minutes at 0° C., then warmed to RT, stirred for 16 h, and concentrated under reduced pressure. The residue was purified by $SiO_2$ gel chromatography (20% EtOAC in hexanes) to give the title compound as a colorless oil (4.82 g, 92%). MS (ES$^+$) $C_{11}H_{14}O_3$ requires: 194, found: 195 [M+H]$^+$.

Step 2: 4-(Methylsulfonyloxy)butyl Benzoate

To a solution of 4-hydroxybutyl benzoate (5.0 g, 18 mmol) and TEA (3.7 g, 36.8 mmol) in DCM (20 ml) was added dropwise MsCl (2.5 g, 22 mmol) as a solution in DCM (10 ml). The mixture was stirred at RT for 30 minutes, diluted with water (30 ml), and extracted with DCM (50 ml). The organic layer was concentrated under reduced pressure to afford 4-(methylsulfonyloxy)butyl benzoate as a colorless oil (5.2 g, 98%). MS (ES$^+$) $C_{12}H_{16}O_5S$ requires: 273, found: 274 [M+H]$^+$.

Step 3: 4-Azidobutyl Benzoate

To a solution of 4-(methylsulfonyloxy)butyl benzoate (3.0 g, 11.0 mmol) in DMF (15 ml) was added $NaN_3$ (1.35 g, 22.1 mmol) and the mixture was stirred at 80° C. for 16 h. The mixture was then cooled to RT, diluted with water (30 mL) and extracted with EtOAc (50 mL). The organic layer was concentrated under reduced pressure to afford 4-azidobutyl benzoate as a yellow oil (3 g, 98%). MS (ES$^+$) $C_{11}H_{13}N_3O_2$ requires: 219, found: 220 [M+H]$^+$.

Step 4: Tert-butyl 1-(4-(benzoyloxy)butyl)-1H-1,2, 3-triazole-4-carboxylate

To a mixture of 4-azidobutyl benzoate (5.0 g, 23 mmol) in $^tBuOH/H_2O$ (20 ml, 1/1 v/v), tert-butyl propiolate (2.90 g, 22.8 mmol) and L-(+)-Ascorbic acid (1.0 g, 5.7 mmol) was added $CuSO_4 \cdot 0.5H_2O$ (2.0 g, 13 mmol). The mixture was stirred at RT for 16 h and concentrated under reduced pressure. The residue was taken up in water (50 ml) and the mixture was stirred for 15 minutes at RT. The resulting solid was collected by filtration to afford the title compound as a white solid (6.5 g, 83%). MS (ES$^+$) $C_{18}H_{23}N_3O_4$ requires: 345.2, found: 346 [M+H]$^+$.

Step 5: 1-(4-(Benzoyloxy)butyl)-1H-1,2,3-triazole-4-carboxylic Acid

A mixture of tert-butyl 1-(4-(benzoyloxy)butyl)-1H-1,2, 3-triazole-4-carboxylate (5.0 g, 15 mmol) in TFA/DCM (40 ml, 1/1 v/v) was stirred at RT for 3 h and then concentrated under reduced pressure. The residue was taken up in water (30 ml) and the mixture was stirred for 15 minutes at RT. The resulting solid was collected by filtration and crystallized from MeCN/$H_2O$ to afford the title compound as a white solid (3.8 g, 90%). MS (ES$^+$) $C_{14}H_{15}N_3O_4$ requires: 289.1, found: 290 [M+H]$^+$.

Steps 6 to 9

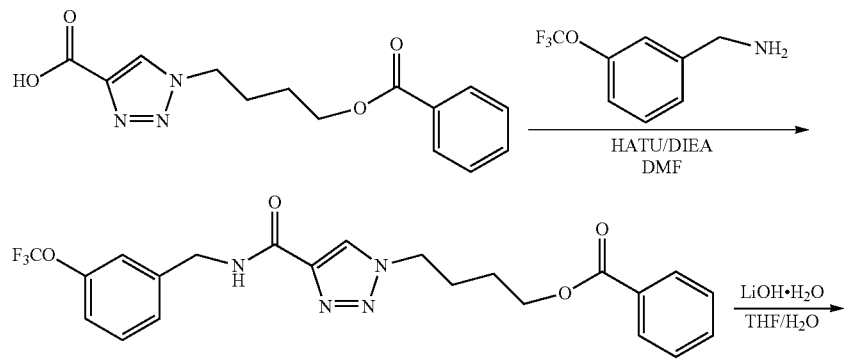

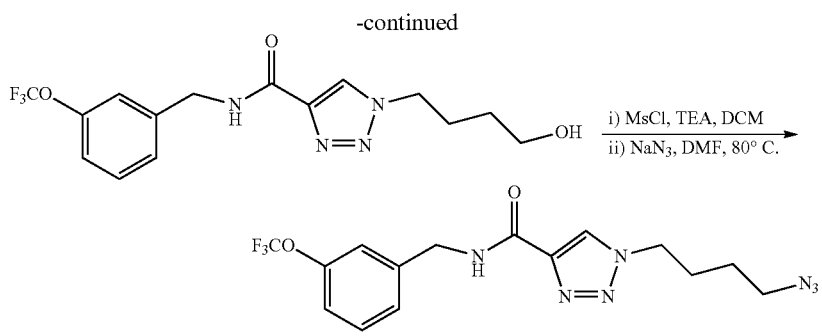

Step 6: 4-(4-(3-(Trifluoromethoxy)benzylcarbamoyl)-1H-1,2,3-triazol-1-yl)butyl Benzoate A mixture of 1-(4-(benzoyloxy)butyl)-1H-1,2,3-triazole-4-carboxylic acid (1.0 g, 3.5 mmol), (3-(trifluoromethoxy)phenyl)methanamine (0.66 g, 3.5 mmol), HATU (1.9 g, 5.0 mmol) and DIPEA (1.30 g, 10.5 mmol) in DMF (10 ml) was stirred at RT for 16 h. The residue was taken up in water (100 ml) and the mixture was stirred for 15 minutes at RT. The resulting solid was filtered to give the title compound as a white solid (1.0 g, 62%). MS (ES$^+$) $C_{22}H_{21}F_3N_4O_4$ requires: 462.2, found: 463 [M+H]$^+$.

Step 7: 1-(4-hydroxybutyl)-N-(3-(trifluoromethoxy)benzyl)-1H-1,2,3-triazole-4-carboxamide A mixture of 4-(4-(3-(trifluoromethoxy)benzylcarbamoyl)-1H-1,2,3-triazol-1-yl)butyl benzoate (1.0 g, 2.2 mmol) and LiOH·H$_2$O (0.27 g, 6.6 mmol) in THF/H$_2$O (10 ml, 1/1 v/v) was stirred at RT for 16 h. The reaction mixture was then partitioned between EtOAc (50 ml) and water (50 ml). The organic layer was collected and concentrated under reduced pressure to give the title compound as a white solid (600 mg, 77%). MS (ES$^+$) $C_{15}H_{17}F_3N_4O_3$ requires: 358.1, found: 359 [M+H]$^+$.

Step 8: 1-(4-azidobutyl)-N-(3-(trifluoromethoxy)benzyl)-1H-1,2,3-triazole-4-carboxamide To a solution of 1-(4-hydroxybutyl)-N-(3-(trifluoromethoxy)benzyl)-1H-1,2,3-triazole-4-carboxamide (600 mg, 1.68 mmol) and TEA (340 mg, 3.36 mmol) in DCM (5 ml) was added dropwise a solution of MsCl (240 mg, 2.10 mmol) in DCM (5 ml). The mixture was stirred at RT for 30 minutes, then diluted with water (10 ml) and extracted with DCM (20 ml). The organic layer was concentrated under reduced pressure. The residue was taken up in DMF (3 ml), NaN$_3$ (110 mg, 1.68 mmol) was added and the mixture was stirred at 80° C. for 1 h, then cooled to RT. The residue was taken up in water (20 ml) and the mixture was stirred for 15 minutes at RT. The resulting solid was collected by filtration to give the title compound as a white solid (600 mg, 93%). MS (ES$^+$) $C_{15}H_{16}F_3N_7O_2$ requires: 383.1, found: 384 [M+H]$^+$.

Step 9: Tert-butyl (1-(4-(4-(3-(trifluoromethoxy)benzylcarbamoyl)-1H-1,2,3-triazol-1-yl)butyl)-1H-1,2,3-triazol-4-yl)methylcarbamate A mixture of 1-(4-Azidobutyl)-N-(3-(trifluoromethoxy)benzyl)-1H-1,2,3-triazole-4-carboxamide (100 mg, 0.26 mmol), tert-butyl prop-2-ynylcarbamate (40 mg, 0.26 mmol), L-(+)-ascorbic acid (40 mg, 0.23 mmol) and CuSO$_4$·0.5H$_2$O (20 mg, 0.12 mmol) in $^t$BuOH/H$_2$O (3 ml, 1/1 v/v) was stirred at RT for 16 h and concentrated under reduced pressure. The residue was taken up in water (10 ml) and the mixture was stirred for 15 minutes at RT. The resulting solid was collected by filtration to give the title compound as a white solid (100 mg, 71%). MS (ES$^+$) $C_{23}H_{29}F_3N_8O_4$ requires: 538.2, found: 539 [M+H]$^+$.

Steps 10 to 11

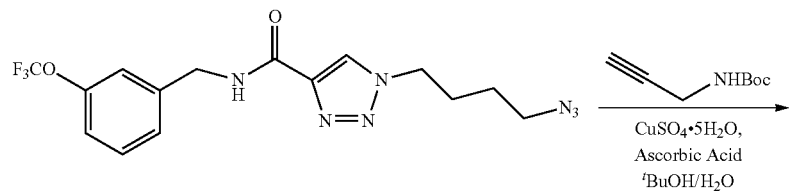

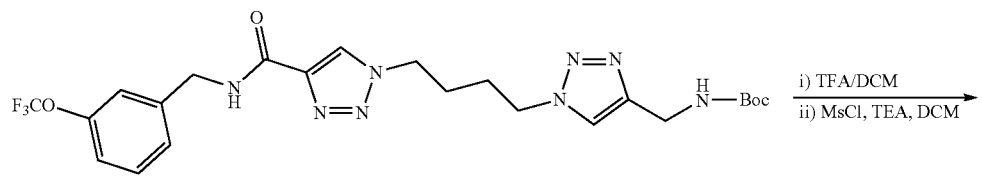

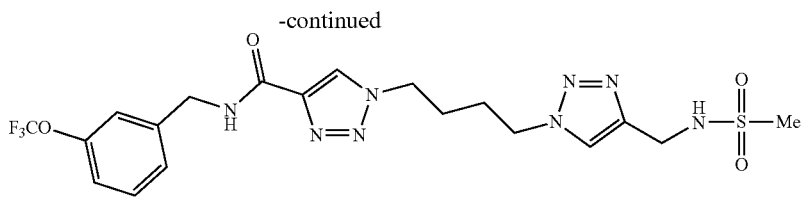

Step 10: 1-(4-(4-(Aminomethyl)-1H-1,2,3-triazol-1-yl)butyl)-N-(3-(trifluoromethoxy)benzyl)-1H-1,2,3-triazole-4-carboxamide A solution of tert-butyl (1-(4-(4-(3-(trifluoromethoxy)benzylcarbamoyl)-1H-1,2,3-triazol-1-yl)butyl)-1H-1,2,3-triazol-4-yl)methylcarbamate (100 mg, 0.19 mmol) in TFA/DCM (3 ml, 1/1 v/v) was stirred at RT for 3 h and concentrated under reduced pressure. The residue was taken up in water (100 ml) and the mixture was stirred for 15 minutes at RT. The resulting solid was collected by filtration to give the title compound as a white solid (70 mg, 86%). MS (ES+) C₁₈H₂₁F₃N₈O₂ requires: 438.2, found: 439 [M+H]+.

Step 11: 1-(4-(4-(methylsulfonamidomethyl)-1H-1,2,3-triazol-1-yl)butyl)-N-(3-(trifluoromethoxy)benzyl)-1H-1,2,3-triazole-4-carboxamide To a solution of 1-(4-(4-(aminomethyl)-1H-1,2,3-triazol-1-yl)butyl)-N-(3-(trifluoromethoxy)benzyl)-1H-1,2,3-triazole-4-carboxamide (70 mg, 0.16 mmol) in DCM (3 ml) were added TEA (48 mg, 0.48 mmol) and methanesulfonyl chloride (36.7 mg, 0.32 mmol). The mixture was stirred at RT for 3 h and concentrated under reduced pressure. The residue was taken up in water (10 ml) and the mixture was stirred for 15 minutes at RT. The resulting solid was collected by filtration to give the title compound as a white solid (37 mg, 45%). MS (ES+) C₁₉H₂₃F₃N₈O₄S requires: 516, found: 517 [M+H]+. ¹H NMR (500 MHz, DMSO) δ 9.21 (t, J=8.0, 1H), 8.60 (s, 1H), 8.01 (s, 1H), 7.51-7.40 (m, 2H), 7.35-7.20 (m, 3H), 4.50-4.32 (m, 6H), 4.10 (d, J=7.5, 2H), 2.88 (s, 3H), 1.78-1.73 (m, 4H).

Example 157: N-methyl-1-(4-(6-(2-(3-(trifluoromethoxy)phenyl)acetamido)pyridazin-3-yl)butyl)-1H-1,2,3-triazole-4-carboxamide

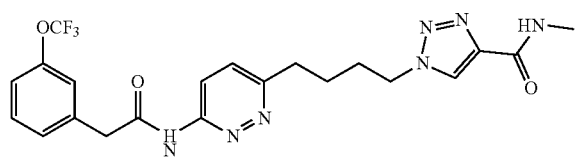 [SMILES: CNC(=O)c1cn(CCCCc2ccc(NC(=O)Cc3cccc(OC(F)(F)F)c3)nn2)nn1]

Steps 1 to 3

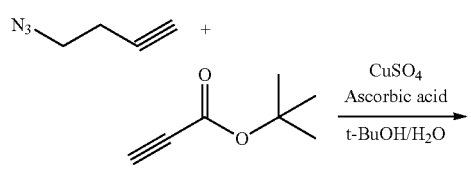

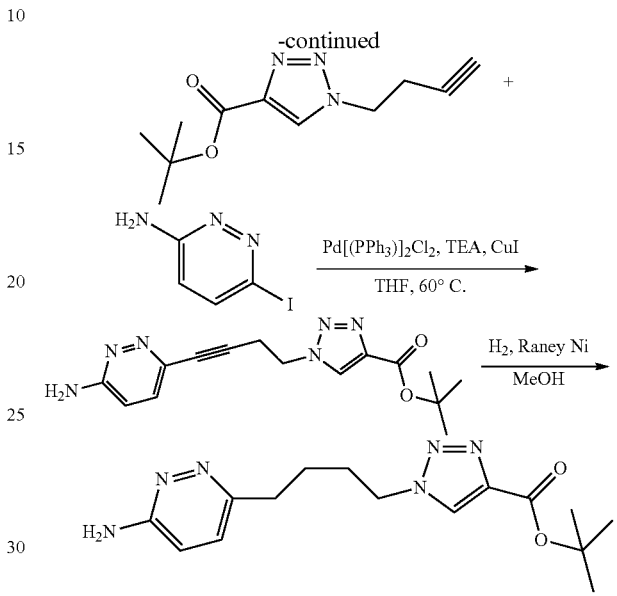

Step 1: tert-butyl 1-(but-3-ynyl)-1H-1,2,3-triazole-4-carboxylate

A mixture of 4-azidobut-1-yne (20 g, 0.21 mol), t-butyl propiolate (26.5 g, 0.21 mol), L-(+)-ascorbic acid (8.0 g, 46 mmol), and CuSO₄ (4.0 g, 25 mmol) in 1:1 v:v t-BuOH/H₂O (400 ml) was stirred at RT for 16 h, then concentrated under reduced pressure. Water (200 ml) was added, and the mixture was extracted with EtOAc (3×300 mL). The combined organic layers were concentrated under reduced pressure to afford a yellow solid. The solid was washed with petroleum ether to give the title compound as a white solid (25 g, 54%). MS (ES+) C₁₁H₁₅N₃O₂ requires: 221, found: 222 [M+H]+.

Step 2: tert-butyl 1-(4-(6-aminopyridazin-3-yl)but-3-ynyl)-1H-1,2,3-triazole-4-carboxylate A mixture of tert-butyl 1-(but-3-ynyl)-1H-1,2,3-triazole-4-carboxylate (15 g, 68 mmol), 6-iodopyridazin-3-amine (15 g, 68 mmol), Pd(PPh₃)₂Cl₂ (4.8 g, 6.8 mmol), CuI (1.3 g, 6.8 mmol), and TEA (34.2 g, 339 mmol) in 300 mL of anhydrous THF was stirred at 60° C. under N₂ for 16 h, then allowed cool to RT. DCM/MeOH (500 mL of a 10:1 v:v mixture) was added, the mixture was filtered and the filtrate concentrated under reduced pressure to give a yellow oil. The oil was purified by SiO₂ gel chromatography (0% to 9% MeOH in DCM) to give the title compound as a yellow solid (18.0 g, 84%). MS (ES+) C₁₅H₁₈N₆O₂ requires: 314, found: 315 [M+H]+.

Step 3: tert-butyl 1-(4-(6-aminopyridazin-3-yl)butyl)-1H-1,2,3-triazole-4-carboxylate A mixture of tert-butyl 1-(4-(6-aminopyridazin-3-yl)but-3-ynyl)-1H-1,2,3-triazole-4-carboxylate (3.5 g, 11 mmol), Raney Ni (300 mg) and MeOH (250 ml) was evacuated and refilled with hydrogen, then stirred under an atmosphere of H$_2$ at 1 atm for 16 h. The mixture was filtered, and the filtrate concentrated under reduced pressure to give a yellow solid. The solid was purified by SiO$_2$ gel chromatography (0% to 9% MeOH in DCM) to give the title compound as a yellow solid (3.17 g, 89%). MS (ES$^+$) C$_{15}$H$_{22}$N$_6$O$_2$ requires: 318, found: 319 [M+H]$^+$. $^1$H NMR (500 MHz, DMSO-d$_6$) δ 8.67 (s, 1H), 7.13 (d, J=9.0 Hz, 1H), 6.71 (d, J=9.0 Hz, 1H), 6.15 (s, 2H), 4.52-4.37 (m, 2H), 2.69 (t, J=7.6 Hz, 2H), 1.96-1.79 (m, 2H), 1.65-1.42 (m, 11H).

Steps 4 to 6

Step 5: 1-(4-(6-(2-(3-(trifluoromethoxy)phenyl)acetamido)pyridazin-3-yl)butyl)-1H-1,2,3-triazole-4-carboxylic Acid A mixture of tert-butyl 1-(4-(6-(2-(3-(trifluoromethoxy)phenyl)acetamido)pyridazin-3-yl)butyl)-1H-1,2,3-triazole-4-carboxylate (134 mg, 0.257 mmol), TFA (0.992 mL, 12.9 mmol) and DCM (1 mL) was stirred at RT for 1 h, then concentrated under reduced pressure, azeotroping with toluene, to give the title compound as a waxy residue (120 mg, 100%). MS (ES$^+$) C$_{20}$H$_{19}$F$_3$N$_6$O$_4$ requires: 464, found: 465 [M+H]$^+$.

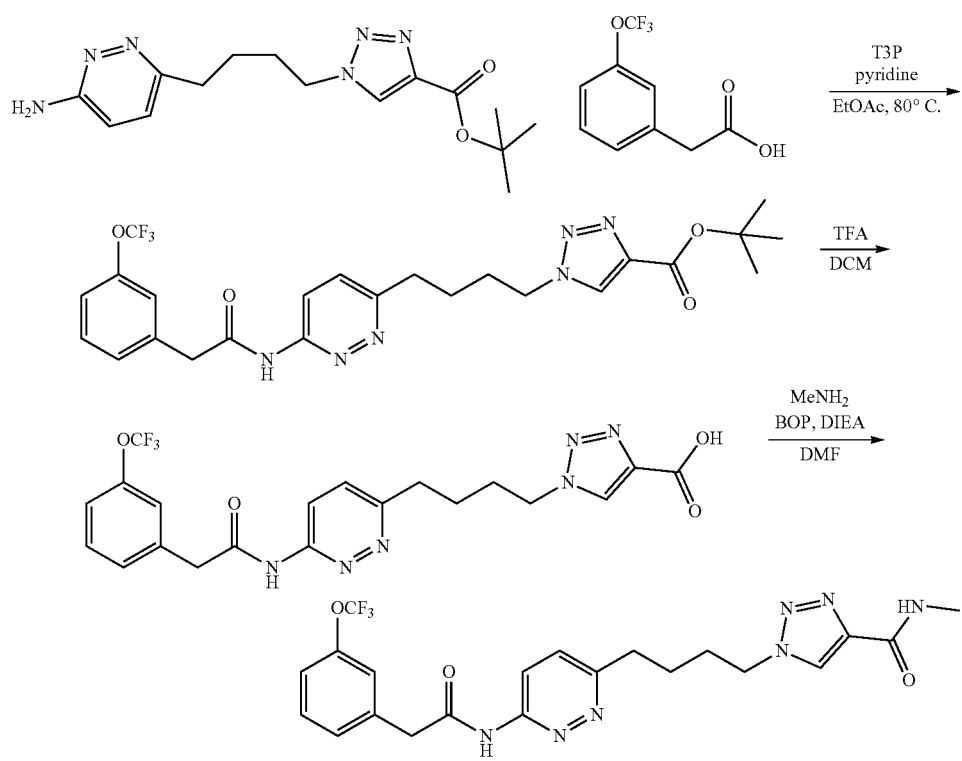

Step 4: tert-butyl 1-(4-(6-(2-(3-(trifluoromethoxy)phenyl)acetamido)pyridazin-3-yl)butyl)-1H-1,2,3-triazole-4-carboxylate To a suspension of tert-butyl 1-(4-(6-aminopyridazin-3-yl)butyl)-1H-1,2,3-triazole-4-carboxylate (80 mg, 0.25 mmol), pyridine (0.101 mL, 1.25 mmol) and 2-(3-(trifluoromethoxy)phenyl)acetic acid (83 mg, 0.37 mmol) was added T3P® (50 wt. %, 795 mg, 1.25 mmol) and the resulting mixture was stirred at 80° C. for 1 h and then RT for 12 h. The reaction was concentrated under reduced pressure and the residue was purified by SiO$_2$ gel chromatography (0% to 15% MeOH in DCM with 1% NH$_4$OH) to give the title compound as an orange solid (136 mg, 78% yield). MS (ES$^+$) C$_{24}$H$_{27}$F$_3$N$_6$O$_4$ requires: 520, found: 521 [M+H]$^+$.

Step 6: N-methyl-1-(4-(6-(2-(3-(trifluoromethoxy)phenyl)acetamido)pyridazin-3-yl)butyl)-1H-1,2,3-triazole-4-carboxamide To a suspension of 1-(4-(6-(2-(3-(trifluoromethoxy)phenyl)acetamido)pyridazin-3-yl)butyl)-1H-1,2,3-triazole-4-carboxylic acid (120 mg, 0.258 mmol), methylamine in THF (2.0 M, 0.258 mL, 0.517 mmol) and BOP (149 mg, 0.336 mmol) in DMF (1.0 mL) was added DIEA (0.135 mL, 0.775 mmol) and the resulting mixture was stirred at RT for 1 h then concentrated under reduced pressure. The residue was purified by mass-triggered preparative HPLC (Mobile phase: A=0.1% TFA/H$_2$O, B=0.1% TFA/MeCN; Gradient: B=20-60%; 20 min; Column: C18) to give the title compound as an off-white solid (35 mg, 28% yield). MS (ES$^+$) C$_{21}$H$_{22}$F$_3$N$_7$O$_3$ requires: 477, found: 478 [M+H]$^+$; $^1$H NMR (600 MHz, DMSO-d$_6$) δ 11.32 (s, 1H), 8.55 (s, 1H), 8.47-8.41 (m, 1H), 8.19 (d, J=9.1 Hz, 1H), 7.54 (d, J=9.1 Hz, 1H), 7.47 (t, J=7.9 Hz, 1H), 7.40-7.34 (m, 2H), 7.29-7.24 (m, 1H), 4.44 (t, J=7.0 Hz, 2H), 3.85 (s, 2H), 2.88 (t, J=7.6 Hz, 2H), 2.75 (d, J=4.7 Hz, 3H), 1.92-1.84 (m, 2H), 1.69-1.59 (m, 2H).

Example 192: N-methyl-1-(4-(6-(2-(4-(3-(trifluoromethoxy)phenyl)pyridin-2-yl)acetamido)pyridazin-3-yl)butyl)-1H-1,2,3-triazole-4-carboxamide

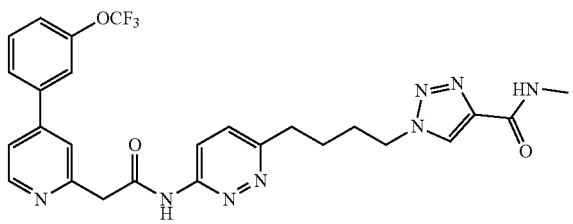 [SMILES: CNC(=O)c1cn(CCCCc2ccc(NC(=O)Cc3cc(-c4cccc(OC(F)(F)F)c4)ccn3)nn2)nn1]

Steps 1-3

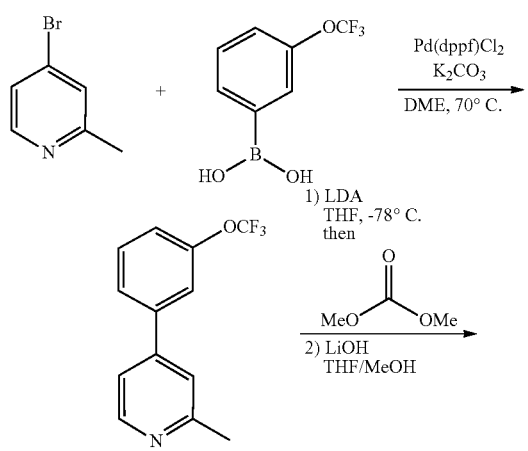

Step 1: 2-methyl-4-(3-(trifluoromethoxy)phenyl)pyridine

A mixture of 4-bromo-2-methylpyridine (1.2 g, 7.0 mmol), (3-(trifluoromethoxy)phenyl)boronic acid (1.87 g, 9.07 mmol) and PdCl$_2$(dppf)-CH$_2$Cl$_2$ (0.285 g, 0.349 mmol) in DME (23 mL) was degassed by bubbling through N$_2$ for 5 min. Aq. K$_2$CO$_3$ (2.0 M, 10.5 mL, 20.9 mmol) was added and the mixture was degassed by bubbling through N$_2$ for an additional 5 min. The mixture was stirred at 70° C. for 12 h, then diluted with EtOAc (25 mL) and water (25 mL) and the layers were separated. The aqueous layer was extracted with EtOAc (2×25 mL), and the combined organic layers were concentrated under reduced pressure. The residue was purified by SiO$_2$ gel chromatography (0% to 100% EtOAc with 20% MeOH in hexanes) to give the title compound as a yellow liquid (1.6 g, 91% yield). MS (ES$^+$) C$_{13}$H$_{10}$F$_3$NO requires: 253, found: 254 [M+H]$^+$.

Step 2: methyl 2-(4-(3-(trifluoromethoxy)phenyl)pyridin-2-yl)acetate

To a solution of 2-methyl-4-(3-(trifluoromethoxy)phenyl)pyridine (1.6 g, 6.3 mmol) in THF (12.6 ml) at −78° C. was added LDA in THF (2.0 M, 9.48 ml, 19.0 mmol) and the resulting mixture was stirred at −78° C. for 30 min. Dimethyl carbonate (0.639 ml, 7.58 mmol) was then added and the mixture was stirred at −78° C. for 1 h. The reaction was quenched with sat. aq. NH$_4$Cl (10 mL) at −78° C. and diluted with water (10 mL). The mixture was extracted with EtOAc (3×10 mL) and the combined organic layers were dried over MgSO$_4$, filtered and concentrated under reduced pressure. The residue was purified by SiO$_2$ gel chromatography (0% to 100% EtOAc with 20% MeOH in hexanes) to give the title compound as a brown liquid (1.8 g, 92% yield). MS (ES$^+$) C$_{15}$H$_{12}$F$_3$NO$_3$ requires: 311, found: 312 [M+H]$^+$.

Step 3: lithium 2-(4-(3-(trifluoromethoxy)phenyl)pyridin-2-yl)acetate

To a solution of methyl 2-(4-(3-(trifluoromethoxy)phenyl)pyridin-2-yl)acetate (1.8 g, 5.8 mmol) in THF (23 mL) and MeOH (5.8 ml) at RT was added aq. LiOH (2.0 M, 3.1 ml, 6.2 mmol) and the resulting mixture was stirred at RT for 1 h. The reaction mixture was concentrated under reduced pressure (bath <35° C.) and lyophilized to give the title compound as a light orange solid (1.75 g, 100% yield). MS (ES$^+$) C$_{14}$H$_{10}$F$_3$NO$_3$ requires: 297, found: 298 [M+H]$^+$.

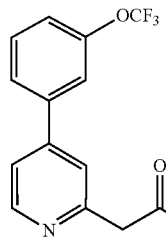

Steps 4 to 6

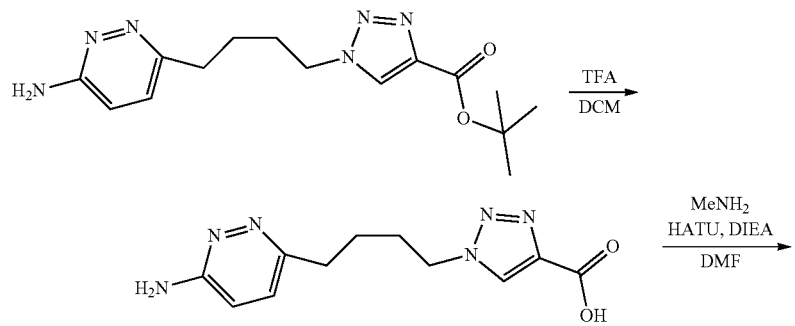

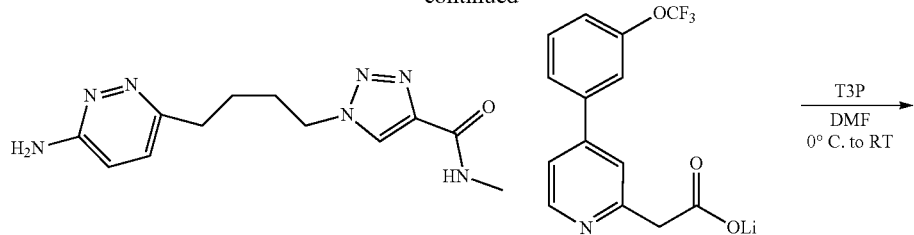

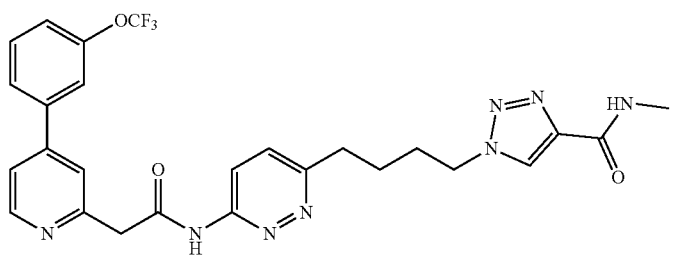

Step 4: 1-(4-(6-aminopyridazin-3-yl)butyl)-1H-1,2,3-triazole-4-carboxylic Acid A mixture of tert-butyl 1-(4-(6-aminopyridazin-3-yl)butyl)-1H-1,2,3-triazole-4-carboxylate (265 mg, 0.832 mmol), TFA (1.0 mL, 13 mmol) and DCM (2.1 mL) was stirred at RT for 1 h, then concentrated under reduced pressure, azeotroping with toluene, to give the title compound as a waxy residue that was immediately used in the next step.

Step 5: 1-(4-(6-aminopyridazin-3-yl)butyl)-N-methyl-1H-1,2,3-triazole-4-carboxamide To a suspension of 1-(4-(6-aminopyridazin-3-yl)butyl)-1H-1,2,3-triazole-4-carboxylic acid (0.832 mmol), methylamine hydrochloride (97 mg, 1.4 mmol) and DIEA (0.499 mL, 2.86 mmol) in DMF (4.8 ml) was added HATU (471 mg, 1.24 mmol) and the resulting mixture was stirred at RT for 1 h. The reaction mixture was concentrated under reduced pressure, and the residue was purified by $SiO_2$ gel chromatography (0% to 30% MeOH in DCM with 1% $NH_4OH$) to give the title compound as a pale yellow solid (66 mg, 29% yield). MS (ES$^+$) $C_{12}H_{17}N_7O$ requires: 275, found: 276 [M+H]$^+$.

Step 6: N-methyl-1-(4-(6-(2-(4-(3-(trifluoromethoxy)phenyl)pyridin-2-yl)acetamido)pyridazin-3-yl)butyl)-1H-1,2,3-triazole-4-carboxamide To a suspension of lithium 2-(4-(3-(trifluoromethoxy)phenyl)pyridin-2-yl)acetate (702 mg, 2.26 mmol) and 1-(4-(6-aminopyridazin-3-yl)butyl)-N-methyl-1H-1,2,3-triazole-4-carboxamide (500 mg, 1.82 mmol) in DMF (6.0 ml) at 0° C. was added T3P® in DMF (50 wt. %, 462 mg, 7.26 mmol) dropwise and the resulting mixture was allowed to warm to RT over 30 min and then stirred for 2 h. The brown mixture was adsorbed onto Celite® and purified by $SiO_2$ gel chromatography (0% to 15% MeOH in DCM with 0.5% $NH_4OH$) to give a tan solid. The solid was then triturated with EtOAc (10 mL) to give the title compound as a light tan solid (361 mg, 34%). MS (ES$^+$) $C_{26}H_{25}F_3N_8O_4$ requires: 554, found: 555 [M+H]$^+$; $^1$H NMR (600 MHz, DMSO-$d_6$) δ 11.31 (s, 1H), 8.61 (d, J=5.1 Hz, 1H), 8.55 (d, J=1.2 Hz, 1H), 8.47-8.37 (m, 1H), 8.22 (d, J=9.1 Hz, 1H), 7.87 (d, J=7.9 Hz, 1H), 7.81 (d, J=10.5 Hz, 2H), 7.72-7.64 (m, 2H), 7.56 (d, J=9.2 Hz, 1H), 7.51 (d, J=8.1 Hz, 1H), 4.45 (t, J=7.0 Hz, 2H), 4.08 (s, 2H), 2.89 (t, J=7.6 Hz, 2H), 2.76 (d, J=4.4 Hz, 3H), 1.96-1.84 (m, 2H), 1.72-1.59 (m, 2H).

Example 211: 1-(2-fluoro-4-(6-(2-(pyridin-2-yl)acetamido)pyridazin-3-yl)butyl)-N-((4-(trifluoromethyl)pyridin-2-yl)methyl)-1H-1,2,3-triazole-4-carboxamide

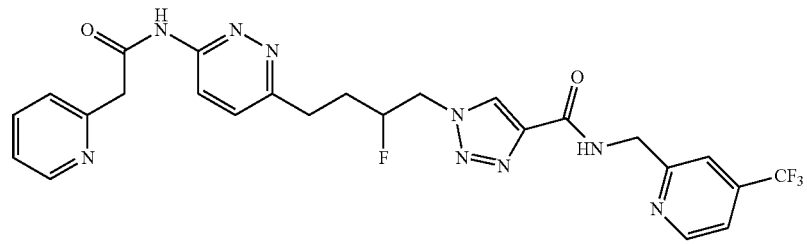 [SMILES: O=C(Cc1ccccn1)Nc1ccc(CCC(F)Cn2cc(C(=O)NCc3cc(C(F)(F)F)ccn3)nn2)nn1]

Steps 1 to 4

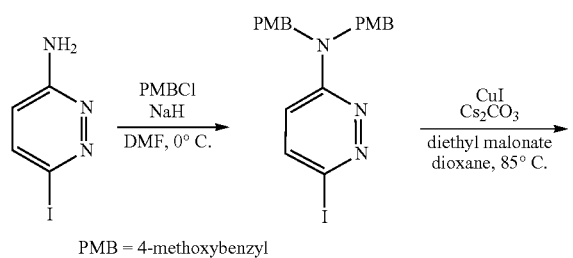

PMB = 4-methoxybenzyl

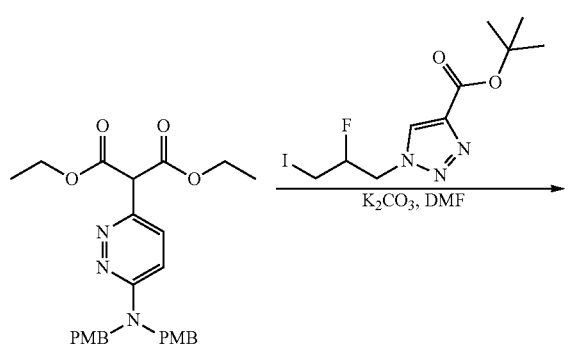

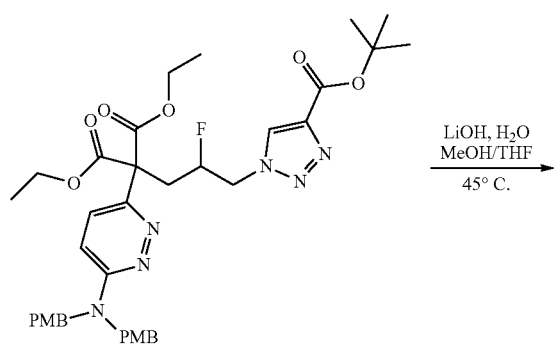

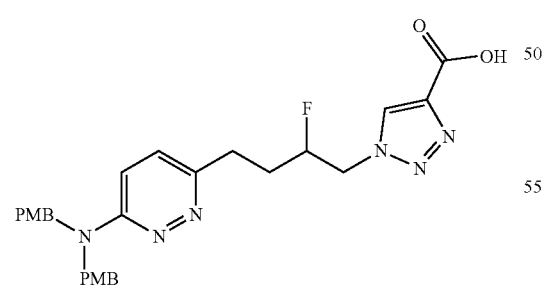

Step 1:
6-iodo-N,N-bis(4-methoxybenzyl)pyridazin-3-amine

To a solution of 6-iodopyridazin-3-amine (1.00 g, 4.52 mmol) in DMF (20 mL) at 0° C. was added sodium hydride (60% in mineral oil, 0.543 g, 13.6 mmol) portionwise. The mixture was stirred for 20 min at RT and then cooled to 0° C. 1-(chloromethyl)-4-methoxybenzene (1.56 g, 9.95 mmol) was then added, then the mixture was stirred at RT for 30 min, quenched with MeOH, concentrated under reduced pressure, diluted with EtOAc, and washed with sat. aq. NaCl. The organic layer was concentrated under reduced pressure, and the residue was purified by SiO$_2$ gel chromatography (0% to 100% EtOAc in hexanes) to give the title compound as a yellow liquid (1.41 g, 68% yield). MS (ES$^+$) $C_{20}H_{20}IN_3O_2$ requires: 461, found: 462 [M+H]$^+$.

Step 2: diethyl 2-(6-(bis(4-methoxybenzyl)amino)
pyridazin-3-yl)malonate

A mixture of copper(I) iodide (0.178 g, 0.932 mmol), picolinic acid (0.230 g, 1.86 mmol), Cs$_2$CO$_3$ (9.11 g, 28.0 mmol), 6-iodo-N,N-bis(4-methoxybenzyl)pyridazin-3-amine (4.30 g, 9.32 mmol) and diethyl malonate (2.99 g, 18.6 mmol) in 1,4-dioxane (40 mL) was evacuated and backfilled with nitrogen three times. The mixture was heated to 85° C. and stirred for 1 h. The mixture was then treated with SiO$_2$ gel (20 g), filtered, and the filtrate was concentrated under reduced pressure. The residue was purified by SiO$_2$ gel chromatography (0% to 75% EtOAc in hexanes) to give the title compound as a brown liquid (3.3 g, 72% yield). MS (ES$^+$) $C_{27}H_{31}N_3O_6$ requires: 493, found: 494 [M+H]$^+$.

Step 3: diethyl 2-(6-(bis(4-methoxybenzyl)amino)
pyridazin-3-yl)-2-(3-(4-(tert-butoxycarbonyl)-1H-1,
2,3-triazol-1-yl)-2-fluoropropyl)malonate A mixture of K$_2$CO$_3$ (428 mg, 3.10 mmol), diethyl 2-(6-(bis(4-methoxybenzyl)amino)pyridazin-3-yl)malonate (1.67 g, 3.38 mmol), and tert-butyl 1-(2-fluoro-3-iodopropyl)-1H-1,2,3-triazole-4-carboxylate (1.00 g, 2.82 mmol) in DMF (10 mL) was stirred at RT for 16 h. The mixture was diluted with water and washed with EtOAc. The organic layer was concentrated under reduced pressure and the residue was purified by SiO$_2$ gel chromatography (0% to 100% EtOAc in hexanes) to give the title compound (1.01 g, 50% yield). MS (ES$^+$) $C_{37}H_{45}FN_6O_8$ requires: 720, found: 721 [M+H]$^+$.

Step 4: 1-(4-(6-(bis(4-methoxybenzyl)amino)
pyridazin-3-yl)-2-fluorobutyl)-1H-1,2,3-triazole-4-
carboxylic Acid A mixture of diethyl 2-(6-(bis(4-methoxybenzyl)amino)pyridazin-3-yl)-2-(3-(4-(tert-butoxycarbonyl)-1H-1,2,3-triazol-1-yl)-2-fluoropropyl)malonate (0.900 g, 1.25 mmol), THF (36 mL), MeOH (12 mL), and water (6 mL) was treated with lithium hydroxide (0.150 g, 6.24 mmol) and stirred at 45° C. for 16 h. The mixture was concentrated under reduced pressure and then 1:1 v:v MeOH/water (20 mL) was added. The pH was adjusted carefully to 4-5 using 1 M aq. HCl, and the mixture was heated up to 90° C. and stirred for 2 h, then concentrated under reduced pressure and treated with 15% MeOH in DCM. The mixture was shaken vigorously, filtered through a Celite®, concentrated under reduced pressure, and dried to give the title compound, which was used without further purification in the following step. MS (ES$^+$) $C_{27}H_{29}FN_6O_4$ requires: 520, found: 521 [M+H]$^+$.

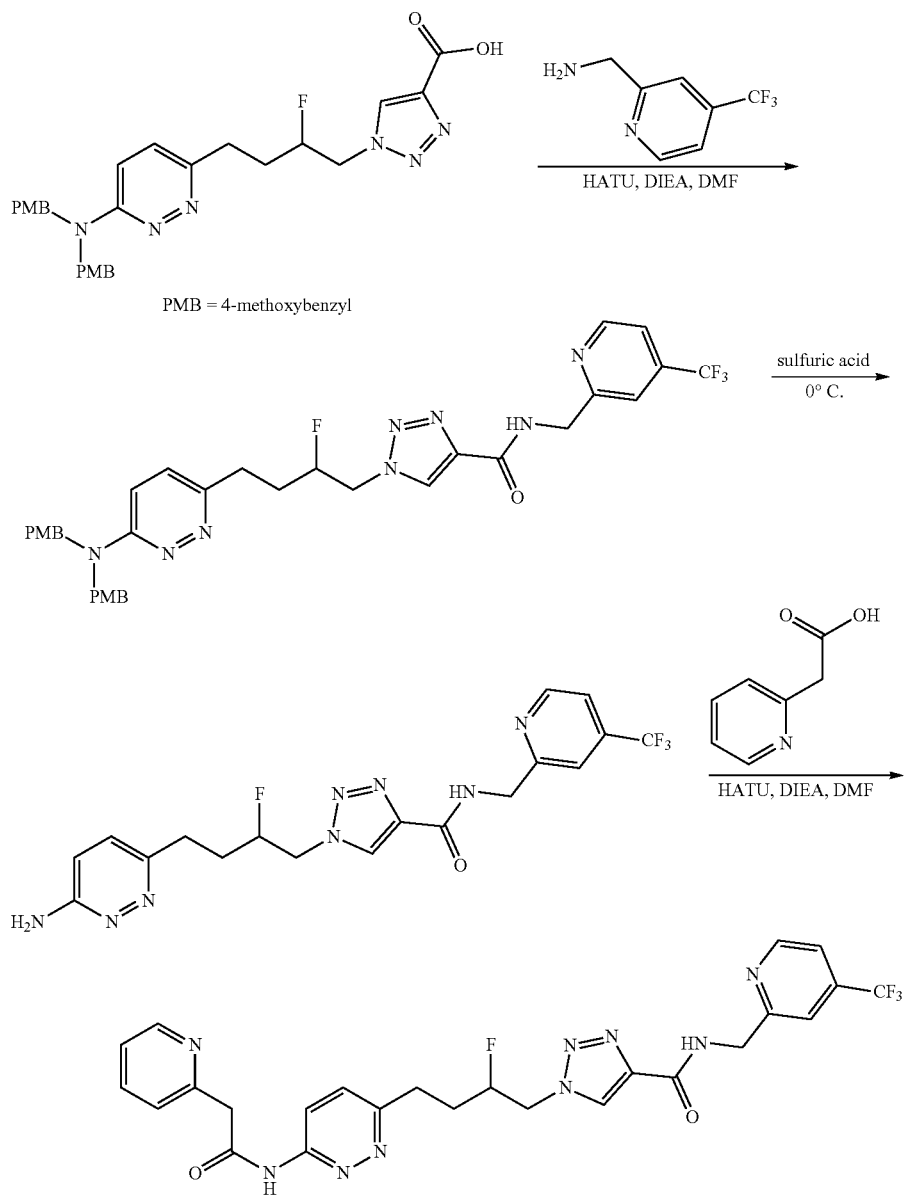

Step 5: 1-(4-(6-(bis(4-methoxybenzyl)amino)pyridazin-3-yl)-2-fluorobutyl)-N-((4-(trifluoromethyl)pyridin-2-yl)methyl)-1H-1,2,3-triazole-4-carboxamide To a solution of 1-(4-(6-(bis(4-methoxybenzyl)amino)pyridazin-3-yl)-2-fluorobutyl)-1H-1,2,3-triazole-4-carboxylic acid (0.36 g, 0.69 mmol) in DMF (0.2 ml) were added HATU (0.315 g, 0.828 mmol), (4-(trifluoromethyl)pyridin-2-yl)methanamine (0.158 g, 0.897 mmol) and DIEA (0.482 ml, 2.76 mmol) and the resulting mixture was stirred at RT for 1 h. The reaction mixture was concentrated under reduced pressure, diluted with water and precipitate was isolated by filtration to give the title compound as a solid, which was used in the following step without further purification. MS (ES$^+$) $C_{34}H_{34}F_4N_8O_3$ requires: 678, found: 679 [M+H]$^+$.

Step 6: 1-(4-(6-aminopyridazin-3-yl)-2-fluorobutyl)-N-((4-(trifluoromethyl)pyridin-2-yl)methyl)-1H-1,2,3-triazole-4-carboxamide To 1-(4-(6-(bis(4-methoxybenzyl)amino)pyridazin-3-yl)-2-fluorobutyl)-N-((4-(trifluoromethyl)pyridin-2-yl)methyl)-1H-1,2,3-triazole-4-carboxamide (0.47 g, 0.69 mmol) at 0° C. was added sulfuric acid (0.736 ml, 13.8 mmol). The mixture was diluted with sat. aq. NaHCO$_3$ and extracted with EtOAc. The organic layer was concentrated under reduced pressure to give the title compound, which was used in the following step without further purification. MS (ES⁺) C$_{18}$H$_{18}$F$_4$N$_8$O requires: 438, found: 439 [M+H]⁺.

Step 7: 1-(2-fluoro-4-(6-(2-(pyridin-2-yl)acetamido) pyridazin-3-yl)butyl)-N-((4-(trifluoromethyl)pyridin-2-yl)methyl)-1H-1,2,3-triazole-4-carboxamide To a solution of 1-(4-(6-aminopyridazin-3-yl)-2-fluorobutyl)-N-((4-(trifluoromethyl)pyridin-2-yl)methyl)-1H-1,2,3-triazole-4-carboxamide (20 mg, 0.046 mmol) in DMF (0.2 ml) were added 2-(pyridin-2-yl)acetic acid hydrochloride (10 mg, 0.059 mmol), HATU (23 mg, 0.059 mmol) and DIEA (0.029 ml, 0.16 mmol). The resulting mixture was stirred at RT for 20 h. The reaction mixture was partitioned between EtOAc and water, and the organic layer was washed with sat. aq. NaCl, dried over Na$_2$SO$_4$, filtered and concentrated under reduced pressure. The resulting bright yellow residue was purified by SiO$_2$ gel chromatography (3% to 5% MeOH in DCM) to give the title compound as an orange solid (12 mg, 47% yield). MS (ES⁺) C$_{25}$H$_{23}$F$_4$N$_9$O$_2$ requires: 557, found: 558 [M+H]⁺. ¹H NMR (MeOH-d$_4$) δ 8.80 (d, J=5.4 Hz, 1H), 8.76 (d, J=5.3 Hz, 1H), 8.76 (dt, J=1.8, 8.5 Hz, 1H), 8.41 (s, 1H), 8.37 (d, J=9.4 Hz, 1H), 7.96 (d, J=7.6 Hz, 1H), 7.90 (m, 1H), 7.67 (s, 1H), 7.65 (d, J=9.4 Hz, 1H), 7.58 (d, J=5.4 Hz, 1H), 5.01 (m, 1H), 4.78 (s, 2H), 4.77 (m, 2H), 3.14 (m, 2H), 2.18 (m, 2H).

Example 259: 1-(2-fluoro-4-(6-(2-(pyridin-2-yl) acetamido)pyridazin-3-yl)butyl)-N-((4-(trifluoromethyl)pyridin-2-yl)methyl)-1H-1,2,3-triazole-4-carboxamide

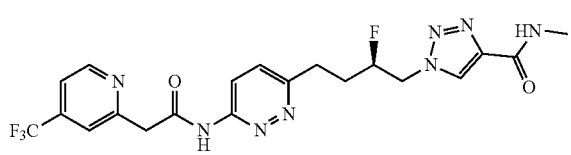 [SMILES: CNC(=O)c1cn(C[C@H](F)CCc2ccc(NC(=O)Cc3cc(C(F)(F)F)ccn3)nn2)nn1]

Steps 1 to 6

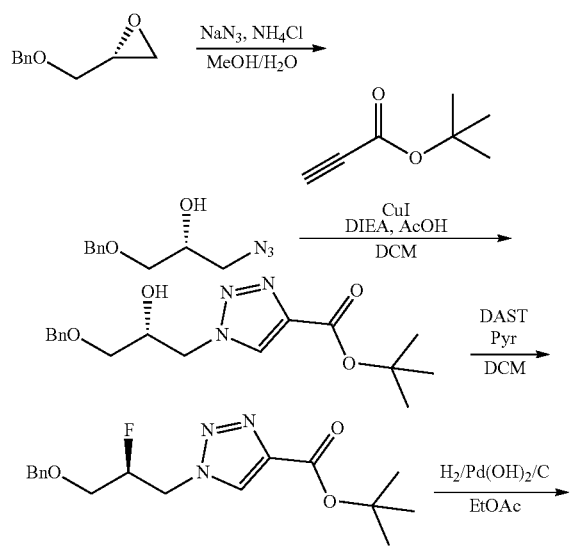

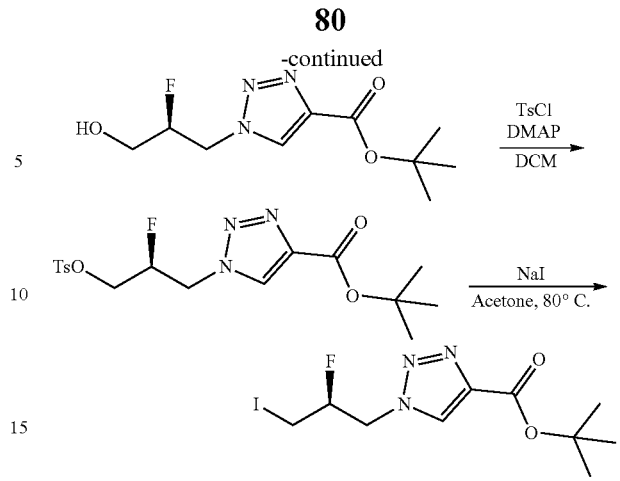

Step 1: (R)-1-azido-3-(benzyloxy)propan-2-ol

To a solution of (R)-2-((benzyloxy)methyl)oxirane (2.42 ml, 15.9 mmol) and NH$_4$Cl (1.7 g, 32 mmol) in MeOH (39.5 ml) and water (5.9 ml) was added NaN$_3$ (5.2 g, 79 mmol) and the resulting mixture was stirred at RT for 16 h. The volatiles were removed under reduced pressure and the residue was partitioned between EtOAc (50 mL) and water (60 mL). The two layers were separated and the aqueous layer was extracted with EtOAc (3×50 mL). The organic layers were combined, dried over MgSO$_4$, filtered, and concentrated under reduced pressure to give the title compound as a colorless oil (3.01 g, 91% yield). MS (ES⁺) C$_{10}$H$_{13}$N$_3$O$_2$ requires: 207, found: 208 [M+H]⁺.

Step 2: (R)-tert-butyl 1-(3-(benzyloxy)-2-hydroxypropyl)-1H-1,2,3-triazole-4-carboxylate To a solution of (R)-1-azido-3-(benzyloxy)propan-2-ol (3.01 g, 14.5 mmol), tert-butyl propiolate (2.33 ml, 17.4 mmol), DIEA (0.253 ml, 1.45 mmol), and AcOH (0.083 ml, 1.4 mmol) in DCM (58.1 ml) was added copper(I) iodide (0.138 g, 0.726 mmol) and the resulting mixture was stirred at RT for 16 h. Silica gel (10 g) was added to the stirring mixture and the resulting suspension was filtered and washed with DCM (20 mL) and EtOAc (20 mL). The filtrate was concentrated under reduced pressure to give the crude title compound as an orange oil, which was used without further purification (3.95 g, 82% yield). MS (ES⁺) C$_{17}$H$_{23}$N$_3$O$_4$ requires: 333, found: 334 [M+H]⁺.

Step 3: (S)-tert-butyl 1-(3-(benzyloxy)-2-fluoropropyl)-1H-1,2,3-triazole-4-carboxylate To a solution of (R)-tert-butyl 1-(3-(benzyloxy)-2-hydroxypropyl)-1H-1,2,3-triazole-4-carboxylate (3.95 g, 11.8 mmol) and pyridine (1.909 ml, 23.70 mmol) in DCM (23.7 ml) at 0° C. was added DAST (3.13 ml, 23.7 mmol). The resulting mixture was stirred at RT for 2.5 h, then filtered through a plug of silica gel, rinsing with DCM (50 mL). The filtrate was concentrated under reduced pressure and the residue was adsorbed onto Celite® and purified by SiO$_2$ gel chromatography (0% to 50% EtOAc in hexanes) to give the title compound as a tan solid (1.78 g, 45% yield). MS (ES⁺) C$_{17}$H$_{22}$FN$_3$O$_3$ requires: 335, found: 336 [M+H]⁺.

Step 4: (S)-tert-butyl 1-(2-fluoro-3-hydroxypropyl)-1H-1,2,3-triazole-4-carboxylate A reaction vessel was charged with (S)-tert-butyl 1-(3-(benzyloxy)-2-fluoropropyl)-1H-1,2,3-triazole-4-carboxylate (1.78 g, 5.31 mmol) and EtOAc (53.1 ml) under an atmosphere of $N_2$. The solution was degassed by bubbling through $N_2$ for 10 min and then with $N_2$ still flowing, palladium hydroxide on carbon (0.746 g, 1.06 mmol) was added. The resulting suspension was purged with $H_2$ for 2 min then stirred under an atmosphere of $H_2$ at 1 atm for 12 h. The reaction mixture was purged with $N_2$, filtered through a Celite® and concentrated under reduced pressure to give the crude title compound as a pale yellow solid (1.32 g, 101% yield). MS (ES$^+$) $C_{10}H_{16}FN_3O_3$ requires: 245, found: 246 [M+H]$^+$.

Step 5: (S)-tert-butyl 1-(2-fluoro-3-(tosyloxy)propyl)-1H-1,2,3-triazole-4-carboxylate To a solution of (S)-tert-butyl 1-(2-fluoro-3-hydroxypropyl)-1H-1,2,3-triazole-4-carboxylate (1.32 g, 5.38 mmol) and DMAP (0.986 g, 8.07 mmol) in DCM (26.9 ml) was added 4-toluenesulfonyl chloride (1.23 g, 6.46 mmol) while maintaining the temperature at RT by a water bath, and the resulting mixture was stirred at RT for 1.5 h. The mixture was diluted with EtOAc (100 mL) and washed with sat. aq. NH$_4$Cl (2×40 mL). The organic layer was dried over MgSO$_4$, filtered, and concentrated under reduced pressure to give crude title compound, which was used without further purification (1.80 g, 84% yield). MS (ES$^+$) $C_{17}H_{22}FN_3O_5S$ requires: 399, found: 400 [M+H]$^+$.

Step 6: (S)-tert-butyl 1-(2-fluoro-3-iodopropyl)-1H-1,2,3-triazole-4-carboxylate To a solution of (S)-tert-butyl 1-(2-fluoro-3-(tosyloxy) propyl)-1H-1,2,3-triazole-4-carboxylate (2.12 g, 5.31 mmol) in acetone (26.5 ml) was added NaI (0.796 g, 5.31 mmol) and the resulting mixture was stirred at 80° C. for 3 h, then at RT for 16 h. Additional NaI (2 eq., 1.6 g) was added and the mixture as stirred at 90° C. for 2 h. The reaction was allowed to cool to RT, diluted with 50:50 v:v EtOAc/Hexanes (150 mL) and washed with water (2×50 mL) and sat. aq. NaCl (50 mL). The organic layer was dried over MgSO$_4$, filtered, and concentrated under reduced pressure. The residue was purified by SiO$_2$ gel chromatography (0% to 50% EtOAc in hexanes) to give the title compound as a white solid (1.71 g, 91% yield). MS (ES$^+$) $C_{10}H_{15}FIN_3O_2$ requires: 355, found: 356 [M+H]$^+$.

Steps 7 to 9

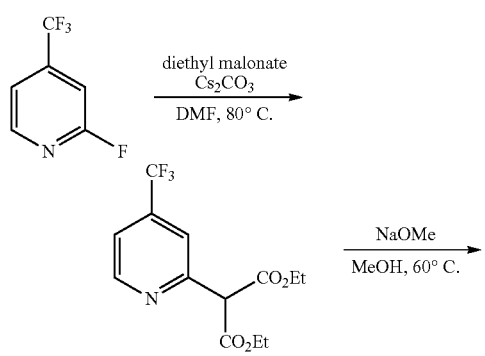

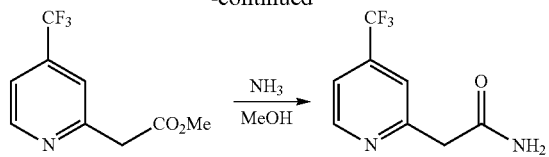

Step 7: diethyl 2-(4-(trifluoromethyl)pyridin-2-yl)malonate

To a suspension of Cs$_2$CO$_3$ (90.8 g, 279 mmol) in DMSO (200 ml) were added 2-fluoro-4-(trifluoromethyl)pyridine (25 g, 150 mmol) and diethyl malonate (46 ml, 300 mmol). The resulting mixture was stirred at 80° C. for 21 h. The resulting bright yellow reaction mixture was allowed to cool to RT, the solution was decanted and the solids were filtered and washed with DCM (using a total of 300-400 mL). The combined organic layers were washed with water (2×400 mL), dried over Na$_2$SO$_4$, filtered and concentrated under reduced pressure. The residue was purified by SiO$_2$ gel chromatography (0% to 10% EtOAc in hexanes) to give the title compound as a bright yellow liquid (32.3 g, 70% yield). MS (ES$^+$) $C_{13}H_{14}F_3NO_4$ requires: 305, found 306 [M+H]$^+$.

Step 8: methyl 2-(4-(trifluoromethyl)pyridin-2-yl)acetate

To a solution of diethyl 2-(4-(trifluoromethyl)pyridin-2-yl)malonate (11.9 g, 39.0 mmol) in MeOH (100 ml) were added sodium methoxide in MeOH (25 wt. %, 10.0 ml, 43.7 mmol) and the resulting mixture was stirred at 60° C. for 4 h. The reaction mixture was concentrated under reduced pressure, and poured onto a slurry of ice. The mixture was neutralized with aq. HCl (1 M, 45 mL, 45 mmol), extracted with EtOAc (200 mL), and the organic layer was dried over Na$_2$SO$_4$, filtered and concentrated under reduced pressure to give a crude dark-yellow liquid. The residue was purified by SiO$_2$ gel chromatography (10% to 20% EtOAc in hexanes) to give the title compound as a pale yellow liquid (5.66 g, 66% yield). MS(ES$^+$) $C_9H_8F_3NO_2$ requires: 219, found 220 [M+H]$^+$.

Step 9: 2-(4-(trifluoromethyl)pyridin-2-yl)acetamide

To a solution of methyl 2-(4-(trifluoromethyl)pyridin-2-yl)acetate (6.04 g, 27.6 mmol) in MeOH (10 ml) was added ammonia (7 M in MeOH, 40 ml, 280 mmol). The reaction mixture was stirred at RT for 21 h, then concentrated under reduced pressure. The residue was taken up in hexanes/EtOAc and filtered. The collected solids were dried to give a crop of product as a white powder and the remaining filtrate was concentrated under reduced pressure to give another crop of product as a pale-yellow solid. The combined product was used without further purification (5.40 g, 96% yield). MS(ES$^+$) $C_8H_7F_3N_2O$ requires: 204, found 205 [M+H]$^+$.

Steps 10 to 13

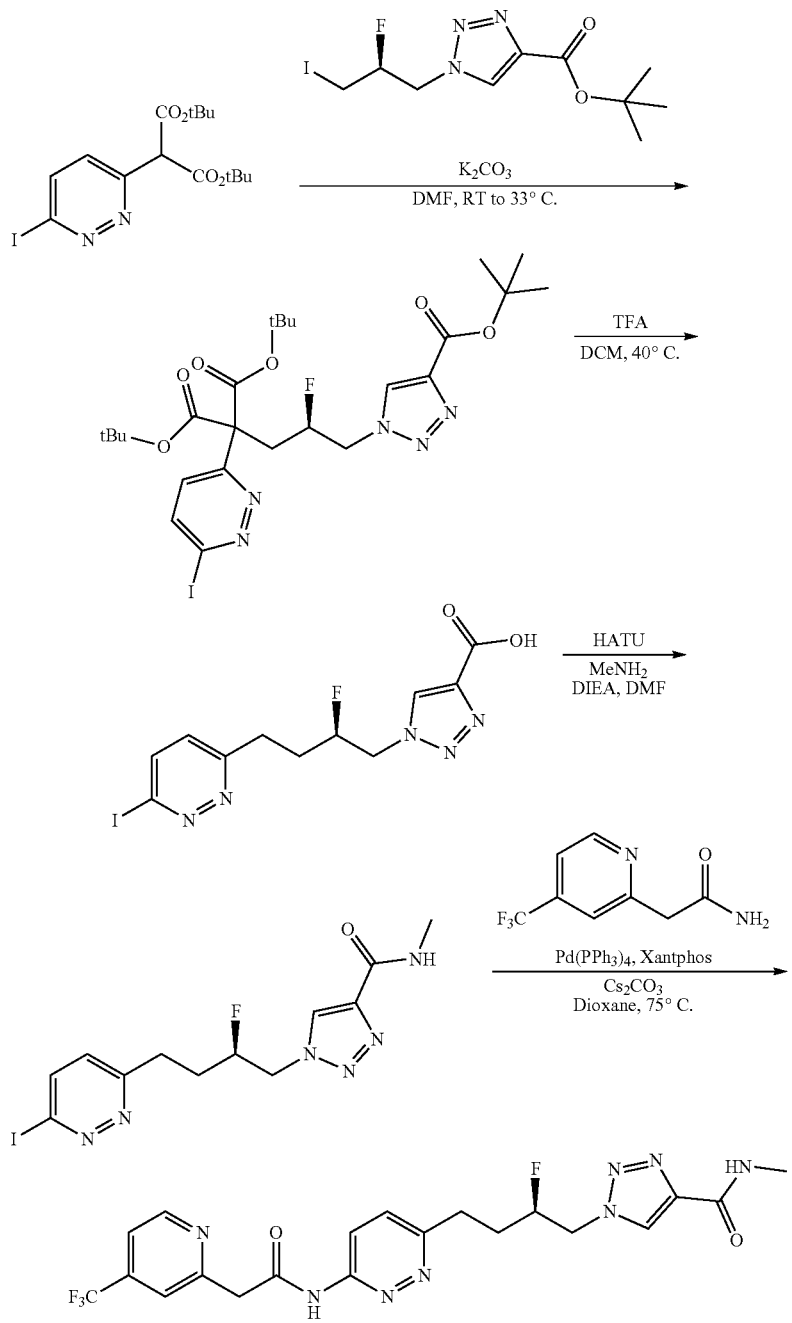

Step 10: (R)-di-tert-butyl 2-(3-(4-(tert-butoxycarbonyl)-1H-1,2,3-triazol-1-yl)-2-fluoropropyl)-2-(6-iodopyridazin-3-yl)malonate A mixture of K$_2$CO$_3$ (257 mg, 1.86 mmol), di-tert-butyl 2-(6-iodopyridazin-3-yl)malonate (781 mg, 1.86 mmol), and (S)-tert-butyl 1-(2-fluoro-3-iodopropyl)-1H-1,2,3-triazole-4-carboxylate (600 mg, 1.69 mmol) was evacuated and backfilled with N$_2$, and then DMF (5.6 mL) was added. The mixture was evacuated and backfilled with N$_2$ three times, then stirred for 24 h at RT and another 24 h at 33° C. The mixture was diluted with 1:1 v:v EtOAc/hexanes (30 mL) and washed twice with water (30 mL then 15 mL). The combined aqueous layers were extracted with 1:1 v:v EtOAc/hexanes (15 mL). The combined organic layers were concentrated under reduced pressure to give crude title compound as a foamy solid, which was used without further purification. MS (ES$^+$) C$_{25}$H$_{35}$FIN$_5$O$_6$ requires: 647, found: 648 [M+H]$^+$.

Step 11: (R)-1-(2-fluoro-4-(6-iodopyridazin-3-yl)butyl)-1H-1,2,3-triazole-4-carboxylic Acid To a solution of (R)-di-tert-butyl 2-(3-(4-(tert-butoxycarbonyl)-1H-1,2,3-triazol-1-yl)-2-fluoropropyl)-2-(6-iodopyridazin-3-yl)malonate (1.09 g, 1.69 mmol) in DCM (14.1 ml) was added TFA (14.1 ml), and the mixture was stirred at 40° C. for 1 h. The mixture was concentrated under reduced pressure to give an oily mixture, which was treated with THF (10 mL) and then concentrated under reduced pressure to give the crude title compound as a solid, which was used in the following step without further purification. MS (ES+) $C_{11}H_{11}FIN_5O_2$ requires: 391, found: 392 [M+H]+.

Step 12: ((R)-1-(2-fluoro-4-(6-iodopyridazin-3-yl)butyl)-N-methyl-1H-1,2,3-triazole-4-carboxamide A mixture of (R)-1-(2-fluoro-4-(6-iodopyridazin-3-yl)butyl)-1H-1,2,3-triazole-4-carboxylic acid (661 mg, 1.69 mmol) and HATU (861 mg, 2.26 mmol) in DMF (8.4 mL) was treated with DIEA (1.475 mL, 8.468 mmol). The mixture was stirred for 20 min and then methylamine in THF (2.0 M, 1.689 mL, 3.378 mmol) was added. The reaction was vigorously stirred for 40 min (precipitate forms over time), diluted with water (5 mL), and then concentrated under reduced pressure to give a solid, which was triturated in water. Precipitate was isolated by filtration, washed with water then EtOAc, and dried to give the crude title compound, which was used in the following step without further purification (380 mg, 56% yield). MS (ES+) $C_{12}H_{14}FIN_6O$ requires: 404, found: 405 [M+H]+.

Step 13: (R)-1-(2-fluoro-4-(6-(2-(4-(trifluoromethyl)pyridin-2-yl)acetamido)pyridazin-3-yl)butyl)-N-methyl-1H-1,2,3-triazole-4-carboxamide A mixture of Pd(PPh3)4 (11.4 mg, 9.90 μmol), Xantphos (11.4 mg, 0.020 mmol), Cs2CO3 (64.5 mg, 0.198 mmol), 2-(4-(trifluoromethyl)pyridin-2-yl)acetamide (20 mg, 0.099 mmol), and (R)-1-(2-fluoro-4-(6-iodopyridazin-3-yl)butyl)-N-methyl-1H-1,2,3-triazole-4-carboxamide (40 mg, 0.099 mmol) in 1,4-dioxane (1 mL) was evacuated and back-filled with N2 three times. The mixture was stirred at 75° C. for 2.5 h. The reaction mixture was directly loaded onto silica gel and purified by SiO2 gel chromatography (0% to 25% DCM in MeOH) to give impure title compound as a brown solid. Further purification by reverse phase preparative HPLC (Mobile phase: A=0.1% TFA/H2O, B=0.1% TFA/MeCN; Gradient: B=20-50%; 12 min; Column: C18) gave the title compound as an off-white solid (27 mg, 57% yield). MS (ES+) $C_{20}H_{20}F_4N_8O_2$ requires: 480, found: 481 [M+H]+. 1H NMR (DMSO-d6) δ 11.38 (s, 1H), 8.80 (d, J=5.2 Hz, 1H), 8.51 (s, 1H), 8.46 (q, J=4.6, Hz, 1H), 8.21 (d, J=9.2 Hz, 1H), 7.81 (s, 1H), 7.67 (d, J=4.6 Hz, 1H), 7.61 (d, J=9.3 Hz, 1H), 5.03 (m, 1H), 4.77 (m, 2H), 4.17 (s, 2H), 3.05 (m, 2H), 2.75 (d, J=5.7 Hz, 3H), 2.08 (m, 2H). The title compound (1 mg/mL, 10 μL per injection) was analyzed on a Shimadzu Prominence HPLC system with a Lux Cellulose 4 column (4.6×150 millimeter, 5 micrometer, 1 mL/min) using a mobile phase of water:acetonitrile (40:60), and showed an ee of >98%.

Example 272: (R)-1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide

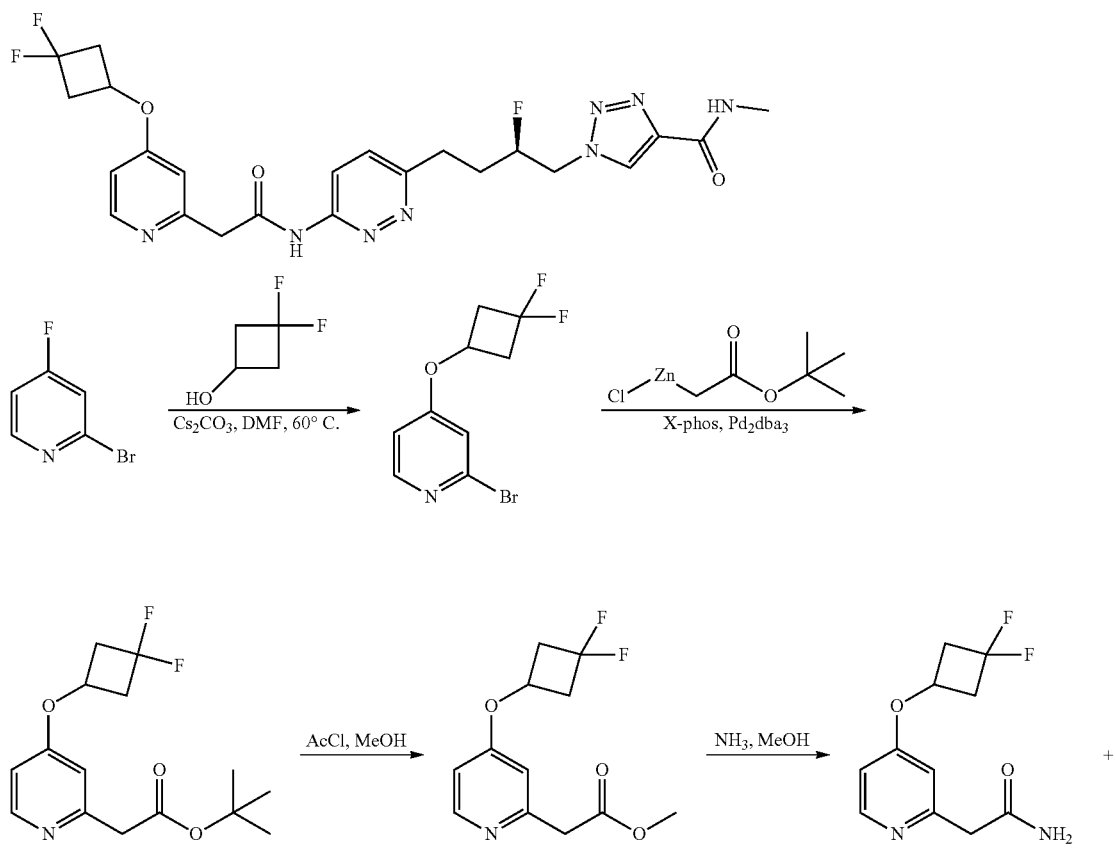

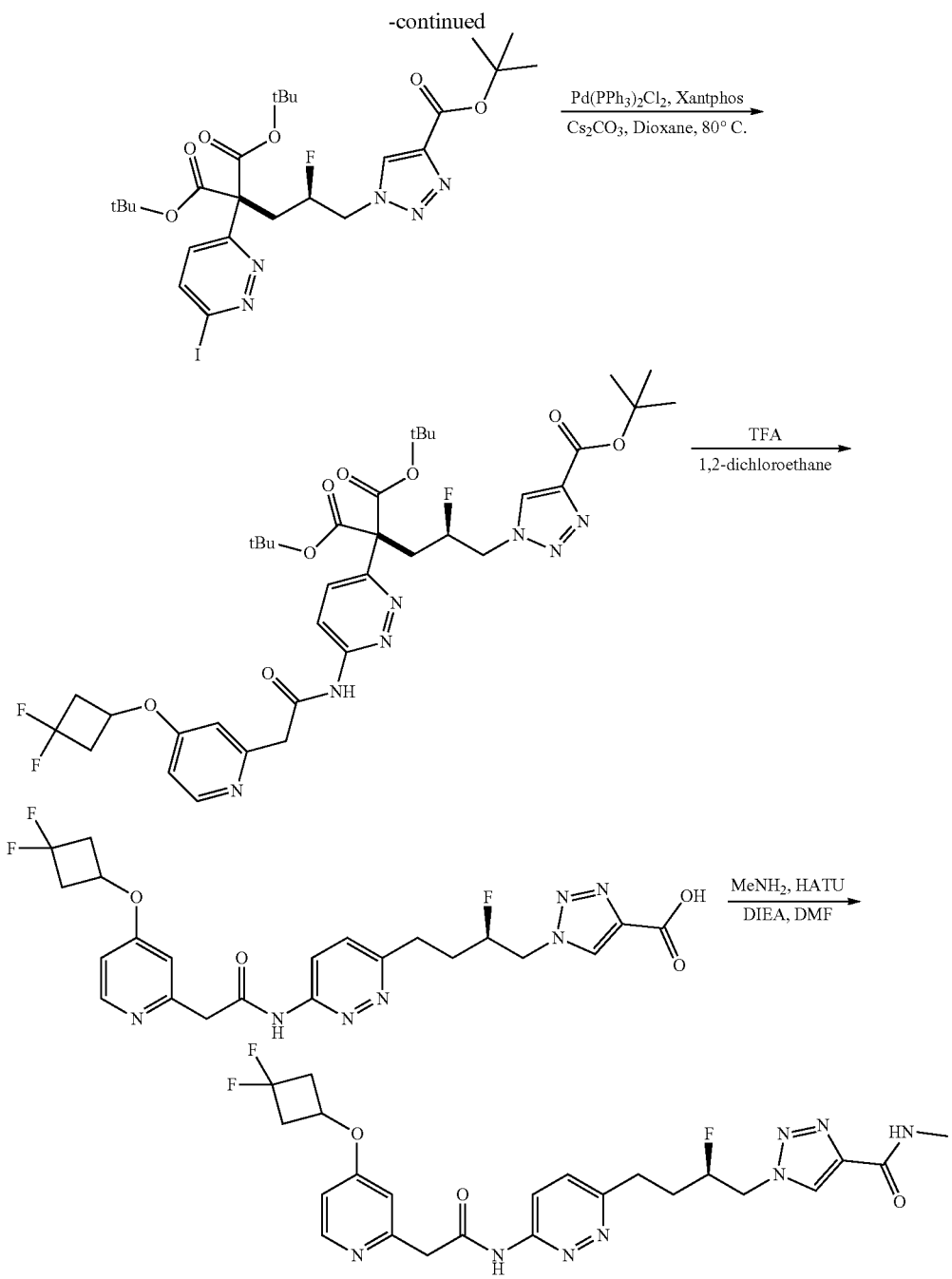

Step 1:
2-bromo-4-(3,3-difluorocyclobutoxy)pyridine

To a solution of 2-bromo-4-fluoropyridine (5.0 g, 28 mmol) in DMF (100 ml) were added 3,3-difluorocyclobutanol (3.07 g, 28.4 mmol) and $Cs_2CO_3$ (18.5 g, 56.8 mmol) and the resulting mixture was stirred at 60° C. for 2 h. The volatiles were removed under reduced pressure. DCM was added and the suspension was filtered. The filtrate was concentrated under reduced pressure. The residue was purified by $SiO_2$ gel chromatography (0% to 30% EtOAc in hexanes) to give the title compound as a pale yellow liquid (2.7 g, 36% yield). MS (ES$^+$) $C_9H_8ClF_2NO$ requires: 263, found: 264 [M+H]$^+$.

Step 2: tert-butyl 2-(4-(3,3-difluorocyclobutoxy)pyridin-2-yl)acetate

A degassed solution of 2-bromo-4-(3,3-difluorocyclobutoxy)pyridine (2.7 g, 10 mmol), (2-(tert-butoxy)-2-oxoethyl)zinc(II) chloride in $Et_2O$ (0.5 M, 40.9 ml, 20.4 mmol), $Pd_2(dba)_3$ (0.468 g, 0.511 mmol) and X-Phos (0.244 g, 0.511 mmol) in THF (30 ml) was stirred at 65° C. for 1 h. The mixture was concentrated under reduced pressure, and sat. aq. $NH_4Cl$ (30 mL) was added. The aqueous phase was extracted with EtOAc (3×20 mL), and the combined organic layers were washed with sat. aq. NaCl, dried over $MgSO_4$, filtered and concentrated under reduced pressure. The residue was purified by $SiO_2$ gel chromatography (0% to 60%

EtOAc in hexanes) to give the title compound as a pale yellow liquid (2.5 g, 82% yield). MS (ES+) C$_{15}$H$_{19}$F$_2$NO$_3$ requires: 299, found: 244 [M−(t−Bu)+2H]+.

Step 3: methyl 2-(4-(3,3-difluorocyclobutoxy)pyridin-2-yl)acetate

To a solution of tert-butyl 2-(4-(3,3-difluorocyclobutoxy)pyridin-2-yl)acetate (2.5 g, 8.4 mmol) in MeOH (50 ml) were added dropwise acetyl chloride (5.9 ml, 84 mmol) and the resulting mixture was stirred at 60° C. for 4 h then concentrated under reduced pressure. The reaction mixture was partitioned between EtOAc (100 mL) and sat. aq. NaHCO$_3$ (100 mL). The aqueous layer was extracted with EtOAc (3×50 mL), and the combined organic layers were washed with sat. aq. NaCl, dried over MgSO$_4$, filtered and concentrated under reduced pressure to give the title compound as a yellow liquid, which was used without further purification (2.1 g, 98% yield). MS (ES+) C$_{12}$H$_{13}$F$_2$NO$_3$ requires: 257, found: 258 [M+H]+.

Step 4: 2-(4-(3,3-difluorocyclobutoxy)pyridin-2-yl)acetamide

A mixture of methyl 2-(4-(3,3-difluorocyclobutoxy)pyridin-2-yl)acetate (2.1 g, 8.2 mmol) and ammonia in MeOH (7 M, 23.3 ml, 163 mmol) was stirred at 80° C. for 16 h in a pressure vessel, allowed to cool to RT, then concentrated under reduced pressure. The residue was triturated with Et$_2$O to give the title compound as a pale yellow solid (1.9 g, 96% yield). MS (ES+) C$_{11}$H$_{12}$F$_2$N$_2$O$_2$ requires: 242, found: 243 [M+H]+.

Step 5: (R)-di-tert-butyl 2-(3-(4-(tert-butoxycarbonyl)-1H-1,2,3-triazol-1-yl)-2-fluoropropyl)-2-(6-(2-(4-(3,3-difluorocyclobutoxy)pyridin-2-yl)acetamido)pyridazin-3-yl)malonate A degassed solution of 2-(4-(3,3-difluorocyclobutoxy)pyridin-2-yl)acetamide (1.12 g, 4.63 mmol), (R)-di-tert-butyl 2-(3-(4-(tert-butoxycarbonyl)-1H-1,2,3-triazol-1-yl)-2-fluoropropyl)-2-(6-iodopyridazin-3-yl)malonate (3.0 g, 4.6 mmol), bis(triphenylphosphine)palladium(II) dichloride (0.65 g, 0.93 mmol), Xantphos (1.072 g, 1.853 mmol) and Cs$_2$CO$_3$ (3.02 g, 9.27 mmol) in 1,4-dioxane (30 ml) was stirred at 80° C. for 16 h. The mixture was concentrated under reduced pressure, and the residue was purified by SiO$_2$ gel chromatography (0% to 4% MeOH in DCM) to give the title compound as a yellow solid (1.21 g, 34% yield). MS (ES+) C$_{36}$H$_{46}$F$_3$N$_7$O$_8$ requires: 761, found: 762 [M+H]+.

Step 6: (R)-1-(4-(6-(2-(4-(3,3-difluorocyclobutoxy)pyridin-2-yl)acetamido)pyridazin-3-yl)-2-fluorobutyl)-1H-1,2,3-triazole-4-carboxylic acid A solution of (R)-di-tert-butyl 2-(3-(4-(tert-butoxycarbonyl)-1H-1,2,3-triazol-1-yl)-2-fluoropropyl)-2-(6-(2-(4-(3,3-difluorocyclobutoxy)pyridin-2-yl)acetamido)pyridazin-3-yl)malonate (1.15 g, 1.51 mmol) in TFA (5 ml) and 1,2-dichloroethane (5 ml) was stirred at 70° C. for 16 h. The mixture was concentrated under reduced pressure, and the residue was diluted with ACN (20 ml) and TEA (1 ml) was added. The resulting precipitate was isolated by filtration and washed with ACN to give the title compound as a pale yellow solid (455 mg, 60% yield). MS (ES+) C$_{22}$H$_{22}$F$_3$N$_7$O$_4$ requires: 505, found: 506 [M+H]+.

Step 7: (R)-1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide To a solution of (R)-1-(4-(6-(2-(4-(3,3-difluorocyclobutoxy)pyridin-2-yl)acetamido)pyridazin-3-yl)-2-fluorobutyl)-1H-1,2,3-triazole-4-carboxylic acid (410 mg, 0.811 mmol) in DMF (4 ml) were added HATU (339 mg, 0.892 mmol), DIEA (0.425 ml, 2.433 mmol) and methylamine in THF (2.0 M, 0.608 ml, 1.22 mmol) and the resulting mixture was stirred at 20° C. for 0.5 h then concentrated under reduced pressure. Water was added and resulting precipitate was isolated by filtration to give the title compound as a yellow solid (395 mg, 94% yield). MS (ES+) C$_{23}$H$_{25}$F$_3$N$_8$O$_3$ requires: 518, found: 519 [M+H]+. $^1$H NMR (DMSO-d$_6$) δ 11.29 (s, 1H), 8.52 (s, 1H), 8.47 (m, 1H), 8.36 (m, 1H), 8.22 (d, J=9.1 Hz, 1H), 7.60 (d, J=9.2 Hz, 1H), 7.00 (m, 1H), 6.87 (m, 1H), 5.03 (m, 1H), 4.90-4.70 (m, 3H), 3.94 (s, 2H), 3.28-3.22 (m, 2H), 3.08-2.98 (m, 2H), 2.79-2.70 (m, 5H), 2.20-1.95 (m, 2H).

Example 255: (R)-1-(2-fluoro-4-(6-(2-(4-(3-(trifluoromethoxy)phenyl)pyridin-2-yl)acetamido)pyridazin-3-yl)butyl)-N-methyl-1H-1,2,3-triazole-4-carboxamide

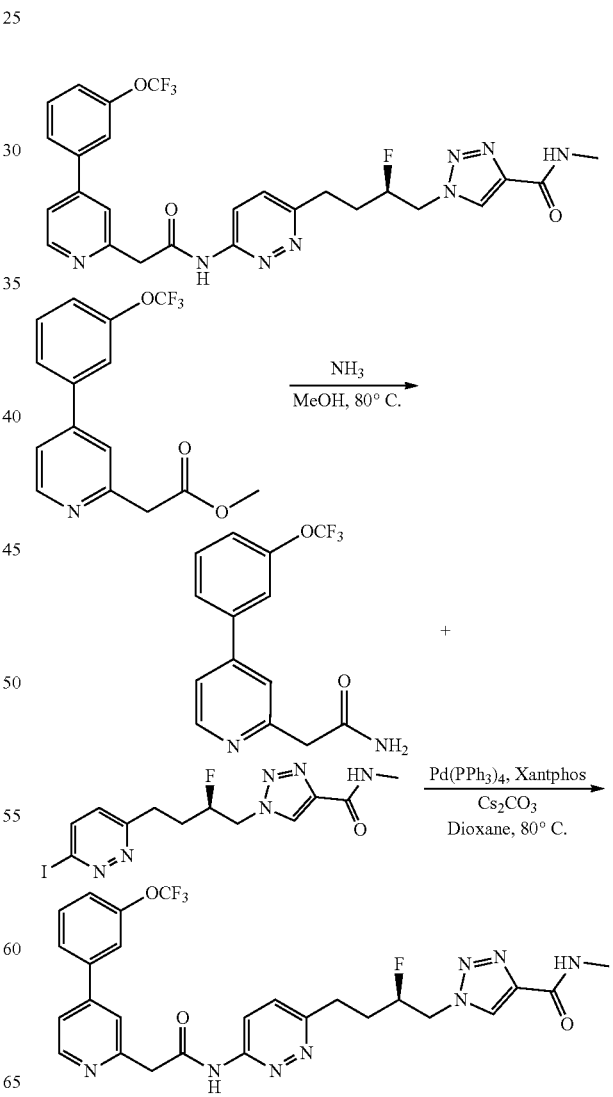

Step 1: 2-(4-(3-(trifluoromethoxy)phenyl)pyridin-2-yl)acetamide

A sealed tube was charged with methyl 2-(4-(3-(trifluoromethoxy)phenyl)pyridin-2-yl)acetate (1.0 g, 3.2 mmol) and ammonia in MeOH (7 M, 11 ml, 77 mmol). The solution was sealed and heated at 80° C. for 24 h, then allowed to cool to RT and concentrated under reduced pressure. The residue was purified by $SiO_2$ gel chromatography (0% to 15% MeOH in DCM with 1% $NH_4OH$) to give the title compound as an off-white solid (0.92 g, 97% yield). MS ($ES^+$) $C_{14}H_{11}F_3N_2O_2$ requires: 296, found: 297 $[M+H]^+$; $^1H$ NMR (600 MHz, DMSO-$d_6$) δ 8.57 (d, J=5.2 Hz, 1H), 7.84 (d, J=7.8 Hz, 1H), 7.77 (s, 1H), 7.71 (d, J=1.8 Hz, 1H), 7.68 (t, J=8.0 Hz, 1H), 7.63 (dd, J=5.3, 1.8 Hz, 1H), 7.56-7.46 (m, 2H), 6.98 (s, 1H), 3.66 (s, 2H).

Step 2: (R)-1-(2-fluoro-4-(6-(2-(4-(3-(trifluoromethoxy)phenyl)pyridin-2-yl)acetamido)pyridazin-3-yl)butyl)-N-methyl-1H-1,2,3-triazole-4-carboxamide A vial was charged with 2-(4-(3-(trifluoromethoxy)phenyl)pyridin-2-yl)acetamide (0.366 g, 1.24 mmol), (R)-1-(2-fluoro-4-(6-iodopyridazin-3-yl)butyl)-N-methyl-1H-1,2,3-triazole-4-carboxamide (0.50 g, 1.2 mmol), $Cs_2CO_3$ (0.806 g, 2.47 mmol), $Pd(PPh_3)_4$ (0.143 g, 0.124 mmol), Xantphos (0.143 g, 0.247 mmol), and 1,4-dioxane (12.4 mL). The mixture was degassed by bubbling $N_2$ through the suspension for 5 min. The mixture was heated at 80° C. for 8 h, then allowed to cool to RT, adsorbed onto Celite® and purified by $SiO_2$ gel chromatography (0% to 15% MeOH in DCM with 0.5% $NH_4OH$) to give a yellow solid (550 mg). The solid was triturated with 2:1 v:v EtOAc/Hexanes (2×10 mL) to give the title compound as an off-white solid (379 mg, 51% yield). MS ($ES^+$) $C_{26}H_{24}F_4N_8O_3$ requires: 572, found: 573 $[M+H]^+$; $^1H$ NMR (600 MHz, DMSO-$d_6$) δ 11.33 (s, 1H), 8.60 (d, J=5.2 Hz, 1H), 8.52 (s, 1H), 8.46 (m, 1H), 8.23 (d, J=9.2 Hz, 1H), 7.86 (dd, J=7.7, 1.5 Hz, 1H), 7.83-7.78 (m, 2H), 7.70-7.66 (m, 2H), 7.61 (d, J=9.2 Hz, 1H), 7.50 (m, 1H), 5.03 (dddd, J=49.4, 11.4, 7.4, 3.3 Hz, 1H), 4.86-4.67 (m, 2H), 4.08 (s, 2H), 3.09-2.96 (m, 2H), 2.76 (d, J=4.7 Hz, 3H), 2.21-1.93 (m, 2H). The title compound (1 mg/mL, 10 µL per injection) was analyzed on a Shimadzu Prominence HPLC system with a Lux Cellulose 4 column (4.6×150 millimeter, 5 micrometer, 1 mL/min) using a mobile phase of water:acetonitrile (20:80), and showed an ee of >98%.

Example 270: (R)-1-(2-fluoro-4-(6-(2-(1-(3-(trifluoromethoxy)phenyl)-1H-imidazol-4-yl)acetamido)pyridazin-3-yl)butyl)-N-methyl-1H-1,2,3-triazole-4-carboxamide

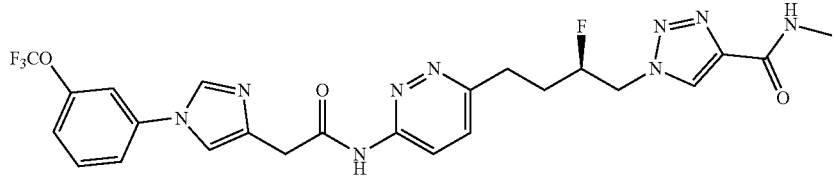 [SMILES: CNC(=O)c1cn(C[C@H](F)CCc2ccc(NC(=O)Cc3cn(-c4cccc(OC(F)(F)F)c4)cn3)nn2)nn1]

Steps 1 to 5

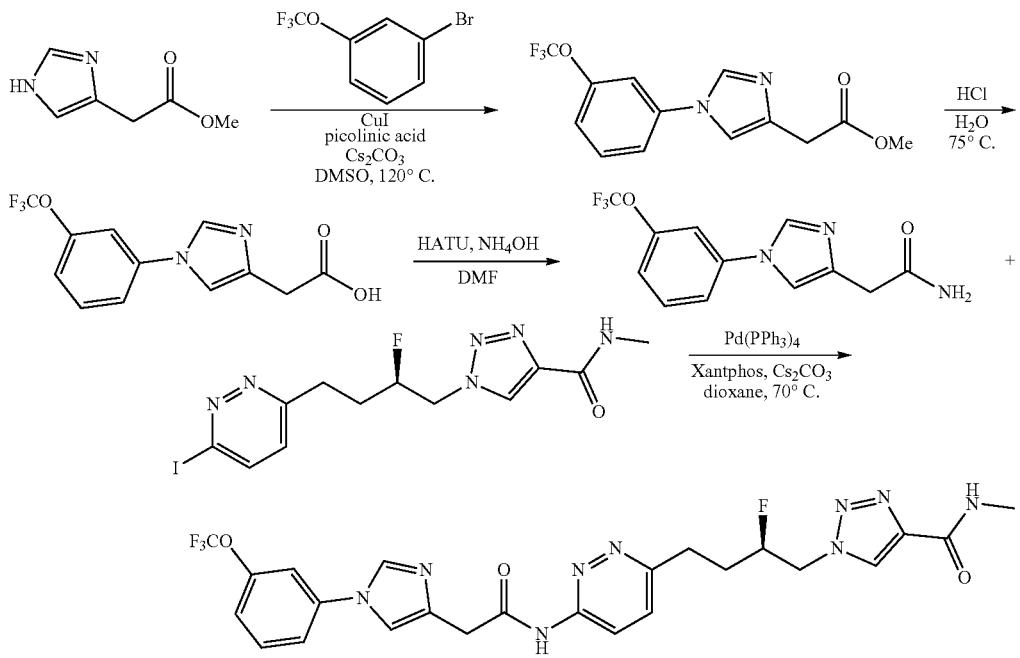

Step 1: methyl 2-(1-(3-(trifluoromethoxy)phenyl)-1H-imidazol-4-yl)acetate

A mixture of 1-bromo-3-(trifluoromethoxy)benzene (2.6 g, 11 mmol), methyl 2-(1H-imidazol-4-yl)acetate (1.5 g, 11 mmol), copper(I) iodide (205 mg, 1.08 mmol), picolinic acid (133 mg, 1.08 mmol), and $Cs_2CO_3$ (10.5 g, 32.4 mmol) in DMSO (50 ml) under Ar was stirred at 120° C. for 16 h. The mixture was treated with water (100 ml), filtered, and the residue was washed with EtOAc. The filtrate layers were separated, and the aqueous layer was extracted with EtOAc (3×100 mL). The combined EtOAc layers were washed with sat. aq. NaCl (100 ml), concentrated under reduced pressure and the residue purified by $SiO_2$ gel chromatography (25% to 75% EtOAc in petroleum ether) to give the title compound as a light brown solid (980 mg, 25%). MS (ES$^+$) $C_{13}H_{11}F_3N_2O_3$ requires: 300, found: 301 [M+H]$^+$.

Step 2: 2-(1-(3-(trifluoromethoxy)phenyl)-1H-imidazol-4-yl)acetic Acid

A mixture of methyl 2-(1-(3-(trifluoromethoxy)phenyl)-1H-imidazol-4-yl)acetate (980 mg, 3.27 mmol) and HCl in 1,4-dioxane (4.0 M, 10 ml, 40 mmol) was stirred at 75° C. for 16 h. The mixture was concentrated under reduced pressure to give the title compound as a light yellow solid (900 mg, 90%). MS (ES$^+$) $C_{12}H_9F_3N_2O_3$ requires: 286, found: 287 [M+H]$^+$.

Step 3: 2-(1-(3-(trifluoromethoxy)phenyl)-1H-imidazol-4-yl)acetamide

To a solution of 2-(1-(3-(trifluoromethoxy)phenyl)-1H-imidazol-4-yl)acetic acid (100 mg, 0.349 mmol) in DMF (1.7 ml) were added TEA (0.146 mL, 1.05 mmol) and HATU (133 mg, 0.349 mmol) and the resulting mixture was stirred at RT for 1 h. Aq. $NH_4OH$ (1 M, 0.110 mL, 1.1 mmol) was added and the mixture was stirred at RT for 12 h, then concentrated under reduced pressure. The residue was purified by mass-triggered preparative HPLC (Mobile phase: A=0.1% TFA/$H_2O$, B=0.1% TFA/MeCN; Gradient: B=10-40%; 20 min; Column: C18) to give the title compound as a yellow liquid (48 mg, 34%). MS (ES$^+$) $C_{12}H_{10}F_3N_3O_2$ requires: 285, found: 286 [M+H]$^+$.

Step 4: (R)-1-(2-fluoro-4-(6-(2-(1-(3-(trifluoromethoxy)phenyl)-1H-imidazol-4-yl)acetamido)pyridazin-3-yl)butyl)-N-methyl-1H-1,2,3-triazole-4-carboxamide A solution of (R)-1-(2-fluoro-4-(6-iodopyridazin-3-yl)butyl)-N-methyl-1H-1,2,3-triazole-4-carboxamide (50 mg, 0.12 mmol), 2-(1-(3-(trifluoromethoxy)phenyl)-1H-imidazol-4-yl)acetamide 2,2,2-trifluoroacetate (49 mg, 0.12 mmol), $Cs_2CO_3$ (141 mg, 0.433 mmol) and Xantphos (14 mg, 0.025 mmol) in 1,4-dioxane (1.24 ml) was degassed by bubbling $N_2$ through for 1 min, then Pd(Ph$_3$)$_4$ (14 mg, 0.012 mmol) was added and the mixture was further degassed for 1 min. The reaction mixture was then stirred at 70° C. for 12 h. The mixture was cooled to RT, diluted with MeOH (2 mL), filtered through Celite® and concentrated under reduced pressure. The residue was purified by $SiO_2$ gel chromatography (3% to 15% MeOH in DCM) to give a pale yellow solid. The residue was recrystallized from hot MeOH (1 mL), and solid was isolated by filtration, washed with MeOH (0.2 mL) and $Et_2O$ (3×0.2 mL) and dried to give the title compound as a white solid (20 mg, 29%). MS (ES$^+$) $C_{24}H_{23}F_4N_9O_3$ requires: 561, found: 562 [M+H]$^+$. $^1$H NMR (600 MHz, DMSO-d$_6$) δ 11.16 (s, 1H), 8.52 (s, 1H), 8.47 (m, 1H), 8.34 (s, 1H), 8.25 (d, J=9.2 Hz, 1H), 7.77 (s, 1H), 7.74-7.71 (m, 2H), 7.68-7.59 (m, 2H), 7.35 (d, J=8.6 Hz, 1H), 5.02 (m, 1H), 4.86-4.65 (m, 2H), 3.76 (s, 2H), 3.14-2.98 (m, 2H), 2.76 (d, J=4.7 Hz, 3H), 2.14 (m, 1H), 2.00 (m, 1H).

Example 268: (R)-1-(2-fluoro-4-(6-(2-(6-methyl-4-(trifluoromethyl)pyridin-2-yl)acetamido)pyridazin-3-yl)butyl)-N-methyl-1H-1,2,3-triazole-4-carboxamide

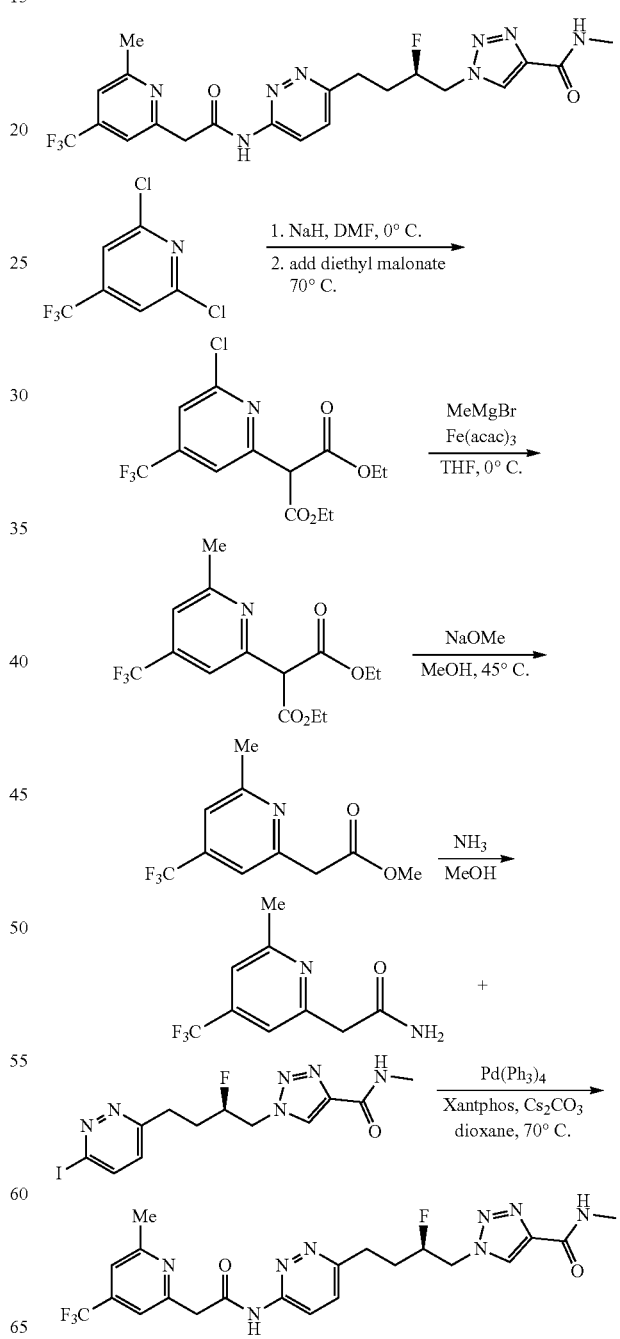

Step 1: diethyl 2-(6-chloro-4-(trifluoromethyl)pyridin-2-yl)malonate

To a suspension of NaH (60% in mineral oil, 1.39 g, 34.7 mmol) in DMF (116 mL) at 0° C. was added diethyl malonate (5.3 ml, 35 mmol) dropwise and the mixture was allowed to warm to RT and stirred for 15 min. 2,6-dichloro-4-(trifluoromethyl)pyridine (2.50 g, 11.6 mmol) was added slowly and then the mixture was stirred at 70° C. for 18 h. The mixture was allowed to cool to RT, quenched with water and the aqueous layer was extracted with EtOAc (3×50 mL). The combined organic layers were washed with water (3×50 mL), dried over $Na_2SO_4$, filtered and concentrated under reduced pressure. The residue was purified by $SiO_2$ gel chromatography (0% to 5% EtOAc in hexanes) to give the title compound as a colorless liquid (2.0 g, 52%). MS (ES$^+$) $C_{12}H_{11}ClF_3NO_4$ requires: 339, found: 340 [M+H]$^+$.

Step 2: diethyl 2-(6-methyl-4-(trifluoromethyl)pyridin-2-yl)malonate

To a solution of diethyl 2-(6-chloro-4-(trifluoromethyl)pyridin-2-yl)malonate (2.0 g, 5.9 mmol) and ferric acetylacetonate (208 mg, 0.589 mmol) in THF (24 mL) and NMP (5.9 mL) at 0° C. was added MeMgBr in diethyl ether (3.0 M, 5.9 mL, 18 mmol) dropwise and the resulting mixture was stirred at 0° C. for 5 min, then allowed to warm to RT and stirred for 30 min. Additional MeMgBr in diethyl ether (3.0 M, 29.5 mL total, 90 mmol total) was added in aliquots of 3.0 equivalents each. The mixture was cooled to 0° C. and slowly quenched with 1 M aq. HCl (100 mL), and the aqueous layer was extracted with EtOAc (3×100 mL). The combined organic layers were washed with water (4×50 mL) and sat. aq. NaCl (50 mL), dried over $Na_2SO_4$, filtered and concentrated under reduced pressure. The residue was purified by $SiO_2$ gel chromatography (0% to 20% EtOAc in hexanes) to give the title compound as a yellow liquid (1.46 g, 78% yield). MS (ES$^+$) $C_{14}H_{16}F_3NO_4$ requires: 319, found: 320 [M+H]$^+$.

Step 3: methyl 2-(6-methyl-4-(trifluoromethyl)pyridin-2-yl)acetate

To a solution of diethyl 2-(6-methyl-4-(trifluoromethyl)pyridin-2-yl)malonate (1.46 g, 4.57 mmol) in MeOH (45.7 mL) at 0° C. was added sodium methoxide (741 mg, 13.7 mmol) and the resulting mixture was stirred at RT for 12 h. The mixture was then stirred at 45° C. for 6 h, then allowed to cool to RT and concentrated under reduced pressure. The residue was partitioned between water (20 mL) and EtOAc (40 mL) and the aqueous layer was extracted with EtOAc (3×20 mL). The combined organic layers were washed with sat. aq. $K_2CO_3$ (2×10 mL) and sat. aq. NaCl (10 mL), dried over $Na_2SO_4$, filtered and concentrated under reduced pressure to give the title compound as a colorless liquid. MS (ES$^+$) $C_{10}H_{10}F_3NO_2$ requires: 233, found: 234 [M+H]$^+$.

Step 4: 2-(6-methyl-4-(trifluoromethyl)pyridin-2-yl)acetamide

A vial was charged with methyl 2-(6-methyl-4-(trifluoromethyl)pyridin-2-yl)acetate (813 mg, 3.49 mmol) and ammonia in MeOH (7 M, 10.0 ml, 69.7 mmol). The vial was sealed and the reaction mixture was stirred at RT for 72 h, then concentrated under reduced pressure to give the title compound as an off-white solid (748 mg, 98%). MS (ES$^+$) $C_9H_9F_3N_2O$ requires: 218, found: 219 [M+H]$^+$.

Step 5: (R)-1-(2-fluoro-4-(6-(2-(6-methyl-4-(trifluoromethyl)pyridin-2-yl)acetamido)pyridazin-3-yl)butyl)-N-methyl-1H-1,2,3-triazole-4-carboxamide A suspension of (R)-1-(2-fluoro-4-(6-iodopyridazin-3-yl)butyl)-N-methyl-1H-1,2,3-triazole-4-carboxamide (500 mg, 1.24 mmol), 2-(6-methyl-4-(trifluoromethyl)pyridin-2-yl)acetamide (297 mg, 1.36 mmol) and $Cs_2CO_3$ (1.01 g, 3.09 mmol) in 1,4-dioxane (12.4 mL) was degassed by bubbling through $N_2$ for 1 min. Xantphos (143 mg, 0.247 mmol) and Pd(Ph$_3$)$_4$ (143 mg, 0.124 mmol) were added and the mixture was degassed by bubbling through $N_2$ for an additional 1 min. The reaction mixture was heated to 70° C. and stirred for 3 h. The mixture was cooled to RT, diluted with 1:1 v:v MeOH/DCM (4 mL), filtered through Celite®, washing with 1:1 v:v MeOH/DCM (4×3 mL) and the filtrate was concentrated under reduced pressure. The residue was purified by $SiO_2$ gel chromatography (0% to 6% MeOH in DCM) to give an off-white solid. The solid was triturated with MeOH (2 mL), collected by vacuum filtration and washed with cold MeOH (3×0.5 mL), then taken up in mixture of ACN/water (1:1), sonicated and lyophilized to give the title compound as a white solid (277 mg, 44%). MS (ES$^+$) $C_{21}H_{22}F_4N_8O_2$ requires: 494, found: 495 [M+H]$^+$. $^1$H NMR (600 MHz, DMSO-d$_6$) δ 11.36 (s, 1H), 8.52 (s, 1H), 8.47 (m, 1H), 8.21 (d, J=9.1 Hz, 1H), 7.63-7.58 (m, 2H), 7.55 (s, 1H), 5.02 (m, 1H), 4.85-4.69 (m, 2H), 4.10 (s, 2H), 3.11-2.96 (m, 2H), 2.76 (d, J=4.7 Hz, 3H), 2.56 (s, 3H), 2.14 (m, 1H), 2.00 (m, 1H).

Example 251: 1-(4-(6-(2-(4-cyclobutoxypyridin-2-yl)acetamido)pyridazin-3-yl)-2-fluorobutyl)-N-methyl-1H-1,2,3-triazole-4-carboxamide 2,2,2-trifluoroacetate

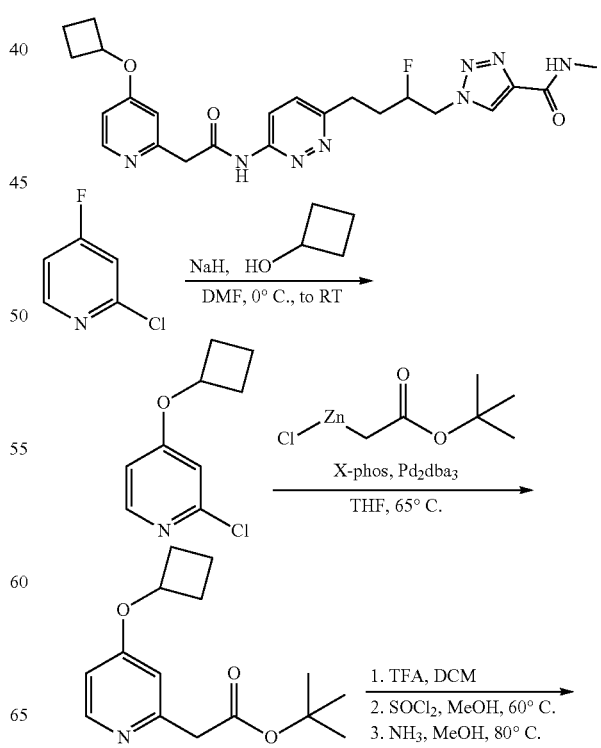

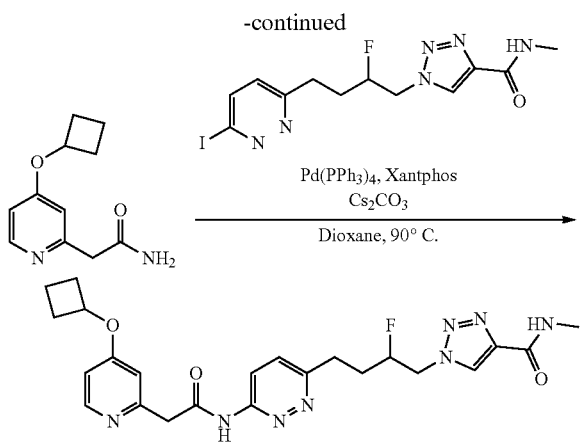

Step 1: 2-chloro-4-cyclobutoxypyridine

To a solution of cyclobutanol (0.327 ml, 4.18 mmol) in DMF (19.01 ml) at 0° C. was added sodium hydride (60% in mineral oil, 0.198 g, 4.94 mmol) and the resulting mixture was stirred at RT for 5 min. 2-chloro-4-fluoropyridine (0.343 ml, 3.80 mmol) was then added dropwise and the resulting mixture was allowed to warm to RT, then diluted with sat. aq. NaHCO₃ (5 mL) and water (10 mL) and extracted with EtOAc (3×10 mL). The combined organic layers were dried over MgSO₄ and concentrated under reduced pressure. The residue was purified by SiO₂ gel chromatography (0% to 100% EtOAc in hexanes) to give the title compound as a colorless liquid (570 mg, 82%). MS (ES⁺) $C_9H_{10}ClNO$ requires: 183, found: 184 [M+H]⁺.

Step 2: tert-butyl 2-(4-(3,3-difluorocyclobutoxy)pyridin-2-yl)acetate 2,2,2-trifluoroacetate A degassed solution of 2-chloro-4-cyclobutoxypyridine (200 mg, 1.09 mmol), (2-(tert-butoxy)-2-oxoethyl)zinc(II) chloride in Et₂O (0.5 M, 5.45 ml, 2.72 mmol), Pd₂(dba)₃ (100 mg, 0.109 mmol) and X-Phos (26 mg, 0.054 mmol) in THF (3 ml) was stirred at 65° C. for 2 h then concentrated under reduced pressure. Water (10 mL) was added, the mixture was extracted with EtOAc (3×5 mL), and the combined organic layers were washed with sat. aq. NaCl, dried over MgSO₄, filtered and concentrated under reduced pressure. The residue was purified by mass-triggered preparative HPLC (Mobile phase: A=0.1% TFA/H₂O, B=0.1% TFA/MeCN; Gradient: B=10-50%; 12 min; Column: C18) to give the title compound as a white solid (187 mg, 46% yield). MS (ES⁺) $C_{15}H_{21}NO_3$ requires: 263, found: 264 [M+H]⁺.

Step 3: 2-(4-(3,3-difluorocyclobutoxy)pyridin-2-yl)acetamide 2,2,2-trifluoroacetate A solution of tert-butyl 2-(4-cyclobutoxypyridin-2-yl)acetate 2,2,2-trifluoroacetate (185 mg, 0.490 mmol) in TFA (3 ml) and DCM (3 ml) was stirred at RT for 2 h, then concentrated under reduced pressure. The residue was taken up in MeOH (3 ml) and treated with thionyl chloride (0.082 ml, 1.1 mmol), and the resulting mixture was stirred at 60° C. for 1 h. The mixture was concentrated under reduced pressure, and to the residue was added ammonia in MeOH (7 M, 3.0 ml, 21 mmol). The reaction mixture was heated in a pressure tube at 80° C. for 16 h, then allowed to cool to RT and concentrated under reduced pressure. The residue was purified by mass-triggered preparative HPLC (Mobile phase: A=0.1% TFA/H₂O, B=0.1% TFA/MeCN; Gradient: B=0-30%; 12 min; Column: C18) to give the title compound as a colorless liquid (102 mg, 85% yield). MS (ES⁺) $C_{11}H_{14}N_2O_2$ requires: 206, found: 207 [M+H]⁺.

Step 4: 1-(4-(6-(2-(4-cyclobutoxypyridin-2-yl)acetamido)pyridazin-3-yl)-2-fluorobutyl)-N-methyl-1H-1,2,3-triazole-4-carboxamide 2,2,2-trifluoroacetate A degassed suspension of 1-(2-fluoro-4-(6-iodopyridazin-3-yl)butyl)-N-methyl-1H-1,2,3-triazole-4-carboxamide (60 mg, 0.15 mmol), 2-(4-cyclobutoxypyridin-2-yl)acetamide 2,2,2-trifluoroacetate (52.3 mg, 0.163 mmol), Pd(PPh₃)₄ (17 mg, 0.015 mmol), Xantphos (17 mg, 0.030 mmol) and Cs₂CO₃ (145 mg, 0.445 mmol) in 1,4-dioxane (2 ml) was stirred at 90° C. for 16 h, then concentrated under reduced pressure. The residue was purified by mass-triggered preparative HPLC (Mobile phase: A=0.1% TFA/H₂O, B=0.1% TFA/MeCN; Gradient: B=10-40%; 20 min; Column: C18) to give the title compound as a white solid (34 mg, 38% yield). MS (ES⁺) $C_{23}H_{27}FN_8O_3$ requires: 482, found: 483 [M+H]⁺. ¹H NMR (MeOH-d₄) δ 8.58 (d, J=7.0 Hz, 1H), 8.39-8.33 (m, 2H), 7.65 (d, J=9.2 Hz, 1H), 7.42 (d, J=2.7 Hz, 1H), 7.36 (dd, J=7.0 Hz, 2.7 Hz, 1H), 5.13-4.68 (m, 6H), 3.19-3.08 (m, 2H), 2.92 (s, 3H), 2.64-2.56 (m, 2H), 2.33-1.77 (m, 6H).

Example 245: 1-(4-(6-(2-(5-(3,3-difluorocyclobutoxy)pyridin-3-yl)acetamido)pyridazin-3-yl)-2-fluorobutyl)-N-methyl-1H-1,2,3-triazole-4-carboxamide

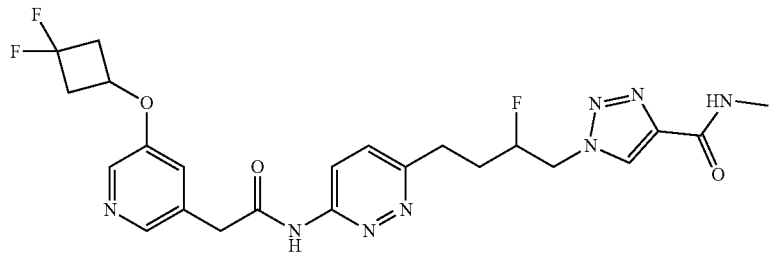

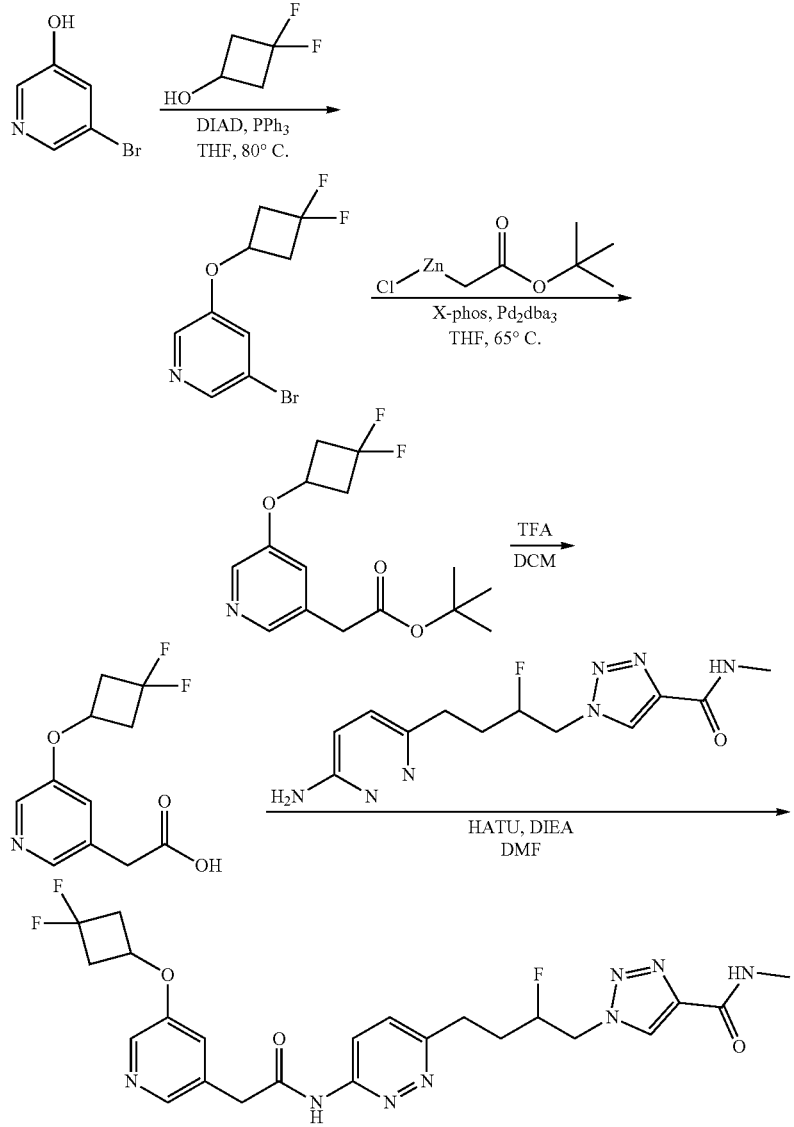

Step 1: 3-bromo-5-(3,3-difluorocyclobutoxy)pyridine 2,2,2-trifluoroacetate

To a solution of 5-bromopyridin-3-ol (174 mg, 1.00 mmol) in THF (5 ml) were added diisopropyl azodicarboxylate (0.389 ml, 2.00 mmol), triphenylphosphine (525 mg, 2.00 mmol) and 3,3-difluorocyclobutanol (130 mg, 1.20 mmol). The mixture was stirred at 80° C. for 2 h, then concentrated under reduced pressure. The residue was purified by mass-triggered preparative HPLC (Mobile phase: A=0.1% TFA/H$_2$O, B=0.1% TFA/MeCN; Gradient: B=30-70%; 12 min; Column: C18) to give the title compound as a yellow liquid (105 mg, 28%). MS (ES$^+$) C$_9$H$_8$BrF$_2$NO requires: 263, found: 264 [M+H]$^+$.

Step 2: tert-butyl 2-(5-(3,3-difluorocyclobutoxy)pyridin-3-yl)acetate 2,2,2-trifluoroacetate A degassed solution of 3-bromo-5-(3,3-difluorocyclobutoxy)pyridine 2,2,2-trifluoroacetate (100 mg, 0.264 mmol), (2-(tert-butoxy)-2-oxoethyl)zinc(II) chloride in Et$_2$O (0.5 M, 2.12 ml, 1.06 mmol), Pd$_2$(dba)$_3$ (12 mg, 0.013 mmol) and X-Phos (6.3 mg, 0.013 mmol) in THF (2 ml) was stirred at 70° C. for 1 h, then concentrated under reduced pressure. The residue was purified by mass-triggered preparative HPLC (Mobile phase: A=0.1% TFA/H$_2$O, B=0.1% TFA/MeCN; Gradient: B=10-40%; 20 min; Column: C18) to give title compound as a white solid (76 mg, 69%). MS (ES$^+$) C$_{15}$H$_{19}$F$_2$NO$_3$ requires: 299, found: 300 [M+H]$^+$.

Step 3: 2-(5-(3,3-difluorocyclobutoxy)pyridin-3-yl)acetic Acid

A solution of tert-butyl 2-(5-(3,3-difluorocyclobutoxy)pyridin-3-yl)acetate 2,2,2-trifluoroacetate (75 mg, 0.18 mmol) in TFA (1 ml) and DCM (1 ml) was stirred at 20° C. for 2 h, then concentrated under reduced pressure. The residue was freeze dried to give the title compound as a white solid (65 mg, 100% yield). MS (ES$^+$) C$_{11}$H$_{11}$F$_2$NO$_3$ requires: 243, found: 244 [M+H]$^+$.

Step 4: 1-(4-(6-(2-(5-(3,3-difluorocyclobutoxy)pyridin-3-yl)acetamido)pyridazin-3-yl)-2-fluorobutyl)-N-methyl-1H-1,2,3-triazole-4-carboxamide 2,2,2-trifluoroacetate To a solution of 2-(5-(3,3-difluorocyclobutoxy)pyridin-3-yl)acetic acid (17.5 mg, 0.072 mmol) in DMF (0.5 ml) were added HATU (18.7 mg, 0.049 mmol), DIEA (8.6 µl, 0.049 mmol) and 1-(4-(6-aminopyridazin-3-yl)-2-fluorobutyl)-N-methyl-1H-1,2,3-triazole-4-carboxamide 2,2,2-trifluoroacetate (20 mg, 0.049 mmol) and the resulting mixture was stirred at 20° C. for 3 h. The volatiles were removed under reduced pressure. The residue was purified by mass-triggered preparative HPLC (Mobile phase: A=0.1% TFA/H$_2$O, B=0.1% TFA/MeCN; Gradient: B=10-40%; 20 min; Column: C18) to give the title compound as a white solid (11 mg, 35%). MS (ES$^+$) C$_{23}$H$_{25}$F$_3$N$_8$O$_3$ requires: 518, found: 519 [M+H]$^+$. $^1$H NMR (DMSO-d$_6$) δ 11.35 (s, 1H), 8.51 (s, 1H), 8.48 (d, J=4.7 Hz, 1H), 8.22-8.18 (m, 3H), 7.61 (d, J=9.3 Hz, 1H), 7.40 (m, 1H), 5.02 (m, 1H), 4.89-4.69 (m, 3H), 3.84 (s, 2H), 3.28-3.18 (m, 2H), 3.07-2.99 (m, 2H), 2.78-2.68 (m, 5H), 2.20-1.93 (m, 2H).

Example 262: 1-(2-Fluoro-4-(6-(2-(4-(2,2,2-trifluoroethoxy)pyridin-2-yl)acetamido)pyridazin-3-yl)butyl)-N-methyl-1H-1,2,3-triazole-4-carboxamide

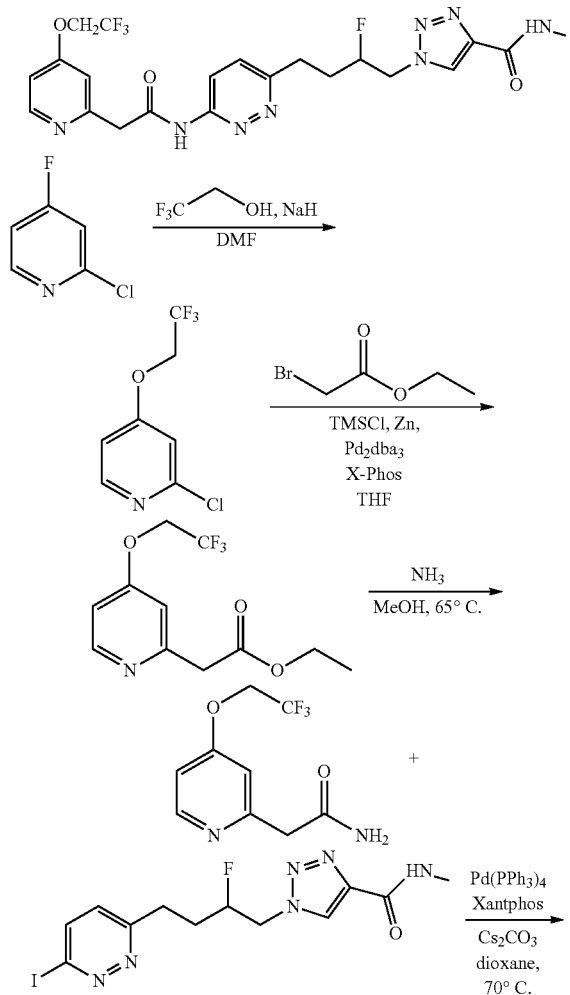

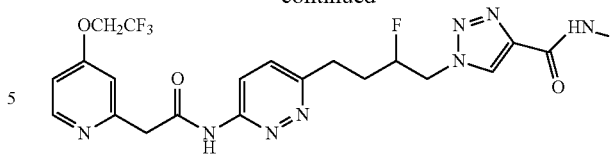

Step 1: 2-chloro-4-(2,2,2-trifluoroethoxy)pyridine

To a solution of 2,2,2-trifluoroethanol (0.72 ml, 9.8 mmol) in DMF (38 ml) was added NaH (60% in mineral oil, 0.39 g, 9.8 mmol) and the resulting mixture was stirred at RT for 5 min. 2-Chloro-4-fluoropyridine (0.68 ml, 7.6 mmol) was added and the reaction was stirred for 18 h. Additional NaH (60% in mineral oil, 0.39 g, 9.8 mmol) and 2,2,2-trifluoroethanol (0.72 ml, 9.8 mmol) were added. After 1 h, the reaction mixture was diluted with sat. aq. NaHCO$_3$ (10 mL) and water (30 mL) and extracted with DCM (3×20 mL). The solution was dried over MgSO$_4$, filtered, and concentrated under reduced pressure. The residue was purified by SiO$_2$ gel chromatography (0% to 100% EtOAc with 20% MeOH in hexanes) to give the title compound as a colorless liquid (1.1 g, 72%). MS (ES$^+$) C$_7$H$_5$ClF$_3$NO requires: 211, found: 212 [M+H]$^+$.

Step 2: Ethyl 2-(4-(2,2,2-trifluoroethoxy)pyridin-2-yl)acetate

Preparation of (2-ethoxy-2-oxoethyl)zinc(II) bromide reagent: To a suspension of Zn (1.2 g, 18 mmol) in THF (4.5 ml) was added chlorotrimethylsilane (0.11 ml, 0.89 mmol) and the resulting mixture was stirred at RT for 15 min. Ethyl 2-bromoacetate (0.99 ml, 8.9 mmol) in THF (13 ml) was added and the resulting mixture was stirred at 30° C. for 30 min. The light green mixture was taken up in a syringe and filtered using a 0.45 uM syringe filter (PTFE) to provide (2-ethoxy-2-oxoethyl)zinc(II) bromide as a ~0.5 M solution in THF.

Reaction: A solution of 2-chloro-4-(2,2,2-trifluoroethoxy)pyridine (200 mg, 0.94 mmol), X-Phos (33 mg, 0.05 mmol) and Pd$_2$(dba)$_3$ (21 mg, 0.024 mmol) in THF (6.3 mL) was degassed by bubbling through N$_2$ for 5 min. (2-Ethoxy-2-oxoethyl)zinc(II) bromide in THF (~0.5 M, 5.6 mL, 2.8 mmol) was added and the mixture was degassed by bubbling through N$_2$ for 10 min. The mixture was stirred for 1 h, then diluted with EtOAc (5 mL) and treated with sat. aq. NH$_4$Cl (5 mL). Layers were separated, the aqueous phase was extracted with EtOAc (3×5 mL), and the combined organic layers were washed with sat. aq. NaCl, dried over Na$_2$SO$_4$, filtered and concentrated under reduced pressure. The residue was purified by SiO$_2$ gel chromatography (0% to 30% MeOH in DCM) to give the title compound as a colorless liquid (249 mg, 99%). MS (ES$^+$) C$_{11}$H$_{12}$F$_3$NO$_3$ requires: 263, found: 264 [M+H]$^+$.

Step 3: 2-(4-(2,2,2-trifluoroethoxy)pyridin-2-yl)acetamide

To ethyl 2-(4-(2,2,2-trifluoroethoxy)pyridin-2-yl)acetate (249 mg, 0.94 mmol) was added ammonia in MeOH (7 M, 2.0 mL, 14 mmol) and the resulting mixture was stirred at 65° C. for 18 h, then allowed to cool to RT and concentrated under reduced pressure. The residue was purified by mass-triggered preparative HPLC (Mobile phase: A=0.1% TFA/H$_2$O, B=0.1% TFA/MeCN; Gradient: B=10-40%; 12 min; Column: C18) to give the title compound as a white powder (192 mg, 58%). MS (ES$^+$) C$_9$H$_9$F$_3$N$_2$O$_2$ requires: 234.0, found: 256.2 [M+Na]$^+$.

Step 4: 1-(2-fluoro-4-(6-(2-(4-(2,2,2-trifluoroethoxy)pyridin-2-yl)acetamido)pyridazin-3-yl)butyl)-N-methyl-1H-1,2,3-triazole-4-carboxamide A solution of 1-(2-fluoro-4-(6-iodopyridazin-3-yl)butyl)-N-methyl-1H-1,2,3-triazole-4-carboxamide (23 mg, 0.057 mmol), 2-(4-(2,2,2-trifluoroethoxy)pyridin-2-yl)acetamide 2,2,2-trifluoroacetate (30 mg, 0.086 mmol), Cs$_2$CO$_3$ (75 mg, 0.23 mmol) and Xantphos (13 mg, 0.023 mmol) in 1,4-dioxane (0.57 mL) was degassed by bubbling through N$_2$ for 10 min. Pd(PPh$_3$)$_4$ (13 mg, 0.011 mmol) was added and the resulting solution was degassed by bubbling through N$_2$ for 10 min. The mixture was stirred at 70° C. for 18 h, then allowed to cool to RT, filtered through Celite®, and concentrated under reduced pressure. The residue was purified by mass-triggered preparative HPLC (Mobile phase: A=0.1% TFA/H$_2$O, B=0.1% TFA/MeCN; Gradient: B=10-40%; 20 min; Column: C18) to give the title compound as an off-white solid (13.1 mg, 36%). MS (ES$^+$) C$_{21}$H$_{22}$F$_4$N$_8$O$_3$ requires: 510, found: 511 [M+H]$^+$. $^1$H NMR (DMSO-d$_6$) δ 11.45 (s, 1H), 8.66 (d, J=7.25 Hz, 1H), 8.52 (s, 1H), 8.48 (q, J=3.86 Hz, 1H) 8.19 (d, J=9.65 Hz, 1H), 7.63 (d, J=9.21 Hz, 1H), 7.46 (s, 1H), 7.37 (d, J=5.25 Hz, 1H), 5.07 (q, J=9.88 Hz, 2H), 4.87-4.67 (m, 2H), 4.14, (2, 2H), 3.09-2.98 (m, 2H), 2.76 (d, J=4.58 Hz, 3H), 2.22-2.06 (m, 1H), 2.06-1.95 (m, 1H), 1.21-1.13 (m, 1H).

Example 253: 1-(2-fluoro-4-(6-(2-(4-(tetrahydro-2H-pyran-4-yl)pyridin-2-yl)acetamido)pyridazin-3-yl)butyl)-N-methyl-1H-1,2,3-triazole-4-carboxamide

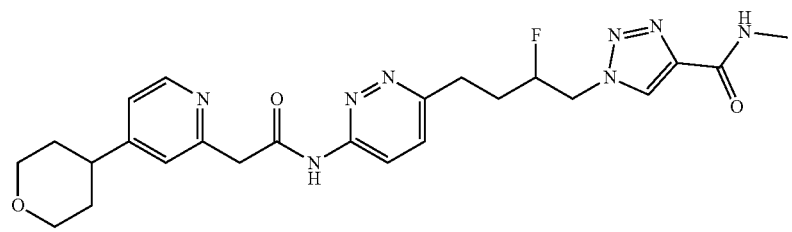

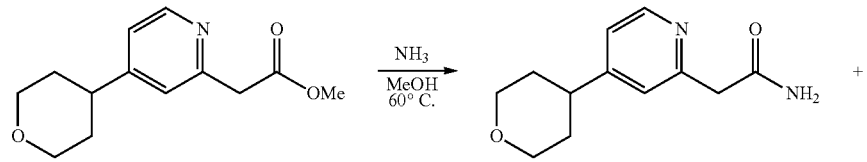

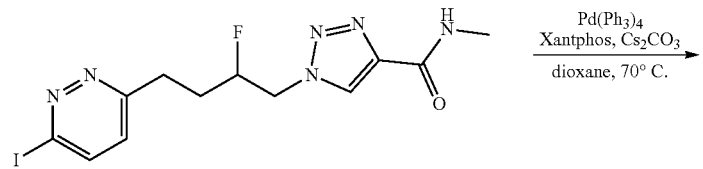

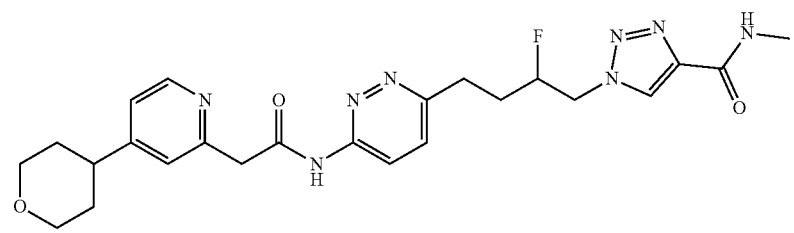

Step 1: 2-(4-(tetrahydro-2H-pyran-4-yl)pyridin-2-yl) acetamide

A vial was charged with methyl 2-(4-(tetrahydro-2H-pyran-4-yl)pyridin-2-yl)acetate (100 mg, 0.425 mmol) and ammonia in MeOH (7 M, 607 μl, 4.25 mmol). The vial was sealed and heated at 60° C. for 12 h, then allowed to cool to RT and concentrated under reduced pressure to give the title compound as a pale yellow liquid (94 mg, 100%). MS (ES$^+$) $C_{12}H_{16}N_2O_2$ requires: 220, found: 221 [M+H]$^+$.

Step 2: 1-(2-fluoro-4-(6-(2-(4-(tetrahydro-2H-pyran-4-yl)pyridin-2-yl)acetamido)pyridazin-3-yl)butyl)-N-methyl-1H-1,2,3-triazole-4-carboxamide trifluoroacetate A solution of 1-(2-fluoro-4-(6-iodopyridazin-3-yl)butyl)-N-methyl-1H-1,2,3-triazole-4-carboxamide (29 mg, 0.073 mmol), 2-(4-(tetrahydro-2H-pyran-4-yl)pyridin-2-yl)acetamide (16 mg, 0.073 mmol), Cs$_2$CO$_3$ (83 mg, 0.25 mmol) and Xantphos (17 mg, 0.029 mmol) in 1,4-dioxane (726 μl) was degassed by bubbling through N$_2$ for 1 min, then Pd(Ph$_3$)$_4$ (17 mg, 0.015 mmol) was added and the mixture was degassed by bubbling through N$_2$ for 1 min. The reaction mixture was stirred at 70° C. for 3 d. The mixture was allowed to cool to RT, filtered through Celite® and concentrated under reduced pressure. The residue was purified by mass-triggered preparative HPLC (Mobile phase: A=0.1% TFA/H$_2$O, B=0.1% TFA/MeCN; Gradient: B=10-40%; 20 min; Column: C18) to give the title compound as an off-white solid (5.3 mg, 12%). MS (ES$^+$) $C_{24}H_{29}FN_8O_3$ requires: 496, found: 497 [M+H]$^+$. $^1$H NMR (500 MHz, MeOH-d$_4$) δ 8.72 (d, J=6.1 Hz, 1H), 8.36-8.30 (m, 1H), 7.94 (d, J=1.8 Hz, 1H), 7.88 (dd, J=6.1, 1.9 Hz, 1H), 7.64 (d, J=9.2 Hz, 1H), 4.99 (m, 1H), 4.83-4.68 (m, 2H), 4.13-4.03 (m, 2H), 3.65-3.55 (m, 2H), 3.22-3.07 (m, 3H), 2.93 (s, 2H), 2.66 (s, 3H), 2.25-2.01 (m, 3H), 1.91-1.86 (m, 3H).

Example 258: N-methyl-1-(4-(6-(2-(4-(1,1,1-trifluoropropan-2-yl)pyridin-2-yl)acetamido)pyridazin-3-yl)butyl)-1H-1,2,3-triazole-4-carboxamide

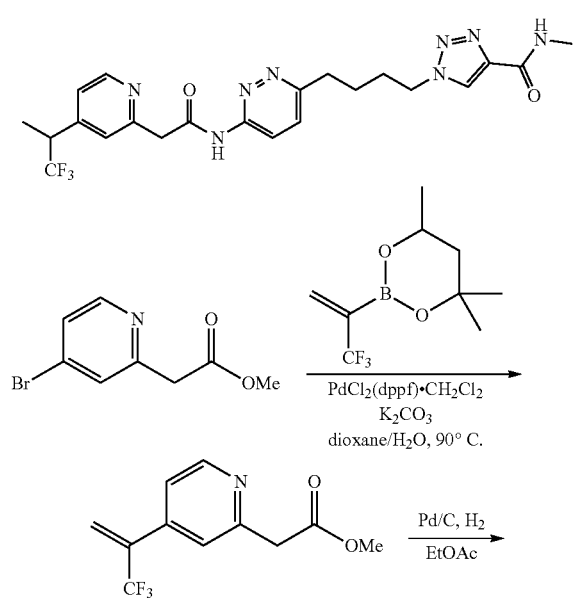

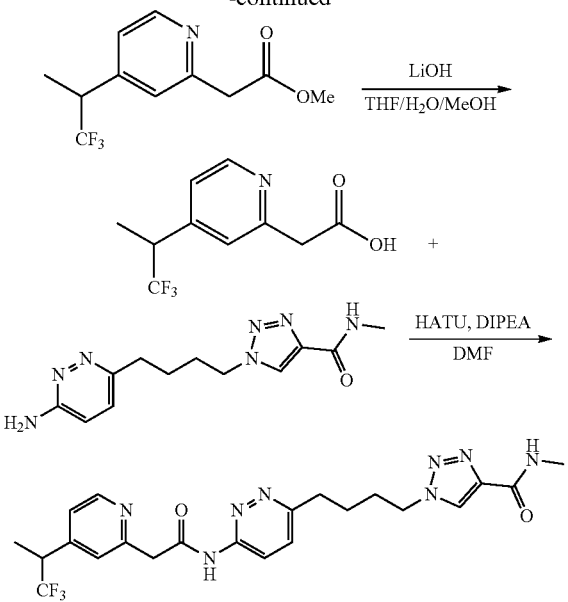

Step 1: methyl 2-(4-(3,3,3-trifluoroprop-1-en-2-yl)pyridin-2-yl)acetate

A suspension of methyl 2-(4-bromopyridin-2-yl)acetate (300 mg, 1.30 mmol), 4,4,6-trimethyl-2-(3,3,3-trifluoroprop-1-en-2-yl)-1,3,2-dioxaborinane (347 mg, 1.57 mmol) and K$_2$CO$_3$ (541 mg, 3.91 mmol) in 1,4-dioxane (5.9 mL) and water (0.6 mL) was degassed by bubbling through N$_2$ for 1 min. PdCl$_2$(dppf)-CH$_2$Cl$_2$ (53 mg, 0.065 mmol) was added and the mixture was degassed by bubbling through N$_2$ for 1 min. The mixture was stirred at 90° C. for 2 h, then allowed to cool to RT, filtered through Celite® and partitioned between water (5 mL) and EtOAc (5 mL). The aqueous layer was extracted with EtOAc (3×5 mL) and the combined organic layers were washed with sat. aq. NaCl (3 mL), dried over Na$_2$SO$_4$, filtered and concentrated under reduced pressure. The residue was purified by SiO$_2$ gel chromatography (0% to 50% EtOAc in hexanes) to give the title compound as a pale yellow liquid (318 mg, 99%). MS (ES$^+$) $C_{11}H_{10}F_3NO_2$ requires: 245, found: 246 [M+H]$^+$.

Step 2: methyl 2-(4-(1,1,1-trifluoropropan-2-yl)pyridin-2-yl)acetate

A reaction vessel was charged with methyl 2-(4-(3,3,3-trifluoroprop-1-en-2-yl)pyridin-2-yl)acetate (100 mg, 0.408 mmol), 10% Pd/C (43 mg, 0.041 mmol) and EtOAc (4.1 ml) under an atmosphere of N$_2$. The suspension was degassed by bubbling through N$_2$ for 1 min, and purged with H$_2$ for 1 min. The reaction mixture was stirred under an atmosphere of H$_2$ at 1 atm for 4 h. The reaction mixture was purged with N$_2$, filtered through Celite® and concentrated under reduced pressure to give the title compound as a pale yellow liquid (98 mg, 97%). MS (ES$^+$) $C_{11}H_{12}F_3NO_2$ requires: 247, found: 248 [M+H]$^+$.

Step 3: lithium 2-(4-(1,1,1-trifluoropropan-2-yl)pyridin-2-yl)acetate

To a solution of methyl 2-(4-(1,1,1-trifluoropropan-2-yl)pyridin-2-yl)acetate (24 mg, 0.097 mmol) in THF (0.69 mL), MeOH (0.14 mL) and water (0.14 mL) was added LiOH (5.8 mg, 0.24 mmol) and the resulting mixture was stirred at RT for 2 h. The mixture was filtered, washing with MeOH, and the filtrate was concentrated under reduced pressure and dried by lyophilization to give the title compound as a white solid (23 mg, 100%). MS (ES+) $C_{10}H_{10}F_3NO_2$ requires: 233, found: 234 [M+H]+.

Step 4: N-methyl-1-(4-(6-(2-(4-(1,1,1-trifluoropropan-2-yl)pyridin-2-yl)acetamido)pyridazin-3-yl)butyl)-1H-1,2,3-triazole-4-carboxamide To a solution of 1-(4-(6-aminopyridazin-3-yl)butyl)-N-methyl-1H-1,2,3-triazole-4-carboxamide (18 mg, 0.065 mmol) and lithium 2-(4-(1,1,1-trifluoropropan-2-yl)pyridin-2-yl)acetate (13 mg, 0.054 mmol) in DMF (0.54 mL) at 0° C. were added TEA (0.023 mL, 0.16 mmol) and T3P® (50 wt. % in EtOAc, 0.048 mL, 0.082 mmol) and the resulting mixture was stirred at 0° C. for 1 h. The mixture was allowed to warm to RT and concentrated under reduced pressure. The residue was purified by mass-triggered preparative HPLC (Mobile phase: A=0.1% TFA/H$_2$O, B=0.1% TFA/MeCN; Gradient: B=20-50%; 16 min; Column: C18) to give the title compound as a pale yellow solid (3.4 mg, 10%). MS (ES+) $C_{22}H_{25}F_3N_8O_2$ requires: 490, found: 491 [M+H]+. $^1$H NMR (600 MHz, MeOH-d$_4$) δ 8.70 (d, J=5.7 Hz, 1H), 8.43 (d, J=9.2 Hz, 1H), 8.32 (s, 1H), 7.82 (m, 1H), 7.72 (m, 1H), 7.69 (d, J=9.2 Hz, 1H), 4.50 (t, J=6.9 Hz, 2H), 3.92 (m, 1H), 2.99 (t, J=7.6 Hz, 2H), 2.92 (s, 3H), 2.04-1.94 (m, 2H), 1.82-1.73 (m, 2H), 1.60-1.57 (m, 3H).

Example 267: (R)-1-(4-(6-(2-(4-(cyclopropyldifluoromethyl)pyridin-2-yl)acetamido)pyridazin-3-yl)-2-fluorobutyl)-N-methyl-1H-1,2,3-triazole-4-carboxamide

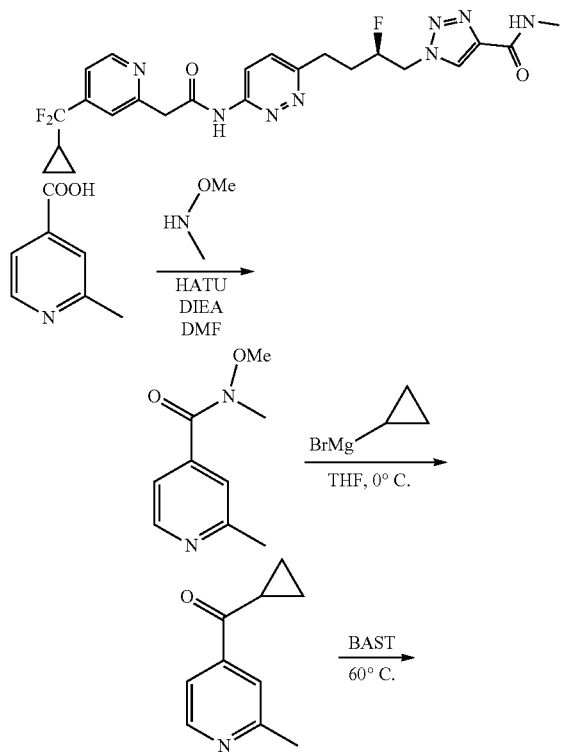

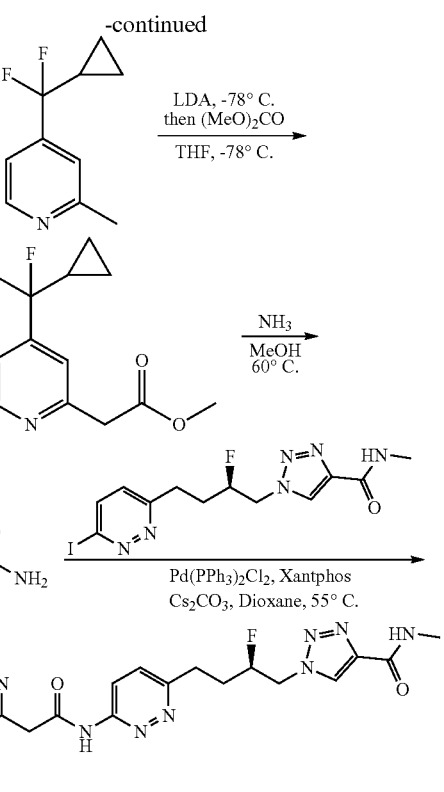

Step 1: N-methoxy-N,2-dimethylisonicotinamide

A mixture of 2-methylisonicotinic acid (4.0 g, 29 mmol), HATU (16.5 g, 1.14 mol) and DIEA (15.0 g, 116 mmol) in DMF (30 ml) was stirred at RT for 30 min, then N,O-dimethylhydroxylamine hydrochloride (3.4 g, 35 mmol) was added. The mixture was stirred at RT for 16 h, then diluted with water (100 ml) and extracted with 10:1 v:v DCM/MeOH (3×200 ml). The combined organic layers were washed with sat. aq. NaCl (3×200 mL), dried over Na$_2$SO$_4$, filtered and concentrated under reduced pressure to give the title compound as a brown oil (4.0 g, 76%) MS (ES+) $C_9H_{12}N_2O_2$ requires: 180, found: 181 [M+H]+.

Step 2: cyclopropyl(2-methylpyridin-4-yl)methanone

To a solution of N-methoxy-N,2-dimethylisonicotinamide (3.8 g, 21 mmol) in THF (100 mL) at 0° C. was slowly added cyclopropylmagnesium bromide in THF (0.5 M, 63 mmol). The mixture was stirred at 0° C. for 2 h, then treated with sat. aq. NH$_4$Cl (20 mL), and the mixture was extracted with DCM (3×300 mL). The combined organic layers were concentrated under reduced pressure, and the residue was purified by SiO$_2$ gel chromatography (0% to 7% MeOH in DCM) to give the title compound as a yellow oil (2.3 g, 67%). MS (ES+) $C_{10}H_{11}NO$ requires: 161, found: 162 [M+H]+.

Step 3: 4-(cyclopropyldifluoromethyl)-2-methylpyridine

A mixture of cyclopropyl(2-methylpyridin-4-yl)methanone (1.0 g, 6.2 mmol) and BAST (5.5 g, 25 mmol) was stirred at 60° C. for 8 h then added to ice water (30 mL). The resulting mixture was extracted with DCM (3×50 mL), and the combined organic layers were concentrated under reduced pressure to a black oil. The oil was purified by preparative HPLC (Mobile phase: A=0.1% ammonium hydroxide/H₂O, B=acetonitrile; Gradient: B=5%-95% in 18 min; Column: C18) to give the title compound as a black oil (150 mg, 13%). MS (ES⁺) C₁₀H₁₁F₂N requires: 183, found: 184 [M+H]⁺.

Step 4: methyl 2-(4-(cyclopropyldifluoromethyl) pyridin-2-yl)acetate

To a solution of 4-(cyclopropyldifluoromethyl)-2-methylpyridine (100 mg, 0.55 mmol) in THF (10 mL) at −78° C. was slowly added LDA in THF (2.0 M, 2.75 mmol). The mixture was stirred at −78° C. for 30 min. Dimethyl carbonate (59 mg, 0.66 mmol) was added. The mixture was stirred at −78° C. for 2 h. The reaction was quenched with water at −78° C., allowed to warm to RT, and extracted with EtOAc (3×50 mL). The combined organic layers were washed with sat. aq. NaCl (100 mL), dried over Na₂SO₄, filtered and concentrated under reduced pressure to give the crude title compound as a yellow oil (130 mg, 100%). MS (ES⁺) C₁₂H₁₃F₂NO₂ requires: 241, found: 242 [M+H]⁺.

Step 5: 2-(4-(cyclopropyldifluoromethyl)pyridin-2-yl)acetamide

A mixture of methyl 2-(4-(cyclopropyldifluoromethyl) pyridin-2-yl)acetate (130 mg, 0.55 mmol) and ammonia in MeOH (7 M, 6 mL) was stirred at 60° C. for 16 h then concentrated under reduced pressure. The residue was purified by preparative HPLC (Mobile phase: A=0.1% ammonium hydroxide/H₂O, B=acetonitrile; Gradient: B=5%-95% in 18 min; Column: C18) to give the title compound as a yellow oil (33 mg, 27%). MS (ES⁺) C₁₁H₁₂F₂N₂O requires: 226, found: 227 [M+H]⁺.

Step 6: (R)-1-(4-(6-(2-(4-(cyclopropyldifluoromethyl)pyridin-2-yl)acetamido)pyridazin-3-yl)-2-fluorobutyl)-N-methyl-1H-1,2,3-triazole-4-carboxamide A mixture of Pd(PPh₃)₄ (9.3 mg, 8.0 μmol), Xantphos (9.3 mg, 0.016 mmol), Cs₂CO₃ (52 mg, 0.16 mmol), 2-(4-(cyclopropyldifluoromethyl)pyridin-2-yl)acetamide (20 mg, 0.088 mmol), and (R)-1-(2-fluoro-4-(6-iodopyridazin-3-yl) butyl)-N-methyl-1H-1,2,3-triazole-4-carboxamide (32 mg, 0.080 mmol) in 1,4-dioxane (0.27 mL) was evacuated and back-filled with N₂ three times. The mixture was stirred at 55° C. for 12 h, then concentrated under reduced pressure, and the residue was partitioned between Et₂O (4 mL) and 1:1 v:v sat. aq. NH₄Cl/water (4 mL). The mixture was vortexed and precipitate was isolated by filtration, rinsing with Et₂O and water, and purified by mass-triggered preparative HPLC (Mobile phase: A=0.1% TFA/H₂O, B=0.1% TFA/MeCN; Gradient: B=20-60%; 12 min; Column: C18) to give the title compound (3.2 mg, 8% yield) as a off-white solid. MS (ES⁺) C₂₃H₂₅F₃N₈O₂ requires: 502, found: 503 [M+H]⁺. ¹H NMR (DMSO-d₆) δ 11.36 (s, 1H), 8.66 (d, J=5.2 Hz, 1H), 8.51 (s, 1H), 8.47 (q, J=4.6, Hz, 1H), 8.22 (d, J=9.2 Hz, 1H), 7.60 (m, 2H), 7.47 (d, J=5.3 Hz, 1H), 5.03 (m, 1H), 4.76 (m, 2H), 4.09 (s, 2H), 3.03 (m, 2H), 2.76 (d, J=5.7 Hz, 3H), 2.06 (m, 2H), 1.71 (m, 1H), 0.72 (m, 4H).

Example 227: N-methyl-1-(4-(6-(2-(2-oxo-4-(3-(trifluoromethoxy)phenyl)piperazin-1-yl)acetamido) pyridazin-3-yl)butyl)-1H-1,2,3-triazole-4-carboxamide

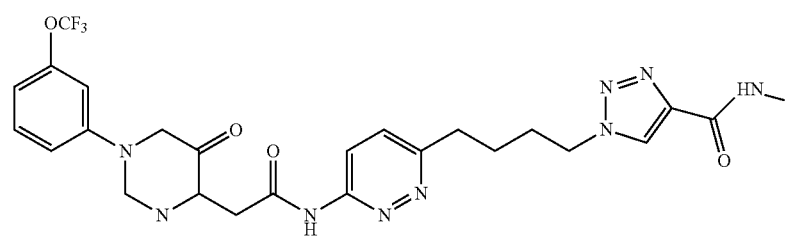

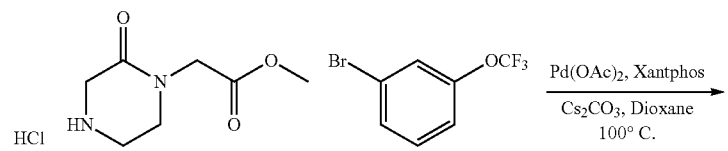

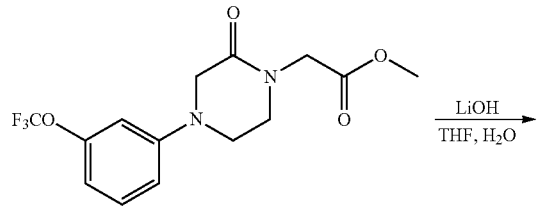

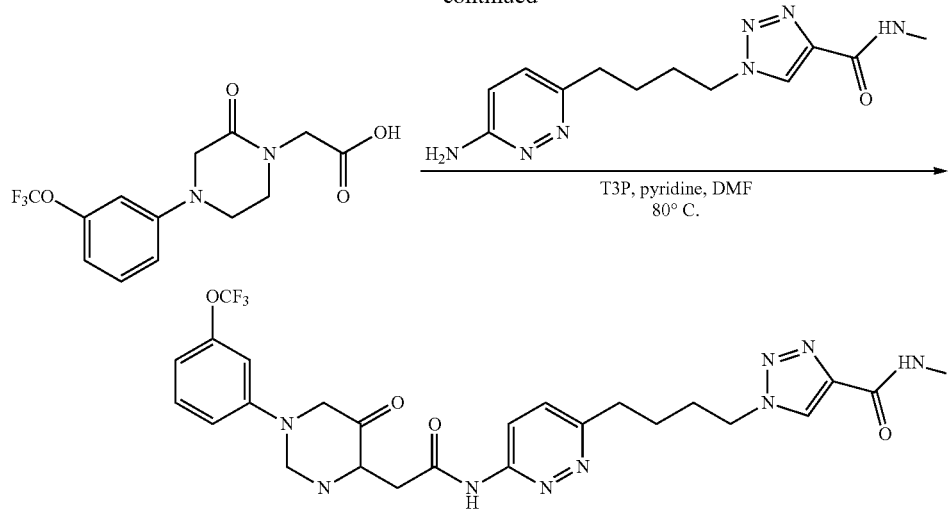

Step 1: methyl 2-(2-oxo-4-(3-(trifluoromethoxy)phenyl)piperazin-1-yl)acetate A degassed suspension of methyl 2-(2-oxopiperazin-1-yl)acetate hydrochloride (104 mg, 0.498 mmol), 1-bromo-3-(trifluoromethoxy)benzene (120 mg, 0.498 mmol), Pd(OAc)$_2$ (11 mg, 0.050 mmol), Xantphos (14 mg, 0.025 mmol) and Cs$_2$CO$_3$ (487 mg, 1.50 mmol) in 1,4-dioxane (3 ml) was stirred at 100° C. for 3 h. The reaction mixture was filtered through Celite®, and the filtrate was concentrated under reduced pressure. The residue was purified by mass-triggered preparative HPLC (Mobile phase: A=0.1% TFA/H$_2$O, B=0.1% TFA/MeCN; Gradient: B=30-70%; 12 min; Column: C18) to give the title compound as a colorless liquid (66 mg, 50%). MS (ES$^+$) C$_{14}$H$_{15}$F$_3$N$_2$O$_4$ requires: 332, found: 333 [M+H]$^+$.

Step 2: 2-(2-oxo-4-(3-(trifluoromethoxy)phenyl)piperazin-1-yl)acetic Acid

To a solution of methyl 2-(2-oxo-4-(3-(trifluoromethoxy)phenyl)piperazin-1-yl)acetate (60 mg, 0.18 mmol) in THF (1 ml) and water (1 ml) was added LiOH (13 mg, 0.54 mmol) and the resulting mixture was stirred at RT for 1 h then concentrated under reduced pressure. The residue was purified by mass-triggered preparative HPLC (Mobile phase: A=0.1% TFA/H$_2$O, B=0.1% TFA/MeCN; Gradient: B=20-60%; 12 min; Column: C18) to give the title compound as a white solid (45 mg, 78%). MS (ES$^+$) C$_{13}$H$_{13}$F$_3$N$_2$O$_4$ requires: 318, found: 319 [M+H]$^+$.

Step 3: N-methyl-1-(4-(6-(2-(2-oxo-4-(3-(trifluoromethoxy)phenyl)piperazin-1-yl)acetamido)pyridazin-3-yl)butyl)-1H-1,2,3-triazole-4-carboxamide 2,2,2-trifluoroacetate A solution of 2-(2-oxo-4-(3-(trifluoromethoxy)phenyl)piperazin-1-yl)acetic acid (16 mg, 0.051 mmol), 1-(4-(6-aminopyridazin-3-yl)butyl)-N-methyl-1H-1,2,3-triazole-4-carboxamide 2,2,2-trifluoroacetate (20 mg, 0.051 mmol), T3P® (50 wt. % in EtOAc, 163 mg, 0.257 mmol) and pyridine (0.021 ml, 0.26 mmol) in DMF (0.5 ml) was stirred at 80° C. for 0.5 h then concentrated under reduced pressure. The residue was purified by mass-triggered preparative HPLC (Mobile phase: A=0.1% TFA/H$_2$O, B=0.1% TFA/MeCN; Gradient: B=0-30%; 20 min; Column: C18) to give the title compound as a white solid (5 mg, 14%). MS (ES$^+$) C$_{25}$H$_{28}$F$_3$N$_9$O$_4$ requires: 575, found: 576 [M+H]$^+$. $^1$H NMR (600 MHz, DMSO-d$_6$) δ 11.23 (s, 1H), 8.55 (s, 1H), 8.43 (m, 1H), 8.20 (m, 1H), 7.57 (d, J=9.1 Hz, 1H), 7.34 (m, 1H), 6.98-6.95 (m, 1H), 6.89 (s, 1H), 6.74 (d, J=8.1 Hz, 1H), 4.45 (t, J=6.9 Hz, 2H), 4.34 (s, 2H), 3.92 (s, 2H), 3.61-3.55 (m, 4H), 2.90 (t, J=7.9 Hz, 2H), 2.76 (d, J=4.7 Hz, 3H), 1.93-1.87 (m, 2H), 1.68-1.62 (m, 2H).

Example 228: N-methyl-1-(4-(6-(2-(4-(3-(trifluoromethoxy)phenyl)piperazin-1-yl)acetamido)pyridazin-3-yl)butyl)-1H-1,2,3-triazole-4-carboxamide

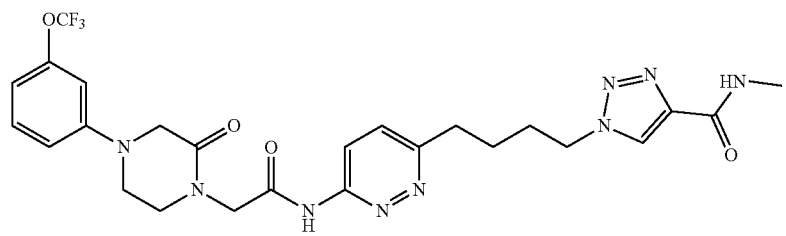

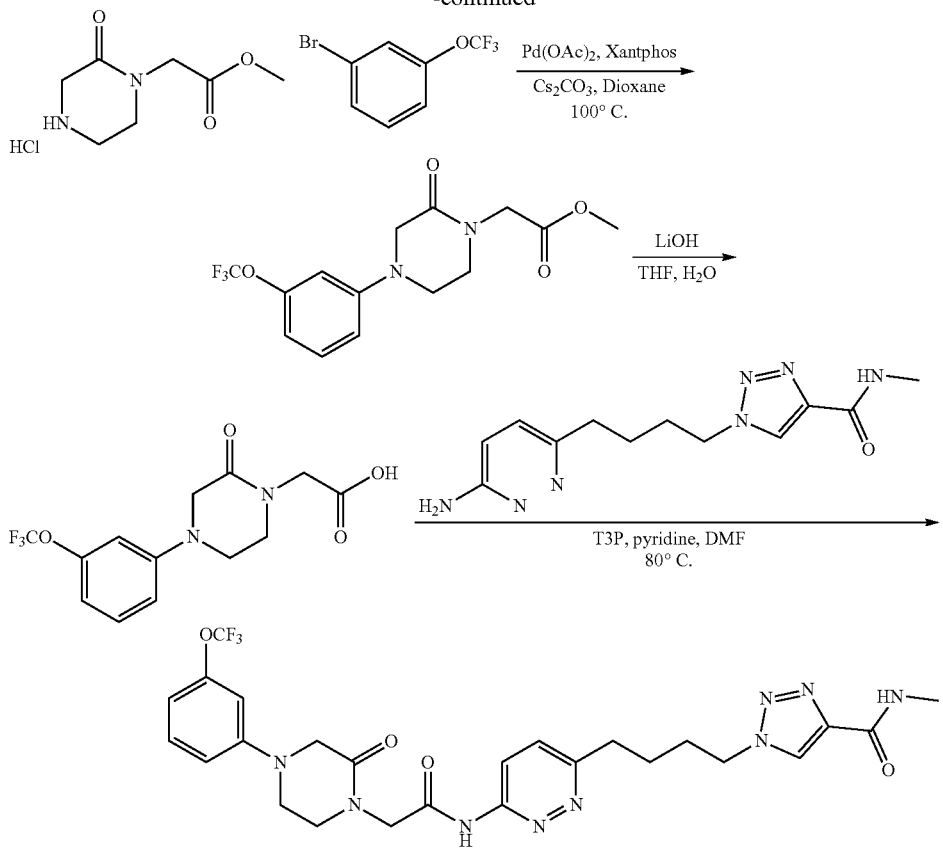

A degassed suspension of ethyl 2-(piperazin-1-yl)acetate (86 mg, 0.50 mmol), 1-bromo-3-(trifluoromethoxy)benzene (120 mg, 0.499 mmol), Pd(OAc)$_2$ (11 mg, 0.050 mmol), Xantphos (14 mg, 0.025 mmol) and Cs$_2$CO$_3$ (488 mg, 1.50 mmol) in 1,4-dioxane (3 ml) was stirred at 100° C. for 3 h. The reaction mixture was filtered through Celite®, and the filtrate was concentrated under reduced pressure. The residue was purified by mass-triggered preparative HPLC (Mobile phase: A=0.1% TFA/H$_2$O, B=0.1% TFA/MeCN; Gradient: B=30-70%; 12 min; Column: C18) to give the title compound as a colorless liquid (108 mg, 65%). MS (ES$^+$) C$_{15}$H$_{19}$F$_3$N$_2$O$_3$ requires: 332, found: 333 [M+H]$^+$.

Step 2: 2-(4-(3-(trifluoromethoxy)phenyl)piperazin-1-yl)acetic acid 2,2,2-trifluoroacetate To a solution of ethyl 2-(4-(3-(trifluoromethoxy)phenyl)piperazin-1-yl)acetate (100 mg, 0.301 mmol) in THF (1 ml) and water (1 ml) were added LiOH (14.4 mg, 0.602 mmol) and the resulting mixture was stirred at RT for 1 h then concentrated under reduced pressure. The residue was purified by mass-triggered preparative HPLC (Mobile phase: A=0.1% TFA/H$_2$O, B=0.1% TFA/MeCN; Gradient: B=10-50%; 12 min; Column: C18) to give the title compound as a white solid (89 mg, 71%). MS (ES$^+$) C$_{13}$H$_{15}$F$_3$N$_2$O$_3$ requires: 304, found: 305 [M+H]$^+$.

Step 3: N-methyl-1-(4-(6-(2-(4-(3-(trifluoromethoxy)phenyl)piperazin-1-yl)acetamido)pyridazin-3-yl)butyl)-1H-1,2,3-triazole-4-carboxamide 2,2,2-trifluoroacetate To a solution of 2-(4-(3-(trifluoromethoxy)phenyl)piperazin-1-yl)acetic acid (21 mg, 0.051 mmol) in DMF (0.5 ml) were added HATU (21 mg, 0.057 mmol), 1-(4-(6-amino-pyridazin-3-yl)butyl)-N-methyl-1H-1,2,3-triazole-4-carboxamide 2,2,2-trifluoroacetate (20 mg, 0.051 mmol) and DIEA (0.045 ml, 0.257 mmol), and the resulting mixture was stirred at RT for 6 h then concentrated under reduced pressure. The residue was purified by mass-triggered preparative HPLC (Mobile phase: A=0.1% TFA/H$_2$O, B=0.1% TFA/MeCN; Gradient: B=10-50%; 12 min; Column: C18) to give the title compound as a white solid (18 mg, 52%). MS (ES$^+$) C$_{25}$H$_{30}$F$_3$N$_9$O$_3$ requires: 561, found: 562 [M+H]$^+$. $^1$H NMR (600 MHz, DMSO-d$_6$) δ 11.71 (s, 1H), 8.59 (s, 1H), 8.42 (m, 1H), 8.21 (m, 1H), 7.64 (d, J=9.1 Hz, 1H), 7.37 (appar t, J=8.3 Hz, 1H), 7.01 (d, J=8.7 Hz, 1H), 6.95 (s, 1H), 6.80 (m, 1H), 4.45 (t, J=7.0 Hz, 2H), 4.35-4.34 (m, br, 2H), 3.99-3.78 (m, 2H), 3.69-3.62 (m, 2H), (3.34-3.21 (m, 4H), 2.91 (t, J=7.6 Hz, 2H), 2.75 (d, J=4.7 Hz, 3H), 1.93-1.87 (m, 2H), 1.68-1.62 (m, 2H).

Example 233: 1-(4-(6-(2-(4-cyclobutoxypyridin-2-yl)acetamido)pyridazin-3-yl)butyl)-N-methyl-1H-1,2,3-triazole-4-carboxamide

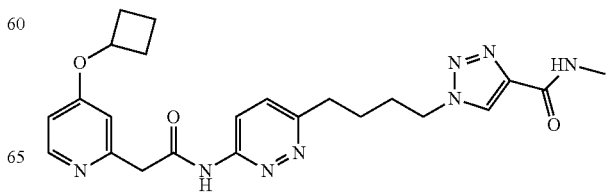

-continued

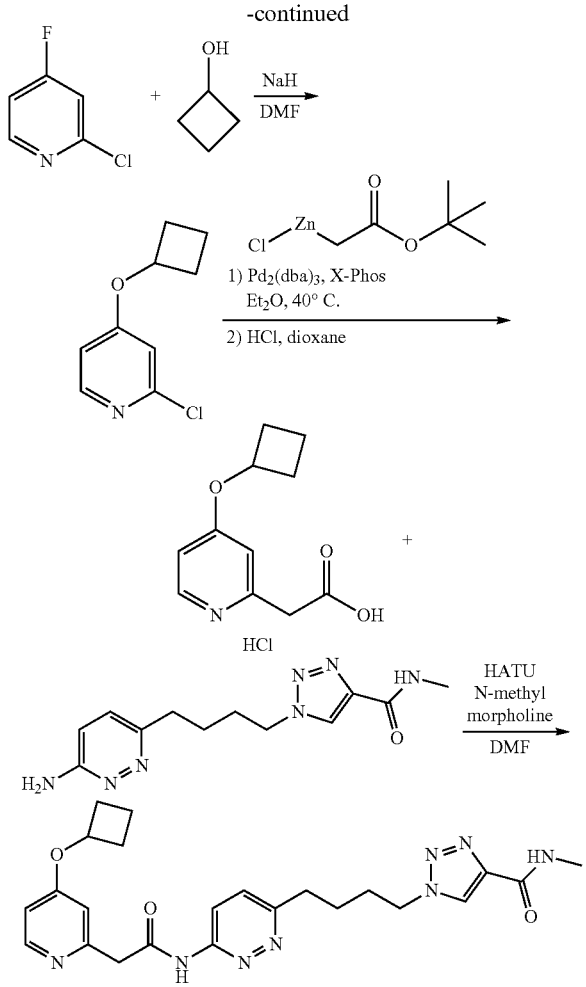

Step 1: 2-chloro-4-cyclobutoxypyridine

To a suspension of NaH (60% in mineral oil, 0.395 g, 9.88 mmol) in DMF (38.0 ml) at 0° C. was added cyclobutanol (0.655 ml, 8.36 mmol) and the resulting mixture was stirred at 0° C. for 15 min. 2-chloro-4-fluoropyridine (0.687 ml, 7.60 mmol) was then added at 0° C. and the mixture was allowed to warm to RT and stirred for 1 h. The reaction mixture was diluted with EtOAc (20 mL), sat. aq. NaHCO$_3$ (20 mL) was added, and the layers were separated. The aqueous layer was extracted with EtOAc (2×20 mL), and the combined organic layers were washed with sat. aq. NaCl, dried over MgSO$_4$, filtered and concentrated under reduced pressure. The residue was purified by SiO$_2$ gel chromatography (0% to 100% EtOAc in hexanes) to give the title compound as a colorless liquid (1.3 g, 93% yield). MS (ES$^+$) C$_9$H$_{10}$ClNO requires: 183, found: 184 [M+H]$^+$.

Step 2: tert-butyl 2-(4-cyclobutoxypyridin-2-yl)acetate

A vial was charged with 2-chloro-4-cyclobutoxypyridine (0.50 g, 2.7 mmol), Pd$_2$(dba)$_3$ (0.125 g, 0.136 mmol), and X-Phos (0.065 g, 0.14 mmol). (2-(Tert-butoxy)-2-oxoethyl) zinc(II) chloride in Et$_2$O (0.5 M, 12 ml, 6.0 mmol) was then added and the resulting mixture degassed by bubbling through N$_2$ for 5 min. The mixture was heated at 40° C. for 1 h, then adsorbed onto silica gel and purified by SiO$_2$ gel chromatography (0% to 10% MeOH in DCM with 1% NH$_4$OH) to give the title compound as a yellow oil (354 mg, 49%). MS (ES$^+$) C$_{15}$H$_{21}$NO$_3$ requires: 263, found: 264 [M+H]$^+$.

Step 3: 2-(4-cyclobutoxypyridin-2-yl)acetic Acid Hydrochloride

HCl in 1,4-dioxane (4.0 M, 0.665 mL, 2.66 mmol) was added to tert-butyl 2-(4-cyclobutoxypyridin-2-yl)acetate (70 mg, 0.27 mmol) at 0° C. The resulting yellow solution was stirred at RT for 2 h. The solution was concentrated under reduced pressure, azeotroping with heptanes, to give the title compound as a light yellow solid (62 mg, 96%). MS (ES$^+$) C$_{11}$H$_{13}$NO$_3$ requires: 207, found: 208 [M+H]$^+$.

Step 4: 1-(4-(6-(2-(4-cyclobutoxypyridin-2-yl)acetamido)pyridazin-3-yl)butyl)-N-methyl-1H-1,2,3-triazole-4-carboxamide To a suspension of 2-(4-cyclobutoxypyridin-2-yl)acetic acid hydrochloride (62 mg, 0.25 mmol), HATU (97 mg, 0.25 mmol), and 1-(4-(6-aminopyridazin-3-yl)butyl)-N-methyl-1H-1,2,3-triazole-4-carboxamide 2,2,2-trifluoroacetate (76 mg, 0.20 mmol) in DMF (0.98 mL) was added 4-methylmorpholine (0.108 mL, 0.979 mmol) and the resulting mixture was stirred at RT for 2 h. The mixture was diluted with MeOH and purified by mass-triggered preparative HPLC (Mobile phase: A=0.1% TFA/H$_2$O, B=0.1% TFA/MeCN; Gradient: B=10-90%; 16 min; Column: C18) to give the title compound as a yellow solid (23 mg, 23% yield). MS (ES$^+$) C$_{23}$H$_{28}$N$_8$O$_3$ requires: 464, found: 465 [M+H]$^+$; $^1$H NMR (500 MHz, MeOH-d$_4$) δ 8.58 (d, J=6.9 Hz, 1H), 8.44 (d, J=9.0 Hz, 1H), 8.31 (s, 1H), 7.72 (d, J=9.2 Hz, 1H), 7.42 (d, J=2.7 Hz, 1H), 7.35 (dd, J=7.0, 2.7 Hz, 1H), 5.08 (m, 1H), 4.50 (t, J=6.9 Hz, 2H), 3.03-2.96 (m, 2H), 2.91 (s, 3H), 2.66-2.53 (m, 3H), 2.34-2.21 (m, 3H), 2.03-1.90 (m, 3H), 1.87-1.71 (m, 3H).

Example 208: N-methyl-1-(4-(6-(2-(4-(tetrahydro-2H-pyran-4-yl)pyridin-2-yl)acetamido)pyridazin-3-yl)butyl)-1H-1,2,3-triazole-4-carboxamide

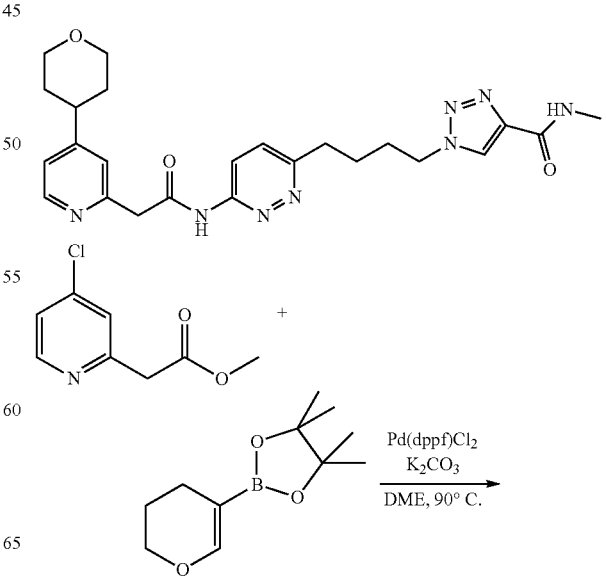

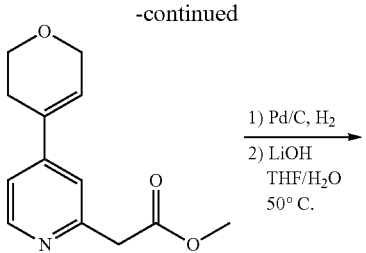

1) Pd/C, H₂
2) LiOH
THF/H₂O
50° C.

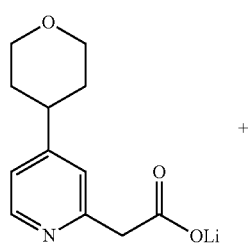

+

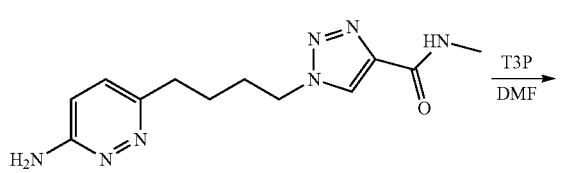

T3P
DMF

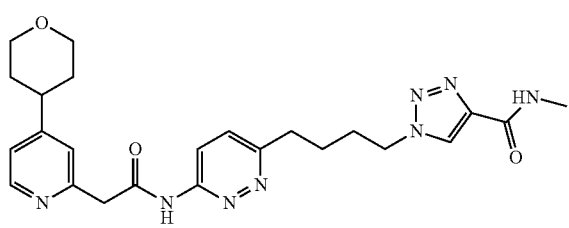

Step 1: methyl 2-(4-(3,6-dihydro-2H-pyran-4-yl)pyridin-2-yl)acetate

A suspension of methyl 2-(4-chloropyridin-2-yl)acetate (300 mg, 1.62 mmol), 2-(3,6-dihydro-2H-pyran-4-yl)-4,4,5,5-tetramethyl-1,3,2-dioxaborolane (407 mg, 1.94 mmol) and PdCl₂(dppf)-CH₂Cl₂ (132 mg, 0.162 mmol) in DME (3 mL) was degassed by bubbling through N₂ for 5 min. Aq. K₂CO₃ (2.0 M, 2.42 ml, 4.85 mmol) was added and the mixture was degassed by bubbling through N₂ for an additional 5 min. The mixture was heated to 90° C. and stirred for 1 h. The mixture was diluted with EtOAc (10 mL) and water (10 mL) and the layers were separated. The aqueous layer was extracted with EtOAc (10 mL) and the combined organic layers were concentrated under reduced pressure. The residue was purified by SiO₂ gel chromatography (0% to 10% MeOH in DCM with 1% NH₄OH) to give the title compound as a brown liquid (154 mg, 41% yield). MS (ES⁺) $C_{13}H_{15}NO_3$ requires: 233, found: 234 [M+H]⁺.

Step 2: methyl 2-(4-(tetrahydro-2H-pyran-4-yl)pyridin-2-yl)acetate

A reaction vessel was charged with methyl 2-(4-(3,6-dihydro-2H-pyran-4-yl)pyridin-2-yl)acetate (150 mg, 0.643 mmol), 10% palladium on carbon (68 mg, 0.064 mmol) and EtOAc (6.4 mL) under an atmosphere of N₂. The suspension was degassed by bubbling through N₂ for 5 min and purged with H₂ for 5 min. The mixture was stirred under an atmosphere of H₂ at 1 atm for 2 h. The reaction mixture was purged with N₂, filtered through Celite®, and concentrated under reduced pressure to give the title compound as a clear liquid (148 mg, 98%). MS (ES⁺) $C_{13}H_{17}NO_3$ requires: 235, found: 236 [M+H]⁺.

Step 3: lithium 2-(4-(tetrahydro-2H-pyran-4-yl)pyridin-2-yl)acetate 2,2,2-trifluoroacetate To a solution of methyl 2-(4-(tetrahydro-2H-pyran-4-yl)pyridin-2-yl)acetate (140 mg, 0.595 mmol) in THF (2.4 mL) and MeOH (0.60 mL) was added aq. LiOH (2.0 M, 0.595 mL, 1.19 mmol) and the resulting mixture was stirred at 50° C. for 1 h then concentrated under reduced pressure. The residue was purified by mass-triggered preparative HPLC (Mobile phase: A=0.1% TFA/H₂O, B=0.1% TFA/MeCN; Gradient: B=0-30%; 20 min; Column: C18) to give the title compound as a pale yellow residue (96 mg, 48% yield). MS (ES⁺) $C_{12}H_{15}NO_3$ requires: 221, found: 222 [M+H]⁺.

Step 4: N-methyl-1-(4-(6-(2-(4-(tetrahydro-2H-pyran-4-yl)pyridin-2-yl)acetamido)pyridazin-3-yl)butyl)-1H-1,2,3-triazole-4-carboxamide To a solution of 2-(4-(tetrahydro-2H-pyran-4-yl)pyridin-2-yl)acetic acid 2,2,2-trifluoroacetate (36 mg, 0.11 mmol) and 1-(4-(6-aminopyridazin-3-yl)butyl)-N-methyl-1H-1,2,3-triazole-4-carboxamide (30 mg, 0.11 mmol) in DMF (0.22 mL) was added T3P® (50 wt. % in EtOAc, 347 mg, 0.545 mmol) and the resulting mixture was stirred at RT for 2 h. The mixture was concentrated under reduced pressure, and the residue was purified by mass-triggered preparative HPLC (Mobile phase: A=0.1% TFA/H₂O, B=0.1% TFA/MeCN; Gradient: B=10-60%; 12 min; Column: C18) to give the title compound as an orange solid (19 mg, 32% yield) after neutralizing residual TFA with an Agilent StratoSpheres® PL-HCO₃ MP resin column (19 mg, 32% yield). MS (ES⁺) $C_{24}H_{30}N_8O_3$ requires: 478, found: 479 [M+H]⁺; ¹H NMR (500 MHz, DMSO-d₆) δ 11.28 (s, 1H), 8.56 (s, 1H), 8.46-8.38 (m, 2H), 8.22 (d, J=9.1 Hz, 1H), 7.55 (d, J=9.1 Hz, 1H), 7.32 (s, 1H), 7.20 (dd, J=5.3 Hz, 1.6 Hz, 1H), 4.45 (t, J=7.0 Hz, 2H), 3.99-3.91 (m, 4H), 3.44 (td, J=11.5 Hz, 2.6 Hz, 2H), 2.91-2.74 (m, 6H), 1.94-1.84 (m, 2H), 1.73-1.62 (m, 6H).

Example 261: 1-(4-(6-(2-(4-(3,3-difluorocyclobutoxy)pyridin-2-yl)acetamido)pyridazin-3-yl)butyl)-N-methyl-1H-1,2,3-triazole-4-carboxamide

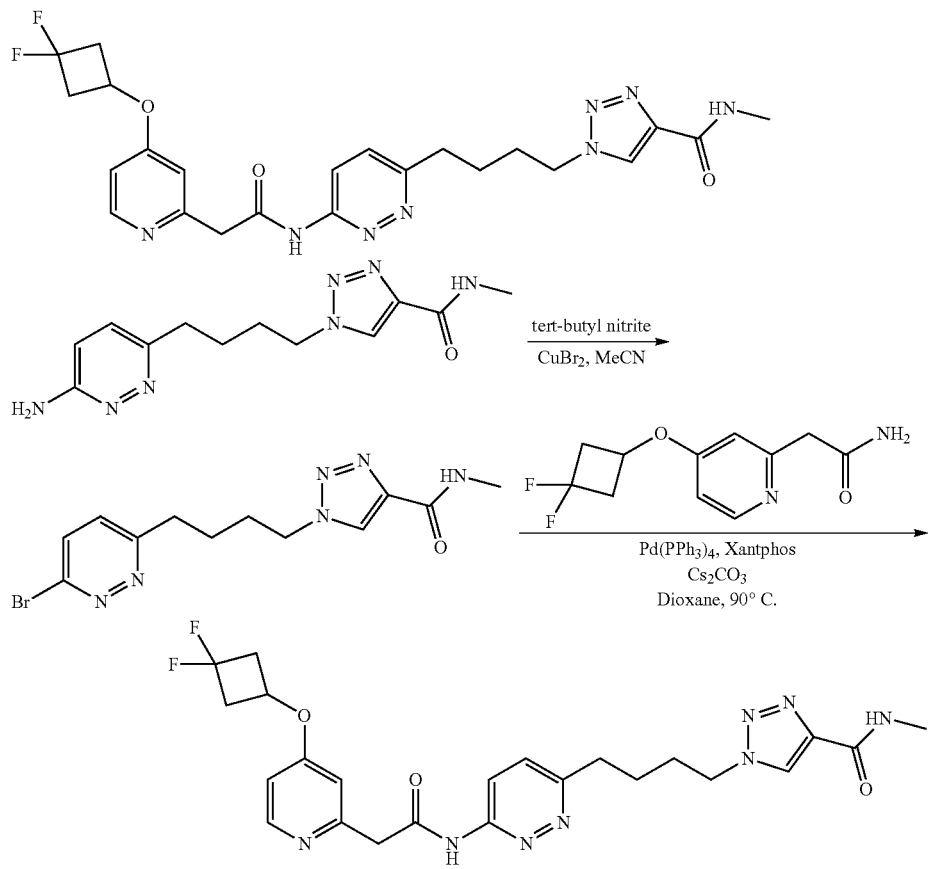

Step 1: 1-(4-(6-bromopyridazin-3-yl)butyl)-N-methyl-1H-1,2,3-triazole-4-carboxamide To a solution of copper (II) bromide (1850 mg, 8.27 mmol) in ACN (35 ml) at 0-5° C. was added dropwise tert-butyl nitrite (0.540 ml, 4.54 mmol) over 1 min. The dark mixture was stirred at 0-5° C. for 5 min, then 1-(4-(6-aminopyridazin-3-yl)butyl)-N-methyl-1H-1,2,3-triazole-4-carboxamide (1020 mg, 3.70 mmol) was added all at once. The mixture was stirred at 0-5° C. for 5 min then RT for 90 h. To the mixture was added 10 mL of a 10% aq. NH$_4$Cl solution. The resulting mixture was partitioned between EtOAc (50 mL) and water (50 mL). The aqueous layer was extracted with EtOAc (50 mL). The combined organic layers were dried over Na$_2$SO$_4$, filtered and concentrated under reduced pressure to give a yellow-orange solid. The solid was triturated in hot MeOH (5 mL), and the mixture was then chilled in a freezer at −RT for 15 min. Precipitate was isolated by filtration, rinsing well with freezer-chilled MeOH and dried by sucking air through to afford the title compound as a yellow solid (76.1 mg, 6%). MS (ES$^+$) C$_{12}$H$_{15}$BrN$_6$O requires: 338/340, found: 361/363 (M+Na)$^+$.

Step 2: 1-(4-(6-(2-(4-(3,3-difluorocyclobutoxy)pyridin-2-yl)acetamido)pyridazin-3-yl)butyl)-N-methyl-1H-1,2,3-triazole-4-carboxamide 2,2,2-trifluoroacetate A degassed solution of 2-(4-(3,3-difluorocyclobutoxy)pyridin-2-yl)acetamide 2,2,2-trifluoroacetate (30 mg, 0.084 mmol), 1-(4-(6-bromopyridazin-3-yl)butyl)-N-methyl-1H-1,2,3-triazole-4-carboxamide (28 mg, 0.084 mmol), Pd(PPh$_3$)$_4$ (9.73 mg, 8.42 μmol), Xantphos (9.8 mg, 0.017 mmol) and Cs$_2$CO$_3$ (82 mg, 0.25 mmol) in 1,4-dioxane (1 ml) was stirred at 90° C. for 16 h then concentrated under reduced pressure. The residue was purified by mass-triggered preparative HPLC (Mobile phase: A=0.1% TFA/H$_2$O, B=0.1% TFA/MeCN; Gradient: B=10-40%; 20 min; Column: C18) to give the title compound as a white solid (10 mg, 19%). MS (ES$^+$) C$_{23}$H$_{26}$F$_2$N$_8$O$_3$ requires: 500, found: 501 [M+H]$^+$. $^1$H NMR (600 MHz, MeOH-d$_4$) δ 8.66 (d, J=7.0 Hz, 1H), 8.41 (d, J=8.8 Hz, 1H), 8.31 (s, 1H), 7.69 (d, J=9.2 Hz, 1H), 7.51 (d, J=2.7 Hz, 1H), 7.45 (dd, J=6.7 Hz, 2.6 Hz, 1H), 5.15-5.09 (m, 1H), 4.50 (t, J=7.0 Hz, 2H), 3.35-3.26 (m, 2H), 2.99 (t, J=7.6 Hz, 2H), 2.95-2.86 (m, 5H), 2.03-1.97 (m, 2H), 1.79-1.73 (m, 2H).

Example 188: N-methyl-1-(4-(6-(2-(5-(3-(trifluoromethoxy)phenyl)pyridin-3-yl)acetamido)pyridazin-3-yl)butyl)-1H-1,2,3-triazole-4-carboxamide

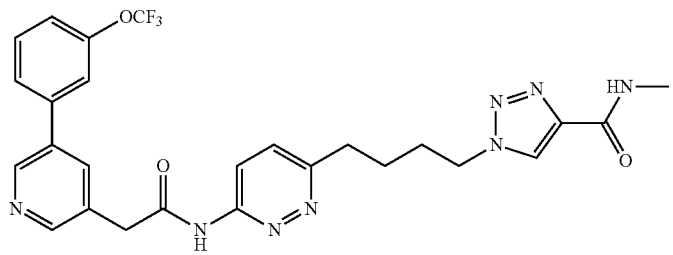

romethoxy)phenyl)boronic acid (74.2 mg, 0.360 mmol), PdCl$_2$(dppf)-CH$_2$Cl$_2$ (12 mg, 0.015 mmol) and aq. K$_2$CO$_3$ (2.0 M, 0.450 ml, 0.900 mmol) in DME (3 ml) was stirred at 90° C. for 1 h. Water (10 mL) was added, and the layers were separated. The aqueous phase was extracted with

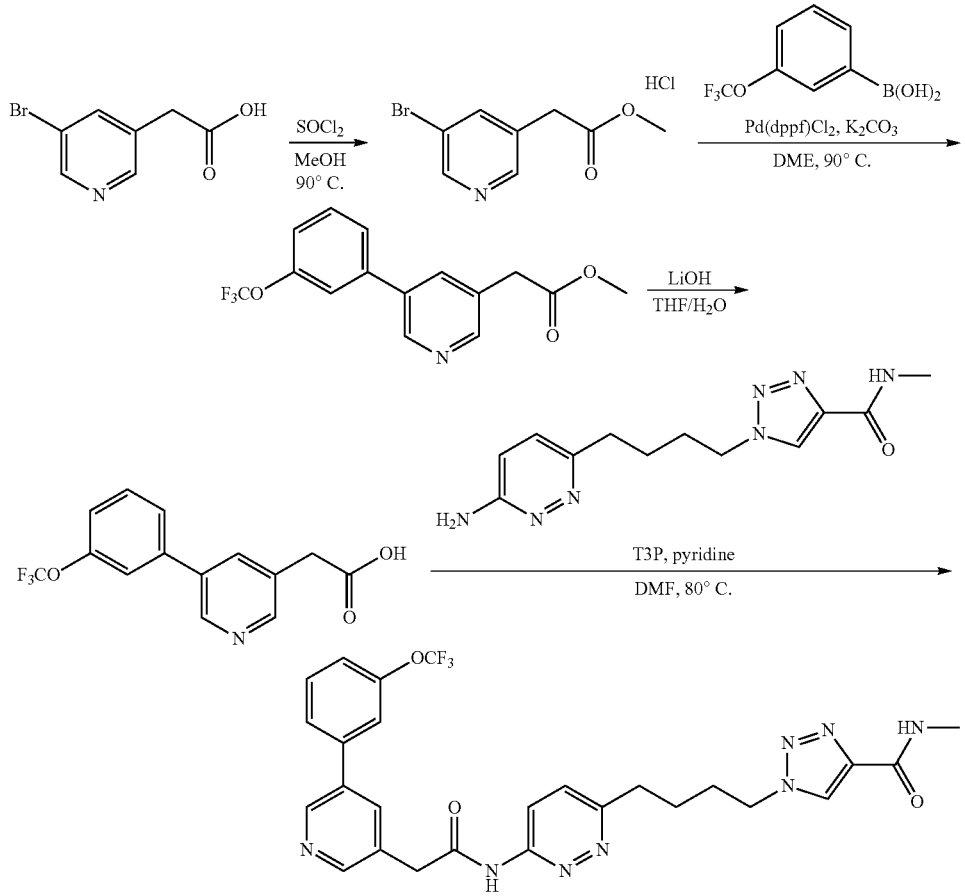

Step 1: methyl 2-(5-bromopyridin-3-yl)acetate Hydrochloride

To a solution of 2-(5-bromopyridin-3-yl)acetic acid (216 mg, 1.00 mmol) in MeOH (5 ml) was added thionyl chloride (0.219 ml, 3.00 mmol) and the resulting mixture was stirred at 90° C. for 2 h. The volatiles were removed under reduced pressure and the residue was lyophilized to give the title compound as a white solid (266 mg, 100%). MS (ES$^+$) C$_8$H$_8$BrNO$_2$ requires: 230, found: 231 [M+H]$^+$.

Step 2: methyl 2-(5-(3-(trifluoromethoxy)phenyl)pyridin-3-yl)acetate

A degassed solution of methyl 2-(5-bromopyridin-3-yl)acetate hydrochloride (80 mg, 0.30 mmol), (3-(trifluo- EtOAc (3×5 mL). The combined organic layers were washed with sat. aq. NaCl, dried over MgSO$_4$, filtered and concentrated under reduced pressure. The residue was purified by SiO$_2$ gel chromatography (0% to 50% EtOAc in hexanes) to give the title compound as a colorless liquid (82 mg, 88%). MS (ES$^+$) C$_{15}$H$_{12}$F$_3$NO$_3$ requires: 311, found: 312 [M+H]$^+$.

Step 3: 2-(5-(3-(trifluoromethoxy)phenyl)pyridin-3-yl)acetic Acid

To a solution of methyl 2-(5-(3-(trifluoromethoxy)phenyl)pyridin-3-yl)acetate (80 mg, 0.26 mmol) in THF (1 ml) and water (1 ml) were added LiOH (12.3 mg, 0.514 mmol) and the resulting mixture was stirred at RT for 1 h then concentrated under reduced pressure. Water (3 ml) was added and the solution was acidified with 10% w/v aq. citric acid to pH 3. Precipitate was isolated by filtration to give the title compound as a white solid (58 mg, 76%). MS (ES+) $C_{14}H_{10}F_3NO_3$ requires: 297, found: 298 [M+H]+.

Step 4: N-methyl-1-(4-(6-(2-(5-(3-(trifluoromethoxy)phenyl)pyridin-3-yl)acetamido)pyridazin-3-yl)butyl)-1H-1,2,3-triazole-4-carboxamide 2,2,2-trifluoroacetate A solution of 2-(5-(3-(trifluoromethoxy)phenyl)pyridin-3-yl)acetic acid (15 mg, 0.052 mmol), 1-(4-(6-aminopyridazin-3-yl)butyl)-N-methyl-1H-1,2,3-triazole-4-carboxamide 2,2,2-trifluoroacetate (20 mg, 0.051 mmol), T3P® (50 wt. % in EtOAc, 165 mg, 0.260 mmol) and pyridine (0.021 mL, 0.26 mmol) in DMF (0.5 ml) was stirred at 80° C. for 0.5 h then concentrated under reduced pressure. The residue was purified by mass-triggered preparative HPLC (Mobile phase: A=0.1% TFA/H$_2$O, B=0.1% TFA/MeCN; Gradient: B=10-50%; 20 min; Column: C18) to give the title compound as a white solid (18 mg, 52%). MS (ES+) $C_{26}H_{25}F_3N_8O_3$ requires: 554, found: 555 [M+H]+. $^1$H NMR (600 MHz, DMSO-d$_6$) δ 11.39 (s, 1H), 8.89 (s, 1H), 8.61 (s, 1H), 8.55 (s, 1H), 8.46-8.41 (m, 1H), 8.23-8.18 (m, 2H), 7.81 (d, J=7.6 Hz, 1H), 7.77 (s, 1H), 7.67 (t, J=8.1 Hz, 1H), 7.56 (d, J=9.2 Hz, 1H), 7.47 (d, J=8.2 Hz, 1H), 4.45 (t, J=6.9 Hz, 2H), 3.97 (s, 2H), 2.89 (t, J=7.5 Hz, 2H), 2.76 (d, J=4.8 Hz, 3H), 1.93-1.84 (m, 2H), 1.68-1.60 (m, 2H).

Example 243: cyclohexyl (6-(4-(4-(methylcarbamoyl)-1H-1,2,3-triazol-1-yl)butyl)pyridazin-3-yl)carbamate

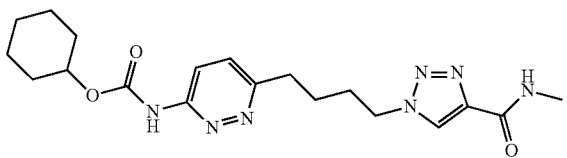

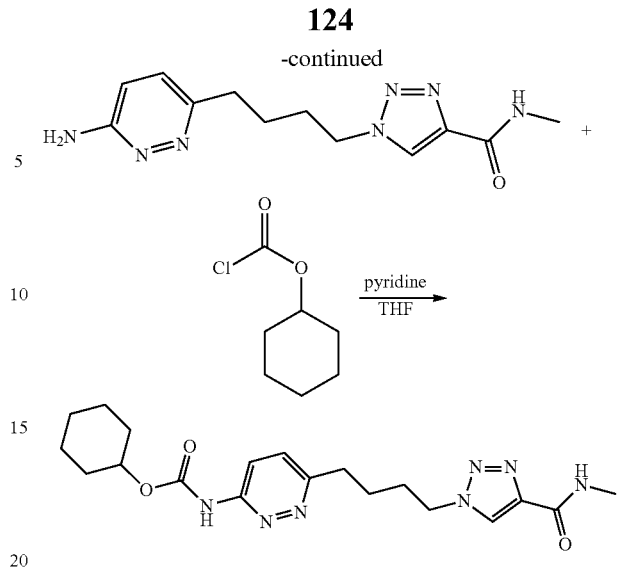

To a solution of 1-(4-(6-aminopyridazin-3-yl)butyl)-N-methyl-1H-1,2,3-triazole-4-carboxamide (30.0 mg, 0.109 mmol) and pyridine (0.013 ml, 0.16 mmol) in THF (1.0 ml) was added cyclohexyl carbonochloridate (21 mg, 0.13 mmol). The mixture was stirred at RT for 4 h, then concentrated under reduced pressure. The residue was purified by mass-triggered preparative HPLC (Mobile phase: A=0.1% TFA/H$_2$O, B=0.1% TFA/MeCN; Gradient: B=20-60%; 12 min; Column: C18) to give the title compound as a yellow solid (7 mg, 16% yield). MS (ES+) $C_{19}H_{27}N_7O_3$ requires: 401, found 402 [M+H]+. $^1$H NMR (600 MHz, DMSO-d$_6$) δ 10.55 (s, 1H), 8.54 (s, 1H), 8.42 (appar br s, 1H), 7.98 (d, J=9.2 Hz, 1H), 7.53 (d, J=9.2 Hz, 1H), 4.72-4.63 (m, 1H), 4.44 (t, J=7.0 Hz, 2H), 2.86 (t, J=7.4 Hz, 2H), 2.75 (d, J=4.6 Hz, 3H), 1.92-1.82 (m, 4H), 1.76-1.67 (m, 2H), 1.67-1.58 (m, 2H), 1.55-1.19 (m, 6H).

Example 269: (R)-1-(2-fluoro-4-(6-(2-(4-(3-(2,2,2-trifluoroethoxy)cyclobutoxy)pyridin-2-yl)acetamido)pyridazin-3-yl)butyl)-N-methyl-1H-1,2,3-triazole-4-carboxamide

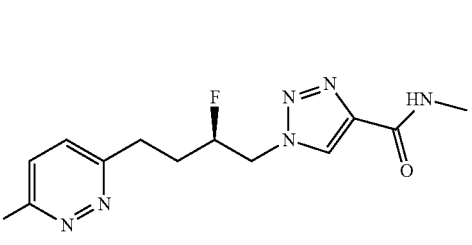

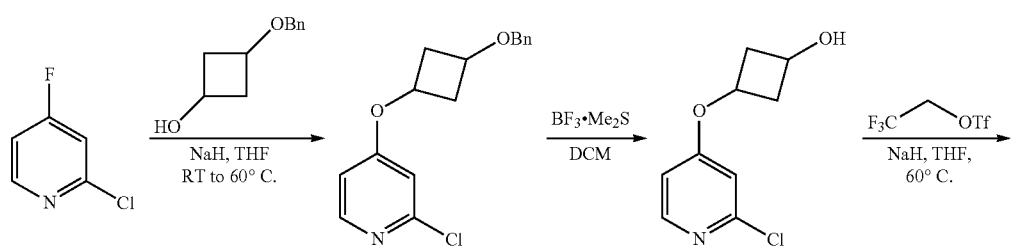

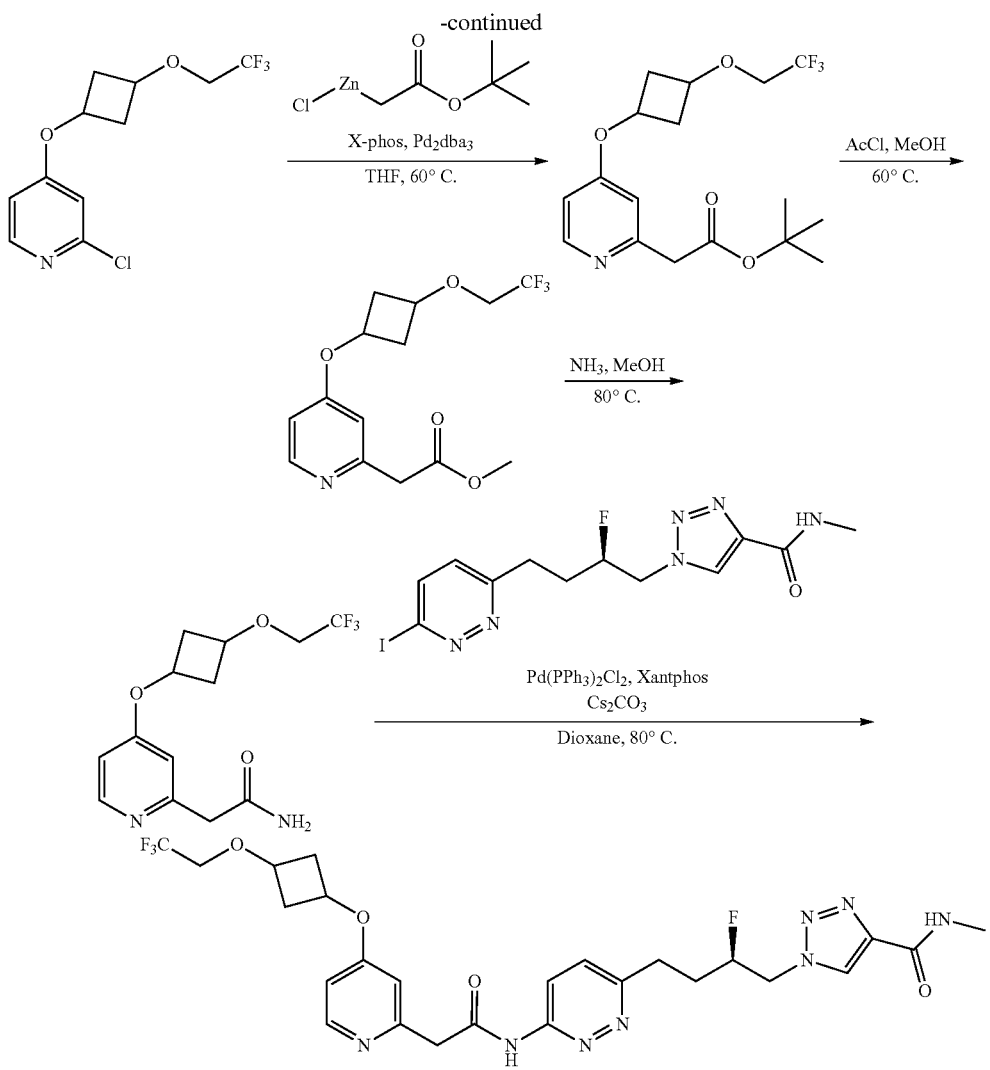

Step 1: 4-(3-(benzyloxy)cyclobutoxy)-2-chloropyridine

To a suspension of NaH (60% in mineral oil, 168 mg, 4.21 mmol) in THF (5 ml) was added 3-(benzyloxy)cyclobutanol (500 mg, 2.81 mmol) and the resulting mixture was stirred at RT for 10 min. 2-chloro-4-fluoropyridine (369 mg, 2.81 mmol) was added, and the mixture was stirred at 60° C. for 2 h. The mixture was allowed to cool to RT, then diluted with EtOAc (20 mL), treated with sat. aq. NH$_4$Cl (20 mL), and the layers were separated. The aqueous layer was extracted with EtOAc (3×15 mL) and the combined organic layers were washed with sat. aq. NaCl, dried over MgSO$_4$, filtered and concentrated under reduced pressure. The residue was purified by SiO$_2$ gel chromatography (0% to 40% EtOAc in hexanes) to give 4-(3-(benzyloxy)cyclobutoxy)-2-chloropyridine as a colorless liquid (585 mg, 72%). MS (ES$^+$) C$_{16}$H$_{16}$ClNO$_2$ requires: 289, found: 290 [M+H]$^+$.

Step 2: 3-((2-chloropyridin-4-yl)oxy)cyclobutanol

To a solution of 4-(3-(benzyloxy)cyclobutoxy)-2-chloropyridine (585 mg, 2.02 mmol) in DCM (10 ml) was added BF$_3$·Me$_2$S (525 mg, 4.04 mmol), and the resulting mixture was stirred at RT for 4 h then concentrated under reduced pressure. The residue was partitioned between EtOAc (50 mL) and sat. aq. NaHCO$_3$ (50 mL), and the layers were separated. The aqueous phase was extracted with EtOAc (3×30 mL) and the combined organic layers were washed with sat. aq. NaCl, dried over MgSO$_4$, filtered and concentrated under reduced pressure. The residue was purified by SiO$_2$ gel chromatography (0% to 5% MeOH in DCM) to give the title compound as a colorless liquid (370 mg, 92%). MS (ES$^+$) C$_9$H$_{10}$ClNO$_2$ requires: 199, found: 200 [M+H]$^+$.

Step 3: 2-chloro-4-(3-(2,2,2-trifluoroethoxy)cyclobutoxy)pyridine

To a suspension of NaH (60% in mineral oil, 44.5 mg, 1.85 mmol) in THF (10 ml) was added 3-((2-chloropyridin-4-yl)oxy)cyclobutanol (370 mg, 1.85 mmol). After bubbling subsided, 2,2,2-trifluoroethyl trifluoromethanesulfonate (1.29 g, 5.56 mmol) was added and the resulting mixture was stirred at 60° C. for 5 h. The reaction mixture was diluted with EtOAc (30 mL), sat. aq. NH$_4$Cl (30 mL) was added, and the layers were separated. The aqueous phase was extracted with EtOAc (3×20 mL), and the combined organic layers were washed with sat. aq. NaCl, dried over MgSO₄, filtered and concentrated under reduced pressure. The residue was purified by SiO₂ gel chromatography (0% to 30% EtOAc in hexanes) to give the title compound as a pale yellow liquid (195 mg, 37%). MS (ES⁺) C₁₁H₁₁ClF₃NO₂ requires: 281, found: 282 [M+H]⁺.

Step 4: tert-butyl 2-(4-(3-(2,2,2-trifluoroethoxy)cyclobutoxy)pyridin-2-yl)acetate A degassed mixture of 2-chloro-4-(3-(2,2,2-trifluoroethoxy)cyclobutoxy)pyridine (195 mg, 0.692 mmol), (2-(tert-butoxy)-2-oxoethyl)zinc(II) chloride in THF (0.5 M, 2.77 mL, 1.38 mmol), Pd₂(dba)₃ (31.7 mg, 0.0350 mmol) and X-Phos (16.5 mg, 0.0350 mmol) was stirred at 60° C. for 0.5 h. The mixture was diluted with EtOAc (20 mL). Sat. aq. NH₄Cl (20 mL) was added, and the layers were separated. The aqueous phase was extracted with EtOAc (3×10 mL), and the combined organic layers were washed with sat. aq. NaCl, dried over MgSO₄, filtered and concentrated under reduced pressure. The residue was purified by SiO₂ gel chromatography (0% to 40% EtOAc in hexanes) to give the title compound as a pale yellow liquid (173 mg, 69%). MS (ES⁺) C₁₇H₂₂F₃NO₄ requires: 361, found: 306 [M−t(Bu)+2H]⁺.

Step 5: methyl 2-(4-(3-(2,2,2-trifluoroethoxy)cyclobutoxy)pyridin-2-yl)acetate

To a solution of tert-butyl 2-(4-(3-(2,2,2-trifluoroethoxy)cyclobutoxy)pyridin-2-yl)acetate (172 mg, 0.476 mmol) in MeOH (5 ml) were added acetyl chloride (0.338 ml, 4.76 mmol) and the resulting mixture was stirred at 60° C. for 3 h then concentrated under reduced pressure. The reaction mixture was taken up in EtOAc (20 mL) and washed with sat. aq. NaHCO₃ (20 mL). The organic layer was further washed with sat. aq. NaCl (10 mL), dried over MgSO₄, filtered and concentrated under reduced pressure to give the title compound as a pale yellow liquid (150 mg, 99%), which was used in the next step without further purification. MS (ES⁺) C₁₄H₁₆F₃NO₄ requires: 319, found: 320 [M+H]⁺.

Step 6: 2-(4-(3-(2,2,2-trifluoroethoxy)cyclobutoxy)pyridin-2-yl)acetamide

A mixture of methyl 2-(4-(3-(2,2,2-trifluoroethoxy)cyclobutoxy)pyridin-2-yl)acetate (150 mg, 0.470 mmol) and ammonia in MeOH (7 M, 2.01 mL, 14.1 mmol) was heated in a sealed tube at 80° C. for 16 h then concentrated under reduced pressure to give the title compound as a yellow solid (140 mg, 98%), which was used without further purification. MS (ES⁺) C₁₃H₁₅F₃N₂O₃ requires: 304, found: 305 [M+H]⁺.

Step 7: (R)-1-(2-fluoro-4-(6-(2-(4-(3-(2,2,2-trifluoroethoxy)cyclobutoxy)pyridin-2-yl)acetamido)pyridazin-3-yl)butyl)-N-methyl-1H-1,2,3-triazole-4-carboxamide 2,2,2-trifluoroacetate A degassed solution of 2-(4-(3-(2,2,2-trifluoroethoxy)cyclobutoxy)pyridin-2-yl)acetamide (22.6 mg, 0.0740 mmol), (R)-1-(2-fluoro-4-(6-iodopyridazin-3-yl)butyl)-N-methyl-1H-1,2,3-triazole-4-carboxamide (30 mg, 0.074 mmol), (PPh₃)₂PdCl₂ (5.21 mg, 7.42 µmol), Xantphos (8.59 mg, 0.0150 mmol) and Cs₂CO₃ (48.4 mg, 0.148 mmol) in 1,4-dioxane (1 ml) was stirred at 80° C. for 16 h then concentrated under reduced pressure. The residue was purified by mass-triggered preparative HPLC (Mobile phase: A=0.1% TFA/H₂O, B=0.1% TFA/MeCN; Gradient: B=10-40%; 20 min; Column: C18) to give the title compound as a white solid (10 mg, 19%). MS (ES⁺) C₂₅H₂₈F₄N₈O₄ requires: 580, found: 581 [M+H]⁺. ¹H NMR (600 MHz, MeOH-d₄) δ 8.60 (d, J=7.0 Hz, 1H), 8.37-8.32 (m, 2H), 7.64 (d, J=9.2 Hz, 1H), 7.44 (d, J=2.5 Hz, 1H), 7.37 (dd, J=7.0 Hz, 2.6 Hz, 1H), 5.24 (m, 1H), 4.98 (m, 1H), 4.82-4.69 (m, 2H), 4.44 (m, 1H), 3.91 (q, J=8.9 Hz, 2H), 3.18-3.07 (m, 2H), 2.92 (s, 3H), 2.71-2.65 (m, 2H), 2.62-2.56 (m, 2H), 2.23-2.02 (m, 2H).

Example 274: 1-(4-(6-(2-(4-(difluoromethoxy)pyridin-2-yl)acetamido)pyridazin-3-yl)-2-fluorobutyl)-N-methyl-1H-1,2,3-triazole-4-carboxamide

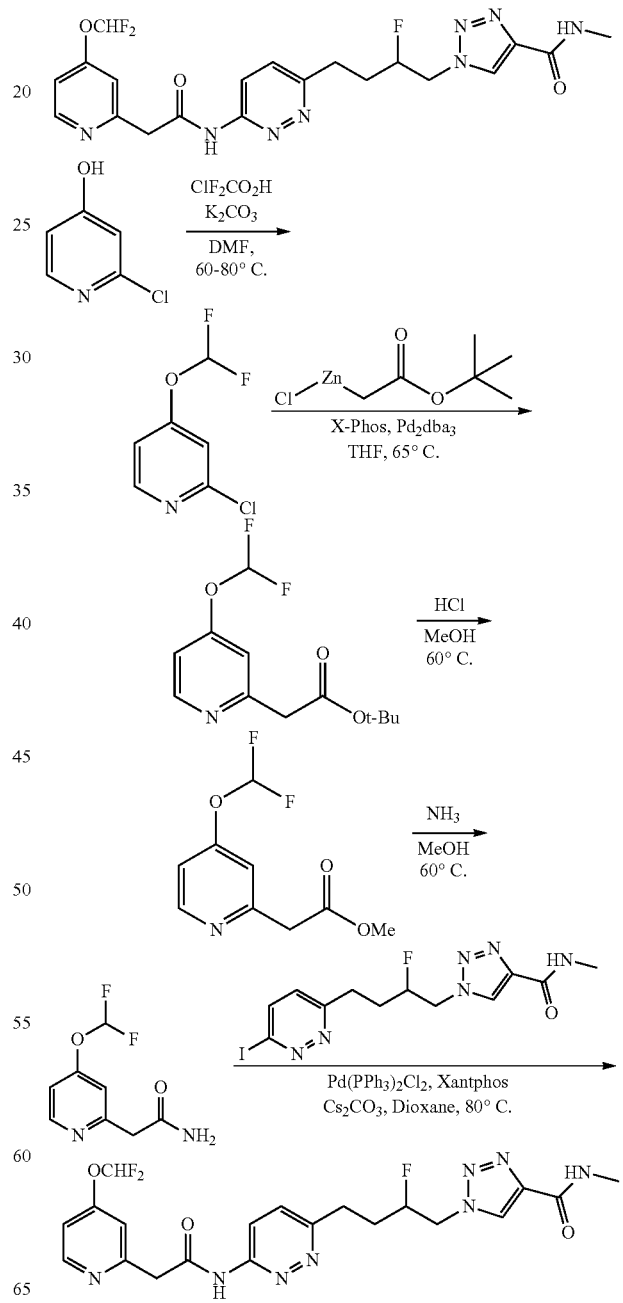

Step 1: 2-chloro-4-(difluoromethoxy)pyridine

To a solution of 2-chloropyridin-4-ol (1.0 g, 7.7 mmol) in DMF (8 ml) were added $K_2CO_3$ (4.6 g, 33 mmol) and 2-chloro-2,2-difluoroacetic acid (1.0 ml, 10 mmol) (note: exothermic!) and the resulting mixture was stirred at RT for 1 h, then stirred at 80° C. for 2 h. An additional amount of 2-chloro-2,2-difluoroacetic acid (2.0 ml, 20 mmol) was added and the mixture was stirred for 16 h at 60° C. then for 30 min at 80° C. The mixture was allowed to cool, filtered, and the filtrate partitioned between EtOAc and water. The organic layer was washed twice with water, dried over $Na_2SO_4$, filtered and concentrated under reduced pressure. The residue was purified by $SiO_2$ gel chromatography (50% to 100% EtOAc in hexanes) to give the title compound as a pale yellow solid (157 mg, 11% yield). MS (ES$^+$) $C_6H_4ClF_2NO$ requires: 179, found: 180 $[M+H]^+$.

Step 2: tert-butyl 2-(4-(difluoromethoxy)pyridin-2-yl)acetate 2,2,2-trifluoroacetate A degassed solution of 2-chloro-4-(difluoromethoxy)pyridine (300 mg, 1.67 mmol), (2-(tert-butoxy)-2-oxoethyl)zinc(II) chloride in $Et_2O$ (0.5 M, 8.35 ml, 4.18 mmol), $Pd_2(dba)_3$ (153 mg, 0.167 mmol), and X-Phos (40 mg, 0.084 mmol) in THF (3 ml) was stirred at 65° C. for 2 h. The mixture was concentrated under reduced pressure, and water (50 mL) was added to the residue. The mixture was extracted with EtOAc (3×25 mL) and the combined organic layers were washed with sat. aq. NaCl, dried over $Na_2SO_4$, filtered, and concentrated under reduced pressure. The residue was purified by mass-triggered preparative HPLC (Mobile phase: A=0.1% TFA/$H_2O$, B=0.1% TFA/MeCN; Gradient: B=30-70%; 16 min; Column: C18) to afford the title compound as a white solid (19 mg, 3% yield). MS (ES$^+$) $C_{12}H_{15}F_2NO_3$ requires: 259, found: 204 $[M-(t-Bu)+2H]^+$.

Step 3: methyl 2-(4-(difluoromethoxy)pyridin-2-yl)acetate

To a solution of tert-butyl 2-(4-(difluoromethoxy)pyridin-2-yl)acetate (20 mg, 0.077 mmol) in MeOH (2.00 ml, 49.4 mmol) was added acetyl chloride (0.055 ml, 0.77 mmol) dropwise over 5 min. The resulting mixture was stirred at 60° C. for 4 h and was then concentrated under reduced pressure to give the title compound as a yellow liquid (16 mg, 96%). MS (ES$^+$) $C_9H_9F_2NO_3$ requires: 217, found 218 $[M+H]^+$.

Step 4: 2-(4-(difluoromethoxy)pyridin-2-yl)acetamide

Methyl 2-(4-(difluoromethoxy)pyridin-2-yl)acetate (16 mg, 0.074 mmol) was treated with ammonia in MeOH (7 M, 1.0 ml, 7.0 mmol), and the reaction mixture was sealed in a reaction vessel and stirred at 60° C. for 16 h. The mixture was allowed to cool, then concentrated under reduced pressure to give the title compound as a yellow solid (12 mg, 81% yield). MS (ES$^+$) $C_8H_8F_2N_2O_2$ requires: 202, found: 203 $[M+H]^+$.

Step 5: 1-(4-(6-(2-(4-(difluoromethoxy)pyridin-2-yl)acetamido)pyridazin-3-yl)-2-fluorobutyl)-N-methyl-1H-1,2,3-triazole-4-carboxamide A suspension of 1-(2-fluoro-4-(6-iodopyridazin-3-yl)butyl)-N-methyl-1H-1,2,3-triazole-4-carboxamide (24 mg, 0.059 mmol), 2-(4-(difluoromethoxy)pyridin-2-yl)acetamide (11 mg, 0.054 mmol), Xantphos (6.0 mg, 0.010 mmol), $Pd(PPh_3)_4$ (6.0 mg, 0.0052 mmol) and $Cs_2CO_3$ (56 mg, 0.17 mmol) in 1,4-dioxane (1.5 ml) was degassed by bubbling through $N_2$ for 5 min. The reaction mixture was heated to 80° C. and stirred for 5 h, then stirred at RT for 16 h. The mixture was concentrated under reduced pressure, dissolved in DMSO, filtered and the filtrate directly purified by mass-triggered preparative HPLC (Mobile phase: A=0.1% TFA/$H_2O$, B=0.1% TFA/MeCN; Gradient: B=10-40%; 20 min; Column: C18) to give the title compound as a yellow solid. MS (ES$^+$) $C_{20}H_{21}F_3N_8O_3$ requires: 478, found: 479 $[M+H]^+$. $^1$H NMR (600 MHz, DMSO-$d_6$) δ 11.35 (s, 1H), 8.55 (d, J=5.8 Hz, 1H), 8.52 (s, 1H), 8.47 (m, 1H), 8.22 (d, J=9.2 Hz, 1H), 7.62 (d, J=9.0 Hz, 1H), 7.50 (t, J=73 Hz, 1H), 7.31 (s, 1H), 7.19 (d, J=4.5 Hz, 1H), 5.03 (m, 1H), 4.86-4.69 (m, 2H), 4.05 (s, 2H), 3.13-2.98 (m, 2H), 2.76 (d, J=4.7 Hz, 3H), 2.21-1.96 (m, 2H).

Example 275: (R)-1-(4-(6-(2-(4-cyclopropylpyridin-2-yl)acetamido)pyridazin-3-yl)-2-fluorobutyl)-N-methyl-1H-1,2,3-triazole-4-carboxamide

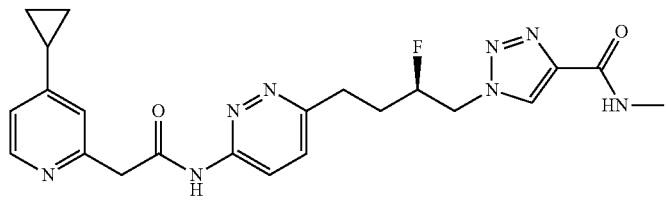

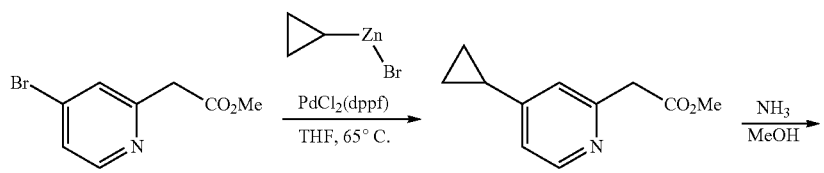

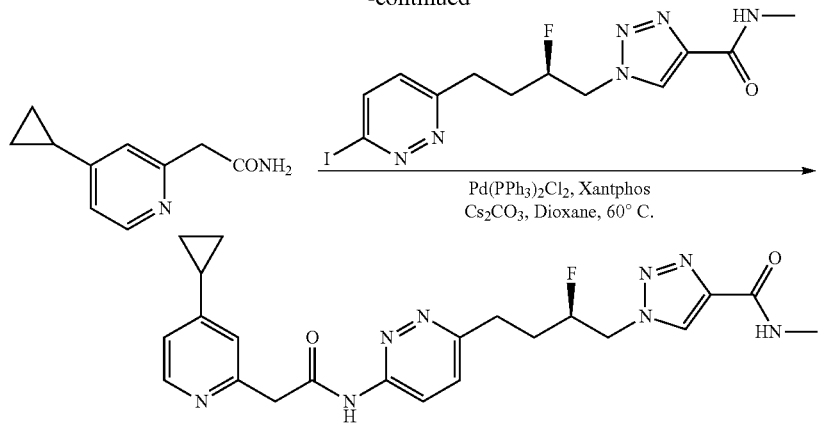

Step 1: methyl 2-(4-cyclopropylpyridin-2-yl)acetate

A degassed solution of methyl 2-(4-bromopyridin-2-yl)acetate (500 mg, 2.17 mmol), cyclopropylzinc(II) bromide in THF (0.5 M, 2.17 mL, 10.9 mmol) and PdCl$_2$(dppf)-CH$_2$Cl$_2$ (89 mg, 0.11 mmol) was stirred at 65° C. for 3 h. The mixture was diluted with EtOAc and washed with sat. aq. NH$_4$Cl. The organic layer was separated, dried over MgSO$_4$, and concentrated under reduced pressure to give the crude title compound, which was used without further purification. MS (ES$^+$) C$_{11}$H$_{13}$NO$_2$ requires: 191, found: 192 [M+H]$^+$.

Step 2: 2-(4-cyclopropylpyridin-2-yl)acetamide

To a solution of methyl 2-(4-cyclopropylpyridin-2-yl)acetate (415 mg, 2.17 mmol) in MeOH (10 ml) was added ammonia in MeOH (7 M, 12.4 ml, 86.8 mmol) and the reaction mixture was stirred at RT for 2 d. The reaction mixture was concentrated under reduced pressure, and the residue was purified by SiO$_2$ gel chromatography (0% to 20% MeOH in DCM) to give the title compound as a tan liquid (250 mg, 65% yield). MS (ES$^+$) C$_{10}$H$_{12}$N$_2$O requires: 176, found: 177 [M+H]$^+$.

Step 3: (R)-1-(4-(6-(2-(4-cyclopropylpyridin-2-yl)acetamido)pyridazin-3-yl)-2-fluorobutyl)-N-methyl-1H-1,2,3-triazole-4-carboxamide 2,2,2-trifluoroacetate A vial was charged with 2-(4-cyclopropylpyridin-2-yl)acetamide (21.8 mg, 0.124 mmol), (R)-1-(2-fluoro-4-(6-iodopyridazin-3-yl)butyl)-N-methyl-1H-1,2,3-triazole-4-carboxamide (50 mg, 0.12 mmol), Cs$_2$CO$_3$ (81.0 mg, 0.247 mmol), Pd(PPh$_3$)$_4$ (11.7 mg, 0.0120 mmol), Xantphos (14.3 mg, 0.0250 mmol), and 1,4-dioxane (1.24 mL). The mixture was evacuated and back-filled with N$_2$ three times then stirred at 60° C. for 16 h. The mixture was diluted with sat. aq. NH$_4$Cl and extracted with DCM. The organic layer was concentrated under reduced pressure and the residue purified by mass-triggered preparative HPLC (Mobile phase: A=0.1% TFA/H$_2$O, B=0.1% TFA/MeCN; Gradient: B=10-30%; 12 min; Column: C18) to give the title compound as an off-white solid (9.0 mg, 16% yield). MS (ES$^+$) C$_{22}$H$_{25}$FN$_8$O$_2$ requires: 452, found: 453 [M+H]$^+$. $^1$H NMR (DMSO-d$_6$) δ 11.48 (s, 1H), 8.58 (d, J=5.2 Hz, 1H), 8.52 (s, 1H), 8.48 (q, J=4.6, Hz, 1H), 8.18 (d, J=9.2 Hz, 1H), 7.63 (d, J=9.2 Hz, 1H), 7.56 (s, 1H), 7.47 (s, 1H), 5.03 (m, 1H), 4.78 (m, 2H), 4.16 (s, 2H), 3.04 (m, 2H), 2.77 (d, J=5.7 Hz, 3H), 2.09 (m, 3H), 1.28 (m, 2H), 1.09 (m, 2H).

Example 605: N-methyl-1-(4-(6-(2-(4-(2-(trifluoromethyl)phenyl)pyridin-2-yl)acetamido)pyridazin-3-yl)butyl)-1H-1,2,3-triazole-4-carboxamide

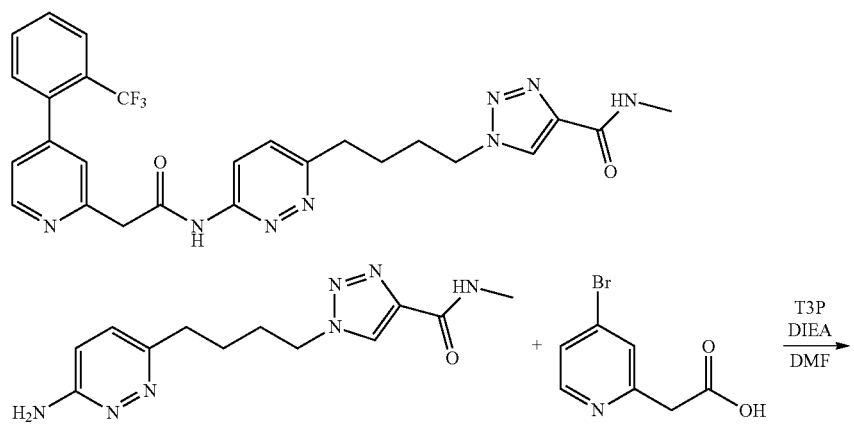

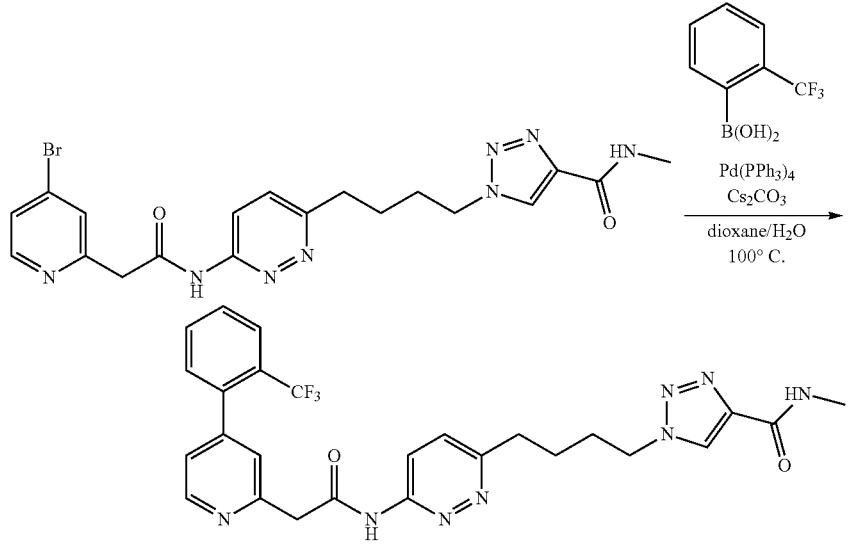

Step 1: 1-(4-(6-(2-(4-bromopyridin-2-yl)acetamido)pyridazin-3-yl)butyl)-N-methyl-1H-1,2,3-triazole-4-carboxamide To a solution of 1-(4-(6-aminopyridazin-3-yl)butyl)-N-methyl-1H-1,2,3-triazole-4-carboxamide (2.0 g, 7.2 mmol) and 2-(4-bromopyridin-2-yl)acetic acid (1.6 g, 7.2 mmol) in DMF (5 ml) were added T3P® (50 wt. % in EtOAc, 9.2 g, 14 mmol) and DIEA (2.7 g, 22 mmol). The mixture was stirred at RT for 3 h, then water (50 mL) was added, the mixture was stirred for 30 min, and precipitate was isolated by filtration to give the title compound as a yellow solid (1 g, 40%). MS (ES$^+$) C$_{19}$H$_{21}$BrN$_8$O$_2$ requires: 473, found: 474 [M+H]$^+$.

Step 2: N-methyl-1-(4-(6-(2-(4-(2-(trifluoromethyl)phenyl)pyridin-2-yl)acetamido)pyridazin-3-yl)butyl)-1H-1,2,3-triazole-4-carboxamide To a solution of 1-(4-(6-(2-(4-bromopyridin-2-yl)acetamido)pyridazin-3-yl)butyl)-N-methyl-1H-1,2,3-triazole-4-carboxamide (60 mg, 0.12 mmol), 2-(trifluoromethyl)phenylboronic acid (60 mg, 0.25 mmol), and Pd(PPh$_3$)$_4$ (15 mg, 0.012 mmol) in 1,4-dioxane (2 ml) and water (0.2 ml) was added Cs$_2$CO$_3$ (12.2 mg, 0.375 mmol), and the mixture was stirred at 100° C. for 16 h. The mixture was concentrated under reduced pressure, DMF (3 mL) was added, the mixture was filtered, and the filtrate was purified by preparatory HPLC (Mobile phase: A=0.1% ammonium hydroxide/H$_2$O, B=acetonitrile; Gradient: B=5%-95% in 18 min; Column: C18) to afford the title compound as a white solid (28 mg, 42%). MS (ES$^+$) C$_{26}$H$_{25}$F$_3$N$_8$O$_2$ requires: 538, found: 539 [M+H]$^+$. $^1$H NMR (500 MHz, DMSO-d$_6$) δ 1.63 (m, 2H), 1.88 (m, 2H), 2.75 (d, J=6 Hz, 3H), 2.89 (t, J=9.5 Hz, 3H), 4.14 (s, 2H), 4.45 (t, J=8.5 Hz, 2H), 7.46 (appar m, 2H), 7.55 (s, 1H), 7.60 (d, J=9.2 Hz, 1H), 7.76 (m, 2H), 7.91 (d, J=7.6 Hz, 1H), 8.23 (d, J=9.2 Hz, 1H), 8.45 (m, 1H), 8.56 (s, 1H), 8.68 (d, J=6.5 Hz, 1H), 11.42 (s, 1H).

Example 229: N-methyl-5-(4-(6-(2-(4-(trifluoromethyl)pyridin-2-yl)acetamido)pyridazin-3-yl)butyl)-1,3,4-thiadiazole-2-carboxamide

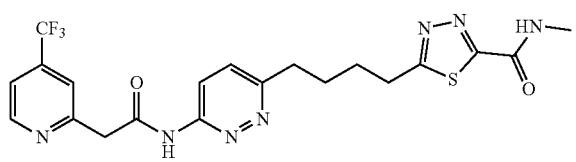 [SMILES: CNC(=O)c1nnc(CCCCc2ccc(NC(=O)Cc3cc(C(F)(F)F)ccn3)nn2)s1]

Steps 1 to 5

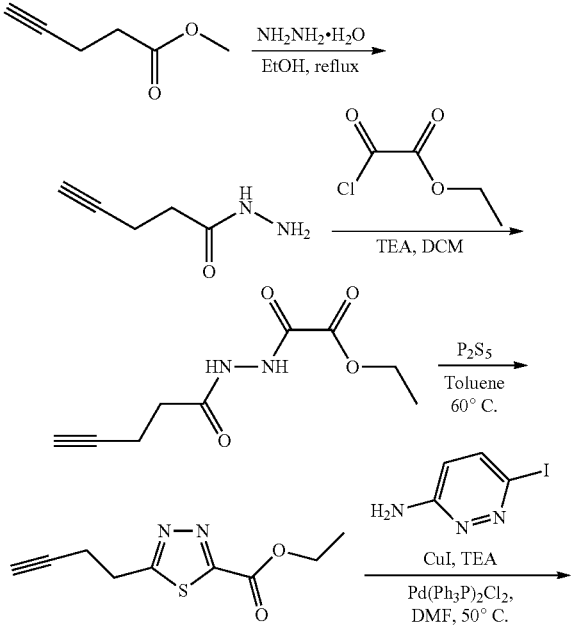

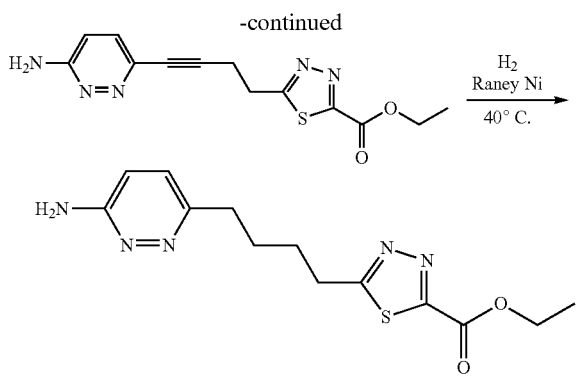

Step 1: pent-4-ynehydrazide

A mixture of methyl pent-4-ynoate (100 g, 510 mmol) and hydrazine hydrate (100 mL, 1530 mmol) in EtOH (800 mL) was stirred at reflux under Ar for 16 h. The mixture was concentrated under reduced pressure, azeotroping with toluene (2×250 mL), to give the title compound as a white solid (61 g, 100%), which was used in the next step without further purification. MS (ES$^+$) C$_5$H$_8$N$_2$O requires: 112, found: 113[M+H]$^+$.

Step 2: ethyl 2-oxo-2-(2-pent-4-ynoylhydrazinyl)acetate

To a mixture of pent-4-ynehydrazide (25.0 g, 223 mmol) and TEA (62.1 mL, 446 mmol) in DCM (500 mL) at 0° C. was added ethyl 2-chloro-2-oxoacetate (27.4 mL, 246 mmol). The mixture was stirred at RT for 30 min then filtered, washing with DCM (2×20 mL). The combined filtrates were concentrated under reduced pressure to give the title compound as a brown oil (60 g, >100%), which was used without further purification. MS (ES$^+$) C$_9$H$_{12}$N$_2$O$_4$ requires: 212, found: 213[M+H]$^+$.

Step 3: ethyl 5-(but-3-ynyl)-1,3,4-thiadiazole-2-carboxylate

A mixture of ethyl 2-oxo-2-(2-pent-4-ynoylhydrazinyl)acetate (17.5 g, 8.20 mmol) in toluene (350 mL) was stirred at 60° C. for 15 min, then P$_2$S$_5$ (20 g, 9.0 mmol) was added in portions. The mixture was stirred at 60° C. for 15 min, then allowed to cool to RT. The toluene layer was separated, and the remaining residue was taken up in sat. aq. NaHCO$_3$ (25 mL) and extracted with EtOAc (3×180 mL). The combined organic layers were concentrated under reduced pressure, and the residue was purified by SiO$_2$ gel chromatography (18% to 30% EtOAc in petroleum ether) to afford the title compound as a yellow solid (3.9 g, 22%). MS (ES$^+$) C$_9$H$_{10}$N$_2$O$_2$S requires: 210, found: 211 [M+H]$^+$.

Step 4: ethyl 5-(4-(6-aminopyridazin-3-yl)but-3-ynyl)-1,3,4-thiadiazole-2-carboxylate A mixture of ethyl 5-(but-3-ynyl)-1,3,4-thiadiazole-2-carboxylate (13.6 g, 64.8 mmol), 6-iodopyridazin-3-amine (15.0 g, 68.0 mmol), Pd(PPh$_3$)$_2$Cl$_2$ (4.55 g, 6.50 mmol), copper (I) iodide (2.47 g, 1.30 mmol) and TEA (27.0 mL, 194 mmol) in THF (200 mL) under Ar was stirred at 50° C. for 1 h, then filtered through a short SiO$_2$ gel column, washing with THF (500 mL) and 4:1 v:v DCM/EtOH (800 mL). The filtrate was concentrated under reduced pressure to afford 44 g of a brown oil, which was washed with Et$_2$O (200 mL×2) and 8:1 v:v Et$_2$O/EtOAc (200 mL). The resulting brown oil was triturated with 95% EtOH (20 mL) and water (160 mL), solid was removed by filtration, and the filtrate was extracted with DCM (150 mL×3). The combined final organic layers were concentrated under reduced pressure to afford the title compound as a brown oil (18.9 g, 96%). MS (ES$^+$) C$_{13}$H$_{13}$N$_5$O$_2$S requires: 303, found: 304 [M+H]$^+$.

Step 5: ethyl 5-(4-(6-aminopyridazin-3-yl)butyl)-1,3,4-thiadiazole-2-carboxylate A reaction vessel containing ethyl 5-(4-(6-aminopyridazin-3-yl)but-3-ynyl)-1,3,4-thiadiazole-2-carboxylate (18.9 g, 62.4 mmol) and Raney Ni (9.0 g) in EtOH (800 mL) was charged with H$_2$ three times, stirred at 40° C. for 1.5 h, purged with N$_2$, filtered, washed with hot EtOH (400 mL, 70-80° C.), and concentrated under reduced pressure to afford 16 g of a brown oil. To this oil was added 40 mL of EtOAc, the mixture was stirred for 10 min, then Et$_2$O (200 mL) was added slowly. The mixture was stirred at RT for 30 min, and solid was isolated by filtration, washed with 1:5 v:v EtOAc/Et$_2$O (2×20), and dried to afford the title compound as a white solid (11.6 g, 61%). MS (ES$^+$) C$_{13}$H$_{17}$N$_5$O$_2$S requires: 307, found: 308[M+H]$^+$.

Steps 6 to 9

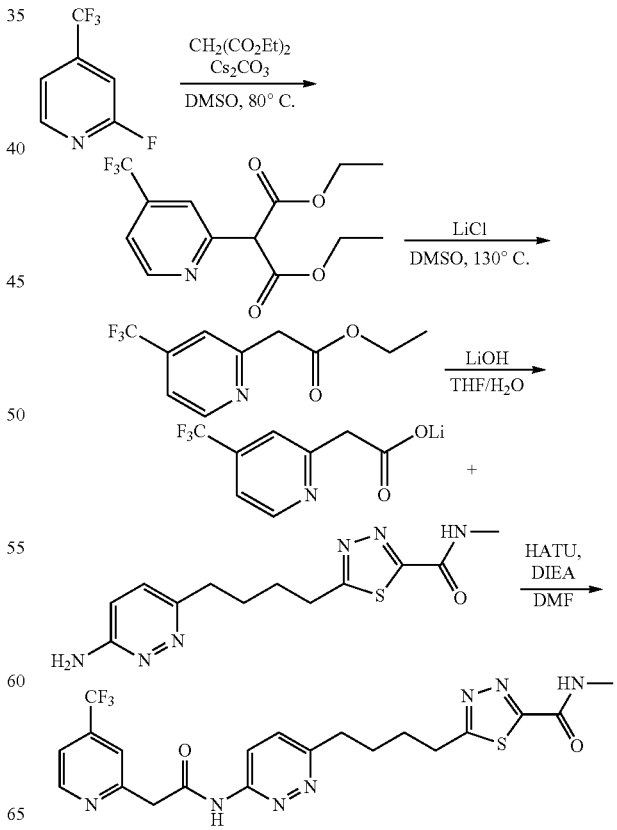

Step 6: diethyl 2-(4-(trifluoromethyl)pyridin-2-yl)malonate

To a solution of 2-fluoro-4-(trifluoromethyl)pyridine (25 g, 0.15 mol) in DMSO (200 mL) were added $Cs_2CO_3$ (97.5 g, 0.300 mol) and diethyl malonate (48 g, 0.30 mol), and the mixture was stirred under $N_2$ at 80° C. for 3 h. The mixture was allowed to cool to RT, filtered, and the filtrate was treated with DCM (200 mL). Crude title compound crystallized from the solution as a white solid, which was used without further purification (40 g, 87%). MS (ES$^+$) $C_{13}H_{14}F_3NO_4$ requires: 305, found: 306 [M+H]$^+$.

Step 7: ethyl 2-(4-(trifluoromethyl)pyridin-2-yl)acetate

To a solution of diethyl 2-(4-(trifluoromethyl)pyridin-2-yl)malonate (4.7 g, 0.015 mol) in DMSO (30 mL) was added lithium chloride (1.9 g, 0.046 mol) and the solution was stirred under $N_2$ at 130° C. for 3 h, then allowed to cool to RT and treated with water (20 mL). The mixture was extracted with EtOAc (2×50 mL), and the combined organic layers were washed with sat. aq. NaCl, dried over $Na_2SO_4$, and concentrated under reduced pressure. The residue was purified by $SiO_2$ gel chromatography (9% EtOAc in petroleum ether) to give the title compound as a yellow oil (1.7 g, 49%). MS (ES$^+$) $C_{10}H_{10}F_3NO_2$ requires: 233, found: 234 [M+H]$^+$.

Step 8: ethyl lithium 2-(4-(trifluoromethyl)pyridin-2-yl)acetate

Lithium hydroxide (0.610 g, 14.4 mmol) was dissolved in ethanol (20 mL), then 2-(4-(trifluoromethyl)pyridin-2-yl) acetate (1.7 g, 7.2 mmol) was added slowly, and the reaction mixture was stirred at RT for 3 h. The mixture was concentrated under reduced pressure to give the crude title compound as a yellow solid, which was used without further purification (1.3 g, 86%). MS (ES$^+$) $C_8H_6F_3NO_2$ requires: 205, found: 206 [M+H]$^+$.

Step 9: N-methyl-5-(4-(6-(2-(4-(trifluoromethyl) pyridin-2-yl)acetamido)pyridazin-3-yl)butyl)-1,3,4-thiadiazole-2-carboxamide 2,2,2-trifluoroacetate To a solution of crude lithium 2-(4-(trifluoromethyl) pyridin-2-yl)acetate (21.7 mg, 0.103 mmol) in DMF (0.5 ml) were added 5-(4-(6-aminopyridazin-3-yl)butyl)-N-methyl-1,3,4-thiadiazole-2-carboxamide (30 mg, 0.10 mmol), HATU (42.9 mg, 0.113 mmol) and DIEA (0.054 ml, 0.31 mmol), and the resulting mixture was stirred at RT for 2 h. The mixture was concentrated under reduced pressure, and the residue was purified by mass-triggered preparative HPLC (Mobile phase: A=0.1% TFA/$H_2O$, B=0.1% TFA/MeCN; Gradient: B=10-50%; 12 min; Column: C18) to give the title compound as a white solid (3 mg, 5%). MS (ES$^+$) $C_{20}H_{20}F_3N_7O_2S$ requires: 479, found: 480 [M+H]$^+$. $^1$H NMR (600 MHz, MeOH-$d_4$) δ 8.77 (d, J=5.2 Hz, 1H), 8.54 (d, J=9.2 Hz, 1H), 7.82 (d, J=9.3 Hz, 1H), 7.79 (s, 1H), 7.63 (d, J=5.3 Hz, 1H), 4.85 (s, 2H), 3.23 (t, J=6.8 Hz, 2H), 3.2 (t, J=7.4 Hz, 2H), 2.94 (s, 3H), 1.95-1.85 (m, 4H).

Example 508: 5-(3-fluoro-4-(4-(methylcarbamoyl)-1H-1,2,3-triazol-1-yl)butyl)-N-((4-(trifluoromethyl) pyridin-2-yl)methyl)-1,3,4-thiadiazole-2-carboxamide

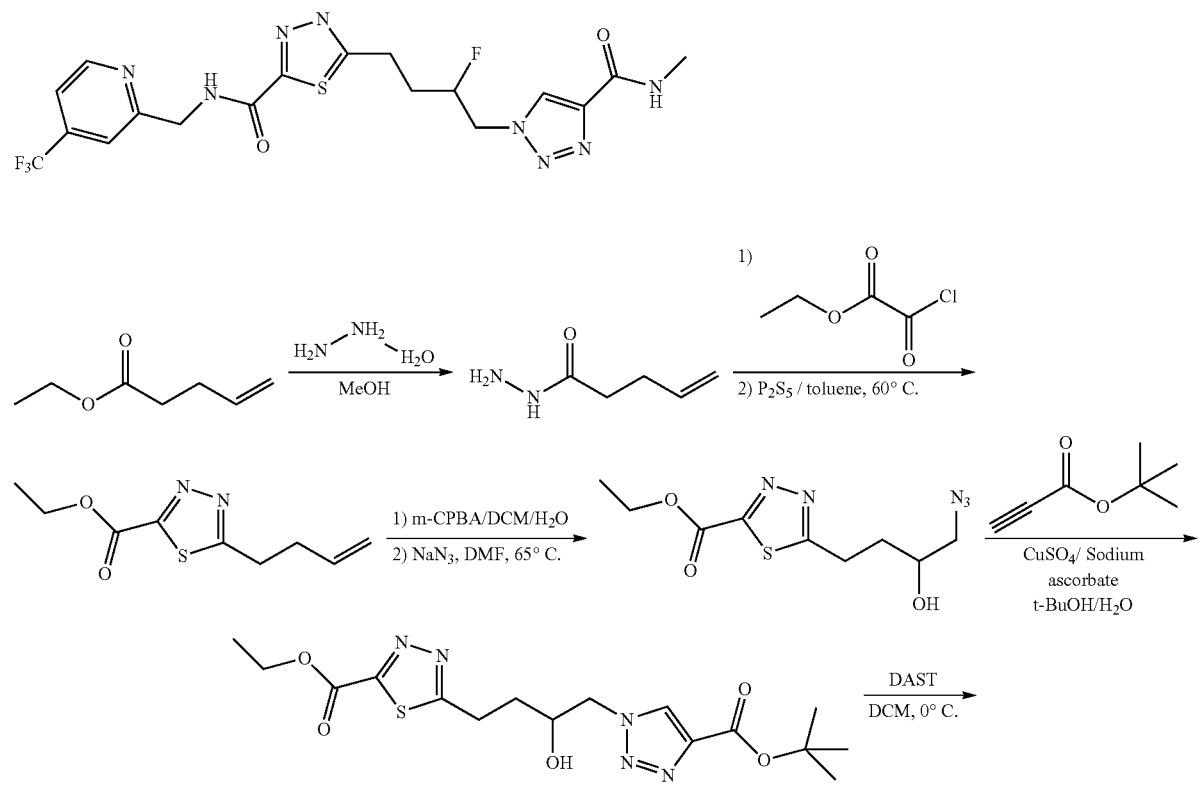

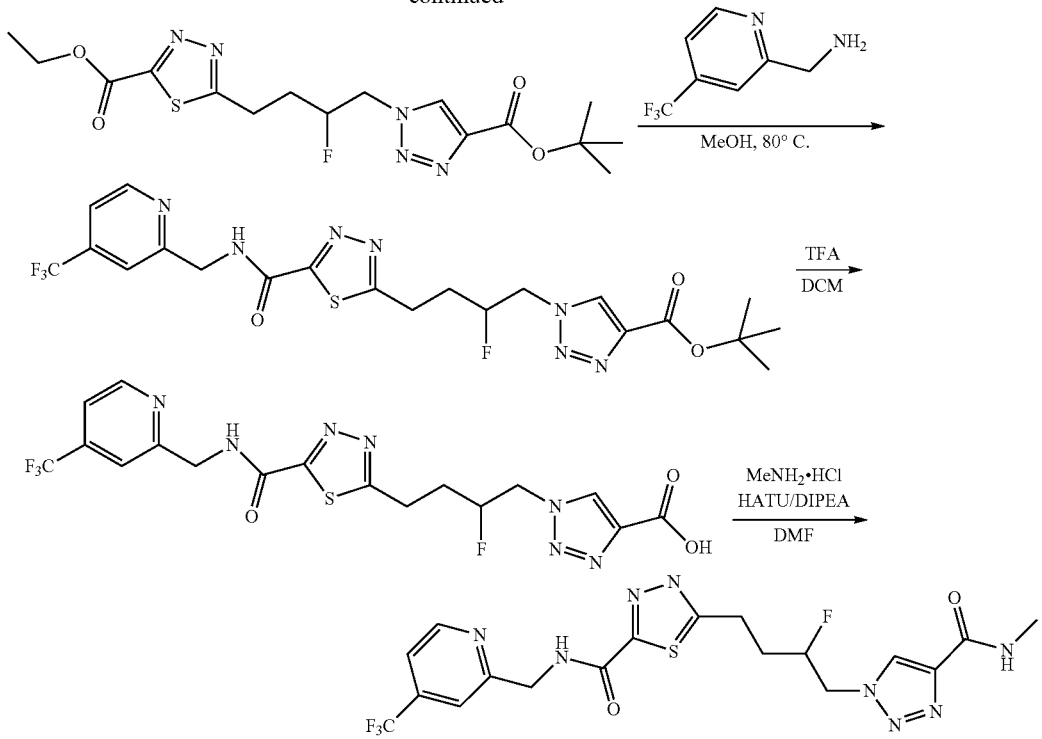

Step 1: pent-4-enehydrazide

Hydrazine hydrate (7.60 g, 152 mmol) was added to a solution of ethyl pent-4-enoate (19.5 g, 152 mmol) in 120 mL of MeOH. The mixture was stirred at RT for 48 h. The mixture was concentrated under reduced pressure to give the title compound as a white solid (11 g, 64%). MS (ES$^+$) $C_5H_{10}N_2O$ requires: 114, found: 115[M+H]$^+$.

Step 2: ethyl 5-(but-3-enyl)-1,3,4-thiadiazole-2-carboxylate

To a mixture of pent-4-enehydrazide (1.14 g, 10.0 mmol) and TEA (2.1 mL, 15 mmol) in anhydrous THF (20 mL) at 0° C. was slowly added ethyl oxalyl chloride (1.34 mL, 12.0 mmol). The mixture was stirred at 0° C. for 30 min. The mixture was concentrated under reduced pressure and the residue dissolved in toluene (20 mL). $P_2S_5$ (4.44 g, 20.0 mmol) was added, and the mixture was stirred at 60° C. for 20 min. The mixture was filtered and the residue was washed with EtOAc. The filtrate was concentrated under reduced pressure and purified by SiO$_2$ gel chromatography (20% EtOAc in petroleum ether) to give the title compound as a yellow oil (1.6 g, 76%). MS (ES$^+$) $C_9H_{12}N_2O_2S$ requires: 212, found: 213[M+H]$^+$.

Step 3: ethyl 5-(4-azido-3-hydroxybutyl)-1,3,4-thiadiazole-2-carboxylate

To a mixture of ethyl 5-(but-3-enyl)-1,3,4-thiadiazole-2-carboxylate (10.0 g, 47.2 mmol) and NaHCO$_3$ (40.0 g, 476 mmol) in 10:1 v:v DCM/water (220 mL) was added m-chloroperbenzoic acid (10.0 g, 56.6 mmol). The mixture was stirred at RT for 40 min then additional m-chloroperbenzoic acid (6.00 g, 37.8 mmol) was added. The mixture was stirred at RT for 2 h then additional m-chloroperbenzoic acid (8.00 g, 47.2 mmol) was added. The mixture was stirred for 2 h, then quenched with water and partitioned between DCM and water. The aqueous layer was extracted with DCM (3×100 mL). The combined organic layers were washed with sat. aq. Na$_2$SO$_3$ and sat. aq. NaHCO$_3$, dried and concentrated under reduced pressure to afford a crude product, which was dissolved in 80 mL of DMF. To the solution was slowly added NaN$_3$ (9.20 g, 142 mmol). The mixture was stirred at 65° C. for 16 h, then diluted with water and extracted with EtOAc (3×150 mL). The combined organic layers were washed with sat. aq. NaCl, dried and concentrated under reduced pressure. The residue was purified by SiO$_2$ gel chromatography (25% to 50% EtOAc in petroleum ether) to give the title compound as a brown oil (10 g, 26%). MS (ES$^+$) $C_9H_{13}N_5O_3S$ requires: 271, found: 272[M+H]$^+$.

Step 4: ethyl 5-(4-(4-(tert-butoxycarbonyl)-1H-1,2,3-triazol-1-yl)-3-hydroxybutyl)-1,3,4-thiadiazole-2-carboxylate A mixture of ethyl 5-(4-azido-3-hydroxybutyl)-1,3,4-thiadiazole-2-carboxylate (1.0 g, 3.7 mmol), tert-butyl propiolate (558 mg, 4.40 mmol), CuSO$_4$ (200 mg) and sodium ascorbate (400 mg) in 1:1 v:v t-BuOH/water (20 mL) was stirred at RT for 2 h. The mixture was diluted with water, then extracted with EtOAc (3×30 mL). The combined organic layers were dried and concentrated under reduced pressure to give the title compound as a yellow solid (1.4 g, 96%). MS (ES$^+$) $C_{16}H_{23}N_5O_5S$ requires: 397, found: 420 [M+Na]$^+$.

Step 5: ethyl 5-(4-(4-(tert-butoxycarbonyl)-1H-1,2,3-triazol-1-yl)-3-fluorobutyl)-1,3,4-thiadiazole-2-carboxylate To a mixture of ethyl 5-(4-(4-(tert-butoxycarbonyl)-1H-1,2,3-triazol-1-yl)-3-hydroxybutyl)-1,3,4-thiadiazole-2-carboxylate (1.4 g, 3.5 mmol) and pyridine (0.150 mL, 1.86 mmol) in DCM (30 mL) at 0° C. was slowly added DAST (2.27 g, 14.1 mmol). The mixture was stirred at 0° C. for 30 min. The mixture was added slowly to an ice-cold saturated NaHCO$_3$ solution, then extracted with DCM (3×30 mL). The combined organic layers were dried and concentrated under reduced pressure. The residue was purified by SiO$_2$ gel chromatography (25% EtOAc in petroleum ether) to give the title compound as an orange solid (440 mg, 31%). MS (ES$^+$) C$_{16}$H$_{22}$FN$_5$O$_4$S requires: 399, found: 422[M+Na]$^+$.

The next steps outline the preparation of racemic EXAMPLE 508. For the preparation of enantiomeric enriched EXAMPLE 220 and EXAMPLE 221, a chiral separation was performed at this stage and the products carried through using the same general procedure. Ethyl 5-(4-(4-(tert-butoxycarbonyl)-1H-1,2,3-triazol-1-yl)-3-fluorobutyl)-1,3,4-thiadiazole-2-carboxylate was separated into its separate enantiomers using chiral SFC separation (column: IC 4.6*150 mm Sum; solvent: MeOH). Enantiomers are arbitrarily assigned in the final products.

Step 6: tert-butyl 1-(2-fluoro-4-(5-((4-(trifluoromethyl)pyridin-2-yl)methylcarbamoyl)-1,3,4-thiadiazol-2-yl)butyl)-1H-1,2,3-triazole-4-carboxylate A mixture of ethyl 5-(4-(4-(tert-butoxycarbonyl)-1H-1,2,3-triazol-1-yl)-3-fluorobutyl)-1,3,4-thiadiazole-2-carboxylate (150 mg, 0.38 mmol) and (4-(trifluoromethyl)pyridin-2-yl)methanamine (100 mg, 0.56 mmol) in MeOH (2 mL) was stirred at 80° C. for 3 d in a sealed tube. The mixture was concentrated under reduced pressure to afford the title compound as a yellow solid (195 mg, 98%). MS (ES$^+$) C$_{21}$H$_{23}$F$_4$N$_7$O$_3$S requires: 529, found: 530[M+H]$^+$.

Step 7: 1-(2-fluoro-4-(5-((4-(trifluoromethyl)pyridin-2-yl)methylcarbamoyl)-1,3,4-thiadiazol-2-yl)butyl)-1H-1,2,3-triazole-4-carboxylic Acid TFA (2 mL) was added to a solution of tert-butyl 1-(2-fluoro-4-(5-((4-(trifluoromethyl)pyridin-2-yl)methylcarbamoyl)-1,3,4-thiadiazol-2-yl)butyl)-1H-1,2,3-triazole-4-carboxylate (195 mg, 0.370 mmol) in DCM (3 mL). The mixture was stirred at RT for 3 h then concentrated under reduced pressure. MeOH was added to the residue, and precipitate was isolated by filtration to give the title compound as a beige solid (170 mg, 98%). MS (ES$^+$) C$_{17}$H$_{15}$F$_4$N$_7$O$_3$S requires: 473, found: 474[M+H]$^+$.

Step 8: 5-(3-fluoro-4-(4-(methylcarbamoyl)-1H-1,2,3-triazol-1-yl)butyl)-N-((4-(trifluoromethyl)pyridin-2-yl)methyl)-1,3,4-thiadiazole-2-carboxamide A mixture of 1-(2-fluoro-4-(5-((4-(trifluoromethyl)pyridin-2-yl)methylcarbamoyl)-1,3,4-thiadiazol-2-yl)butyl)-1H-1,2,3-triazole-4-carboxylic acid (40 mg, 0.085 mmol), methylamine hydrochloride (9.0 mg, 0.13 mmol), HATU (48 mg, 0.13 mmol) and DIEA (33 mg, 0.25 mmol) in DMF (1 mL) was stirred at RT for 2 h then treated with water. Precipitate was isolated by filtration and washed with MeOH to give the title compound as a white solid (20 mg, 49%). MS (ES$^+$) C$_{18}$H$_{18}$F$_4$N$_8$O$_2$S requires: 486, found: 487[M+H]$^+$; 1H NMR (500 MHz, DMSO-d$_6$) δ 9.81 (t, J=6.1 Hz, 1H), 8.81 (m, 1H), 8.53 (s, 1H), 8.50 (m, 1H), 7.73 (s, 1H), 7.69 (m, 1H), 5.06 (m, 1H), 4.88-4.73 (m, 2H), 4.70 (d, J=6.1 Hz, 2H), 3.34 (appar s, 2H), 2.76 (d, J=4.7 Hz, 3H), 2.36-2.07 (m, 2H).

Example 540: 1-(2-fluoro-4-(5-(2-(pyridin-2-yl)acetamido)-1,3,4-thiadiazol-2-yl)butyl)-N-((4-(trifluoromethyl)pyridin-2-yl)methyl)-1H-1,2,3-triazole-4-carboxamide

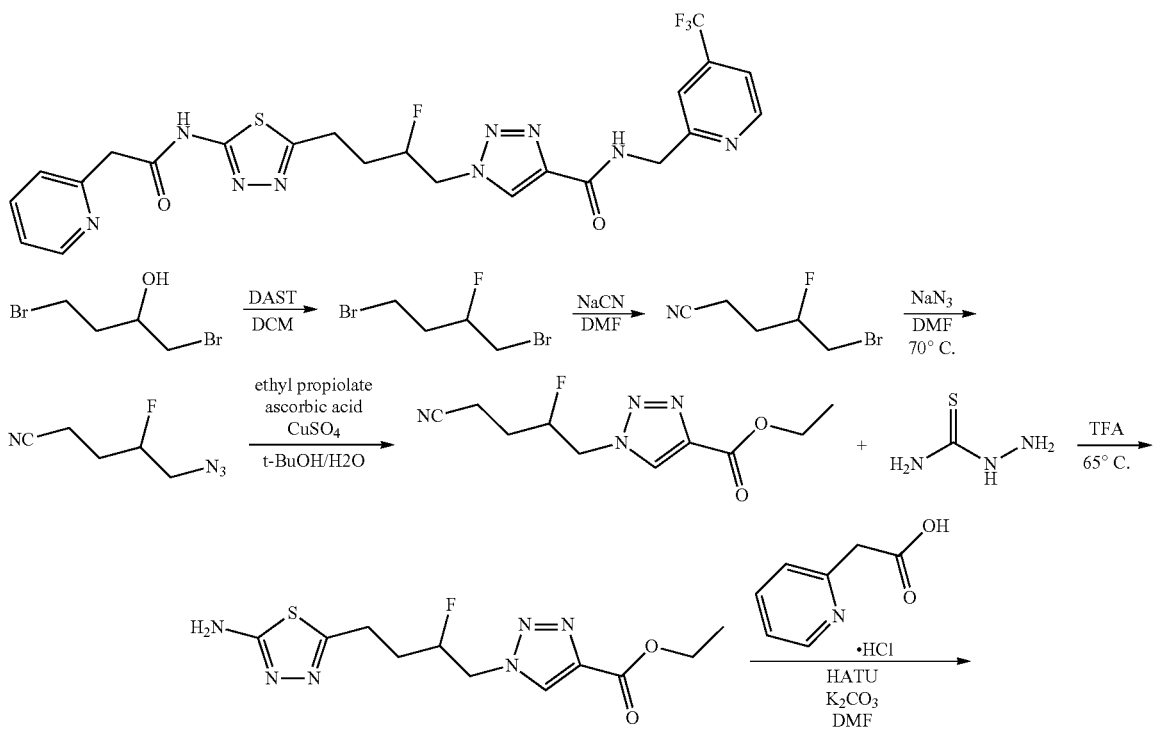

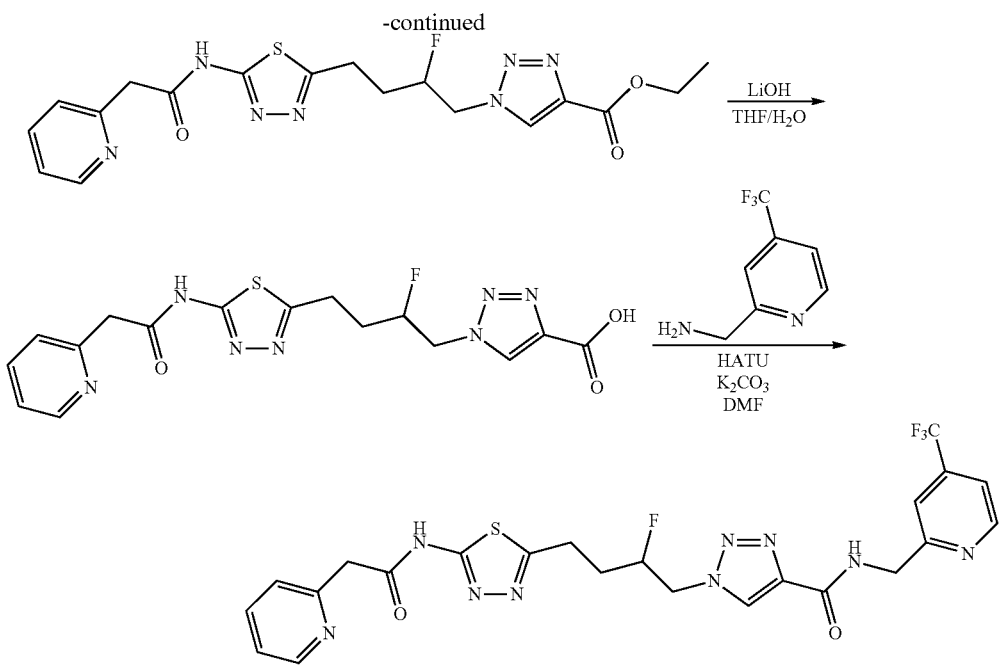

Step 1: 1,4-dibromo-2-fluorobutane

To a solution of 1,4-dibromobutan-2-ol (50.0 g, 216 mmol) in DCM (200 ml) at 0-5° C. was added DAST (38.2 g, 237 mmol). The mixture was allowed to warm to RT and stirred for 16 h. The mixture was added to a solution of sat. aq. NaHCO$_3$ (200 ml) at 0-5° C. and extracted with DCM (2×200 ml). The combined organic layers were washed with sat. aq. NaCl (300 mL), dried over Na$_2$SO$_4$, filtered and concentrated under reduced pressure to give the presumed title compound as a yellow oil (40.0 g, 80%).

Step 2: 5-bromo-4-fluoropentanenitrile

A solution of 1,4-dibromo-2-fluorobutane (5.0 g, 21 mmol) and NaCN (1.05 g, 21.0 mmol) in DMF (10 mL) was stirred at RT for 16 h. Water (50 ml) was added, and the mixture was extracted with EtOAc (3×60 mL). The combined organic layers were washed with sat. aq. NaCl (100 mL), dried over Na$_2$SO$_4$, filtered and concentrated under reduced pressure to give the crude title compound as a yellow oil (3.78 g, 100%).

Step 3: 5-azido-4-fluoropentanenitrile

A solution of 5-bromo-4-fluoropentanenitrile (540 mg, 3.00 mmol) and sodium azide (195 mg, 3.00 mmol) in DMF (5 mL) was stirred at 70° C. for 16 h to give the title compound as a solution, which was used in the next step without purification (assumed 426 mg, 100% crude).

Step 4: ethyl 1-(4-cyano-2-fluorobutyl)-1H-1,2,3-triazole-4-carboxylate

A solution of crude 5-azido-4-fluoropentanenitrile (426 mg, 3.00 mmol), ethyl propiolate (441 mg, 4.50 mmol) L-(+)-ascorbic acid (192 mg, 0.970 mmol) and CuSO$_4$-5H$_2$O (86 mg, 0.34 mmol) in 1:1 v:v t-BuOH/water (20 ml) was stirred at RT for 3 h, then extracted with EtOAc (3×60 mL). The combined organic layers were washed with sat. aq. NaCl (100 mL), dried over Na$_2$SO$_4$, filtered and concentrated under reduced pressure to give the title compound as a yellow oil (450 mg, 62%). MS (ES$^+$) C$_{10}$H$_{13}$FN$_4$O$_2$ requires: 240, found: 241 [M+H]$^+$.

Step 5: ethyl 1-(4-cyano-2-fluorobutyl)-1H-1,2,3-triazole-4-carboxylate

A solution of ethyl 1-(4-cyano-2-fluorobutyl)-1H-1,2,3-triazole-4-carboxylate (450 mg, 1.88 mmol) and hydrazinecarbothioamide (341 mg, 3.75 mmol) in TFA (5 mL) was stirred at 70° C. for 16 h. The mixture was concentrated under reduced pressure, and to the residue was added sat. aq. NaHCO$_3$ (20 mL). The mixture was extracted with EtOAc (3×50 mL). The combined organic layers were concentrated under reduced pressure to give a yellow solid, which was washed with water (20 mL) and Et$_2$O (30 mL) to give the title compound as a white solid (200 mg, 33%). MS (ES$^+$) C$_{11}$H$_{15}$FN$_6$O$_2$S requires: 314, found: 315 [M+H]$^+$.

Step 6: ethyl 1-(2-fluoro-4-(5-(2-(pyridin-2-yl)acetamido)-1,3,4-thiadiazol-2-yl)butyl)-1H-1,2,3-triazole-4-carboxylate A solution of ethyl 1-(4-(5-amino-1,3,4-thiadiazol-2-yl)-2-fluorobutyl)-1H-1,2,3-triazole-4-carboxylate (160 mg, 0.50 mmol), 2-(pyridin-2-yl)acetic acid hydrochloride (87 mg, 0.50 mmol), HATU (285 mg, 0.75 mmol) and K$_2$CO$_3$ (207 mg, 1.50 mmol) in DMF (5 mL) was stirred at RT for 16 h. The mixture was diluted with water (30 mL), then extracted with 10:1 v:v DCM/MeOH (3×50 mL). The combined organic layers were washed with sat. aq. NaCl (100 mL), dried over Na$_2$SO$_4$, filtered and concentrated under reduced pressure to give the title compound as a white solid (194 mg, 89%). MS (ES$^+$) C$_{18}$H$_{20}$FN$_7$O$_3$S requires: 433, found: 434 [M+H]$^+$.

Step 7: 1-(2-fluoro-4-(5-(2-(pyridin-2-yl)acetamido)-1,3,4-thiadiazol-2-yl)butyl)-1H-1,2,3-triazole-4-carboxylic Acid A solution of ethyl 1-(2-fluoro-4-(5-(2-(pyridin-2-yl)acetamido)-1,3,4-thiadiazol-2-yl)butyl)-1H-1,2,3-triazole-4-carboxylate (150 mg, 0.35 mmol) and LiOH (17 mg, 0.70 mmol) in 1:1 v:v THF/H$_2$O (5 mL) was stirred at RT for 16 h. The solvent was removed, and the residue was purified by preparative HPLC (Mobile phase: A=0.1% ammonium hydroxide/H$_2$O, B=acetonitrile; Gradient: B=5%-95% in 18 min; Column: C18) to give the title compound as a white solid (120 mg, 66%). MS (ES$^+$) C$_{16}$H$_{16}$FN$_7$O$_3$S requires: 405, found: 406 [M+H]$^+$.

Step 8: 1-(2-fluoro-4-(5-(2-(pyridin-2-yl)acetamido)-1,3,4-thiadiazol-2-yl)butyl)-N-((4-(trifluoromethyl)pyridin-2-yl)methyl)-1H-1,2,3-triazole-4-carboxamide A solution of 1-(2-fluoro-4-(5-(2-(pyridin-2-yl)acetamido)-1,3,4-thiadiazol-2-yl)butyl)-1H-1,2,3-triazole-4-carboxylic acid (41 mg, 0.10 mmol), (4-(trifluoromethyl)pyridin-2-yl)methanamine (18 mg, 0.10 mmol), HATU (57 mg, 0.15 mmol) and K$_2$CO$_3$ (42 mg, 0.30 mmol) in DMF (1 mL) was stirred at RT for 16 h. The mixture was purified by preparative HPLC (Mobile phase: A=0.1% ammonium hydroxide/H$_2$O, B=acetonitrile; Gradient: B=5%-95% in 18 min; Column: C18) to afford the title compound as a white solid (25 mg, 45%). MS (ES$^+$) C$_{23}$H$_{21}$F$_4$N$_9$O$_2$S requires: 563, found: 564 [M+H]$^+$. $^1$H NMR (500 MHz, DMSO-d$_6$) δ 12.83 (br s, 1H), 9.25 (t, J=6.0 Hz, 1H), 8.81 (d, J=5.0 Hz, 1H), 8.65 (m, 1H), 8.61 (s, 1H), 8.06 (s, 1H), 7.74-7.62 (m, 3H), 7.54 (m, 1H) 5.06 (m, 1H), 4.89-4.65 (m, 4H), 4.15 (s, 2H), 3.17 (m, 2H), 2.25-1.98 (m, 2H).

Example 397: 1-(2-fluoro-4-(5-(2-(4-(3-(trifluoromethoxy)phenyl)pyridin-2-yl)acetamido)-1,3,4-thiadiazol-2-yl)butyl)-N-methyl-1H-1,2,3-triazole-4-carboxamide 2,2,2-trifluoroacetate

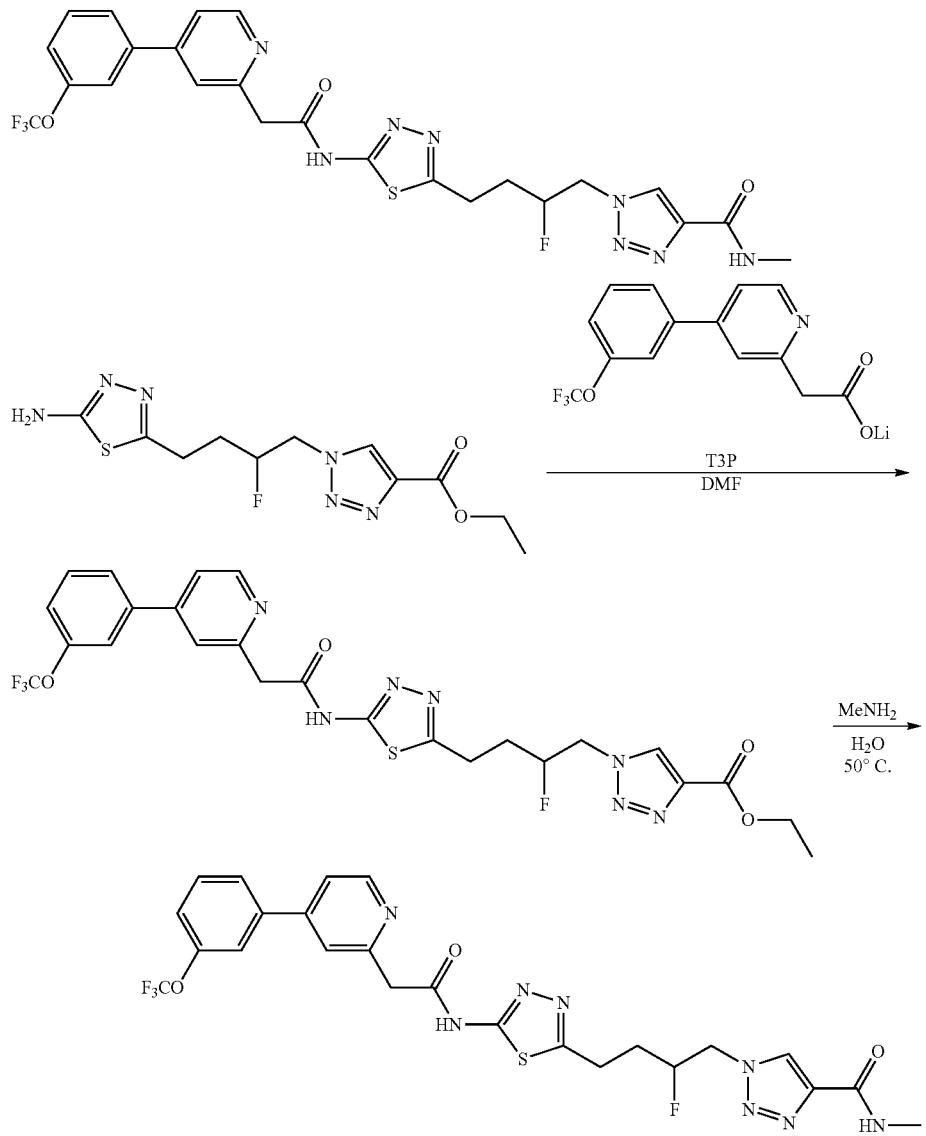

Step 1: ethyl 1-(2-fluoro-4-(5-(2-(4-(3-(trifluoromethoxy)phenyl)pyridin-2-yl)acetamido)-1,3,4-thiadiazol-2-yl)butyl)-1H-1,2,3-triazole-4-carboxylate To a suspension of lithium 2-(4-(3-(trifluoromethoxy)phenyl)pyridin-2-yl)acetate (0.104 g, 0.343 mmol) and ethyl 1-(4-(5-amino-1,3,4-thiadiazol-2-yl)-2-fluorobutyl)-1H-1,2,3-triazole-4-carboxylate (0.073 g, 0.23 mmol) in DMF (2 ml) at 0° C. was added T3P® (50 wt. % in DMF, 0.55 ml, 0.86 mmol), and the mixture was stirred for 1 h at 0° C. then 1 h at RT. The resulting bright yellow-orange mixture was partitioned between EtOAc and water, and the organic layer was washed with water, dried over $Na_2SO_4$, filtered, and concentrated under reduced pressure. The residue was purified by $SiO_2$ gel chromatography (2% to 5% MeOH in DCM) to give the title compound as a yellow solid (67 mg, 49% yield). MS (ES$^+$) $C_{25}H_{23}F_4N_7O_4S$ requires: 593, found: 594 [M+H]$^+$.

Step 2: 1-(2-fluoro-4-(5-(2-(4-(3-(trifluoromethoxy)phenyl)pyridin-2-yl)acetamido)-1,3,4-thiadiazol-2-yl)butyl)-N-methyl-1H-1,2,3-triazole-4-carboxamide 2,2,2-trifluoroacetate To a solution of ethyl 1-(2-fluoro-4-(5-(2-(4-(3-(trifluoromethoxy)phenyl)pyridin-2-yl)acetamido)-1,3,4-thiadiazol-2-yl)butyl)-1H-1,2,3-triazole-4-carboxylate (10 mg, 0.017 mmol) in 1,4-dioxane (0.2 ml) was added aq. methylamine (40% w/v, 0.10 mL, 1.3 mmol) and the mixture was stirred at 50° C. for 1 h. The mixture was concentrated under reduced pressure, and the residue was dissolved in DMSO and directly purified by mass-triggered preparative HPLC (Mobile phase: A=0.1% TFA/$H_2O$, B=0.1% TFA/MeCN; Gradient: B=30-70%; 12 min; Column: C18) to give the title compound as a white powder (7.0 mg, 60% yield). MS (ES$^+$) $C_{24}H_{22}F_4N_8O_3S$ requires: 578, found: 579 [M+H]$^+$. $^1$H NMR (600 MHz, DMSO-$d_6$) δ 12.74 (s, 1H), 8.62 (d, J=5.0 Hz, 1H), 8.51 (s, 1H), 8.48 (m, 1H), 7.87 (m, 2H), 7.82 (s, 1H), 7.73 (d, J=4.7 Hz, 1H), 7.69 (t, J=8.0 Hz, 1H), 7.52 (d, J=8.2 Hz, 1H), 5.04 (m, 1H), 4.85-4.69 (m, 2H), 4.11 (s, 2H), 3.15 (m, 2H), 2.76 (d, J=4.6 Hz, 3H), 2.21-1.96 (m, 2H).

Example 250: (R)-1-(2-fluoro-4-(5-(2-(pyridin-2-yl)acetamido)-1,3,4-thiadiazol-2-yl)butyl)-N-((4-(trifluoromethyl)pyridin-2-yl)methyl)-1H-1,2,3-triazole-4-carboxamide

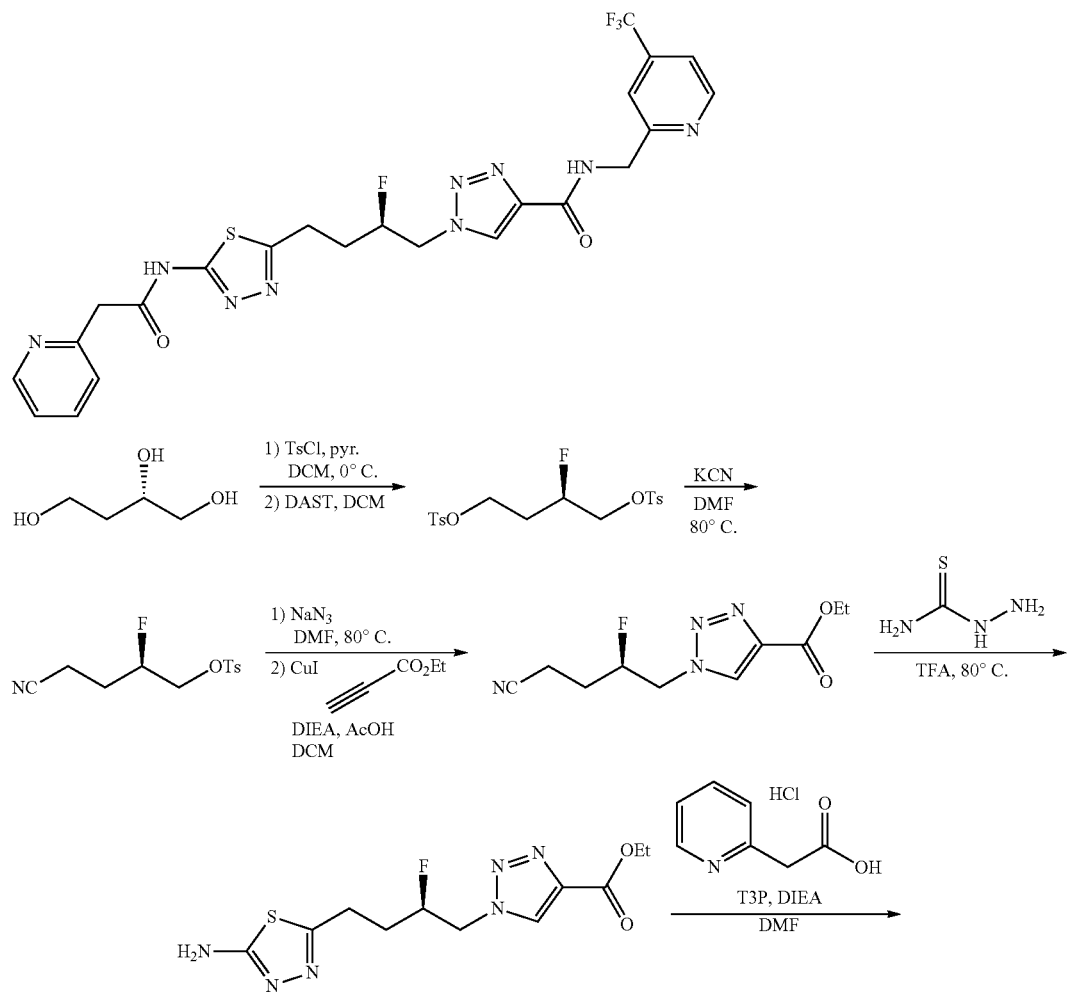

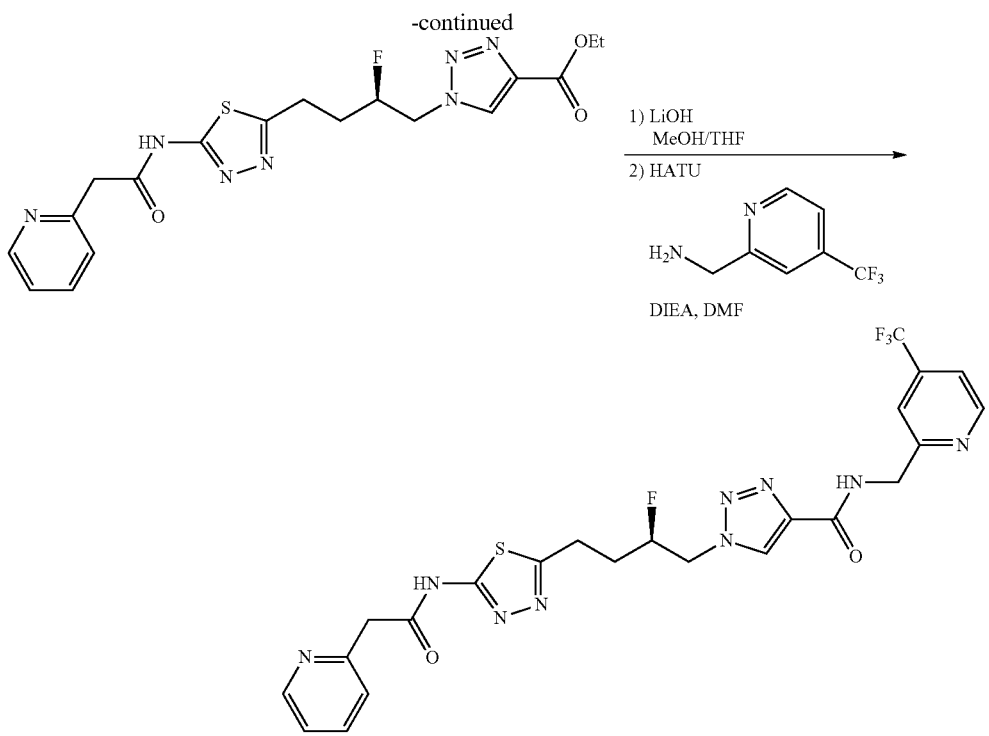

Step 1: (S)-2-hydroxybutane-1,4-diyl bis(4-methylbenzenesulfonate)

To a cooled 0° C. solution of (S)-butane-1,2,4-triol (2.10 ml, 23.6 mmol) in DCM (47 ml) was added 4-toluenesulfonyl chloride (11.2 g, 58.9 mmol) followed by pyridine (5.69 ml, 70.7 mmol). The resulting mixture was stirred at 0° C. for 12 h. The mixture was concentrated under reduced pressure and the residue was purified by $SiO_2$ gel chromatography (0% to 100% EtOAc in hexanes) to give the title compound as a colorless liquid (4.98 g, 51% yield). MS (ES$^+$) $C_{18}H_{22}O_7S_2$ requires: 414, found: 415 [M+H]$^+$.

Step 2: (R)-2-fluorobutane-1,4-diyl bis(4-methylbenzenesulfonate)

To a cooled 0° C. solution of (S)-2-hydroxybutane-1,4-diyl bis(4-methylbenzenesulfonate) (4.98 g, 12.0 mmol) in DCM (60 ml) was added DAST (2.39 ml, 18.1 mmol) and the resulting mixture was stirred as it warmed to RT for 4 h. The mixture was filtered through a plug of $SiO_2$ gel, eluting with EtOAc. The filtrate was concentrated under reduced pressure to give the title compound as a red liquid (4.29 g, 85% yield). MS (ES$^+$) $C_{18}H_{21}FO_6S_2$ requires: 416, found: 439 [M+Na]$^+$.

Step 3: (R)-4-cyano-2-fluorobutyl 4-methylbenzenesulfonate

To a solution of (R)-2-fluorobutane-1,4-diyl bis(4-methylbenzenesulfonate) (4.29 g, 10.3 mmol) in DMF (24 ml) was added KCN (0.957 g, 14.7 mmol) and the resulting mixture was stirred at 80° C. for 4 h. The mixture was allowed to cool to RT, diluted with EtOAc (24 mL), and filtered through a plug of $SiO_2$ gel, eluting with EtOAc (50 mL). The filtrate was concentrated under reduced pressure to give the title compound as a colorless liquid (2.41 g, 86% yield). MS (ES$^+$) $C_{12}H_{14}FNO_3S$ requires: 271, found: 294 [M+Na]$^+$.

Step 4: Ethyl (R)-1-(4-cyano-2-fluorobutyl)-1H-1,2,3-triazole-4-carboxylate

To a solution of (R)-4-cyano-2-fluorobutyl 4-methylbenzenesulfonate (2.4 g, 8.8 mmol) in DMF (8.9 ml) was added $NaN_3$ (0.690 g, 10.6 mmol) and the resulting mixture was stirred at 80° C. for 3 h. The reaction mixture was allowed to cool to RT and diluted with DCM (88 ml). DIEA (0.153 ml, 0.879 mmol), ethyl propiolate (1.34 ml, 13.2 mmol), and AcOH (0.050 ml, 0.879 mmol) were added to the reaction mixture. Copper (I) iodide (0.084 g, 0.44 mmol) was then added and the mixture was stirred for 15 h at RT. The reaction was concentrated under reduced pressure and the residue was purified by $SiO_2$ gel chromatography (0% to 100% EtOAc in hexanes) to give the title compound as a pale orange solid (675 mg, 32% yield). MS (ES$^+$) $C_{10}H_{13}FN_4O_2$ requires: 240, found: 241 [M+H]$^+$.

Step 5: ethyl (R)-1-(4-(5-amino-1,3,4-thiadiazol-2-yl)-2-fluorobutyl)-1H-1,2,3-triazole-4-carboxylate To a suspension of (R)-ethyl 1-(4-cyano-2-fluorobutyl)-1H-1,2,3-triazole-4-carboxylate (675 mg, 2.81 mmol) in TFA (14 ml) was added hydrazinecarbothioamide (307 mg, 3.37 mmol) and the resulting mixture was stirred at 80° C. for 5 h. The mixture was concentrated under reduced pressure and the residue was purified by $SiO_2$ gel chromatography (0% to 10% MeOH in DCM) to give the title compound as a pale yellow solid (550 mg, 62% yield). MS (ES$^+$) $C_{11}H_{15}FN_6O_2S$ requires: 314, found: 315 [M+H]$^+$. Enantiopurity was analyzed by chiral SFC (30% MeOH/$CO_2$ with 0.5% $NH_4OH$, ChiralPak IC column, 4.6×150 mm, 5 um, 3 mL/min), which indicated >98% ee.

Step 6: ethyl (R)-1-(2-fluoro-4-(5-(2-(pyridin-2-yl)acetamido)-1,3,4-thiadiazol-2-yl)butyl)-1H-1,2,3-triazole-4-carboxylate To a 0° C. solution of (R)-ethyl 1-(4-(5-amino-1,3,4-thiadiazol-2-yl)-2-fluorobutyl)-1H-1,2,3-triazole-4-carboxylate (100 mg, 0.318 mmol) and 2-(pyridin-2-yl)acetic acid hydrochloride (61 mg, 0.35 mmol) in DMF (1.59 mL) was added triethylamine (0.133 mL, 0.954 mmol) and, after 5 min of stirring, T3P® (50 wt. % in DMF, 0.284 mL, 0.477 mmol) was added dropwise. The resulting mixture was stirred at RT for 15 h. The mixture was concentrated under reduced pressure and the residue was purified by SiO$_2$ gel chromatography (0% to 10% MeOH in DCM with 1% NH$_4$OH) to give the title compound as a yellow solid (123 mg, 89% yield). MS (ES$^+$) C$_{18}$H$_{10}$FN$_7$O$_3$S requires: 433, found: 434 [M+H]$^+$.

Step 7: lithium (R)-1-(2-fluoro-4-(5-(2-(pyridin-2-yl)acetamido)-1,3,4-thiadiazol-2-yl)butyl)-1H-1,2,3-triazole-4-carboxylate To a solution of (R)-ethyl 1-(2-fluoro-4-(5-(2-(pyridin-2-yl)acetamido)-1,3,4-thiadiazol-2-yl)butyl)-1H-1,2,3-triazole-4-carboxylate (123 mg, 0.284 mmol) in MeOH (0.284 mL) and THF (1.135 mL) was added aq. LiOH (2.0 M, 0.17 mL, 0.34 mmol) and the resulting mixture was stirred at RT for 4 h. The mixture was concentrated under reduced pressure to give the title compound as a yellow solid (126 mg, >100% yield), which was used without further purification. MS (ES$^+$) C$_{16}$H$_{16}$FN$_7$O$_3$S requires: 405, found: 406 [M+H]$^+$.

Step 8: (R)-1-(2-fluoro-4-(5-(2-(pyridin-2-yl)acetamido)-1,3,4-thiadiazol-2-yl)butyl)-N-((4-(trifluoromethyl)pyridin-2-yl)methyl)-1H-1,2,3-triazole-4-carboxamide To a suspension of lithium (R)-1-(2-fluoro-4-(5-(2-(pyridin-2-yl)acetamido)-1,3,4-thiadiazol-2-yl)butyl)-1H-1,2,3-triazole-4-carboxylate (126 mg, 0.306 mmol), HATU (175 mg, 0.459 mmol), and (4-(trifluoromethyl)pyridin-2-yl)methanamine dihydrochloride (92 mg, 0.37 mmol) in DMF (1.53 mL) was added DIEA (0.160 mL, 0.919 mmol) and the resulting mixture was stirred at RT for 72 h. The mixture was concentrated under reduced pressure and the residue was adsorbed onto Celite® and purified by SiO$_2$ gel chromatography (0% to 10% MeOH in DCM with 1% NH$_4$OH) to give the title compound as a tan solid (51 mg, 30% yield). MS (ES$^+$) C$_{23}$H$_{21}$F$_4$N$_9$O$_2$S requires: 563, found: 564 [M+H]$^+$; $^1$H NMR (600 MHz, DMSO-d$_6$) δ 12.72 (s, 1H), 9.23 (t, J=5.9 Hz, 1H), 8.81 (d, J=4.9 Hz, 1H), 8.61 (s, 1H), 8.49 (d, J=4.8 Hz, 1H), 7.77 (appar t, J=7.7 Hz, 1H), 7.71-7.60 (m, 2H), 7.40 (d, J=7.8 Hz, 1H), 7.29 (appar t, J=6.3 Hz, 1H), 5.08 (m, 1H), 4.89-4.70 (m, 2H), 4.67 (d, J=6.0 Hz, 2H), 4.01 (s, 2H), 3.22-3.10 (m, 2H), 2.26-1.98 (m, 2H).

Example 80: N-(3-(trifluoromethoxy)benzyl)-1-(4-(4-(((5-(trifluoromethyl)pyridin-3-yl)methyl)carbamoyl)-1H-1,2,3-triazol-1-yl)butyl)-1H-1,2,3-triazole-4-carboxamide

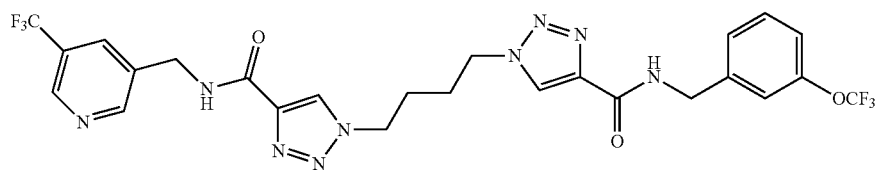 [SMILES: O=C(NCc1cccc(OC(F)(F)F)c1)c1cn(CCCCn2cc(C(=O)NCc3cncc(C(F)(F)F)c3)nn2)nn1]

Steps 1 to 8

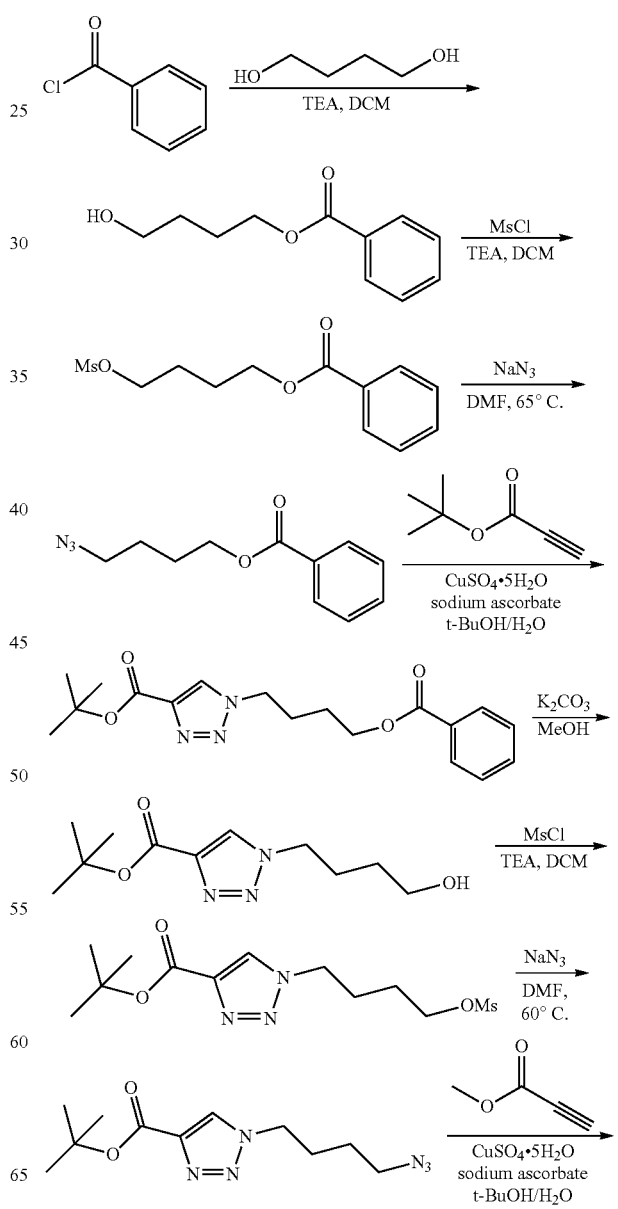

-continued

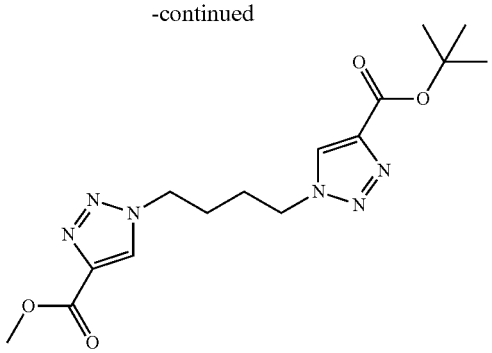

Step 1: 4-hydroxybutyl Benzoate

To a stirred solution of 1,4-butanediol (82.60 mL, 931.2 mmol) and TEA (43.26 mL, 310.4 mmol) in DCM (750 mL) at 0° C. was added benzoyl chloride (36 mL, 31 mmol). The resulting mixture was allowed to warm to RT and stirred for 6 h before quenching with sat. aq. NaHCO$_3$ (150 mL). Layers were separated and the aqueous layer was extracted with DCM (2×100 mL). The combined organic layers were washed with sat. aq. NH$_4$Cl (150 mL) and water (150 mL), dried over Na$_2$SO$_4$, filtered and concentrated under reduced pressure. The residue was purified by SiO$_2$ gel chromatography (9% to 50% EtOAc in hexanes) to give the title compound as a colorless oil (49.6 g; 82% yield). MS (ES$^+$) C$_{11}$H$_{14}$O$_3$ requires: 194, found: 195 [M+H]$^+$.

Step 2: 4-methylsulfonyloxybutyl Benzoate

To a stirred solution of 4-hydroxybutyl benzoate (20.0 g, 103 mmol) and TEA (28.70 mL, 205.9 mmol) in DCM (300 mL) at 0° C. was added methanesulfonyl chloride (11.95 mL, 154.5 mmol). The resulting mixture was allowed to warm to RT and stirred for 6 h before quenching with sat. aq. NaHCO$_3$ (120 mL). The layers were separated and the aqueous layer was extracted with CH$_2$Cl$_2$ (2×60 mL). The combined organic layers were then washed with sat. aq. NaCl (150 mL×2), dried over Na$_2$SO$_4$, filtered and concentrated under reduced pressure to obtain the title compound as a colorless oil (28.02 g; 100% yield). $^1$H NMR (400 MHz, CDCl$_3$) δ 1.91-1.93 (m, 4H), 3.01 (s, 3H), 4.29-4.38 (m, 4H), 7.42-8.04 (m, 5H).

Step 3: 4-azidobutyl Benzoate 4-methylsulfonyloxybutyl benzoate (42.06 g, 154.4 mmol) was dissolved in DMF (300 mL). NaN$_3$ (20.28 g, 308.9 mmol) was added cautiously. The solution was slowly heated to 65° C. and stirred for 16 h. The mixture was allowed to cool to RT, transferred to a separation funnel and diluted with Et$_2$O (600 mL), then washed with water (3×90 mL). The organic layer was dried over Na$_2$SO$_4$, filtered and concentrated under reduced pressure to give the title compound as a yellow oil, which was used without further purification (33.86 g; 100% yield). $^1$H NMR (400 MHz, CDCl$_3$) δ 1.74-1.89 (m, 4H), 3.37 (t, 2H), 4.35 (t, 2H), 7.42-8.05 (m, 5H).

Step 4: tert-butyl 1-(4-benzoyloxybutyl)triazole-4-carboxylate

To a solution of 1-(4-azidobutyl)-N-[[3-(trifluoromethoxy)phenyl]methyl]triazole-4-carboxamide (12.0 g, 54.7 mmol) in t-BuOH (100 mL) and water (100 mL) were added CuSO$_4$-5H$_2$O (1.38 g, 5.47 mmol), L-ascorbic acid sodium salt (2.20 g, 11.0 mmol) and tert-butyl prop-2-ynoate (8.29 g, 65.7 mmol). The suspension was stirred vigorously at RT for 16 h. The mixture was concentrated under reduced pressure to remove the organic layer, diluted with ice-cold water, and precipitate was isolated by filtration, washed with water and dried to give the title compound as a light brown solid (18.1 g; 96% yield). MS (ES$^+$) C$_{18}$H$_{23}$N$_3$O$_4$ requires: 345, found: 346 [M+H]$^+$.

Step 5: tert-butyl 1-(4-hydroxybutyl)triazole-4-carboxylate

To a solution of tert-butyl 1-(4-benzoyloxybutyl)triazole-4-carboxylate (31 g; 90 mmol) in MeOH (300 mL) was added K$_2$CO$_3$ (12.40 g, 89.75 mmol). The mixture was stirred at RT for 4 h, filtered, and the filtrate was concentrated under reduced pressure. The residue was purified by SiO$_2$ gel chromatography (2% to 10% MeOH in DCM) to give the title compound as a light yellow oil (9.27 g, 43% yield). MS (ES$^+$) C$_{11}$H$_{19}$N$_3$O$_3$ requires: 241, found: 242 [M+H]$^+$.

Step 6: tert-butyl 1-(4-methylsulfonyloxybutyl)triazole-4-carboxylate

To a stirred solution of tert-butyl 1-(4-hydroxybutyl)triazole-4-carboxylate (8.8 g, 36 mmol) and TEA (10.17 mL, 72.94 mmol) in DCM (120 mL) at 0° C. was added methanesulfonyl chloride (4.23 mL, 54.7 mmoles). The resulting mixture was allowed to warm to RT and stirred for 30 min before quenching with sat. aq. NaHCO$_3$ (90 mL). The layers were separated and the aqueous layer was extracted with DCM (2×30 mL). The combined organic layers were washed with sat. aq. NaCl (80 mL), dried over MgSO$_4$, filtered and concentrated under reduced pressure to give the title compound as a colorless oil, which was used without further purification (11.27 g; 97% yield). MS (ES$^+$) C$_{12}$H$_{21}$N$_3$O$_5$S requires: 319, found: 320[M+H]$^+$.

Step 7: tert-butyl 1-(4-azidobutyl)triazole-4-carboxylate

Tert-butyl 1-(4-methylsulfonyloxybutyl)triazole-4-carboxylate (11.27 g, 35.29 mmol) was dissolved in DMF (80 mL). NaN$_3$ (4.63 g, 70.6 mmol) was added cautiously. The solution was slowly heated to 60° C. and stirred for 16 h. The mixture was allowed to cool to RT, transferred to a separation funnel and diluted with Et$_2$O (250 mL), then washed with water (3×60 mL). The organic layer was dried over Na$_2$SO$_4$, filtered and concentrated under reduced pressure to afford the title compound as a yellow oil (9.1 g; 97% yield), which was used without further purification. $^1$H NMR (400 MHz, CDCl3) δ 1.61 (m, 11H), 2.03 (m, 2H), 3.35 (t, 2H), 4.45 (t, 2H), 8.01 (s, 1H).

Step 8: methyl 1-(4-(4-(tert-butoxycarbonyl)-1H-1,2,3-triazol-1-yl)butyl)-1H-1,2,3-triazole-4-carboxylate To a solution of tert-butyl 1-(4-azidobutyl)triazole-4-carboxylate (9.1 g, 34 mmol) in t-BuOH (40 mL) and water (40 mL) were added CuSO$_4$·5H$_2$O (862 mg, 3.42 mmol), L-ascorbic acid sodium salt (1.37 g, 6.83 mmol) and methyl prop-2-ynoate (2.87 g, 34.2 mmol). The suspension was stirred vigorously at RT for 16 h. The mixture was concentrated under reduced pressure to remove the organic layer, diluted with ice-cold water, and precipitate was isolated by filtration, washed with water and dried to give the title compound as a solid (9.64 g; 81% yield). MS (ES$^+$) C$_{15}$H$_{22}$N$_6$O$_4$ requires: 350, found: 351 [M+H]$^+$.

Steps 9 to 12
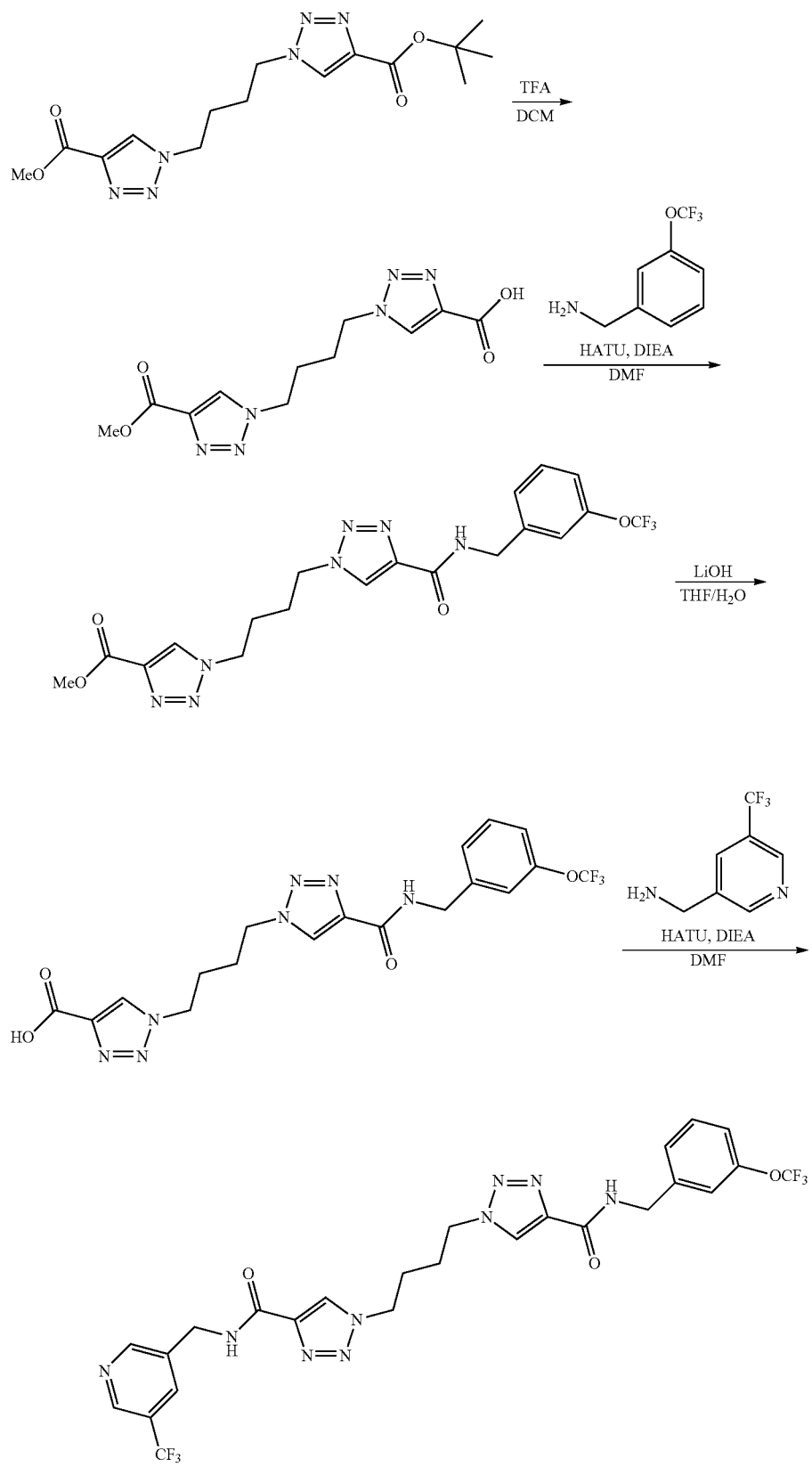

Step 9: 1-(4-(4-(methoxycarbonyl)-1H-1,2,3-triazol-1-yl)butyl)-1H-1,2,3-triazole-4-carboxylic Acid To a 0° C. solution of tert-butyl 1-(4-(4-(methoxycarbonyl)-1H-1,2,3-triazol-1-yl)butyl)-1H-1,2,3-triazole-4-carboxylate (1.00 g, 2.85 mmol) in DCM (28 ml) was added dropwise TFA (4.40 mL, 57.1 mmol), and the resulting mixture was stirred at RT for 4 h. The mixture was concentrated under reduced pressure, azeotroping with toluene (3×25 mL), to give crude title compound, which was used without further purification. MS (ES$^+$) $C_{11}H_{14}N_6O_4$ requires: 294, found: 295 [M+H]$^+$.

Step 10: methyl 1-(4-(4-((3-(trifluoromethoxy)benzyl)carbamoyl)-1H-1,2,3-triazol-1-yl)butyl)-1H-1,2,3-triazole-4-carboxylate To a solution of crude 1-(4-(4-(methoxycarbonyl)-1H-1,2,3-triazol-1-yl)butyl)-1H-1,2,3-triazole-4-carboxylic acid (840 mg, 2.85 mmol) in DMF (28 mL) were added (3-(trifluoromethoxy)phenyl)methanamine (0.650 mL, 3.43 mmol), HATU (1.3 g, 3.4 mmol), and DIEA (0.750 mL, 4.28 mmol). The resulting mixture was stirred at RT for 16 h. Precipitated solid was collected by filtration to give the title compound as an off-white powder (700 mg, 52% yield). MS (ES$^+$) $C_{19}H_{20}F_3N_7O_4$ requires: 467, found: 468 [M+H]$^+$.

Step 11: 1-(4-(4-((3-(trifluoromethoxy)benzyl)carbamoyl)-1H-1,2,3-triazol-1-yl)butyl)-1H-1,2,3-triazole-4-carboxylic Acid To a solution of methyl 1-(4-(4-((3-(trifluoromethoxy)benzyl)carbamoyl)-1H-1,2,3-triazol-1-yl)butyl)-1H-1,2,3-triazole-4-carboxylate (100 mg, 0.214 mmol) in THF (1.8 mL) and water (0.18 mL) was added LiOH (51 mg, 2.1 mmol), and the resulting mixture was stirred at RT for 4 h. The solution was neutralized with HCl in MeOH (1.25 M, 1.7 mL, 2.12 mmol) and the mixture was concentrated under reduced pressure under reduced pressure to give the crude title compound as a white solid (96 mg, 99%), which was used as is. MS (ES$^+$) $C_{18}H_{18}F_3N_7O_4$ requires: 453, found: 454 [M+H]$^+$.

Step 12: N-(3-(trifluoromethoxy)benzyl)-1-(4-(4-(((5-(trifluoromethyl)pyridin-3-yl)methyl)carbamoyl)-1H-1,2,3-triazol-1-yl)butyl)-1H-1,2,3-triazole-4-carboxamide To a solution of 1-(4-(4-((3-(trifluoromethoxy)benzyl)carbamoyl)-1H-1,2,3-triazol-1-yl)butyl)-1H-1,2,3-triazole-4-carboxylic acid (194 mg, 0.428 mmol) in DMF (4.3 mL) were added (5-(trifluoromethyl)pyridin-3-yl)methanamine dihydrochloride (117 mg, 0.471 mmol), HATU (244 mg, 0.642 mmol) and DIEA (0.262 mL, 1.49 mmol). The resulting mixture was stirred at RT for 18 h. Precipitated solid was collected by filtration and rinsed with MeOH to give the title compound as a white solid (180 mg, 69% yield). MS (ES$^+$) $C_{25}H_{23}F_6N_9O_3$ requires: 611, found: 612.5 [M+H]$^+$. $^1$H NMR (600 MHz, DMSO-d$_6$) δ 9.27 (t, J=6.2 Hz, 1H), 9.19 (t, J=6.3 Hz, 1H), 8.89-8.82 (m, 2H), 8.61 (s, 1H), 8.60 (s, 1H), 8.12 (appar t, J=2.1 Hz, 1H), 7.45 (appar t, J=7.9 Hz, 1H), 7.34 (m, 1H), 7.28 (m, 1H), 7.24 (m, 1H), 4.56 (d, J=6.1 Hz, 2H), 4.50-4.39 (m, 6H), 1.87-1.77 (m, 4H).

Example 475: 1-(3-fluoro-4-(4-((4-(trifluoromethyl)pyridin-2-yl)methylcarbamoyl)-1H-1,2,3-triazol-1-yl)butyl)-N-methyl-1H-1,2,3-triazole-4-carboxamide

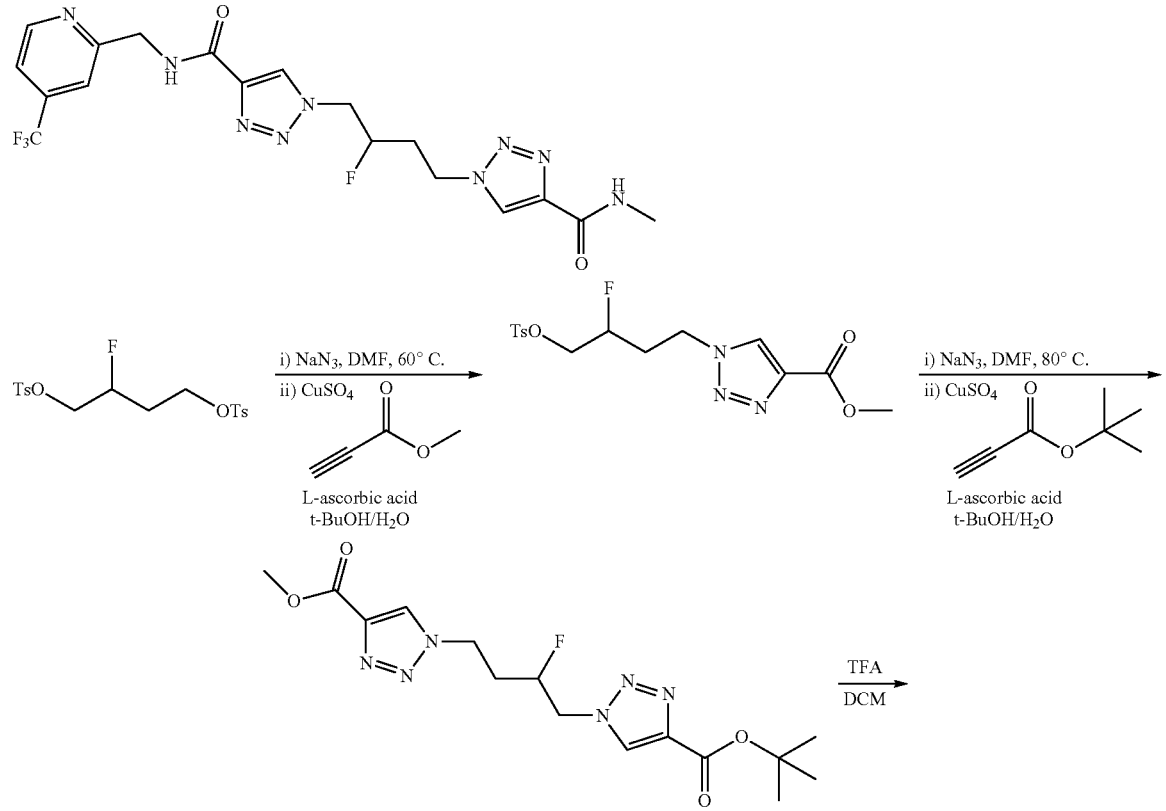

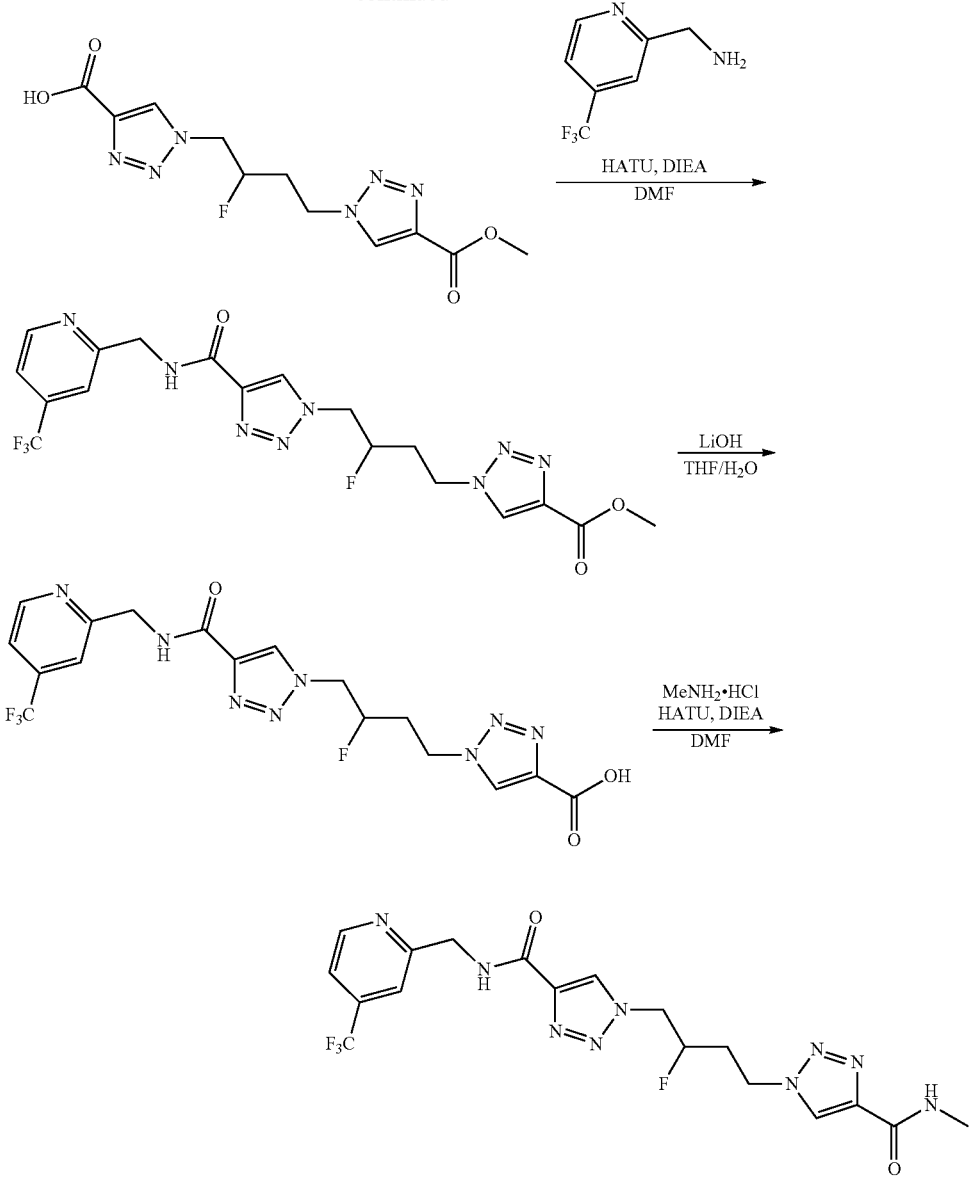

Step 1: methyl 1-(3-fluoro-4-(tosyloxy)butyl)-1H-1,2,3-triazole-4-carboxylate

A mixture of 2-fluorobutane-1,4-diyl bis(4-methylbenzenesulfonate) (20 g, 48 mol), NaN$_3$ (3.1 g, 48 mmol), and DMF (100 ml) was stirred at 60° C. for 16 h, then water (500 mL) was added. The mixture was extracted with DCM (800 mL), and the organic layer was concentrated under reduced pressure. To the residue was added 1:1 v:v t-BuOH/water (200 mL), methyl propiolate (4.0 g, 48 mmol), CuSO$_4$ (1.2 g, 7.5 mmol), and L-ascorbic acid (2.4 g, 14 mmol). The mixture was stirred at RT for 16 h, then concentrated under reduced pressure. To the residue was added water (150 mL), the mixture was stirred for 30 min, and precipitate was isolated by filtration to give the title compound as a white solid (12 g, 60%). MS (ES$^+$) C$_{15}$H$_{18}$FN$_3$O$_5$S requires: 371, found: 372 [M+H]$^+$.

Step 2: tert-butyl 1-(2-fluoro-4-(4-(methoxycarbonyl)-1H-1,2,3-triazol-1-yl)butyl)-1H-1,2,3-triazole-4-carboxylate A mixture of methyl 1-(3-fluoro-4-(tosyloxy)butyl)-1H-1,2,3-triazole-4-carboxylate (8.9 g, 24 mmol), NaN$_3$ (1.56 g, 24.0 mmol), and DMF (50 ml) was stirred at 80° C. for 16 h, then water (500 mL) was added. The mixture was extracted with DCM (600 mL), and the organic layer was concentrated under reduced pressure. To the residue was added 1:1 v:v t-BuOH/water (200 mL), tert-butyl propiolate (3.0 g, 24 mmol), CuSO$_4$ (0.60 g, 3.8 mmol), and L-ascorbic acid (1.2 g, 6.8 mmol). The mixture was stirred at RT for 16 h then concentrated under reduced pressure. To the residue was added water (150 ml), the mixture was stirred for 30 min, and precipitate was isolated by filtration to give the title compound as a white solid (7 g, 80%). MS (ES$^+$) C$_{15}$H$_{21}$FN$_6$O$_4$ requires: 368, found: 369 [M+H]$^+$.

Step 3: 1-(2-fluoro-4-(4-(methoxycarbonyl)-1H-1,2,3-triazol-1-yl)butyl)-1H-1,2,3-triazole-4-carboxylic Acid A mixture of tert-butyl 1-(2-fluoro-4-(4-(methoxycarbonyl)-1H-1,2,3-triazol-1-yl)butyl)-1H-1,2,3-triazole-4-carboxylate (1.0 g, 2.7 mmol) and 1:1 v:v TFA/DCM (20 ml) was stirred at RT for 3 h, then concentrated under reduced pressure. To the residue was added water (100 ml), the mixture was stirred for 20 min, and precipitate was isolated by filtration to give the title compound as a white solid (500 mg, 64%). MS (ES+) $C_{11}H_{13}FN_6O_4$ requires: 312, found: 313 [M+H]+.

Step 4: methyl 1-(3-fluoro-4-(4-((4-(trifluoromethyl)pyridin-2-yl)methylcarbamoyl)-1H-1,2,3-triazol-1-yl)butyl)-1H-1,2,3-triazole-4-carboxylate A mixture of 1-(2-fluoro-4-(4-(methoxycarbonyl)-1H-1,2,3-triazol-1-yl)butyl)-1H-1,2,3-triazole-4-carboxylic acid (500 mg, 1.6 mmol), (4-(trifluoromethyl)pyridin-2-yl) methanamine (282 mg, 1.60 mmol), HATU (912 mg, 2.4 mmol), DIEA (600 mg, 4.8 mmol), and DMF (5 ml) was stirred at RT for 2 h, then water (100 mL) was added and the mixture was stirred for 10 min. Precipitate was isolated by filtration to give the title compound as a light brown solid (700 mg, 90%). MS (ES+) $C_{18}H_{18}F_4N_8O_3$ requires: 470, found: 471 [M+H]+.

Step 5: 1-(3-fluoro-4-(4-((4-(trifluoromethyl)pyridin-2-yl)methylcarbamoyl)-1H-1,2,3-triazol-1-yl)butyl)-1H-1,2,3-triazole-4-carboxylic Acid A mixture of methyl 1-(3-fluoro-4-(4-((4-(trifluoromethyl)pyridin-2-yl)methylcarbamoyl)-1H-1,2,3-triazol-1-yl)butyl)-1H-1,2,3-triazole-4-carboxylate (700 mg, 1.4 mmol), LiOH (70 mg, 2.8 mmol), and 1:1 v:v THF/H2O (8 ml) was stirred at RT for 3 h, then concentrated under reduced pressure to remove organics. The pH value was adjusted to 4.0 with 1 M aq. HCl. Precipitate was isolated by filtration to give the title compound as a white solid (600 mg, 91%). MS (ES+) $C_{17}H_{16}F_4N_8O_3$ requires: 456, found: 457[M+H]+.

Step 6: 1-(3-fluoro-4-(4-((4-(trifluoromethyl)pyridin-2-yl)methylcarbamoyl)-1H-1,2,3-triazol-1-yl)butyl)-N-methyl-1H-1,2,3-triazole-4-carboxamide A mixture of 1-(3-fluoro-4-(4-((4-(trifluoromethyl)pyridin-2-yl)methylcarbamoyl)-1H-1,2,3-triazol-1-yl)butyl)-1H-1,2,3-triazole-4-carboxylic acid (40 mg, 0.085 mmol), methylamine hydrochloride (6 mg, 0.09 mmol), HATU (50 mg, 0.13 mmol), DIEA (33 mg, 0.26 mmol), and DMF (1 ml) was stirred at RT for 16 h, then purified by preparative HPLC (Mobile phase: A=0.1% ammonium hydroxide/H2O, B=acetonitrile; Gradient: B=5%-95% in 18 min; Column: C18) to afford the title compound as a white solid (26 mg, 60%). MS (ES+) $C_{18}H_{19}F_4N_9O_2$ requires: 469, found: 470 [M+H]+. 1H NMR (400 MHz, DMSO) δ 9.24 (t, J=6.0 Hz, 1H), 8.81 (d, J=4.9 Hz, 1H), 8.60 (d, J=6.5 Hz, 2H), 8.46 (m, 1H), 7.77-7.50 (m, 2H), 5.00 (m, 1H), 4.89-4.71 (m, 2H), 4.65 (m, 2H), 4.59 (m, 2H), 2.76 (d, J=4.6 Hz, 3H), 2.38-2.10 (m, 2H).

Example 297: 1-[4-[4-[[2-(2-pyridyl)acetyl]amino]triazol-1-yl]butyl]-N-(2-pyridylmethyl)triazole-4-carboxamide

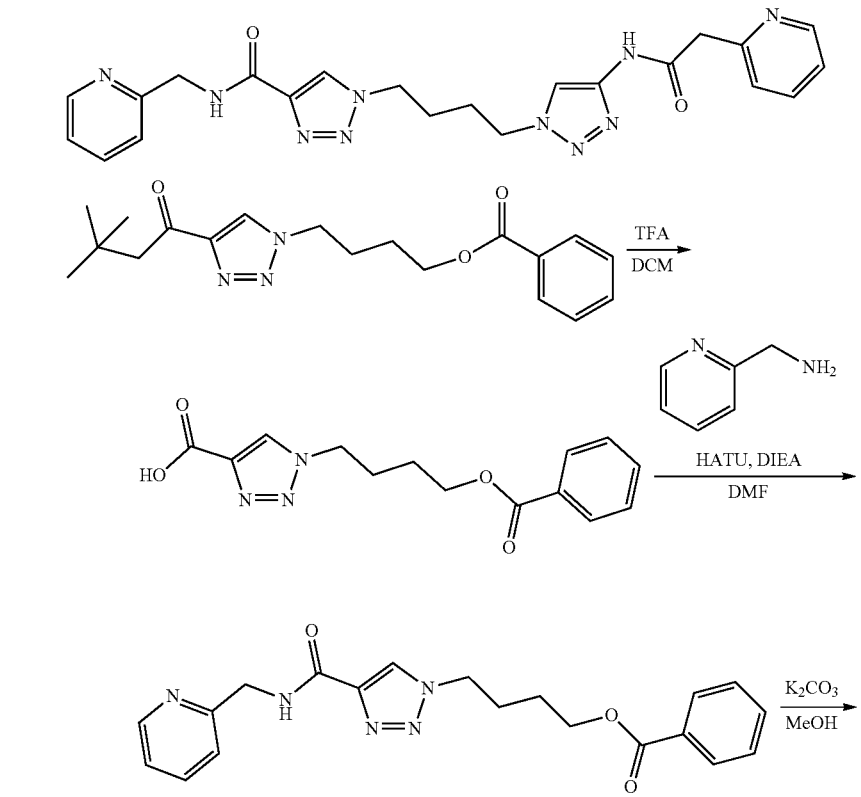

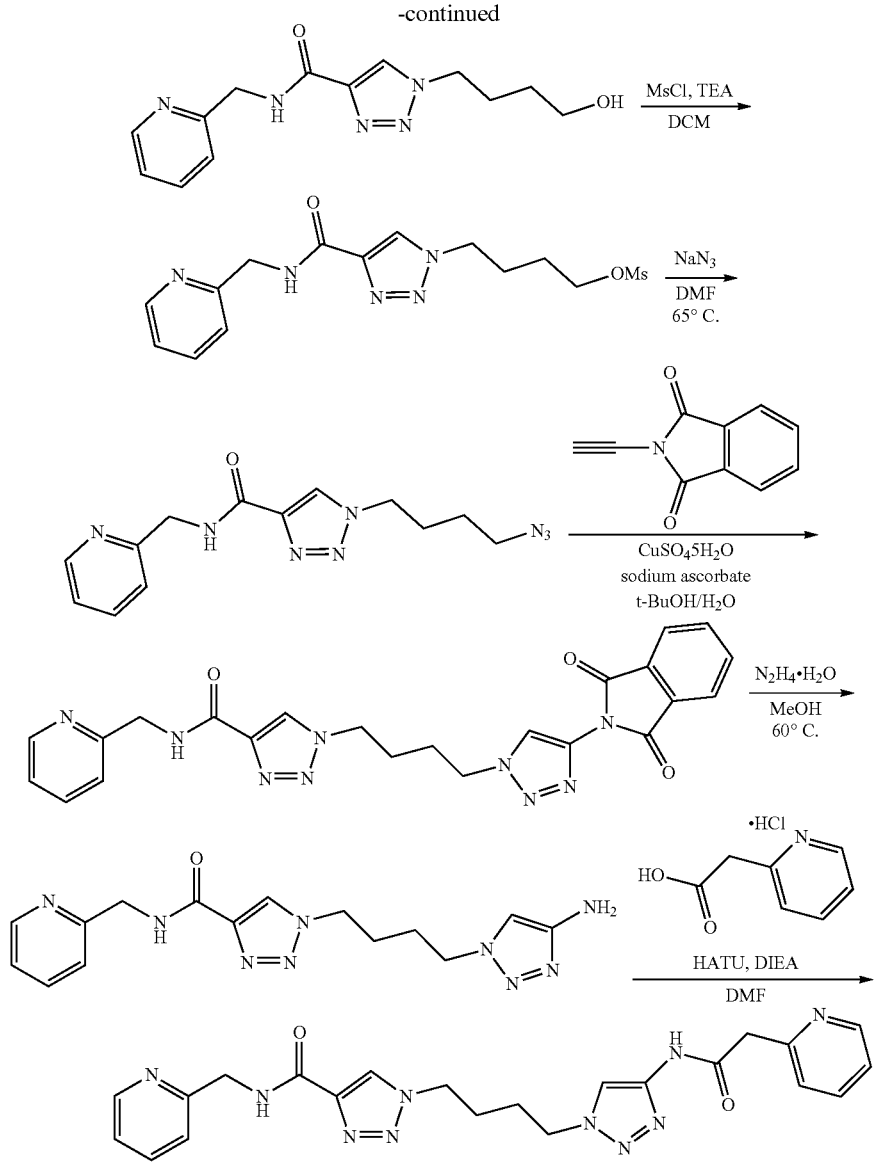

Step 1: 1-(4-(benzoyloxy)butyl)-1H-1,2,3-triazole-4-carboxylic Acid

A solution of tert-butyl 1-(4-(benzoyloxy)butyl)-1H-1,2,3-triazole-4-carboxylate (5 g, 14.5 mmol) in 1:1 v:v TFA/DCM (40 ml) was stirred at RT for 3 h, then concentrated under reduced pressure. Water (30 ml) was added, the mixture was stirred for 15 min, and precipitate was isolated by filtration then recrystallized from acetonitrile/water to afford the presumed title product as a white solid (3.8 g, 90%).

Step 2: 4-(4-(pyridin-2-ylmethylcarbamoyl)-1H-1,2,3-triazol-1-yl)butyl Benzoate

To a stirred solution of 1-(4-(benzoyloxy)butyl)-1H-1,2,3-triazole-4-carboxylic acid (1.00 g, 3.46 mmol) in DMF (10 mL) were added HATU (1.84 g, 4.84 mmol), DIEA (1.21 mL, 6.91 mmol) and 2-pyridinemethanamine (449 mg, 4.15 mmol). The reaction mixture was stirred at RT for 16 h. Water (90 mL) was added and precipitate was isolated by filtration, washed with water, and dried to give the title compound as a brown solid (1.27 g; 97% yield). MS (ES$^+$) $C_{20}H_{21}N_5O_3$ requires: 379, found: 380 [M+H]$^+$.

Step 3: 1-(4-hydroxybutyl)-N-(pyridin-2-ylmethyl)-1H-1,2,3-triazole-4-carboxamide To a solution of 4-(4-(pyridin-2-ylmethylcarbamoyl)-1H-1,2,3-triazol-1-yl)butyl benzoate (1.27 g, 3.35 mmol) in MeOH (80 mL) was added $K_2CO_3$ (463 mg, 3.35 mmol). The suspension was stirred vigorously at RT for 3 d. The reaction mixture was extracted with DCM (3×45 mL), and the combined organic layers were dried over MgSO$_4$, filtered through of Celite® and concentrated under reduced pressure. The residue was purified by SiO$_2$ gel chromatography (25% EtOAc in petroleum ether) to give the title compound as a white solid (0.86 g, 93% yield). MS (ES$^+$) $C_{13}H_{17}N_5O_2$ requires: 275, found: 276[M+H]$^+$.

Step 4: 4-[4-(2-pyridylmethylcarbamoyl)triazol-1-yl]butyl methanesulfonate

To a stirred solution of 1-(4-hydroxybutyl)-N-(2-pyridylmethyl)triazole-4-carboxamide (0.85 g; 3.1 mmol) and TEA (0.861 mL, 6.17 mmol) in DCM (20 mL) at 0° C. was added methanesulfonyl chloride (0.358 mL, 14.6 mmol). The resulting mixture was allowed to warm to RT and stirred for 30 min before quenching with sat. aq. NaHCO$_3$ (150 mL). Layers were separated and the aqueous layer was extracted with DCM (2×60 mL). The combined organic layers were washed with sat. aq. NaCl (150 mL), dried over Na$_2$SO$_4$, filtered and concentrated under reduced pressure to give the title compound as a colorless oil (1.09 g, 100% yield). MS (ES$^+$) C$_{14}$H$_{19}$N$_5$O$_4$S requires: 353, found: 354 [M+H]$^+$.

Step 5: 1-(4-azidobutyl)-N-(2-pyridylmethyl)triazole-4-carboxamide

4-[4-(2-Pyridylmethylcarbamoyl)triazol-1-yl]butyl methanesulfonate (1.09 g, 3.08 mmol) was dissolved in DMF (15 mL). NaN$_3$ (405 mg, 6.17 mmol) was added cautiously. The solution was slowly heated to 65° C. and stirred for 16 h, then allowed to cool to RT. The mixture was transferred to a separation funnel and diluted with Et$_2$O (90 mL), then washed with water (3×30 mL). The organic layer was dried over Na$_2$SO$_4$, filtered and concentrated under reduced pressure to give the title compound as a yellow solid (0.9 g; 97% yield). MS (ES$^+$) C$_{13}$H$_{16}$N$_8$O requires: 300, found: 301 [M+H]$^+$.

Step 6: 1-(4-(4-(1,3-dioxoisoindolin-2-yl)-1H-1,2,3-triazol-1-yl)butyl)-N-(pyridin-2-ylmethyl)-1H-1,2,3-triazole-4-carboxamide To a solution of 1-(4-azidobutyl)-N-(pyridin-2-ylmethyl)-1H-1,2,3-triazole-4-carboxamide (900 mg, 3 mmol) in t-BuOH (10 mL) and water (10 mL) were added CuSO$_4$·5H$_2$O (75.6 mg, 0.303 mmol), L-ascorbic acid sodium salt (120 mg, 0.600 mmol) and 2-ethynylisoindoline-1,3-dione (513 mg, 3.00 mmol). This suspension was stirred vigorously at RT for 16 h, then concentrated under reduced pressure to remove the organic layer. The mixture was diluted with ice-cold water, and precipitate was isolated by filtration, washed with water, and dried to give the title compound as a solid (1.28 g, 91% yield). MS (ES$^+$) C$_{23}$H$_{21}$N$_9$O$_3$ requires: 471, found: 472 [M+H]$^+$.

Step 7: 1-(4-(4-amino-1H-1,2,3-triazol-1-yl)butyl)-N-(pyridin-2-ylmethyl)-1H-1,2,3-triazole-4-carboxamide To a suspension of 1-(4-(4-(1,3-dioxoisoindolin-2-yl)-1H-1,2,3-triazol-1-yl)butyl)-N-(pyridin-2-ylmethyl)-1H-1,2,3-triazole-4-carboxamide (1.28 g, 2.71 mmol) in MeOH (45 mL) was added hydrazine monohydrate (0.660 mL, 13.6 mmol). The mixture was stirred at 60° C. for 30 min, then concentrated under reduced pressure to obtain a solid, which was washed with cold water (3×15 mL) to give the title compound as a brown solid (0.574 g, 62% yield). MS (ES$^+$) C$_{15}$H$_{19}$N$_9$O requires: 341, found: 342 [M+H]$^+$.

Step 8: 1-[4-[4-[[2-(2-pyridyl)acetyl]amino]triazol-1-yl]butyl]-N-(2-pyridylmethyl)triazole-4-carboxamide To a solution of 2-pyridylacetic acid hydrochloride (27.9 mg, 0.159 mmol), HATU (77.5 mg, 0.197 mmol) and DIEA (0.460 mL, 0.264 mmol) in DMF (1 mL) was added 1-(4-(4-amino-1H-1,2,3-triazol-1-yl)butyl)-N-(pyridin-2-ylmethyl)-1H-1,2,3-triazole-4-carboxamide (45.0 mg, 0.131 mmol), and the resulting mixture was stirred at RT for 16 h. The mixture was directly purified by preparative HPLC (Mobile phase: A=0.1% ammonium hydroxide/H$_2$O, B=acetonitrile; Gradient: B=5%-95% in 18 min; Column: C18) to give the title compound as a white solid (15 mg; 25% yield). MS (ES$^+$) C$_{22}$H$_{24}$N$_{10}$O$_2$ requires: 460, found: 461 [M+H]$^+$; $^1$H NMR (400 MHz, MeOH-d$_4$) δ 8.52 (m, 2H), 8.40 (s, 1H), 8.12 (s, 1H), 7.82 (m, 2H), 7.53-7.26 (m, 4H), 4.71 (s, 2H), 4.51-4.43 (m, 4H), 3.96 (m, 2H), 1.94 (appar s, 4H).

Example 332: 1-(4-(4-(2-(4,4-difluoropiperidin-1-yl)acetamido)-1H-1,2,3-triazol-1-yl)butyl)-N-(3-(trifluoromethoxy)benzyl)-1H-1,2,3-triazole-4-carboxamide

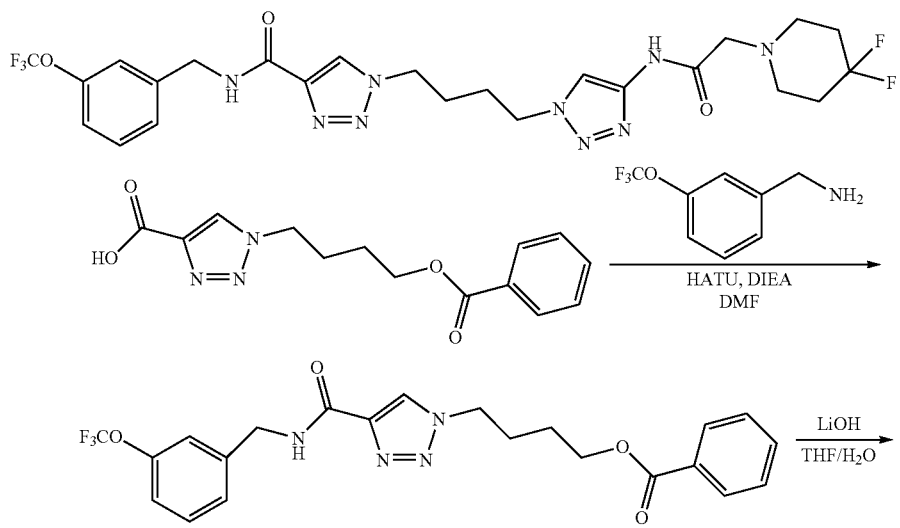

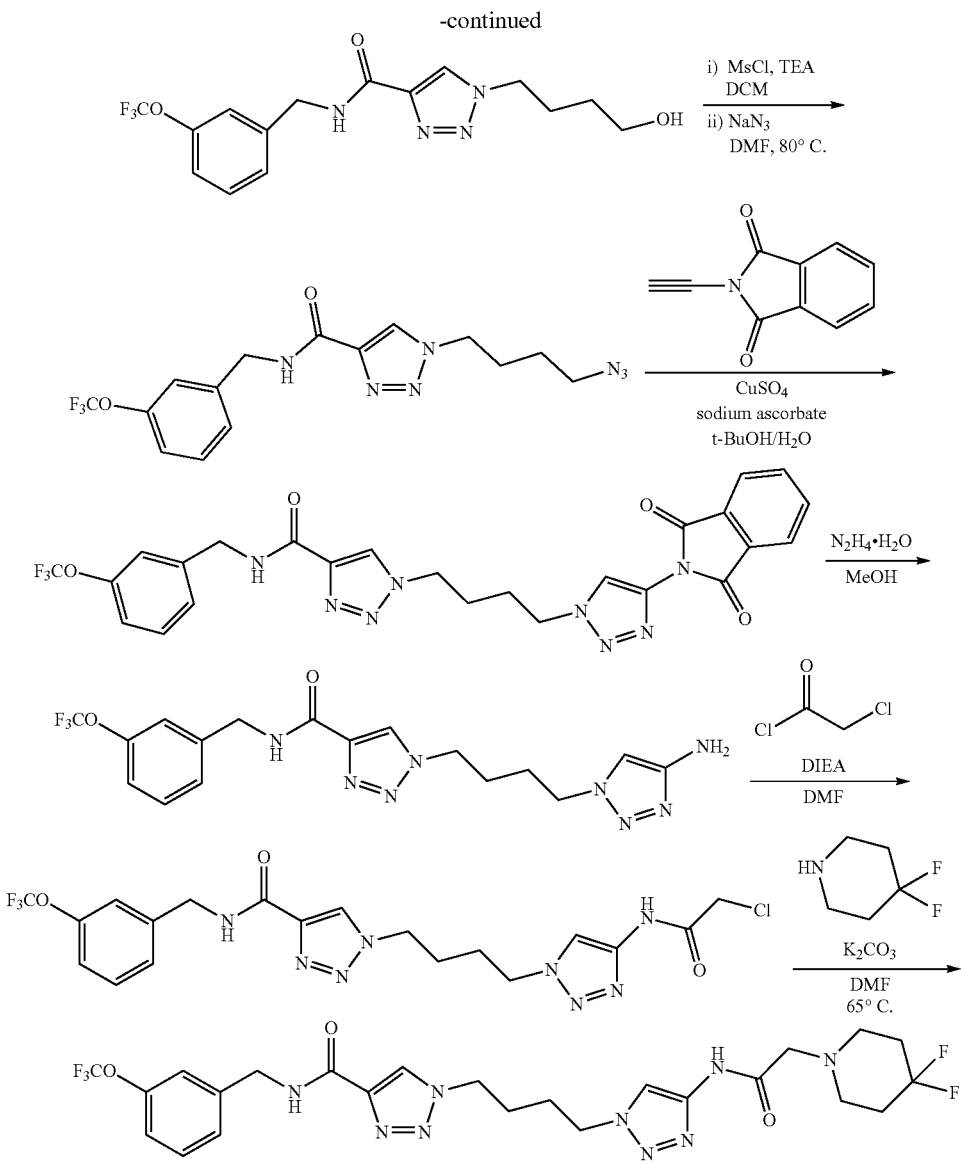

Step 1: 4-(4-(3-(trifluoromethoxy)benzylcarbamoyl)-1H-1,2,3-triazol-1-yl)butyl benzoate A mixture of 1-(4-(benzoyloxy)butyl)-1H-1,2,3-triazole-4-carboxylic acid (1.0 g, 3.5 mmol), (3-(trifluoromethoxy)phenyl)methanamine (0.66 g, 3.5 mmol), HATU (1.9 g, 5.2 mmol), and DIEA (1.3 g, 10 mmol) in DMF (10 ml) was stirred at RT for 16 h. Water (100 ml) was added, the mixture was stirred for 10 min, and precipitate was isolated by filtration to give the title compound as a white solid (1 g, 62%). MS (ES⁺) $C_{22}H_{21}F_3N_4O_4$ requires: 462, found: 463 [M+H]⁺.

Step 2: 1-(4-hydroxybutyl)-N-(3-(trifluoromethoxy)benzyl)-1H-1,2,3-triazole-4-carboxamide A mixture of 4-(4-(3-(trifluoromethoxy)benzylcarbamoyl)-1H-1,2,3-triazol-1-yl)butyl benzoate (1.0 g, 2.2 mmol) and LiOH·H₂O (0.27 g, 6.6 mmol) in THF (5 ml) and water (5 ml) was stirred at RT for 16 h, then extracted with EtOAc (50 mL). The combined organic layers were concentrated under reduced pressure to afford the title compound as a white solid (600 mg, 77%). MS (ES⁺) $C_{15}H_{17}F_3N_4O_3$ requires: 358, found: 359 [M+H]⁺.

Step 3: 1-(4-azidobutyl)-N-(3-(trifluoromethoxy)benzyl)-1H-1,2,3-triazole-4-carboxamide To a stirred solution of 1-(4-hydroxybutyl)-N-(3-(trifluoromethoxy)benzyl)-1H-1,2,3-triazole-4-carboxamide (600 mg, 1.68 mmol) and TEA (340 mg, 3.36 mmol) in DCM (5 ml) at RT was added methanesulfonyl chloride (240 mg, 2.1 mmol) in DCM (5 ml) dropwise. The mixture was stirred at RT for 30 min then treated with water (10 ml) and extracted with DCM (20 ml). The organic layer was concentrated under reduced pressure to afford a white solid (presumed crude 4-(4-(3-(trifluoromethoxy)benzylcarbamoyl)-1H-1,2,3-triazol-1-yl)butyl methanesulfonate), which was dissolved in DMF (3 mL). To the solution was added NaN₃ (110 mg, 1.68 mmol), and the mixture was stirred at 80° C. for 1 hr, then allowed to cool to RT. Water (20 ml) was added, the mixture was stirred for 15 min, and precipitate was isolated by filtration to give the title compound as a white solid (600 mg, 93%). MS (ES⁺) $C_{15}H_{16}F_3N_7O_2$ requires: 383, found: 384 $[M+H]^+$.

Step 4: 1-(4-(4-(1,3-dioxoisoindolin-2-yl)-1H-1,2,3-triazol-1-yl)butyl)-N-(3-(trifluoromethoxy)benzyl)-1H-1,2,3-triazole-4-carboxamide A mixture of 1-(4-azidobutyl)-N-(3-(trifluoromethoxy)benzyl)-1H-1,2,3-triazole-4-carboxamide (600 mg, 0.78 mmol), 2-ethynylisoindoline-1,3-dione (133 mg, 0.780 mmol), L(+)-ascorbic acid (40 mg, 0.23 mmol), and $CuSO_4$ (20 mg, 0.12 mmol) in 1:1 v:v t-BuOH/$H_2O$ (10 mL) was stirred at RT for 16 h, then concentrated under reduced pressure. Water (30 ml) was added, the mixture was stirred for 15 min, and precipitate was isolated by filtration to give the title compound as a white solid (600 mg, 71%). MS (ES⁺) $C_{25}H_{21}F_3N_8O_4$ requires: 554, found: 555 $[M+H]^+$.

Step 5: 1-(4-(4-amino-1H-1,2,3-triazol-1-yl)butyl)-N-(3-(trifluoromethoxy)benzyl)-1H-1,2,3-triazole-4-carboxamide A mixture of 1-(4-(4-(1,3-dioxoisoindolin-2-yl)-1H-1,2,3-triazol-1-yl)butyl)-N-(3-(trifluoromethoxy)benzyl)-1H-1,2,3-triazole-4-carboxamide (500 mg, 0.90 mmol) and hydrazine hydrate (90 mg, 1.8 mmol) in MeOH (10 ml) was stirred at RT for 3 h, then concentrated under reduced pressure. To the residue was added EtOAc (50 mL), and the mixture was stirred for 15 min, filtered, and the filtrate was concentrated under reduced pressure to give the title compound as a white solid (300 mg, 86%). MS (ES⁺) $C_{17}H_{19}F_3N_8O_2$ requires: 424, found: 425 $[M+H]^+$.

Step 6: 1-(4-(4-(2-chloroacetamido)-1H-1,2,3-triazol-1-yl)butyl)-N-(3-(trifluoromethoxy)benzyl)-1H-1,2,3-triazole-4-carboxamide A mixture of 1-(4-(4-amino-1H-1,2,3-triazol-1-yl)butyl)-N-(3-(trifluoromethoxy)benzyl)-1H-1,2,3-triazole-4-carboxamide (300 mg, 0.705 mmol), 2-chloroacetyl chloride (120 mg, 1.06 mmol) and DIEA (177 mg, 1.41 mmol) in DMF (5 ml) was stirred at RT for 2 h. Water (50 ml) was added, the mixture was stirred for 10 min, and precipitate was isolated by filtration to give the title compound as a yellow solid (220 mg, 63%). MS (ES⁺) $C_{19}H_{20}ClF_3N_8O_3$ requires: 501, found: 502 $[M+H]^+$.

Step 7: 1-(4-(4-(2-(4,4-difluoropiperidin-1-yl)acetamido)-1H-1,2,3-triazol-1-yl)butyl)-N-(3-(trifluoromethoxy)benzyl)-1H-1,2,3-triazole-4-carboxamide A mixture of 1-(4-(4-(2-chloroacetamido)-1H-1,2,3-triazol-1-yl)butyl)-N-(3-(trifluoromethoxy)benzyl)-1H-1,2,3-triazole-4-carboxamide (30 mg, 0.06 mmol), 3-fluoroazetidine (7 mg, 0.09 mmol) and $K_2CO_3$ (25 mg, 0.18 mmol) in DMF (1 ml) was stirred at 65° C. for 2 h. Precipitate was isolated by filtration and purified by preparative HPLC (Mobile phase: A=0.1% ammonium hydroxide/$H_2O$, B=acetonitrile; Gradient: B=5%-95% in 18 min; Column: C18) to afford the title compound as a white solid (12.7 mg, 57%). MS (ES⁺) $C_{24}H_{28}F_5N_9O_3$ requires: 585, found: 586 $[M+H]^+$. ¹H NMR (500 MHz, DMSO-$d_6$) δ 1.78 (m, 4H), 2.24 (m, 4H), 3.16 (m, 4H), 3.90 (m, 2H), 4.40-4.49 (m, 6H), 7.24 (d, J=8.4 Hz, 1H), 7.29 (s, 1H), 7.35 (d, J=7.6 Hz, 1H), 7.46 (appar t, J=8.0 Hz, 1H), 8.20 (s, 1H), 8.59 (s, 1H), 9.20 (t, J=6.0 Hz, 1H), 11.45 (br s, 1H).

Example 347: 1-(3-fluoro-4-(4-(2-(pyridin-2-yl)acetamido)-1H-1,2,3-triazol-1-yl)butyl)-N-(3-(trifluoromethoxy)benzyl)-1H-1,2,3-triazole-4-carboxamide

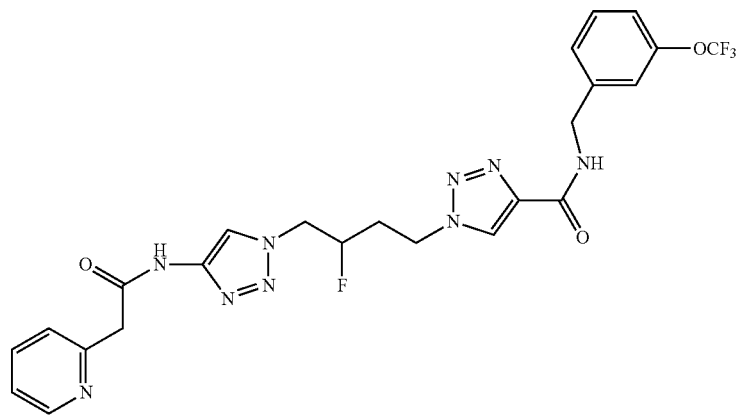

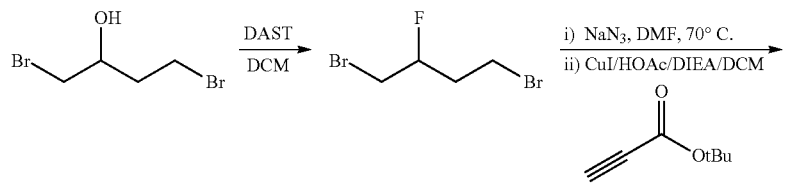

-continued

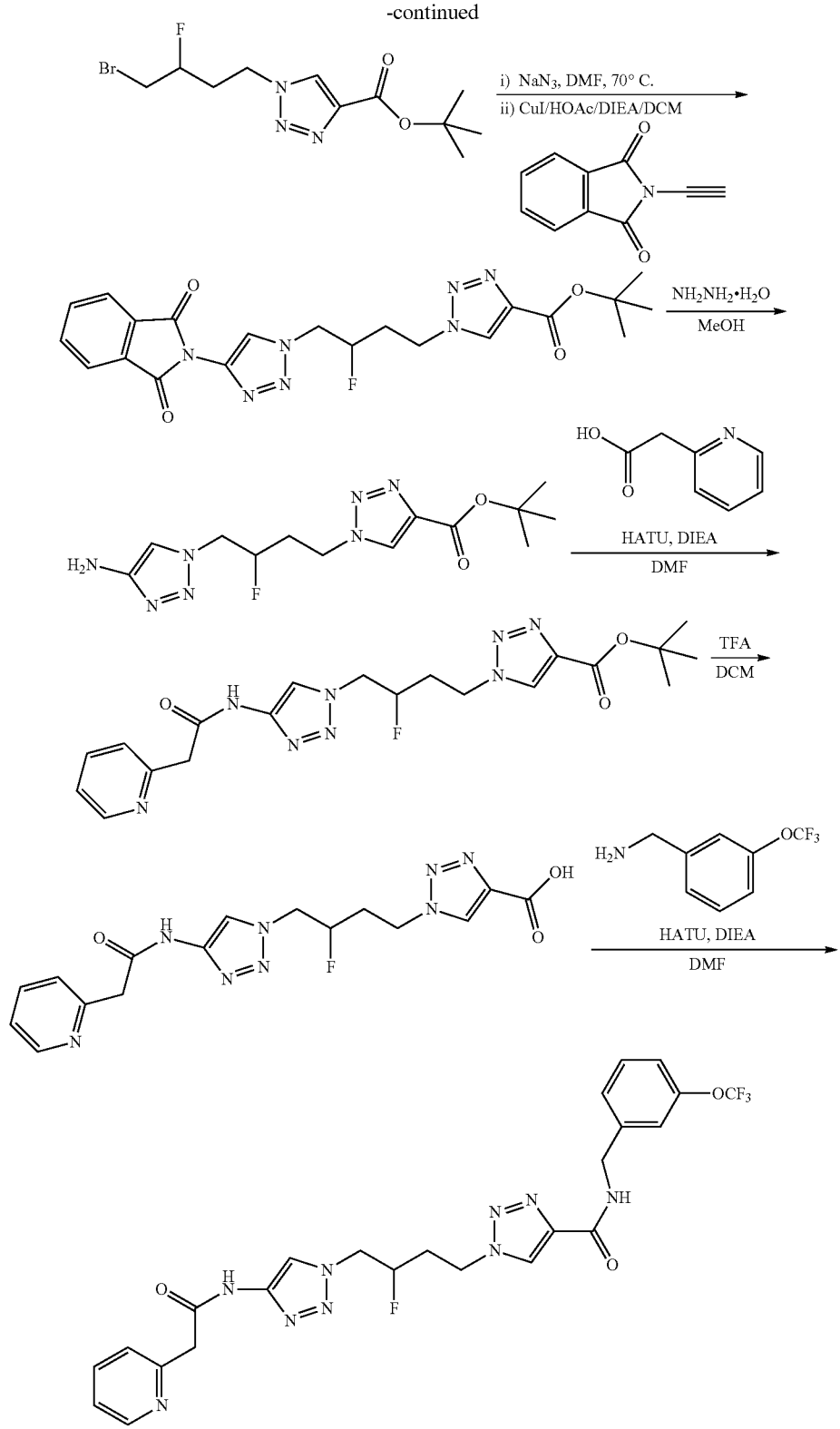

Step 1: 1,4-dibromo-2-fluorobutane

To a solution of 1,4-dibromobutan-2-ol (10 g, 43 mmol) in DCM (140 mL) at 0° C. was slowly added DAST (13.9 g, 86.2 mmol). The mixture was stirred at RT for 16 h, then carefully quenched with sat. aq. NaHCO. The mixture was extracted with DCM (3×100 mL), and the combined organic layers were dried and concentrated under reduced pressure to give the presumed title compound (9.5 g, 94%) as a yellow oil.

Step 2: tert-butyl 1-(4-bromo-3-fluorobutyl)-1H-1,2,3-triazole-4-carboxylate A mixture of 1,4-dibromo-2-fluorobutane (5.0 g, 21 mmol) and NaN$_3$ (1.32 g, 20.3 mmol) in DMF (10 mL) was stirred at 70° C. for 1 h then allowed to cool to RT. DCM (100 mL) was added, followed by AcOH (130 mg, 2.14 mmol), DIEA (280 mg, 2.14 mmol), tert-butyl propiolate (4.04 g, 32.1 mmol) and copper(I) iodide (203 mg, 1.10 mmol). The mixture was stirred at RT for 5 h, diluted with water, and extracted with DCM (2×80 mL). The combined organic layers were dried and concentrated under reduced pressure, and solid was washed with Et$_2$O and isolated by filtration to give the title compound as a brown solid (3.5 g, 51%). MS (ES$^+$) C$_{10}$H$_{17}$BrFN$_3$O$_2$ requires: 321/323, found: 322/324[M+H]$^+$.

Step 3: tert-butyl 1-(4-(4-(1,3-dioxoisoindolin-2-yl)-1H-1,2,3-triazol-1-yl)-3-fluorobutyl)-1H-1,2,3-triazole-4-carboxylate A mixture of tert-butyl 1-(4-bromo-3-fluorobutyl)-1H-1,2,3-triazole-4-carboxylate (1.0 g, 3.1 mmol) and NaN$_3$ (400 mg, 6.2 mmol) in DMF (2 mL) was stirred at 70° C. for 16 h, then allowed to cool to RT. DCM (20 mL) was added, followed by AcOH (19 mg, 0.31 mmol), DIEA (40 mg, 0.31 mmol), 2-ethynylisoindoline-1,3-dione (640 mg, 3.73 mmol) and copper(I) iodide (30 mg, 0.16 mmol). The mixture was stirred at RT for 5 h, then diluted with water and treated with sat. aq. NH$_4$OH (2 mL). The mixture was extracted with EtOAc (3×30 mL). The combined organic layers were dried and concentrated under reduced pressure to give the title compound as a yellow oil (1.3 g, 92%). MS (ES$^+$) C$_{21}$H$_{22}$FN$_7$O$_4$ requires: 455, found: 456[M+H]$^+$.

Step 4: tert-butyl 1-(4-(4-amino-1H-1,2,3-triazol-1-yl)-3-fluorobutyl)-1H-1,2,3-triazole-4-carboxylate Hydrazine hydrate (715 mg, 14.3 mmol) was added to a solution of tert-butyl 1-(4-(4-(1,3-dioxoisoindolin-2-yl)-1H-1,2,3-triazol-1-yl)-3-fluorobutyl)-1H-1,2,3-triazole-4-carboxylate (1.3 g, 2.9 mmol) in MeOH (15 mL). The mixture was stirred at RT for 1 h, then concentrated under reduced pressure and the residue purified by SiO$_2$ gel chromatography (10% MeOH in DCM) to give the title compound as a yellow solid (650 mg, 70%). MS (ES$^+$) C$_{13}$H$_{20}$FN$_7$O$_2$ requires: 325, found: 326 [M+H]$^+$.

Step 5: tert-butyl 1-(3-fluoro-4-(4-(2-(pyridin-2-yl)acetamido)-1H-1,2,3-triazol-1-yl)butyl)-1H-1,2,3-triazole-4-carboxylate A mixture of tert-butyl 1-(4-(4-amino-1H-1,2,3-triazol-1-yl)-3-fluorobutyl)-1H-1,2,3-triazole-4-carboxylate (350 mg, 1.08 mmol), 2-(pyridin-2-yl)acetic acid (220 mg, 1.62 mmol), HATU (614 mg, 1.62 mmol) and DIEA (209 mg, 1.62 mmol) in DMF (10 mL) was stirred at RT for 2 h. The mixture was diluted with water and extracted with 10:1 v:v DCM/MeOH. The organic layer was dried and concentrated under reduced pressure to afford the title compound as a brown oil (500 mg, 60%). MS (ES$^+$) C$_{20}$H$_{25}$FN$_8$O$_3$ requires: 444, found: 445[M+H]$^+$.

Step 6: 1-(3-fluoro-4-(4-(2-(pyridin-2-yl)acetamido)-1H-1,2,3-triazol-1-yl)butyl)-1H-1,2,3-triazole-4-carboxylic Acid TFA (2 mL) was added to a solution of tert-butyl 1-(3-fluoro-4-(4-(2-(pyridin-2-yl)acetamido)-1H-1,2,3-triazol-1-yl)butyl)-1H-1,2,3-triazole-4-carboxylate (500 mg, 1.13 mmol) in DCM (5 mL). The mixture was stirred at 50° C. for 16 h. Water was added and the mixture was concentrated under reduced pressure to remove the organic layer. The aqueous mixture was washed with EtOAc (3×20 mL), then concentrated under reduced pressure. The residue was washed with MeOH and solid was isolated by filtration to give the title compound as a beige solid (300 mg, 68%). MS (ES$^+$) C$_{16}$H$_{17}$FN$_8$O$_3$ requires: 388, found: 389 [M+H]$^+$.

Step 7: 1-(3-fluoro-4-(4-(2-(pyridin-2-yl)acetamido)-1H-1,2,3-triazol-1-yl)butyl)-N-(3-(trifluoromethoxy)benzyl)-1H-1,2,3-triazole-4-carboxamide A mixture of 1-(3-fluoro-4-(4-(2-(pyridin-2-yl)acetamido)-1H-1,2,3-triazol-1-yl)butyl)-1H-1,2,3-triazole-4-carboxylic acid (40 mg, 0.10 mmol), (3-(trifluoromethoxy)phenyl)methanamine (24 mg, 0.12 mmol), HATU (57 mg, 0.15 mmol) and DIEA (20 mg, 0.15 mmol) in DMF (1 mL) was stirred at RT for 2 h. Water (10 mL) was added, and precipitated solid was isolated by filtration and washed with MeOH to give the title compound as a white solid. MS (ES$^+$) C$_{24}$H$_{23}$F$_4$N$_9$O$_3$ requires: 561, found: 562[M+H]$^+$; $^1$H NMR (500 MHz, DMSO-d$_6$) δ 11.17 (s, 1H), 9.20 (t, J=6.1 Hz, 1H), 8.63 (s, 1H), 8.48 (m, 1H), 8.12 (s, 1H), 7.75 (t, J=8.2 Hz, 1H), 7.45 (t, J=7.9 Hz, 1H), 7.36 (dd, J=17.6, 7.8 Hz, 2H), 7.31-7.20 (m, 3H), 4.94 (m, 1H), 4.68 (m, 2H), 4.58 (t, J=6.9 Hz, 2H), 4.48 (d, J=6.2 Hz, 2H), 3.87 (s, 2H), 2.36-2.09 (m, 2H).

Example 372: 1-(3-fluoro-4-(4-(2-(3-fluoroazetidin-1-yl)acetamido)-1H-1,2,3-triazol-1-yl)butyl)-N-(2-fluoro-5-(trifluoromethoxy)benzyl)-1H-1,2,3-triazole-4-carboxamide

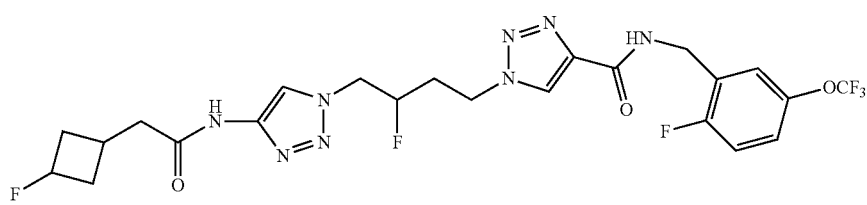

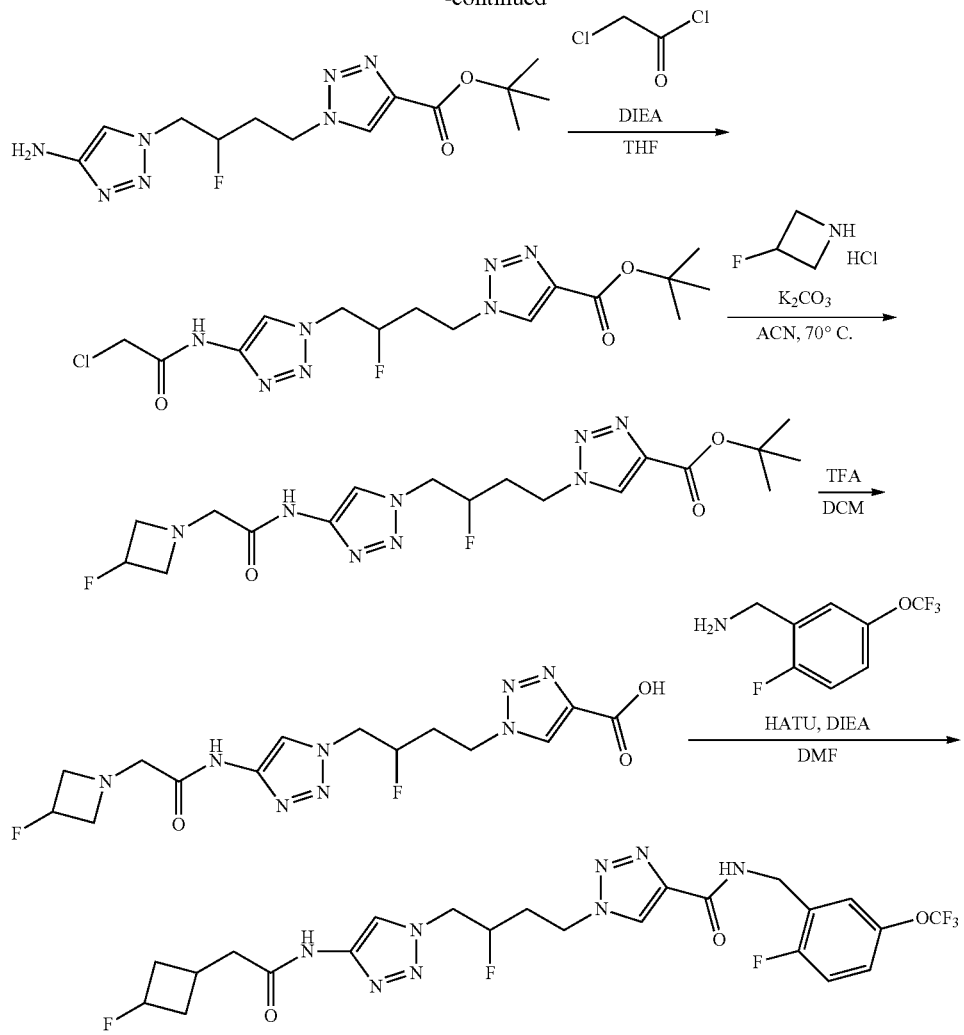

Step 1: tert-butyl 1-(4-(4-(2-chloroacetamido)-1H-1,2,3-triazol-1-yl)-3-fluorobutyl)-1H-1,2,3-triazole-4-carboxylate To a mixture of tert-butyl 1-(4-(4-amino-1H-1,2,3-triazol-1-yl)-3-fluorobutyl)-1H-1,2,3-triazole-4-carboxylate (800 mg, 2.46 mmol) and DIEA (635 mg, 4.92 mmol) in THF (10 mL) at 0° C. was added 2-chloroacetyl chloride (556 mg, 4.92 mmol). The mixture was stirred at 0° C. for 30 min. The mixture was concentrated under reduced pressure, and the residue was partitioned between EtOAc and H$_2$O. The aqueous layer was extracted with EtOAc (3×30 mL). The combined organic layers were dried and concentrated under reduced pressure to afford the title compound as a yellow oil (950 mg, 96%). MS (ES$^+$) C$_{15}$H$_{21}$ClFN$_7$O$_3$ requires: 401, found: 402[M+H]$^+$.

Step 2: tert-butyl 1-(3-fluoro-4-(4-(2-(3-fluoroazetidin-1-yl)acetamido)-1H-1,2,3-triazol-1-yl)butyl)-1H-1,2,3-triazole-4-carboxylate A mixture of tert-butyl 1-(4-(4-(2-chloroacetamido)-1H-1,2,3-triazol-1-yl)-3-fluorobutyl)-1H-1,2,3-triazole-4-carboxylate (450 mg, 1.12 mmol), 3-fluoroazetidine hydrochloride (138 mg, 1.23 mmol) and K$_2$CO$_3$ (310 mg, 2.24 mmol) in ACN (5 mL) was stirred at 70° C. for 5 h. The mixture was concentrated under reduced pressure and the residue purified by SiO$_2$ gel chromatography (10% MeOH in DCM) to give the title compound as a yellow solid (330 mg, 67%). MS (ES$^+$) C$_{18}$H$_{26}$F$_2$N$_8$O$_3$ requires: 440, found: 441[M+H]$^+$.

Step 3: 1-(3-fluoro-4-(4-(2-(3-fluoroazetidin-1-yl)acetamido)-1H-1,2,3-triazol-1-yl)butyl)-1H-1,2,3-triazole-4-carboxylic Acid TFA (2 mL) was added to a solution of tert-butyl 1-(3-fluoro-4-(4-(2-(3-fluoroazetidin-1-yl)acetamido)-1H-1,2,3-triazol-1-yl)butyl)-1H-1,2,3-triazole-4-carboxylate (330 mg, 0.75 mmol) in DCM (10 mL). The mixture was stirred at 50° C. for 4 h. Water was added and the mixture lyophilized to give the title compound as a yellow oil (350 mg, 94%). MS (ES$^+$) C$_{14}$H$_{18}$F$_2$N$_8$O$_3$ requires: 384, found: 385[M+H]$^+$.

Step 8: 1-(3-fluoro-4-(4-(2-(3-fluoroazetidin-1-yl)acetamido)-1H-1,2,3-triazol-1-yl)butyl)-N-(2-fluoro-5-(trifluoromethoxy)benzyl)-1H-1,2,3-triazole-4-carboxamide A mixture of 1-(3-fluoro-4-(4-(2-(3-fluoroazetidin-1-yl)acetamido)-1H-1,2,3-triazol-1-yl)butyl)-1H-1,2,3-triazole- 4-carboxylic acid (40 mg, 0.1 mmol), (2-fluoro-5-(trifluoromethoxy)phenyl)methanamine (25 mg, 0.12 mmol), HATU (59 mg, 0.15 mmol) and DIEA (20 mg, 0.15 mmol) in DMF (1 mL) was stirred at RT for 2 h. Water was added, and precipitated solid was isolated by filtration and purified by preparatory HPLC (Mobile phase: A=0.1% ammonium hydroxide/H$_2$O, B=acetonitrile; Gradient: B=5%-95% in 18 min; Column: C18) to give the title compound as a white solid (6 mg, 10%). MS (ES$^+$) C$_{22}$H$_{23}$F$_6$N$_9$O$_3$ requires: 575, found: 576[M+H]$^+$; $^1$H NMR (500 MHz, DMSO-d$_6$) δ 10.64 (s, 1H), 9.17 (t, J=6.1 Hz, 1H), 8.64 (s, 1H), 8.16 (s, 1H), 7.36-7.30 (m, 3H), 5.18 (m, 1H), 4.96 (m, 1H), 4.73-4.63 (m, 2H), 4.59 (t, J=6.9 Hz, 2H), 4.50 (d, J=5.8 Hz, 2H), 3.71-3.63 (m, 2H), 3.29-3.24 (m, 4H), 2.33-2.13 (m, 2H).

Non-limiting examples include the following compounds and pharmaceutically acceptable salts thereof:

TABLE 1

Synthesized Examples

| Ex. No. | Structure | Name |
|---|---|---|
| 10 | 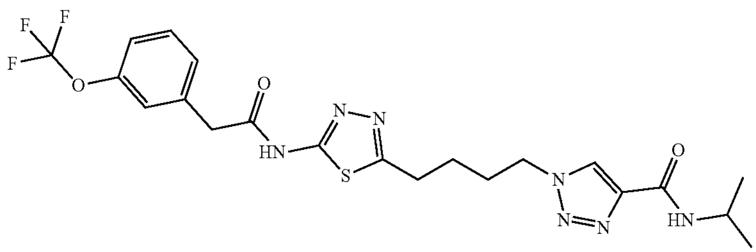 [SMILES: CC(C)NC(=O)c1cn(CCCCc2nnc(NC(=O)Cc3cccc(OC(F)(F)F)c3)s2)nn1] | N-(propan-2-yl)-1-[4-(5-{2-[3-(trifluoromethoxy)phenyl)acetamido}-1,3,4-thiadiazol-2-yl)butyl]-1H-1,2,3-triazole-4-carboxamide |
| 11 | 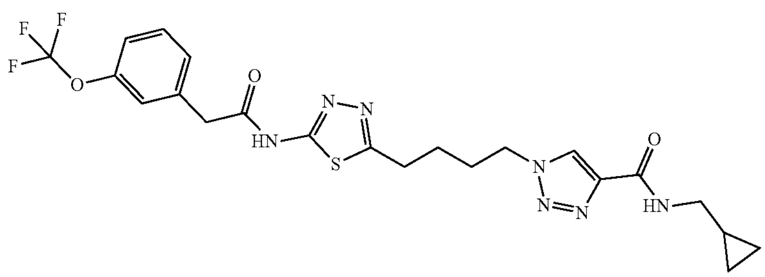 [SMILES: O=C(Cc1cccc(OC(F)(F)F)c1)Nc1nnc(CCCCn2cc(C(=O)NCC3CC3)nn2)s1] | N-(cyclopropylmethyl)-1-[4-(5-{2-[3-(trifluoromethoxy)phenyl]acetamido}-1,3,4-thiadiazol-2-yl)butyl]-1H-1,2,3-triazole-4-carboxamide |
| 12 | 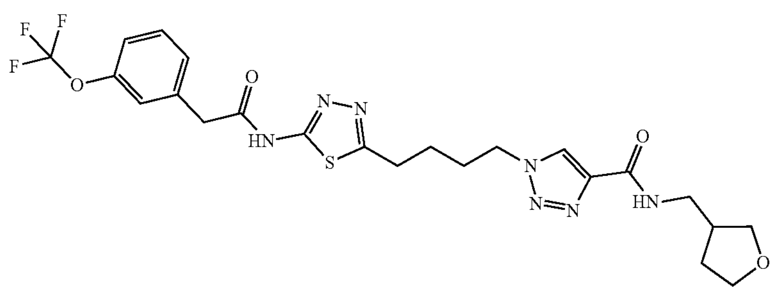 [SMILES: O=C(Cc1cccc(OC(F)(F)F)c1)Nc1nnc(CCCCn2cc(C(=O)NCC3CCOC3)nn2)s1] | N-(oxolan-3-ylmethyl)-1-[4-(5-{2-[3-(trifluoromethoxy)phenyl]acetamido}-1,3,4-thiadiazol-2-yl)butyl]-1H-1,2,3-triazole-4-carboxamide |
| 13 | 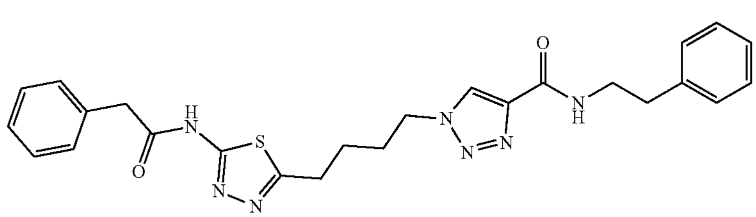 [SMILES: O=C(Cc1ccccc1)Nc1nnc(CCCCn2cc(C(=O)NCCc3ccccc3)nn2)s1] | 1-{4-[5-(2-phenylacetamido)-1,3,4-thiadiazol-2-yl]butyl}-N-(2-phenylethyl)-1H-1,2,3-triazole-4-carboxamide |
| 14 | 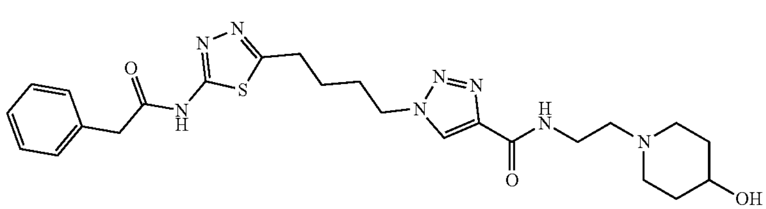 [SMILES: O=C(Cc1ccccc1)Nc1nnc(CCCCn2cc(C(=O)NCCN3CCC(O)CC3)nn2)s1] | N-[2-(4-hydroxypiperidin-1-yl)ethyl]-1-{4-[5-(2-phenylacetamido)-1,3,4-thiadiazol-2-yl]butyl}-1H-1,2,3-triazole-4-carboxamide |

TABLE 1-continued

Synthesized Examples

| Ex. No. | Structure | Name |
|---|---|---|
| 15 | 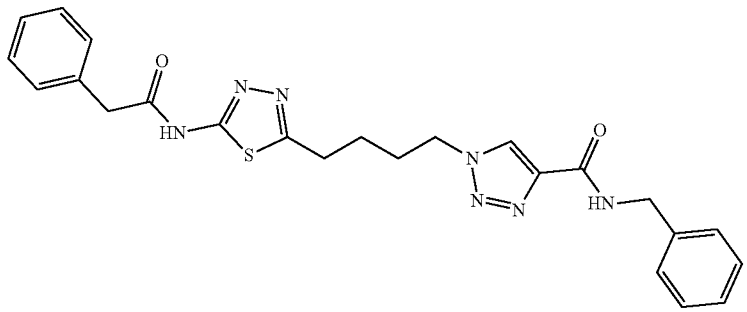 [SMILES: O=C(Cc1ccccc1)Nc1nnc(CCCCn2cc(C(=O)NCc3ccccc3)nn2)s1] | N-benzyl-1-{4-[5-(2-phenylacetamido)-1,3,4-thiadiazol-2-yl]butyl}-1H-1,2,3-triazole-4-carboxamide |
| 16 | 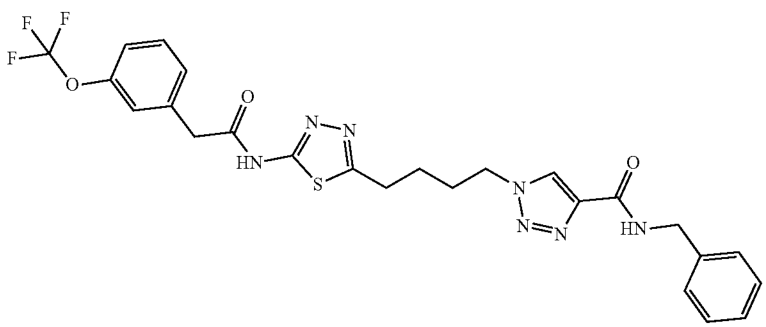 [SMILES: O=C(Cc1cccc(OC(F)(F)F)c1)Nc1nnc(CCCCn2cc(C(=O)NCc3ccccc3)nn2)s1] | N-benzyl-1-[4-(5-{2-[3-(trifluoromethoxy)phenyl]acetamido}-1,3,4-thiadiazol-2-yl)butyl]-1H-1,2,3-triazole-4-carboxamide |
| 17 | 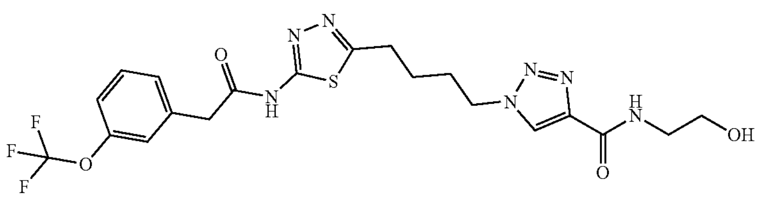 [SMILES: O=C(Cc1cccc(OC(F)(F)F)c1)Nc1nnc(CCCCn2cc(C(=O)NCCO)nn2)s1] | N-(2-hydroxyethyl)-1-[4-(5-{2-[3-(trifluoromethoxy)phenyl]acetamido}-1,3,4-thiadiazol-2-yl)butyl]-1H-1,2,3-triazole-4-carboxamide |
| 18 | 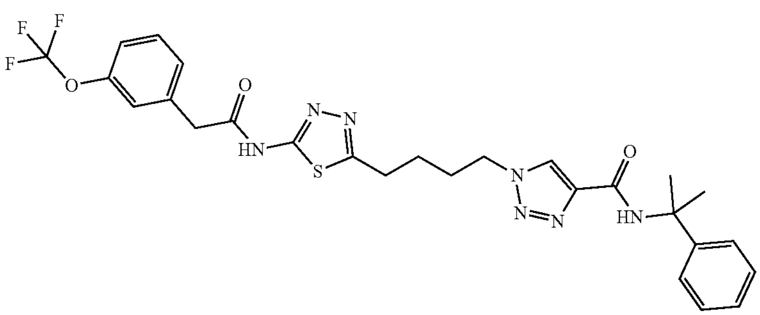 [SMILES: CC(C)(NC(=O)c1cn(CCCCc2nnc(NC(=O)Cc3cccc(OC(F)(F)F)c3)s2)nn1)c1ccccc1] | N-(2-phenylpropan-2-yl)-1-[4-(5-{2-[3-(trifluoromethoxy)phenyl]acetamido}-1,3,4-thiadiazol-2-yl)butyl]-1H-1,2,3-triazole-4-carboxamide |
| 19 | 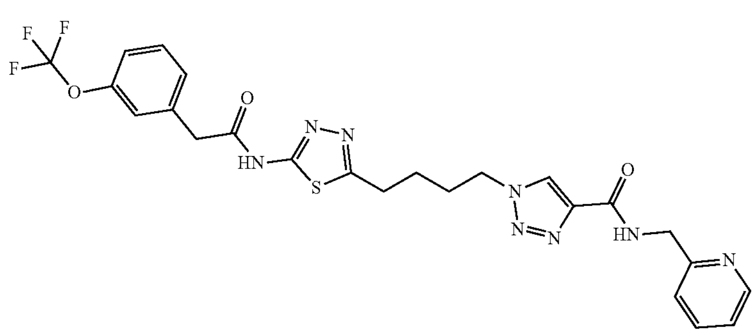 [SMILES: O=C(Cc1cccc(OC(F)(F)F)c1)Nc1nnc(CCCCn2cc(C(=O)NCc3ccccn3)nn2)s1] | N-(pyridin-2-ylmethyl)-1-[4-(5-{2-[3-(trifluoromethoxy)phenyl]acetamido}-1,3,4-thiadiazol-2-yl)butyl]-1H-1,2,3-triazole-4-carboxamide |

TABLE 1-continued

Synthesized Examples

| Ex. No. | Structure | Name |
|---|---|---|
| 20 | 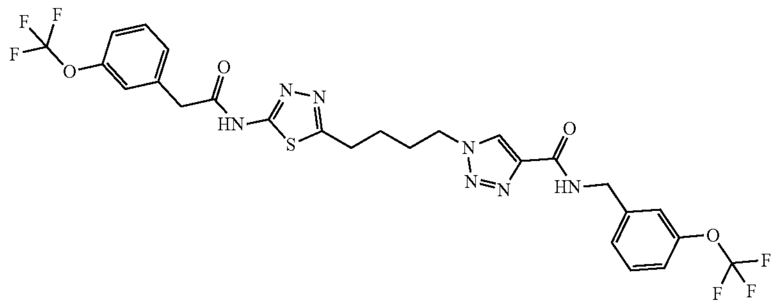 [SMILES: O=C(Cc1cccc(OC(F)(F)F)c1)Nc1nnc(CCCCn2cc(C(=O)NCc3cccc(OC(F)(F)F)c3)nn2)s1] | 1-[4-(5-{2-[3-(trifluoromethoxy)phenyl]acetamido}-1,3,4-thiadiazol-2-yl)butyl]-N-{[3-(trifluoromethoxy)phenyl]methyl}-1H-1,2,3-triazole-4-carboxamide |
| 21 | 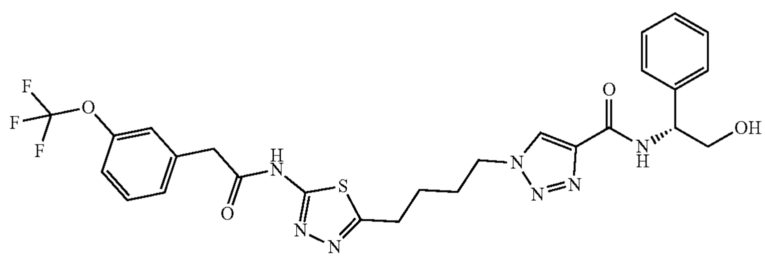 [SMILES: O=C(Cc1cccc(OC(F)(F)F)c1)Nc1nnc(CCCCn2cc(C(=O)N[C@@H](CO)c3ccccc3)nn2)s1] | N-[(1R)-2-hydroxy-1-phenylethyl]-1-[4-(5-{2-[3-(trifluoromethoxy)phenyl]acetamido}-1,3,4-thiadiazol-2-yl)butyl]-1H-1,2,3-triazole-4-carboxamide |
| 22 | 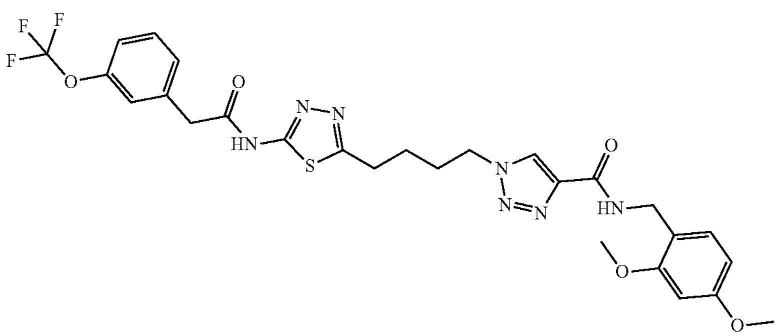 [SMILES: COc1ccc(CNC(=O)c2cn(CCCCc3nnc(NC(=O)Cc4cccc(OC(F)(F)F)c4)s3)nn2)c(OC)c1] | N-[(2,4-dimethoxyphenyl)methyl]-1-[4-(5-{2-[3-(trifluoromethoxy)phenyl]acetamido}-1,3,4-thiadiazol-2-yl)butyl]-1H-1,2,3-triazole-4-carboxamide |
| 23 | 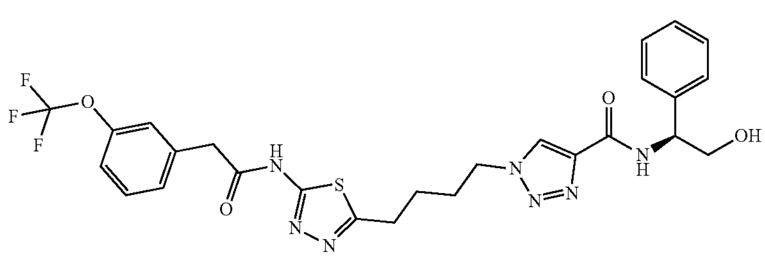 [SMILES: O=C(Cc1cccc(OC(F)(F)F)c1)Nc1nnc(CCCCn2cc(C(=O)N[C@H](CO)c3ccccc3)nn2)s1] | N-[(1S)-2-hydroxy-1-phenylethyl]-1-[4-(5-{2-[3-(trifluoromethoxy)phenyl]acetamido}-1,3,4-thiadiazol-2-yl)butyl]-1H-1,2,3-triazole-4-carboxamide |
| 24 | 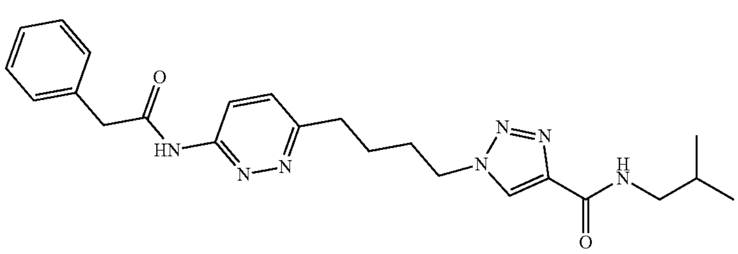 [SMILES: CC(C)CNC(=O)c1cn(CCCCc2ccc(NC(=O)Cc3ccccc3)nn2)nn1] | N-(2-methylpropyl)-1-{4-[6-(2-phenylacetamido)pyridazin-3-yl]butyl}-1H-1,2,3-triazole-4-carboxamide |

TABLE 1-continued

Synthesized Examples

| Ex. No. | Structure | Name |
|---|---|---|
| 25 | 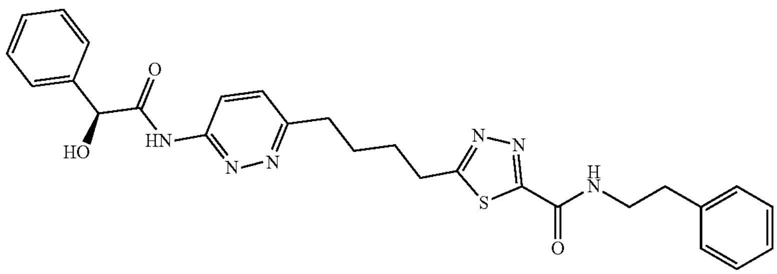 [SMILES: O=C(NCCc1ccccc1)c1nnc(CCCCc2ccc(NC(=O)[C@@H](O)c3ccccc3)nn2)s1] | 5-(4-{6-[(2S)-2-hydroxy-2-phenylacetamido]pyridazin-3-yl}butyl)-N-(2-phenylethl)-1,3,4-thiadiazole-2-carboxamide |
| 26 | 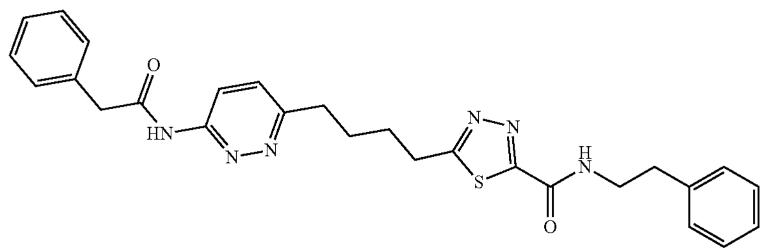 [SMILES: O=C(Cc1ccccc1)Nc1ccc(CCCCc2nnc(C(=O)NCCc3ccccc3)s2)nn1] | 5-{4-[6-(2-phenylacetamido)pyridazin-3-yl]butyl}-N-(2-phenylethyl)-1,3,4-thiadiazole-2-carboxamide |
| 27 | 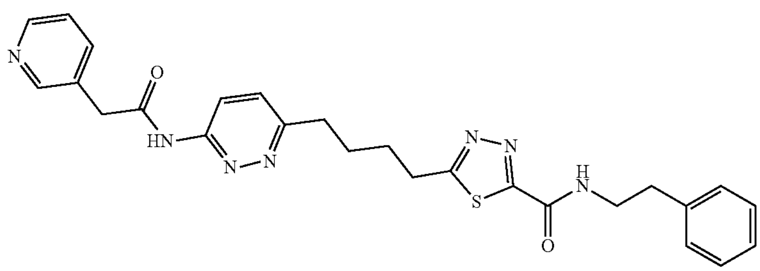 [SMILES: O=C(Cc1cccnc1)Nc1ccc(CCCCc2nnc(C(=O)NCCc3ccccc3)s2)nn1] | N-(2-phenylethyl)-5-(4-{6-[2-(pyridin-3-yl)acetamido]pyridazin-3-yl}butyl)-1,3,4-thiadiazole-2-carboxamide |
| 28 | 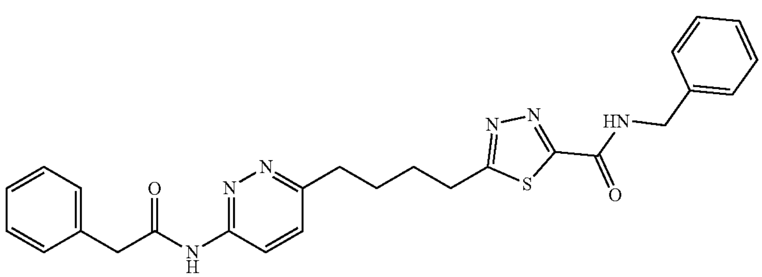 [SMILES: O=C(Cc1ccccc1)Nc1ccc(CCCCc2nnc(C(=O)NCc3ccccc3)s2)nn1] | N-benzyl-5-{4-[6-(2-phenylacetamido)pyridazin-3-yl]butyl}-1,3,4-thiadiazole-2-carboxamide |
| 29 | 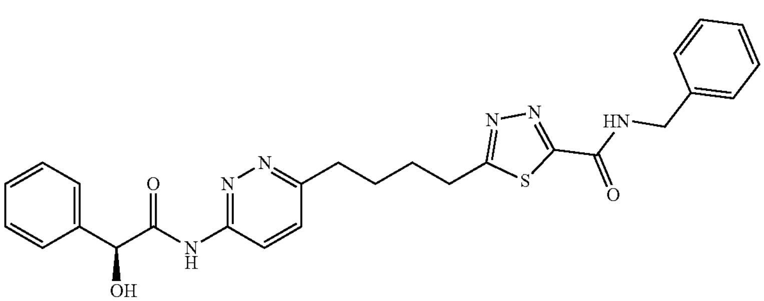 [SMILES: O=C(NCc1ccccc1)c1nnc(CCCCc2ccc(NC(=O)[C@@H](O)c3ccccc3)nn2)s1] | N-benzyl-5-(4-{6-[(2S)-2-hydroxy-2-phenylacetamido]pyridazin-3-yl}butyl)-1,3,4-thiadiazole-2-carboxamide |

TABLE 1-continued

Synthesized Examples

| Ex. No. | Structure | Name |
|---|---|---|
| 30 | 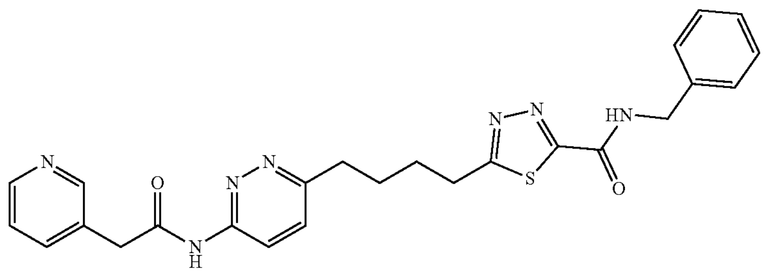 [SMILES: O=C(Cc1cccnc1)Nc1ccc(CCCCc2nnc(C(=O)NCc3ccccc3)s2)nn1] | N-benzyl-5-(4-{6-[2-(pyridin-3-yl)acetamido]pyridazin-3-yl}butyl)-1,3,4-thiadiazole-2-carboxamide |
| 31 | 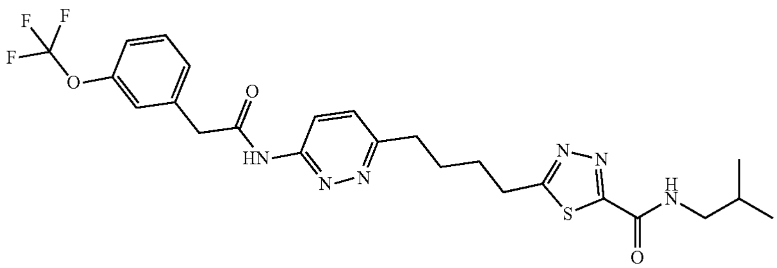 [SMILES: CC(C)CNC(=O)c1nnc(CCCCc2ccc(NC(=O)Cc3cccc(OC(F)(F)F)c3)nn2)s1] | N-(2-methylpropyl)-5-[4-(6-{2-[3-(trifluoromethoxy)phenyl]acetamido}pyridazin-3-yl)butyl]-1,3,4-thiadiazole-2-carboxamide |
| 32 | 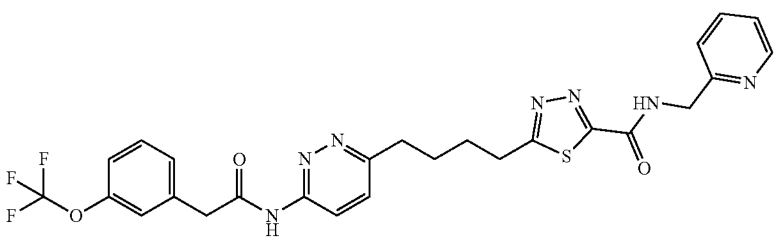 [SMILES: O=C(Cc1cccc(OC(F)(F)F)c1)Nc1ccc(CCCCc2nnc(C(=O)NCc3ccccn3)s2)nn1] | N-(pyridin-2-ylmethyl)-5-[4-(6-{2-[3-(trifluoromethoxy)phenyl]acetamido}pyridazin-3-yl)butyl]-1,3,4-thiadiazole-2-carboxamide |
| 33 | 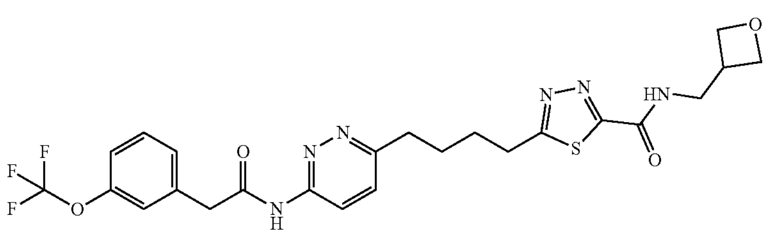 [SMILES: O=C(Cc1cccc(OC(F)(F)F)c1)Nc1ccc(CCCCc2nnc(C(=O)NCC3COC3)s2)nn1] | N-(oxetan-3-ylmethyl)-5-[4-(6-{2-[3-(trifluoromethoxy)phenyl]acetamido}pyridazin-3-yl)butyl]-1,3,4-thiadiazole-2-carboxamide |
| 34 | | N-(2-hydroxy-2-methylpropyl)-5-[4-(6-{2-[3-(trifluoromethoxy)phenyl]acetamido}pyridazin-3-yl)butyl]-1,3,4-thiadiazole-2-carboxamide |
| 34 | | N-[2-(pyrrolidin-1-yl)ethyl]-5-[5-(6-{2-[3-(trifluoromethoxy)phenyl]acetamido}pyridazin-3-yl)butyl]-1,3,4-thiadiazole-2-carboxamide |

TABLE 1-continued

Synthesized Examples

| Ex. No. | Structure | Name |
|---|---|---|
| 36 | 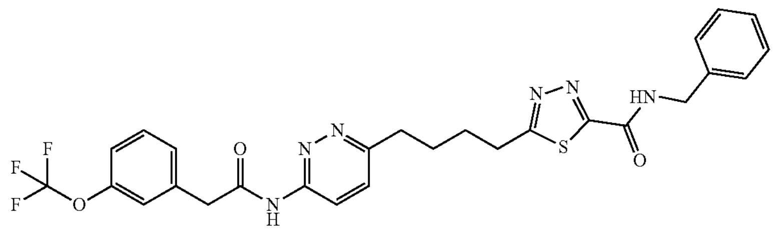 [SMILES: O=C(Cc1cccc(OC(F)(F)F)c1)Nc1ccc(CCCCc2nnc(C(=O)NCc3ccccc3)s2)nn1] | N-benzyl-5-[4-(6-{2-[3-(trifluoromethoxy)phenyl]acetamido}pyridazin-3-yl)butyl]-1,3,4-thiadiazole-2-carboxamide |
| 37 | 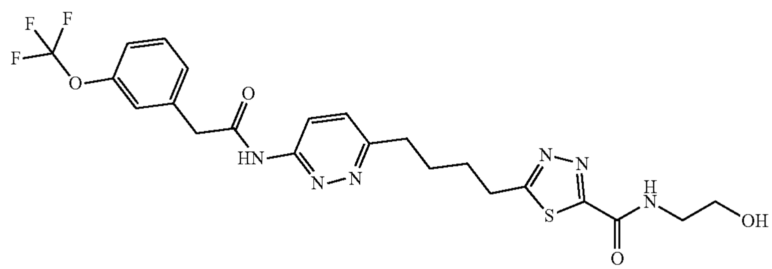 [SMILES: O=C(Cc1cccc(OC(F)(F)F)c1)Nc1ccc(CCCCc2nnc(C(=O)NCCO)s2)nn1] | N-(2-hydroxyethyl)-5-[4-(6-{2-[3-(trifluoromethoxy)phenyl]acetamido}pyridazin-3-yl)butyl]-1,3,4-thiadiazole-2-carboxamide |
| 38 | 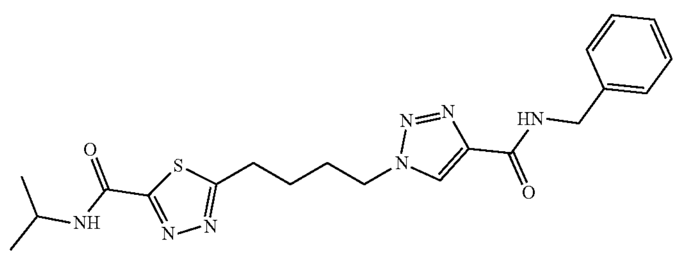 [SMILES: CC(C)NC(=O)c1nnc(CCCCn2cc(C(=O)NCc3ccccc3)nn2)s1] | 5-{4-[4-(benzylcarbamoyl)-1H-1,2,3-triazol-1-yl]butyl}-N-(propan-2-yl)-1,3,4-thiadiazole-2-carboxamide |
| 39 | 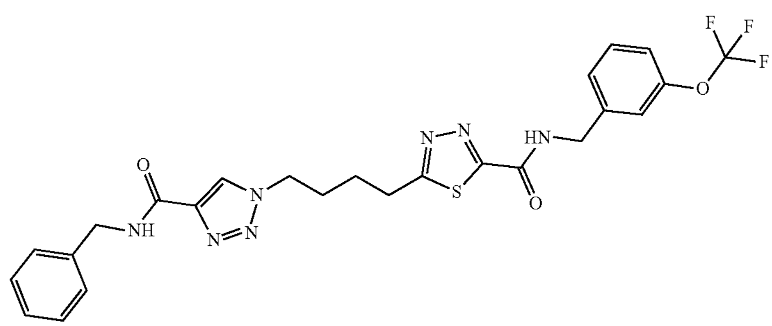 [SMILES: O=C(NCc1ccccc1)c1cn(CCCCc2nnc(C(=O)NCc3cccc(OC(F)(F)F)c3)s2)nn1] | 5-{4-[4-(benzylcarbamoyl)-1H-1,2,3-triazol-1-yl]butyl}-N-{[3-(trifluoromethoxy)phenyl]methyl}-1,3,4-thiadiazole-2-carboxamide |
| 40 | 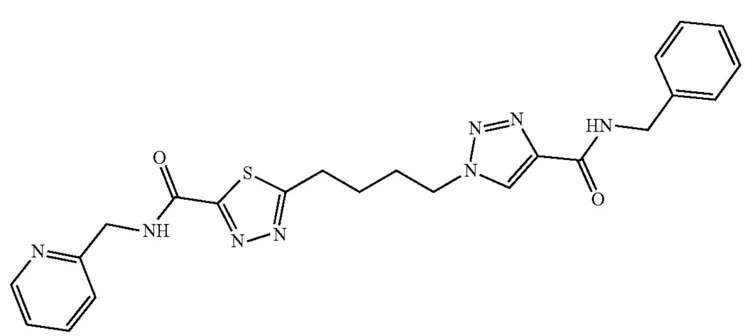 [SMILES: O=C(NCc1ccccc1)c1cn(CCCCc2nnc(C(=O)NCc3ccccn3)s2)nn1] | 5-{4-[4-(benzylcarbamoyl)-1H-1,2,3-triazol-1-yl]butyl}-N-(pyridin-2-ylmethyl)-1,3,4-thiadiazole-2-carboxamide |

TABLE 1-continued

Synthesized Examples

| Ex. No. | Structure | Name |
|---|---|---|
| 41 | 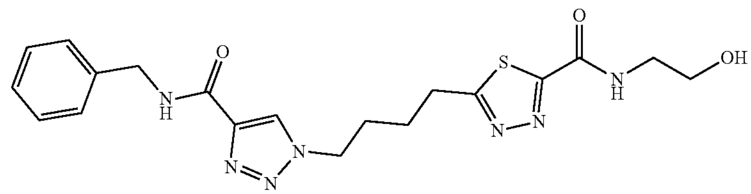 [SMILES: O=C(NCc1ccccc1)c1cn(CCCCc2nnc(C(=O)NCCO)s2)nn1] | 5-{4-[4-(benzylcarbamoyl)-1H-1,2,3-triazol-1-yl]butyl}-N-(2-hydroxyethyl)-1,3,4-thiadiazole-2-carboxamide |
| 42 | 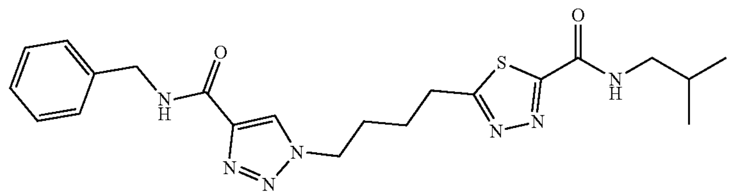 [SMILES: CC(C)CNC(=O)c1nnc(CCCCn2cc(C(=O)NCc3ccccc3)nn2)s1] | 5-{4-[4-(benzylcarbamoyl)-1H-1,2,3-triazol-1-yl]butyl}-N-(2-methylpropyl)-1,3,4-thiadiazole-2-carboxamide |
| 43 | 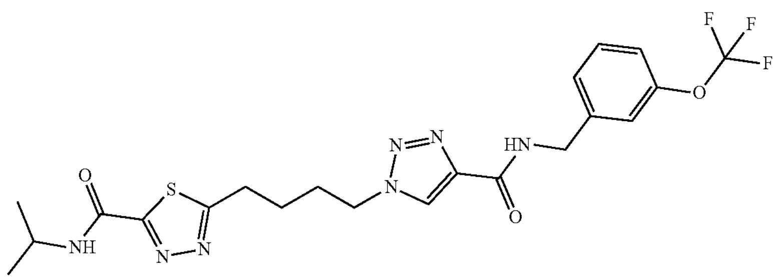 [SMILES: CC(C)NC(=O)c1nnc(CCCCn2cc(C(=O)NCc3cccc(OC(F)(F)F)c3)nn2)s1] | N-(propan-2-yl)-5-{4-[4-({[3-(trifluoromethoxy)phenyl]methyl}carbamoyl)-1H-1,2,3-triazol-1-yl]butyl}-1,3,4-thiadiazole-2-carboxamide |
| 44 | 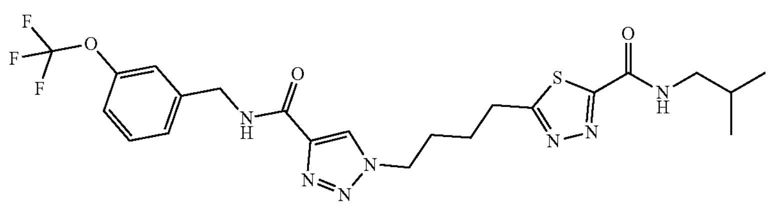 [SMILES: CC(C)CNC(=O)c1nnc(CCCCn2cc(C(=O)NCc3cccc(OC(F)(F)F)c3)nn2)s1] | N-(2-methylpropyl)-5-{4-[4-({[3-(trifluoromethoxy)phenyl]methyl}carbamoyl)-1H-1,2,3-triazol-1-yl]butyl}-1,3,4-thiadiazole-2-carboxamide |
| 45 | 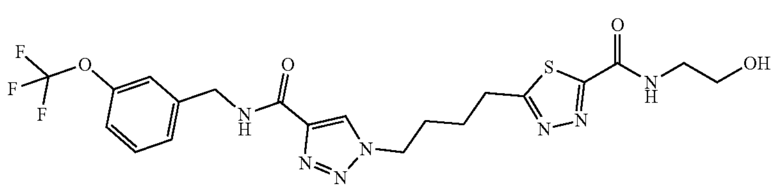 [SMILES: O=C(NCc1cccc(OC(F)(F)F)c1)c1cn(CCCCc2nnc(C(=O)NCCO)s2)nn1] | N-(2-hydroxyethyl)-5-{4-[4-({[3-(trifluoromethoxy)phenyl]methyl}carbamoyl)-1H-1,2,3-triazol-1-yl]butyl}-1,3,4-thiadiazole-2-carboxamide |
| 46 | 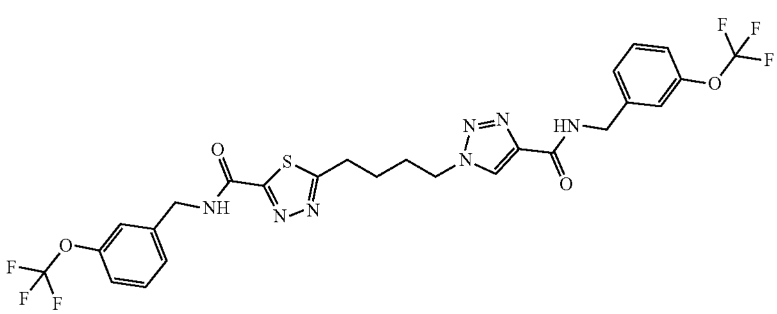 [SMILES: O=C(NCc1cccc(OC(F)(F)F)c1)c1cn(CCCCc2nnc(C(=O)NCc3cccc(OC(F)(F)F)c3)s2)nn1] | N-{[3-(trifluoromethoxy)phenyl]methyl}-5-{4-[4-({[3-(trifluoromethoxy)phenyl]methyl}carbamoyl)-1H-1,2,3-triazol-1-yl]butyl}-1,3,4-thiadiazole-2-carboxamide |

TABLE 1-continued

Synthesized Examples

| Ex. No. | Structure | Name |
|---|---|---|
| 47 | 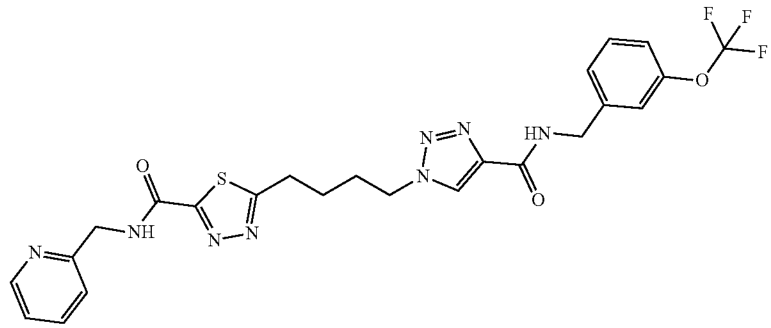 [SMILES: O=C(NCc1cccc(OC(F)(F)F)c1)c1cn(CCCCc2nnc(C(=O)NCc3ccccn3)s2)nn1] | N-(pyridin-2-ylmethyl)-5-{4-[4-({[3-(trifluoromethoxy)phenyl]methyl}carbamoyl)-1H-1,2,3-triazol-1-yl]butyl}-1,3,4-thiadiazole-2-carboxamide |
| 48 | 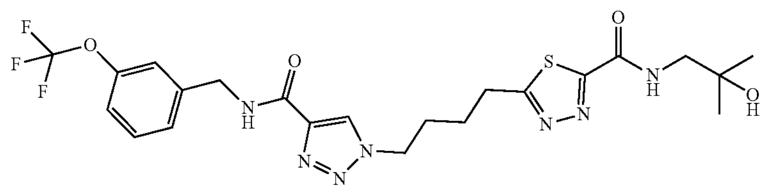 [SMILES: CC(C)(O)CNC(=O)c1nnc(CCCCn2cc(C(=O)NCc3cccc(OC(F)(F)F)c3)nn2)s1] | N-(2-hydroxy-2-methylpropyl)-5-{4-[4-({[3-(trifluoromethoxy)phenyl]methyl}carbamoyl)-1H-1,2,3-triazol-1-yl]butyl}-1,3,4-thiadiazole-2-carboxamide |
| 49 | 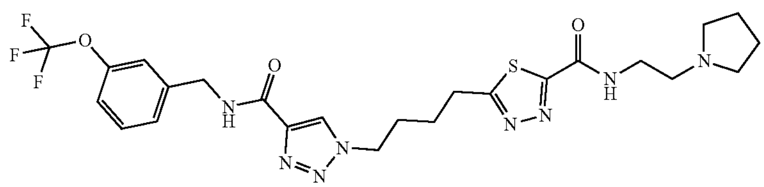 [SMILES: O=C(NCc1cccc(OC(F)(F)F)c1)c1cn(CCCCc2nnc(C(=O)NCCN3CCCC3)s2)nn1] | N-[2-(pyrrolidin-1-yl)ethyl]-5-{4-[4-({[3-(trifluoromethoxy)phenyl]methyl}carbamoyl)-1H-1,2,3-triazol-1-yl]butyl}-1,3,4-thiadiazole-2-carboxamide |
| 50 | 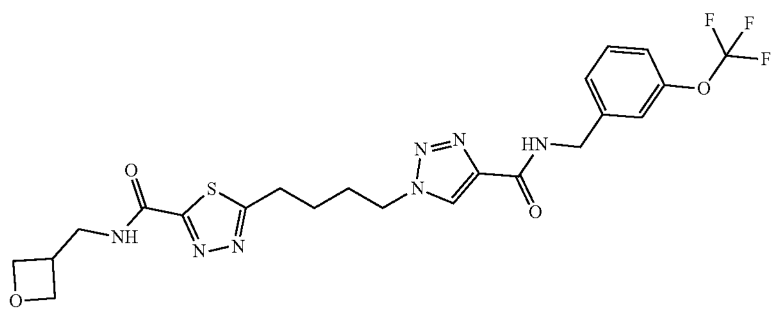 [SMILES: O=C(NCc1cccc(OC(F)(F)F)c1)c1cn(CCCCc2nnc(C(=O)NCC3COC3)s2)nn1] | N-(oxetan-3-ylmethyl)-5-{4-[4-({[3-(trifluoromethoxy)phenyl]methyl}carbamoyl)-1H-1,2,3-triazol-1-yl]butyl}-1,3,4-thiadiazole-2-carboxamide |
| 51 | 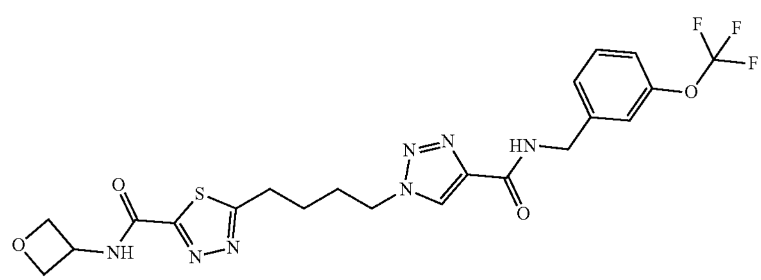 [SMILES: O=C(NCc1cccc(OC(F)(F)F)c1)c1cn(CCCCc2nnc(C(=O)NC3COC3)s2)nn1] | N-(oxetan-3-yl)-5-{4-[4-({[3-(trifluoromethoxy)phenyl]methyl}carbamoyl)-1H-1,2,3-triazol-1-yl]butyl}-1,3,4-thiadiazole-2-carboxamide |
| 52 | 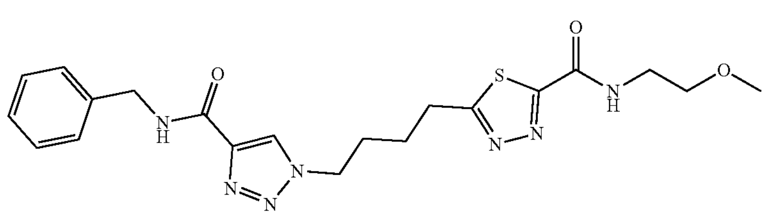 [SMILES: COCCNC(=O)c1nnc(CCCCn2cc(C(=O)NCc3ccccc3)nn2)s1] | 5-{4-[4-(benzylcarbamoyl)-1H-1,2,3-triazol-1-yl]butyl}-N-(2-methoxyethyl)-1,3,4-thiadiazole-2-carboxamide |

TABLE 1-continued

Synthesized Examples

| Ex. No. | Structure | Name |
|---|---|---|
| 53 | 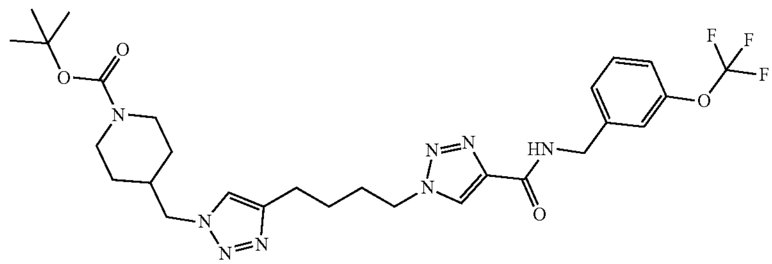 [SMILES: CC(C)(C)OC(=O)N1CCC(Cn2cc(CCCCn3cc(C(=O)NCc4cccc(OC(F)(F)F)c4)nn3)nn2)CC1] | tert-butyl 4-[(4-{4-[4-({[3-(trifluoromethoxy)phenyl]methyl}carbamoyl)-1H-1,2,3-triazol-1-yl]butyl}-1H-1,2,3-triazol-1-yl)methyl]piperidine-1-carboxylate |
| 54 | 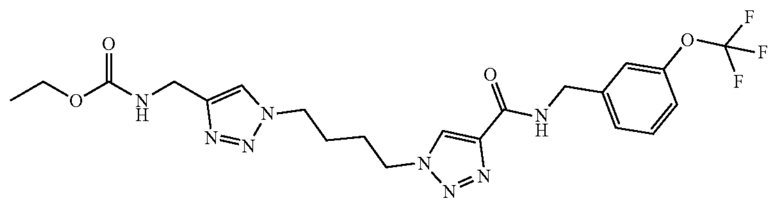 [SMILES: CCOC(=O)NCc1cn(CCCCn2cc(C(=O)NCc3cccc(OC(F)(F)F)c3)nn2)nn1] | ethyl N-[(1-{4-[4-({[3-(trifluoromethoxy)phenyl]methyl}carbamoyl)-1H-1,2,3-triazol-1-yl]butyl}-1H-1,2,3-triazol-4-yl)methyl]carbamate |
| 55 | 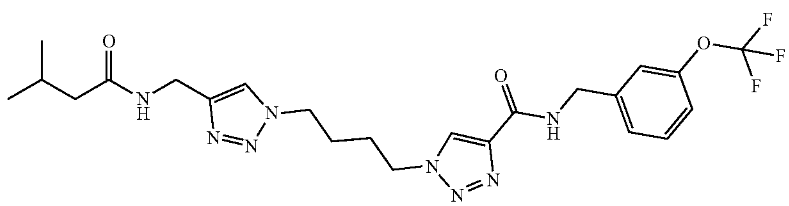 [SMILES: CC(C)CC(=O)NCc1cn(CCCCn2cc(C(=O)NCc3cccc(OC(F)(F)F)c3)nn2)nn1] | 1-(4-{4-[(3-methylbutanamido)methyl]-1H-1,2,3-triazol-1-yl}butyl)-N-{[3-(trifluoromethoxy)phenyl]methyl}-1H-1,2,3-triazole-4-carboxamide |
| 56 | 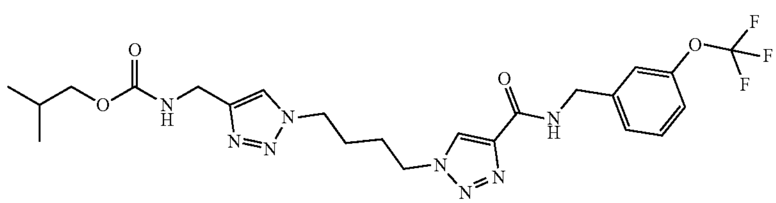 [SMILES: CC(C)COC(=O)NCc1cn(CCCCn2cc(C(=O)NCc3cccc(OC(F)(F)F)c3)nn2)nn1] | 2-methylpropyl N-[(1-{4-[4-({[3-(trifluoromethoxy)phenyl]methyl}carbamoyl)-1H-1,2,3-triazol-1-yl]butyl}-1H-1,2,3-triazol-4-yl)methyl]carbamate |
| 57 | 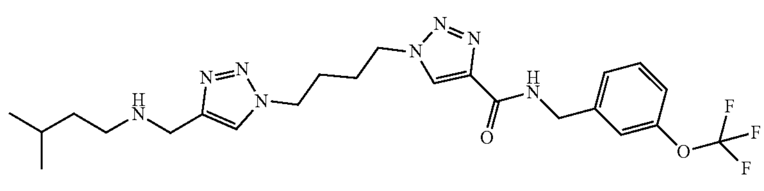 [SMILES: CC(C)CCNCc1cn(CCCCn2cc(C(=O)NCc3cccc(OC(F)(F)F)c3)nn2)nn1] | 1-(4-(4-((isopentylamino)methyl)-1H-1,2,3-triazol-1-yl)butyl)-N-(3-(trifluoromethoxy)benzyl)-1H-1,2,3-triazole-4-carboxamide |
| 58 | 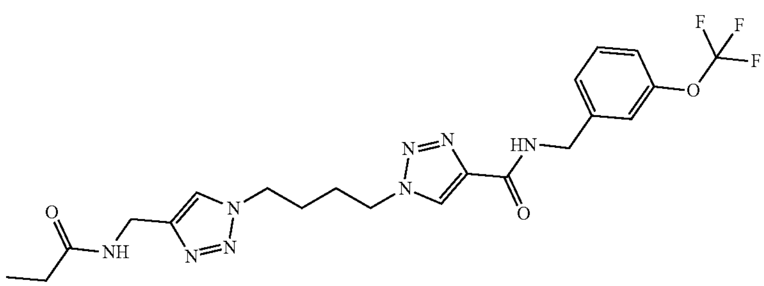 [SMILES: CCC(=O)NCc1cn(CCCCn2cc(C(=O)NCc3cccc(OC(F)(F)F)c3)nn2)nn1] | 1-(4-(4-(propionamidomethyl)-1H-1,2,3-triazol-1-yl)butyl)-N-(3-(trifluoromethoxy)benzyl)-1H-1,2,3-triazole-4-carboxamide |

TABLE 1-continued

Synthesized Examples

| Ex. No. | Structure | Name |
|---|---|---|
| 59 | 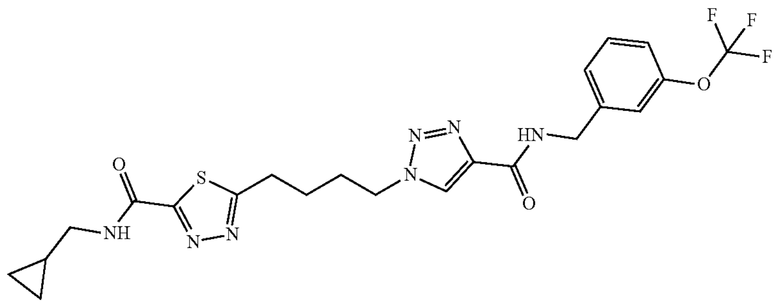 [SMILES: O=C(NCc1cccc(OC(F)(F)F)c1)c1cn(CCCCc2nnc(C(=O)NCC3CC3)s2)nn1] | N-(cyclopropylmethyl)-5-{4-[4-({[3-(trifluoromethoxy)phenyl]methyl}carbamoyl)-1H-1,2,3-triazol-1-yl]butyl}-1,3,4-thiadiazole-2-carboxamide |
| 60 | 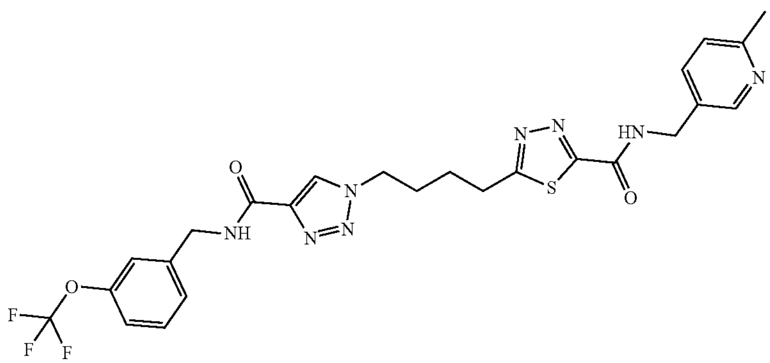 [SMILES: Cc1ccc(CNC(=O)c2nnc(CCCCn3cc(C(=O)NCc4cccc(OC(F)(F)F)c4)nn3)s2)cn1] | N-[(6-methylpyridin-3-yl)methyl]-5-{4-[4-({[3-(trifluoromethoxy)phenyl]methyl}carbamoyl)-1H-1,2,3-triazol-1-yl]butyl}-1,3,4-thiadiazole-2-carboxamide |
| 61 | 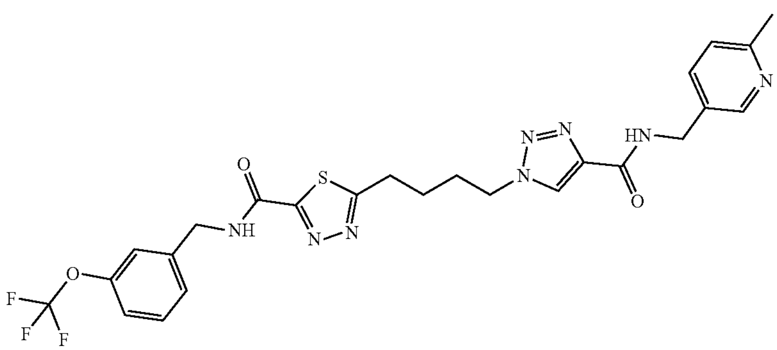 [SMILES: Cc1ccc(CNC(=O)c2cn(CCCCc3nnc(C(=O)NCc4cccc(OC(F)(F)F)c4)s3)nn2)cn1] | 5-[4-(4-{[(6-methylpyridin-3-yl)methyl]carbamoyl}-1H-1,2,3-triazol-1-yl)butyl]-N-{[3-(trifluoromethoxy)phenyl]methyl}-1,3,4-thiadiazole-2-carboxamide |
| 62 | 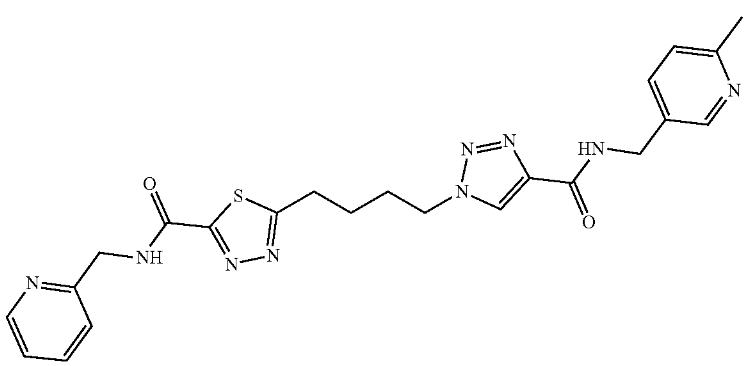 [SMILES: Cc1ccc(CNC(=O)c2cn(CCCCc3nnc(C(=O)NCc4ccccn4)s3)nn2)cn1] | 5-[4-(4-{[(6-methylpyridin-3-yl)methyl]carbamoyl}-1H-1,2,3-triazol-1-yl)butyl]-N-(pyridin-2-ylmethyl)-1,3,4-thiadiazole-2-carboxamide |

TABLE 1-continued

Synthesized Examples

| Ex. No. | Structure | Name |
|---|---|---|
| 63 | 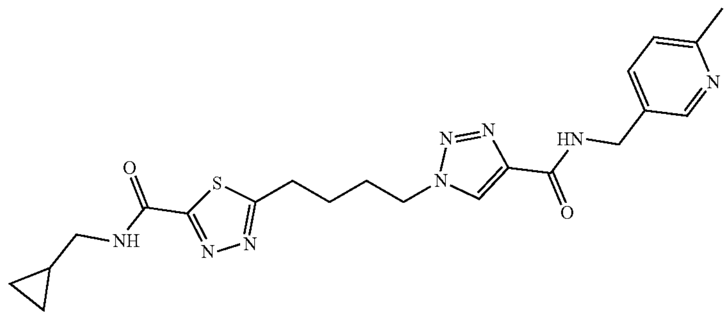 [SMILES: Cc1ccc(CNC(=O)c2cn(CCCCc3nnc(C(=O)NCC4CC4)s3)nn2)cn1] | N-(cyclopropylmethyl)-5-[4-(4-{[(6-methylpyridin-3-yl)methyl]carbamoyl}-1H-1,2,3-triazol-1-yl)butyl]-1,3,4-thiadiazole-2-carboxamide |
| 64 | 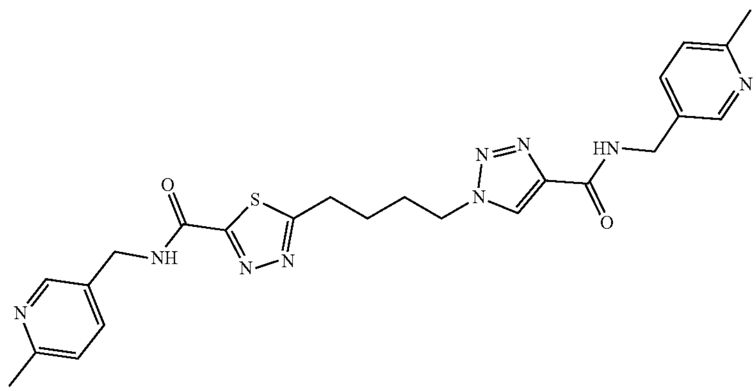 | N-[(6-methylpyridin-3-yl)methyl]-5-[4-(4-{[(6-methylpyridin-3-yl)methyl]carbamoyl}-1H-1,2,3-triazol-1-yl)butyl]-1,3,4-thiadiazole-2-carboxamide |
| 65 | 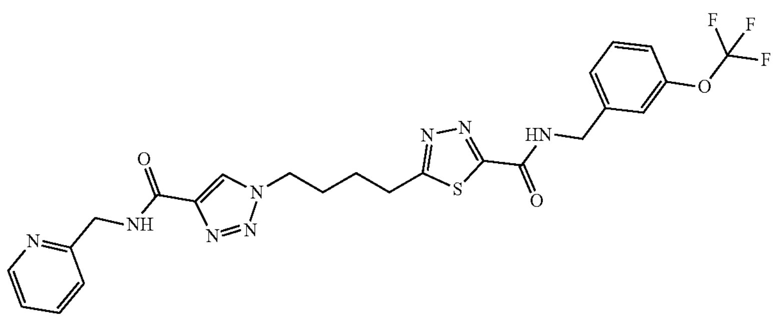 [SMILES: O=C(NCc1ccccn1)c1cn(CCCCc2nnc(C(=O)NCc3cccc(OC(F)(F)F)c3)s2)nn1] | 5-(4-{4-[(pyridin-2-ylmethyl)carbamoyl]-1H-1,2,3-triazol-1-yl}butyl)-N-{[3-(trifluoromethoxy)phenyl]methyl}-1,3,4-thiadiazole-2-carboxamide |
| 66 | 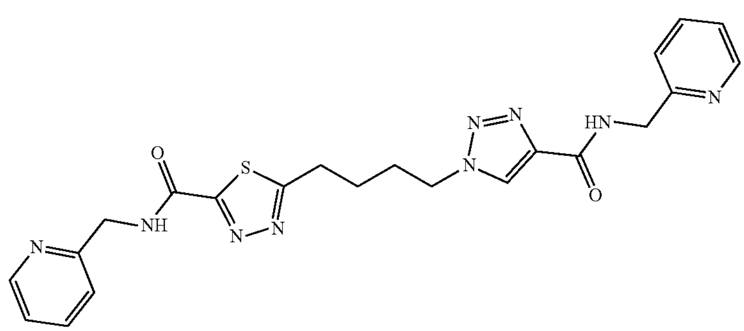 [SMILES: O=C(NCc1ccccn1)c1cn(CCCCc2nnc(C(=O)NCc3ccccn3)s2)nn1] | N-(pyridin-2-ylmethyl)-5-(4-{4-[(pyridin-2-ylmethyl)carbamoyl]-1H-1,2,3-triazol-1-yl}butyl)-1,3,4-thiadiazole-2-carboxamide |

TABLE 1-continued

Synthesized Examples

| Ex. No. | Structure | Name |
|---|---|---|
| 67 | 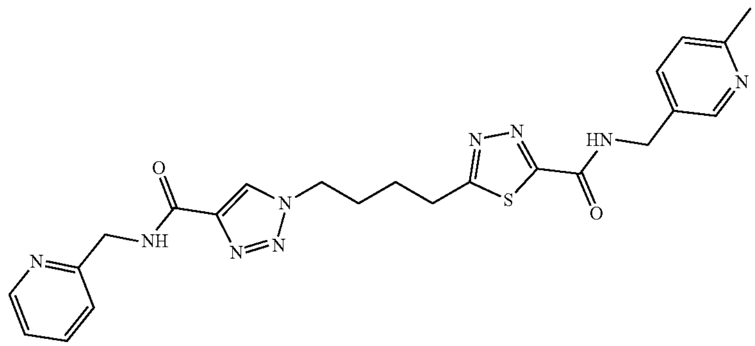 [SMILES: Cc1ccc(CNC(=O)c2nnc(CCCCn3cc(C(=O)NCc4ccccn4)nn3)s2)cn1] | N-[(6-methylpyridin-3-yl)methyl]-5-(4-{4-[(pyridin-2-ylmethyl)carbamoyl]-1H-1,2,3-triazol-1-yl}butyl)-1,3,4-thiadiazole-2-carboxamide |
| 68 | 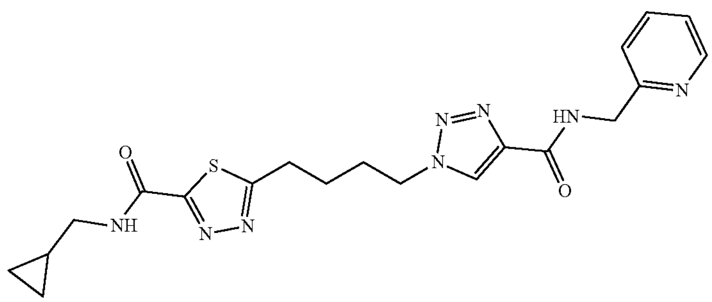 [SMILES: O=C(NCc1ccccn1)c1cn(CCCCc2nnc(C(=O)NCC3CC3)s2)nn1] | N-(cyclopropylmethyl)-5-(4-{4-[(pyridin-2-ylmethyl)carbamoyl]-1H-1,2,3-triazol-1-yl}butyl)-1,3,4-thiadiazole-2-carboxamide |
| 69 | 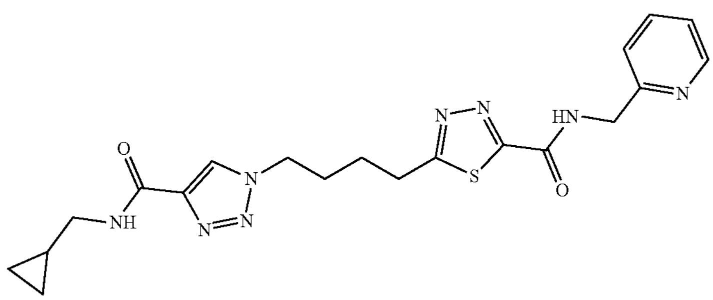 [SMILES: O=C(NCC1CC1)c1cn(CCCCc2nnc(C(=O)NCc3ccccn3)s2)nn1] | 5-(4-{4-[(cyclopropylmethyl)carbamoyl]-1H-1,2,3-triazol-1-yl}butyl)-N-(pyridin-2-ylmethyl)-1,2,3-thiadiazole-2-carboxamide |
| 70 | 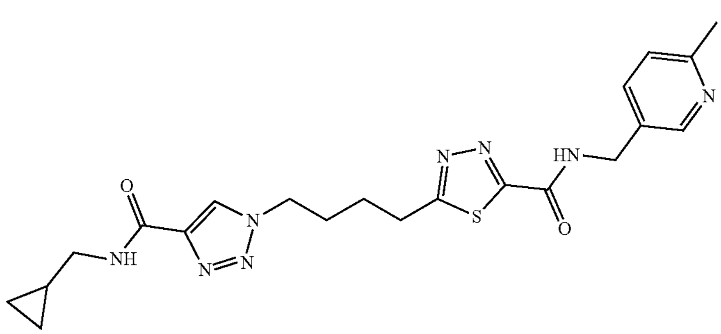 [SMILES: Cc1ccc(CNC(=O)c2nnc(CCCCn3cc(C(=O)NCC4CC4)nn3)s2)cn1] | 5-(4-{4-[(cyclopropylmethyl)carbamoyl]-1H-1,2,3-triazol-1-yl}butyl)-N-[(6-methylpyridin-3-yl)methyl]-1,3,4-thiadiazole-2-carboxamide |

TABLE 1-continued

Synthesized Examples

| Ex. No. | Structure | Name |
|---|---|---|
| 71 | 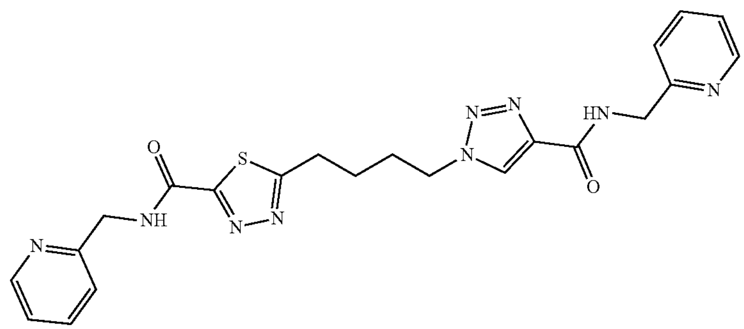 [SMILES: O=C(NCc1ccccn1)c1cn(CCCCc2nnc(C(=O)NCc3ccccn3)s2)nn1] | N-(pyridin-2-ylmethyl)-1-(4-{4-[(pyridin-2-ylmethyl)carbamoyl]-1H-1,2,3-triazol-1-yl}butyl)-1H-1,2,3-triazole-4-carboxamide |
| 72 | 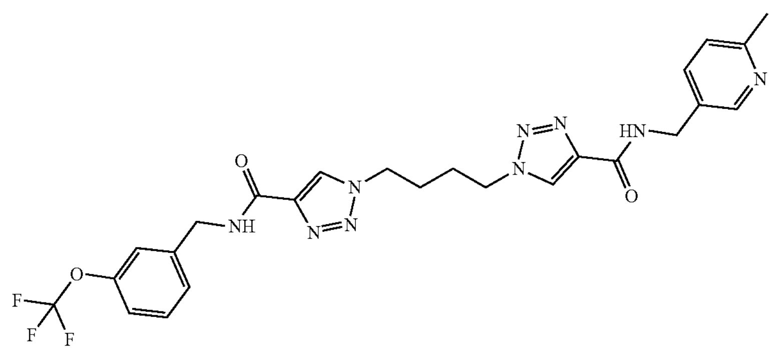 [SMILES: Cc1ccc(CNC(=O)c2cn(CCCCn3cc(C(=O)NCc4cccc(OC(F)(F)F)c4)nn3)nn2)cn1] | 1-[4-(4-{[(6-methylpyridin-3-yl)methyl]carbamoyl}-1H-1,2,3-triazol-1-yl)butyl]-N-{[3-(trifluoromethoxy)phenyl]methyl}-1H-1,2,3-triazole-4-carboxamide |
| 73 | 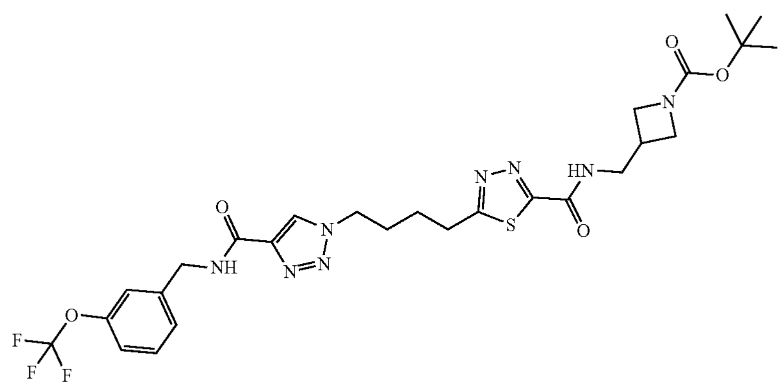 [SMILES: CC(C)(C)OC(=O)N1CC(CNC(=O)c2nnc(CCCCn3cc(C(=O)NCc4cccc(OC(F)(F)F)c4)nn3)s2)C1] | tert-butyl 3-{[(5-{4-[4-({[3-(trifluoromethoxy)phenyl]methyl}carbamoyl)-1H-1,2,3-triazol-1-yl]butyl}-1,3,4-thiadiazol-2-yl)formamido]methyl}azetidine-1-carboxylate |
| 74 | 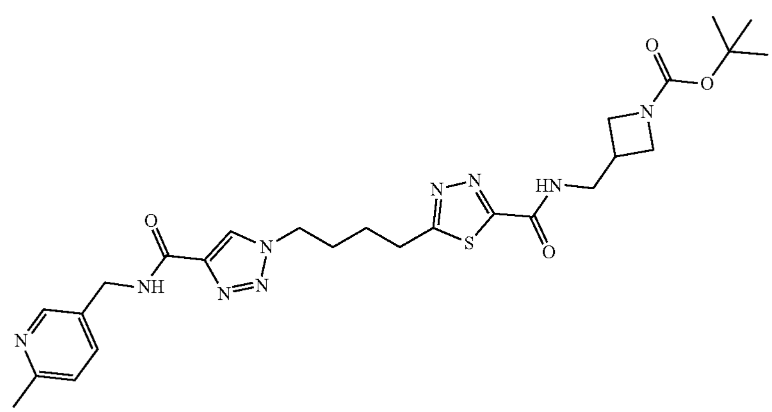 [SMILES: Cc1ccc(CNC(=O)c2cn(CCCCc3nnc(C(=O)NCC4CN(C(=O)OC(C)(C)C)C4)s3)nn2)cn1] | tert-butyl 3-[({5-[4-(4-{[(6-methylpyridin-3-yl)methyl]carbamoyl}-1H-1,2,3-triazol-1-yl)butyl]-1,3,4-thiadiazol-2-yl}formamido)methyl]azetidine-1-carboxylate |

TABLE 1-continued

Synthesized Examples

| Ex. No. | Structure | Name |
|---|---|---|
| 75 | 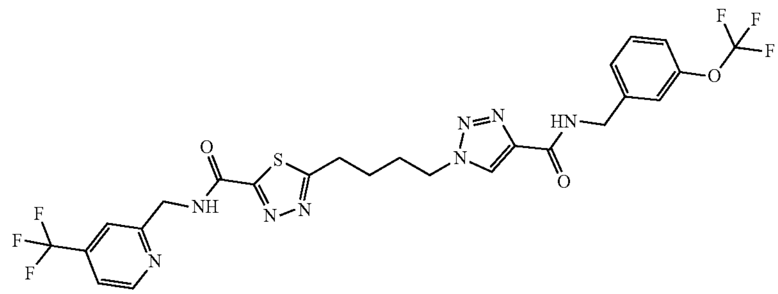 [SMILES: O=C(NCc1cccc(OC(F)(F)F)c1)c1cn(CCCCc2nnc(C(=O)NCc3cc(C(F)(F)F)ccn3)s2)nn1] | 5-{4-[4-({[3-(trifluoromethoxy)phenyl]methyl}carbamoyl)-1H-1,2,3-triazol-1-yl]butyl}-N-{[4-(trifluoromethyl)pyridin-2-yl]methyl}-1,3,4-thiadiazole-2-carboxamide |
| 76 | 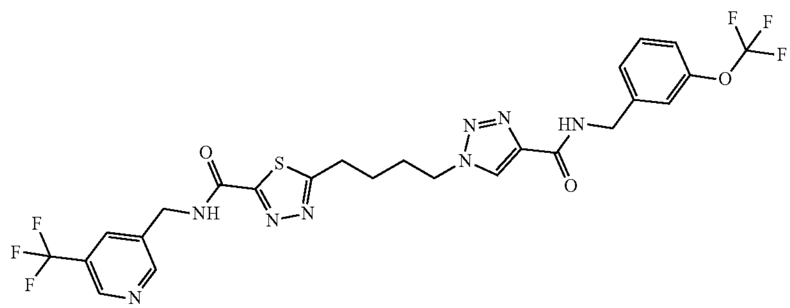 [SMILES: O=C(NCc1cccc(OC(F)(F)F)c1)c1cn(CCCCc2nnc(C(=O)NCc3cncc(C(F)(F)F)c3)s2)nn1] | 5-{4-[4-({[3-(trifluoromethoxy)phenyl]methyl}carbamoyl)-1H-1,2,3-triazol-1-yl]butyl}-N-{[5-(trifluoromethyl)pyridin-3-yl]methyl}-1,3,4-thiadiazole-2-carboxamide |
| 77 | 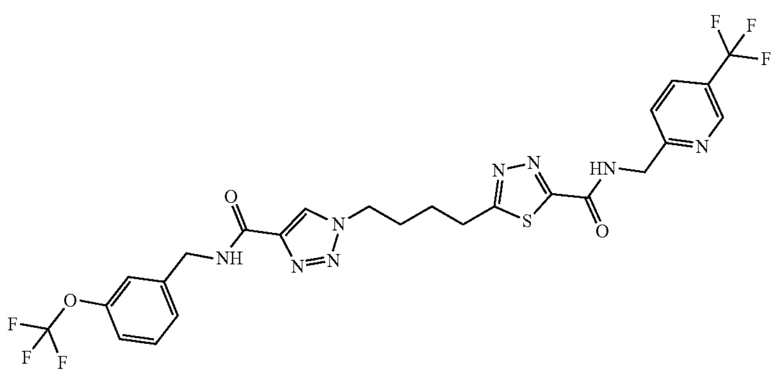 [SMILES: O=C(NCc1cccc(OC(F)(F)F)c1)c1cn(CCCCc2nnc(C(=O)NCc3ccc(C(F)(F)F)cn3)s2)nn1] | 5-{4-[4-({[3-(trifluoromethoxy)phenyl]methyl}carbamoyl)-1H-1,2,3-triazol-1-yl]butyl}-N-{[5-(trifluoromethyl)pyridin-2-yl]methyl}-1,3,4-thiadiazole-2-carboxamide |
| 78 | 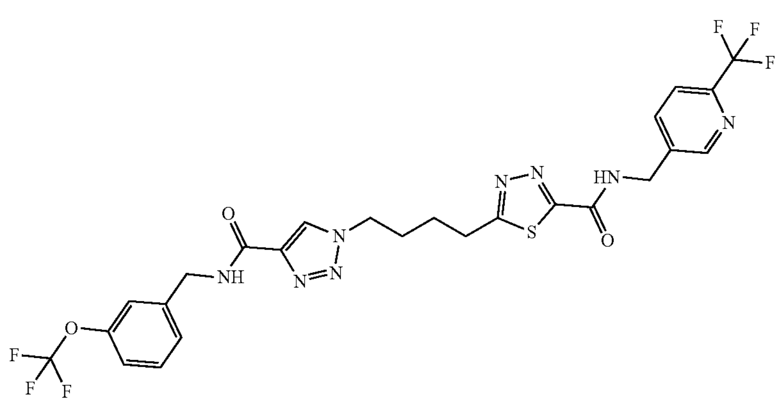 [SMILES: O=C(NCc1cccc(OC(F)(F)F)c1)c1cn(CCCCc2nnc(C(=O)NCc3ccc(C(F)(F)F)nc3)s2)nn1] | 5-{4-[4-({[3-(trifluoromethoxy)phenyl]methyl}carbamoyl)-1H-1,2,3-triazol-1-yl]butyl}-N-{[6-(trifluoromethyl)pyridin-3-yl]methyl}-1,3,4-thiadiazole-2-carboxamide |

TABLE 1-continued

Synthesized Examples

| Ex. No. | Structure | Name |
|---|---|---|
| 79 | 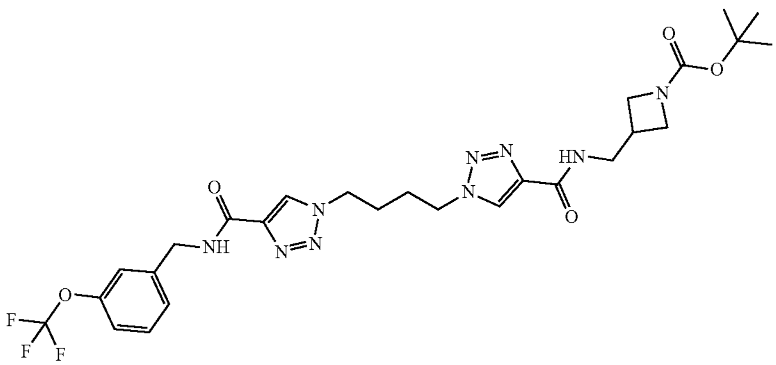 [SMILES: CC(C)(C)OC(=O)N1CC(CNC(=O)c2cn(CCCCn3cc(C(=O)NCc4cccc(OC(F)(F)F)c4)nn3)nn2)C1] | tert-butyl 3-{[(1-{4-[4-({[3-(trifluoromethoxy)phenyl]methyl}carbamoyl)-1H-1,2,3-triazol-1-yl]butyl}-1H-1,2,3-triazol-4-yl)formamido]methyl}azetidine-1-carboxylate |
| 80 | 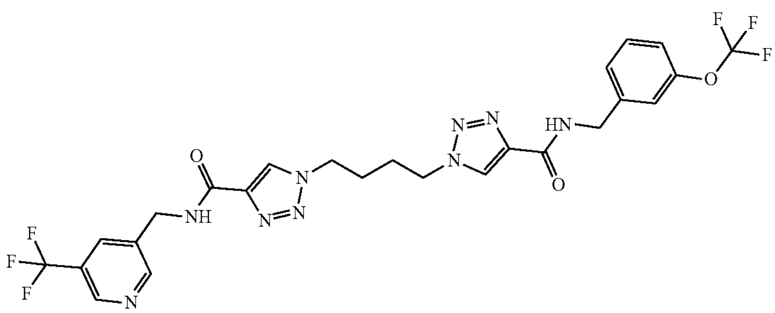 [SMILES: O=C(NCc1cccc(OC(F)(F)F)c1)c1cn(CCCCn2cc(C(=O)NCc3cncc(C(F)(F)F)c3)nn2)nn1] | 1-{4-[4-({[3-(trifluoromethoxy)phenyl]methyl}carbamoyl)-1H-1,2,3-triazol-1-yl]butyl}-N-{[5-(trifluoromethyl)pyridin-3-yl]methyl}-1H-1,2,3-triazole-4-carboxamide |
| 81 | 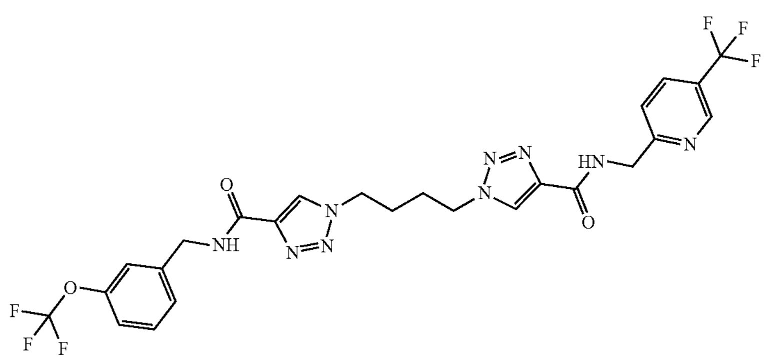 [SMILES: O=C(NCc1cccc(OC(F)(F)F)c1)c1cn(CCCCn2cc(C(=O)NCc3ccc(C(F)(F)F)cn3)nn2)nn1] | 1-{4-[4-({[3-(trifluoromethoxy)phenyl]methyl}carbamoyl)-1H-1,2,3-triazol-1-yl]butyl}-N-{[5-(trifluoromethyl)pyridin-2-yl]methyl}-1H-1,2,3-triazole-4-carboxamide |
| 82 | 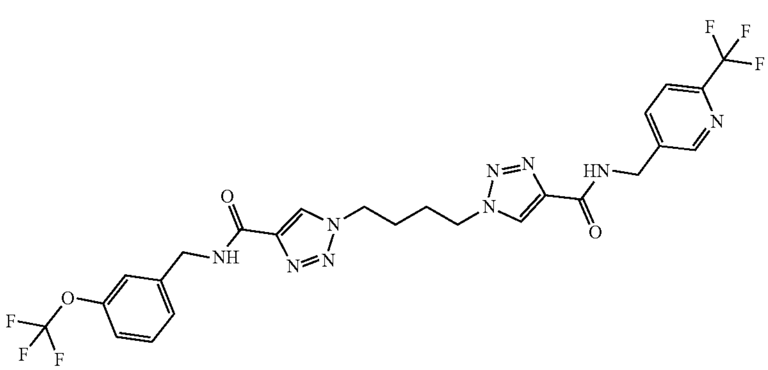 [SMILES: O=C(NCc1ccc(C(F)(F)F)nc1)c1cn(CCCCn2cc(C(=O)NCc3cccc(OC(F)(F)F)c3)nn2)nn1] | 1-{4-[4-({[3-(trifluoromethoxy)phenyl]methyl}carbamoyl)-1H-1,2,3-triazol-1-yl]butyl}-N-{[6-(trifluoromethyl)pyridin-3-yl]methyl}-1H-1,2,3-triazole-4-carboxamide |

TABLE 1-continued

Synthesized Examples

| Ex. No. | Structure | Name |
|---|---|---|
| 83 | 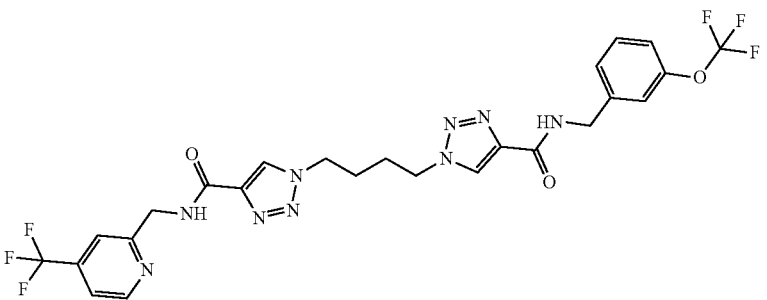 [SMILES: O=C(NCc1cccc(OC(F)(F)F)c1)c1cn(CCCCn2cc(C(=O)NCc3cc(C(F)(F)F)ccn3)nn2)nn1] | N-{[3-(trifluoromethoxy)phenyl]methyl}-1-{4-[4-({[4-(trifluoromethyl)pyridin-2-yl]methyl}carbamoyl)-1H-1,2,3-triazol-1-yl]butyl}-1H-1,2,3-triazole-4-carboxamide |
| 84 | 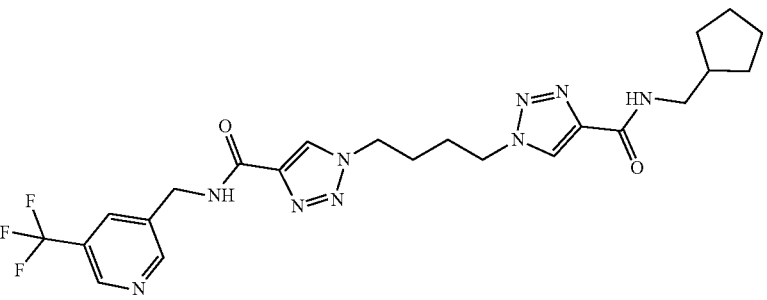 [SMILES: O=C(NCc1cncc(C(F)(F)F)c1)c1cn(CCCCn2cc(C(=O)NCC3CCCC3)nn2)nn1] | N-(cyclopentylmethyl)-1-{4-[4-({[5-(trifluoromethyl)pyridin-3-yl]methyl}carbamoyl)-1H-1,2,3-triazol-1-yl]butyl}-1H-1,2,3-triazole-4-carboxamide |
| 85 | 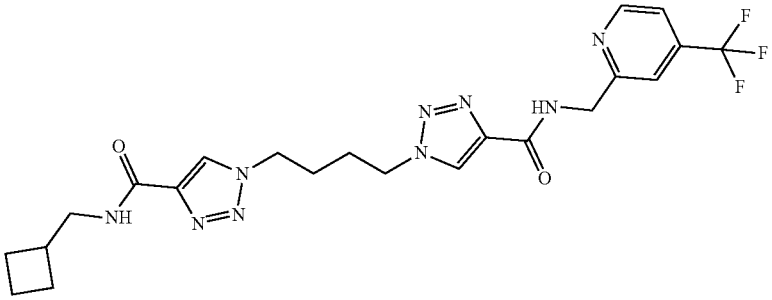 [SMILES: O=C(NCc1cc(C(F)(F)F)ccn1)c1cn(CCCCn2cc(C(=O)NCC3CCC3)nn2)nn1] | 1-(4-{4-[(cyclobutylmethyl)carbamoyl]-1H-1,2,3-triazol-1-yl}butyl)-N-{[4-(trifluoromethyl)pyridin-2-yl]methyl}-1H-1,2,3-triazole-4-carboxamide |
| 86 | 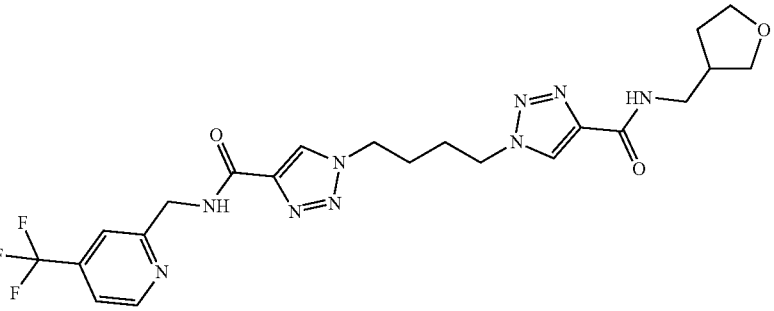 | 1-(4-{4-[(oxolan-3-ylmethyl)carbamoyl]-1H-1,2,3-triazol-1-yl}butyl)-N-{[4-(trifluoromethyl)pyridin-2-yl]methyl}-1H-1,2,3-triazole-4-carboxamide |
| 87 | 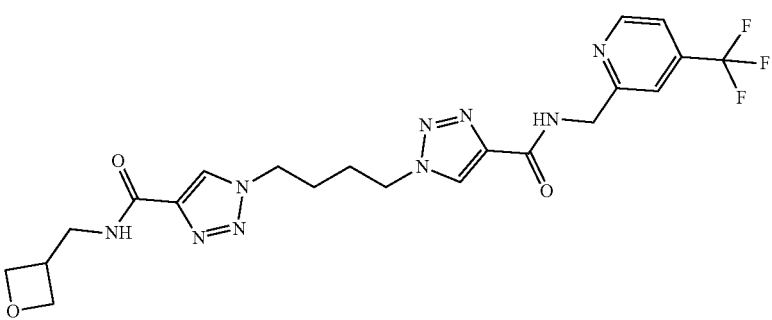 [SMILES: O=C(NCc1cc(C(F)(F)F)ccn1)c1cn(CCCCn2cc(C(=O)NCC3COC3)nn2)nn1] | 1-(4-{4-[(oxetan-3-ylmethyl)carbamoyl]-1H-1,2,3-triazol-1-yl}butyl)-N-{[4-(trifluoromethyl)pyridin-2-yl]methyl}-1H-1,2,3-triazole-4-carboxamide |

TABLE 1-continued

Synthesized Examples

| Ex. No. | Structure | Name |
|---|---|---|
| 88 | 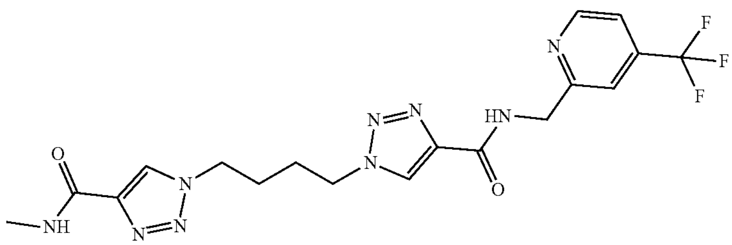 [SMILES: CNC(=O)c1cn(CCCCn2cc(C(=O)NCc3cc(C(F)(F)F)ccn3)nn2)nn1] | 1-{4-[4-(methylcarbamoyl)-1H-1,2,3-triazol-1-yl]butyl}-N-{[4-(trifluoromethyl)pyridin-2-yl]methyl}-1H-1,2,3-triazole-4-carboxamide |
| 89 | 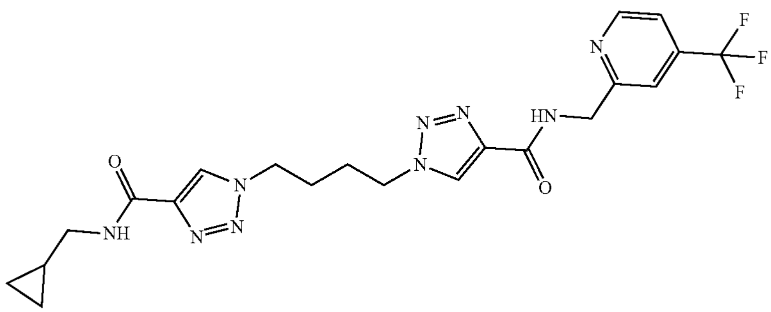 [SMILES: O=C(NCc1cc(C(F)(F)F)ccn1)c1cn(CCCCn2cc(C(=O)NCC3CC3)nn2)nn1] | 1-(4-{4-[(cyclopropylmethyl)carbamoyl]-1H-1,2,3-triazol-1-yl}butyl)-N-{[4-(trifluoromethyl)pyridin-2-yl]methyl}-1H-1,2,3-triazole-4-carboxamide |
| 90 | 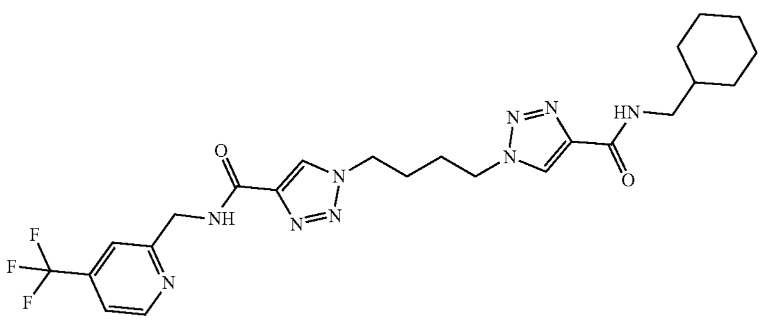 [SMILES: O=C(NCc1cc(C(F)(F)F)ccn1)c1cn(CCCCn2cc(C(=O)NCC3CCCCC3)nn2)nn1] | 1-(4-{4-[(cyclohexylmethyl)carbamoyl]-1H-1,2,3-triazol-1-yl}butyl)-N-{[4-(trifluoromethyl)pyridin-2-yl]methyl}-1H-1,2,3-triazol-4-carboxamide |
| 91 | 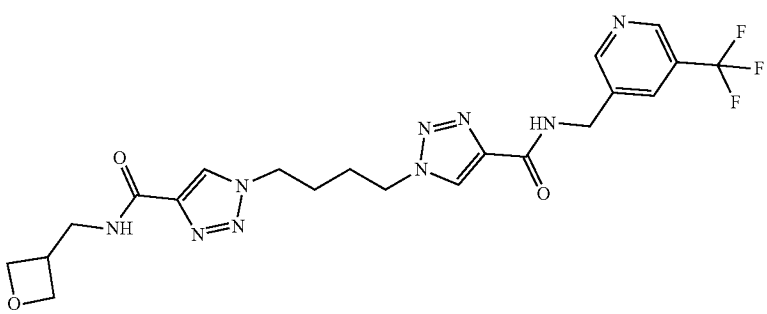 [SMILES: O=C(NCc1cncc(C(F)(F)F)c1)c1cn(CCCCn2cc(C(=O)NCC3COC3)nn2)nn1] | N-(oxetan-3-ylmethyl)-1-{4-[4-({[5-(trifluoromethyl)pyridin-3-yl]methyl}carbamoyl)-1H-1,2,3-triazol-1-yl]butyl}-1H-1,2,3-triazole-4-carboxamide |
| 92 | 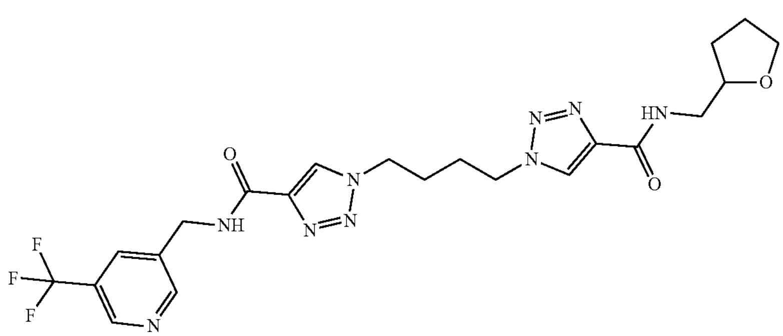 [SMILES: O=C(NCc1cncc(C(F)(F)F)c1)c1cn(CCCCn2cc(C(=O)NCC3CCCO3)nn2)nn1] | N-(oxolan-2-ylmethyl)-1-{4-[4-({[5-(trifluoromethyl)pyridin-3-yl]methyl}carbamoyl)-1H-1,2,3-triazol-1-yl]butyl}-1H-1,2,3-triazole-4-carboxamide |

TABLE 1-continued

Synthesized Examples

| Ex. No. | Structure | Name |
|---|---|---|
| 93 | 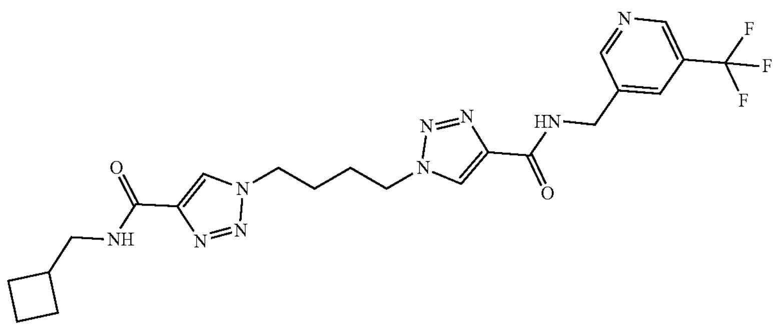 [SMILES: O=C(NCc1cncc(C(F)(F)F)c1)c1cn(CCCCn2cc(C(=O)NCC3CCC3)nn2)nn1] | N-(cyclobutylmethyl)-1-{4-[4-({[5-(trifluoromethyl)pyridin-3-yl]methyl}carbamoyl)-1H-1,2,3-triazol-1-yl]butyl}-1H-1,2,3-triazole-4-carboxamide |
| 94 | 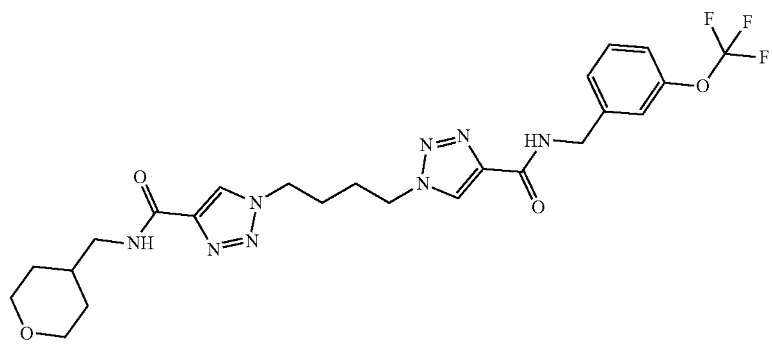 [SMILES: O=C(NCc1cccc(OC(F)(F)F)c1)c1cn(CCCCn2cc(C(=O)NCC3CCOCC3)nn2)nn1] | N-(oxan-4-ylmethyl)-1-{4-[4-({[3-(trifluoromethoxy)phenyl]methyl}carbamoyl)-1H-1,2,3-triazol-1-yl]butyl}-1H-1,2,3-triazole-4-carboxamide |
| 95 | 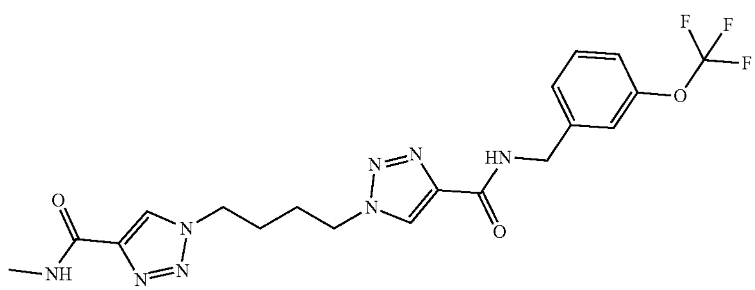 [SMILES: CNC(=O)c1cn(CCCCn2cc(C(=O)NCc3cccc(OC(F)(F)F)c3)nn2)nn1] | N-methyl-1-{4-[4-({[3-(trifluoromethoxy)phenyl]methyl}carbamoyl)-1H-1,2,3-triazol-1-yl]butyl}-1H-1,2,3-triazole-4-carboxamide |
| 96 | 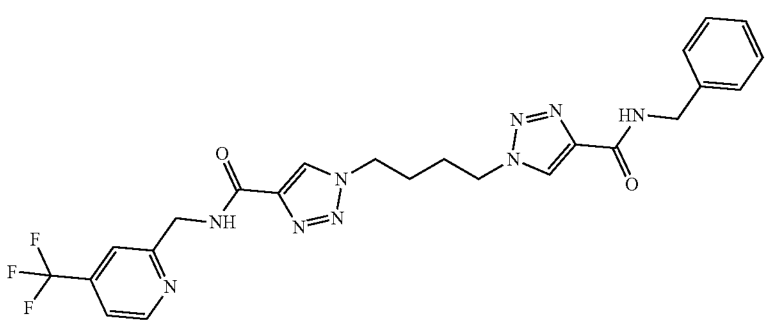 [SMILES: O=C(NCc1ccccc1)c1cn(CCCCn2cc(C(=O)NCc3cc(C(F)(F)F)ccn3)nn2)nn1] | 1-{4-[4-(benzylcarbamoyl)-1H-1,2,3-triazol-1-yl]butyl}-N-{[4-(trifluoromethyl)pyridin-2-yl]methyl}-1H-1,2,3-triazole-4-carboxamide |

TABLE 1-continued

Synthesized Examples

| Ex. No. | Structure | Name |
|---|---|---|
| 97 | 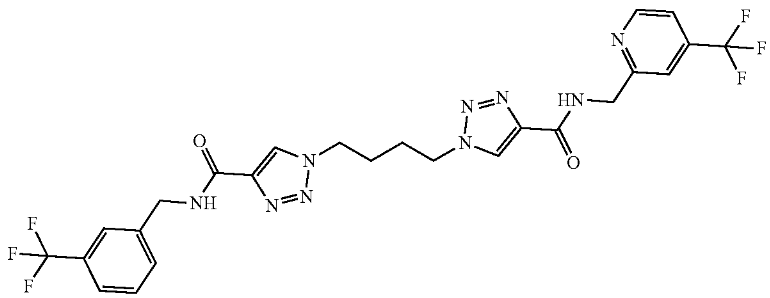 [SMILES: O=C(NCc1cccc(C(F)(F)F)c1)c1cn(CCCCn2cc(C(=O)NCc3cc(C(F)(F)F)ccn3)nn2)nn1] | 1-{4-[4-({[3-(trifluoromethyl)phenyl]methyl}carbamoyl)-1H-1,2,3-triazol-1-yl]butyl}-N-{[4-(trifluoromethyl)pyridin-2-yl]methyl}-1H-1,2,3-triazole-4-carboxamide |
| 98 | 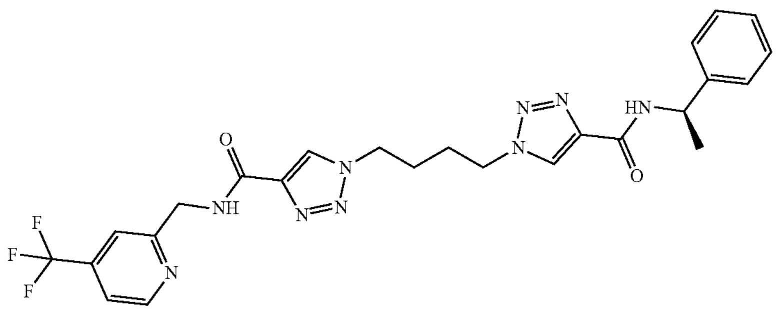 [SMILES: C[C@@H](NC(=O)c1cn(CCCCn2cc(C(=O)NCc3cc(C(F)(F)F)ccn3)nn2)nn1)c1ccccc1] | 1-[4-(4-{[(1R)-1-phenylethyl]carbamoyl}-1H-1,2,3-triazol-1-yl)butyl]-N-{[4-(trifluoromethyl)pyridin-2-yl]methyl}-1H-1,2,3-triazole-4-carboxamide |
| 99 | 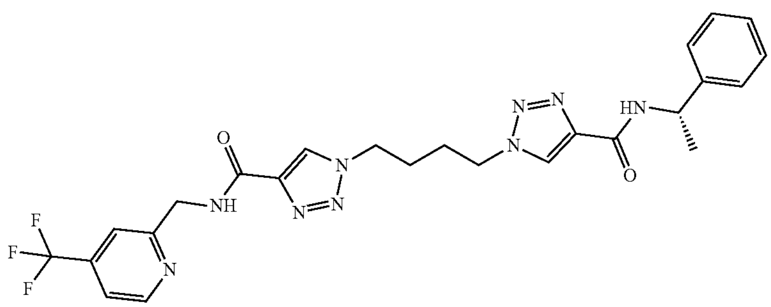 [SMILES: C[C@H](NC(=O)c1cn(CCCCn2cc(C(=O)NCc3cc(C(F)(F)F)ccn3)nn2)nn1)c1ccccc1] | 1-[4-(4-{[(1S)-1-phenyethyl]carbamoyl}-1H-1,2,3-triazol-1-yl)butyl]-N-{[4-(trifluoromethyl)pyridin-2-yl]methyl}-1H-1,2,3-triazole-4-carboxamide |
| 100 | 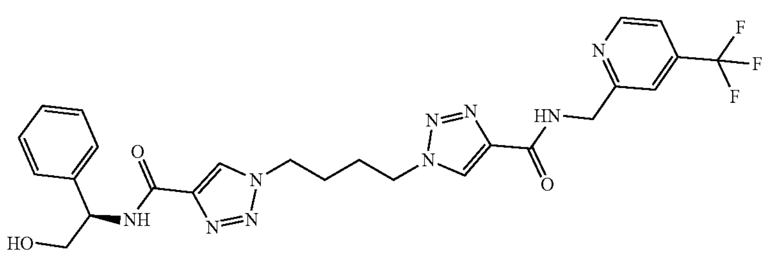 [SMILES: O=C(NCc1cc(C(F)(F)F)ccn1)c1cn(CCCCn2cc(C(=O)N[C@@H](CO)c3ccccc3)nn2)nn1] | 1-[4-(4-{[(1R)-2-hydroxy-1-phenylethyl]carbamoyl}-1H-1,2,3-triazol-1-yl)butyl]-N-{[4-(trifluoromethyl)pyridin-2-yl]methyl}-1H-1,2,3-triazole-4-carboxamide |
| 101 | 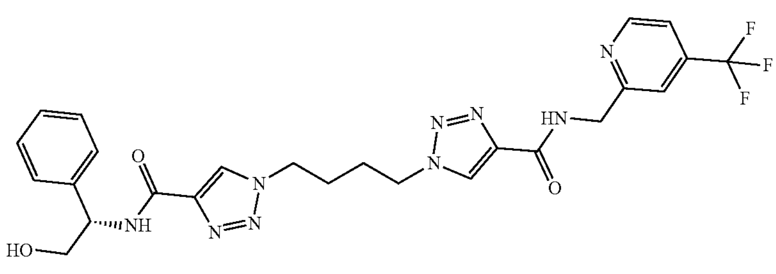 [SMILES: O=C(NCc1cc(C(F)(F)F)ccn1)c1cn(CCCCn2cc(C(=O)N[C@H](CO)c3ccccc3)nn2)nn1] | 1-[4-(4-{[(1S)-2-hydroxy-1-phenylethyl]carbamoyl}-1H-1,2,3-triazol-1-yl)butyl]-N-{[4-(trifluoromethyl)pyridin-2-yl]methyl}-1H-1,2,3-triazole-4-carboxamide |

TABLE 1-continued

Synthesized Examples

| Ex. No. | Structure | Name |
| --- | --- | --- |
| 102 | 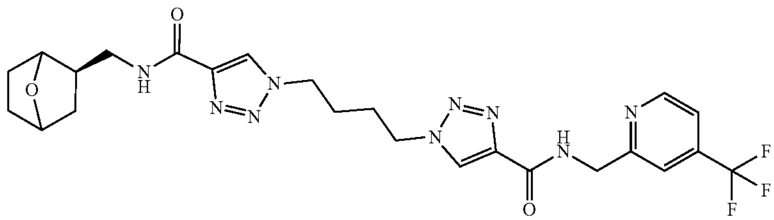 [SMILES: O=C(NCc1cc(C(F)(F)F)ccn1)c1cn(CCCCn2cc(C(=O)NC[C@H]3CC4CCC3O4)nn2)nn1] | 1-[4-(4-{[(2R)-7-oxabicyclo[2.2.1]heptan-2-ylmethyl]carbamoyl}-1H-1,2,3-triazol-1-yl)butyl]-N-{[4-(trifluoromethyl)pyridin-2-yl]methyl}-1H-1,2,3-triazole-4-carboxamide |
| 103 | 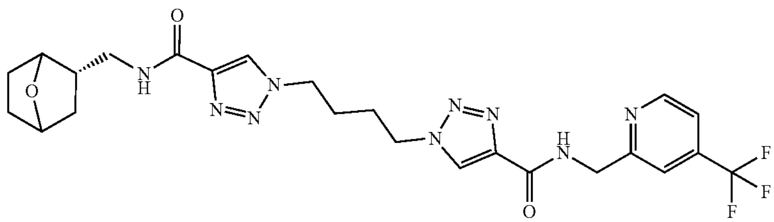 [SMILES: O=C(NCc1cc(C(F)(F)F)ccn1)c1cn(CCCCn2cc(C(=O)NC[C@@H]3CC4CCC3O4)nn2)nn1] | 1-[4-(4-{[(2S)-7-oxabicyclo[2.2.1]heptan-2-ylmethyl]carbamoyl}-1H-1,2,3-triazol-1-yl)butyl]-N-{[4-(trifluoromethyl)pyridin-2-yl]methyl}-1H-1,2,3-triazole-4-carboxamide |
| 104 | 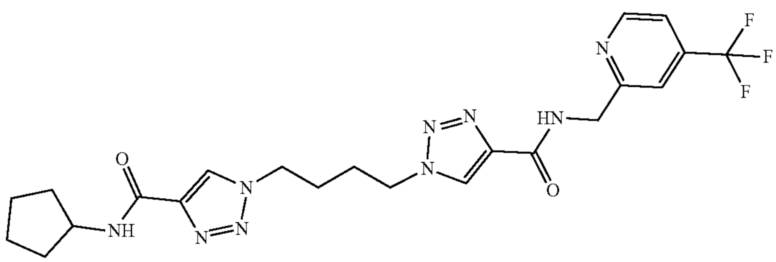 [SMILES: O=C(NCc1cc(C(F)(F)F)ccn1)c1cn(CCCCn2cc(C(=O)NC3CCCC3)nn2)nn1] | 1-{4-[4-(cyclopentylcarbamoyl)-1H-1,2,3-triazol-1-yl]butyl}-N-{[4-(trifluoromethyl)pyridin-2-yl]methyl}-1H-1,2,3-triazole-4-carboxamide |
| 105 | 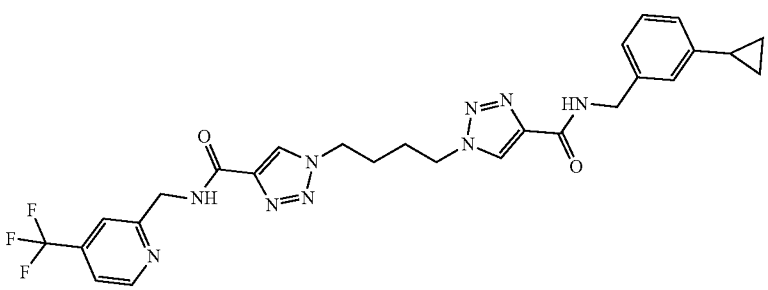 [SMILES: O=C(NCc1cccc(C2CC2)c1)c1cn(CCCCn2cc(C(=O)NCc3cc(C(F)(F)F)ccn3)nn2)nn1] | 1-[4-(4-{[(3-cyclopropylphenyl)methyl]carbamoyl}-1H-1,2,3-triazol-1-yl)butyl]-N-{[4-(trifluoromethyl)pyridin-2-yl]methyl}-1H-1,2,3-triazole-4-carboxamide |
| 106 | 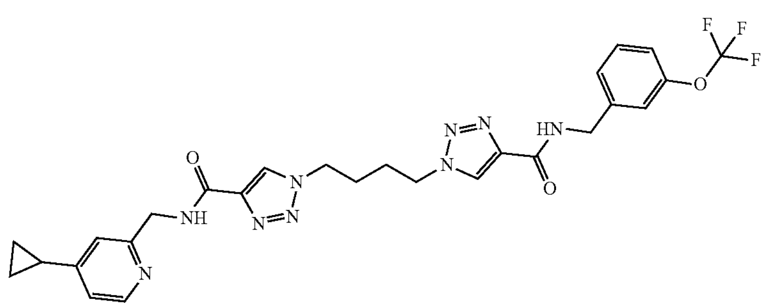 [SMILES: O=C(NCc1cccc(OC(F)(F)F)c1)c1cn(CCCCn2cc(C(=O)NCc3cc(C4CC4)ccn3)nn2)nn1] | N-[(4-cyclopropylpyridin-2-yl)methyl]-1-{4-[4-({[3-(trifluoromethoxy)phenyl]methyl}carbamoyl)-1H-1,2,3-triazol-1-yl]butyl}-1H-1,2,3-triazole-4-carboxamide |

TABLE 1-continued

Synthesized Examples

| Ex. No. | Structure | Name |
|---|---|---|
| 107 | 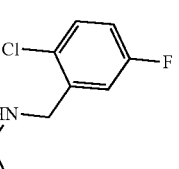 | 1-[4-(4-{[(2-chloro-5-fluorophenyl)methyl]carbamoyl}-1H-1,2,3-triazol-1-yl)butyl]-N-{[4-(trifluoromethyl)pyridin-2-yl]methyl}-1H-1,2,3-triazole-4-carboxamide |
| 108 | 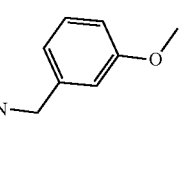 | 1-[4-(4-{[(3-methoxyphenyl)methyl]carbamoyl}-1H-1,2,3-triazol-1-yl)butyl]-N-{[4-(trifluoromethyl)pyridin-2-yl]methyl}-1H-1,2,3-triazole-4-carboxamide |
| 109 | 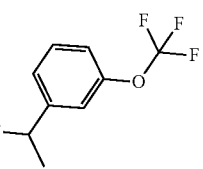 | 1-{4-[4-({1-[3-(trifluoromethoxy)phenyl]ethyl}carbamoyl)-1H-1,2,3-triazol-1-yl]butyl}-N-{[4-(trifluoromethyl)pyridin-2-yl]methyl}-1H-1,2,3-triazole-4-carboxamide |
| 110 | 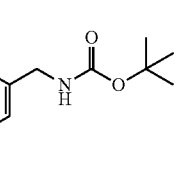 | tert-butyl N-[(3-{[(1-{4-[4-({[4-(trifluoromethyl)pyridin-2-yl]methyl}carbamoyl)-1H-1,2,3-triazol-1-yl]butyl}-1H-1,2,3-triazol-4-yl)formamido]methyl}phenyl)methyl]carbamate |
| 111 | 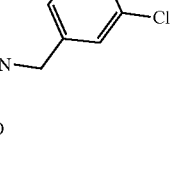 | 1-[4-(4-{[(3-chlorophenyl)methyl]carbamoyl}-1H-1,2,3-triazol-1-yl)butyl]-N-{[4-(trifluoromethyl)pyridin-2-yl]methyl}-1H-1,2,3-triazole-4-carboxamide |

TABLE 1-continued

Synthesized Examples

| Ex. No. | Structure | Name |
|---|---|---|
| 112 | 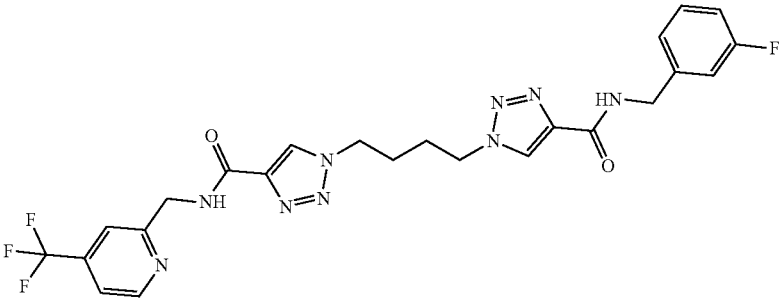 [SMILES: O=C(NCc1cccc(F)c1)c1cn(CCCCn2cc(C(=O)NCc3cc(C(F)(F)F)ccn3)nn2)nn1] | 1-[4-(4-{[(3-fluorophenyl)methyl]carbamoyl}-1H-1,2,3-triazol-1-yl)butyl]-N-{[4-(trifluoromethyl)pyridin-2-yl]methyl}-1H-1,2,3-triazole-4-carboxamide |
| 113 | 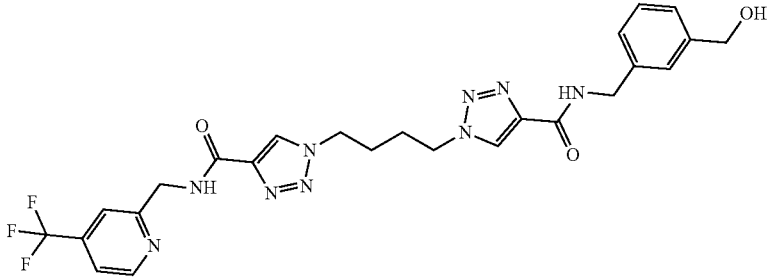 [SMILES: O=C(NCc1cccc(CO)c1)c1cn(CCCCn2cc(C(=O)NCc3cc(C(F)(F)F)ccn3)nn2)nn1] | 1-{4-(4-({[3-(hydroxymethyl)phenyl]methyl}carbamoyl)-1H-1,2,3-triazol-1-yl]butyl}-N-{[4-(trifluoromethyl)pyridin-2-yl]methyl}-1H-1,2,3-triazole-4-carboxamide |
| 114 | 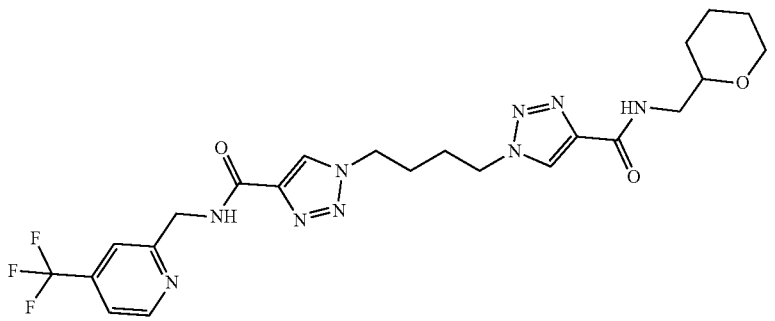 [SMILES: O=C(NCc1cc(C(F)(F)F)ccn1)c1cn(CCCCn2cc(C(=O)NCC3CCCCO3)nn2)nn1] | 1-(4-{4-[(oxan-2-ylmethyl)carbamoyl]-1H-1,2,3-triazol-1-yl}butyl)-N-{[4-(trifluoromethyl)pyridin-2-yl]methyl}-1H-1,2,3-triazole-4-carboxamide |
| 115 | 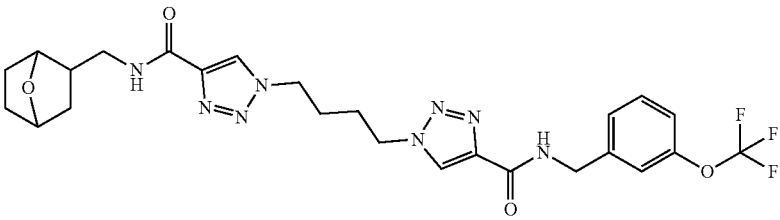 [SMILES: O=C(NCc1cccc(OC(F)(F)F)c1)c1cn(CCCCn2cc(C(=O)NCC3CC4CCC3O4)nn2)nn1] | N-{7-oxabicyclo[2.2.1]heptan-2-ylmethyl}-1-{4-[4-({[3-(trifluoromethoxy)phenyl]methyl}carbamoyl)-1H-1,2,3-triazol-1-yl]butyl}-1H-1,2,3-triazole-4-carboxamide |
| 116 | 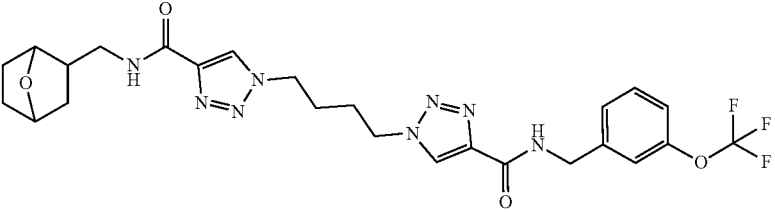 [SMILES: O=C(NCc1cccc(OC(F)(F)F)c1)c1cn(CCCCn2cc(C(=O)NCC3CC4CCC3O4)nn2)nn1] | N-{7-oxabicyclo[2.2.1]heptan-2-ylmethyl}-1-{4-[4-({[3-(trifluoromethoxy)phenyl]methyl}carbamoyl)-1H-1,2,3-triazol-1-yl]butyl}-1H-1,2,3-triazole-4-carboxamide |

TABLE 1-continued

Synthesized Examples

| Ex. No. | Structure | Name |
|---|---|---|
| 117 | 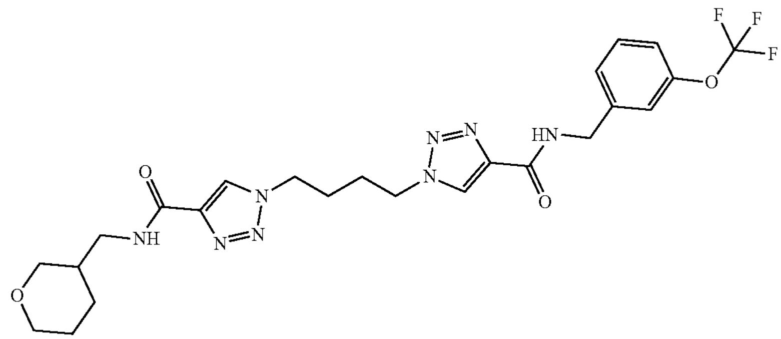 [SMILES: O=C(NCc1cccc(OC(F)(F)F)c1)c1cn(CCCCn2cc(C(=O)NCC3CCCOC3)nn2)nn1] | N-(oxan-3-ylmethyl)-1-{4-[4-({[3-(trifluoromethoxy)phenyl]methyl}carbamoyl)-1H-1,2,3-triazol-1-yl]butyl}-1H-1,2,3-triazole-4-carboxamide |
| 118 | 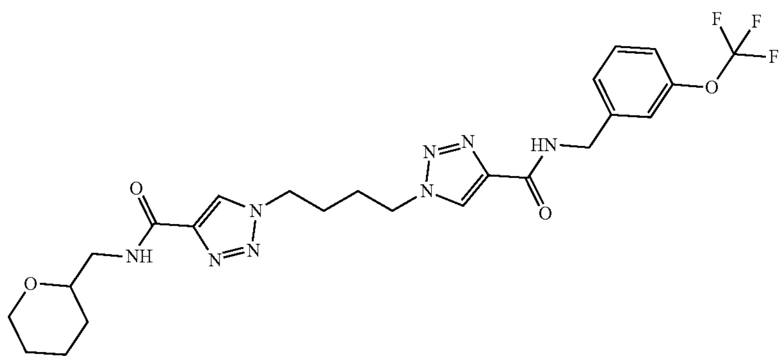 [SMILES: O=C(NCc1cccc(OC(F)(F)F)c1)c1cn(CCCCn2cc(C(=O)NCC3CCCCO3)nn2)nn1] | N-(oxan-2-ylmethyl)-1-{4-[4-({[3-(trifluoromethoxy)phenyl]methyl}carbamoyl)-1H-1,2,3-triazol-1-yl]butyl}-1H-1,2,3-triazole-4-carboxamide |
| 119 | 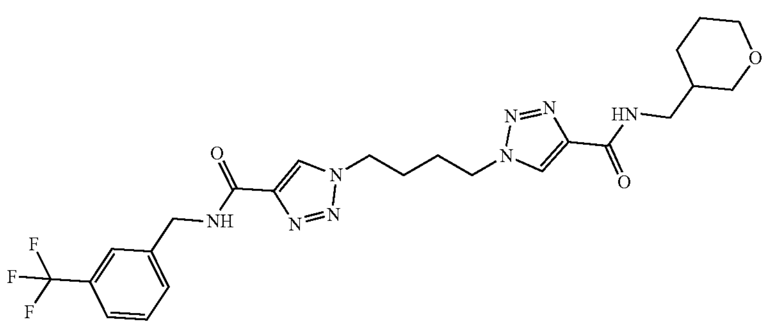 [SMILES: O=C(NCc1cccc(C(F)(F)F)c1)c1cn(CCCCn2cc(C(=O)NCC3CCCOC3)nn2)nn1] | N-(oxan-3-ylmethyl)-1-{4-[4-({[3-(trifluoromethyl)phenyl]methyl}carbamoyl)-1H-1,2,3-triazol-1-yl]butyl}-1H-1,2,3-triazole-4-carboxamide |
| 120 | 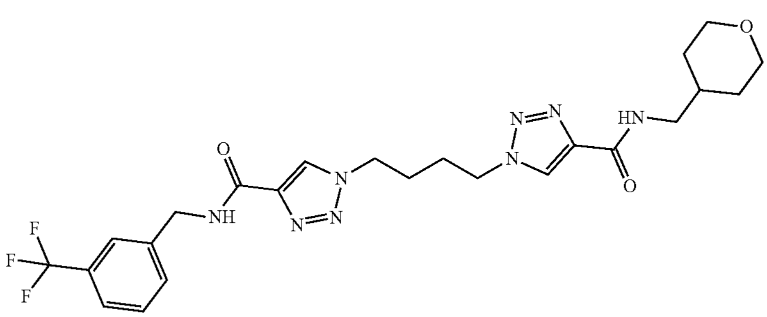 [SMILES: O=C(NCc1cccc(C(F)(F)F)c1)c1cn(CCCCn2cc(C(=O)NCC3CCOCC3)nn2)nn1] | N-(oxan-4-ylmethyl)-1-{4-[4-({[3-(trifluoromethyl)phenyl]methyl}carbamoyl)-1H-1,2,3-triazol-1-yl]butyl}-1H-1,2,3-triazole-4-carboxamide |

TABLE 1-continued

Synthesized Examples

| Ex. No. | Structure | Name |
|---|---|---|
| 121 | 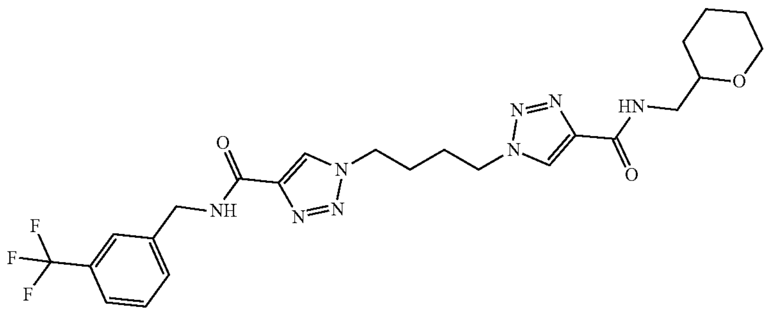 [SMILES: O=C(NCc1cccc(C(F)(F)F)c1)c1cn(CCCCn2cc(C(=O)NCC3CCCCO3)nn2)nn1] | N-(oxan-2-ylmethyl)-1-{4-[4-({[3-(trifluoromethyl)phenyl]methyl}carbamoyl)-1H-1,2,3-triazol-1-yl]butyl}-1H-1,2,3-triazole-4-carboxamide |
| 122 | 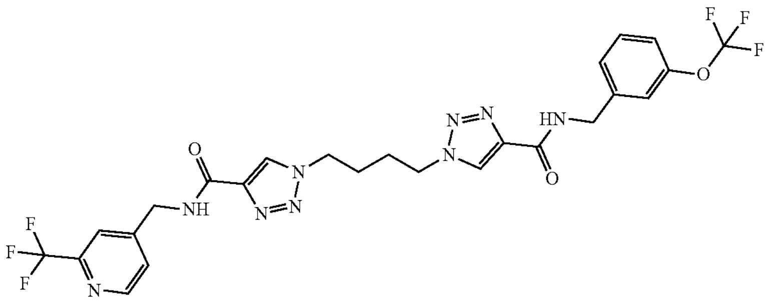 [SMILES: O=C(NCc1cccc(OC(F)(F)F)c1)c1cn(CCCCn2cc(C(=O)NCc3ccnc(C(F)(F)F)c3)nn2)nn1] | 1-{4-[4-({[3-(trifluoromethoxy)phenyl]methyl}carbamoyl)-1H-1,2,3-triazol-1-yl]butyl}-N-{[2-(trifluoromethyl)pyridin-4-yl]methyl}-1H-1,2,3-triazole-4-carboxamide |
| 123 | 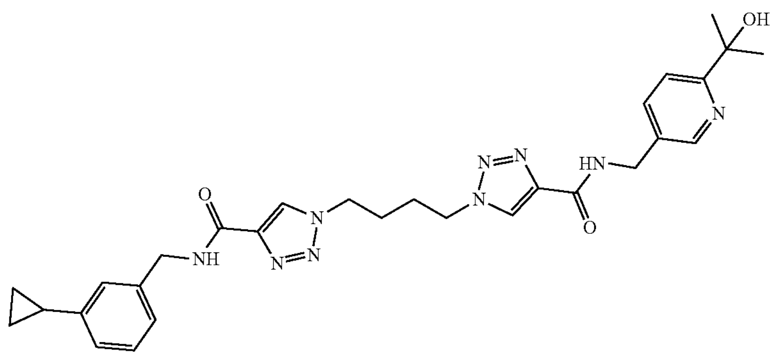 [SMILES: CC(C)(O)c1ccc(CNC(=O)c2cn(CCCCn3cc(C(=O)NCc4cccc(C5CC5)c4)nn3)nn2)cn1] | N-[(3-cyclopropylphenyl)methyl]-1-{4-[4-({[6-(2-hydroxypropan-2-yl)pyridin-3-yl]methyl}carbamoyl)-1H-1,2,3-triazol-1-yl]butyl}-1H-1,2,3-triazole-4-carboxamide |
| 124 | 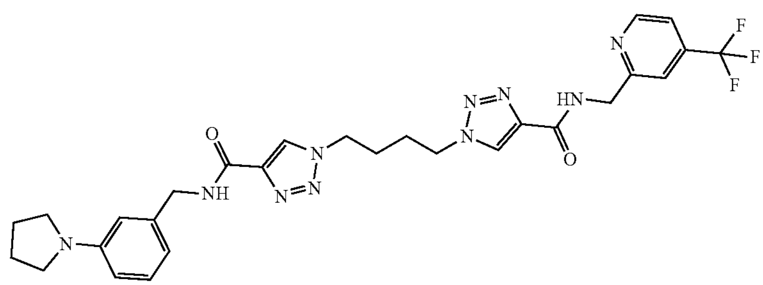 [SMILES: O=C(NCc1cccc(N2CCCC2)c1)c1cn(CCCCn2cc(C(=O)NCc3cc(C(F)(F)F)ccn3)nn2)nn1] | 1-{4-[4-({[3-(pyrrolidin-1-yl)phenyl]methyl}carbamoyl)-1H-1,2,3-triazol-1-yl]butyl}-N-{[4-(trifluoromethyl)pyridin-2-yl]methyl}-1H-1,2,3-triazole-4-carboxamide |
| 125 | 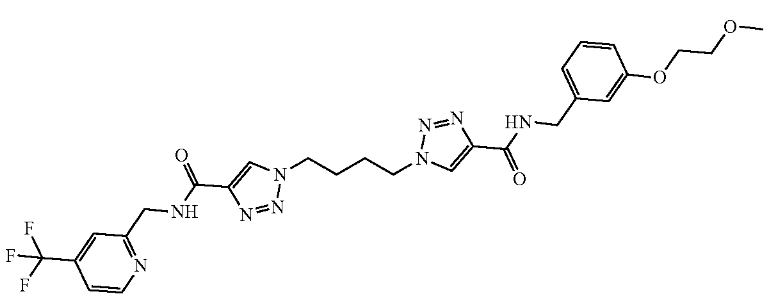 [SMILES: COCCOc1cccc(CNC(=O)c2cn(CCCCn3cc(C(=O)NCc4cc(C(F)(F)F)ccn4)nn3)nn2)c1] | 1-{4-[4-({[3-(2-methoxyethoxy)phenyl]methyl}carbamoyl)-1H-1,2,3-triazol-1-yl]butyl}-N-{[4-(trifluoromethyl)pyridin-2-yl]methyl}-1H-1,2,3-triazole-4-carboxamide |

TABLE 1-continued

Synthesized Examples

| Ex. No. | Structure | Name |
|---|---|---|
| 126 | 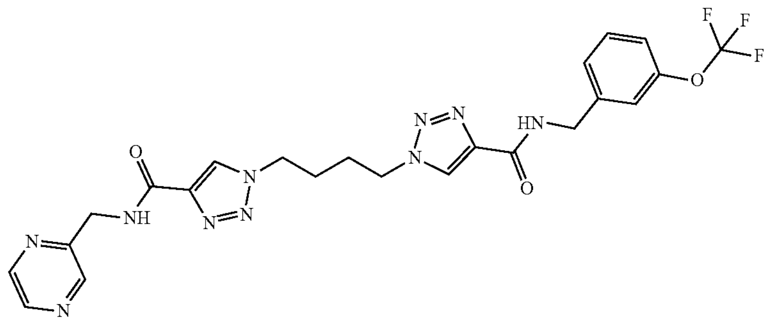 [SMILES: O=C(NCc1cccc(OC(F)(F)F)c1)c1cn(CCCCn2cc(C(=O)NCc3cnccn3)nn2)nn1] | N-(pyrazin-2-ylmethyl)-1-{4-[4-({[3-(trifluoromethoxy)phenyl]methyl}carbamoyl)-1H-1,2,3-triazol-1-yl]butyl}-1H-1,2,3-triazole-4-carboxamide |
| 127 | 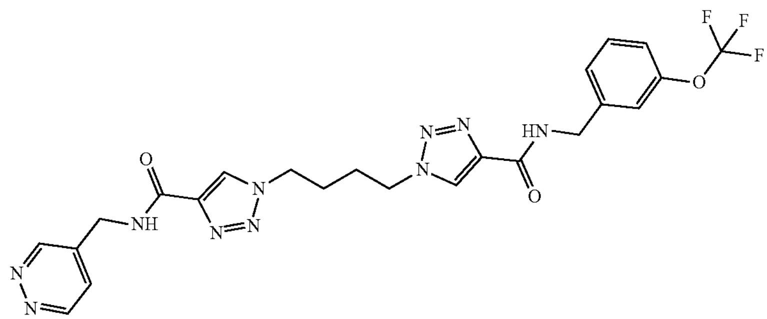 [SMILES: O=C(NCc1ccnnc1)c1cn(CCCCn2cc(C(=O)NCc3cccc(OC(F)(F)F)c3)nn2)nn1] | 1-(4-{4-[(pyridazin-4-ylmethyl)carbamoyl]-1H-1,2,3-triazol-1-yl}butyl)-N-{[3-(trifluoromethoxy)phenyl]methyl}-1H-1,2,3-triazole-4-carboxamide |
| 128 | 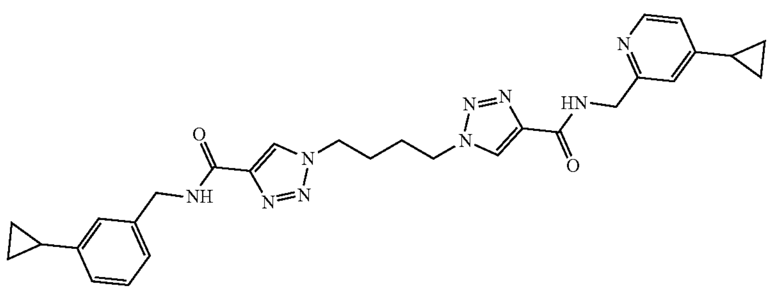 [SMILES: O=C(NCc1cccc(C2CC2)c1)c1cn(CCCCn2cc(C(=O)NCc3cc(C4CC4)ccn3)nn2)nn1] | N-[(3-cyclopropylphenyl)methyl]-1-[4-(4-{[(4-cyclopropylpyridin-2-yl)methyl]carbamoyl}-1H-1,2,3-triazol-1-yl)butyl]-1H-1,2,3-triazole-4-carboxamide |
| 129 | 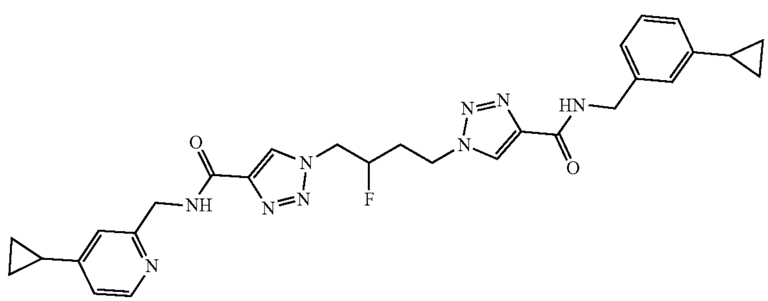 [SMILES: O=C(NCc1cccc(C2CC2)c1)c1cn(CCC(F)Cn2cc(C(=O)NCc3cc(C4CC4)ccn3)nn2)nn1] | N-[(3-cyclopropylphenyl)methyl]-1-[4-(4-{[(4-cyclopropylpyridin-2-yl)methyl]carbamoyl}-1H-1,2,3-triazol-1-yl)-3-fluorobutyl]-1H-1,2,3-triazole-4-carboxamide |
| 130 | 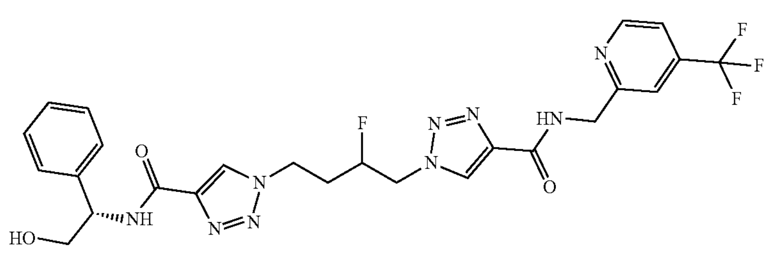 [SMILES: O=C(NCc1cc(C(F)(F)F)ccn1)c1cn(CC(F)CCn2cc(C(=O)N[C@H](CO)c3ccccc3)nn2)nn1] | 1-[2-fluoro-4-(4-{[(1S)-2-hydroxy-1-phenylethyl]carbamoyl}-1H-1,2,3-triazol-1-yl)butyl)-N-{[4-(trifluoromethyl)pyridin-2-yl]methyl}-1H-1,2,3-triazole-4-carboxamide |

TABLE 1-continued

Synthesized Examples

| Ex. No. | Name |
|---|---|
| 131 | 1-[2-fluoro-4-(4-{[(1R)-1-phenylethyl]carbamoyl}-1H-1,2,3-triazol-1-yl)butyl]-N-{[4-(trifluoromethyl)pyridin-2-yl]methyl}-1H-1,2,3-triazole-4-carboxamide |
| 132 | 1-{4-[4-({[3-(difluoromethoxy)phenyl]methyl}carbamoyl)-1H-1,2,3-triazol-1-yl]butyl}-N-{[4-(trifluoromethyl)pyridin-2-yl]methyl}-1H-1,2,3-triazole-4-carboxamide |
| 133 | 1-[4-(4-{[(3-cyclopropylphenyl)methyl]carbamoyl}-1H-1,2,3-triazol-1-yl)butyl]-N-{[5-(trifluoromethyl)pyridin-3-yl]methyl}-1H-1,2,3-triazole-4-carboxamide |
| 134 | 1-[4-(4-{[(3-cyclopropylphenyl)methyl]carbamoyl}-1H-1,2,3-triazol-1-yl)-3-fluorobutyl]-N-[(4-cyclopropylpyridin-2-yl)methyl]-1H-1,2,3-triazole-4-carboxamide |
| 135 | 1-[4-(4-{[(4-cyclopropylpyridin-2-yl)methyl]carbamoyl}-1H-1,2,3-triazol-1-yl)butyl]-N-{[5-(trifluoromethyl)pyridin-3-yl]methyl}-1H-1,2,3-triazole-4-carboxamide |

TABLE 1-continued

Synthesized Examples

| Ex. No. | Structure | Name |
|---|---|---|
| 136 | 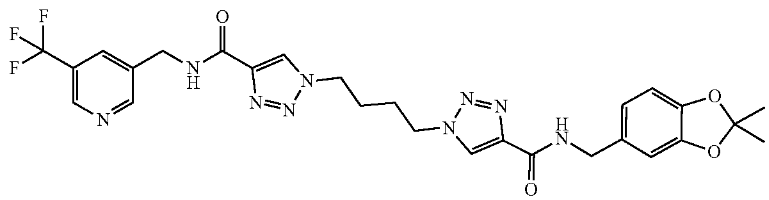 [SMILES: CC1(C)Oc2ccc(CNC(=O)c3cn(CCCCn4cc(C(=O)NCc5cncc(C(F)(F)F)c5)nn4)nn3)cc2O1] | 1-[4-(4-{[(2,2-dimethyl-2H-1,3-benzodioxol-5-yl)methyl]carbamoyl}-1H-1,2,3-triazol-1-yl)butyl]-N-{[5-(trifluoromethyl)pyridin-3-yl]methyl}-1H-1,2,3-triazole-4-carboxamide |
| 137 | 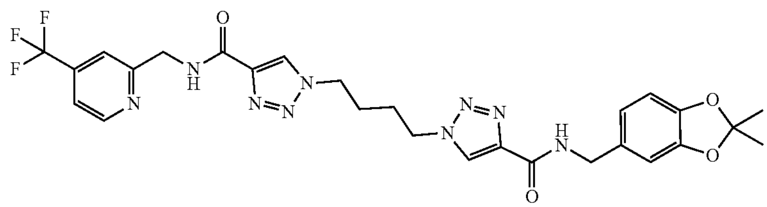 [SMILES: CC1(C)Oc2ccc(CNC(=O)c3cn(CCCCn4cc(C(=O)NCc5cc(C(F)(F)F)ccn5)nn4)nn3)cc2O1] | 1-[4-(4-{[(2,2-dimethyl-2H-1,3-benzodioxol-5-yl)methyl]caramoyl}-1H-1,2,3-triazol-1-yl)butyl]-N-{[4-(trifluoromethyl)pyridin-2-yl]methyl}-1H-1,2,3-triazole-4-carboxamide |
| 138 | 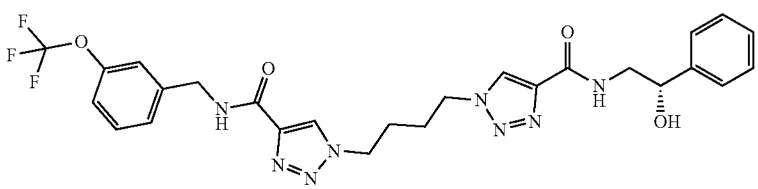 [SMILES: O=C(NCc1cccc(OC(F)(F)F)c1)c1cn(CCCCn2cc(C(=O)NC[C@@H](O)c3ccccc3)nn2)nn1] | N-[(2S)-2-hydroxy-2-phenylethyl]-1-{4-[4-({[3-(trifluoromethoxy)phenyl]methyl}carbamoyl)-1H-1,2,3-triazol-1-yl]butyl}-1H-1,2,3-triazole-4-carboxamide |
| 139 | 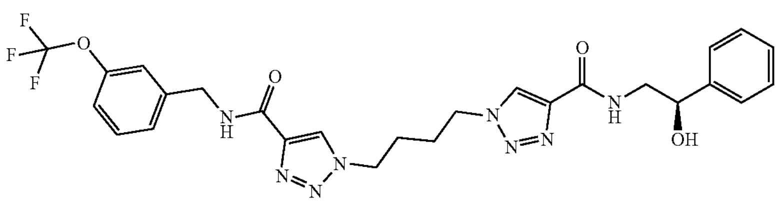 [SMILES: O=C(NCc1cccc(OC(F)(F)F)c1)c1cn(CCCCn2cc(C(=O)NC[C@H](O)c3ccccc3)nn2)nn1] | N-[(2R)-2-hydroxy-2-phenylethyl]-1-{4-[4-({[3-(trifluoromethoxy)phenyl]methyl}carbamoyl)-1H-1,2,3-triazol-1-yl]butyl}-1H-1,2,3-triazole-4-carboxamide |
| 140 | 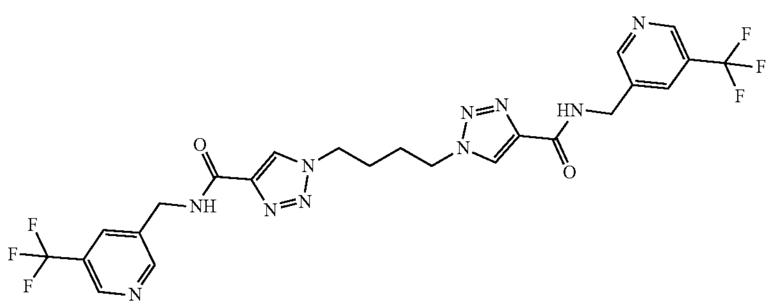 [SMILES: O=C(NCc1cncc(C(F)(F)F)c1)c1cn(CCCCn2cc(C(=O)NCc3cncc(C(F)(F)F)c3)nn2)nn1] | N-{[5-(trifluoromethyl)pyridin-3-yl]methyl}-1-{4-[4-({[5-(trifluoromethyl)pyridin-3-yl]methyl}carbamoyl)-1H-1,2,3-triazol-1-yl]butyl}-1H-1,2,3-triazole-4-carboxamide |
| 141 | 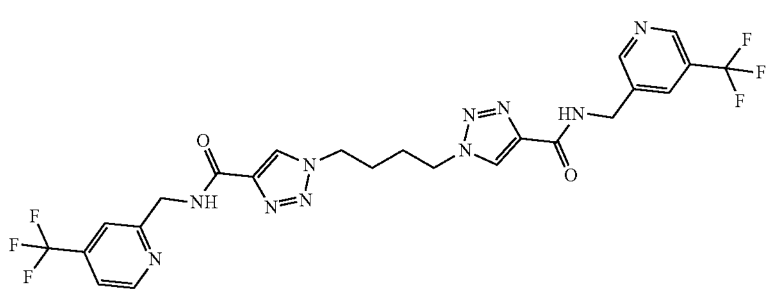 [SMILES: O=C(NCc1cncc(C(F)(F)F)c1)c1cn(CCCCn2cc(C(=O)NCc3cc(C(F)(F)F)ccn3)nn2)nn1] | 1-{4-[4-({[4-(trifluoromethyl)pyridin-2-yl]methyl}carbamoyl)-1H-1,2,3-triazol-1-yl]butyl}-N-{[5-(trifluoromethyl)pyridin-3-yl]methyl}-1H-1,2,3-triazole-4-carboxamide |

TABLE 1-continued

Synthesized Examples

| Ex. No. | Structure | Name |
|---|---|---|
| 142 | 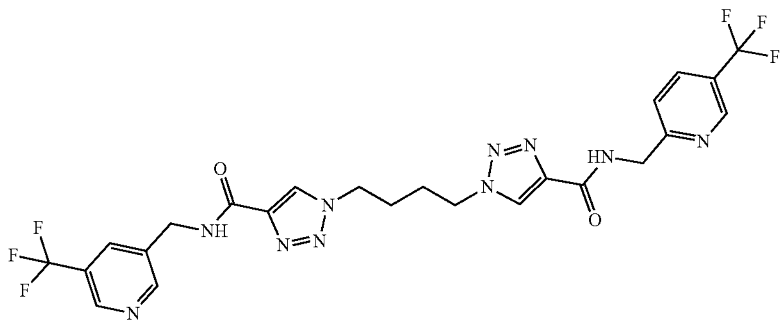 [SMILES: O=C(NCc1cncc(C(F)(F)F)c1)c1cn(CCCCn2cc(C(=O)NCc3ccc(C(F)(F)F)cn3)nn2)nn1] | 1-{4-[4-({[5-(trifluoromethyl)pyridin-2-yl]methyl}carbamoyl)-1H-1,2,3-triazol-1-yl]butyl}-N-{[5-(trifluoromethyl)pyridin-3-yl]methyl}-1H-1,2,3-triazole-4-carboxamide |
| 143 | 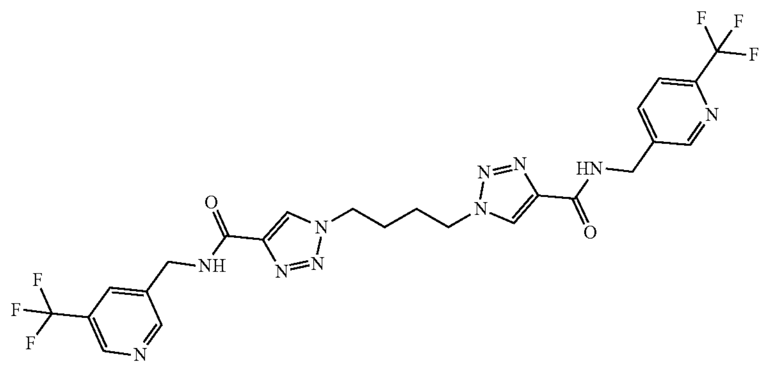 [SMILES: O=C(NCc1ccc(C(F)(F)F)nc1)c1cn(CCCCn2cc(C(=O)NCc3cncc(C(F)(F)F)c3)nn2)nn1] | N-{[5-(trifluoromethyl)pyridin-3-yl]methyl}-1-{4-[4-({[6-(trifluoromethyl)pyridin-3-yl]methyl}carbamoyl)-1H-1,2,3-triazol-1-yl]butyl}-1H-1,2,3-triazole-4-carboxamide |
| 144 | 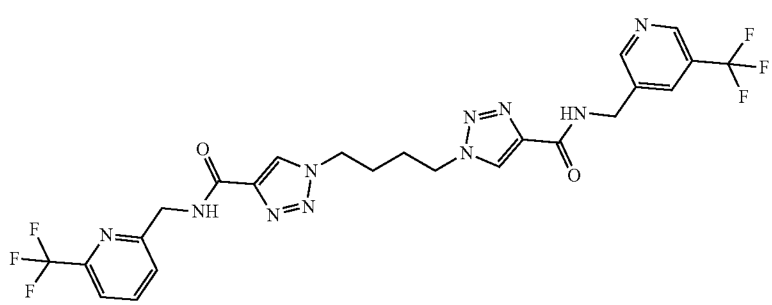 [SMILES: O=C(NCc1cncc(C(F)(F)F)c1)c1cn(CCCCn2cc(C(=O)NCc3cccc(C(F)(F)F)n3)nn2)nn1] | 1-{4-[4-({[6-(trifluoromethyl)pyridin-2-yl]methyl}carbamoyl)-1H-1,2,3-triazol-1-yl]butyl}-N-{[5-(trifluoromethyl)pyridin-3-yl]methyl}-1H-1,2,3-triazole-4-carboxamide |
| 145 | 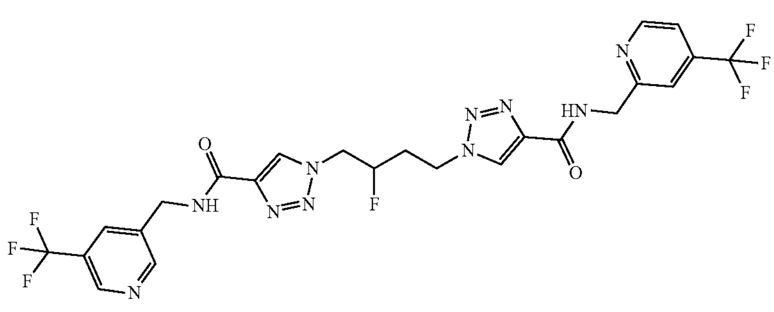 [SMILES: O=C(NCc1cc(C(F)(F)F)ccn1)c1cn(CCC(F)Cn2cc(C(=O)NCc3cncc(C(F)(F)F)c3)nn2)nn1] | 1-{3-fluoro-4-[4-({[5-(trifluoromethyl)pyridin-3-yl]methyl}carbamoyl)-1H-1,2,3-triazol-1-yl]butyl}-N-{[4-(trifluoromethyl)pyridin-2-yl]methyl}-1H-1,2,3-triazole-4-carboxamide |

TABLE 1-continued

Synthesized Examples

| Ex. No. | Structure | Name |
|---|---|---|
| 146 | 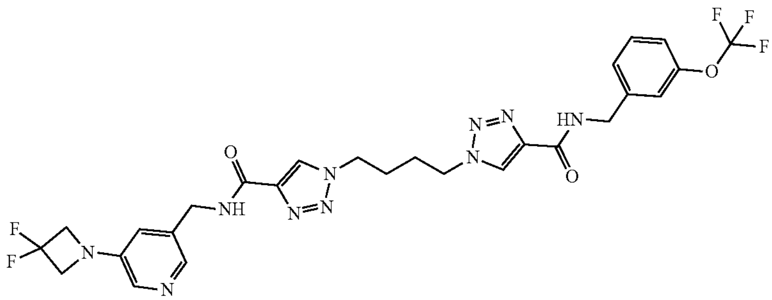 [SMILES: O=C(NCc1cccc(OC(F)(F)F)c1)c1cn(CCCCn2cc(C(=O)NCc3cncc(N4CC(F)(F)C4)c3)nn2)nn1] | N-{[5-(3,3-difluoroazetidin-1-yl)pyridin-3-yl]methyl}-1-{4-[4-({[3-(trifluoromethoxy)phenyl]methyl}carbamoyl)-1H-1,2,3-triazol-1-yl]butyl}-1H-1,2,3-triazole-4-carboxamide |
| 147 | 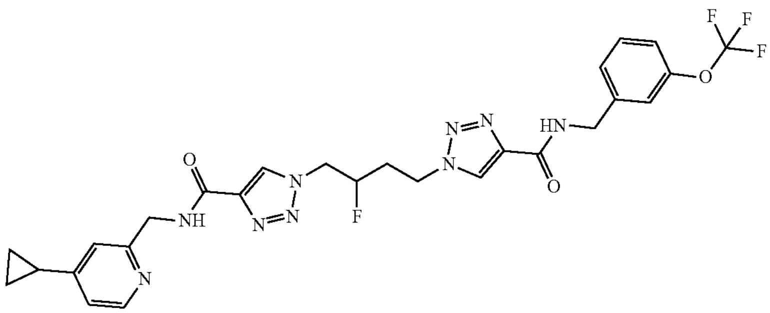 [SMILES: O=C(NCc1cccc(OC(F)(F)F)c1)c1cn(CCC(F)Cn2cc(C(=O)NCc3cc(C4CC4)ccn3)nn2)nn1] | 1-[4-(4-{[(4-cyclopropylpyridin-2-yl)methyl]carbamoyl}-1H-1,2,3-triazol-1-yl)-3-fluorobutyl]-N-{[3-(trifluoromethoxy)phenyl]methyl}-1H-1,2,3-triazole-4-carboxamide |
| 148 | 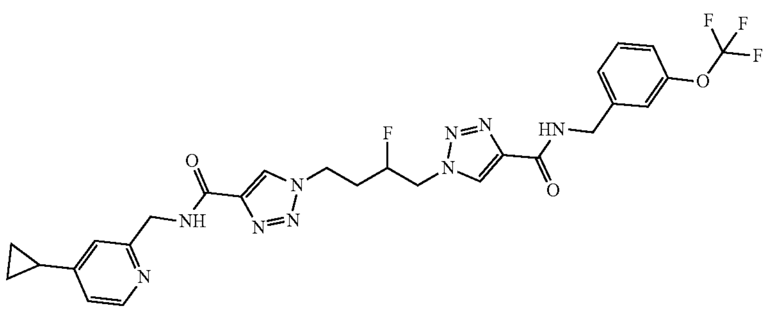 [SMILES: O=C(NCc1cc(C2CC2)ccn1)c1cn(CCC(F)Cn2cc(C(=O)NCc3cccc(OC(F)(F)F)c3)nn2)nn1] | 1-[4-(4-{[(4-cyclopropylpyridin-2-yl)methyl]carbamoyl}-1H-1,2,3-triazol-1-yl)-2-fluorobutyl]-N-{[3-(trifluoromethoxy)phenyl]methyl}-1H-1,2,3-triazole-4-carboxamide |
| 149 | 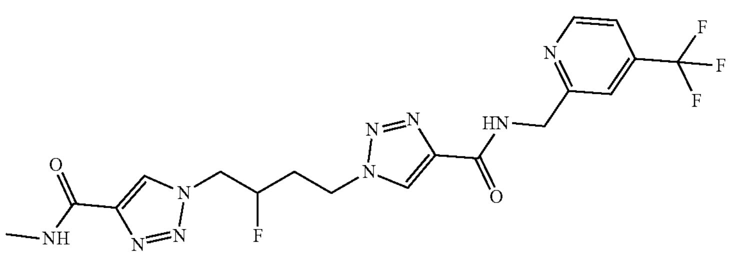 [SMILES: CNC(=O)c1cn(CC(F)CCn2cc(C(=O)NCc3cc(C(F)(F)F)ccn3)nn2)nn1] | 1-{2-fluoro-4-[4-({[4-(trifluoromethyl)pyridin-2-yl]methyl}carbamoyl)-1H-1,2,3-triazol-1-yl]butyl}-N-methyl-1H-1,2,3-triazole-4-carboxamide |
| 150 | 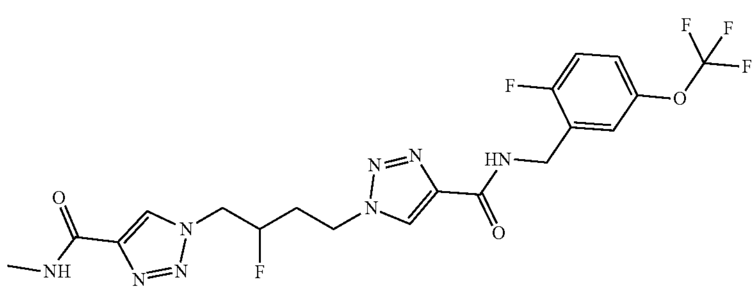 [SMILES: CNC(=O)c1cn(CC(F)CCn2cc(C(=O)NCc3cc(OC(F)(F)F)ccc3F)nn2)nn1] | 1-{2-fluoro-4-[4-({[2-fluoro-5-(trifluoromethoxy)phenyl]methyl}carbamoyl)-1H-1,2,3-triazol-1-yl]butyl}-N-methyl-1H-1,2,3-triazole-4-carboxamide |

TABLE 1-continued

Synthesized Examples

| Ex. No. | Structure | Name |
|---|---|---|
| 151 | 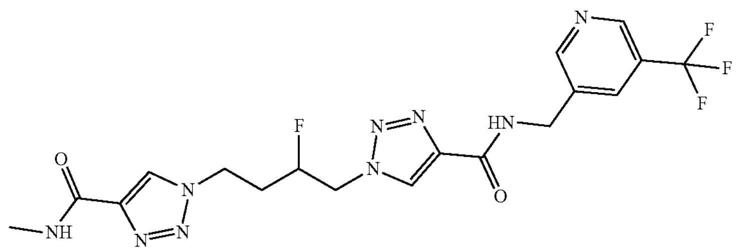 [SMILES: CNC(=O)c1cn(CCC(F)Cn2cc(C(=O)NCc3cncc(C(F)(F)F)c3)nn2)nn1] | 1-{3-fluoro-4-[4-({[5-(trifluoromethyl)pyridin-3-yl]methyl}carbamoyl)-1H-1,2,3-triazol-1-yl]butyl}-N-methyl-1H-1,2,3-triazole-4-carboxamide |
| 152 | 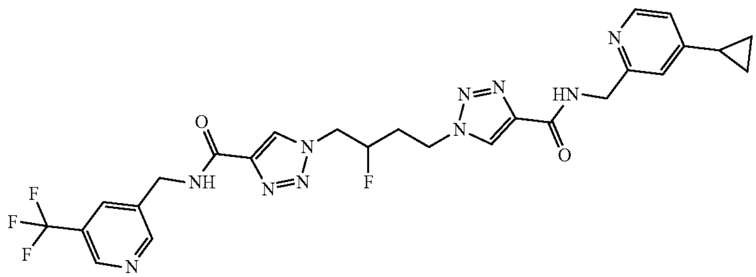 [SMILES: O=C(NCc1cc(C2CC2)ccn1)c1cn(CCC(F)Cn2cc(C(=O)NCc3cncc(C(F)(F)F)c3)nn2)nn1] | N-[(4-cyclopropylpyridin-2-yl)methyl]-1-{3-fluoro-4-[4-({[5-(trifluoromethyl)pyridin-3-yl]methyl}carbamoyl)-1H-1,2,3-triazol-1-yl]butyl}-1H-1,2,3-triazole-4-carboxamide |
| 153 | 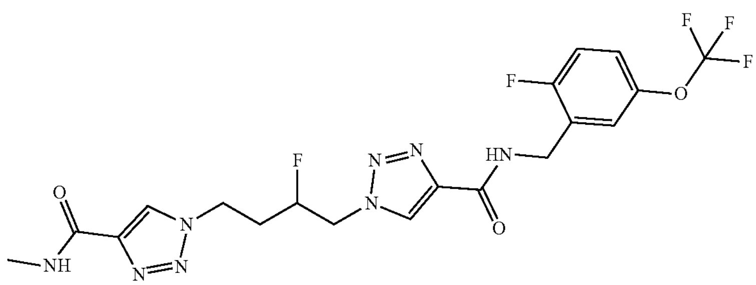 [SMILES: CNC(=O)c1cn(CCC(F)Cn2cc(C(=O)NCc3cc(OC(F)(F)F)ccc3F)nn2)nn1] | 1-{3-fluoro-4-[4-({[2-fluoro-5-(trifluoromethoxy)phenyl]methyl}carbamoyl)-1H-1,2,3-triazol-1-yl]butyl}-N-methyl-1H-1,2,3-triazole-4-carboxamide |
| 154 | 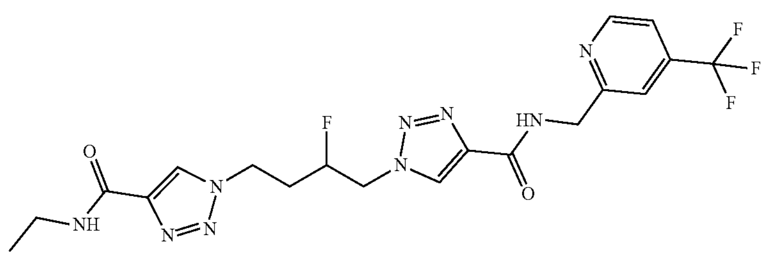 [SMILES: CCNC(=O)c1cn(CCC(F)Cn2cc(C(=O)NCc3cc(C(F)(F)F)ccn3)nn2)nn1] | N-ethyl-1-{3-fluoro-4-[4-({[4-(trifluoromethyl)pyridin-2-yl]methyl}carbamoyl)-1H-1,2,3-triazol-1-yl]butyl}-1H-1,2,3-triazole-4-carboxamide |
| 155 | 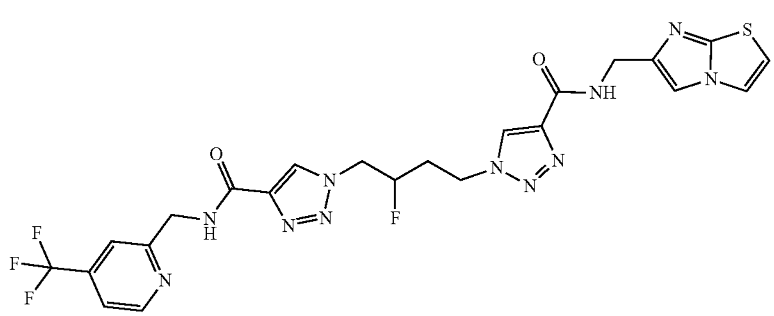 [SMILES: O=C(NCc1cn2ccsc2n1)c1cn(CCC(F)Cn2cc(C(=O)NCc3cc(C(F)(F)F)ccn3)nn2)nn1] | 1-{3-fuoro-4-[4-({[4-(trifluoromethyl)pyridin-2-yl]methyl}carbamoyl)-1H-1,2,3-triazol-1-yl]butyl}-N-{imidazo[2,1-b][1,3]thiazol-6-ylmethyl}-1H-1,2,3-triazole-4-carboxamide |

TABLE 1-continued

Synthesized Examples

| Ex. No. | Structure | Name |
|---|---|---|
| 156 | 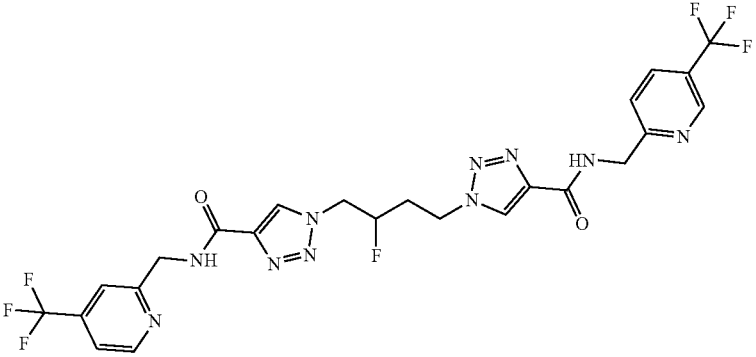 [SMILES: O=C(NCc1ccc(C(F)(F)F)cn1)c1cn(CCC(F)Cn2cc(C(=O)NCc3cc(C(F)(F)F)ccn3)nn2)nn1] | 1-{2-fluoro-4-[4-({[5-(trifluoromethyl)pyridin-2-yl]methyl}carbamoyl)-1H-1,2,3-triazol-1-yl]butyl}-N-{[4-(trifluoromethyl)pyridin-2-yl]methyl}-1H-1,2,3-triazole-4-carboxamide |
| 157 | 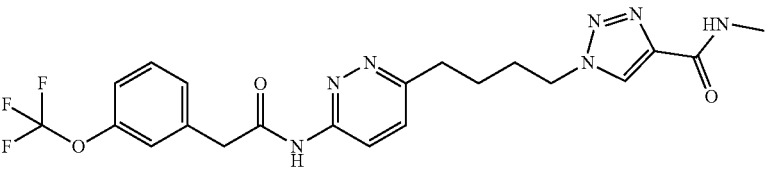 [SMILES: CNC(=O)c1cn(CCCCc2ccc(NC(=O)Cc3cccc(OC(F)(F)F)c3)nn2)nn1] | N-methyl-1-[4-(6-{2-[3-(trifluoromethoxy)phenyl]acetamido}pyridazin-3-yl)butyl]-1H-1,2,3-triazole-4-carboxamide |
| 158 | 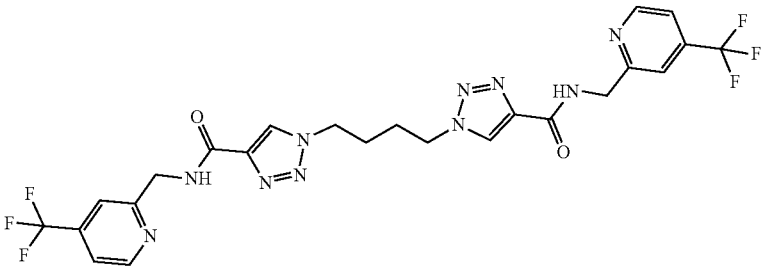 [SMILES: O=C(NCc1cc(C(F)(F)F)ccn1)c1cn(CCCCn2cc(C(=O)NCc3cc(C(F)(F)F)ccn3)nn2)nn1] | N-{[4-(trifluoromethyl)pyridin-2-yl]methyl}-1-{4-[4-({[4-(trifluoromethyl)pyridin-2-yl]methyl}carbamoyl)-1H-1,2,3-triazol-1-yl]butyl}-1,2,3-triazole-4-carboxamide |
| 159 | 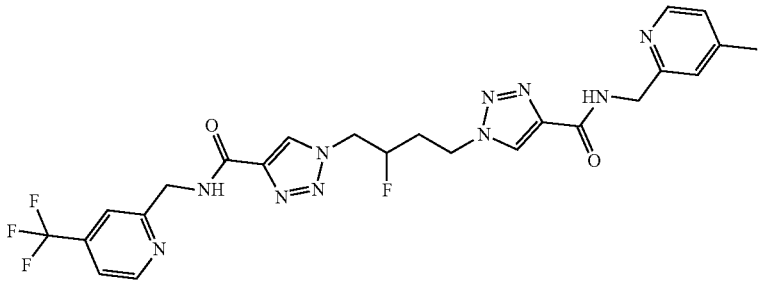 [SMILES: Cc1ccnc(CNC(=O)c2cn(CCC(F)Cn3cc(C(=O)NCc4cc(C(F)(F)F)ccn4)nn3)nn2)c1] | 1-[2-fluoro-4-(4-{[(4-methylpyridin-2-yl)methyl]carbamoyl}-1H-1,2,3-triazol-1-yl)butyl]-N-{[4-(trifluoromethyl)pyridin-2-yl]methyl}-1H-1,2,3-triazole-4-carboxamide |
| 160 | 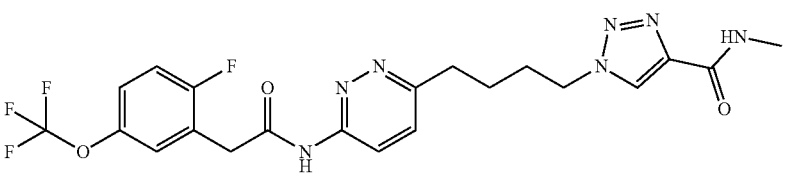 [SMILES: CNC(=O)c1cn(CCCCc2ccc(NC(=O)Cc3cc(OC(F)(F)F)ccc3F)nn2)nn1] | 1-[4-(6-{2-[2-fluoro-5-(trifluoromethoxy)phenyl]acetamido}pyridazin-3-yl)butyl]-N-methyl-1H-1,2,3-triazole-4-carboxamide |
| 161 | 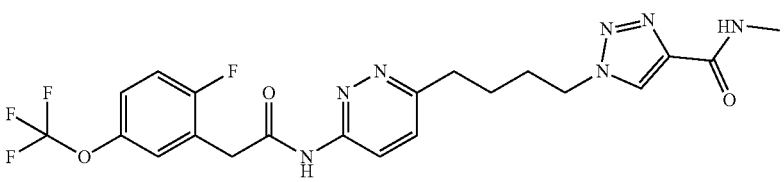 [SMILES: CNC(=O)c1cn(CCCCc2ccc(NC(=O)Cc3cc(OC(F)(F)F)ccc3F)nn2)nn1] | N-methyl-1-{4-[6-(2-phenylacetamido)pyridazin-3-yl]butyl}-1H-1,2,3-triazole-4-carboxamide |

TABLE 1-continued

Synthesized Examples

| Ex. No. | Structure | Name |
|---|---|---|
| 162 | 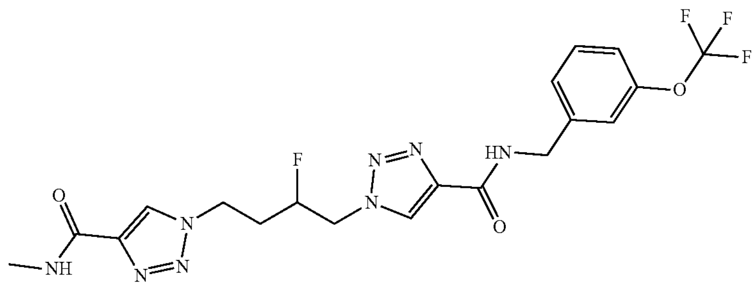 [SMILES: CNC(=O)c1cn(CCC(F)Cn2cc(C(=O)NCc3cccc(OC(F)(F)F)c3)nn2)nn1] | 1-{3-fluoro-4-[4-({[3-(trifluoromethoxy)phenyl]methyl}carbamoyl)-1H-1,2,3-triazol-1-yl]butyl}-N-methyl-1H-1,2,3-triazole-4-carboxamide |
| 163 | 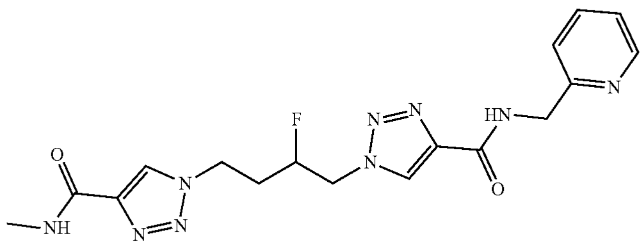 [SMILES: CNC(=O)c1cn(CCC(F)Cn2cc(C(=O)NCc3ccccn3)nn2)nn1] | 1-(3-fluoro-4-{4-[(pyridin-2-ylmethyl)carbamoyl]-1H-1,2,3-triazol-1-yl}butyl)-N-methyl-1H-1,2,3-triazole-4-carboxamide |
| 164 | 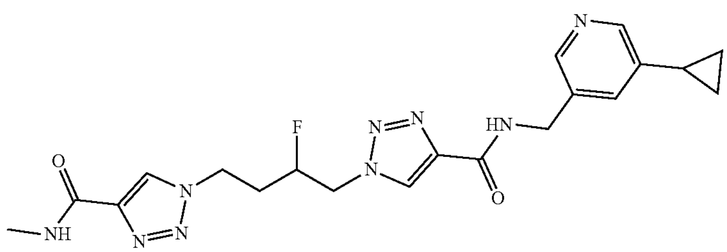 [SMILES: CNC(=O)c1cn(CCC(F)Cn2cc(C(=O)NCc3cncc(C4CC4)c3)nn2)nn1] | 1-[4-(4-{[(5-cyclopropylpyridin-3-yl)methyl]carbamoyl}-1H-1,2,3-triazol-1-yl)-3-fluorobutyl]-N-methyl-1H-1,2,3-triazole-4-carboxamide |
| 165 | 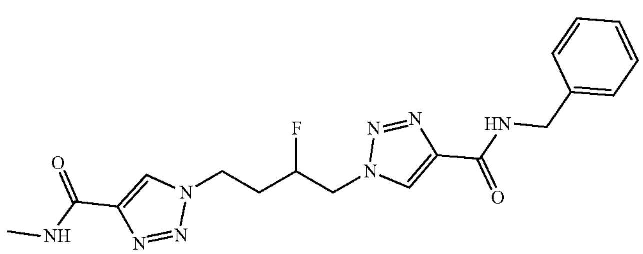 [SMILES: CNC(=O)c1cn(CCC(F)Cn2cc(C(=O)NCc3ccccc3)nn2)nn1] | 1-{4-[4-(benzylcarbamoyl)-1H-1,2,3-triazol-1-yl]-3-fluorobutyl}-N-methyl-1H-1,2,3-triazole-4-carboxamide |
| 166 | 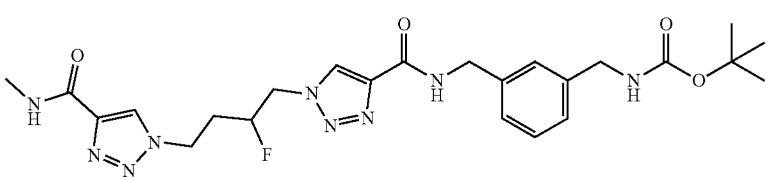 [SMILES: CNC(=O)c1cn(CCC(F)Cn2cc(C(=O)NCc3cccc(CNC(=O)OC(C)(C)C)c3)nn2)nn1] | tert-butyl N-[(3-{[(1-{2-fluoro-4-[4-(methylcarbamoyl)-1H-1,2,3-triazol-1-yl]butyl}-1H-1,2,3-triazol-4-yl)formamido]methyl}phenyl)methyl]carbamate |
| 167 | 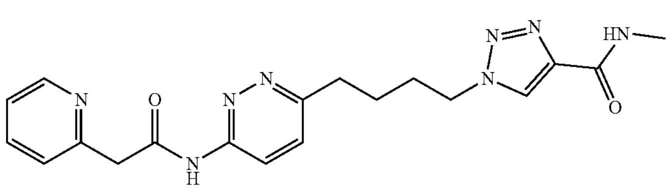 [SMILES: CNC(=O)c1cn(CCCCc2ccc(NC(=O)Cc3ccccn3)nn2)nn1] | N-methyl-1-(4-{6-[2-(pyridin-2-yl)acetamido]pyridazin-3-yl}butyl)-1H-1,2,3-triazole-4-carboxamide |

TABLE 1-continued

Synthesized Examples

| Ex. No. | Structure | Name |
|---|---|---|
| 168 | 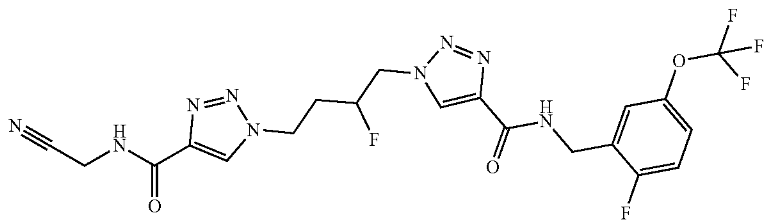 [SMILES: N#CCNC(=O)c1cn(CCC(F)Cn2cc(C(=O)NCc3cc(OC(F)(F)F)ccc3F)nn2)nn1] | N-(cyanomethyl)-1-{3-fluoro-4-[4-({[2-fluoro-5-(trifluoromethoxy)phenyl]methyl}carbamoyl)-1H-1,2,3-triazol-1-yl]butyl}-1H-1,2,3-triazole-4-carboxamide |
| 169 | 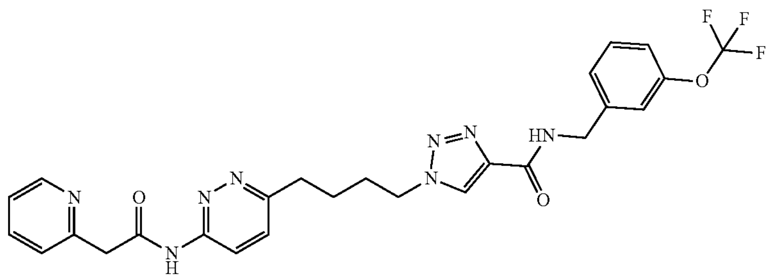 [SMILES: O=C(Cc1ccccn1)Nc1ccc(CCCCn2cc(C(=O)NCc3cccc(OC(F)(F)F)c3)nn2)nn1] | 1-(4-{6-[2-(pyridin-2-yl)acetamido]pyridazin-3-yl}butyl)-N-{[3-(trifluoromethoxy)phenyl]methyl}-1H-1,2,3-triazole-4-carboxamide |
| 170 | 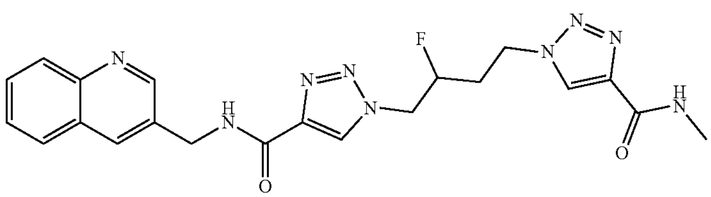 [SMILES: CNC(=O)c1cn(CCC(F)Cn2cc(C(=O)NCc3cnc4ccccc4c3)nn2)nn1] | 1-(3-fuoro-4-{4-[(quinolin-3-ylmethyl)carbamoyl]-1H-1,2,3-triazol-1-yl}butyl)-N-methyl-1H-1,2,3-triazole-4-carboxamide |
| 171 | 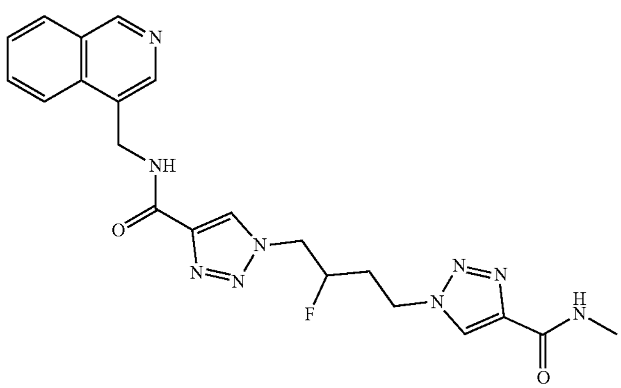 [SMILES: CNC(=O)c1cn(CCC(F)Cn2cc(C(=O)NCc3cncc4ccccc34)nn2)nn1] | 1-(3-fluoro-4-{4-[(isoquinolin-4-ylmethyl)carbamoyl]-1H-1,2,3-triazol-1-yl}butyl)-N-methyl-1H-1,2,3-triazole-4-carboxamide |
| 172 | 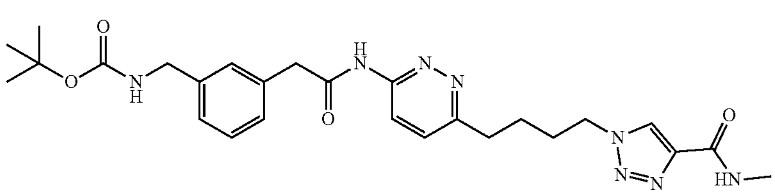 [SMILES: CNC(=O)c1cn(CCCCc2ccc(NC(=O)Cc3cccc(CNC(=O)OC(C)(C)C)c3)nn2)nn1] | tert-butyl N-[(3-{[(6-{4-[4-(methylcarbamoyl)-1H-1,2,3-triazol-1-yl]butyl}pyridazin-3-yl)carbamoyl]methyl}phenyl)methyl]carbamate |
| 173 | 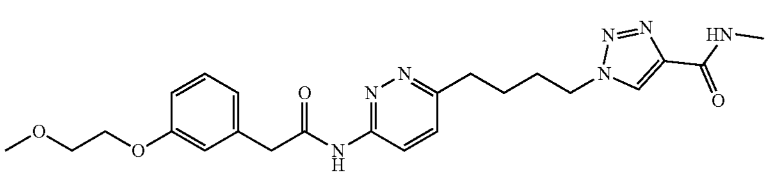 | 1-[4-(6-{2-[3-(2-methoxyethoxy)phenyl]acetamido}pyridazin-3-yl)butyl]-N-methyl-1H-1,2,3-triazole-4-carboxamide |

TABLE 1-continued

Synthesized Examples

| Ex. No. | Structure | Name |
|---|---|---|
| 174 | 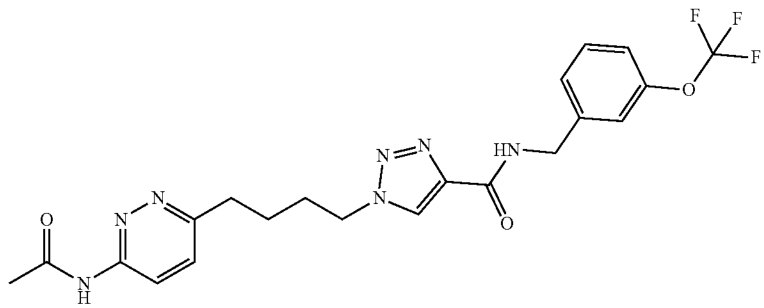 [SMILES: CC(=O)Nc1ccc(CCCCn2cc(C(=O)NCc3cccc(OC(F)(F)F)c3)nn2)nn1] | 1-[4-(6-acetamidopyridazin-3-yl)butyl]-N-{[3-(trifluoromethoxy)phenyl]methyl}-1H-1,2,3-triazole-4-carboxamide |
| 175 | 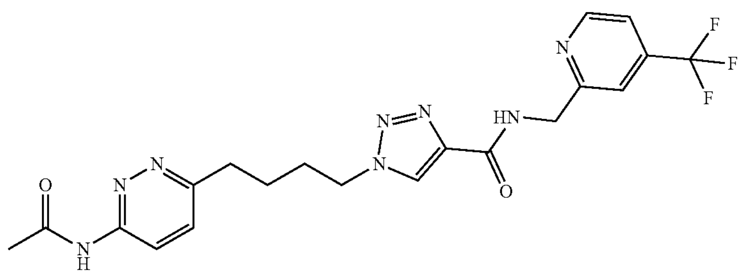 [SMILES: CC(=O)Nc1ccc(CCCCn2cc(C(=O)NCc3cc(C(F)(F)F)ccn3)nn2)nn1] | 1-[4-(6-acetamidopyridazin-3-yl)butyl]-N-{[4-(trifluoromethyl)pyridin-2-yl]methyl}-1H-1,2,3-triazole-4-carboxamide |
| 176 | 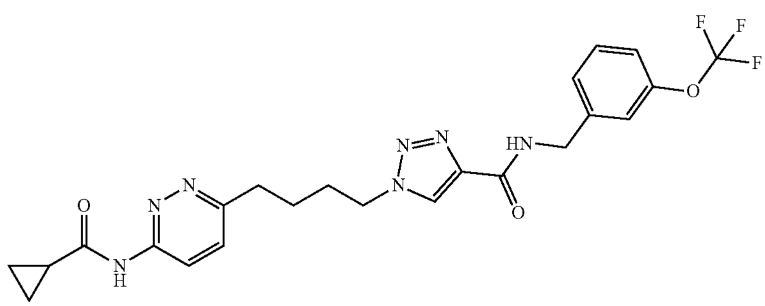 [SMILES: O=C(NCc1cccc(OC(F)(F)F)c1)c1cn(CCCCc2ccc(NC(=O)C3CC3)nn2)nn1] | 1-[4-(6-cyclopropaneamidopyridazin-3-yl)butyl]-N-{[3-(trifluoromethoxy)phenyl]methyl}-1H-1,2,3-triazole-4-carboxamide |
| 177 | 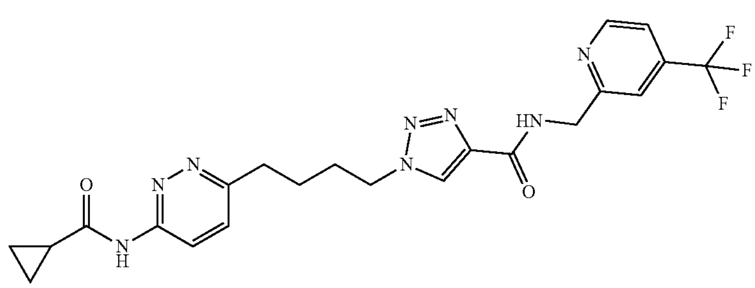 [SMILES: O=C(NCc1cc(C(F)(F)F)ccn1)c1cn(CCCCc2ccc(NC(=O)C3CC3)nn2)nn1] | 1-[4-(6-cyclopropaneamidopyridazin-3-yl)butyl]-N-{[4-(trifluoromethyl)pyridin-2-yl]methyl}-1H-1,2,3-triazole-4-carboxamide |
| 178 | 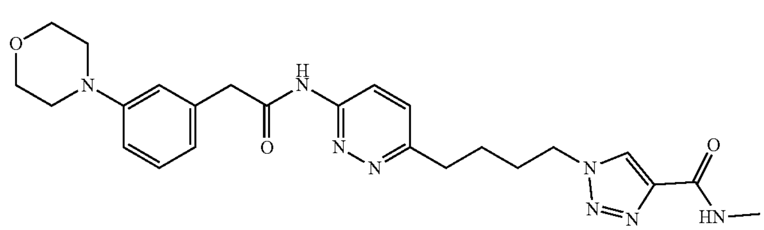 [SMILES: CNC(=O)c1cn(CCCCc2ccc(NC(=O)Cc3cccc(N4CCOCC4)c3)nn2)nn1] | N-methyl-1-[4-(6-{2-[3-(morpholin-4-yl)phenyl]acetamido}pyridazin-3-yl)butyl]-1H-1,2,3-triazole-4-carboxamide |

TABLE 1-continued

Synthesized Examples

| Ex. No. | Structure | Name |
|---|---|---|
| 179 | 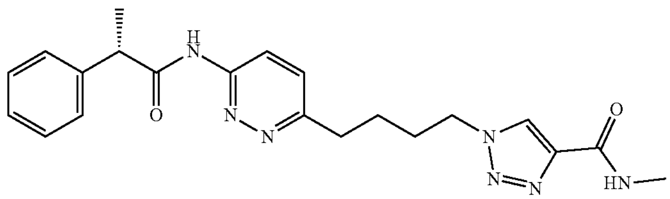 [SMILES: CNC(=O)c1cn(CCCCc2ccc(NC(=O)[C@@H](C)c3ccccc3)nn2)nn1] | N-methyl-1-(4-{6-[(2S)-2-phenylpropanamido]pyridazin-3-yl}butyl)-1H-1,2,3-triazole-4-carboxamide |
| 180 | 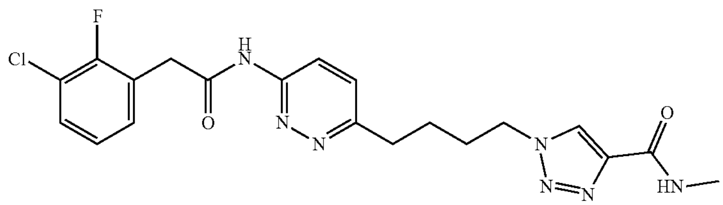 [SMILES: CNC(=O)c1cn(CCCCc2ccc(NC(=O)Cc3cccc(Cl)c3F)nn2)nn1] | 1-(4-{6-[2-(3-chloro-2-fluorophenyl)acetamido]pyridazin-3-yl}butyl)-N-methyl-1H-1,2,3-triazole-4-carboxamide |
| 181 | 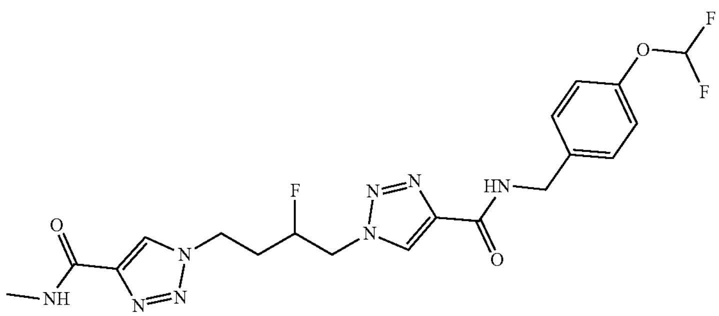 [SMILES: CNC(=O)c1cn(CCC(F)Cn2cc(C(=O)NCc3ccc(OC(F)F)cc3)nn2)nn1] | 1-{4-[4-({[4-(difluoromethoxy)phenyl]methyl}carbamoyl)-1H-1,2,3-triazol-1-yl]-3-fluorobutyl}-N-methyl-1H-1,2,3-triazole-4-carboxamide |
| 182 | 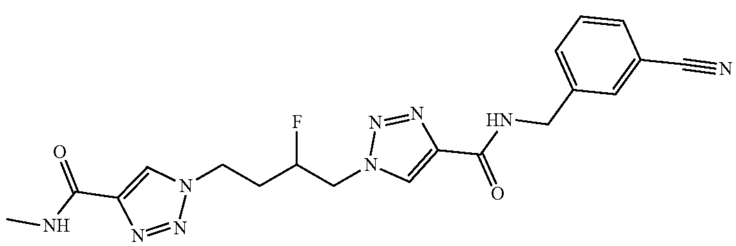 [SMILES: CNC(=O)c1cn(CCC(F)Cn2cc(C(=O)NCc3cccc(C#N)c3)nn2)nn1] | 1-[4-(4-{[(3-cyanophenyl)methyl]carbamoyl}-1H-1,2,3-triazol-1-yl)-3-fluorobutyl]-N-methyl-1H-1,2,3-triazole-4-carboxamide |
| 183 | 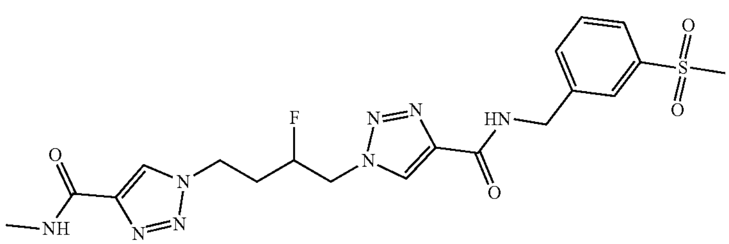 | 1-[3-fluoro-4-(4-{[3-methanesulfonylphenyl)methyl]carbamoyl}-1H-1,2,3-triazol-1-yl)butyl]-N-methyl-1H-1,2,3-triazole-4-carboxamide |
| 184 | 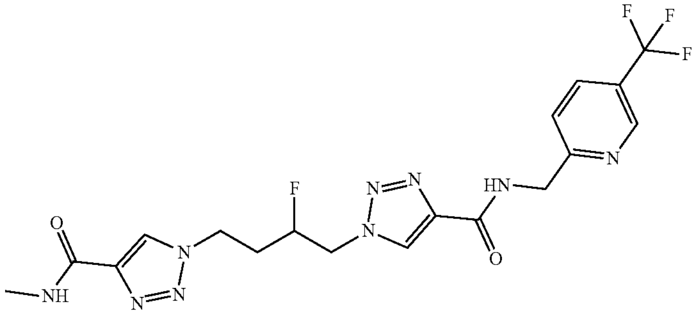 [SMILES: CNC(=O)c1cn(CCC(F)Cn2cc(C(=O)NCc3ccc(C(F)(F)F)cn3)nn2)nn1] | 1-{3-fluoro-4-[4-({[5-(trifluoromethyl)pyridin-2-yl]methyl}carbamoyl)-1H-1,2,3-triazol-1-yl]butyl}-N-methyl-1H-1,2,3-triazole-4-carboxamide |

TABLE 1-continued

Synthesized Examples

| Ex. No. | Name |
|---|---|
| 185 | methyl 3-{[(1-{2-fluoro-4-[4-(methylcarbamoyl)-1H-1,2,3-triazol-1-yl]butyl}-1H-1,2,3-triazol-4-yl)formamido]methyl}benzoate |
| 186 | 1-{3-fluoro-4-[4-({[6-(trifluoromethyl)pyridin-3-yl]methyl}carbamoyl)-1H-1,2,3-triazol-1-yl]butyl}-N-methyl-1H-1,2,3-triazole-4-carboxamide |
| 187 | 1-[3-fluoro-4-(4-{[(6-methylpyridin-3-yl)methyl]carbamoyl}-1H-1,2,3-triazol-1-yl)butyl]-N-methyl-1H-1,2,3-triazole-4-carboxamide |
| 188 | N-methyl-1-{4-[6-(2-{5-[3-(trifluoromethoxy)phenyl]pyridin-3-yl}acetamido)pyridazin-3-yl]butyl}-1H-1,2,3-triazole-4-carboxamide |
| 189 | 5-{3-fluoro-4-[4-(methylcarbamoyl)-1H-1,2,3-triazol-1-yl]butyl}-N-{[5-(trifluoromethyl)pyridin-2-yl]methyl}-1,3,4-thiadiazole-2-carboxamide |

TABLE 1-continued

Synthesized Examples

| Ex. No. | Structure | Name |
|---|---|---|
| 190 | 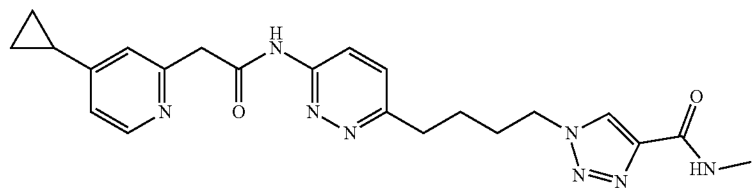 [SMILES: CNC(=O)c1cn(CCCCc2ccc(NC(=O)Cc3cc(C4CC4)ccn3)nn2)nn1] | 1-(4-{6-[2-(4-cyclopropylpyridin-2-yl)acetamido]pyridazin-3-yl}butyl)-N-methyl-1H-1,2,3-triazole-4-carboxamide |
| 191 | 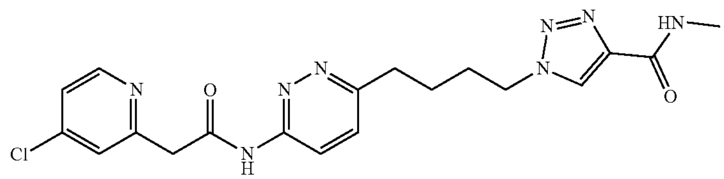 [SMILES: CNC(=O)c1cn(CCCCc2ccc(NC(=O)Cc3cc(Cl)ccn3)nn2)nn1] | 1-(4-{6-[2-(4-chloropyridin-2-yl)acetamido]pyridazin-3-yl}butyl)-N-methyl-1H-1,2,3-triazole-4-carboxamide |
| 192 | 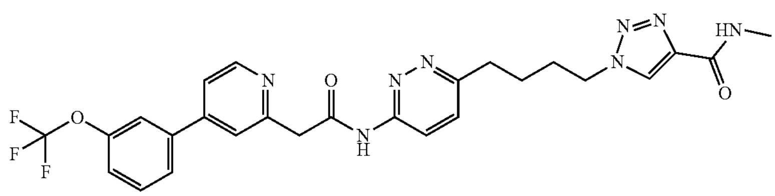 [SMILES: CNC(=O)c1cn(CCCCc2ccc(NC(=O)Cc3cc(-c4cccc(OC(F)(F)F)c4)ccn3)nn2)nn1] | N-methyl-1-{4-[6-(2-{4-[3-(trifluoromethoxy)phenyl]pyridin-2-yl}acetamido)pyridazin-3-yl]butyl}-1H-1,2,3-triazole-4-carboxamide |
| 193 | 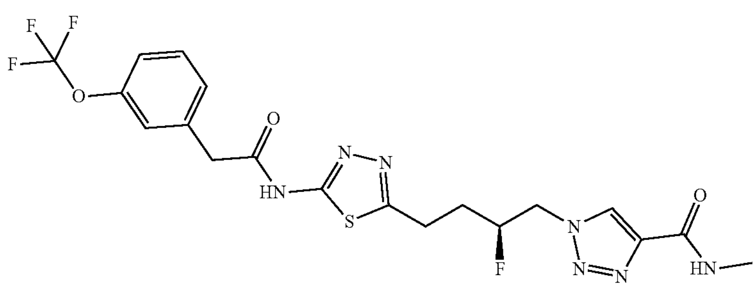 [SMILES: CNC(=O)c1cn(C[C@@H](F)CCc2nnc(NC(=O)Cc3cccc(OC(F)(F)F)c3)s2)nn1] | (S)-1-(2-fluoro-4-(5-(2-(3-(trifluoromethoxy)phenyl)acetamido)-1,3,4-thiadiazol-2-yl)butyl)-N-methyl-1H-1,2,3-triazole-4-carboxamide |
| 194 | 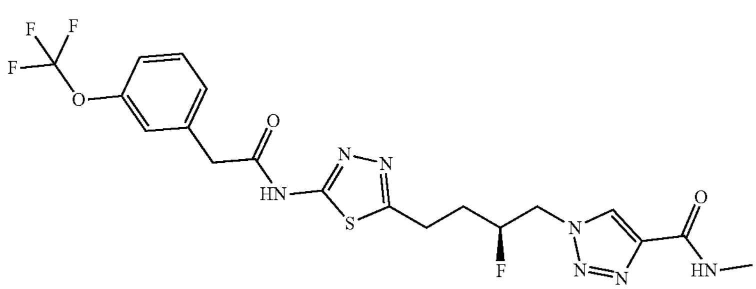 [SMILES: CNC(=O)c1cn(C[C@@H](F)CCc2nnc(NC(=O)Cc3cccc(OC(F)(F)F)c3)s2)nn1] | (S)-1-(2-fluoro-4-(5-(2-(3-(trifluoromethoxy)phenyl)acetamido)-1,3,4-thiadiazol-2-yl)butyl)-N-methyl-1H-1,2,3-triazole-4-carboxamide |
| 195 | 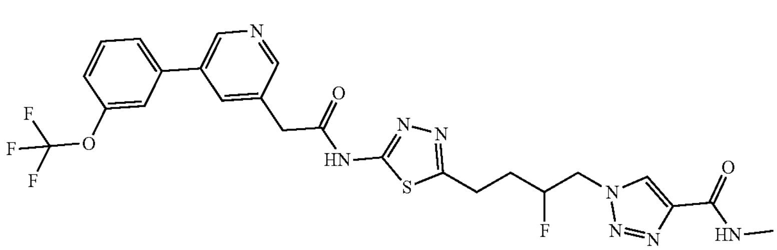 [SMILES: CNC(=O)c1cn(CC(F)CCc2nnc(NC(=O)Cc3cncc(-c4cccc(OC(F)(F)F)c4)c3)s2)nn1] | 1-(2-fluoro-4-(5-(2-(5-(3-(trifluoromethoxy)phenyl)pyridin-3-yl)acetamido)-1,3,4-thiadiazol-2-yl)butyl)-N-methyl-1H-1,2,3-triazole-4-carboxamide |

TABLE 1-continued

Synthesized Examples

| Ex. No. | Structure | Name |
|---|---|---|
| 196 | 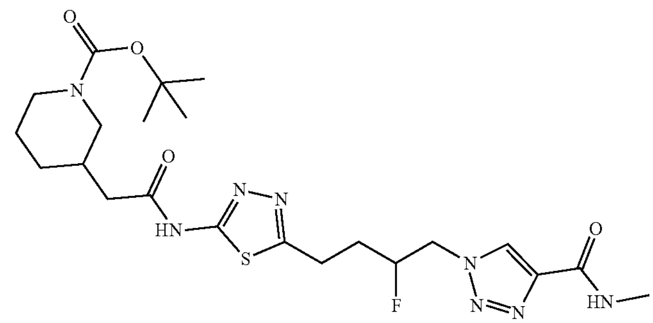 [SMILES: CNC(=O)c1cn(CC(F)CCc2nnc(NC(=O)CC3CCCN(C(=O)OC(C)(C)C)C3)s2)nn1] | tert-butyl 3-((5-(3-fluoro-4-(4-(methylcarbamoyl)-1H-1,2,3-triazol-1-yl)butyl)-1,3,4-thiadiazole-2-carboxamido)methyl)piperidine-1-carboxylate |
| 197 | 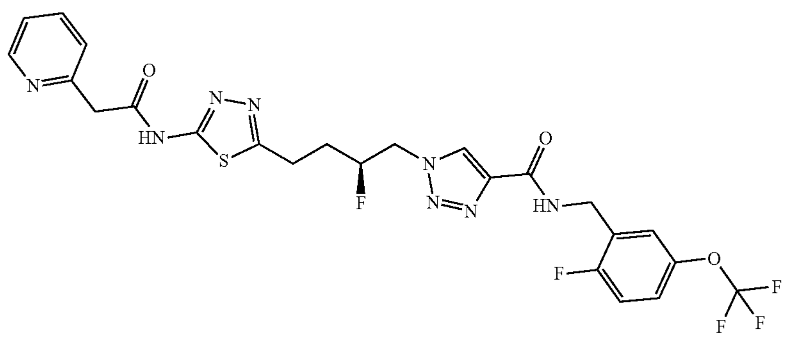 [SMILES: O=C(Cc1ccccn1)Nc1nnc(CC[C@H](F)Cn2cc(C(=O)NCc3cc(OC(F)(F)F)ccc3F)nn2)s1] | (S)-1-(2-fluoro-4-(5-(2-(pyridin-2-yl)acetamido)-1,3,4-thiadiazol-2-yl)butyl)-N-(2-fluoro-5-(trifluoromethoxy)benzyl)-1H-1,2,3-triazole-4-carboxamide |
| 198 | 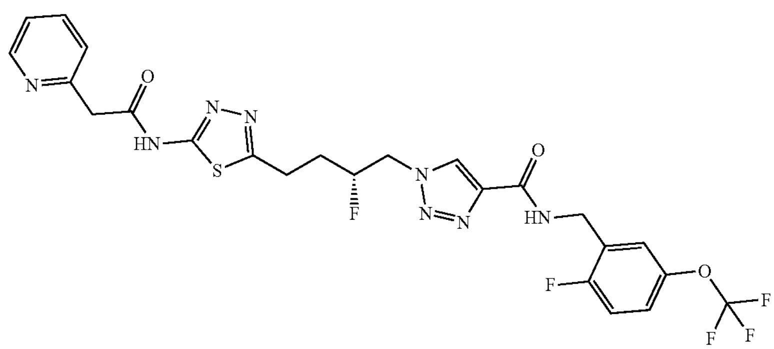 [SMILES: O=C(Cc1ccccn1)Nc1nnc(CC[C@@H](F)Cn2cc(C(=O)NCc3cc(OC(F)(F)F)ccc3F)nn2)s1] | (R)-1-(2-fluoro-4-(5-(2-(pyridin-2-yl)acetamido)-1,3,4-thiadiazol-2-yl)butyl)-N-(2-fluoro-5-(trifluoromethoxy)benzyl)-1H-1,2,3-triazole-4-carboxamide |
| 199 | 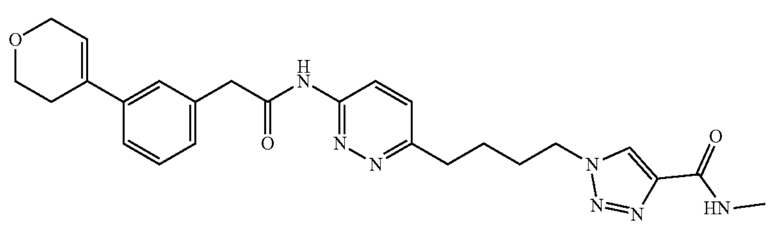 [SMILES: CNC(=O)c1cn(CCCCc2ccc(NC(=O)Cc3cccc(C4=CCOCC4)c3)nn2)nn1] | 1-(4-(6-(2-(3-(3,6-dihydro-2H-pyran-4-yl)phenyl)acetamido)pyridazin-3-yl)butyl)-N-methyl-1H-1,2,3-triazole-4-carboxamide |
| 200 | 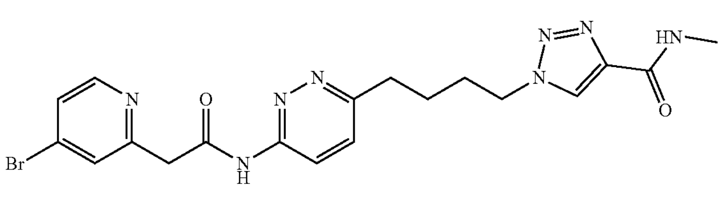 [SMILES: CNC(=O)c1cn(CCCCc2ccc(NC(=O)Cc3cc(Br)ccn3)nn2)nn1] | 1-(4-(6-(2-(4-bromopyridin-2-yl)acetamido)pyridazin-3-yl)butyl)-N-methyl-1H-1,2,3-triazole-4-carboxamide |

TABLE 1-continued

Synthesized Examples

| Ex. No. | Structure | Name |
|---|---|---|
| 201 | 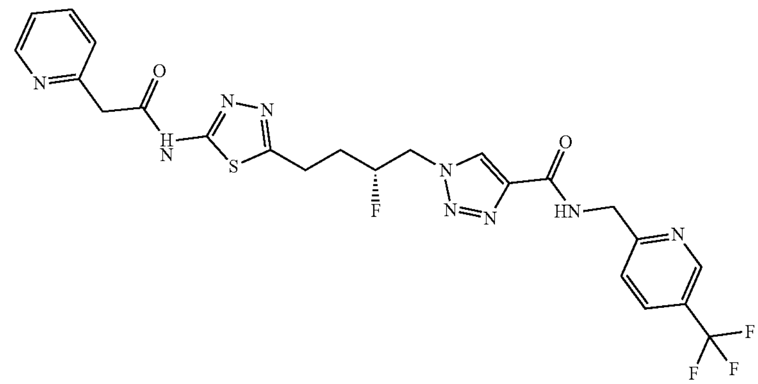 [SMILES: O=C(Cc1ccccn1)Nc1nnc(CC[C@@H](F)Cn2cc(C(=O)NCc3ccc(C(F)(F)F)cn3)nn2)s1] | (R)-1-(2-fluoro-4-(5-(2-(pyridin-2-yl)acetamido)-1,3,4-thiadiazol-2-yl)butyl)-N-((5-(trifluoromethyl)pyridin-2-yl)methyl)-1H-1,2,3-triazole-4-carboxamide |
| 202 | 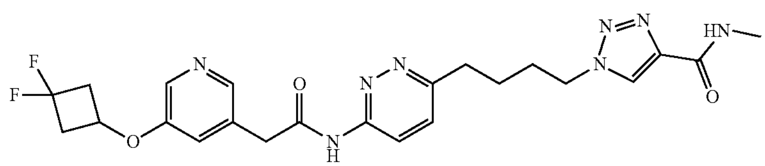 [SMILES: CNC(=O)c1cn(CCCCc2ccc(NC(=O)Cc3cncc(OC4CC(F)(F)C4)c3)nn2)nn1] | 1-(4-(6-(2-(5-(3,3-difluorocyclobutoxy)pyridin-3-yl)acetamido)pyridazin-3-yl)butyl)-N-methyl-1H-1,2,3-triazole-4-carboxamide |
| 203 | 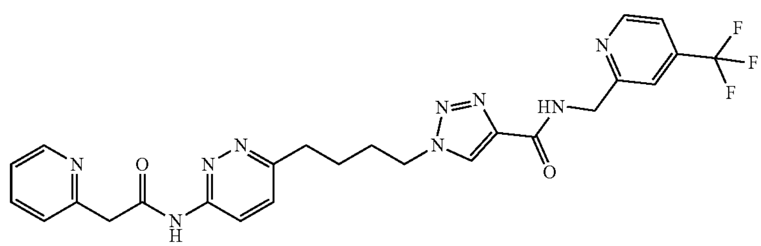 [SMILES: O=C(Cc1ccccn1)Nc1ccc(CCCCn2cc(C(=O)NCc3cc(C(F)(F)F)ccn3)nn2)nn1] | 1-(4-(6-(2-(pyridin-2-yl)acetamido)pyridazin-3-yl)butyl)-N-((4-(trifluoromethyl)pyridin-2-yl)methyl)-1H-1,2,3-triazole-4-carboxamide |
| 204 | 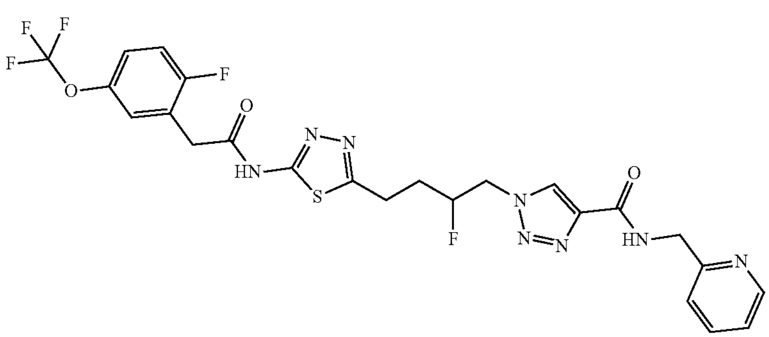 [SMILES: O=C(Cc1cc(OC(F)(F)F)ccc1F)Nc1nnc(CCC(F)Cn2cc(C(=O)NCc3ccccn3)nn2)s1] | 1-(2-fluoro-4-(5-(2-(2-fluoro-5-(trifluoromethoxy)phenyl)acetamido)-1,3,4-thiadiazol-2-yl)butyl)-N-(pyridin-2-ylmethyl)-1H-1,2,3-triazole-4-carboxamide |
| 205 | 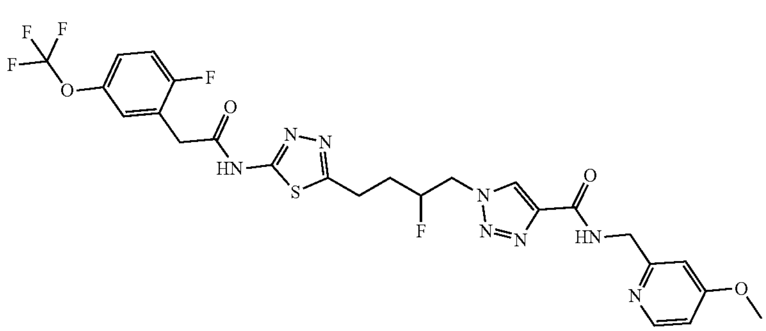 [SMILES: COc1ccnc(CNC(=O)c2cn(CC(F)CCc3nnc(NC(=O)Cc4cc(OC(F)(F)F)ccc4F)s3)nn2)c1] | 1-(2-fluoro-4-(5-(2-(2-fluoro-5-(trifluoromethoxy)phenyl)acetamido)-1,3,4-thiadiazol-2-yl)butyl)-N-((4-methoxypyridin-2-yl)methyl)-1H-1,2,3-triazole-4-carboxamide |

TABLE 1-continued

Synthesized Examples

| Ex. No. | Structure | Name |
|---|---|---|
| 206 | 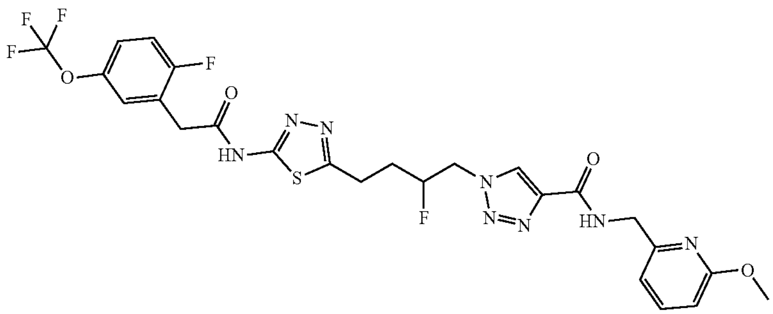 [SMILES: COc1cccc(CNC(=O)c2cn(CC(F)CCc3nnc(NC(=O)Cc4cc(OC(F)(F)F)ccc4F)s3)nn2)n1] | 1-(2-fluoro-4-(5-(2-(2-fluoro-5-(trifluoromethoxy)phenyl)acetamido)-1,3,4-thiadiazol-2-yL)butyl)-N-((6-methoxypyridin-2-yl)methyl)-1H-1,2,3-triazole-4-carboxamide |
| 207 | 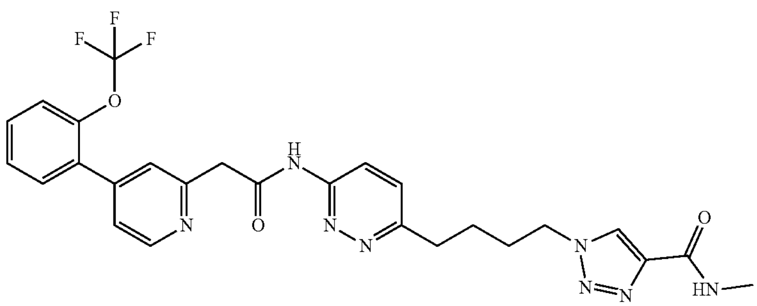 [SMILES: CNC(=O)c1cn(CCCCc2ccc(NC(=O)Cc3cc(-c4ccccc4OC(F)(F)F)ccn3)nn2)nn1] | N-methyl-1-(4-(6-(2-(4-(2 (trifluoromethoxy)phenyl)pyridin-2-yl)acetamido)pyridazin-3-yl)butyl)-1H-1,2,3-triazole-4-carboxamide |
| 208 | 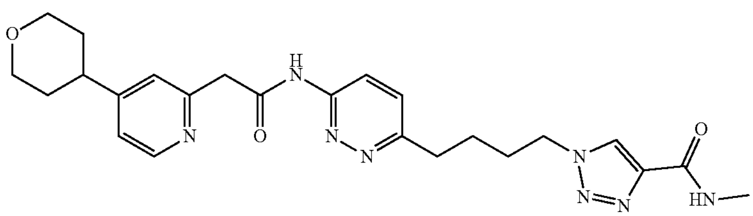 [SMILES: CNC(=O)c1cn(CCCCc2ccc(NC(=O)Cc3cc(C4CCOCC4)ccn3)nn2)nn1] | N-methyl-1-(4-(6-(2-(4-(tetrahydro-2H-pyran-4-yl)pyridin-2-yl)acetamido)pyridazin-3-yl)butyl)-1H-1,2,3-triazole-4-carboxamide |
| 209 | 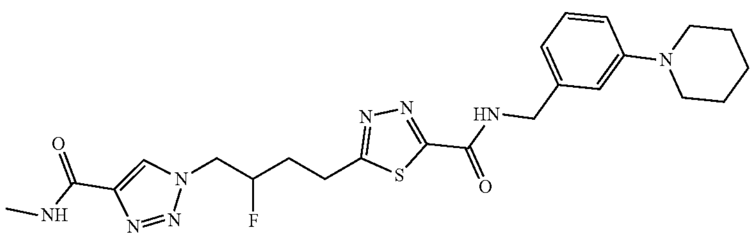 [SMILES: CNC(=O)c1cn(CC(F)CCc2nnc(C(=O)NCc3cccc(N4CCCCC4)c3)s2)nn1] | 5-(3-fluoro-4-(4-(methylcarbamoyl)-1H-1,2,3-triazol-1-yl)butyl)-N-(3-(piperidin-1-yl)benzyl)-1,3,4-thiadiazole-2-carboxamide |
| 210 | 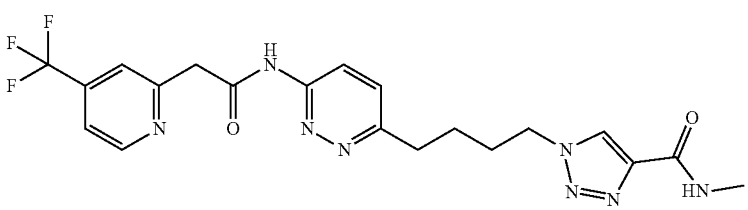 [SMILES: CNC(=O)c1cn(CCCCc2ccc(NC(=O)Cc3cc(C(F)(F)F)ccn3)nn2)nn1] | N-methyl-1-(4-(6-(2-(4-(trifluoromethyl)pyridin-2-yl)acetamido)pyridazin-3-yl)butyl)-1H-1,2,3-triazole-4-carboxamide |
| 211 | 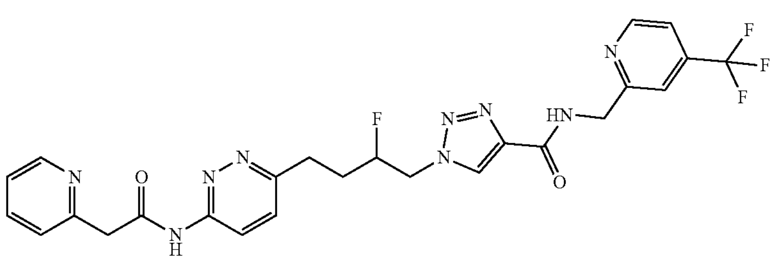 [SMILES: O=C(Cc1ccccn1)Nc1ccc(CCC(F)Cn2cc(C(=O)NCc3cc(C(F)(F)F)ccn3)nn2)nn1] | 1-(2-fluoro-4-(6-(2-(pyridin-2-yl)acetamido)pyridazin-3-yl)butyl)-N-((4-(trifluoromethyl)pyridin-2-yl)methyl)-1H-1,2,3-triazole-4-carboxamide |

TABLE 1-continued

Synthesized Examples

| Ex. No. | Structure | Name |
|---|---|---|
| 212 | 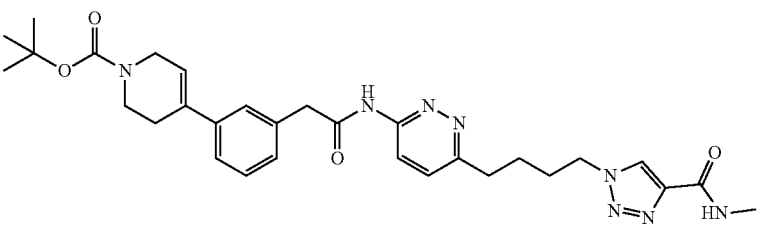 [SMILES: CNC(=O)c1cn(CCCCc2ccc(NC(=O)Cc3cccc(C4=CCN(C(=O)OC(C)(C)C)CC4)c3)nn2)nn1] | tert-butyl 4-(3-(2-((6-(4-(4-(methylcarbamoyl)-1H-1,2,3-triazol-1-yl)butyl)pyridazin-3-yl)amino)-2-oxoethyl)phenyl)-3,6-dihydropyridine-1(2H)-carboxylate |
| 213 | 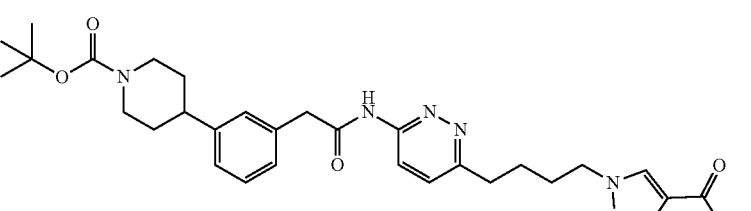 | tert-butyl 4-(3-(2-((6-(4-(4-(methylcarbamoyl)-1H-1,2,3-triazol-1-yl)butyl)pyridazin-3-yl)amino)-2-oxoethyl)phenyl)piperidine-1-carboxylate |
| 214 | 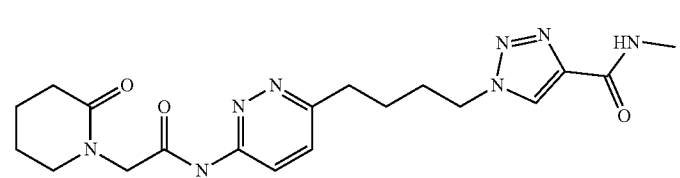 | N-methyl-1-(4-(6-(2-(2-oxopiperidin-1-yl)acetamido)pyridazin-3-yl)butyl)-1H-1,2,3-triazole-4-carboxamide |
| 215 | 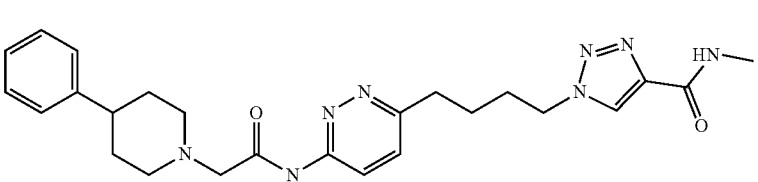 | N-methyl-1-(4-(6-(2-(4-phenylpiperidin-1-yl)acetamido)pyridazin-3-yl)butyl)-1H-1,2,3-triazole-4-carboxamide |
| 216 | 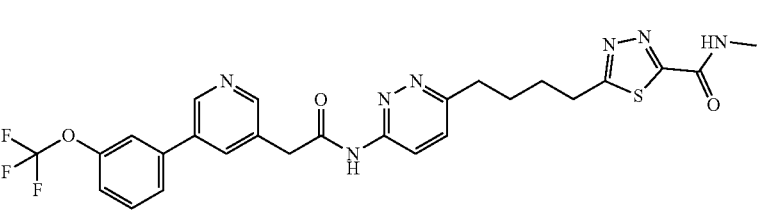 [SMILES: CNC(=O)c1nnc(CCCCc2ccc(NC(=O)Cc3cncc(-c4cccc(OC(F)(F)F)c4)c3)nn2)s1] | N-methyl-5-(4-(6-(2-(5-(3-(trifluoromethoxy)phenyl)pyridin-3-yl)acetamido)pyridazin-3-yl)butyl)-1,2,3-thiadiazole-2-carboxamide |
| 217 | 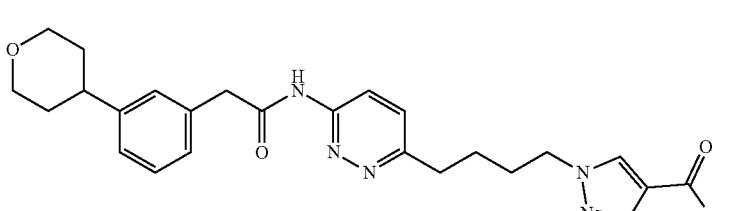 | N-methyl-1-(4-(6-(2-(3-(tetrahydro-2H-pyran-2-yl)phenyl)acetamido)pyridazin-3-yl)butyl)-1H-1,2,3-triazole-4-carboxamide |

TABLE 1-continued

Synthesized Examples

| Ex. No. | Structure | Name |
|---|---|---|
| 218 | 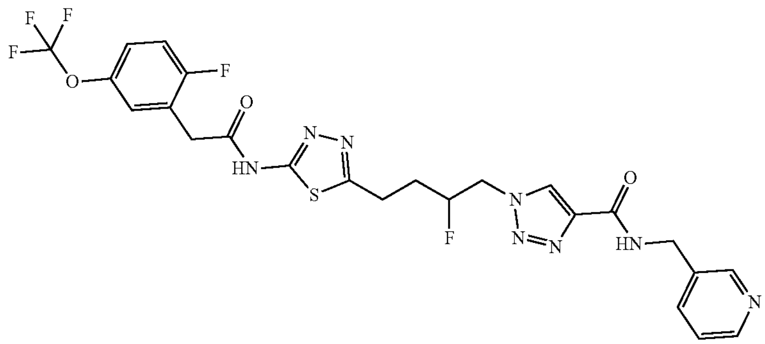 [SMILES: O=C(Cc1cc(OC(F)(F)F)ccc1F)Nc1nnc(CCC(F)Cn2cc(C(=O)NCc3cccnc3)nn2)s1] | 1-(2-fluoro-4-(5-(2-(2-fluoro-5-(trifluoromethoxy)phenyl)acetamido)-1,3,4-thiadiazol-2-yl)butyl)-N-(pyridin-3-ylmethyl)-1H-1,2,3-triazole-4-carboxamide |
| 219 | 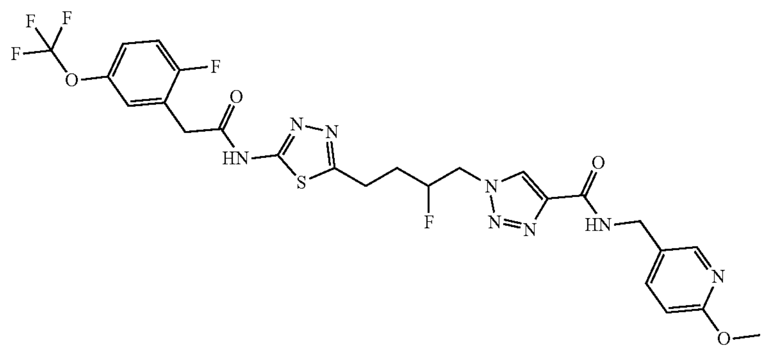 [SMILES: COc1ccc(CNC(=O)c2cn(CC(F)CCc3nnc(NC(=O)Cc4cc(OC(F)(F)F)ccc4F)s3)nn2)cn1] | 1-(2-fluoro-4-(5-(2-(2-fluoro-5-(trifluoromethoxy)phenyl)acetamido)-1,3,4-thidiazol-2-yl)butyl)-N-((6-methoxypyridin-3-yl)methyl)-1H-1,2,3-triazole-4-carboxamide |
| 220 | 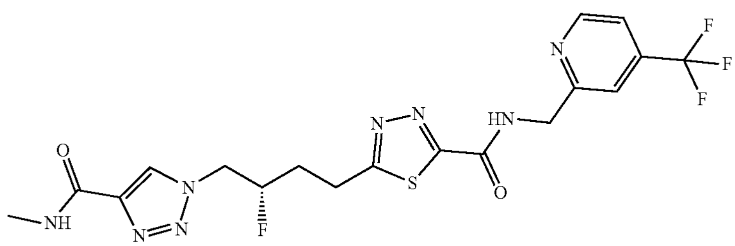 [SMILES: CNC(=O)c1cn(C[C@@H](F)CCc2nnc(C(=O)NCc3cc(C(F)(F)F)ccn3)s2)nn1] | (S)-5-(3-fluoro-4-(4-(methylcarbamoyl)-1H-1,2,3-triazol-1-yl)butyl)-N-((4-(trifluoromethyl)pyridin-2-yl)methyl)-1,3,4-thiadiazole-2-carboxamide |
| 221 | 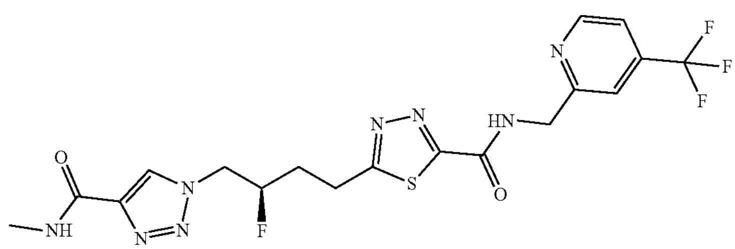 [SMILES: CNC(=O)c1cn(C[C@H](F)CCc2nnc(C(=O)NCc3cc(C(F)(F)F)ccn3)s2)nn1] | (R)-5-(3-fluoro-4-(4-(methylcarbamoyl)-1H-1,2,3-triazol-1-yl)butyl)-N-((4-(trifluoromethyl)pyridin-2-yl)methyl)-1,3,4-thiadiazole-2-carboxamide |
| 222 | 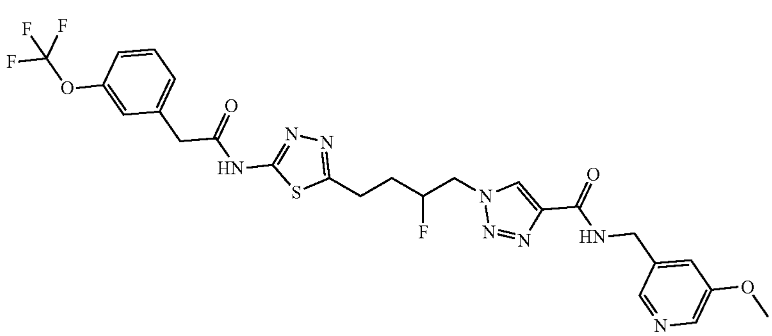 [SMILES: COc1cncc(CNC(=O)c2cn(CC(F)CCc3nnc(NC(=O)Cc4cccc(OC(F)(F)F)c4)s3)nn2)c1] | 1-(2-fluoro-4-(5-(2-(3-(trifluoromethoxy)phenyl)acetamido)-1,3,4-thiadiazol-2-yl)butyl)-N-((5-methoxypyridin-3-yl)methyl)-1H-1,2,3-triazole-4-carboxamide |

TABLE 1-continued

Synthesized Examples

| Ex. No. | Structure | Name |
|---|---|---|
| 223 | 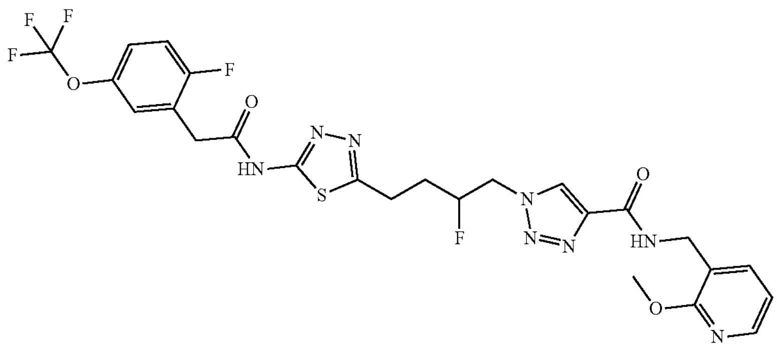 [SMILES: COc1ncccc1CNC(=O)c1cn(CC(F)CCc2nnc(NC(=O)Cc3cc(OC(F)(F)F)ccc3F)s2)nn1] | 1-(2-fluoro-4-(5-(2-(2-fluoro-5-(trifluoromethoxy)phenyl)acetamido)-1,3,4-thiadiazol-2-yl)butyl)-N-((2-methoxypyridin-3-yl)methyl)-1H-1,2,3-triazole-4-carboxamide |
| 224 | 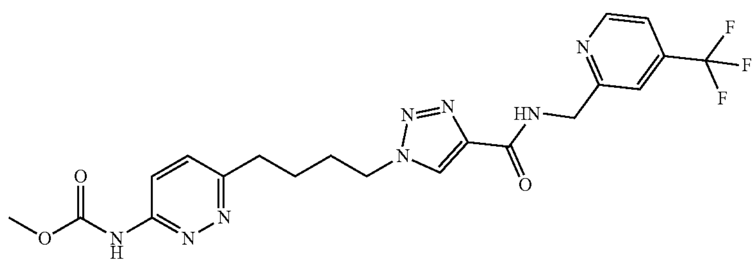 [SMILES: COC(=O)Nc1ccc(CCCCn2cc(C(=O)NCc3cc(C(F)(F)F)ccn3)nn2)nn1] | methyl 6-(4-(4-(((4-(trifluoromethyl)pyridin-2-yl)methyl)carbamoyl)-1H-1,2,3-triazol-1-yl)butyl)pyridazin-3-yl)carbamate |
| 225 | 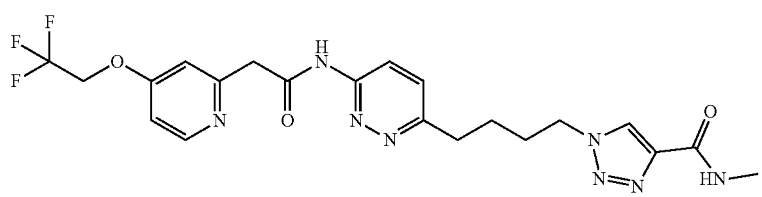 [SMILES: CNC(=O)c1cn(CCCCc2ccc(NC(=O)Cc3cc(OCC(F)(F)F)ccn3)nn2)nn1] | N-methyl-1-(4-(6-(2-(4-(2,2,2-trifluoroethoxy)pyridin-2-yl)acetamido)pyridazin-3-yl)butyl)-1H-1,2,3-triazole-4-carboxamide |
| 226 | 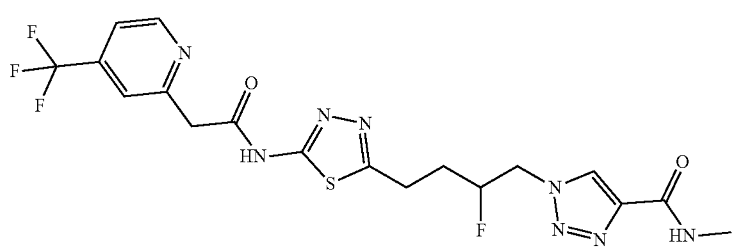 [SMILES: CNC(=O)c1cn(CC(F)CCc2nnc(NC(=O)Cc3cc(C(F)(F)F)ccn3)s2)nn1] | 1-(2-fluoro-4-(5-(2-(4-(trifluoromethyl)pyridin-2-yl)acetamido)-1,3,4-thiadiazol-2-yl)butyl)-N-methyl-1H-1,2,3-triazole-4-carboxamide |
| 227 | 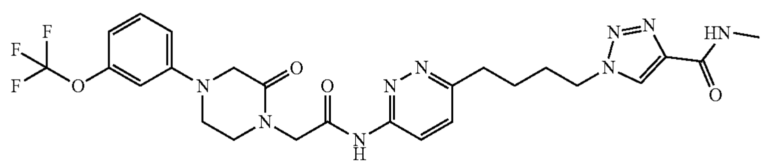 [SMILES: CNC(=O)c1cn(CCCCc2ccc(NC(=O)CN3CCN(c4cccc(OC(F)(F)F)c4)CC3=O)nn2)nn1] | N-methyl-1-(4-(6-(2-(2-oxo-4-(3-(trifluoromethoxy)phenyl)piperazin-1-yl)acetamido)pyridazin-3-yl)butyl)-1H-1,2,3-triazole-4-carboxamide |
| 228 | 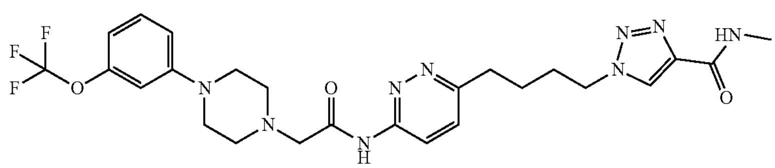 [SMILES: CNC(=O)c1cn(CCCCc2ccc(NC(=O)CN3CCN(c4cccc(OC(F)(F)F)c4)CC3)nn2)nn1] | N-methyl-1-(4-(6-(2-(4-(3-(trifluoromethoxy)phenyl)piperazin-1-yl)acetamido)pyridazin-3-yl)butyl)-1H-1,2,3-triazole-4-carboxamide |

TABLE 1-continued

Synthesized Examples

| Ex. No. | Structure | Name |
|---|---|---|
| 229 | 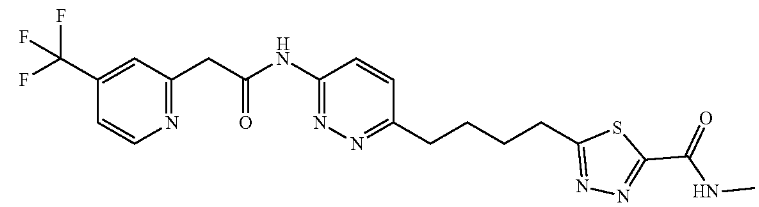 [SMILES: CNC(=O)c1nnc(CCCCc2ccc(NC(=O)Cc3cc(C(F)(F)F)ccn3)nn2)s1] | N-methyl-5-(4-(6-(2-(4-(trifluoromethyl)pyridin-2-yl)acetamido)pyridazin-3-yl)butyl)-1,3,4-thiadiazole-2-carboxamide |
| 230 | 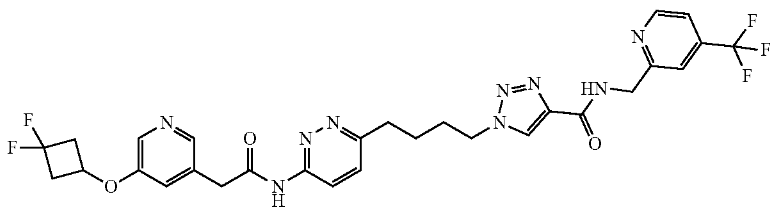 [SMILES: O=C(Cc1cncc(OC2CC(F)(F)C2)c1)Nc1ccc(CCCCn2cc(C(=O)NCc3cc(C(F)(F)F)ccn3)nn2)nn1] | 1-(4-(6-(2-(5-(3,3-difluorocyclobutoxy)pyridin-3-yl)acetamido)pyridazin-3-yl)butyl)-N-((4-(trifluoromethyl)pyridin-2-yl)methyl)-1H-1,2,3-triazole-4-carboxamide |
| 231 | 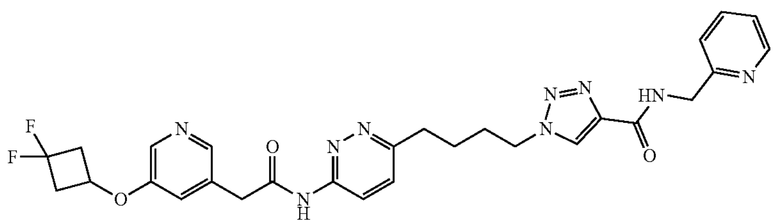 [SMILES: O=C(Cc1cncc(OC2CC(F)(F)C2)c1)Nc1ccc(CCCCn2cc(C(=O)NCc3ccccn3)nn2)nn1] | 1-(4-(6-(2-(5-(3,3-difluorocyclobutoxy)pyridin-3-yl)acetamido)pyridazin-3-yl)butyl)-N-(pyridin-2-ylmethyl)-1H-1,2,3-triazole-4-carboxamide |
| 232 | 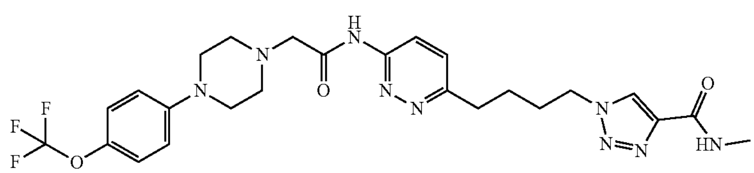 [SMILES: CNC(=O)c1cn(CCCCc2ccc(NC(=O)CN3CCN(c4ccc(OC(F)(F)F)cc4)CC3)nn2)nn1] | N-methyl-1-(4-(6-(2-(4-(4-(trifluoromethoxy)phenyl)piperazin-1-yl)acetamido)pyridazin-3-yl)butyl)-1H-1,2,3-triazole-4-carboxamide |
| 233 | 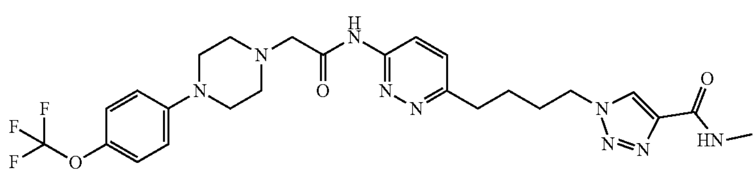 [SMILES: CNC(=O)c1cn(CCCCc2ccc(NC(=O)CN3CCN(c4ccc(OC(F)(F)F)cc4)CC3)nn2)nn1] | N-methyl-1-(4-(6-(2-(4-(4-(trifluoromethoxy)phenyl)piperazin-1-yl)acetamido)pyridazin-3-yl)butyl)-1H-1,2,3-triazole-4-carboxamide |
| 234 | 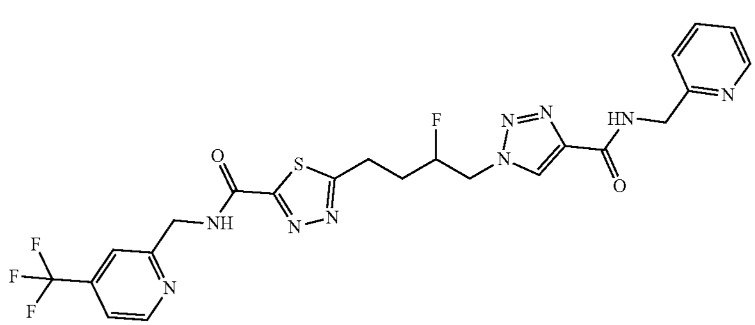 [SMILES: O=C(NCc1ccccn1)c1cn(CC(F)CCc2nnc(C(=O)NCc3cc(C(F)(F)F)ccn3)s2)nn1] | 5-(3-fluoro-4-(4-((pyridin-2-ylmethyl)carbamoyl)-1H-1,2,3-triazol-1-yl)butyl)-N-((4-(trifluoromethyl)pyridin-2-yl)methyl)-1,3,4-thiadiazole-2-carboxamide |

TABLE 1-continued

Synthesized Examples

| Ex. No. | Structure | Name |
|---|---|---|
| 235 | 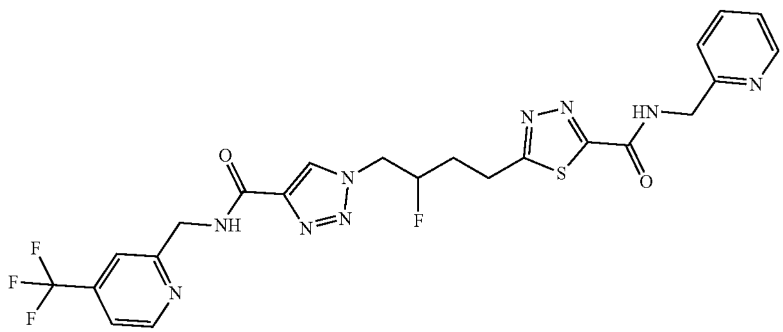 [SMILES: O=C(NCc1cc(C(F)(F)F)ccn1)c1cn(CC(F)CCc2nnc(C(=O)NCc3ccccn3)s2)nn1] | 5-(3-fluoro-4-(4-(((4-(trifluoromethyl)pyridin-2-yl)methyl)carbamoyl)-1H-1,2,3-triazol-1-yl)butyl)-N-(pyridin-2-ylmethyl)-1,3,4-thiadiazole-2-carboxamide |
| 236 | 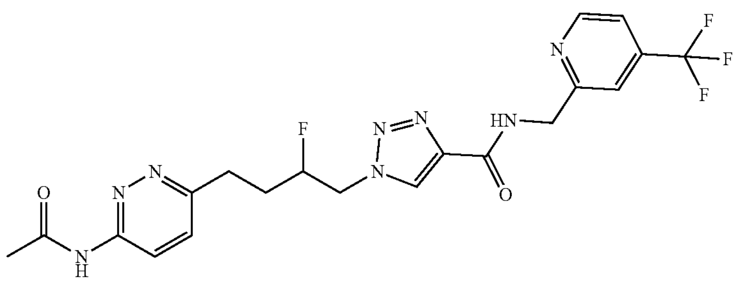 [SMILES: CC(=O)Nc1ccc(CCC(F)Cn2cc(C(=O)NCc3cc(C(F)(F)F)ccn3)nn2)nn1] | 1-(4-(6-acetamidopyridazin-3-yl)-2-fluorobutyl)-N-((4-(trifluoromethyl)pyridin-2-yl)methyl)-1H-1,2,3-triazole-4-carboxamide |
| 237 | 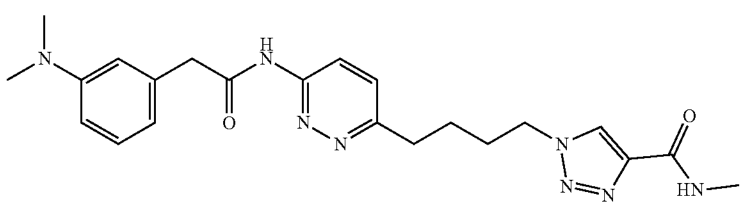 | 1-(4-(6-(2-(3-(dimethylamino)phenyl)acetamido)pyridazin-3-yl)butyl)-N-methyl-1H-1,2,3-triazole-4-carboxamide |
| 238 | 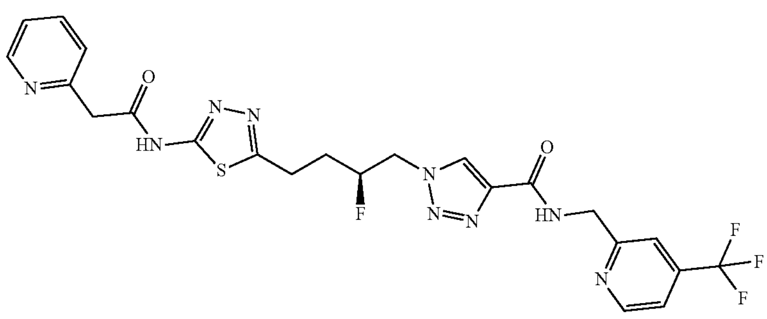 [SMILES: O=C(Cc1ccccn1)Nc1nnc(CC[C@H](F)Cn2cc(C(=O)NCc3cc(C(F)(F)F)ccn3)nn2)s1] | (S)-1-(2-fluoro-4-(5-(2-(pyridin-2-yl)acetamido)-1,3,4-thiadiazol-2-yl)butyl)-N-((4-(trifluoromethyl)pyridin-2-yl)methyl)-1H-1,2,3-triazole-4-carboxamide |
| 239 | 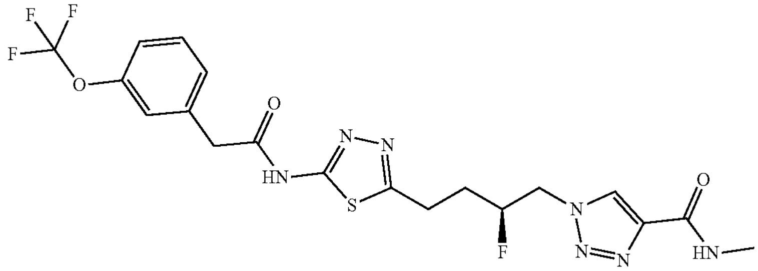 [SMILES: CNC(=O)c1cn(C[C@@H](F)CCc2nnc(NC(=O)Cc3cccc(OC(F)(F)F)c3)s2)nn1] | (S)-1-(2-fluoro-4-(5-(2-(3-(trifluoromethoxy)phenyl)acetamido)-1,3,4-thiadiazol-2-yl)butyl)-N-methyl-1H-1,2,3-triazole-4-carboxamide |

TABLE 1-continued

Synthesized Examples

| Ex. No. | Structure | Name |
|---|---|---|
| 240 | 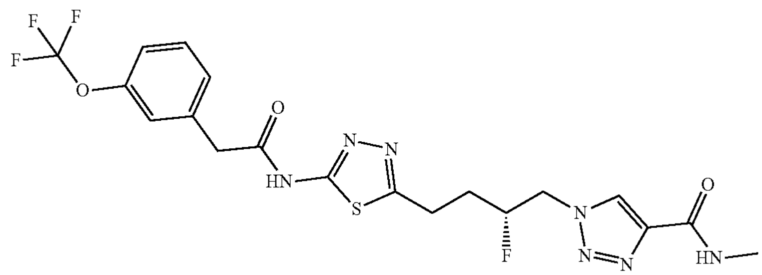 [SMILES: CNC(=O)c1cn(C[C@H](F)CCc2nnc(NC(=O)Cc3cccc(OC(F)(F)F)c3)s2)nn1] | (R)-1-(2-fluoro-4-(5-(2-(3-(trifluoromethoxy)phenyl)acetamido)-1,3,4-thiadiazol-2-yl)butyl)-N-methyl-1H-1,2,3-triazole-4-carboxamide |
| 241 | 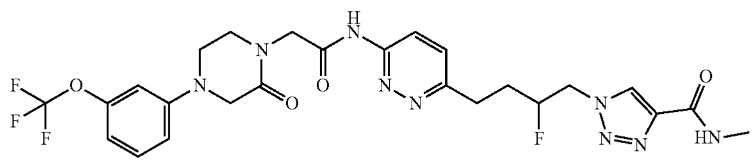 [SMILES: CNC(=O)c1cn(CC(F)CCc2ccc(NC(=O)CN3CCN(c4cccc(OC(F)(F)F)c4)CC3=O)nn2)nn1] | 1-(2-fluoro-4-(6-(2-(2-oxo-4-(3-(trifluoromethoxy)phenyl)piperazin-1-yl)acetamido)pyridazin-3-yl)butyl)-N-methyl-1H-1,2,3-triazole-4-carboxamide |
| 242 | 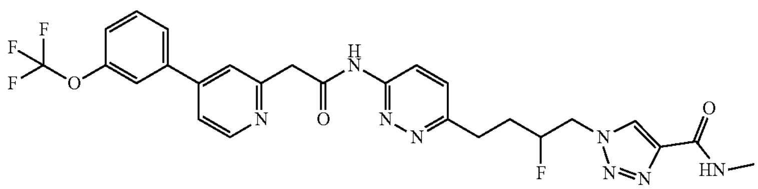 [SMILES: CNC(=O)c1cn(CC(F)CCc2ccc(NC(=O)Cc3cc(-c4cccc(OC(F)(F)F)c4)ccn3)nn2)nn1] | 1-(2-fluoro-4-(6-(2-(4-(3-(trifluoromethoxy)phenyl)pyridin-2-yl)acetamido)pyridazin-3-yl)butyl)-N-methyl-1H-1,2,3-triazole-4-carboxamide |
| 243 | 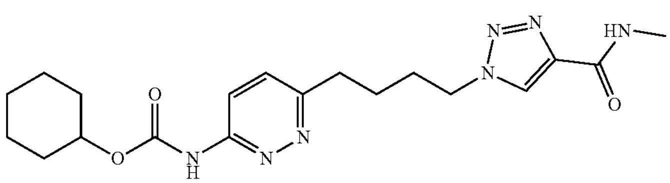 [SMILES: CNC(=O)c1cn(CCCCc2ccc(NC(=O)OC3CCCCC3)nn2)nn1] | cyclohexyl (6-(4-(4-(methylcarbamoyl)-1H-1,2,3-triazol-1-yl)butyl)pyridazin-3-yl)carbamate |
| 244 | 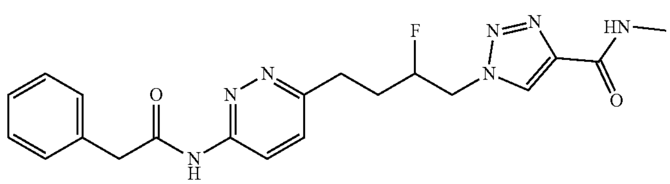 [SMILES: CNC(=O)c1cn(CC(F)CCc2ccc(NC(=O)Cc3ccccc3)nn2)nn1] | 1-(2-fluoro-4-(6-(2-phenylacetamido)pyridazin-3-yl)butyl)-N-methyl-1H-1,2,3-triazole-4-carboxamide |
| 245 | 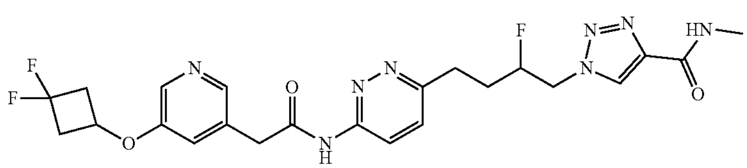 [SMILES: CNC(=O)c1cn(CC(F)CCc2ccc(NC(=O)Cc3cncc(OC4CC(F)(F)C4)c3)nn2)nn1] | 1-(4-(6-(2-(5-(3,3-difluorocyclobutoxy)pyridin-3-yl)acetamido)pyridazin-3-yl)-2-fluorobutyl)-N-methyl-1H-1,2,3-triazole-4-carboxamide |
| 246 | 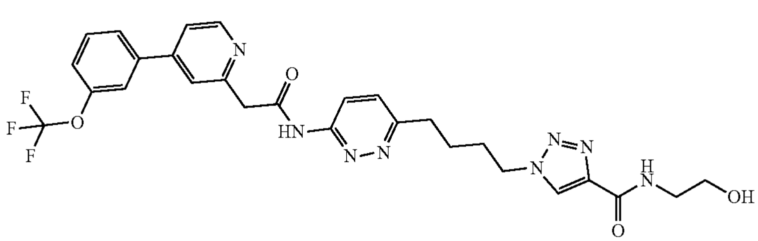 [SMILES: O=C(Cc1cc(-c2cccc(OC(F)(F)F)c2)ccn1)Nc1ccc(CCCCn2cc(C(=O)NCCO)nn2)nn1] | N-(2-hydroxyethyl)-1-(4-(6-(2-(4-(3-(trifluoromethoxy)phenyl)pyridin-2-yl)acetamido)pyridazin-3-yl)butyl)-1H-1,2,3-triazole-4-carboxamide |

TABLE 1-continued

Synthesized Examples

| Ex. No. | Structure | Name |
|---|---|---|
| 247 | 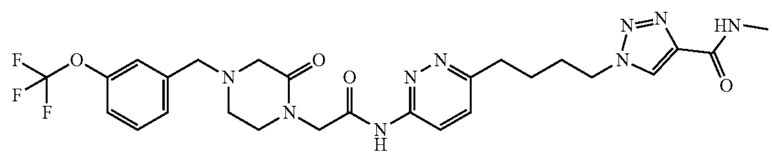 [SMILES: CNC(=O)c1cn(CCCCc2ccc(NC(=O)CN3CCN(Cc4cccc(OC(F)(F)F)c4)CC3=O)nn2)nn1] | N-methyl-1-(4-(6-(2-(2-oxo-4-(3-(trifluoromethoxy)benzyl)piperazin-1-yl)acetamido)pyridazin-3-yl)butyl)-1H-1,2,3-triazole-4-carboxamide |
| 248 | 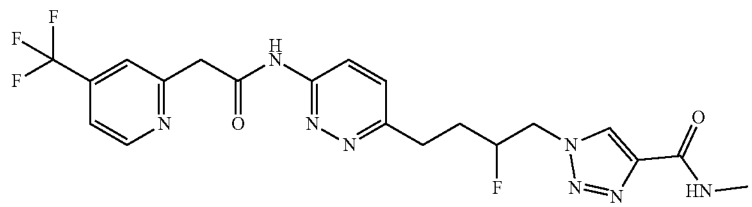 | 1-(2-fluoro-4-(6-(2-(4-(trifluoromethyl)pyridin-2-yl)acetamido)pyridazin-3-yl)butyl)-N-methyl-1H-1,2,3-triazole-4-carboxamide |
| 249 | 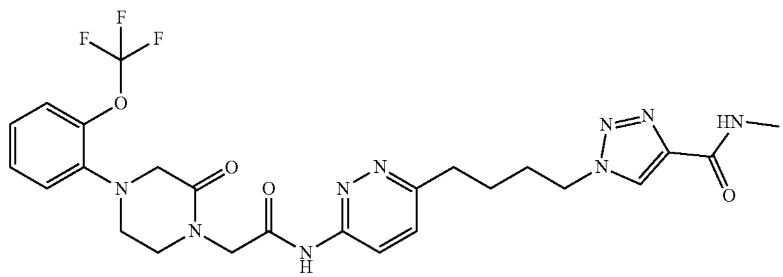 [SMILES: CNC(=O)c1cn(CCCCc2ccc(NC(=O)CN3CCN(c4ccccc4OC(F)(F)F)CC3=O)nn2)nn1] | N-methyl-1-(4-(6-(2-(2-oxo-4-(2-(trifluoromethoxy)phenyl)piperazin-1-yl)acetamido)pyridazin-3-yl)butyl)-1H-1,2,3-triazole-4-carboxamide |
| 250 | 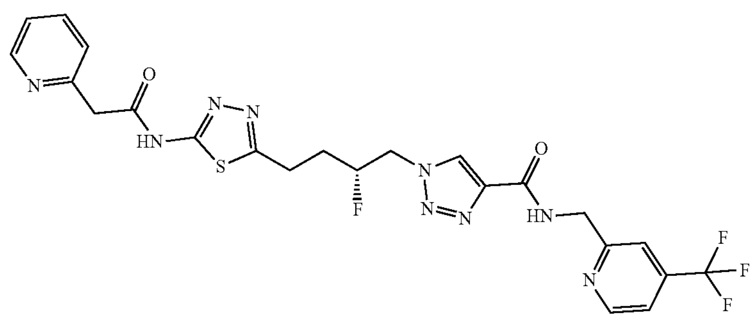 [SMILES: O=C(Cc1ccccn1)Nc1nnc(CC[C@@H](F)Cn2cc(C(=O)NCc3cc(C(F)(F)F)ccn3)nn2)s1] | (R)-1-(2-fluoro-4-(5-(2-(pyridin-2-yl)acetamido)-1,3,4-thiadiazol-2-yl)butyl)-N-((4-(trifluoromethyl)pyridin-2-yl)methyl)-1H-1,2,3-triazole-4-carboxamide |
| 251 | 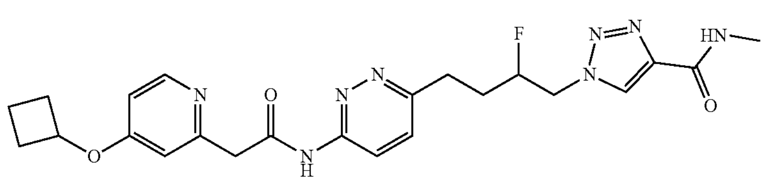 [SMILES: CNC(=O)c1cn(CC(F)CCc2ccc(NC(=O)Cc3cc(OC4CCC4)ccn3)nn2)nn1] | 1-(4-(6-(2-(4-cyclobutoxypyridin-2-yl)acetamido)pyridazin-3-yl)-2-fluorobutyl)-N-methyl-1H-1,2,3-triazole-4-carboxamide |
| 252 | 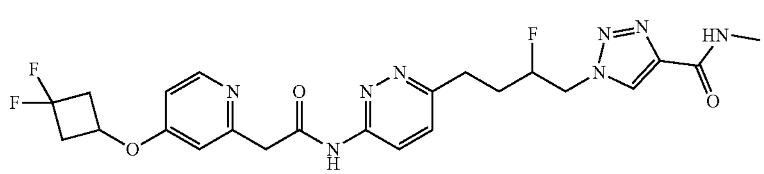 [SMILES: CNC(=O)c1cn(CC(F)CCc2ccc(NC(=O)Cc3cc(OC4CC(F)(F)C4)ccn3)nn2)nn1] | 1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide |
| 253 | 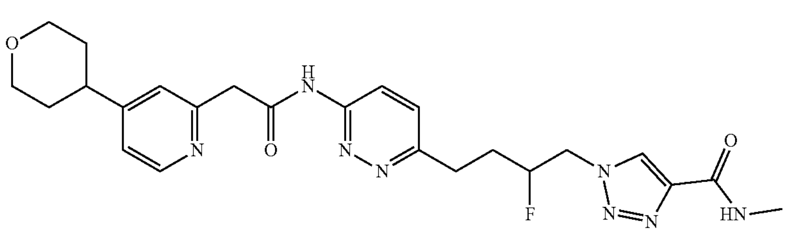 [SMILES: CNC(=O)c1cn(CC(F)CCc2ccc(NC(=O)Cc3cc(C4CCOCC4)ccn3)nn2)nn1] | 1-(2-fluoro-4-(6-(2-(4-(tetrahydro-2H-pyran-4-yl)pyridin-2-yl)acetamido)pyridazin-3-yl)butyl)-N-methyl-1H-1,2,3-triazole-4-carboxamide |

TABLE 1-continued

Synthesized Examples

| Ex. No. | Structure | Name |
|---|---|---|
| 254 | 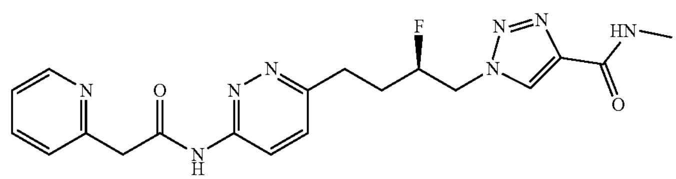 [SMILES: CNC(=O)c1cn(C[C@H](F)CCc2ccc(NC(=O)Cc3ccccn3)nn2)nn1] | (R)-1-(2-fluoro-4-(6-(2-(pyridin-2-yl)acetamido)pyridazin-3-yl)butyl)-N-methyl-1H-1,2,3-triazole-4-carboxamide |
| 255 | 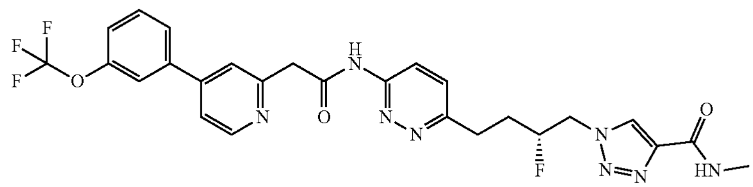 [SMILES: CNC(=O)c1cn(C[C@H](F)CCc2ccc(NC(=O)Cc3cc(-c4cccc(OC(F)(F)F)c4)ccn3)nn2)nn1] | (R)-1-(2-fluoro-4-(6-(2-(4-(3-(trifluoromethoxy)phenyl)pyridin-2-yl)acetamido)pyridazin-3-yl)butyl)-N-methyl-1H-1,2,3-triazole-4-carboxamide |
| 256 | 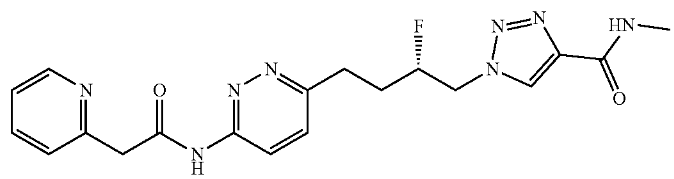 [SMILES: CNC(=O)c1cn(C[C@@H](F)CCc2ccc(NC(=O)Cc3ccccn3)nn2)nn1] | (S)-1-(2-fluoro-4-(6-(2-(pyridin-2-yl)acetamido)pyridazin-3-yl)butyl)-N-methyl-1H-1,2,3-triazole-4-carboxamide |
| 257 | 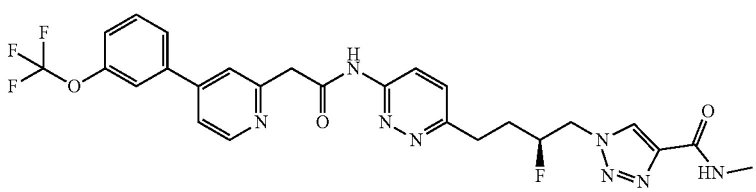 [SMILES: CNC(=O)c1cn(C[C@@H](F)CCc2ccc(NC(=O)Cc3cc(-c4cccc(OC(F)(F)F)c4)ccn3)nn2)nn1] | (S)-1-(2-fluoro-4-(6-(2-(4-(3-(trifluoromethoxy)phenyl)pyridin-2-yl)acetamido)pyridazin-3-yl)butyl)-N-methyl-1H-1,2,3-triazole-4-carboxamide |
| 258 | 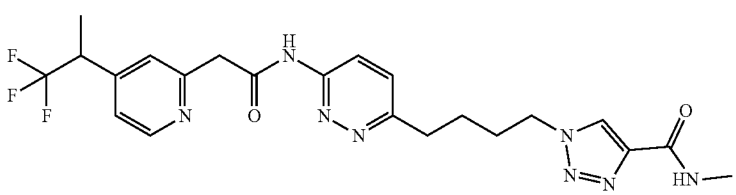 [SMILES: CNC(=O)c1cn(CCCCc2ccc(NC(=O)Cc3cc(C(C)C(F)(F)F)ccn3)nn2)nn1] | N-methyl-1-(4-(6-(2-(4-(1,1,1-trifluoropropan-2-yl)pyridin-2-yl)acetamido)pyridazin-3-yl)butyl)-1H-1,2,3-triazole-4-carboxamide |
| 259 | 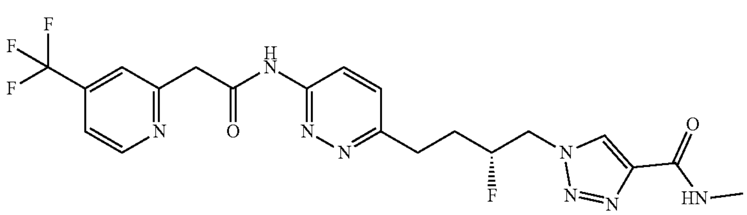 [SMILES: CNC(=O)c1cn(C[C@H](F)CCc2ccc(NC(=O)Cc3cc(C(F)(F)F)ccn3)nn2)nn1] | (R)-1-(2-fluoro-4-(6-(2-(4-(trifluoromethyl)pyridin-2-yl)acetamido)pyridazin-3-yl)butyl)-N-methyl-1H-1,2,3-triazole-4-carboxamide |
| 260 | 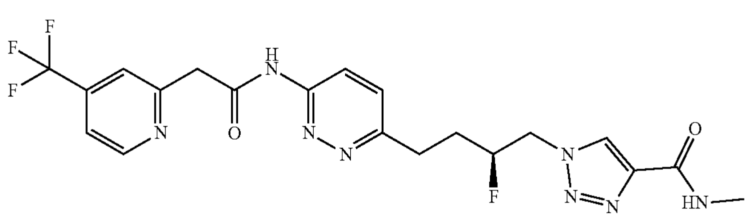 [SMILES: CNC(=O)c1cn(C[C@@H](F)CCc2ccc(NC(=O)Cc3cc(C(F)(F)F)ccn3)nn2)nn1] | (S)-1-(2-fluoro-4-(6-(2-(4-(trifluoromethyl)pyridin-2-yl)acetamido)pyridazin-3-yl)butyl)-N-methyl-1H-1,2,3-triazole-4-carboxamide |

TABLE 1-continued

Synthesized Examples

| Ex. No. | Structure | Name |
|---|---|---|
| 261 | 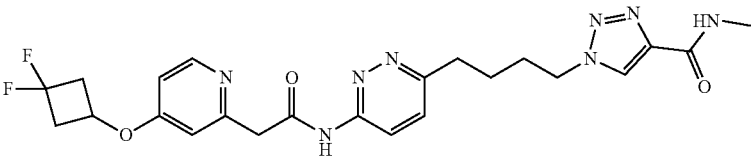 [SMILES: CNC(=O)c1cn(CCCCc2ccc(NC(=O)Cc3cc(OC4CC(F)(F)C4)ccn3)nn2)nn1] | 1-(4-(6-(2-(4-(3,3-difluorocyclobutoxy)pyridin-2-yl)acetamido)pyridazin-3-yl)butyl)-N-methyl-1H-1,2,3-triazole-4-carboxamide |
| 262 | 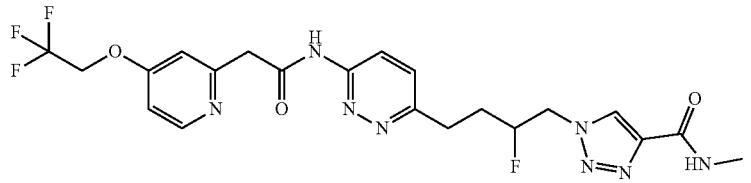 [SMILES: CNC(=O)c1cn(CC(F)CCc2ccc(NC(=O)Cc3cc(OCC(F)(F)F)ccn3)nn2)nn1] | 1-(2-fluoro-4-(6-(2-(4-(2,2,2-trifluoroethoxy)pyridin-2-yl)acetamido)pyridazin-3-yl)butyl)-N-methyl-1H-1,2,3-triazole-4-carboxamide |
| 263 | 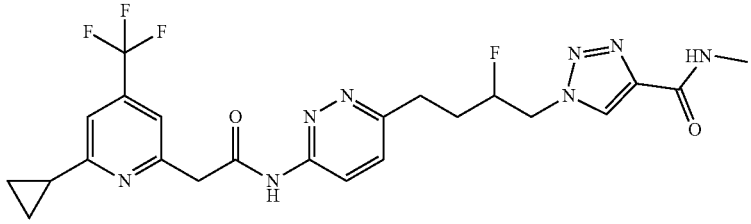 [SMILES: CNC(=O)c1cn(CC(F)CCc2ccc(NC(=O)Cc3cc(C(F)(F)F)cc(C4CC4)n3)nn2)nn1] | 1-(4-(6-(2-(6-cyclopropyl-4-(trifluoromethyl)pyridin-2-yl)acetamido)pyridazin-3-yl)-2-fluorobutyl)-N-methyl-1H-1,2,3-triazole-4-carboxamide |
| 264 | 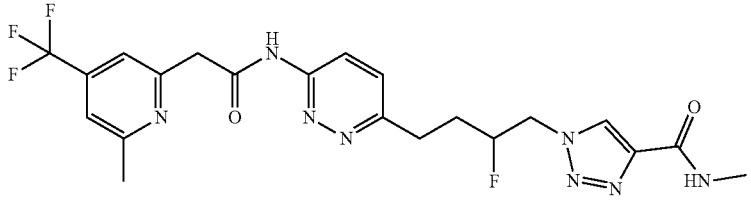 [SMILES: CNC(=O)c1cn(CC(F)CCc2ccc(NC(=O)Cc3cc(C(F)(F)F)cc(C)n3)nn2)nn1] | 1-(2-fluoro-4-(6-(2-(6-methyl-4-(trifluoromethyl)pyridin-2-yl)acetamido)pyridazin-3-yl)butyl)-N-methyl-1H-1,2,3-triazole-4-carboxamide |
| 265 | 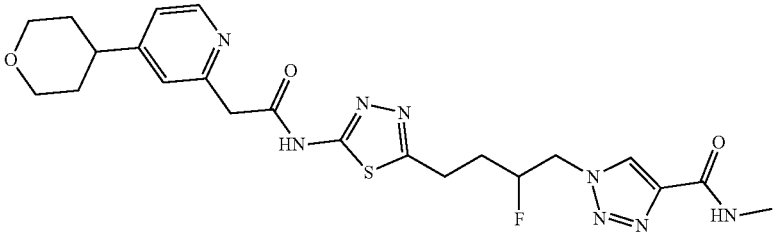 [SMILES: CNC(=O)c1cn(CC(F)CCc2nnc(NC(=O)Cc3cc(C4CCOCC4)ccn3)s2)nn1] | 1-(2-fluoro-4-(5-(2-(4-(tetrahydro-2H-pyran-4-yl)pyridin-2-yl)acetamido)-1,3,4-thiadiazol-2-yl)butyl)-N-methyl-1H-1,2,3-triazole-4-carboxamide |
| 266 | 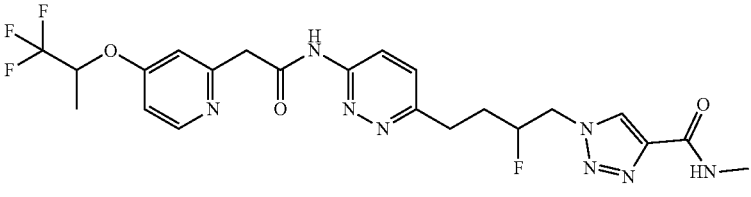 [SMILES: CNC(=O)c1cn(CC(F)CCc2ccc(NC(=O)Cc3cc(OC(C)C(F)(F)F)ccn3)nn2)nn1] | 1-(2-fluoro-4-(6-(2-(4-((1,1,1-trifluoropropan-2-yl)oxy)pyridin-2-yl)acetamido)pyridazin-3-yl)butyl)-N-methyl-1H-1,2,3-triazole-4-carboxamide |
| 267 | 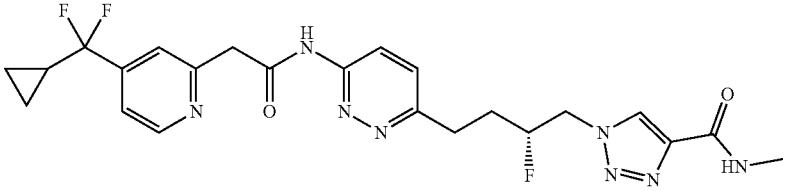 [SMILES: CNC(=O)c1cn(C[C@H](F)CCc2ccc(NC(=O)Cc3cc(C(F)(F)C4CC4)ccn3)nn2)nn1] | (R)-1-(4-(6-(2-(4-(cyclopropyldifluoromethyl)pyridin-2-yl)acetamido)pyridazin-3-yl)-2-fluorobutyl)-N-methyl-1H-1,2,3-triazole-4-carboxamide |

TABLE 1-continued

Synthesized Examples

| Ex. No. | Structure | Name |
|---|---|---|
| 268 | 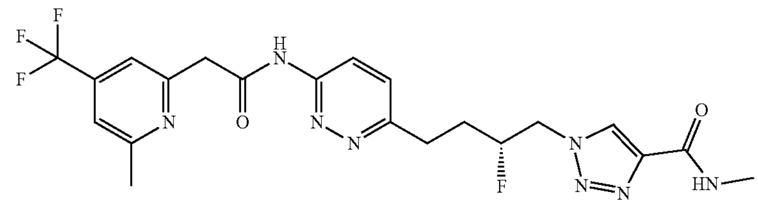 [SMILES: CNC(=O)c1cn(C[C@H](F)CCc2ccc(NC(=O)Cc3cc(C(F)(F)F)cc(C)n3)nn2)nn1] | (R)-1-(2-fluoro-4-(6-(2-(6-methyl-4-(trifluoromethyl)pyridin-2-yl)acetamido)pyridazin-3-yl)butyl)-N-methyl-1H-1,2,3-triazole-4-carboxamide |
| 269 | 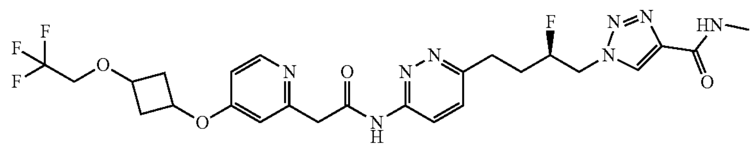 [SMILES: CNC(=O)c1cn(C[C@H](F)CCc2ccc(NC(=O)Cc3cc(OC4CC(OCC(F)(F)F)C4)ccn3)nn2)nn1] | (R)-1-(2-fluoro-4-(6-(2-(4-(3-(2,2,2-trifluoroethoxy)cyclobutoxy)pyridin-2-yl)acetamido)pyridazin-3-yl)butyl)-N-methyl-1H-1,2,3-triazole-4-carboxamide |
| 270 | 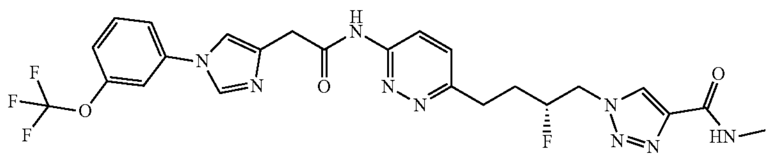 [SMILES: CNC(=O)c1cn(C[C@H](F)CCc2ccc(NC(=O)Cc3cn(-c4cccc(OC(F)(F)F)c4)cn3)nn2)nn1] | (R)-1-(2-fluoro-4-(6-(2-(1-(3-(tifluoromethoxy)phenyl)-1H-imidazol-4-yl)acetamido)pyridazin-3-yl)butyl)-N-methyl-1H-1,2,3-triazole-4-carboxamide |
| 271 | 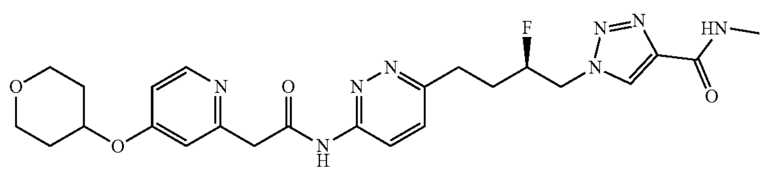 [SMILES: CNC(=O)c1cn(C[C@H](F)CCc2ccc(NC(=O)Cc3cc(OC4CCOCC4)ccn3)nn2)nn1] | (R)-1-(2-fluoro-4-(6-(2-(4-((tetrahydro-2H-pyran-4-yl)oxy)pyridin-2-yl)acetamido)pyridazin-3-yl)butyl)-N-methyl-1H-1,2,3-triazole-4-carboxamide |
| 272 | 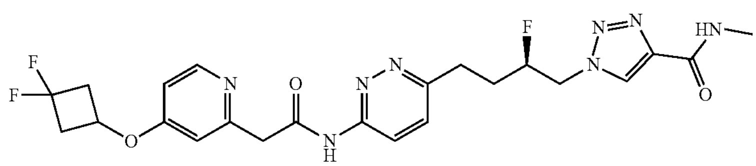 [SMILES: CNC(=O)c1cn(C[C@H](F)CCc2ccc(NC(=O)Cc3cc(OC4CC(F)(F)C4)ccn3)nn2)nn1] | (R)-1-(4-(6-(2-(4-(3,3-difluorocyclobutoxy)pyridin-2-yl)acetamido)pyridazin-3-yl)-2-fluorobutyl)-N-methyl-1H-1,2,3-triazole-4-carboxamide |
| 273 | 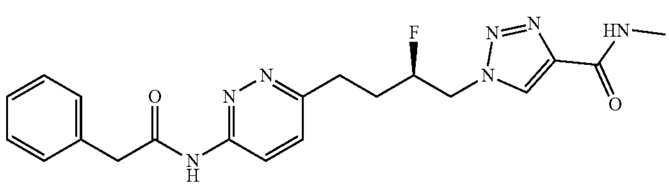 [SMILES: CNC(=O)c1cn(C[C@H](F)CCc2ccc(NC(=O)Cc3ccccc3)nn2)nn1] | (R)-1-(2-fluoro-4-(6-(2-phenylacetamido)pyridazin-3-yl)butyl)-N-methyl-1H-1,2,3-triazole-4-carboxamide |
| 274 | 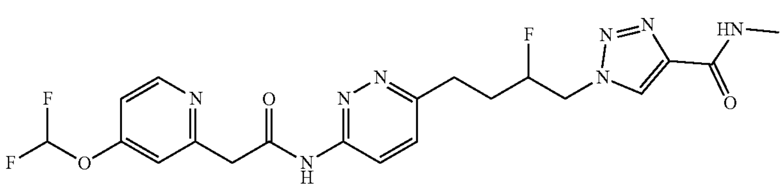 [SMILES: CNC(=O)c1cn(CC(F)CCc2ccc(NC(=O)Cc3cc(OC(F)F)ccn3)nn2)nn1] | 1-(4-(6-(2-(4-(difluoromethoxy)pyridin-2-yl)acetamido)pyridazin-3-yl)-2-fluorobutyl)-N-methyl-1,2,3-triazole-4-carboxamide |
| 275 | 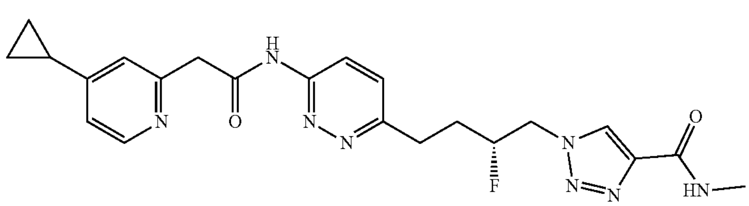 [SMILES: CNC(=O)c1cn(C[C@H](F)CCc2ccc(NC(=O)Cc3cc(C4CC4)ccn3)nn2)nn1] | (R)-1-(4-(6-(2-(4-cyclopropylpyridin-2-yl)acetamido)pyridazin-3-yl)-2-fluorobutyl)-N-methyl-1H-1,2,3-triazole-4-carboxamide |

TABLE 1-continued

Synthesized Examples

| Ex. No. | Structure | Name |
|---|---|---|
| 276 | 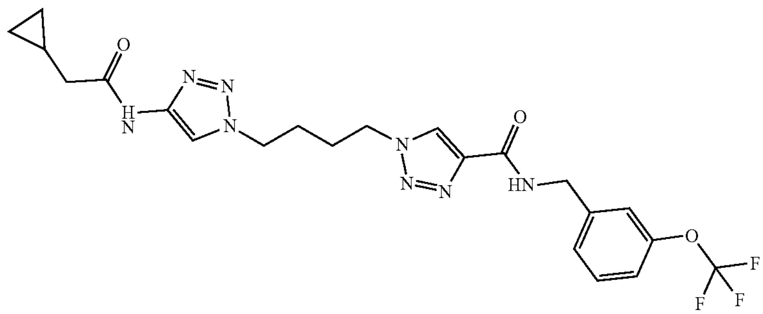 [SMILES: O=C(CC1CC1)Nc1cn(CCCCn2cc(C(=O)NCc3cccc(OC(F)(F)F)c3)nn2)nn1] | 1-{4-[4-(2-cyclopropylacetamido)-1H-1,2,3-triazol-1-yl]butyl}-N-{[3-(trifluoromethoxy)phenyl]methyl}-1H-1,2,3-triazole-4-carboxamide |
| 277 | 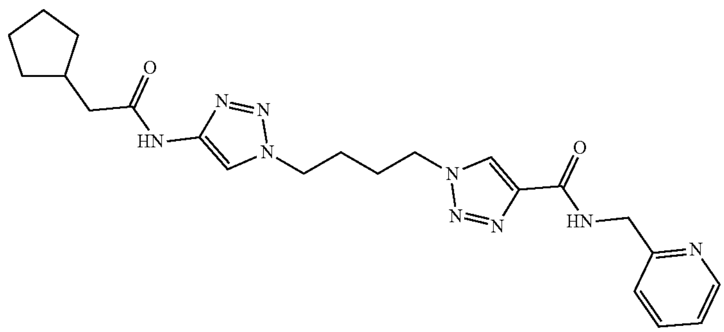 [SMILES: O=C(CC1CCCC1)Nc1cn(CCCCn2cc(C(=O)NCc3ccccn3)nn2)nn1] | 1-{4-[4-(cyclopentylacetamido)-1H-1,2,3-triazol-1-yl]butyl}-N-(pyridin-2-ylmethyl)-1H-1,2,3-triazole-4-carboxamide |
| 278 | 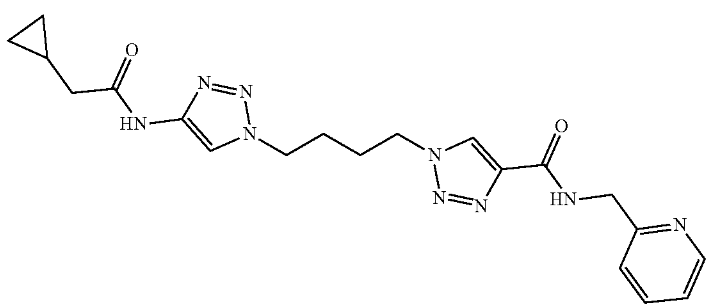 [SMILES: O=C(CC1CC1)Nc1cn(CCCCn2cc(C(=O)NCc3ccccn3)nn2)nn1] | 1-{4-[4-(2-cyclopropylacetamido)-1H-1,2,3-triazol-1-yl]butyl}-N-(pyridin-2-ylmethyl)-1H-1,2,3-triazole-4-carboxamide |
| 279 | 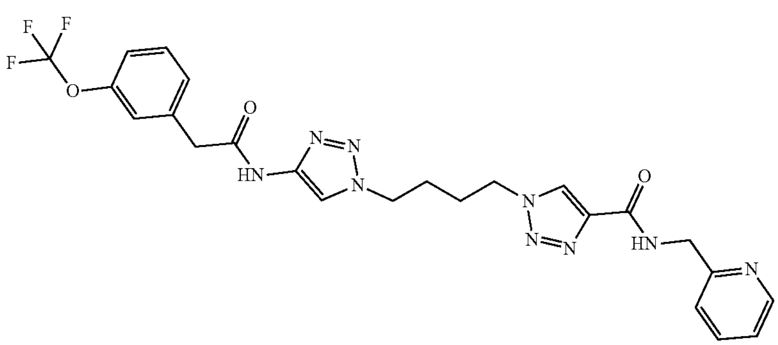 [SMILES: O=C(Cc1cccc(OC(F)(F)F)c1)Nc1cn(CCCCn2cc(C(=O)NCc3ccccn3)nn2)nn1] | N-(pyridin-2-ylmethyl)-1-[4-(4-{2-[3-(trifluoromethoxy)phenyl]acetamido}-1H-1,2,3-triazol-1-yl)butyl]-1H-1,2,3-triazole-4-carboxamide |

TABLE 1-continued

Synthesized Examples

| Ex. No. | Structure | Name |
|---|---|---|
| 280 | 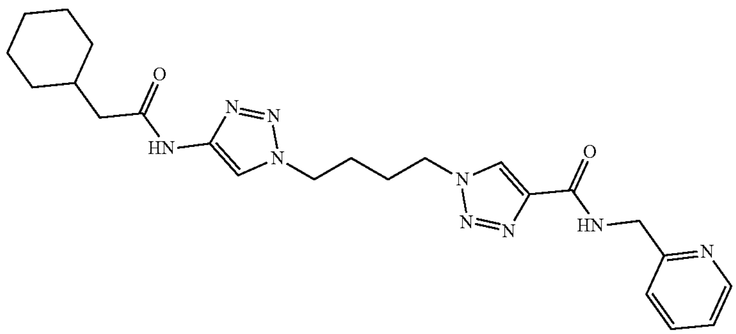 [SMILES: O=C(CC1CCCCC1)Nc1cn(CCCCn2cc(C(=O)NCc3ccccn3)nn2)nn1] | 1-{4-[4-(2-cyclohexylacetamido)-1H-1,2,3-triazol-1-yl]butyl}-N-(pyridin-2-ylmethyl)-1H-1,2,3-triazole-4-carboxamide |
| 281 | 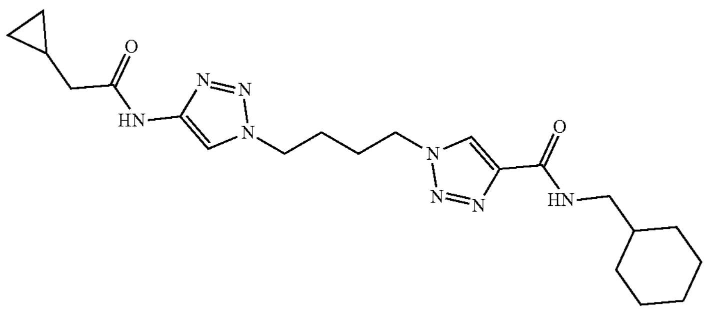 [SMILES: O=C(CC1CC1)Nc1cn(CCCCn2cc(C(=O)NCC3CCCCC3)nn2)nn1] | N-(cyclohexylmethyl)-1-{4-[4-(2-cyclopropylacetamido)-1H-1,2,3-triazol-1-yl]butyl}-1H-1,2,3-triazole-4-carboxamide |
| 282 | 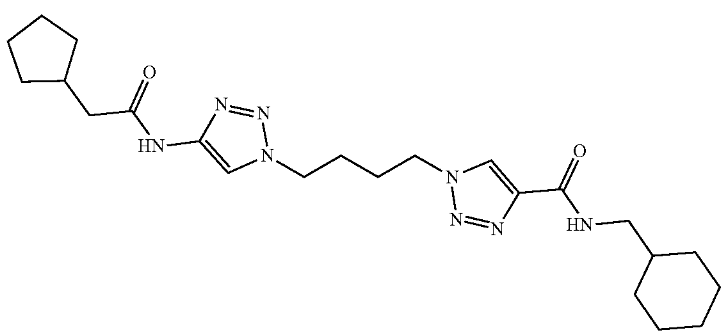 [SMILES: O=C(CC1CCCC1)Nc1cn(CCCCn2cc(C(=O)NCC3CCCCC3)nn2)nn1] | N-(cyclohexylmethyl)-1-{4-[4-(2-cyclopentylacetamido)-1H-1,2,3-triazol-1-yl]butyl}-1H-1,2,3-triazole-4-carboxamide |
| 283 | 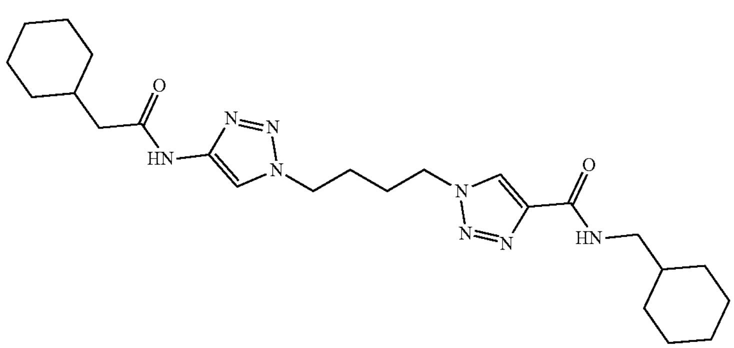 [SMILES: O=C(CC1CCCCC1)Nc1cn(CCCCn2cc(C(=O)NCC3CCCCC3)nn2)nn1] | 1-{4-[4-(2-cyclohexylacetamido)-1H-1,2,3-triazol-1-yl]butyl}-N-(cyclohexylmethyl)-1H-1,2,3-triazole-4-carboxamide |

TABLE 1-continued

Synthesized Examples

| Ex. No. | Structure | Name |
|---|---|---|
| 284 | 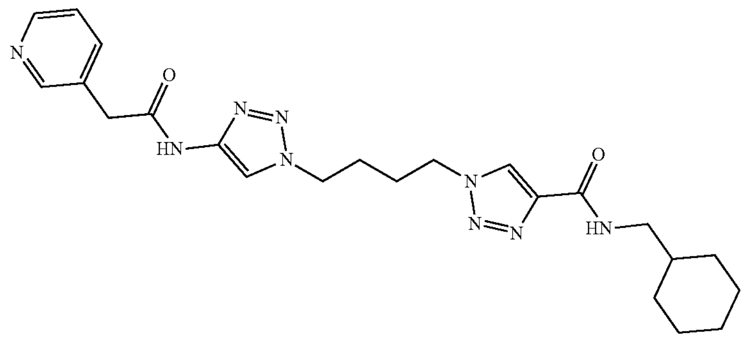 [SMILES: O=C(Cc1cccnc1)Nc1cn(CCCCn2cc(C(=O)NCC3CCCCC3)nn2)nn1] | N-(cyclohexylmethyl)-1-(4-{4-[2-(pyridin-3-yl)acetamido]-1H-1,2,3-triazol-1-yl}butyl)-1H-1,2,3-triazole-4-carboxamide |
| 285 | 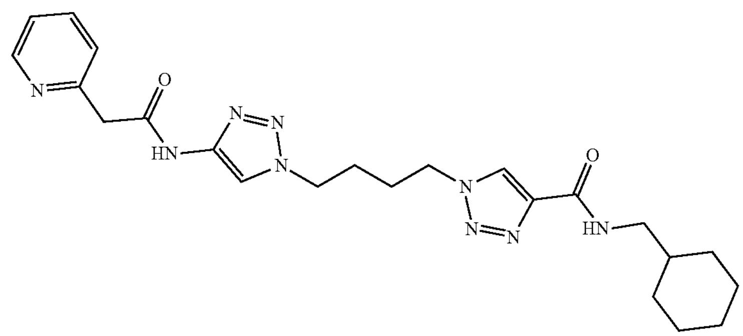 [SMILES: O=C(Cc1ccccn1)Nc1cn(CCCCn2cc(C(=O)NCC3CCCCC3)nn2)nn1] | N-(cyclohexylmethyl)-1-(4-{4-[2-(pyridin-2-yl)acetamido]-1H-1,2,3-triazol-1-yl}butyl)-1H-1,2,3-triazole-4-carboxamide |
| 286 | 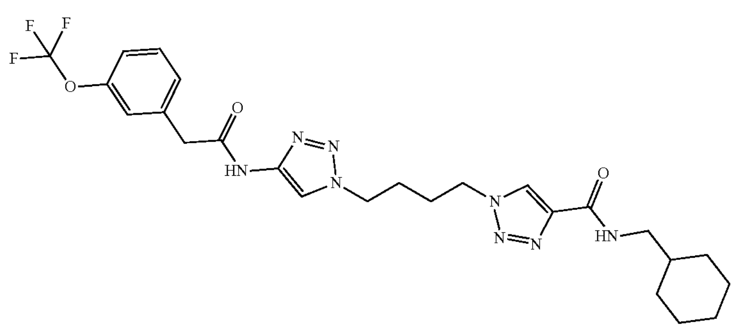 [SMILES: O=C(Cc1cccc(OC(F)(F)F)c1)Nc1cn(CCCCn2cc(C(=O)NCC3CCCCC3)nn2)nn1] | N-(cyclohexylmethyl)-1-[4-(4-{2-[3-(trifluoromethoxy)phenyl]acetamido}-1H-1,2,3-triazol-1-yl)butyl]-1H-1,2,3-triazole-4-carboxamide |
| 287 | 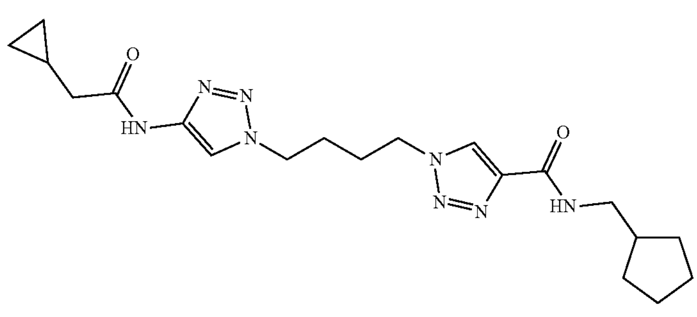 [SMILES: O=C(CC1CC1)Nc1cn(CCCCn2cc(C(=O)NCC3CCCC3)nn2)nn1] | N-(cyclopentylmethyl)-1-{4-[4-(2-cyclopropylacetamido)-1H-1,2,3-triazol-1-yl]butyl}-1H-1,2,3-triazole-4-carboxamide |

TABLE 1-continued

Synthesized Examples

| Ex. No. | Structure | Name |
|---|---|---|
| 288 | 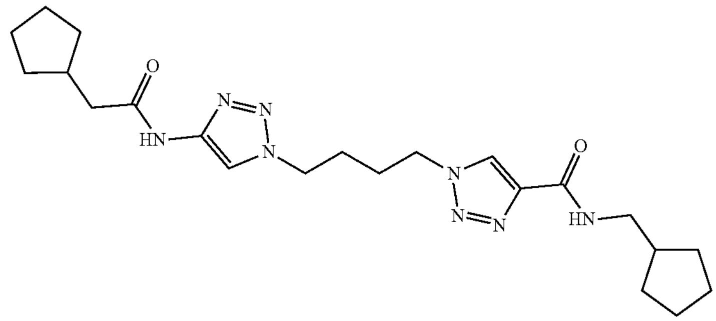 [SMILES: O=C(CC1CCCC1)Nc1cn(CCCCn2cc(C(=O)NCC3CCCC3)nn2)nn1] | 1-{4-[4-(2-cyclopentylacetamido)-1H-1,2,3-triazol-1-yl]butyl}-N-(cyclopentylmethyl)-1H-1,2,3-triazole-4-carboxamide |
| 289 | 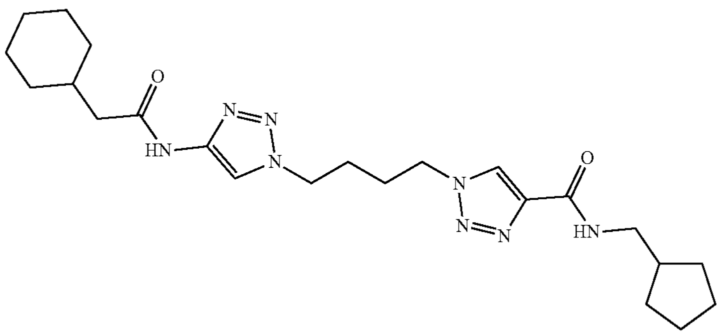 [SMILES: O=C(CC1CCCCC1)Nc1cn(CCCCn2cc(C(=O)NCC3CCCC3)nn2)nn1] | 1-{4-[4-(2-cyclohexylacetamido)-1H-1,2,3-triazol-1-yl]butyl}-N-(cyclopentylmethyl)-1H-1,2,3-triazole-4-carboxamide |
| 290 | 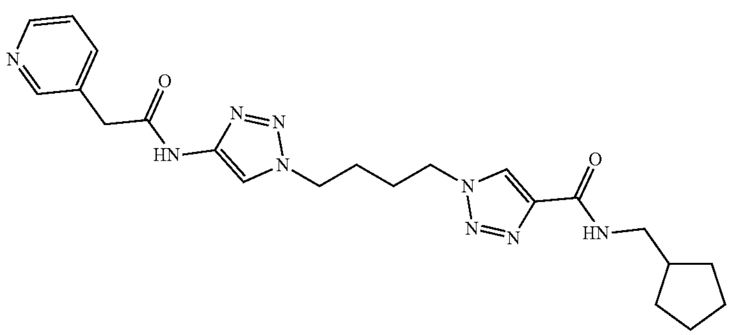 [SMILES: O=C(Cc1cccnc1)Nc1cn(CCCCn2cc(C(=O)NCC3CCCC3)nn2)nn1] | N-(cyclopentylmethyl)-1-(4-{4-[2-(pyridin-3-yl)acetamido]-1H-1,2,3-triazol-1-yl}butyl)-1H-1,2,3-triazole-4-carboxamide |
| 291 | 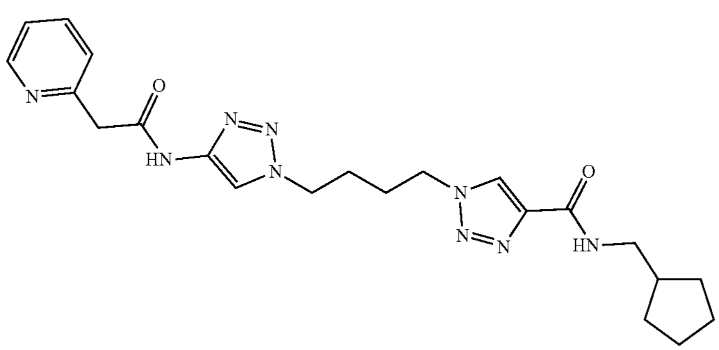 [SMILES: O=C(Cc1ccccn1)Nc1cn(CCCCn2cc(C(=O)NCC3CCCC3)nn2)nn1] | N-(cyclopentylmethyl)-1-(4-{4-[2-(pyridin-2-yl)acetamido]-1H-1,2,3-triazol-1-yl}butyl)-1H-1,2,3-triazole-4-carboxamide |

TABLE 1-continued

Synthesized Examples

| Ex. No. | Structure | Name |
|---|---|---|
| 292 | 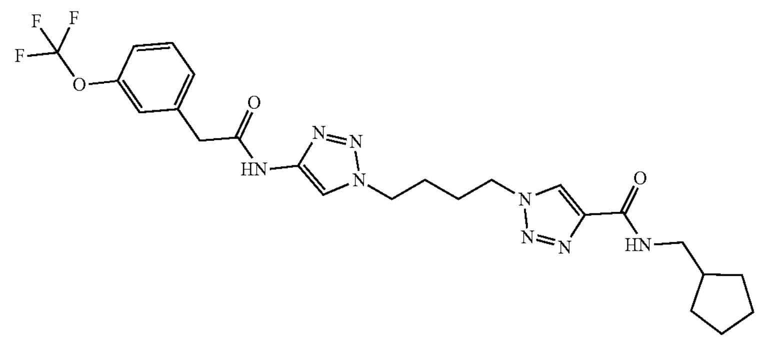 [SMILES: O=C(Cc1cccc(OC(F)(F)F)c1)Nc1cn(CCCCn2cc(C(=O)NCC3CCCC3)nn2)nn1] | N-(cyclopentylmethyl)-1-[4-(4-{2-[3-(trifluoromethoxy)phenyl]acetamido}-1H-1,2,3-triazol-1-yl)butyl]-1H-1,2,3-triazole-4-carboxamide |
| 293 | 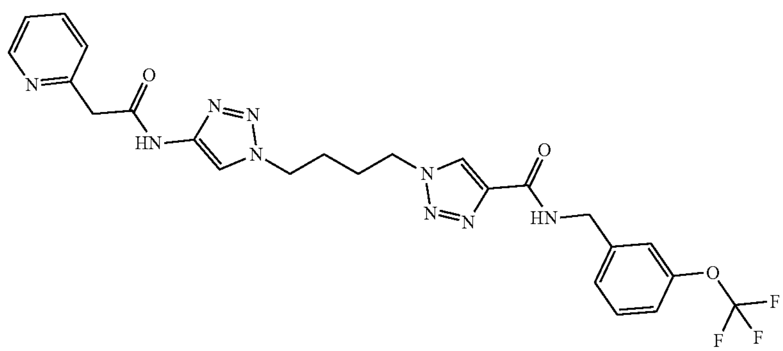 [SMILES: O=C(Cc1ccccn1)Nc1cn(CCCCn2cc(C(=O)NCc3cccc(OC(F)(F)F)c3)nn2)nn1] | 1-(4-{4-[2-(pyridin-2-yl)acetamido]-1H-1,2,3-triazol-1-yl}butyl)-N-{[3-(trifluoromethoxy)phenyl]methyl}-1H-1,2,3-triazole-4-carboxamide |
| 294 | 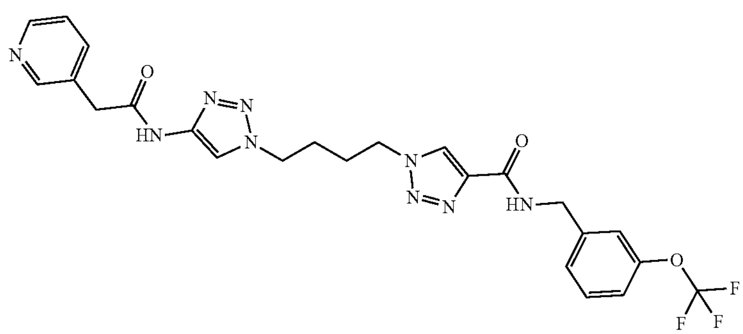 [SMILES: O=C(Cc1cccnc1)Nc1cn(CCCCn2cc(C(=O)NCc3cccc(OC(F)(F)F)c3)nn2)nn1] | 1-(4-{4-[2-(pyridin-3-yl)acetamido]-1H-1,2,3-triazol-1-yl}butyl)-N-{[3-(trifluoromethoxy)phenyl]methyl}-1H-1,2,3-triazole-4-carboxamide |
| 295 | 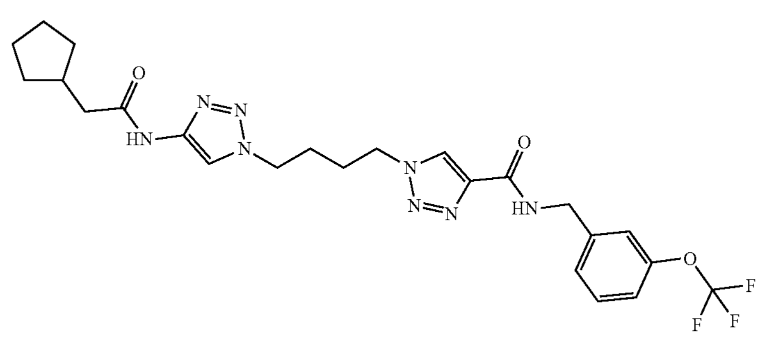 [SMILES: O=C(CC1CCCC1)Nc1cn(CCCCn2cc(C(=O)NCc3cccc(OC(F)(F)F)c3)nn2)nn1] | 1-{4-[4-(2-cyclopentylacetamido)-1H-1,2,3-triazol-1-yl]butyl}-N-{[3-(trifluoromethoxy)phenyl]methyl}-1H-1,2,3-triazole-4-carboxamide |

TABLE 1-continued

Synthesized Examples

| Ex. No. | Structure | Name |
|---|---|---|
| 296 | 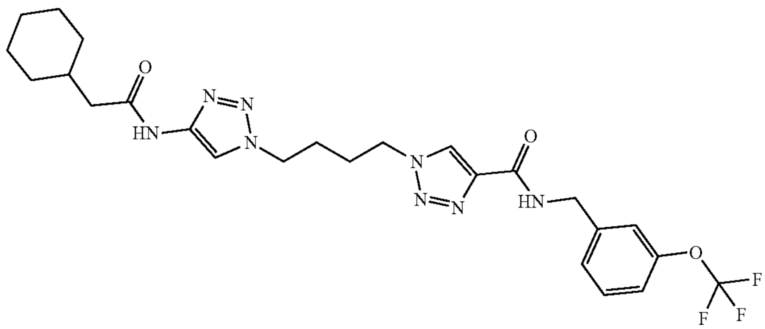 [SMILES: O=C(CC1CCCCC1)Nc1cn(CCCCn2cc(C(=O)NCc3cccc(OC(F)(F)F)c3)nn2)nn1] | 1-{4-[4-(2-cyclohexylacetamido)-1H-1,2,3-triazol-1-yl]butyl}-N-{[3-(trifluoromethoxy)phenyl]methyl}-1H-1,2,3-triazole-4-carboxamide |
| 297 | 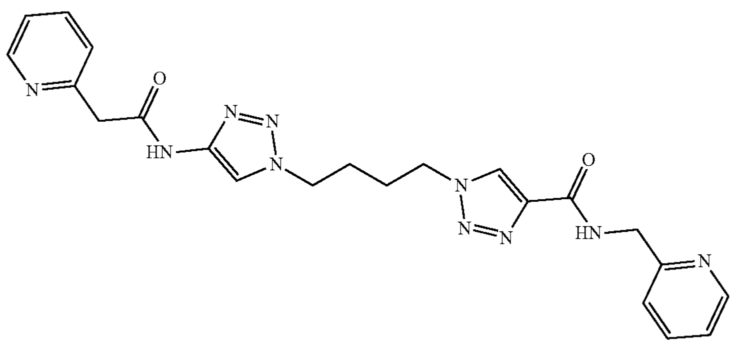 [SMILES: O=C(Cc1ccccn1)Nc1cn(CCCCn2cc(C(=O)NCc3ccccn3)nn2)nn1] | 1-(4-{4-[2-(pyridin-2-yl)acetamido]-1H-1,2,3-triazol-1-yl}butyl)-N-(pyridin-2-ylmethyl)-1H-1,2,3-triazole-4-carboxamide |
| 298 | 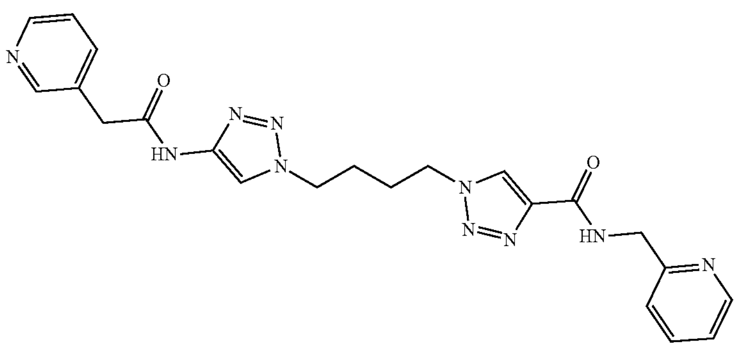 [SMILES: O=C(Cc1cccnc1)Nc1cn(CCCCn2cc(C(=O)NCc3ccccn3)nn2)nn1] | N-(pyridin-2-ylmethyl)-1-(4-{4-[2-(pyridin-3-yl)acetamido]-1H-1,2,3-triazol-1-yl}butyl)-1H-1,2,3-triazole-4-carboxamide |
| 299 | 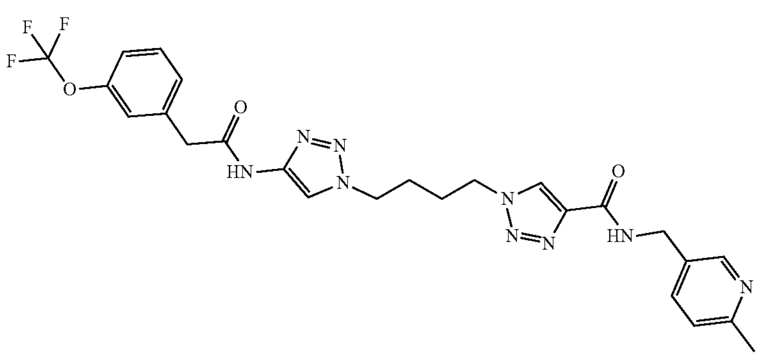 [SMILES: Cc1ccc(CNC(=O)c2cn(CCCCn3cc(NC(=O)Cc4cccc(OC(F)(F)F)c4)nn3)nn2)cn1] | N-[(6-methylpyridin-3-yl)methyl]-1-[4-(4-{2-[3-(trifluoromethoxy)phenyl]acetamido}-1H-1,2,3-triazol-1-yl)butyl]-1H-1,2,3-triazole-4-carboxamide |

TABLE 1-continued

Synthesized Examples

| Ex. No. | Structure | Name |
|---|---|---|
| 300 | 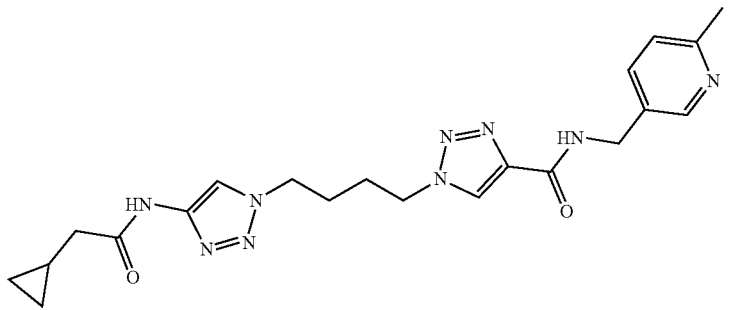 [SMILES: Cc1ccc(CNC(=O)c2cn(CCCCn3cc(NC(=O)CC4CC4)nn3)nn2)cn1] | 1-{4-[4-(2-cyclopropylacetamido)-1H-1,2,3-triazol-1-yl]butyl}-N-[(6-methylpyridin-3-yl)methyl]-1H-1,2,3-triazole-4-carboxamide |
| 301 | 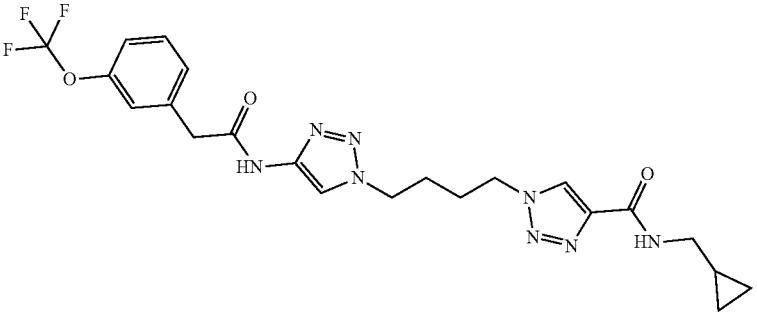 [SMILES: O=C(Cc1cccc(OC(F)(F)F)c1)Nc1cn(CCCCn2cc(C(=O)NCC3CC3)nn2)nn1] | N-(cyclopropylmethyl)-1-[4-(4-{2-[3-(trifluoromethoxy)phenyl]acetamido}-1H-1,2,3-triazol-1-yl)butyl]-1H-1,2,3-triazole-4-carboxamide |
| 302 | 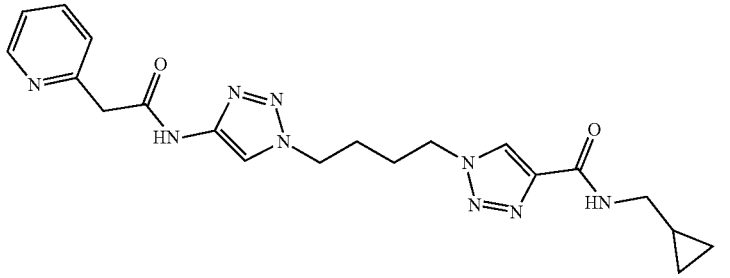 [SMILES: O=C(Cc1ccccn1)Nc1cn(CCCCn2cc(C(=O)NCC3CC3)nn2)nn1] | N-(cyclopropylmethyl)-1-(4-{4-[2-(pyridin-2-yl)acetamido]-1H-1,2,3-triazol-1-yl}butyl)-1H-1,2,3-triazole-4-carboxamide |
| 303 | 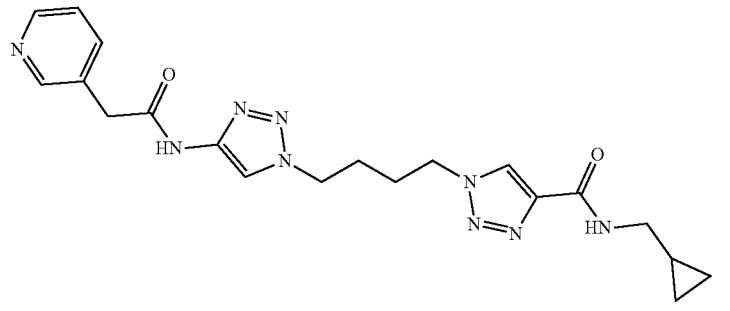 [SMILES: O=C(Cc1cccnc1)Nc1cn(CCCCn2cc(C(=O)NCC3CC3)nn2)nn1] | N-(cyclopropylmethyl)-1-(4-{4-[2-(pyridin-3-yl)acetamido]-1H-1,2,3-triazol-1-yl}butyl)-1H-1,2,3-triazole-4-carboxamide |
| 304 | 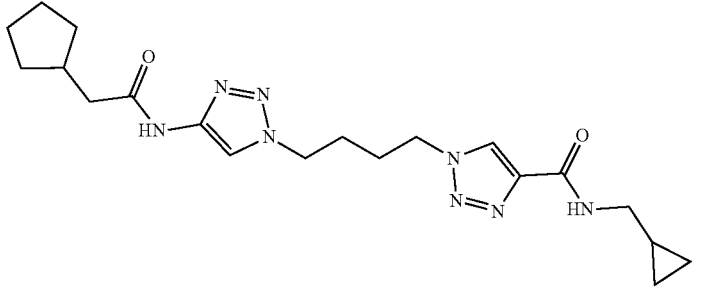 [SMILES: O=C(CC1CCCC1)Nc1cn(CCCCn2cc(C(=O)NCC3CC3)nn2)nn1] | 1-{4-[4-(2-cyclopentylacetamido)-1H-1,2,3-triazol-1-yl]butyl}-N-(cyclopropylmethyl)-1H-1,2,3-triazole-4-carboxamide |

TABLE 1-continued

Synthesized Examples

| Ex. No. | Structure | Name |
|---|---|---|
| 305 | 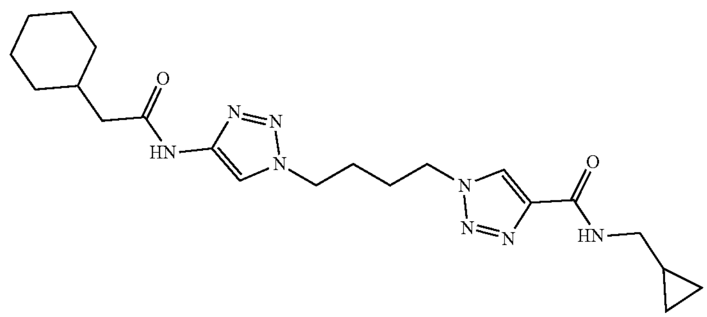 [SMILES: O=C(CC1CCCCC1)Nc1cn(CCCCn2cc(C(=O)NCC3CC3)nn2)nn1] | 1-{4-[4-(2-cyclohexylacetamido)-1H-1,2,3-triazol-1-yl]butyl}-N-(cyclopropylmethyl)-1H-1,2,3-triazole-4-carboxamide |
| 306 | 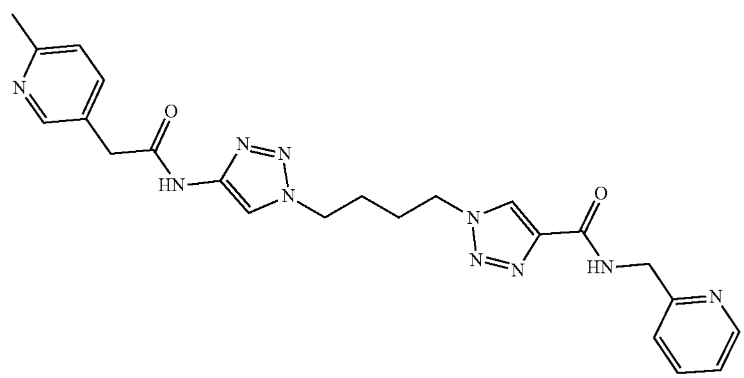 [SMILES: Cc1ccc(CC(=O)Nc2cn(CCCCn3cc(C(=O)NCc4ccccn4)nn3)nn2)cn1] | 1-(4-{4-[2-(6-methylpyridin-3-yl)acetamido]-1H-1,2,3-triazol-1-yl}butyl)-N-(pyridin-2-ylmethyl)-1H-1,2,3-triazole-4-carboxamide |
| 307 | 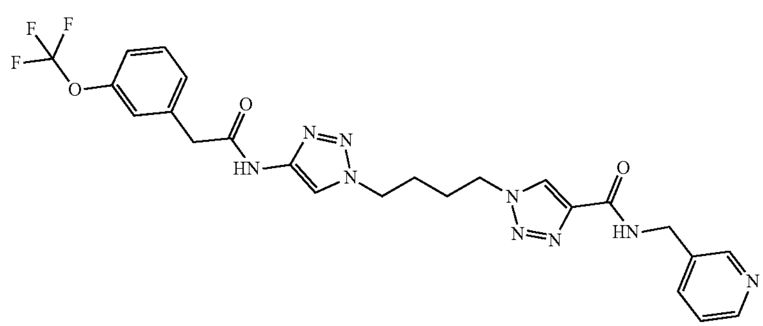 [SMILES: O=C(Cc1cccc(OC(F)(F)F)c1)Nc1cn(CCCCn2cc(C(=O)NCc3cccnc3)nn2)nn1] | N-(pyridin-3-ylmethyl)-1-[4-(4-{2-[3-(trifluoromethoxy)phenyl]acetamido}-1H-1,2,3-triazol-1-yl)butyl]-1H-1,2,3-triazole-4-carboxamide |
| 308 | 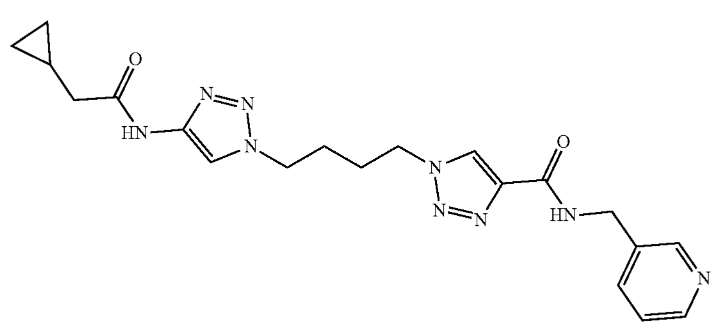 [SMILES: O=C(CC1CC1)Nc1cn(CCCCn2cc(C(=O)NCc3cccnc3)nn2)nn1] | 1-{4-[4-(2-cyclopropylacetamido)-1H-1,2,3-triazol-1-yl]butyl}-N-(pyridin-3-ylmethyl)-1H-1,2,3-triazole-4-carboxamide |

TABLE 1-continued

Synthesized Examples

| Ex. No. | Structure | Name |
|---|---|---|
| 309 | 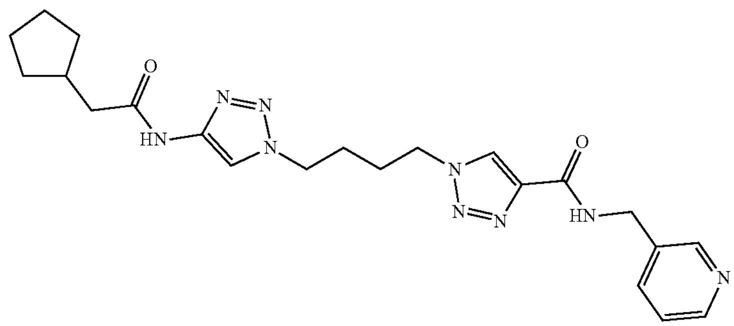 [SMILES: O=C(CC1CCCC1)Nc1cn(CCCCn2cc(C(=O)NCc3cccnc3)nn2)nn1] | 1-{4-[4-(2-cyclopentylacetamido)-1H-1,2,3-triazol-1-yl]butyl}-N-(pyridin-3-ylmethyl)-1H-1,2,3-triazole-4-carboxamide |
| 310 | 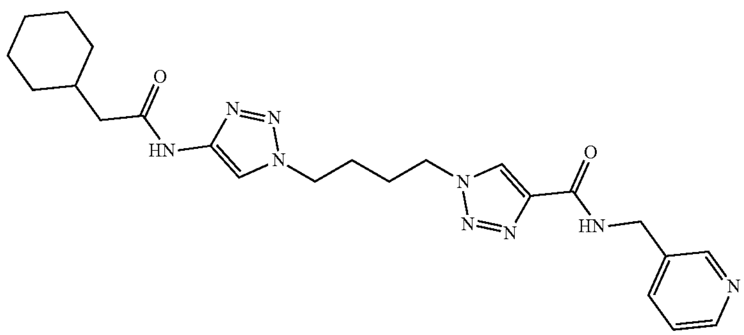 [SMILES: O=C(CC1CCCCC1)Nc1cn(CCCCn2cc(C(=O)NCc3cccnc3)nn2)nn1] | 1-{4-[4-(2-cyclohexylacetamido)-1H-1,2,3-triazol-1-yl]butyl}-N-(pyridin-3-ylmethyl)-1H-1,2,3-triazole-4-carboxamide |
| 311 | 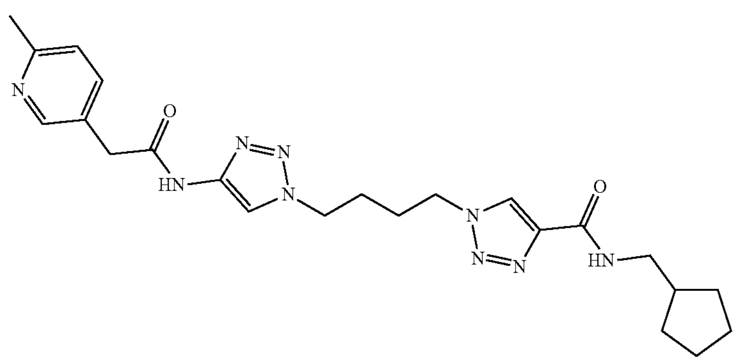 [SMILES: Cc1ccc(CC(=O)Nc2cn(CCCCn3cc(C(=O)NCC4CCCC4)nn3)nn2)cn1] | N-(cyclopentylmethyl)-1-(4-{4-[2-(6-methylpyridin-3-yl)acetamido]-1H-1,2,3-triazol-1-yl}butyl)-1H-1,2,3-triazole-4-carboxamide |
| 312 | 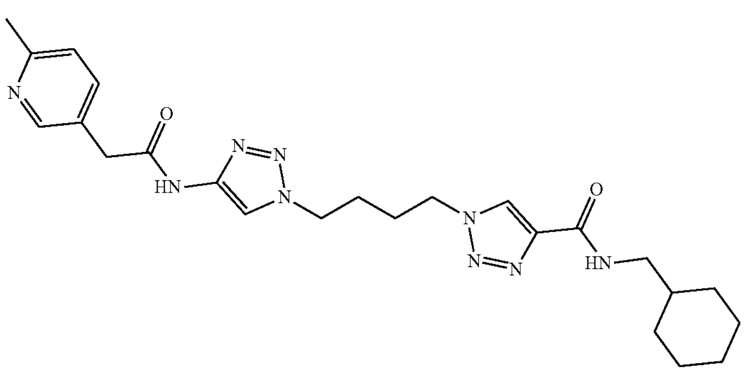 [SMILES: Cc1ccc(CC(=O)Nc2cn(CCCCn3cc(C(=O)NCC4CCCCC4)nn3)nn2)cn1] | N-(cyclohexylmethyl)-1-(4-{4-[2-(6-methylpyridin-3-yl)acetamido]-1H-1,2,3-triazol-1-yl}butyl)-1H-1,2,3-triazole-4-carboxamide |

TABLE 1-continued

Synthesized Examples

| Ex. No. | Structure | Name |
|---|---|---|
| 313 | 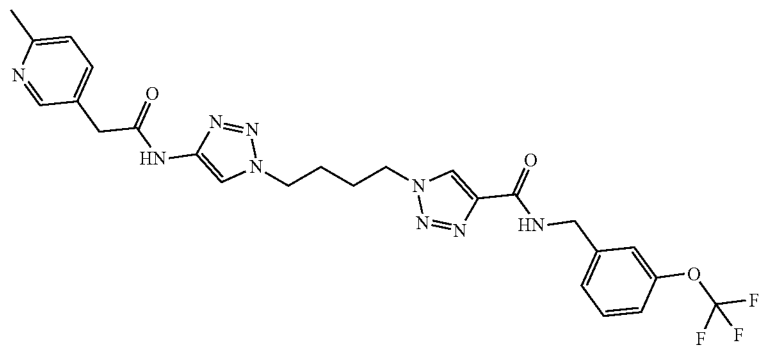 [SMILES: Cc1ccc(CC(=O)Nc2cn(CCCCn3cc(C(=O)NCc4cccc(OC(F)(F)F)c4)nn3)nn2)cn1] | 1-(4-{4-[2-(6-methylpyridin-3-yl)acetamido]-1H-1,2,3-triazol-1-yl}butyl)-N-{[3-(trifluoromethoxy)phenyl]methyl}-1H-1,2,3-triazole-4-carboxamide |
| 314 | 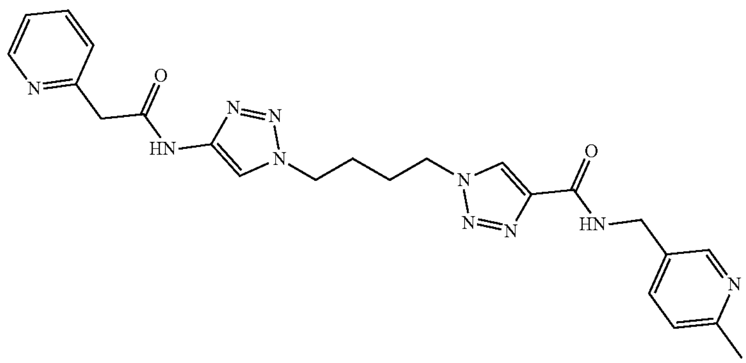 [SMILES: Cc1ccc(CNC(=O)c2cn(CCCCn3cc(NC(=O)Cc4ccccn4)nn3)nn2)cn1] | N-[(6-methylpyridin-3-yl)methyl]-1-(4-{4-[2-(pyridin-2-yl)acetamido]-1H-1,2,3-triazol-1-yl}butyl)-1H-1,2,3-triazole-4-carboxamide |
| 315 | 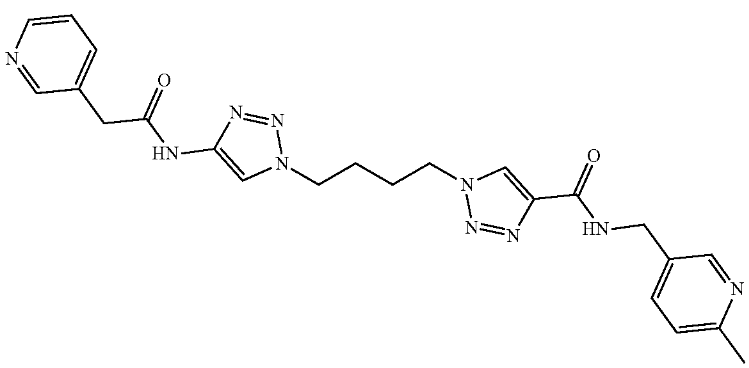 [SMILES: Cc1ccc(CNC(=O)c2cn(CCCCn3cc(NC(=O)Cc4cccnc4)nn3)nn2)cn1] | N-[(6-methylpyridin-3-yl)methyl]-1-(4-{4-[2-(pyridin-3-yl)acetamido]-1H-1,2,3-triazol-1-yl}butyl)-1H-1,2,3-triazole-4-carboxamide |
| 316 | 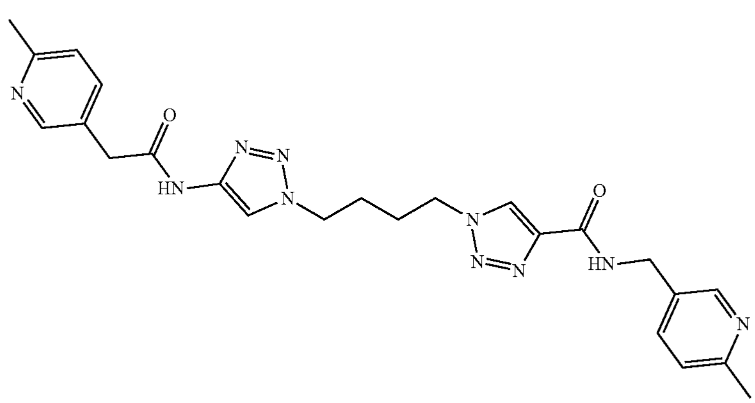 | 1-(4-{4-[2-(6-methylpyridin-3-yl)acetamido]-1H-1,2,3-triazol-1-yl}butyl)-N-[(6-methylpyridin-3-yl)methyl]-1H-1,2,3-triazole-4-carboxamide |

TABLE 1-continued

Synthesized Examples

| Ex. No. | Structure | Name |
|---|---|---|
| 317 | 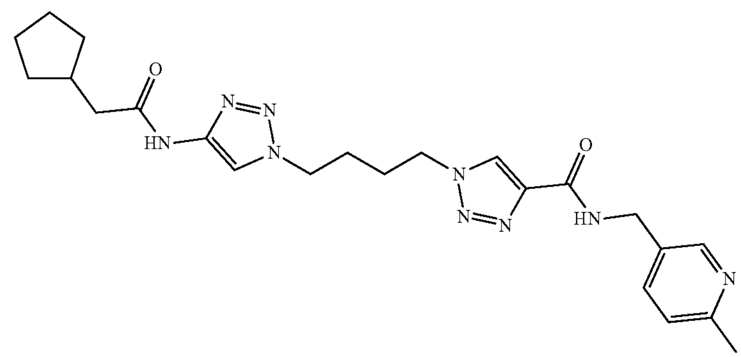 [SMILES: Cc1ccc(CNC(=O)c2cn(CCCCn3cc(NC(=O)CC4CCCC4)nn3)nn2)cn1] | 1-{4-[4-(2-cyclopentylacetamido)-1H-1,2,3-triazol-1-yl]butyl}-N-[(6-methylpyridin-3-yl)methyl]-1H-1,2,3-triazole-4-carboxamide |
| 318 | 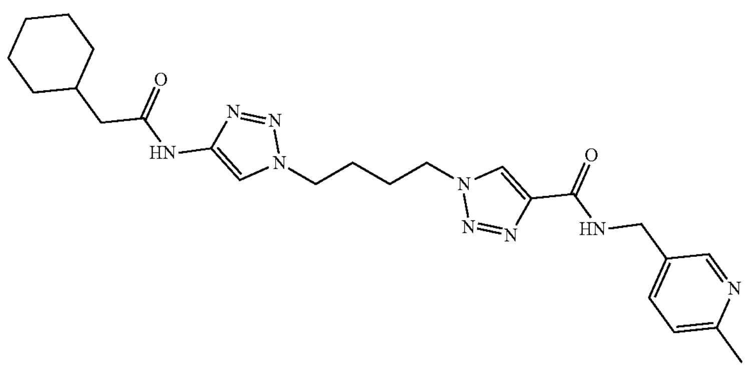 [SMILES: Cc1ccc(CNC(=O)c2cn(CCCCn3cc(NC(=O)CC4CCCCC4)nn3)nn2)cn1] | 1-{4-[4-(2-cyclohexylacetamido)-1H-1,2,3-triazol-1-yl]butyl}-N-[(6-methylpyridin-3-yl)methyl]-1H-1,2,3-triazole-4-carboxamide |
| 319 | 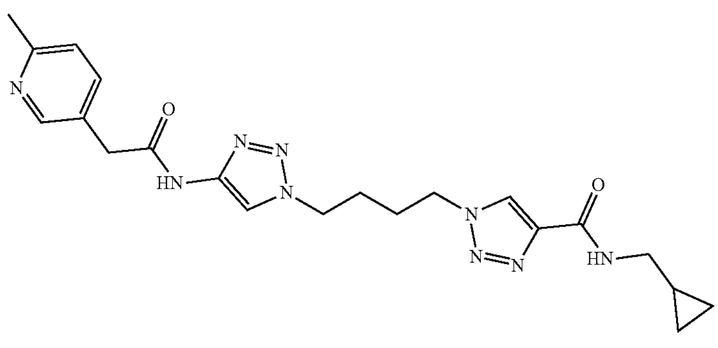 [SMILES: Cc1ccc(CC(=O)Nc2cn(CCCCn3cc(C(=O)NCC4CC4)nn3)nn2)cn1] | N-(cyclopropylmethyl)-1-(4-{4-[2-(6-methylpyridin-3-yl)acetamido]-1H-1,2,3-triazol-1-yl}butyl)-1H-1,2,3-triazole-4-carboxamide |
| 320 | 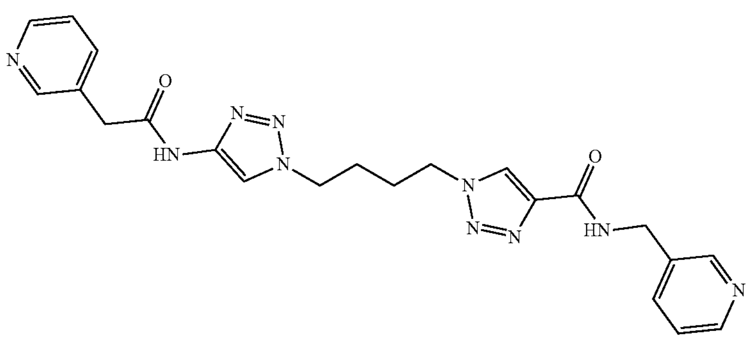 [SMILES: O=C(Cc1cccnc1)Nc1cn(CCCCn2cc(C(=O)NCc3cccnc3)nn2)nn1] | 1-(4-{4-[2-(pyridin-3-yl)acetamido]-1H-1,2,3-triazol-1-yl}butyl)-N-(pyridin-3-ylmethyl)-1H-1,2,3-triazole-4-carboxamide |

TABLE 1-continued

Synthesized Examples

| Ex. No. | Structure | Name |
|---|---|---|
| 321 | 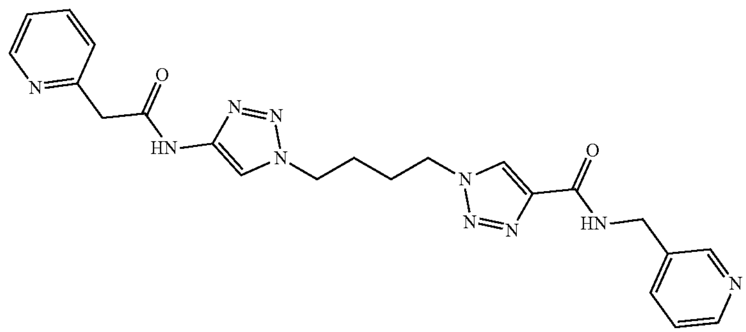 [SMILES: O=C(Cc1ccccn1)Nc1cn(CCCCn2cc(C(=O)NCc3cccnc3)nn2)nn1] | 1-(4-{4-[2-(pyridin-2-yl)acetamido]-1H-1,2,3-triazol-1-yl}butyl)-N-(pyridin-3-ylmethyl)-1H-1,2,3-triazole-4-carboxamide |
| 322 | 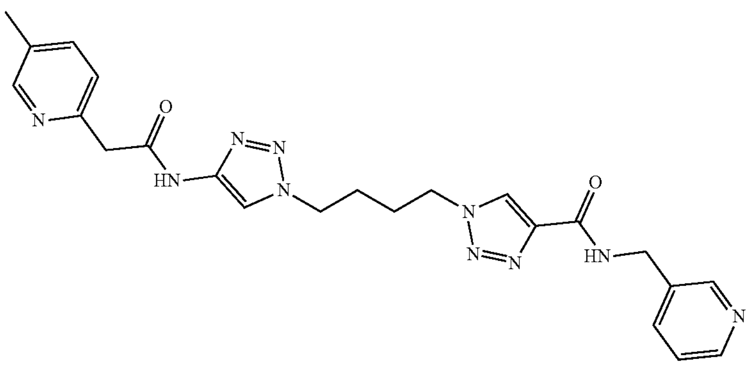 [SMILES: Cc1ccc(CC(=O)Nc2cn(CCCCn3cc(C(=O)NCc4cccnc4)nn3)nn2)nc1] | 1-(4-{4-[2-(6-methylpyridin-3-yl)acetamido]-1H-1,2,3-triazol-1-yl}butyl)-N-(pyridin-3-ylmethyl)-1H-1,2,3-triazole-4-carboxamide |
| 323 | 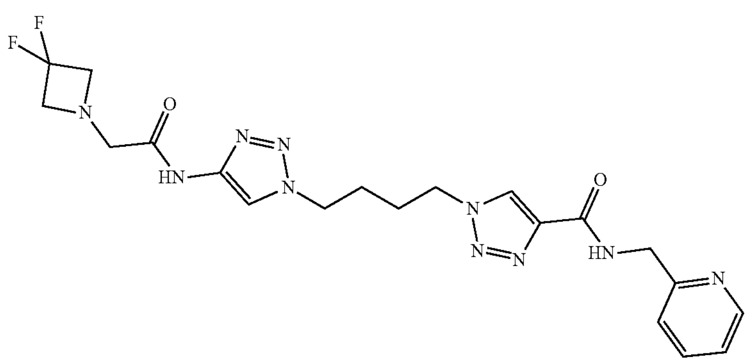 [SMILES: O=C(CN1CC(F)(F)C1)Nc1cn(CCCCn2cc(C(=O)NCc3ccccn3)nn2)nn1] | 1-(4-{4-[2-(3,3-difluoroazetidin-1-yl)acetamido]-1H-1,2,3-triazol-1-yl}butyl)-N-(pyridin-2-ylmethyl)-1H-1,2,3-triazole-4-carboxamide |
| 324 | 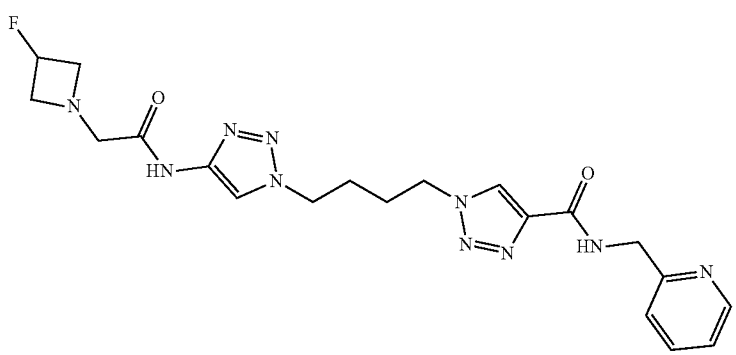 [SMILES: O=C(CN1CC(F)C1)Nc1cn(CCCCn2cc(C(=O)NCc3ccccn3)nn2)nn1] | 1-(4-{4-[2-(3-fluoroazetidin-1-yl)acetamido]-1H-1,2,3-triazol-1-yl}butyl)-N-(pyridin-2-ylmethyl)-1H-1,2,3-triazole-4-carboxamide |

TABLE 1-continued

Synthesized Examples

| Ex. No. | Structure | Name |
|---|---|---|
| 325 | 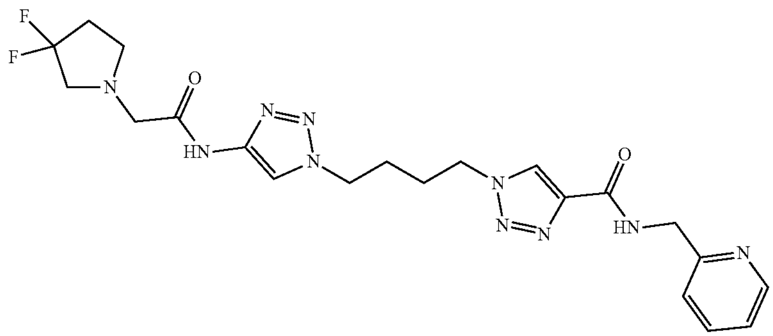 [SMILES: O=C(CN1CCC(F)(F)C1)Nc1cn(CCCCn2cc(C(=O)NCc3ccccn3)nn2)nn1] | 1-(4-{4-[2-(3,3-difluoropyrrolidin-1-yl)acetamido]-1H-1,2,3-triazol-1-yl}butyl)-N-(pyridin-2-ylmethyl)-1H-1,2,3-triazole-4-carboxamide |
| 326 | 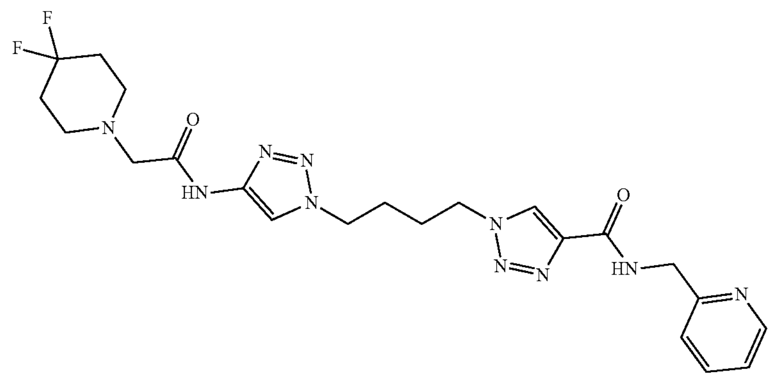 [SMILES: O=C(CN1CCC(F)(F)CC1)Nc1cn(CCCCn2cc(C(=O)NCc3ccccn3)nn2)nn1] | 1-(4-{4-[2-(4,4-difluoropiperidin-1-yl)acetamido]-1H-1,2,3-triazol-1-yl}butyl)-N-(pyridin-2-ylmethyl)-1H-1,2,3-triazole-4-carboxamide |
| 327 | 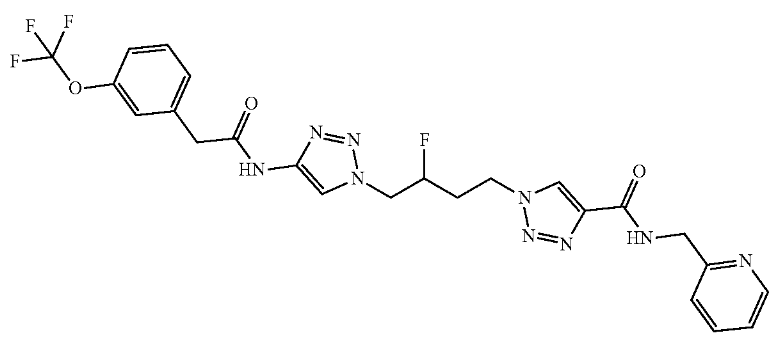 [SMILES: O=C(Cc1cccc(OC(F)(F)F)c1)Nc1cn(CC(F)CCn2cc(C(=O)NCc3ccccn3)nn2)nn1] | 1-[3-fluoro-4-(4-{2-[3-(trifluoromethoxy)phenyl]acetamido}-1H-1,2,3-triazol-1-yl)butyl]-N-(pyridin-2-ylmethyl)-1H-1,2,3-triazole-4-carboxamide |
| 328 | 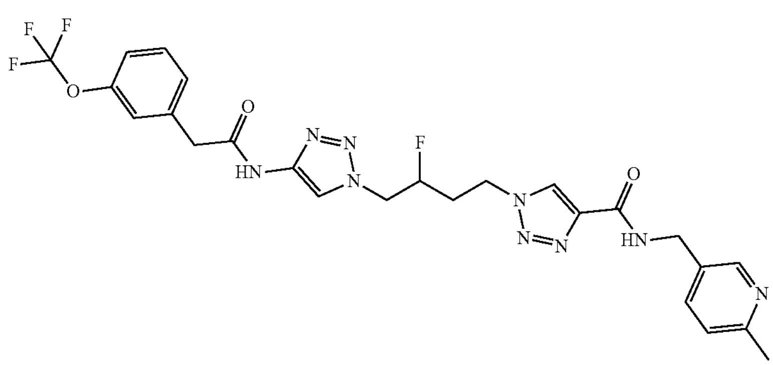 [SMILES: Cc1ccc(CNC(=O)c2cn(CCC(F)Cn3cc(NC(=O)Cc4cccc(OC(F)(F)F)c4)nn3)nn2)cn1] | 1-[3-fluoro-4-(4-{2-[3-(trifluoromethoxy)phenyl]acetamido}-1H-1,2,3-triazol-1-yl)butyl]-N-[(6-methylpyridin-3-yl)methyl]-1H-1,2,3-triazole-4-carboxamide |

TABLE 1-continued

Synthesized Examples

| Ex. No. | Structure | Name |
|---|---|---|
| 329 | 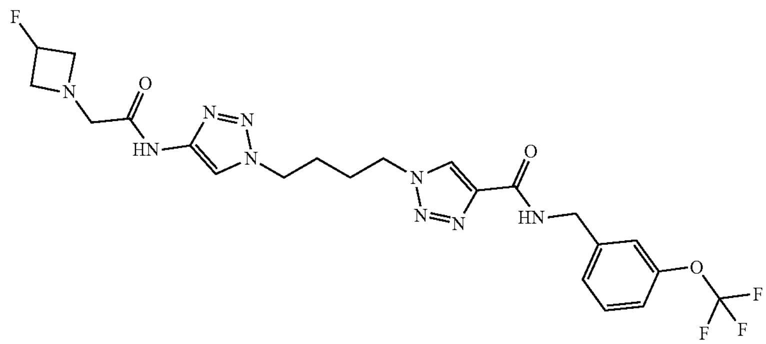 [SMILES: O=C(CN1CC(F)C1)Nc1cn(CCCCn2cc(C(=O)NCc3cccc(OC(F)(F)F)c3)nn2)nn1] | 1-(4-{4-[2-(3-fluoroazetidin-1-yl)acetamido]-1H-1,2,3-triazol-1-yl}butyl)-N-{[3-(trifluoromethoxy)phenyl]methyl}-1H-1,2,3-triazole-4-carboxamide |
| 330 | 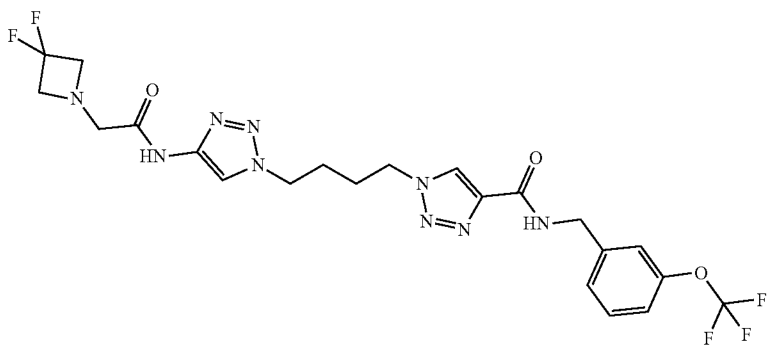 [SMILES: O=C(CN1CC(F)(F)C1)Nc1cn(CCCCn2cc(C(=O)NCc3cccc(OC(F)(F)F)c3)nn2)nn1] | 1-(4-{4-[2-(3,3-difluoroazetidin-1-yl)acetamido]-1H-1,2,3-triazol-1-yl}butyl)-N-{[3-(trifluoromethoxy)phenyl]methyl}-1H-1,2,3-triazole-4-carboxamide |
| 331 | 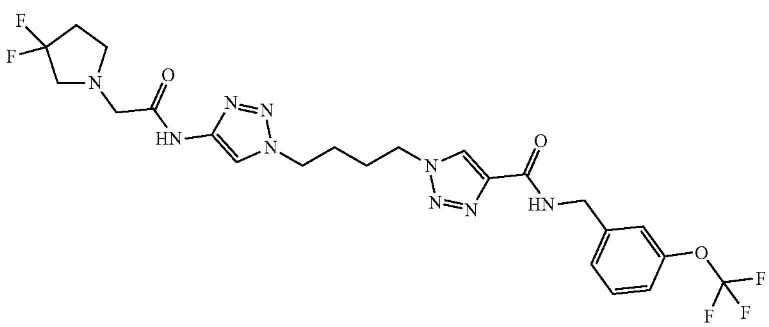 [SMILES: O=C(CN1CCC(F)(F)C1)Nc1cn(CCCCn2cc(C(=O)NCc3cccc(OC(F)(F)F)c3)nn2)nn1] | 1-(4-{4-[2-(3,3-difluoropyrrolidin-1-yl)acetamido]-1H-1,2,3-triazol-1-yl}butyl)-N-{[3-(trifluoromethoxy)phenyl]methyl}-1H-1,2,3-triazole-4-carboxamide |
| 332 | 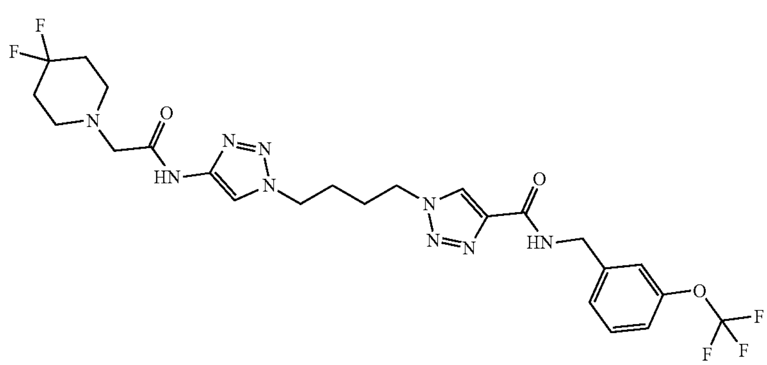 [SMILES: O=C(CN1CCC(F)(F)CC1)Nc1cn(CCCCn2cc(C(=O)NCc3cccc(OC(F)(F)F)c3)nn2)nn1] | 1-(4-{4-[2-(4,4-difluoropiperidin-1-yl)acetamido]-1H-1,2,3-triazol-1-yl}butyl)-N-{[3-(trifluoromethoxy)phenyl]methyl}-1H-1,2,3-triazole-4-carboxamide |

TABLE 1-continued

Synthesized Examples

| Ex. No. | Structure | Name |
|---|---|---|
| 333 | 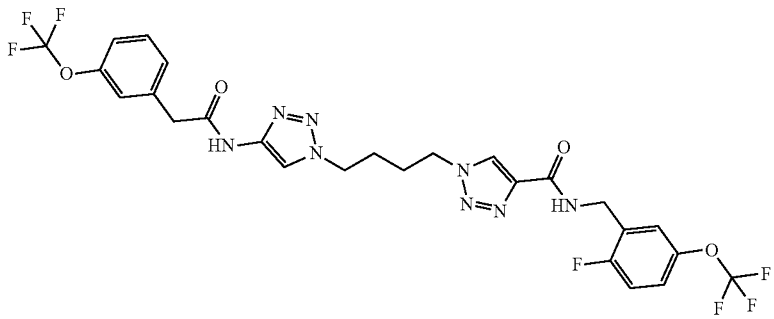 [SMILES: O=C(Cc1cccc(OC(F)(F)F)c1)Nc1cn(CCCCn2cc(C(=O)NCc3cc(OC(F)(F)F)ccc3F)nn2)nn1] | N-{[2-fluoro-5-(trifluoromethoxy)phenyl]methyl}-1-[4-(4-{2-[3-(trifluoromethoxy)phenyl]acetamido}-1H-1,2,3-triazol-1-yl)butyl]-1H-1,2,3-triazole-4-carboxamide |
| 334 | 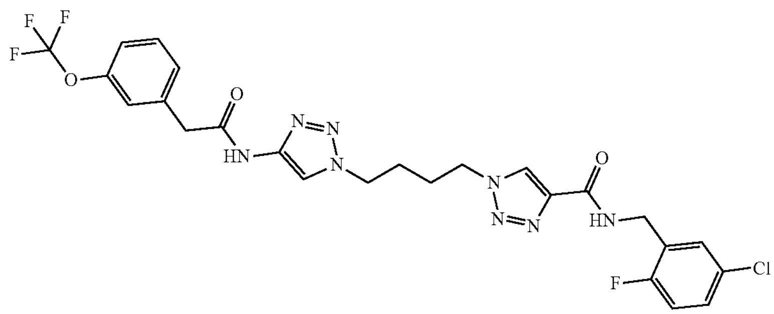 [SMILES: O=C(Cc1cccc(OC(F)(F)F)c1)Nc1cn(CCCCn2cc(C(=O)NCc3cc(Cl)ccc3F)nn2)nn1] | N-[(5-chloro-2-fluorophenyl)methyl]-1-[4-(4-{2-[3-(trifluoromethoxy)phenyl]acetamido}-1H-1,2,3-triazol-1-yl)butyl]-1H-1,2,3-triazole-4-carboxamide |
| 335 | 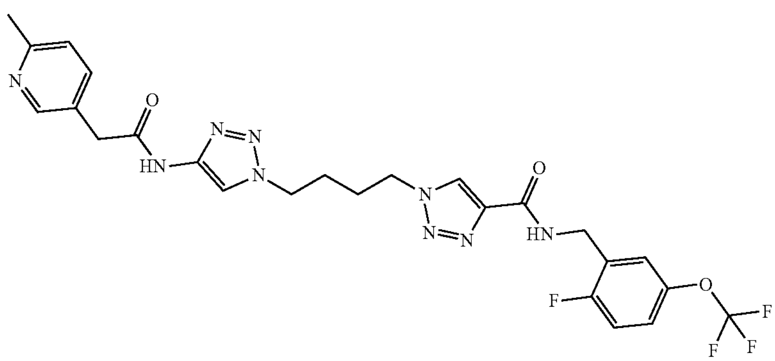 [SMILES: Cc1ccc(CC(=O)Nc2cn(CCCCn3cc(C(=O)NCc4cc(OC(F)(F)F)ccc4F)nn3)nn2)cn1] | N-{[2-fluoro-5-(trifluoromethoxy)phenyl]methyl}-1-(4-{4-[2-(6-methylpyridin-3-yl)acetamido]-1H-1,2,3-triazol-1-yl}butyl)-1H-1,2,3-triazole-4-carboxamide |
| 336 | 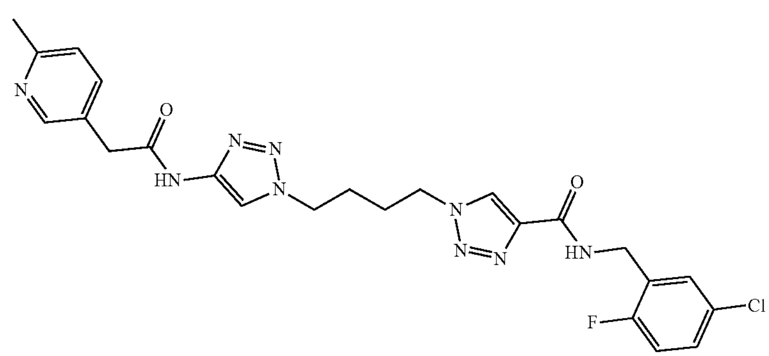 [SMILES: Cc1ccc(CC(=O)Nc2cn(CCCCn3cc(C(=O)NCc4cc(Cl)ccc4F)nn3)nn2)cn1] | N-[(5-chloro-2-fluorophenyl)methyl]-1-(4-{4-[2-(6-methylpyridin-3-yl)acetamido]-1H-1,2,3-triazol-1-yl}butyl)-1H-1,2,3-triazole-4-carboxamide |

TABLE 1-continued

Synthesized Examples

| Ex. No. | Structure | Name |
|---|---|---|
| 337 | 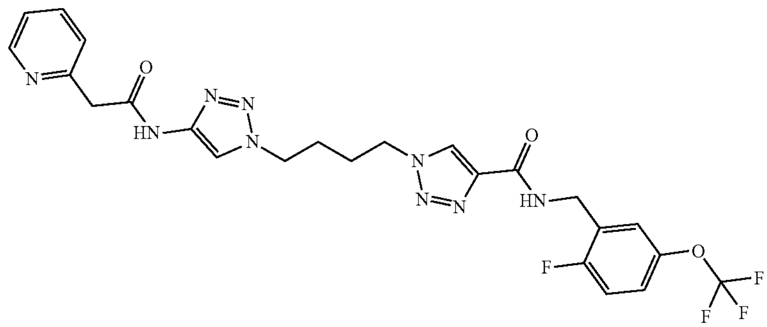 [SMILES: O=C(Cc1ccccn1)Nc1cn(CCCCn2cc(C(=O)NCc3cc(OC(F)(F)F)ccc3F)nn2)nn1] | N-{[2-fluoro-5-(trifluoromethoxy)phenyl]methyl}-1-(4-{4-[2-(pyridin-2-yl)acetamido]-1H-1,2,3-triazol-1-yl}butyl)-1H-1,2,3-triazole-4-carboxamide |
| 338 | 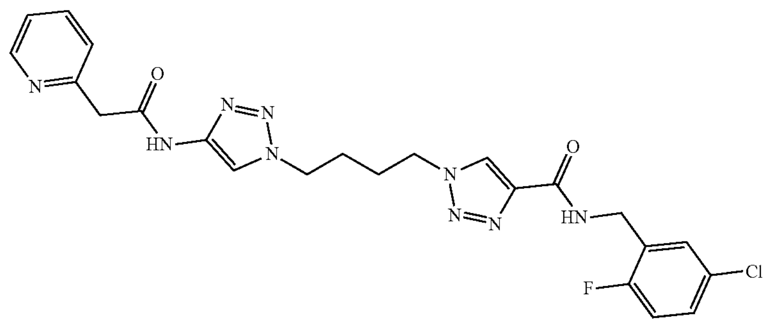 [SMILES: O=C(Cc1ccccn1)Nc1cn(CCCCn2cc(C(=O)NCc3cc(Cl)ccc3F)nn2)nn1] | N-[(5-chloro-2-fluorophenyl)methyl]-1-(4-{4-[2-(pyridin-2-yl)acetamido]-1H-1,2,3-triazol-1-yl}butyl)-1H-1,2,3-triazole-4-carboxamide |
| 339 | 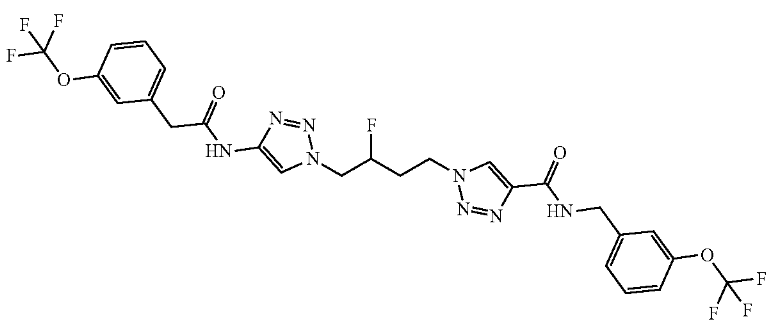 [SMILES: O=C(Cc1cccc(OC(F)(F)F)c1)Nc1cn(CC(F)CCn2cc(C(=O)NCc3cccc(OC(F)(F)F)c3)nn2)nn1] | 1-[3-fluoro-4-(4-{2-[3-(trifluoromethoxy)phenyl]acetamido}-1H-1,2,3-triazol-1-yl)butyl]-N-{[3-(trifluoromethoxy)phenyl]methyl}-1H-1,2,3-triazole-4-carboxamide |
| 340 | 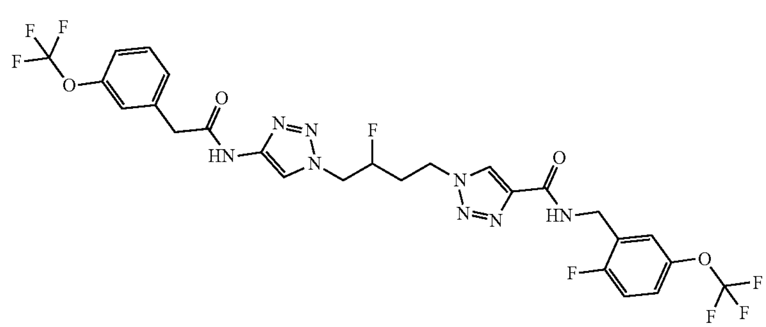 [SMILES: O=C(Cc1cccc(OC(F)(F)F)c1)Nc1cn(CC(F)CCn2cc(C(=O)NCc3cc(OC(F)(F)F)ccc3F)nn2)nn1] | 1-[3-fluoro-4-(4-{2-[3-(trifluoromethoxy)phenyl]acetamido}-1H-1,2,3-triazol-1-yl)butyl]-N-{[2-fluoro-5-(trifluoromethoxy)phenyl]methyl}-1H-1,2,3-triazole-4-carboxamide |

TABLE 1-continued

Synthesized Examples

| Ex. No. | Structure | Name |
|---|---|---|
| 341 | 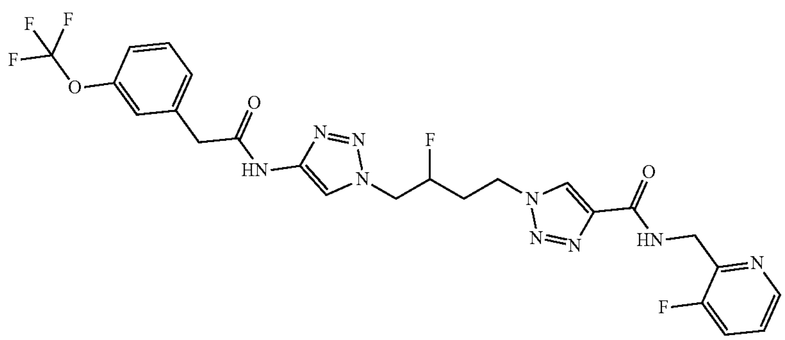 [SMILES: O=C(Cc1cccc(OC(F)(F)F)c1)Nc1cn(CC(F)CCn2cc(C(=O)NCc3ncccc3F)nn2)nn1] | 1-[3-fluoro-4-(4-{2-[3-(trifluoromethoxy)phenyl]acetamido}-1H-1,2,3-triazol-1-yl)butyl]-N-[(3-fluoropyridin-2-yl)methyl]-1H-1,2,3-triazole-4-carboxamide |
| 342 | 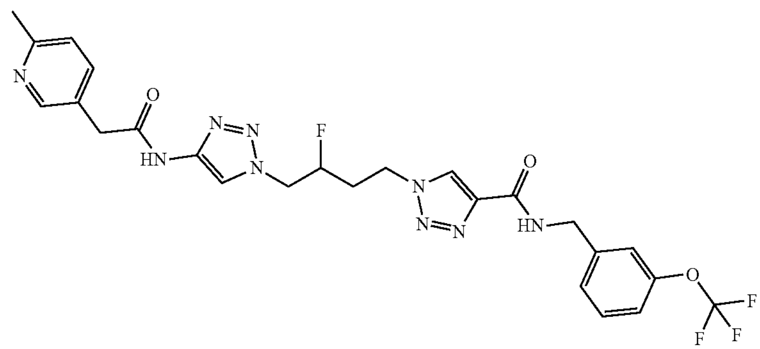 [SMILES: Cc1ccc(CC(=O)Nc2cn(CC(F)CCn3cc(C(=O)NCc4cccc(OC(F)(F)F)c4)nn3)nn2)cn1] | 1-(3-fluoro-4-{4-[2-(6-methylpyridin-3-yl)acetamido]-1H-1,2,3-triazol-1-yl}butyl)-N-{[3-(trifluoromethoxy)phenyl]methyl}-1H-1,2,3-triazole-4-carboxamide |
| 343 | 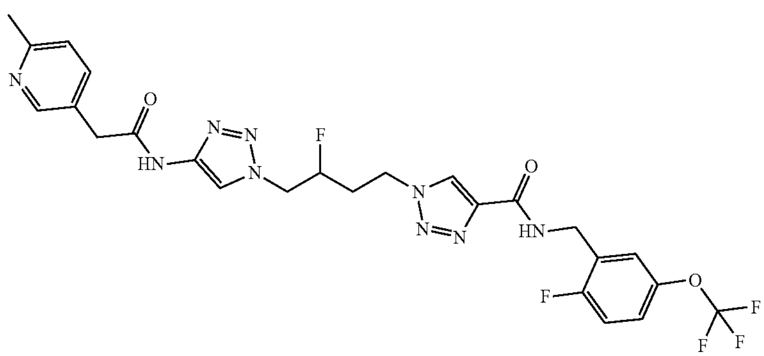 [SMILES: Cc1ccc(CC(=O)Nc2cn(CC(F)CCn3cc(C(=O)NCc4cc(OC(F)(F)F)ccc4F)nn3)nn2)cn1] | 1-(3-fluoro-4-{4-[2-(6-methylpyridin-3-yl)acetamido]-1H-1,2,3-triazol-1-yl}butyl)-N-{[2-fluoro-5-(trifluoromethoxy)phenyl]methy}-1H-1,2,3-triazole-4-carboxamide |
| 344 | 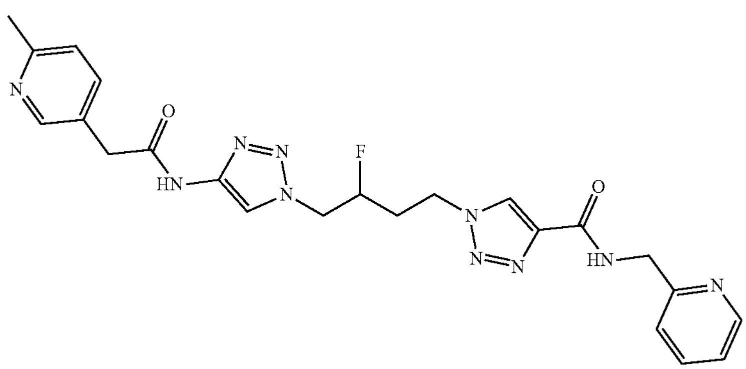 [SMILES: Cc1ccc(CC(=O)Nc2cn(CC(F)CCn3cc(C(=O)NCc4ccccn4)nn3)nn2)cn1] | 1-(3-fluoro-4-{4-[2-(6-methylpyridin-3-yl)acetamido]-1H-1,2,3-triazol-1-yl}butyl)-N-(pyridin-2-ylmethyl)-1H-1,2,3-triazole-4-carboxamide |

TABLE 1-continued

Synthesized Examples

| Ex. No. | Structure | Name |
|---|---|---|
| 345 | 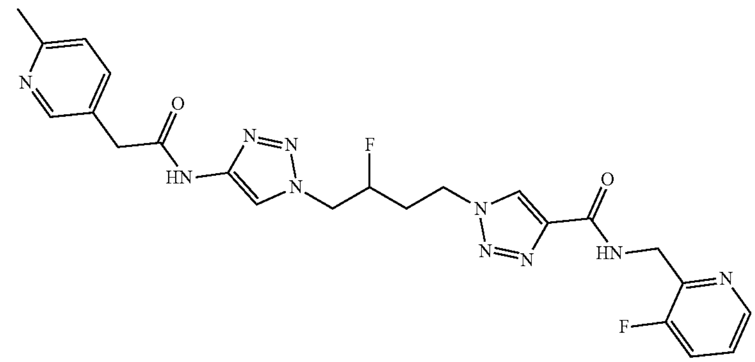 [SMILES: Cc1ccc(CC(=O)Nc2cn(CC(F)CCn3cc(C(=O)NCc4ncccc4F)nn3)nn2)cn1] | 1-(3-fluoro-4-{4-[2-(6-methylpyridin-3-yl)acetamido]-1H-1,2,3-triazol-1-yl}butyl)-N-[(3-fluoropyridin-2-yl)methyl]-1H-1,2,3-triazole-4-carboxamide |
| 346 | 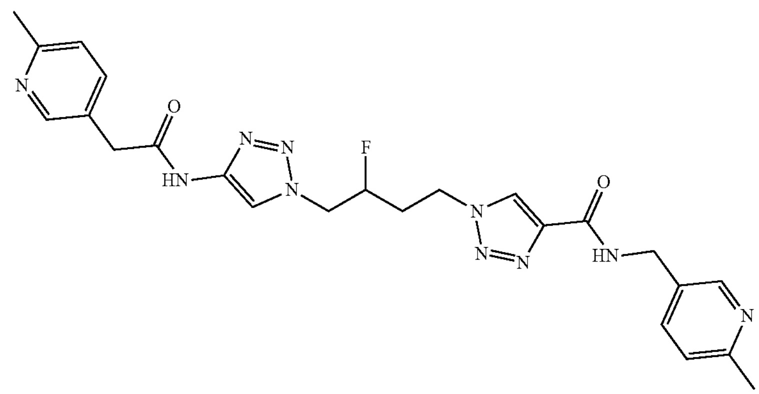 | 1-(3-fluoro-4-{4-[2-(6-methylpyridin-3-yl)acetamido]-1H-1,2,3-triazol-1-yl}butyl)-N-[(6-methylpyridin-3-yl)methyl-1H-1,2,3-triazole-4-carboxamide |
| 347 | 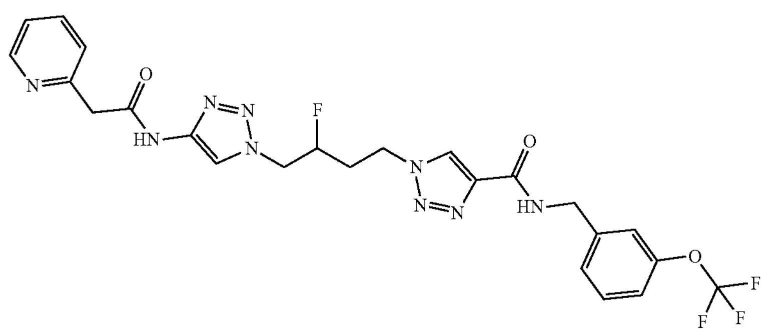 [SMILES: O=C(Cc1ccccn1)Nc1cn(CC(F)CCn2cc(C(=O)NCc3cccc(OC(F)(F)F)c3)nn2)nn1] | 1-(3-fluoro-4-{4-[2-(pyridin-2-yl)acetamido]-1H-1,2,3-triazol-1-yl}butyl)-N-{[3-(trifluoromethoxy)phenyl]methyl}-1H-1,2,3-triazole-4-carboxamide |
| 348 | 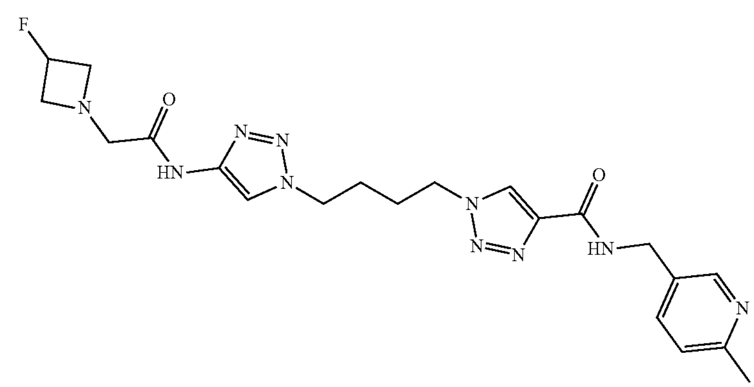 [SMILES: Cc1ccc(CNC(=O)c2cn(CCCCn3cc(NC(=O)CN4CC(F)C4)nn3)nn2)cn1] | 1-(4-{4-[2-(3-fluoroazetidin-1-yl)acetamido]-1H-1,2,3-triazol-1-yl}butyl)-N-[(6-methylpyridin-3-yl)methyl]-1H-1,2,3-triazole-4-carboxamide |

TABLE 1-continued

Synthesized Examples

| Ex. No. | Structure | Name |
|---|---|---|
| 349 | 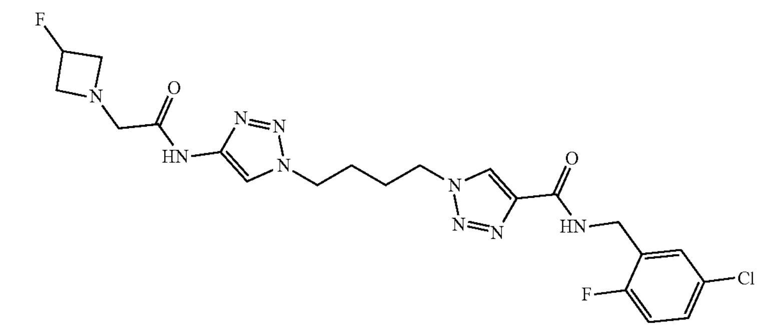 [SMILES: O=C(CN1CC(F)C1)Nc1cn(CCCCn2cc(C(=O)NCc3cc(Cl)ccc3F)nn2)nn1] | N-[(5-chloro-2-fluorophenyl)methyl]-1-(4-{4-[2-(3-fluoroazetidin-1-yl)acetamido]-1H-1,2,3-triazol-1-yl}butyl)-1H-1,2,3-triazole-4-carboxamide |
| 350 | 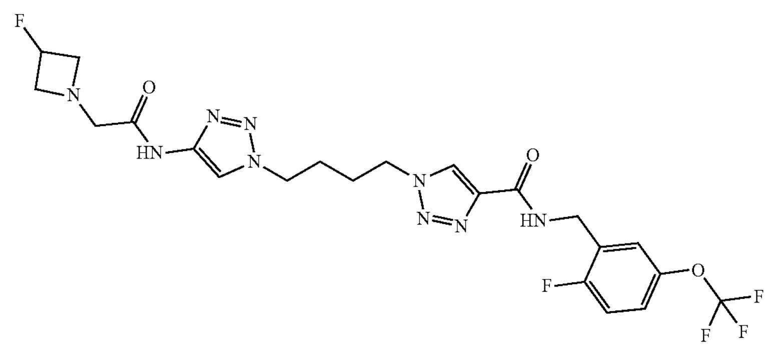 [SMILES: O=C(CN1CC(F)C1)Nc1cn(CCCCn2cc(C(=O)NCc3cc(OC(F)(F)F)ccc3F)nn2)nn1] | N-{[2-fluoro-5-(trifluoromethoxy)phenyl]methyl}-1-(4-{4-[2-(3-fluoroazetidin-1-yl)acetamido]-1H-1,2,3-triazol-1-yl}butyl)-1H-1,2,3-triazole-4-carboxamide |
| 351 | 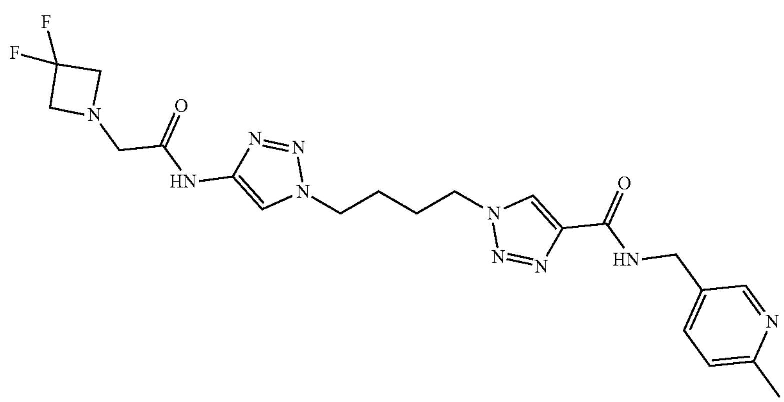 [SMILES: Cc1ccc(CNC(=O)c2cn(CCCCn3cc(NC(=O)CN4CC(F)(F)C4)nn3)nn2)cn1] | 1-(4-{4-[2-(3,3-difluoroazetidin-1-yl)acetamido]-1H-1,2,3-triazol-1-yl}butyl)-N-[(6-methylpyridin-3-yl)methyl]-1H-1,2,3-triazole-4-carboxamide |
| 352 | 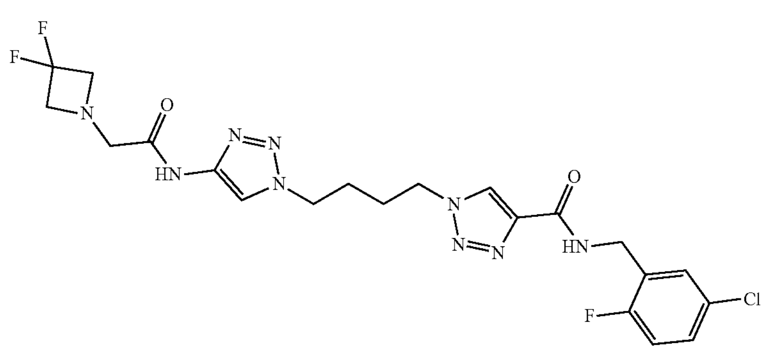 [SMILES: O=C(CN1CC(F)(F)C1)Nc1cn(CCCCn2cc(C(=O)NCc3cc(Cl)ccc3F)nn2)nn1] | N-[(5-chloro-2-fluorophenyl)methyl]-1-(4-{4-[2-(3,3-difluoroazetidin-1-yl)acetamido]-1H-1,2,3-triazol-1-yl}butyl)-1H-1,2,3-triazole-4-carboxamide |

TABLE 1-continued

Synthesized Examples

| Ex. No. | Structure | Name |
|---|---|---|
| 353 | 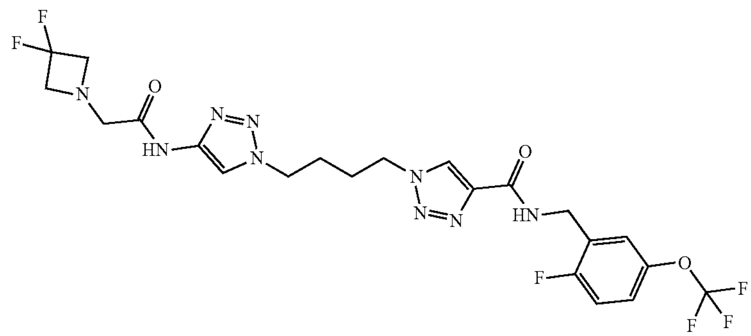 [SMILES: O=C(CN1CC(F)(F)C1)Nc1cn(CCCCn2cc(C(=O)NCc3cc(OC(F)(F)F)ccc3F)nn2)nn1] | 1-(4-{4-[2-(3,3-difluoroazetidin-1-yl)acetamido]-1H-1,2,3-triazol-1-yl}butyl)-N-{[2-fluoro-5-(trifluoromethoxy)phenyl]methyl}-1H-1,2,3-triazole-4-carboxamide |
| 354 | 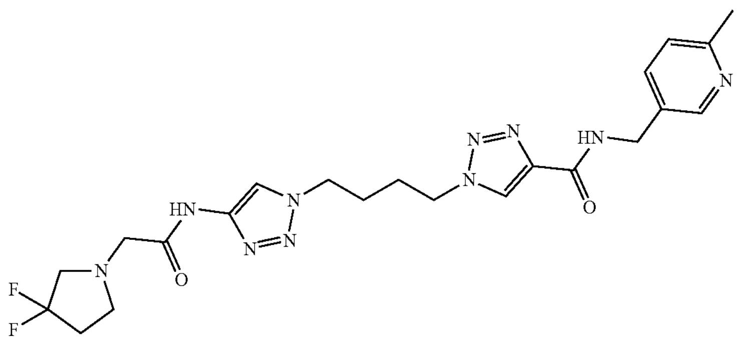 [SMILES: Cc1ccc(CNC(=O)c2cn(CCCCn3cc(NC(=O)CN4CCC(F)(F)C4)nn3)nn2)cn1] | 1-(4-{4-[2-(3,3-difluoropyrrolidin-1-yl)acetamido]-1H-1,2,3-triazol-1-yl}butyl)-N-[(6-methylpyridin-3-yl)methyl]-1H-1,2,3-triazole-4-carboxamide |
| 355 | 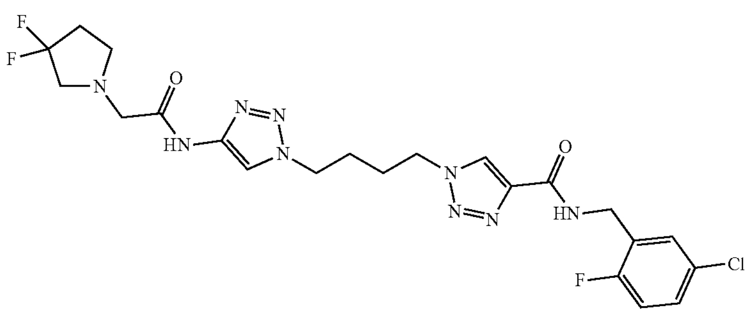 [SMILES: O=C(CN1CCC(F)(F)C1)Nc1cn(CCCCn2cc(C(=O)NCc3cc(Cl)ccc3F)nn2)nn1] | N-[(5-chloro-2-fluorophenyl)methyl]-1-(4-{4-[2-(3,3-difluoropyrrolidin-1-yl)acetamido]-1H-1,2,3-triazol-1-yl}butyl)-1H-1,2,3-triazole-4-carboxamide |
| 356 | 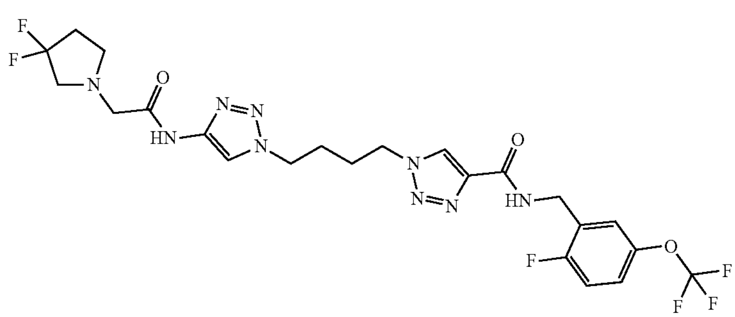 [SMILES: O=C(CN1CCC(F)(F)C1)Nc1cn(CCCCn2cc(C(=O)NCc3cc(OC(F)(F)F)ccc3F)nn2)nn1] | 1-(4-{4-[2-(3,3-difluoropyrrolidin-1-yl)acetamido]-1H-1,2,3-triazol-1-yl}butyl)-N-{[2-fluoro-5-(trifluoromethoxy)phenyl]methyl}-1H-1,2,3-triazole-4-carboxamide |

TABLE 1-continued

Synthesized Examples

| Ex. No. | Structure | Name |
|---|---|---|
| 357 | 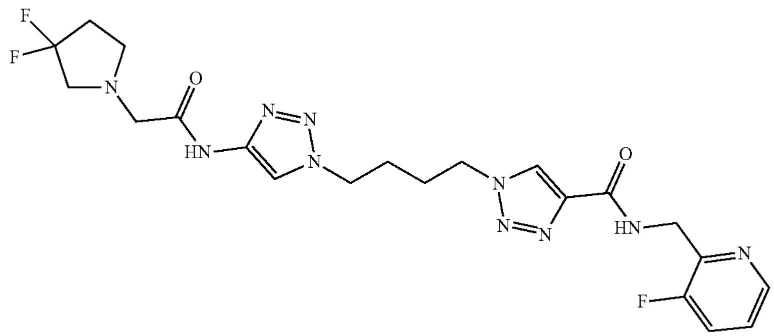 [SMILES: O=C(CN1CCC(F)(F)C1)Nc1cn(CCCCn2cc(C(=O)NCc3ncccc3F)nn2)nn1] | 1-(4-{4-[2-(3,3-difluoropyrrolidin-1-yl)acetamido]-1H-1,2,3-triazol-1-yl}butyl)-N-[(3-fluoropyridin-2-yl)methyl]-1H-1,2,3-triazole-4-carboxamide |
| 358 | 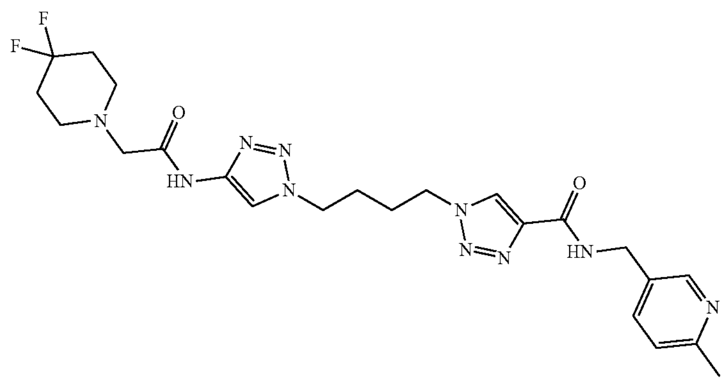 [SMILES: Cc1ccc(CNC(=O)c2cn(CCCCn3cc(NC(=O)CN4CCC(F)(F)CC4)nn3)nn2)cn1] | 1-(4-{4-[2-(4,4-difluoropiperidin-1-yl)acetamido]-1H-1,2,3-triazol-1-yl}butyl)-N-[(6-methylpyridin-3-yl)methyl]-1H-1,2,3-triazole-4-carboxamide |
| 359 | 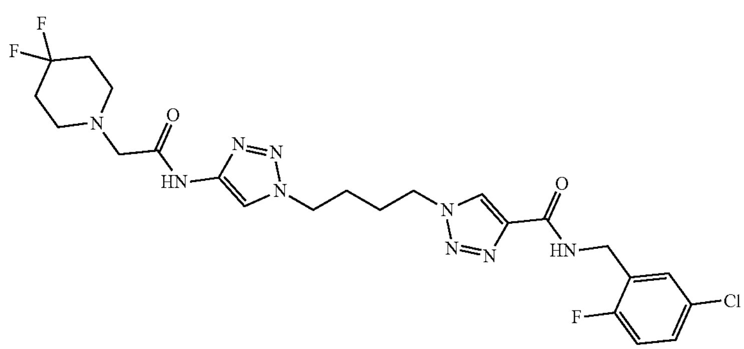 [SMILES: O=C(CN1CCC(F)(F)CC1)Nc1cn(CCCCn2cc(C(=O)NCc3cc(Cl)ccc3F)nn2)nn1] | N-[(5-chloro-2-fluorophenyl)methyl]-1-(4-{4-[2-(4,4-difluoropiperidin-1-yl)acetamido]-1H-1,2,3-triazol-1-yl}butyl)-1H-1,2,3-triazole-4-carboxamide |
| 360 | 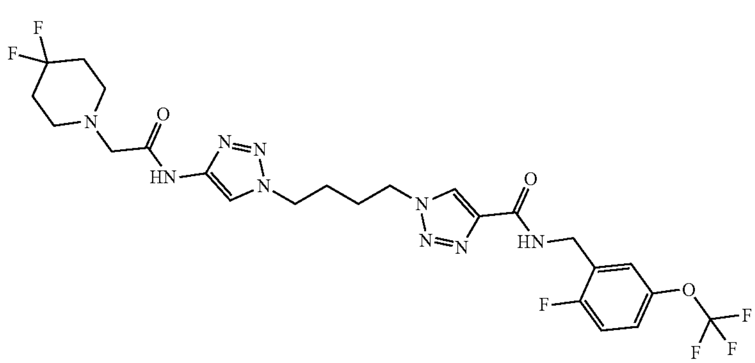 [SMILES: O=C(CN1CCC(F)(F)CC1)Nc1cn(CCCCn2cc(C(=O)NCc3cc(OC(F)(F)F)ccc3F)nn2)nn1] | 1-(4-{4-[2-(4,4-difluoropiperidin-1-yl)acetamido]-1H-1,2,3-triazol-1-yl}butyl)-N-{[2-fluoro-5-(trifluoromethoxy)phenyl]methyl}-1H-1,2,3-triazole-4-carboxamide |

TABLE 1-continued

Synthesized Examples

| Ex. No. | Structure | Name |
|---|---|---|
| 361 | 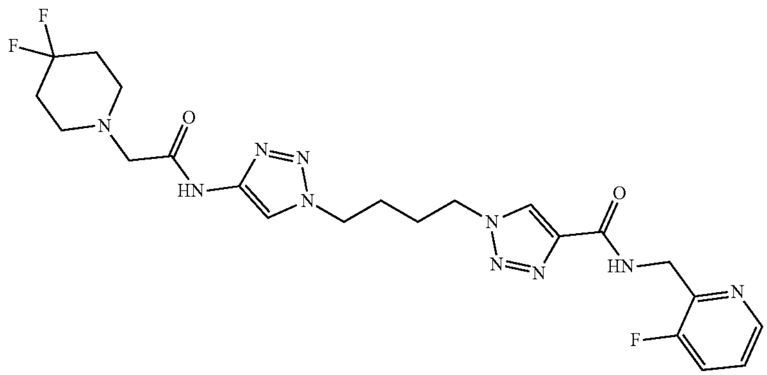 [SMILES: O=C(CN1CCC(F)(F)CC1)Nc1cn(CCCCn2cc(C(=O)NCc3ncccc3F)nn2)nn1] | 1-(4-{4-[2-(4,4-difluoropiperidin-1-yl)acetamido]-1H-1,2,3-triazol-1-yl}butyl)-N-[(3-fluoropyridin-2-yl)methyl]-1H-1,2,3-triazole-4-carboxamide |
| 362 | 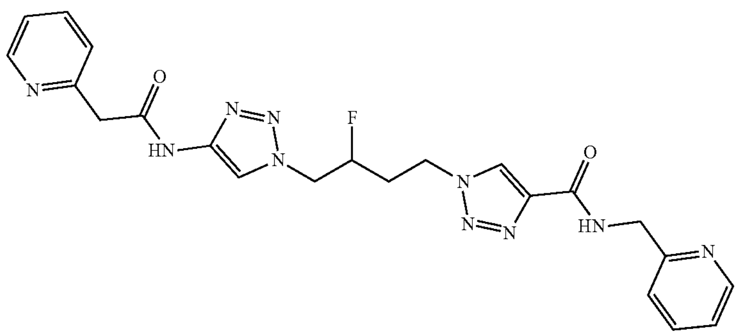 [SMILES: O=C(Cc1ccccn1)Nc1cn(CC(F)CCn2cc(C(=O)NCc3ccccn3)nn2)nn1] | 1-(3-fluoro-4-{4-[2-(pyridin-2-yl)acetamido]-1H-1,2,3-triazol-1-yl}butyl)-N-(pyridin-2-ylmethyl)-1H-1,2,3-triazole-4-carboxamide |
| 363 | 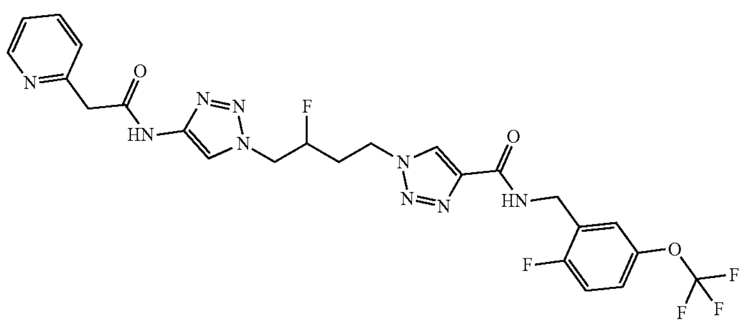 [SMILES: O=C(Cc1ccccn1)Nc1cn(CC(F)CCn2cc(C(=O)NCc3cc(OC(F)(F)F)ccc3F)nn2)nn1] | 1-(3-fluoro-4-{4-[2-(pyridin-2-yl)acetamido]-1H-1,2,3-triazol-1-yl}butyl)-N-{[2-fluoro-5-(trifluoromethoxy)phenyl]methyl}-1H-1,2,3-triazole-4-carboxamide |
| 364 | 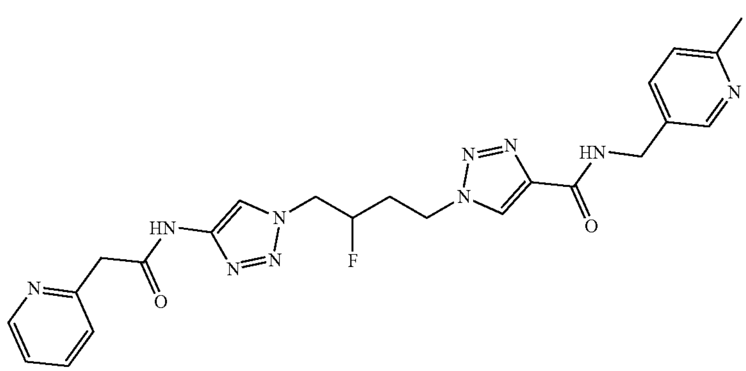 [SMILES: Cc1ccc(CNC(=O)c2cn(CCC(F)Cn3cc(NC(=O)Cc4ccccn4)nn3)nn2)cn1] | 1-(3-fluoro-4-{4-[2-(pyridin-2-yl)acetamido]-1H-1,2,3-triazol-1-yl}butyl)-N-[(6-methylpyridin-3-yl)methyl]-1H-1,2,3-triazole-4-carboxamide |

TABLE 1-continued

Synthesized Examples

| Ex. No. | Structure | Name |
|---|---|---|
| 365 | 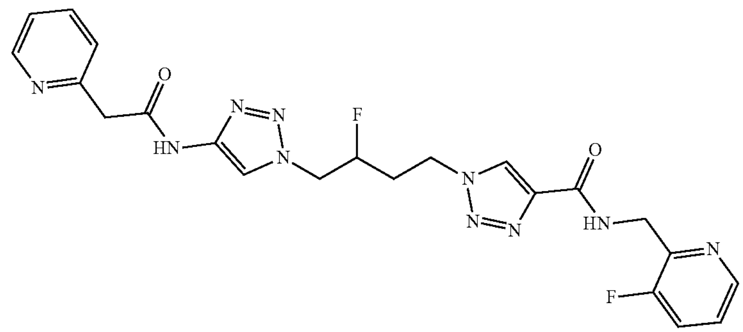 [SMILES: O=C(Cc1ccccn1)Nc1cn(CC(F)CCn2cc(C(=O)NCc3ncccc3F)nn2)nn1] | 1-(3-fluoro-4-{4-[2-(pyridin-2-yl)acetamido]-1H-1,2,3-triazol-1-yl}butyl)-N-[(3-fluoropyridin-2-yl)methyl]-1H-1,2,3-triazole-4-carboxamide |
| 366 | 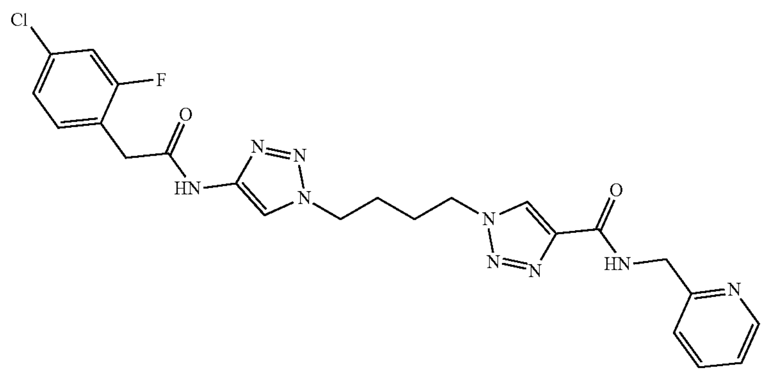 [SMILES: O=C(Cc1ccc(Cl)cc1F)Nc1cn(CCCCn2cc(C(=O)NCc3ccccn3)nn2)nn1] | 1-(4-{4-[2-(4-chloro-2-fluorophenyl)acetamido]-1H-1,2,3-triazol-1-yl}butyl)-N-(pyridin-2-ylmethyl)-1H-1,2,3-triazole-4-carboxamide |
| 367 | 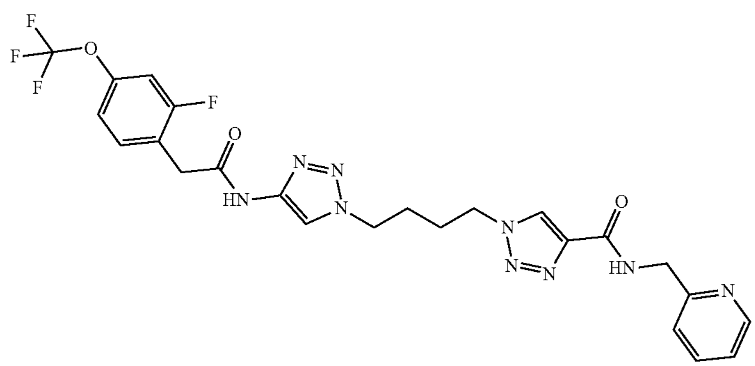 [SMILES: O=C(Cc1ccc(OC(F)(F)F)cc1F)Nc1cn(CCCCn2cc(C(=O)NCc3ccccn3)nn2)nn1] | 1-[4-(4-{2-[2-fluoro-4-(trifluoromethoxy)phenyl]acetamido}-1H-1,2,3-triazol-1-yl)butyl]-N-(pyridin-2-ylmethy)-1H-1,2,3-triazole-4-carboxamide |
| 368 | 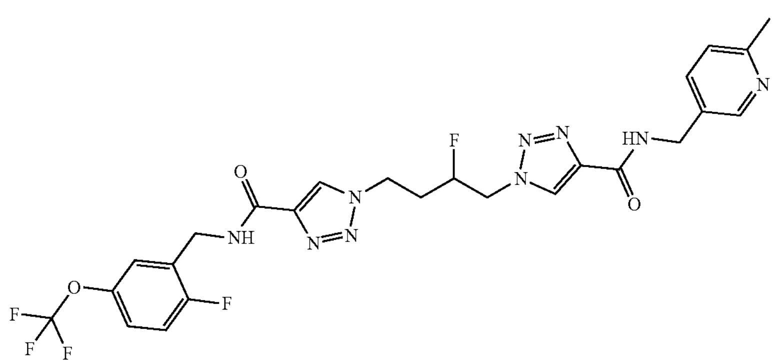 [SMILES: Cc1ccc(CNC(=O)c2cn(CC(F)CCn3cc(C(=O)NCc4cc(OC(F)(F)F)ccc4F)nn3)nn2)cn1] | 1-{2-fluoro-4-[4-({[2-fluoro-5-(trifluoromethoxy)phenyl]methyl}carbamoyl-1H-1,2,3-triazol-1-yl]butyl}-N-[(6-methylpyridin-3-yl)methyl]-1H-1,2,3-triazole-4-carboxamide |

TABLE 1-continued

Synthesized Examples

| Ex. No. | Structure | Name |
|---|---|---|
| 369 | 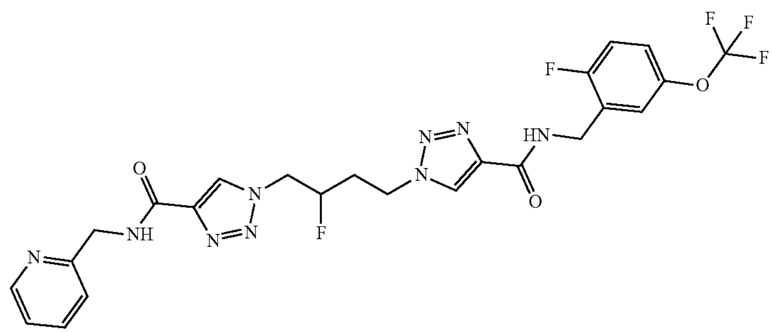 [SMILES: O=C(NCc1cc(OC(F)(F)F)ccc1F)c1cn(CCC(F)Cn2cc(C(=O)NCc3ccccn3)nn2)nn1] | 1-{2-fluoro-4-[4-({[2-fluoro-5-(trifluoromethoxy)phenyl]methyl}carbamoyl)-1H-1,2,3-triazol-1-yl]butyl}-N-(pyridin-2-ylmethyl)-1H-1,2,3-triazole-4-carboxamide |
| 370 | 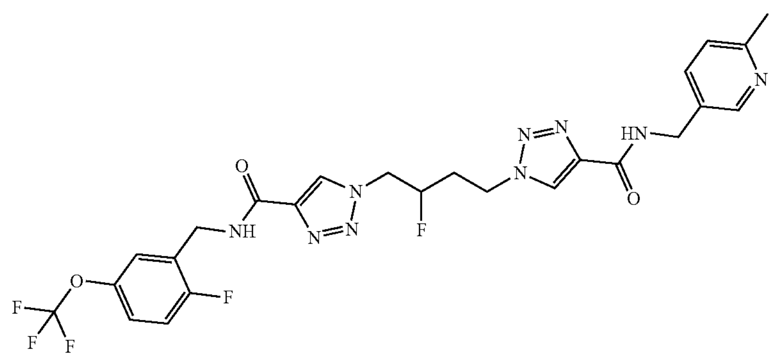 [SMILES: Cc1ccc(CNC(=O)c2cn(CCC(F)Cn3cc(C(=O)NCc4cc(OC(F)(F)F)ccc4F)nn3)nn2)cn1] | 1-{3-fluoro-4-[4-({[2-fluoro-5-(trifluoromethoxy)phenyl]methyl}carbamoyl)-1H-1,2,3-triazol-1-yl]butyl}-N-[(6-methylpyridin-3-yl)methyl]-1H-1,2,3-triazole-4-carboxamide |
| 371 | 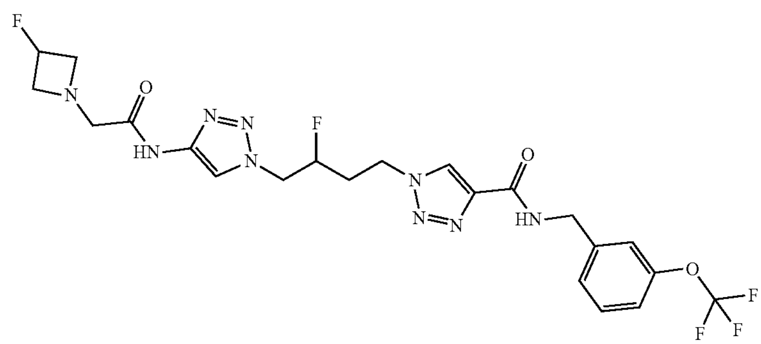 [SMILES: O=C(CN1CC(F)C1)Nc1cn(CC(F)CCn2cc(C(=O)NCc3cccc(OC(F)(F)F)c3)nn2)nn1] | 1-(3-fluoro-4-{4-[2-(3-fluoroazetidin-1-yl)acetamido]-1H-1,2,3-triazol-1-yl}butyl)-N-{[3-(trifluoromethoxy)phenyl]methyl}-1H-1,2,3-triazole-4-carboxamide |
| 372 | 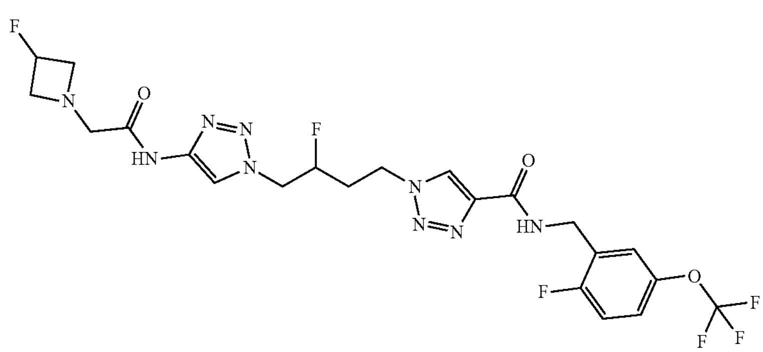 [SMILES: O=C(CN1CC(F)C1)Nc1cn(CC(F)CCn2cc(C(=O)NCc3cc(OC(F)(F)F)ccc3F)nn2)nn1] | 1-(3-fluoro-4-{4-[2-(3-fluoroazetidin-1-yl)acetamido]-1H-1,2,3-triazol-1-yl}butyl)-N-{[2-fluoro-5-(trifluoromethoxy)phenyl]methyl}-1H-1,2,3-triazole-4-carboxamide |

TABLE 1-continued

Synthesized Examples

| Ex. No. | Structure | Name |
|---|---|---|
| 373 | 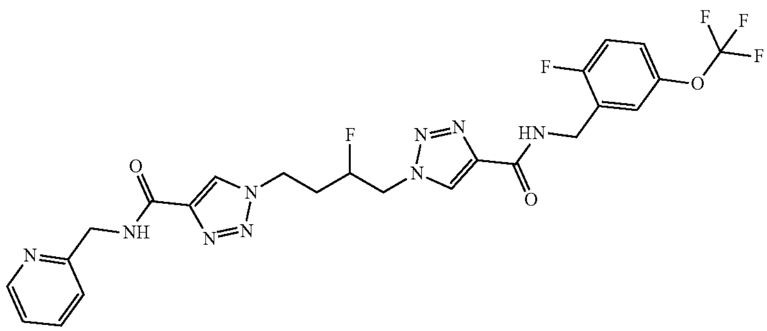 [SMILES: O=C(NCc1ccccn1)c1cn(CCC(F)Cn2cc(C(=O)NCc3cc(OC(F)(F)F)ccc3F)nn2)nn1] | 1-{3-fluoro-4-[4-({[2-fluoro-5-(trifluoromethoxy)phenyl]methyl}carbamoyl)-1H-1,2,3-triazol-1-yl]butyl}-N-(pyridin-2-ylmethyl)-1H-1,2,3-triazole-4-carboxamide |
| 374 | 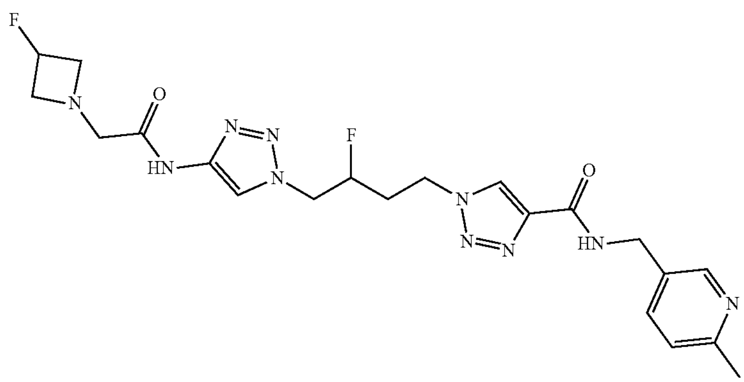 [SMILES: Cc1ccc(CNC(=O)c2cn(CCC(F)Cn3cc(NC(=O)CN4CC(F)C4)nn3)nn2)cn1] | 1-(3-fluoro-4-{4-[2-(3-fluoroazetidin-1-yl)acetamido]-1H-1,2,3-triazol-1-yl}butyl)-N-[(6-methylpyridin-3-yl)methyl]-1H-1,2,3-triazole-4-carboxamide |
| 375 | 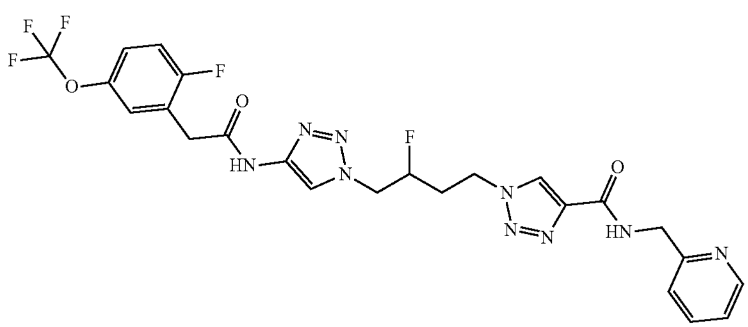 [SMILES: O=C(Cc1cc(OC(F)(F)F)ccc1F)Nc1cn(CC(F)CCn2cc(C(=O)NCc3ccccn3)nn2)nn1] | 1-[3-fluoro-4-(4-{2-[2-fluoro-5-(trifluoromethoxy)phenyl]acetamido}-1H-1,2,3-triazol-1-yl)butyl]-N-(pyridin-2-ylmethyl)-1H-1,2,3-triazole-4-carboxamide |
| 376 | 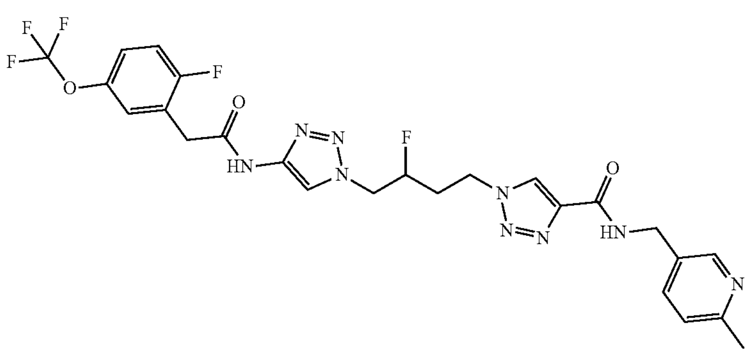 [SMILES: Cc1ccc(CNC(=O)c2cn(CCC(F)Cn3cc(NC(=O)Cc4cc(OC(F)(F)F)ccc4F)nn3)nn2)cn1] | 1-[3-fluoro-4-(4-{2-[2-fluoro-5-(trifluoromethoxy)phenyl]acetamido}-1H-1,2,3-triazol-1-yl)butyl]-N-[(6-methylpyridin-3-yl)methyl]-1H-1,2,3-triazole-4-carboxamide |

TABLE 1-continued

Synthesized Examples

| Ex. No. | Structure | Name |
|---|---|---|
| 377 | 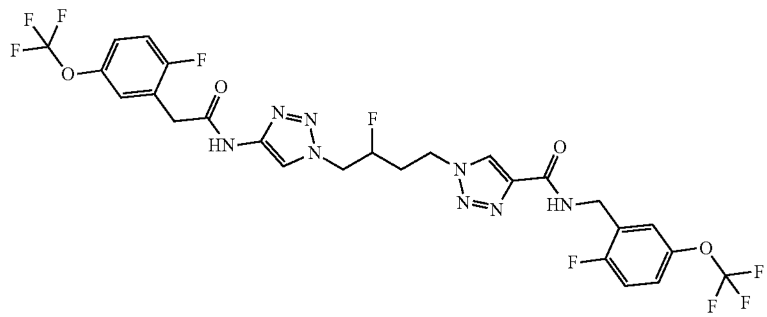 [SMILES: O=C(Cc1cc(OC(F)(F)F)ccc1F)Nc1cn(CC(F)CCn2cc(C(=O)NCc3cc(OC(F)(F)F)ccc3F)nn2)nn1] | 1-[3-fluoro-4-(4-{2-[2-fluoro-5-(trifluoromethoxy)phenyl]acetamido}-1H-1,2,3-triazol-1-yl)butyl]-N-{[2-fluoro-5-(trifluoromethoxy)phenyl]methyl}-1H-1,2,3-triazole-4-carboxamide |
| 378 | 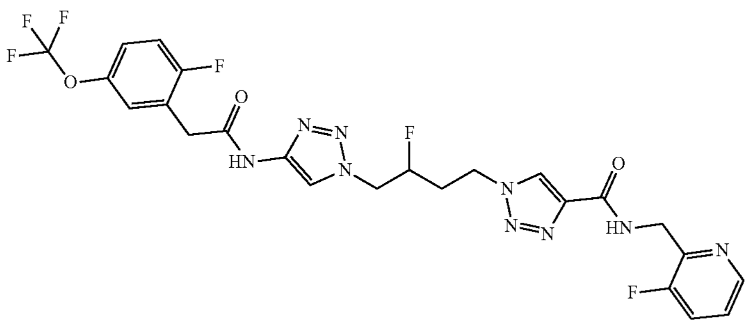 [SMILES: O=C(Cc1cc(OC(F)(F)F)ccc1F)Nc1cn(CC(F)CCn2cc(C(=O)NCc3ncccc3F)nn2)nn1] | 1-[3-fluoro-4-(4-{2-[2-fluoro-5-(trifluoromethoxy)phenyl]acetamido}-1H-1,2,3-triazol-1-yl)butyl]-N-[(3-fluoropyridin-2-yl)methyl]-1H-1,2,3-triazole-4-carboxamide |
| 379 | 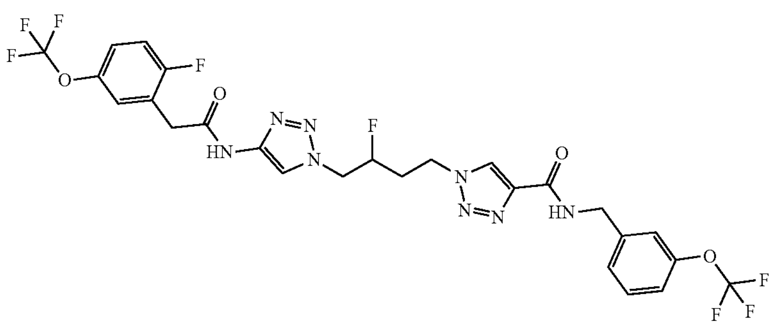 [SMILES: O=C(Cc1cc(OC(F)(F)F)ccc1F)Nc1cn(CC(F)CCn2cc(C(=O)NCc3cccc(OC(F)(F)F)c3)nn2)nn1] | 1-[3-fluoro-4-(4-{2-[2-fluoro-5-(trifluoromethoxy)phenyl]acetamido}-1H-1,2,3-triazol-1-yl)butyl]-N-{[3-(trifluoromethoxy)phenyl]methyl}-1H-1,2,3-triazole-4-carboxamide |
| 380 | 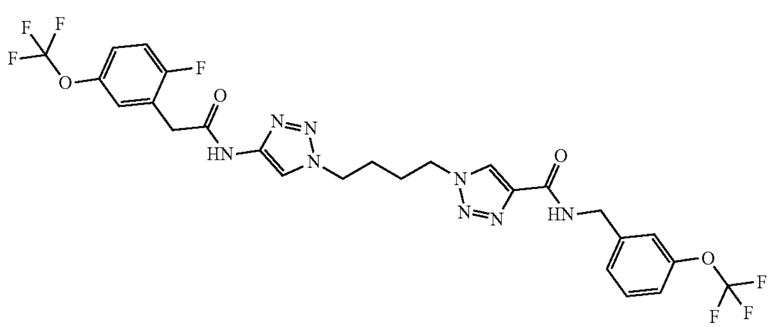 [SMILES: O=C(Cc1cc(OC(F)(F)F)ccc1F)Nc1cn(CCCCn2cc(C(=O)NCc3cccc(OC(F)(F)F)c3)nn2)nn1] | 1-[4-(4-{2-[2-fluoro-5-(trifluoromethoxy)phenyl]acetamido}-1H-1,2,3-triazol-1-yl)butyl]-N-{[3-(trifluoromethoxy)phenyl]methyl}-1H-1,2,3-triazole-4-carboxamide |

TABLE 1-continued

Synthesized Examples

| Ex. No. | Structure | Name |
|---|---|---|
| 381 | 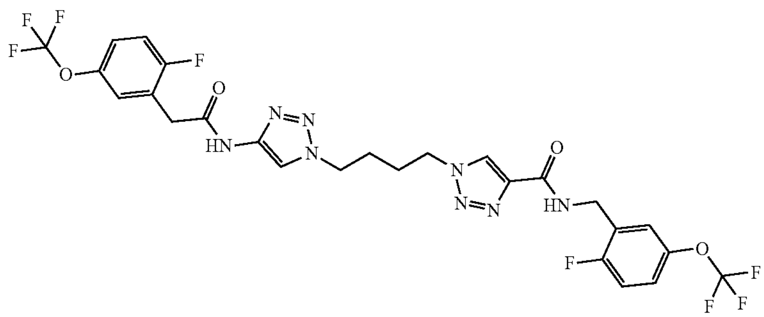 [SMILES: O=C(Cc1cc(OC(F)(F)F)ccc1F)Nc1cn(CCCCn2cc(C(=O)NCc3cc(OC(F)(F)F)ccc3F)nn2)nn1] | 1-[4-(4-{2-[2-fluoro-5-(trifluoromethoxy)phenyl]acetamido}-1H-1,2,3-triazol-1-yl)butyl]-N-{[2-fluoro-5-(trifluoromethoxy)phenyl]methyl}-1H-1,2,3-triazole-4-carboxamide |
| 382 | 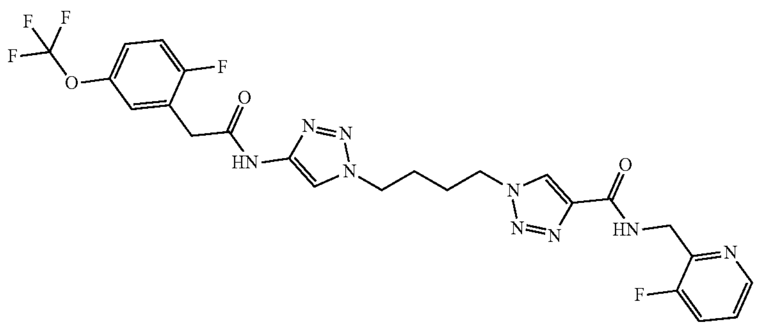 [SMILES: O=C(Cc1cc(OC(F)(F)F)ccc1F)Nc1cn(CCCCn2cc(C(=O)NCc3ncccc3F)nn2)nn1] | 1-[4-(4-{2-[2-fluoro-5-(trifluoromethoxy)phenyl]acetamido}-1H-1,2,3-triazol-1-yl)butyl]-N-[(3-fluoropyridin-2-yl)methyl]-1H-1,2,3-triazole-4-carboxamide |
| 383 | 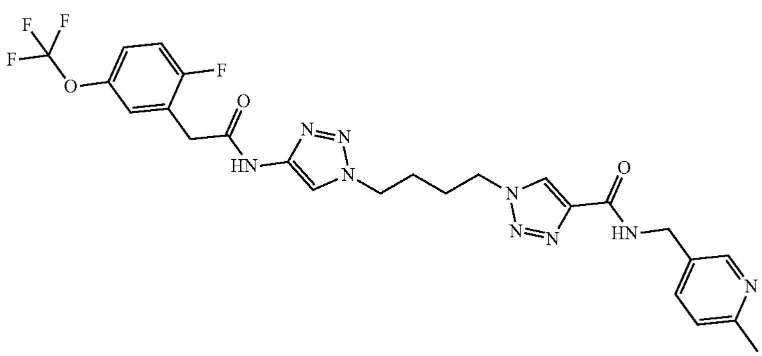 [SMILES: Cc1ccc(CNC(=O)c2cn(CCCCn3cc(NC(=O)Cc4cc(OC(F)(F)F)ccc4F)nn3)nn2)cn1] | 1-[4-(4-{2-[2-fluoro-5-(trifluoromethoxy)phenyl]acetamido}-1H-1,2,3-triazol-1-yl)butyl]-N-[(6-methylpyridin-3-yl)methyl]-1H-1,2,3-triazole-4-carboxamide |
| 384 | 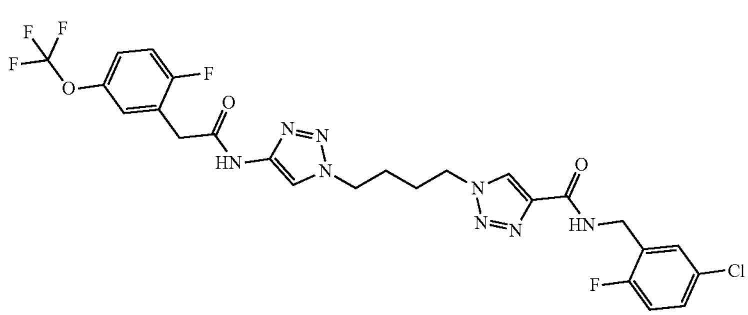 [SMILES: O=C(Cc1cc(OC(F)(F)F)ccc1F)Nc1cn(CCCCn2cc(C(=O)NCc3cc(Cl)ccc3F)nn2)nn1] | N-[(5-chloro-2-fluorophenyl)methyl]-1-[4-(4-{2-[2-fluoro-5-(trifluoromethoxy)phenyl]acetamido}-1H-1,2,3-triazol-1-yl)butyl]-1H-1,2,3-triazole-4-carboxamide |

TABLE 1-continued

Synthesized Examples

| Ex. No. | Structure | Name |
| --- | --- | --- |
| 385 | 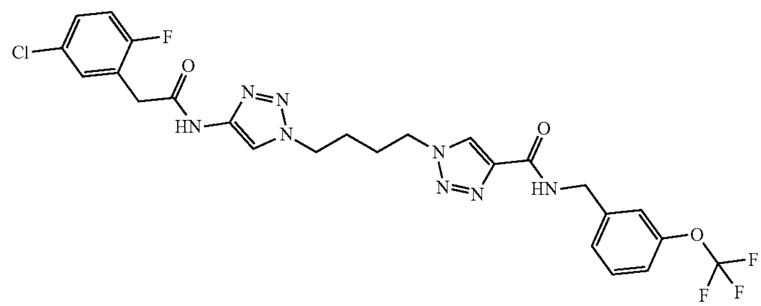 [SMILES: O=C(Cc1cc(Cl)ccc1F)Nc1cn(CCCCn2cc(C(=O)NCc3cccc(OC(F)(F)F)c3)nn2)nn1] | 1-(4-{4-[2-(5-chloro-2-fluorophenyl)acetamido]-1H-1,2,3-triazol-1-yl}butyl)-N-{[3-(trifluoromethoxy)phenyl]methyl}-1H-1,2,3-triazole-4-carboxamide |
| 386 | 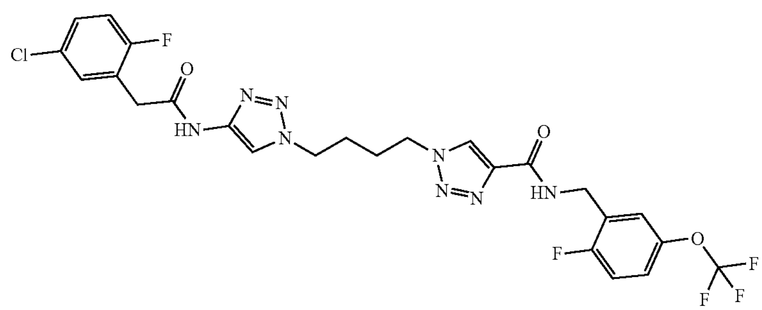 [SMILES: O=C(Cc1cc(Cl)ccc1F)Nc1cn(CCCCn2cc(C(=O)NCc3cc(OC(F)(F)F)ccc3F)nn2)nn1] | 1-(4-{4-[2-(5-chloro-2-fluorophenyl)acetamido]-1H-1,2,3-triazol-1-yl}butyl)-N-{[2-fluoro-5-(trifluoromethoxy)phenyl]methyl}-1H-1,2,3-triazole-4-carboxamide |
| 387 | 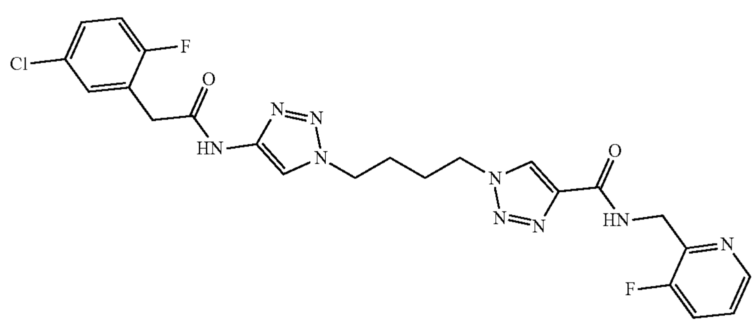 [SMILES: O=C(Cc1cc(Cl)ccc1F)Nc1cn(CCCCn2cc(C(=O)NCc3ncccc3F)nn2)nn1] | 1-(4-{4-[2-(5-chloro-2-fluorophenyl)acetamido]-1H-1,2,3-triazol-1-yl}butyl)-N-[(3-fluoropyridin-2-yl)methyl]-1H-1,2,3-triazole-4-carboxamide |
| 388 | 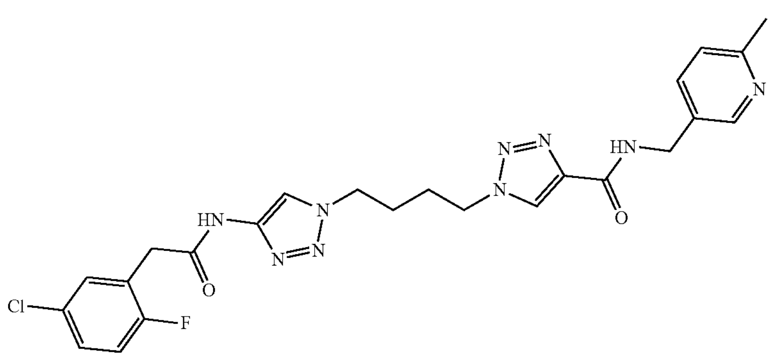 [SMILES: Cc1ccc(CNC(=O)c2cn(CCCCn3cc(NC(=O)Cc4cc(Cl)ccc4F)nn3)nn2)cn1] | 1-(4-{4-[2-(5-chloro-2-fluorophenyl)acetamido]-1H-1,2,3-triazol-1-yl}butyl)-N-[(6-methylpyridin-3-yl)methyl]-1H-1,2,3-triazole-4-carboxamide |

TABLE 1-continued

Synthesized Examples

| Ex. No. | Structure | Name |
|---|---|---|
| 389 | 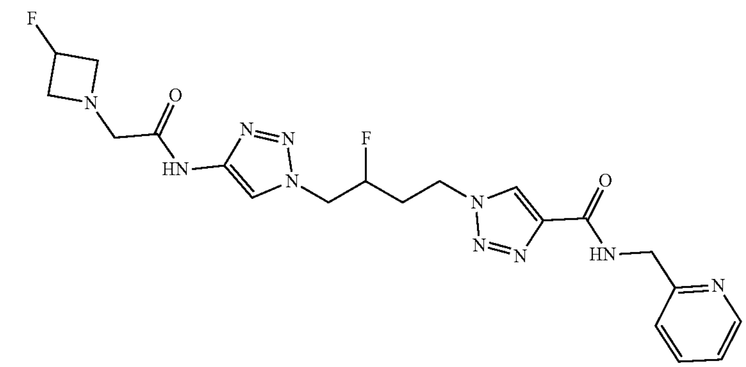 [SMILES: O=C(CN1CC(F)C1)Nc1cn(CC(F)CCn2cc(C(=O)NCc3ccccn3)nn2)nn1] | 1-(3-fluoro-4-{4-[2-(3-fluoroazetidin-1-yl)acetamido]-1H-1,2,3-triazol-1-yl}butyl)-N-(pyridin-2-ylmethyl)-1H-1,2,3-triazole-4-carboxamide |
| 390 | 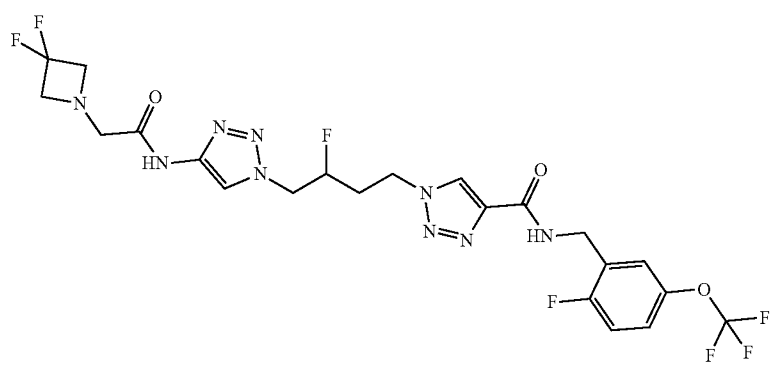 [SMILES: O=C(CN1CC(F)(F)C1)Nc1cn(CC(F)CCn2cc(C(=O)NCc3cc(OC(F)(F)F)ccc3F)nn2)nn1] | 1-(4-{4-[2-(3,3-difluoroazetidin-1-yl)acetamido]-1H-1,2,3-triazol-1-yl}-3-fluorobutyl)-N-{[2-fluoro-5-(trifluoromethoxy)phenyl]methyl}-1H-1,2,3-triazole-4-carboxamide |
| 391 | 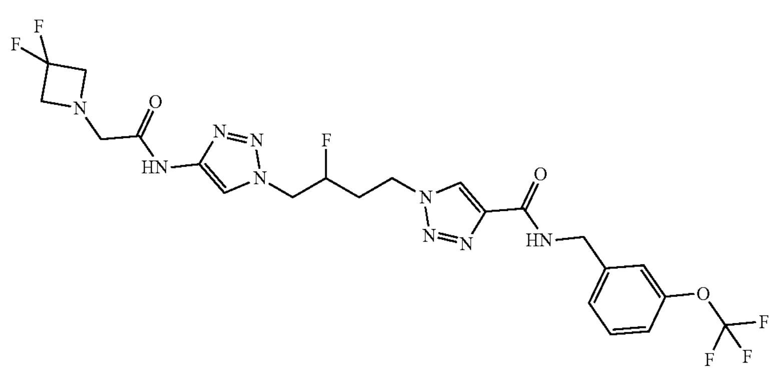 [SMILES: O=C(CN1CC(F)(F)C1)Nc1cn(CC(F)CCn2cc(C(=O)NCc3cccc(OC(F)(F)F)c3)nn2)nn1] | 1-(4-{4-[2-(3,3-difluoroazetidin-1-yl)acetamido]-1H-1,2,3-triazol-1-yl}-3-fluorobutyl)-N-{[3-(trifluoromethoxy)phenyl]methyl}-1H-1,2,3-triazole-4-carboxamide |
| 392 | 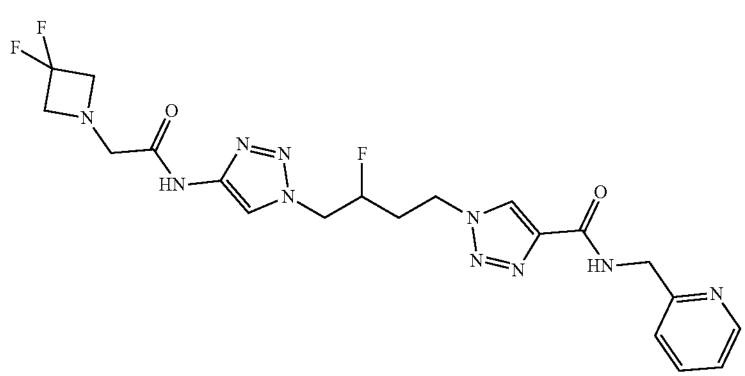 [SMILES: O=C(CN1CC(F)(F)C1)Nc1cn(CC(F)CCn2cc(C(=O)NCc3ccccn3)nn2)nn1] | 1-(4-{4-[2-(3,3-difluoroazetidin-1-yl)acetamido]-1H-1,2,3-triazol-1-yl}-3-fluorobutyl)-N-(pyridin-2-ylmethyl)-1H-1,2,3-triazole-4-carboxamide |

TABLE 1-continued

Synthesized Examples

| Ex. No. | Structure | Name |
| --- | --- | --- |
| 393 | 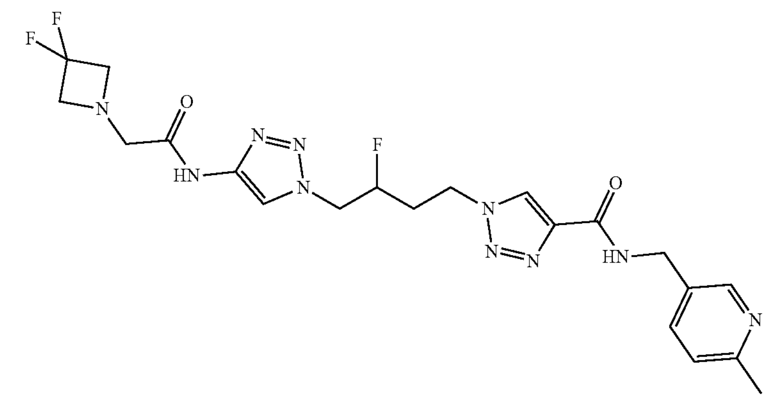 [SMILES: Cc1ccc(CNC(=O)c2cn(CCC(F)Cn3cc(NC(=O)CN4CC(F)(F)C4)nn3)nn2)cn1] | 1-(4-{4-[2-(3,3-difluoroazetidin-1-yl)acetamido]-1H-1,2,3-triazol-1-yl}-3-fluorobutyl)-N-[(6-methylpyridin-3-yl)methyl]-1H-1,2,3-triazole-4-carboxamide |
| 394 | 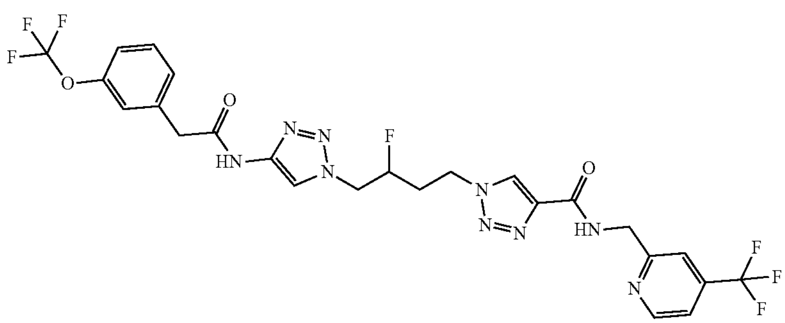 [SMILES: O=C(Cc1cccc(OC(F)(F)F)c1)Nc1cn(CC(F)CCn2cc(C(=O)NCc3cc(C(F)(F)F)ccn3)nn2)nn1] | 1-[3-fluoro-4-(4-{2-[3-(trifluoromethoxy)phenyl]acetamido}-1H-1,2,3-triazol-1-yl)butyl]-N-{[4-(trifluoromethyl)pyridin-2-yl]methyl}-1H-1,2,3-triazole-4-carboxamide |
| 395 | 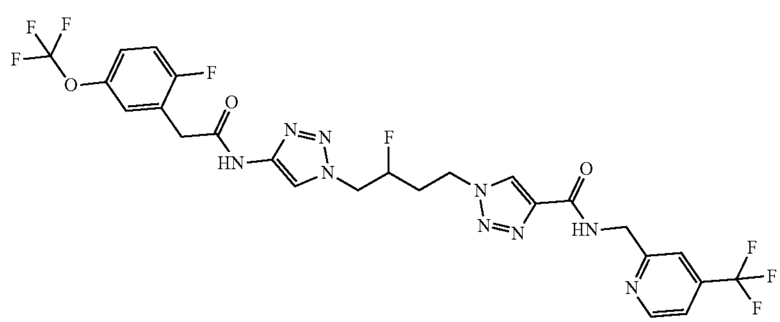 [SMILES: O=C(Cc1cc(OC(F)(F)F)ccc1F)Nc1cn(CC(F)CCn2cc(C(=O)NCc3cc(C(F)(F)F)ccn3)nn2)nn1] | 1-[3-fluoro-4-(4-{2-[2-fluoro-5-(trifluoromethoxy)phenyl]acetamido}-1H-1,2,3-triazol-1-yl)butyl]-N-{[4-(trifluoromethyl)pyridin-2-yl]methyl}-1H-1,2,3-triazole-4-carboxamide |
| 396 | 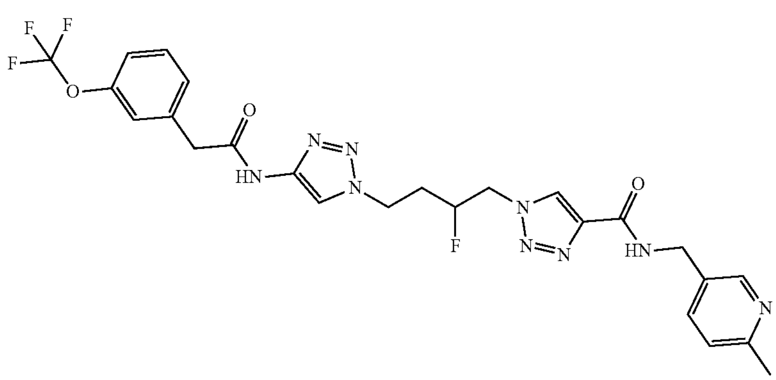 [SMILES: Cc1ccc(CNC(=O)c2cn(CC(F)CCn3cc(NC(=O)Cc4cccc(OC(F)(F)F)c4)nn3)nn2)cn1] | 1-[2-fluoro-4-(4-{2-[3-(trifluoromethoxy)phenyl]acetamido}-1H-1,2,3-triazol-1-yl)butyl]-N-[(6-methylpyridin-3-yl)methyl]-1H-1,2,3-triazole-4-carboxamide |

TABLE 1-continued

Synthesized Examples

| Ex. No. | Structure | Name |
|---|---|---|
| 397 | 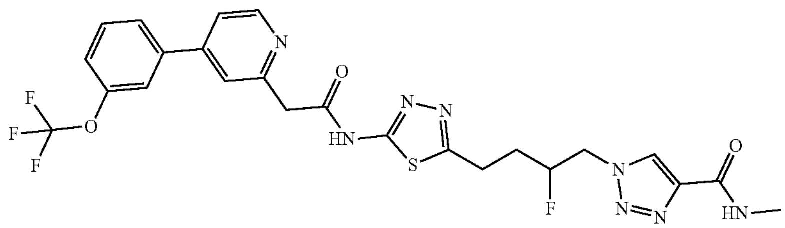 [SMILES: CNC(=O)c1cn(CC(F)CCc2nnc(NC(=O)Cc3cc(-c4cccc(OC(F)(F)F)c4)ccn3)s2)nn1] | 1-(2-fluoro-4-(5-(2-(4-(3-(trifluoromethoxy)phenyl)pyridin-2-yl)acetamido)-1,3,4-thiadiazol-2-yl)butyl)-N-methyl-1H-1,2,3-triazole-4-carboxamide |
| 398 | 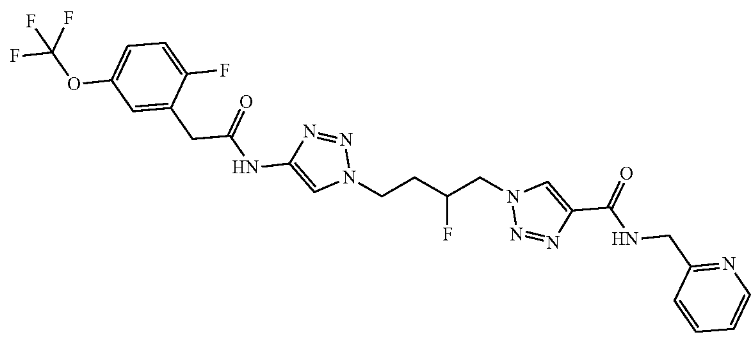 [SMILES: O=C(Cc1cc(OC(F)(F)F)ccc1F)Nc1cn(CCC(F)Cn2cc(C(=O)NCc3ccccn3)nn2)nn1] | 1-[2-fluoro-4-(4-{2-[2-fluoro-5-(trifluoromethoxy)phenyl]acetamido}-1H-1,2,3-triazol-1-yl)butyl]-N-(pyridin-2-ylmethyl)-1H-1,2,3-triazole-4-carboxamide |
| 399 | 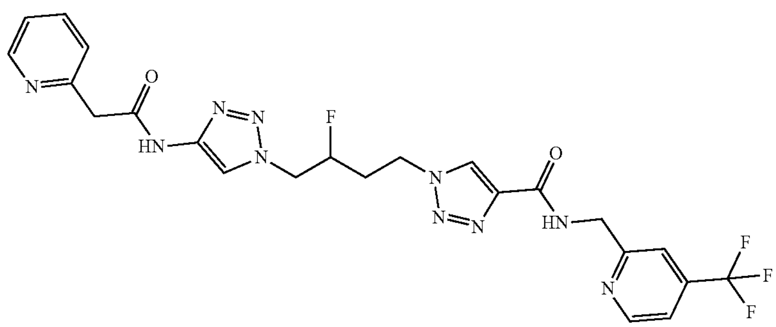 [SMILES: O=C(Cc1ccccn1)Nc1cn(CC(F)CCn2cc(C(=O)NCc3cc(C(F)(F)F)ccn3)nn2)nn1] | 1-(3-fluoro-4-{4-[2-(pyridin-2-yl)acetamido]-1H-1,2,3-triazol-1-yl}butyl)-N-{[4-(trifluoromethyl)pyridin-2-yl]methyl}-1H-1,2,3-triazole-4-carboxamide |
| 400 | 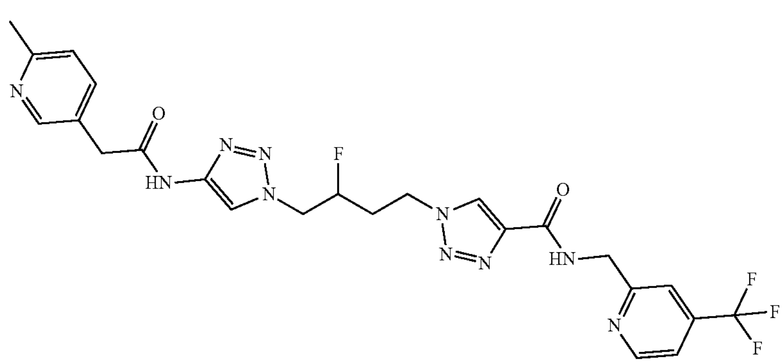 [SMILES: Cc1ccc(CC(=O)Nc2cn(CC(F)CCn3cc(C(=O)NCc4cc(C(F)(F)F)ccn4)nn3)nn2)cn1] | 1-(3-fluoro-4-{4-[2-(6-methylpyridin-3-yl)acetamido]-1H-1,2,3-triazol-1-yl}butyl)-N-{[4-(trifluoromethyl)pyridin-2-yl]methyl}-1H-1,2,3-triazole-4-carboxamide |

TABLE 1-continued

Synthesized Examples

| Ex. No. | Structure | Name |
|---|---|---|
| 401 | 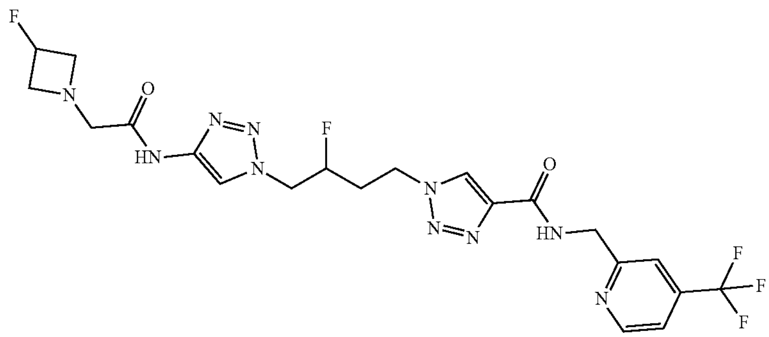 [SMILES: O=C(CN1CC(F)C1)Nc1cn(CC(F)CCn2cc(C(=O)NCc3cc(C(F)(F)F)ccn3)nn2)nn1] | 1-(3-fluoro-4-{4-[2-(3-fluoroazetidin-1-yl)acetamido]-1H-1,2,3-triazol-1-yl}butyl)-N-{[4-(trifluoromethyl)pyridin-2-yl]methyl}-1H-1,2,3-triazole-4-carboxamide |
| 402 | 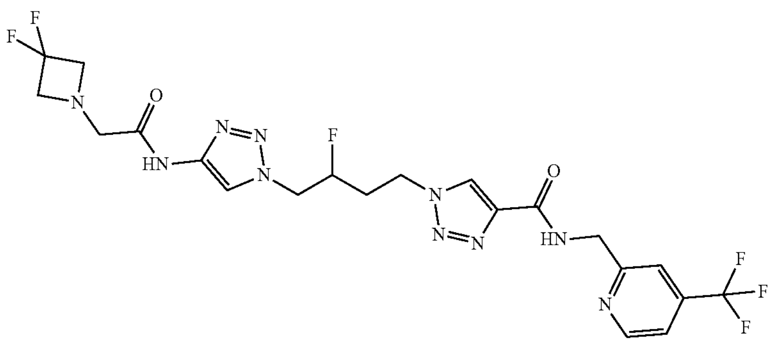 [SMILES: O=C(CN1CC(F)(F)C1)Nc1cn(CC(F)CCn2cc(C(=O)NCc3cc(C(F)(F)F)ccn3)nn2)nn1] | 1-(4-{4-[2-(3,3-difluoroazetidin-1-yl)acetamido]-1H-1,2,3-triazol-1-yl}-3-fluorobutyl)-N-{[4-(trifluoromethyl)pyridin-2-yl]methyl}-1H-1,2,3-triazole-4-carboxamide |
| 403 | 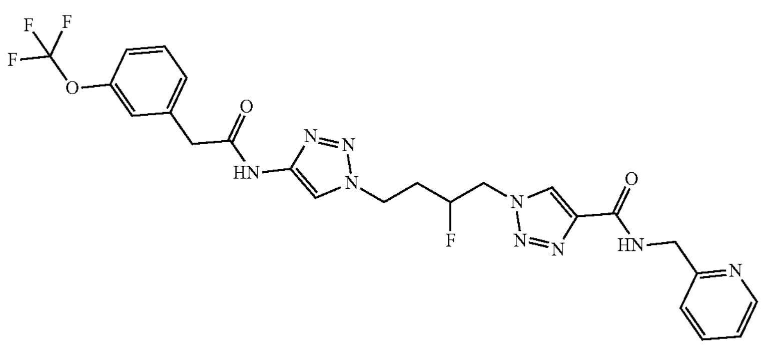 [SMILES: O=C(Cc1cccc(OC(F)(F)F)c1)Nc1cn(CCC(F)Cn2cc(C(=O)NCc3ccccn3)nn2)nn1] | 1-[2-fluoro-4-(4-{2-[3-(trifluoromethoxy)phenyl]acetamido}-1H-1,2,3-triazol-1-yl)butyl]-N-(pyridin-2-ylmethyl)-1H-1,2,3-triazole-4-carboxamide |
| 404 | 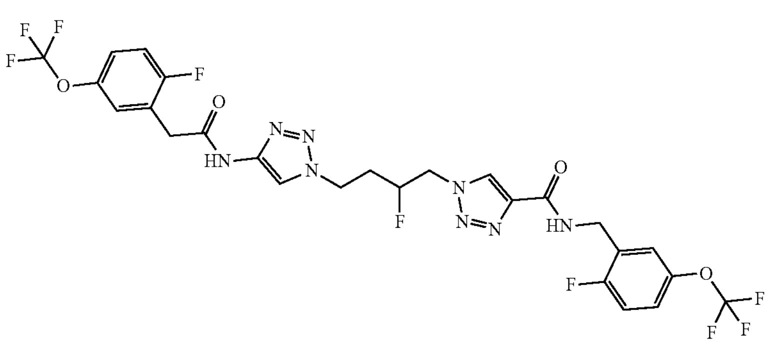 [SMILES: O=C(Cc1cc(OC(F)(F)F)ccc1F)Nc1cn(CCC(F)Cn2cc(C(=O)NCc3cc(OC(F)(F)F)ccc3F)nn2)nn1] | 1-[2-fluoro-4-(4-{2-[2-fluoro-5-(trifluoromethoxy)phenyl]acetamido}-1H-1,2,3-triazol-1-yl)butyl]-N-{[2-fluoro-5-(trifluoromethoxy)phenyl]methyl}-1H-1,2,3-triazole-4-carboxamide |

TABLE 1-continued

Synthesized Examples

| Ex. No. | Structure | Name |
|---|---|---|
| 405 | 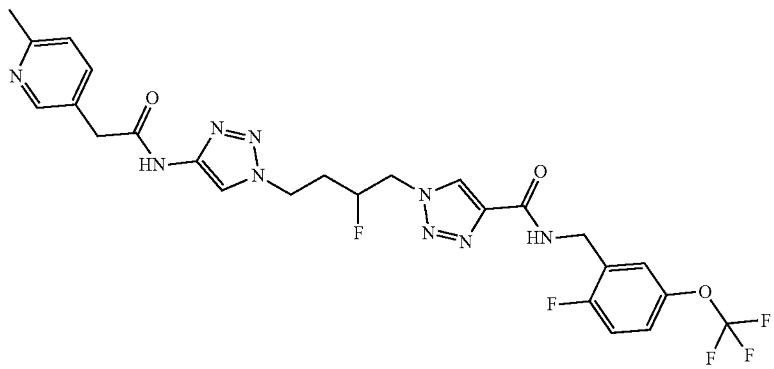 [SMILES: Cc1ccc(CC(=O)Nc2cn(CCC(F)Cn3cc(C(=O)NCc4cc(OC(F)(F)F)ccc4F)nn3)nn2)cn1] | 1-(2-fluoro-4-{4-[2-(6-methylpyridin-3-yl)acetamido]-1H-1,2,3-triazol-1-yl}butyl)-N-{[2-fluoro-5-(trifluoromethoxy)phenyl]methyl}-1H-1,2,3-triazole-4-carboxamide |
| 406 | 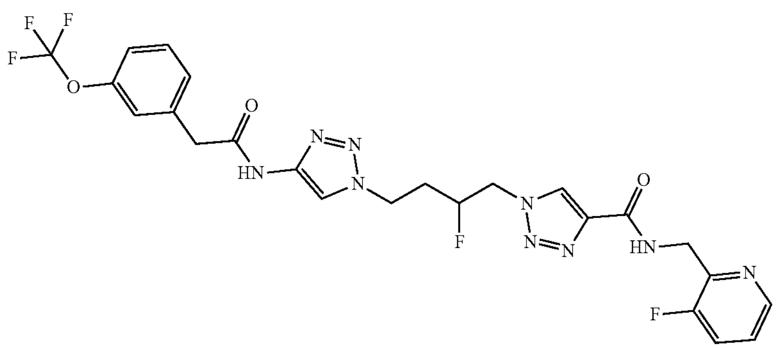 [SMILES: O=C(Cc1cccc(OC(F)(F)F)c1)Nc1cn(CCC(F)Cn2cc(C(=O)NCc3ncccc3F)nn2)nn1] | 1-[2-fluoro-4-(4-{2-[3-(trifluoromethoxy)phenyl]acetamido}-1H-1,2,3-triazol-1-yl)butyl]-N-[(3-fluoropyridin-2-yl)methyl]-1H-1,2,3-triazole-4-carboxamide |
| 407 | 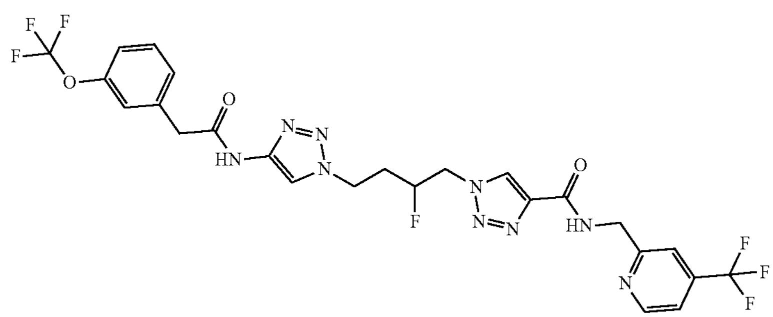 [SMILES: O=C(Cc1cccc(OC(F)(F)F)c1)Nc1cn(CCC(F)Cn2cc(C(=O)NCc3cc(C(F)(F)F)ccn3)nn2)nn1] | 1-[2-fluoro-4-(4-{2-[3-(trifluoromethoxy)phenyl]acetamido}-1H-1,2,3-triazol-1-yl)butyl]-N-{[4-(trifluoromethyl)pyridin-2-yl]methyl}-1H-1,2,3-triazole-4-carboxamide |
| 408 | 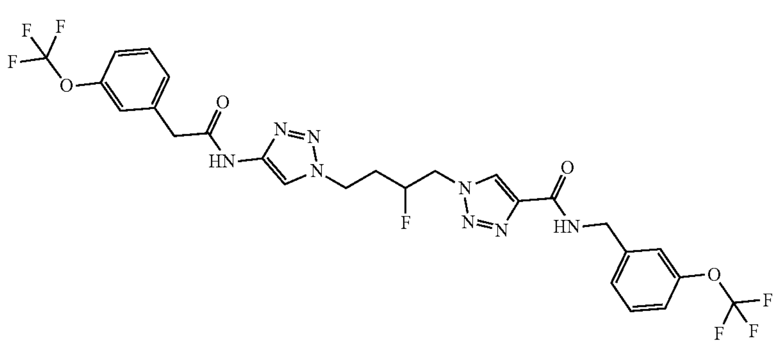 [SMILES: O=C(Cc1cccc(OC(F)(F)F)c1)Nc1cn(CCC(F)Cn2cc(C(=O)NCc3cccc(OC(F)(F)F)c3)nn2)nn1] | 1-[2-fluoro-4-(4-{2-[3-(trifluoromethoxy)phenyl]acetamido}-1H-1,2,3-triazol-1-yl)butyl]-N-{[3-(trifluoromethoxy)phenyl]methyl}-1H-1,2,3-triazole-4-carboxamide |

TABLE 1-continued

Synthesized Examples

| Ex. No. | Structure | Name |
|---|---|---|
| 409 | 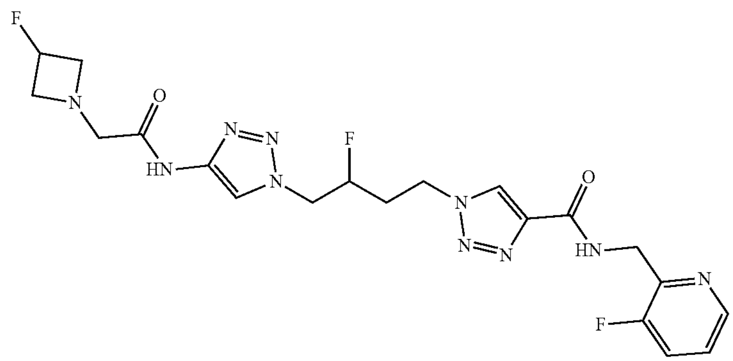 [SMILES: O=C(CN1CC(F)C1)Nc1cn(CC(F)CCn2cc(C(=O)NCc3ncccc3F)nn2)nn1] | 1-(3-fluoro-4-{4-[2-(3-fluoroazetidin-1-yl)acetamido]-1H-1,2,3-triazol-1-yl}butyl)-N-[(3-fluoropyridin-2-yl)methyl]-1H-1,2,3-triazole-4-carboxamide |
| 410 | 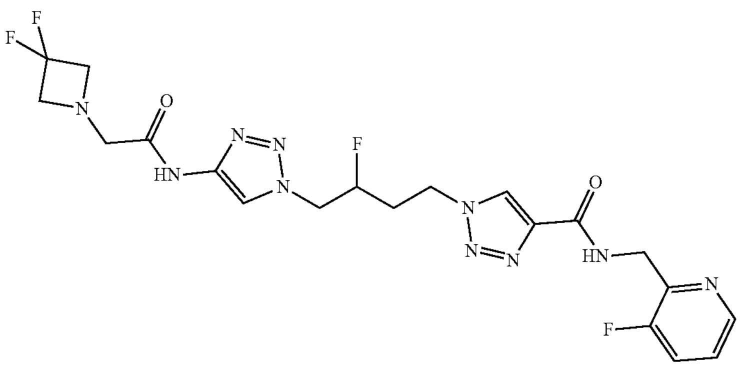 [SMILES: O=C(CN1CC(F)(F)C1)Nc1cn(CC(F)CCn2cc(C(=O)NCc3ncccc3F)nn2)nn1] | 1-(4-{4-[2-(3,3-difluoroazetidin-1-yl)acetamido]-1H-1,2,3-triazol-1-yl}-3-fluorobutyl)-N-[(3-fluoropyridin-2-yl)methyl]-1H-1,2,3-triazole-4-carboxamide |
| 411 | 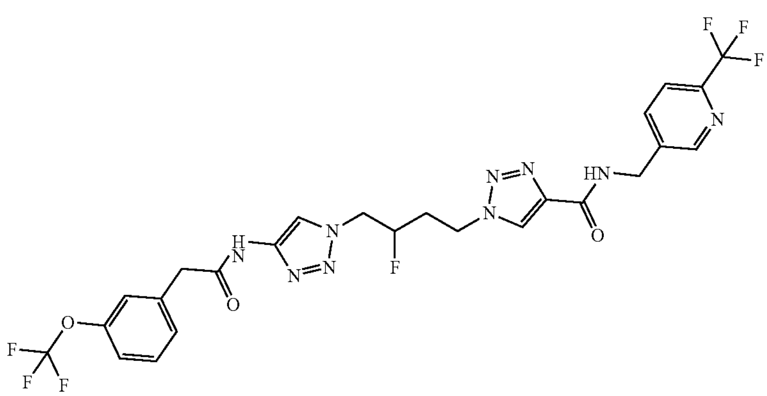 [SMILES: O=C(Cc1cccc(OC(F)(F)F)c1)Nc1cn(CC(F)CCn2cc(C(=O)NCc3ccc(C(F)(F)F)nc3)nn2)nn1] | 1-[3-fluoro-4-(4-{2-[3-(trifluoromethoxy)phenyl]acetamido}-1H-1,2,3-triazol-1-yl)butyl]-N-{[6-(trifluoromethyl)pyridin-3-yl]methyl}-1H-1,2,3-triazole-4-carboxamide |
| 412 | 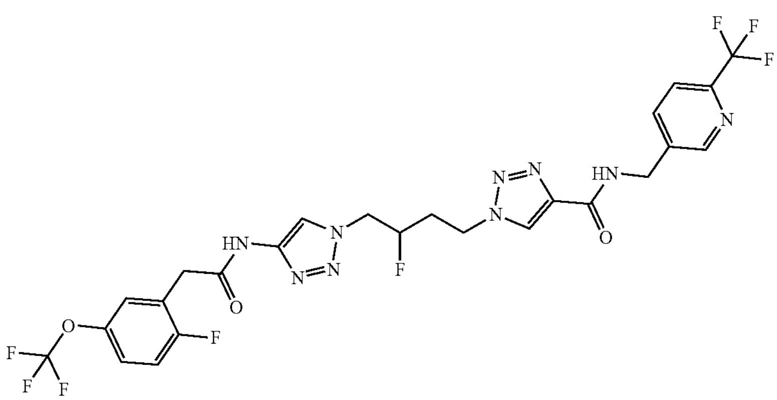 [SMILES: O=C(Cc1cc(OC(F)(F)F)ccc1F)Nc1cn(CC(F)CCn2cc(C(=O)NCc3ccc(C(F)(F)F)nc3)nn2)nn1] | 1-[3-fluoro-4-(4-{2-[2-fluoro-5-(trifluoromethoxy)phenyl]acetamido}-1H-1,2,3-triazol-1-yl)butyl]-N-{[6-(trifluoromethyl)pyridin-3-yl]methyl}-1H-1,2,3-triazole-4-carboxamide |

TABLE 1-continued

Synthesized Examples

| Ex. No. | Structure | Name |
|---|---|---|
| 413 | 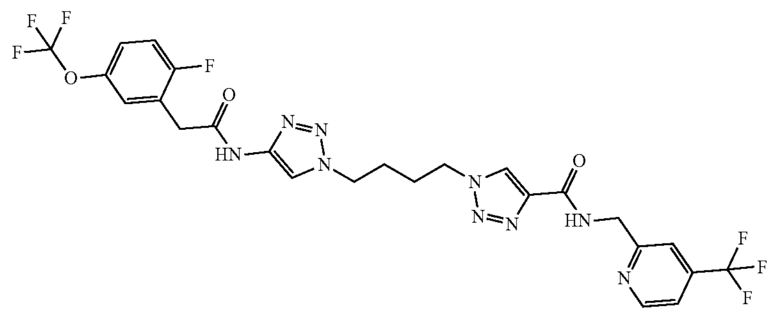 [SMILES: O=C(Cc1cc(OC(F)(F)F)ccc1F)Nc1cn(CCCCn2cc(C(=O)NCc3cc(C(F)(F)F)ccn3)nn2)nn1] | 1-[4-(4-{2-[2-fluoro-5-(trifluoromethoxy)phenyl]acetamido}-1H-1,2,3-triazol-1-yl)butyl]-N-{[4-(trifluoromethyl)pyridin-2-yl]methyl}-1H-1,2,3-triazole-4-carboxamide |
| 414 | 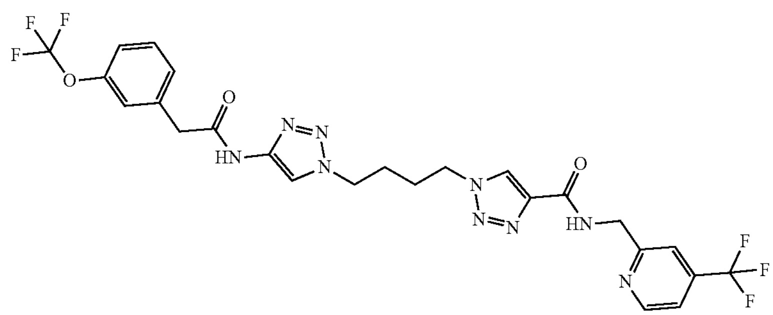 [SMILES: O=C(Cc1cccc(OC(F)(F)F)c1)Nc1cn(CCCCn2cc(C(=O)NCc3cc(C(F)(F)F)ccn3)nn2)nn1] | 1-[4-(4-{2-[3-(trifluoromethoxy)phenyl]acetamido}-1H-1,2,3-triazol-1-yl)butyl]-N-{[4-(trifluoromethyl)pyridin-2-yl]methyl}-1H-1,2,3-triazole-4-carboxamide |
| 415 | 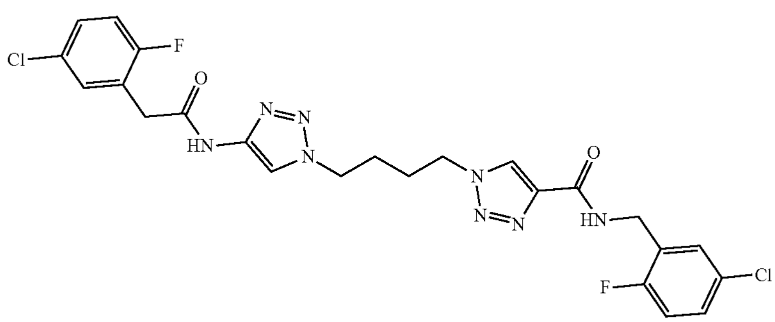 [SMILES: O=C(Cc1cc(Cl)ccc1F)Nc1cn(CCCCn2cc(C(=O)NCc3cc(Cl)ccc3F)nn2)nn1] | 1-(4-{4-[2-(5-chloro-2-fluorophenyl)acetamido]-1H-1,2,3-triazol-1-yl}butyl)-N-[(5-chloro-2-fluorophenyl)methyl]-1H-1,2,3-triazole-4-carboxamide |
| 416 | 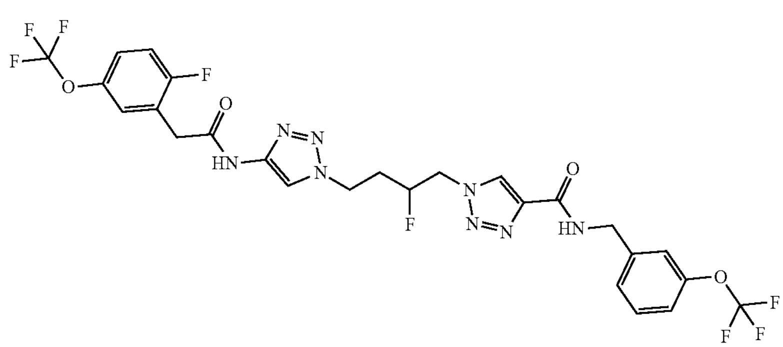 [SMILES: O=C(Cc1cc(OC(F)(F)F)ccc1F)Nc1cn(CCC(F)Cn2cc(C(=O)NCc3cccc(OC(F)(F)F)c3)nn2)nn1] | 1-[2-fluoro-4-(4-{2-[2-fluoro-5-(trifluoromethoxy)phenyl]acetamido}-1H-1,2,3-triazol-1-yl)butyl]-N-{[3-(trifluoromethoxy)phenyl]methyl}-1H-1,2,3-triazole-4-carboxamide |

TABLE 1-continued

Synthesized Examples

| Ex. No. | Structure | Name |
|---|---|---|
| 417 | 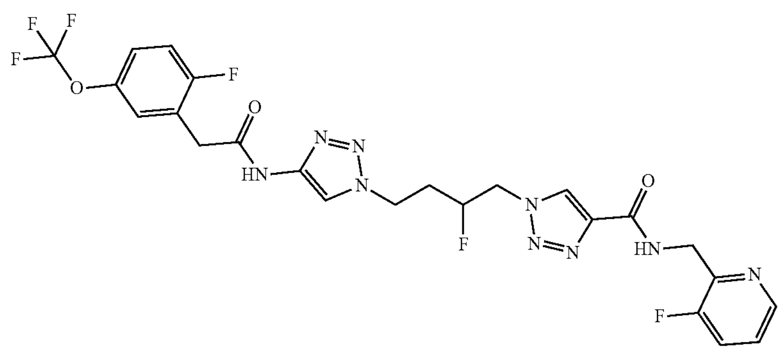 [SMILES: O=C(Cc1cc(OC(F)(F)F)ccc1F)Nc1cn(CCC(F)Cn2cc(C(=O)NCc3ncccc3F)nn2)nn1] | 1-[2-fluoro-4-(4-{2-[2-fluoro-5-(trifluoromethoxy)phenyl]acetamido}-1H-1,2,3-triazol-1-yl)butyl]-N-[(3-fluoropyridin-2-yl)methyl]-1H-1,2,3-triazole-4-carboxamide |
| 418 | 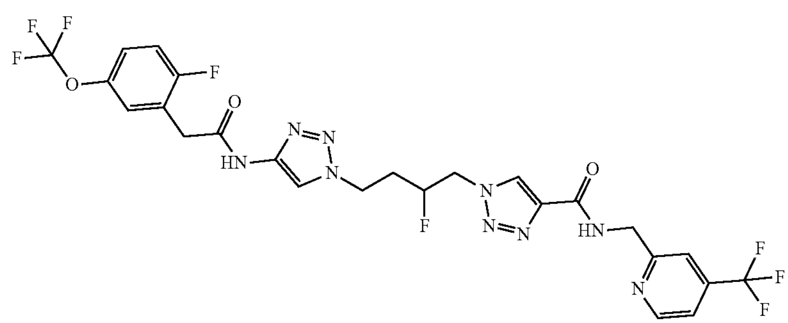 [SMILES: O=C(Cc1cc(OC(F)(F)F)ccc1F)Nc1cn(CCC(F)Cn2cc(C(=O)NCc3cc(C(F)(F)F)ccn3)nn2)nn1] | 1-[2-fluoro-4-(4-{2-[2-fluoro-5-(trifluoromethoxy)phenyl]acetamido}-1H-1,2,3-triazol-1-yl)butyl]-N-{[4-(trifluoromethyl)pyridin-2-yl]methyl}-1H-1,2,3-triazole-4-carboxamide |
| 419 | 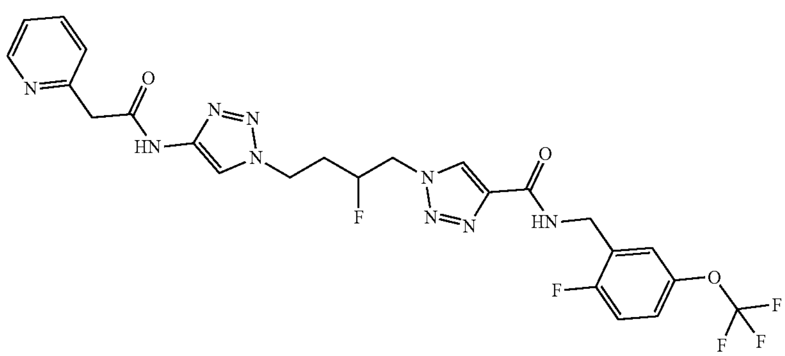 [SMILES: O=C(Cc1ccccn1)Nc1cn(CCC(F)Cn2cc(C(=O)NCc3cc(OC(F)(F)F)ccc3F)nn2)nn1] | 1-(2-fluoro-4-{4-[2-(pyridin-2-yl)acetamido]-1H-1,2,3-triazol-1-yl}butyl)-N-{[2-fluoro-5-(trifluoromethoxy)phenyl]methyl}-1H-1,2,3-triazole-4-carboxamide |
| 420 | 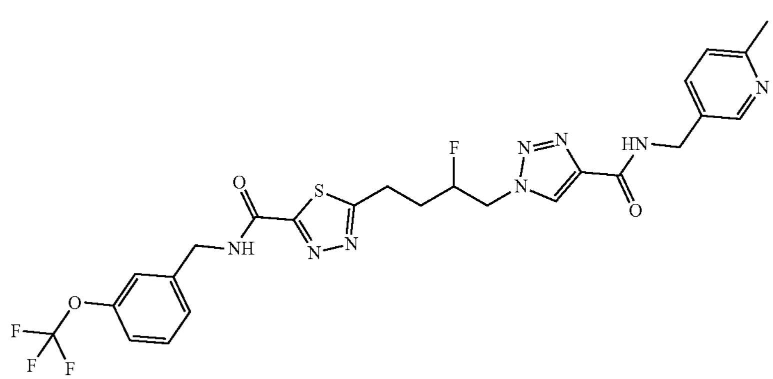 [SMILES: Cc1ccc(CNC(=O)c2cn(CC(F)CCc3nnc(C(=O)NCc4cccc(OC(F)(F)F)c4)s3)nn2)cn1] | 5-[3-fluoro-4-(4-{[(6-methylpyridin-3-yl)methyl]carbamoyl}-1H-1,2,3-triazol-1-yl)butyl]-N-{[3-(trifluoromethoxy)phenyl]methyl}-1,3,4-thiadiazole-2-carboxamide |

TABLE 1-continued

Synthesized Examples

| Ex. No. | Structure | Name |
|---|---|---|
| 421 | 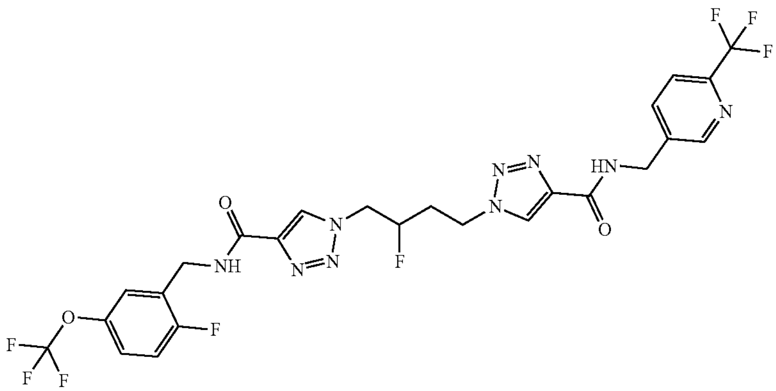 [SMILES: O=C(NCc1ccc(C(F)(F)F)nc1)c1cn(CCC(F)Cn2cc(C(=O)NCc3cc(OC(F)(F)F)ccc3F)nn2)nn1] | 1-{2-fluoro-4-[4-({[6-(trifluoromethyl)pyridin-3-yl]methyl}carbamoyl)-1H-1,2,3-triazol-1-yl]butyl}-N-{[2-fluoro-5-(trifluoromethoxy)phenyl]methyl}-1H-1,2,3-triazole-4-carboxamide |
| 422 | 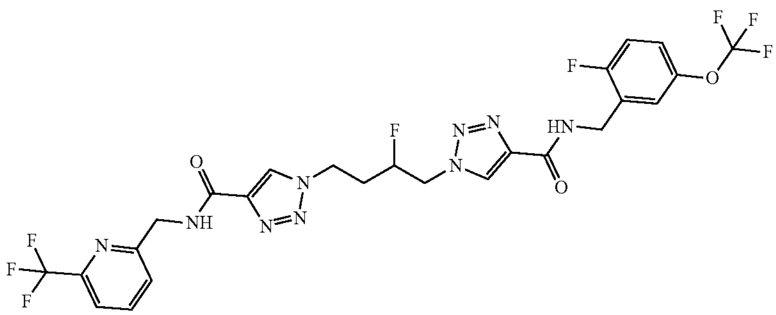 [SMILES: O=C(NCc1cccc(C(F)(F)F)n1)c1cn(CCC(F)Cn2cc(C(=O)NCc3cc(OC(F)(F)F)ccc3F)nn2)nn1] | 1-{2-fluoro-4-[5-({[6-(trifluoromethyl)pyridin-2-yl]methyl}carbamoyl)-1H-1,2,3-triazol-1-yl]butyl}-N-{[2-fluoro-5-(trifluoromethoxy)phenyl]methyl}-1H-1,2,3-triazole-4-carboxamide |
| 423 | 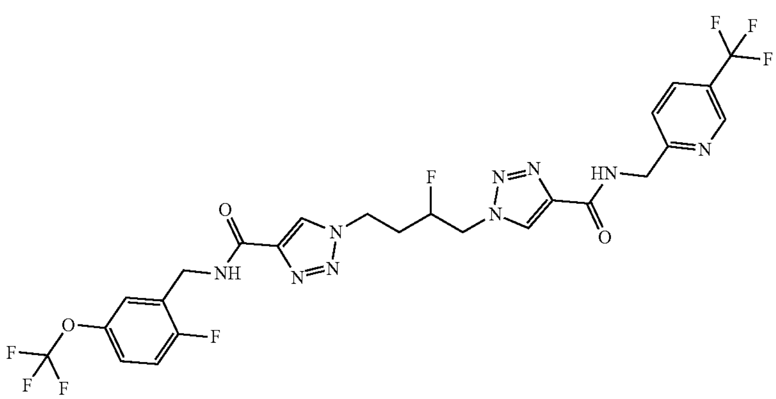 [SMILES: O=C(NCc1cc(OC(F)(F)F)ccc1F)c1cn(CCC(F)Cn2cc(C(=O)NCc3ccc(C(F)(F)F)cn3)nn2)nn1] | 1-{2-fluoro-4-[4-({[2-fluoro-5-(trifluoromethoxy)phenyl]methyl}carbamoyl)-1H-1,2,3-triazol-1-yl]butyl}-N-{[5-(trifluoromethyl)pyridin-2-yl]methyl}-1H-1,2,3-triazole-4-carboxamide |
| 424 | 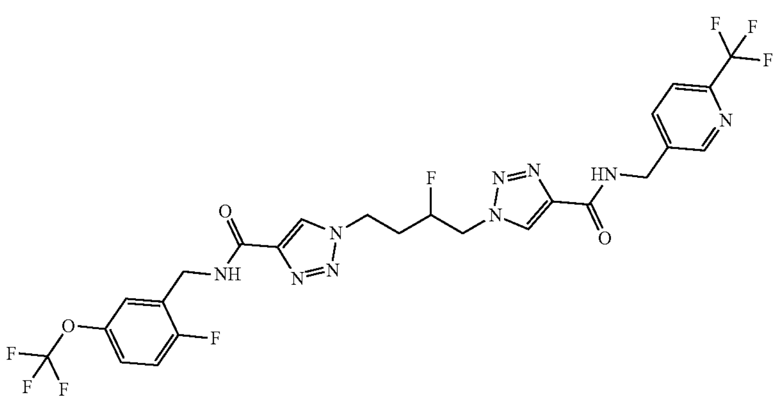 [SMILES: O=C(NCc1cc(OC(F)(F)F)ccc1F)c1cn(CCC(F)Cn2cc(C(=O)NCc3ccc(C(F)(F)F)nc3)nn2)nn1] | 1-{2-fluoro-4-[4-({[2-fluoro-5-(trifluoromethoxy)phenyl]methyl}carbamoyl)-1H-1,2,3-triazol-1-yl]butyl}-N-{[6-(trifluoromethyl)pyridin-3-yl]methyl}-1H-1,2,3-triazole-4-carboxamide |

TABLE 1-continued

Synthesized Examples

| Ex. No. | Structure | Name |
|---|---|---|
| 425 | 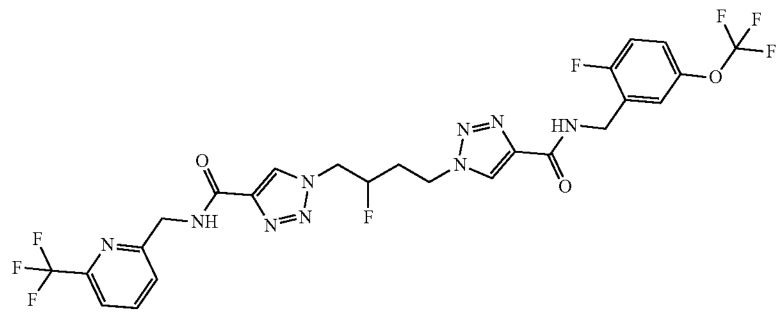 [SMILES: O=C(NCc1cc(OC(F)(F)F)ccc1F)c1cn(CCC(F)Cn2cc(C(=O)NCc3cccc(C(F)(F)F)n3)nn2)nn1] | 1-{2-fluoro-4-[4-({[2-fluoro-5-(trifluoromethoxy)phenyl]methyl}carbamoyl)-1H-1,2,3-triazol-1-yl]butyl}-N-{[6-(trifluoromethyl)pyridin-2-yl]methyl}-1H-1,2,3-triazole-4-carboxamide |
| 426 | 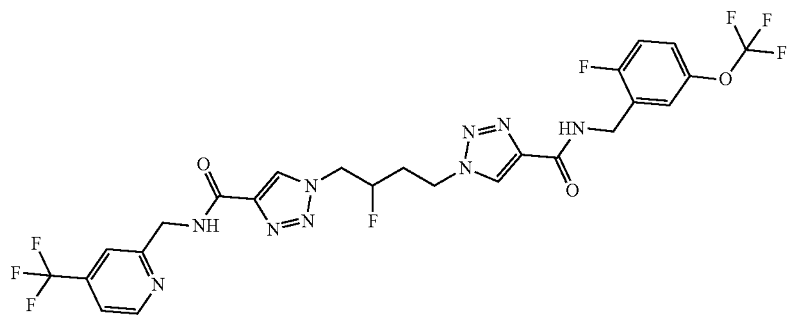 [SMILES: O=C(NCc1cc(OC(F)(F)F)ccc1F)c1cn(CCC(F)Cn2cc(C(=O)NCc3cc(C(F)(F)F)ccn3)nn2)nn1] | 1-{2-fluoro-4-[4-({[2-fluoro-5-(trifluoromethoxy)phenyl]methyl}carbamoyl)-1H-1,2,3-triazol-1-yl]butyl}-N-{[4-(trifluoromethyl)pyridin-2-yl]methyl}-1H-1,2,3-triazole-4-carboxamide |
| 427 | 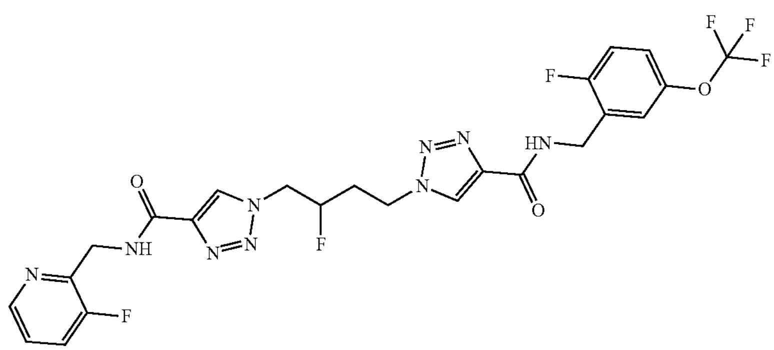 [SMILES: O=C(NCc1cc(OC(F)(F)F)ccc1F)c1cn(CCC(F)Cn2cc(C(=O)NCc3ncccc3F)nn2)nn1] | 1-{2-fluoro-4-[4-({[2-fluoro-5-(trifluoromethoxy)phenyl]methyl}carbamoyl)-1H-1,2,3-triazol-1-yl]butyl}-N-[(3-fluoropyridin-2-yl)methyl]-1H-1,2,3-triazole-4-carboxamide |
| 428 | 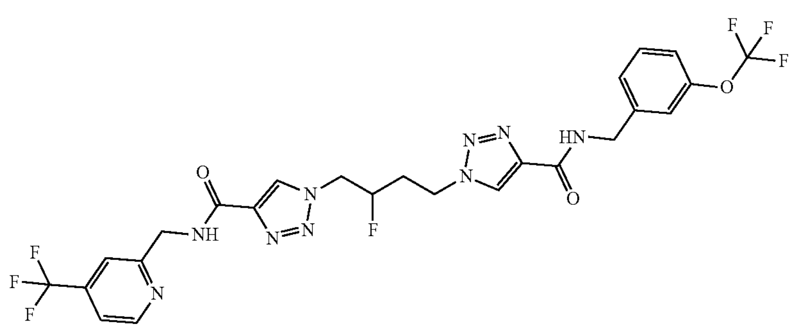 [SMILES: O=C(NCc1cccc(OC(F)(F)F)c1)c1cn(CCC(F)Cn2cc(C(=O)NCc3cc(C(F)(F)F)ccn3)nn2)nn1] | 1-{2-fluoro-4-[4-({[3-(trifluoromethoxy)phenyl]methyl}carbamoyl)-1H-1,2,3-triazol-1-yl]butyl}-N-{[4-(trifluoromethyl)pyridin-2-yl]methyl}-1H-1,2,3-triazole-4-carboxamide |

TABLE 1-continued

Synthesized Examples

| Ex. No. | Structure | Name |
|---|---|---|
| 429 | 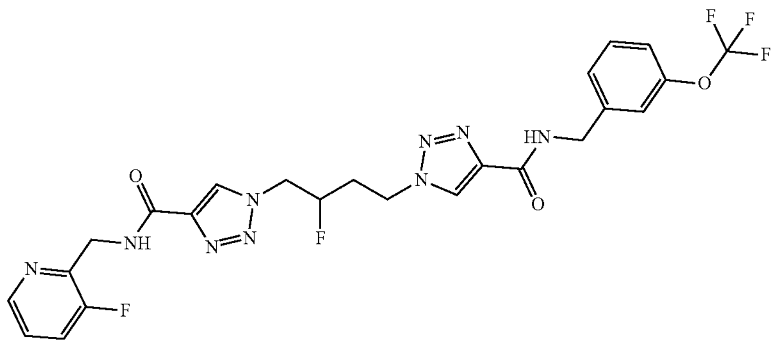 [SMILES: O=C(NCc1cccc(OC(F)(F)F)c1)c1cn(CCC(F)Cn2cc(C(=O)NCc3ncccc3F)nn2)nn1] | 1-{2-fluoro-4-[4-({[3-(trifluoromethoxy)phenyl]methyl}carbamoyl)-1H-1,2,3-triazol-1-yl]butyl}-N-[(3-fluoropyridin-2-yl)methyl]-1H-1,2,3-triazole-4-carboxamide |
| 430 | 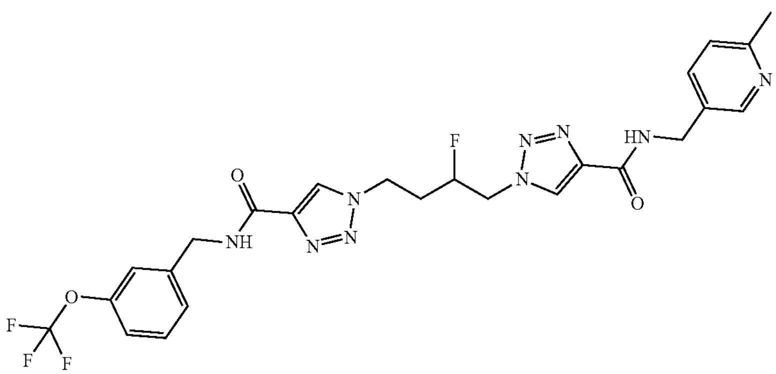 [SMILES: Cc1ccc(CNC(=O)c2cn(CC(F)CCn3cc(C(=O)NCc4cccc(OC(F)(F)F)c4)nn3)nn2)cn1] | 1-{2-fluoro-4-[4-({[3-(trifluoromethoxy)phenyl]methyl}carbamoyl)-1H-1,2,3-triazol-1-yl]butyl}-N-[(6-methylpyridin-3-yl)methyl]-1H-1,2,3-triazole-4-carboxamide |
| 431 | 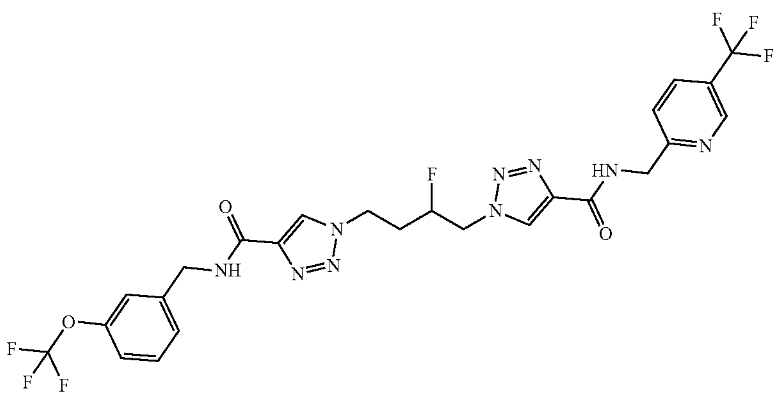 [SMILES: O=C(NCc1cccc(OC(F)(F)F)c1)c1cn(CCC(F)Cn2cc(C(=O)NCc3ccc(C(F)(F)F)cn3)nn2)nn1] | 1-{2-fluoro-4-[4-({[3-(trifluoromethoxy)phenyl]methyl}carbamoyl)-1H-1,2,3-triazol-1-yl]butyl}-N-{[5-(trifluoromethyl)pyridin-2-yl]methyl}-1H-1,2,3-triazole-4-carboxamide |
| 432 | 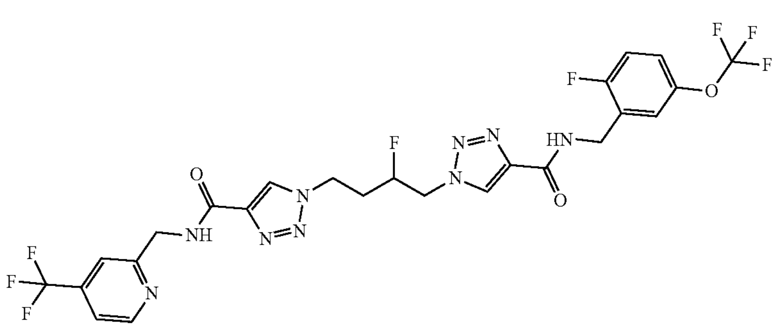 [SMILES: O=C(NCc1cc(C(F)(F)F)ccn1)c1cn(CCC(F)Cn2cc(C(=O)NCc3cc(OC(F)(F)F)ccc3F)nn2)nn1] | 1-{2-fluoro-4-[4-({[4-(tifluoromethyl)pyridin-2-yl]methyl}carbamoyl)-1H-1,2,3-triazol-1-yl]butyl}-N-{[2-fluoro-5-(trifluoromethoxy)phenyl]methyl}-1H-1,2,3-triazole-4-carboxamide |

TABLE 1-continued

Synthesized Examples

| Ex. No. | Structure | Name |
|---|---|---|
| 433 | 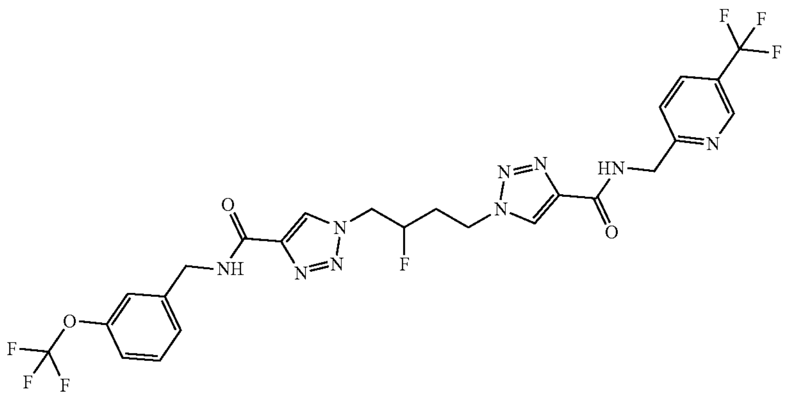 [SMILES: O=C(NCc1ccc(C(F)(F)F)cn1)c1cn(CCC(F)Cn2cc(C(=O)NCc3cccc(OC(F)(F)F)c3)nn2)nn1] | 1-{2-fluoro-4-[4-({[5-(trifluoromethyl)pyridin-2-yl]methyl}carbamoyl)-1H-1,2,3-triazol-1-yl]butyl}-N-{[3-(trifluoromethoxy)phenyl]methyl}-1H-1,2,3-triazole-4-carboxamide |
| 434 | 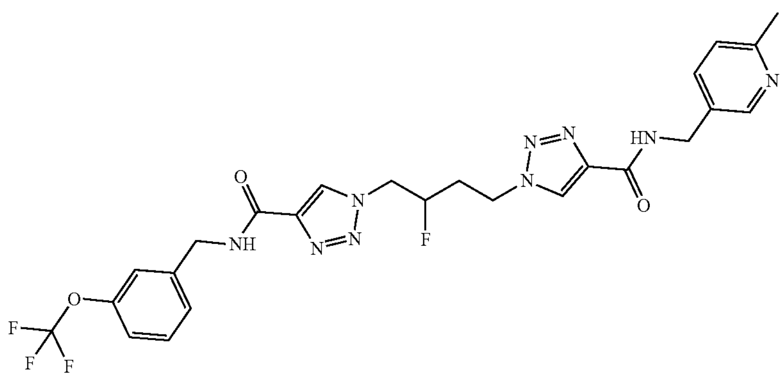 [SMILES: Cc1ccc(CNC(=O)c2cn(CCC(F)Cn3cc(C(=O)NCc4cccc(OC(F)(F)F)c4)nn3)nn2)cn1] | 1-[2-fluoro-4-(4-{[(6-methylpyridin-3-yl)methyl]carbamoyl}-1H-1,2,3-triazol-1-yl)butyl]-N-{[3-(trifluoromethoxy)phenyl]methyl}-1H-1,2,3-triazole-4-carboxamide |
| 435 | 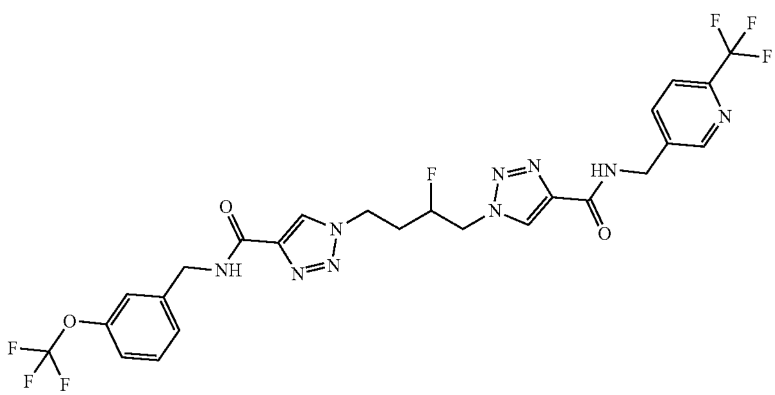 [SMILES: O=C(NCc1cccc(OC(F)(F)F)c1)c1cn(CCC(F)Cn2cc(C(=O)NCc3ccc(C(F)(F)F)nc3)nn2)nn1] | 1-{2-fluoro-4-[4-({[3-(trifluoromethoxy)phenyl]methyl}carbamoyl]-1H-1,2,3-triazol-1-yl]butyl}-N-{[6-(trifluoromethyl)pyridin-3-yl]methyl}-1H-1,2,3-triazole-4-carboxamide |
| 436 | 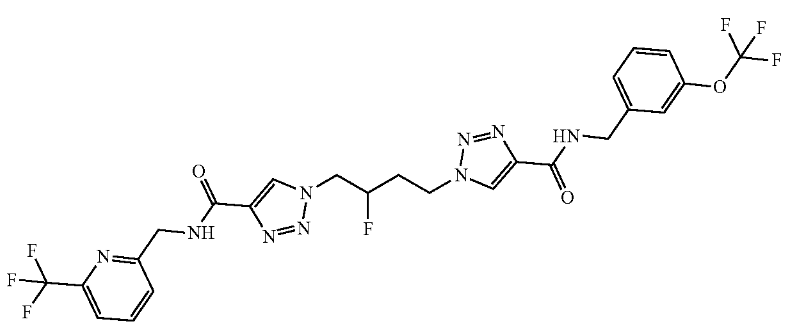 [SMILES: O=C(NCc1cccc(OC(F)(F)F)c1)c1cn(CCC(F)Cn2cc(C(=O)NCc3cccc(C(F)(F)F)n3)nn2)nn1] | 1-{2-fluoro-4-[4-({[3-(trifluoromethoxy)phenyl]methyl}carbamoyl]-1H-1,2,3-triazol-1-yl]butyl}-N-{[6-(trifluoromethyl)pyridin-2-yl]methyl}-1H-1,2,3-triazole-4-carboxamide |

TABLE 1-continued

Synthesized Examples

| Ex. No. | Structure | Name |
|---|---|---|
| 437 | 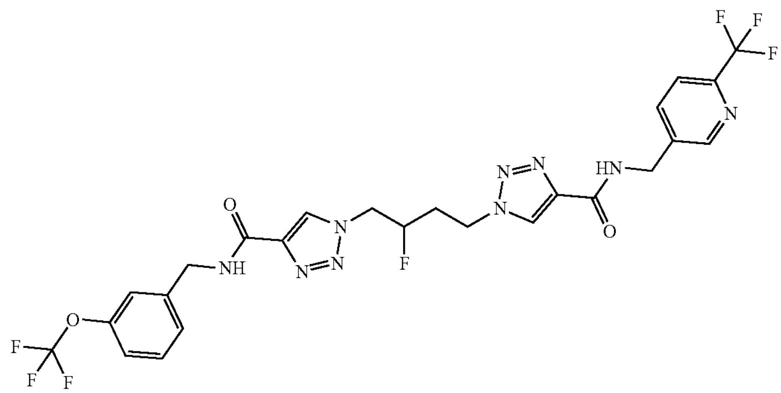 [SMILES: O=C(NCc1ccc(C(F)(F)F)nc1)c1cn(CCC(F)Cn2cc(C(=O)NCc3cccc(OC(F)(F)F)c3)nn2)nn1] | 1-{3-fluoro-4-[4-({[3-(trifluoromethoxy)phenyl]methyl}carbamoyl)-1H-1,2,3-triazol-1-yl]butyl}-N-{[6-(trifluoromethyl)pyridin-3-yl]methyl}-1H-1,2,3-triazole-4-carboxamide |
| 438 | 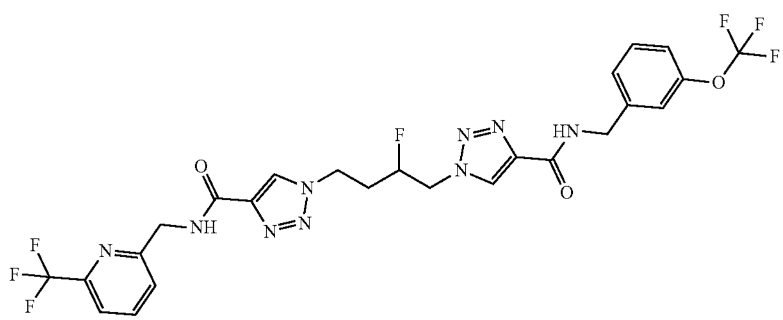 [SMILES: O=C(NCc1cccc(C(F)(F)F)n1)c1cn(CCC(F)Cn2cc(C(=O)NCc3cccc(OC(F)(F)F)c3)nn2)nn1] | 1-{3-fluoro-4-[4-({[3-(trifluoromethoxy)phenyl]methyl}carbamoyl)-1H-1,2,3-triazol-1-yl]butyl}-N-{[6-(trifluoromethyl)pyridin-2-yl]methyl}-1H-1,2,3-triazole-4-carboxamide |
| 439 | 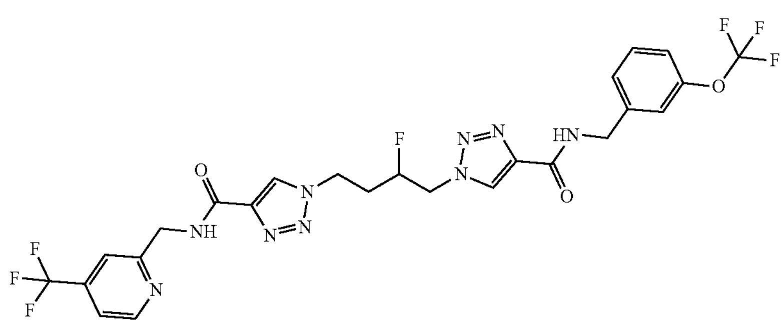 [SMILES: O=C(NCc1cc(C(F)(F)F)ccn1)c1cn(CCC(F)Cn2cc(C(=O)NCc3cccc(OC(F)(F)F)c3)nn2)nn1] | 1-{3-fluoro-4-[4-({[3-(trifluoromethoxy)phenyl]methyl}carbamoyl)-1H-1,2,3-triazol-1-yl]butyl}-N-{[4-(trifluoromethyl)pyridin-2-yl]methyl}-1H-1,2,3-triazole-4-carboxamide |
| 440 | 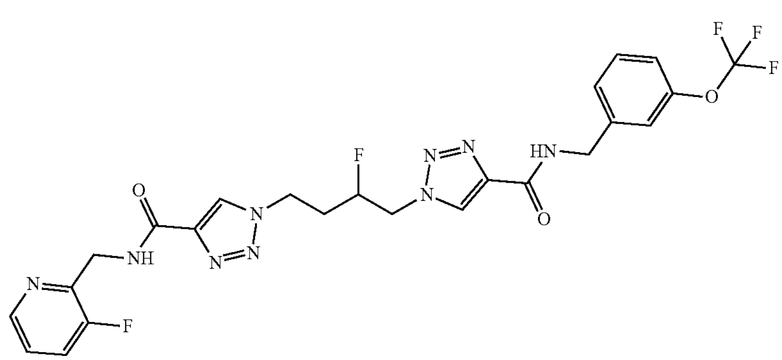 [SMILES: O=C(NCc1ncccc1F)c1cn(CCC(F)Cn2cc(C(=O)NCc3cccc(OC(F)(F)F)c3)nn2)nn1] | 1-{3-fluoro-4-[4-({[3-(trifluoromethoxy)phenyl]methyl}carbamoyl)-1H-1,2,3-triazol-1-yl]butyl}-N-[(3-fluoropyridin-2-yl)methyl]-1H-1,2,3-triazole-4-carboxamide |

TABLE 1-continued

Synthesized Examples

| Ex. No. | Structure | Name |
|---|---|---|
| 441 | 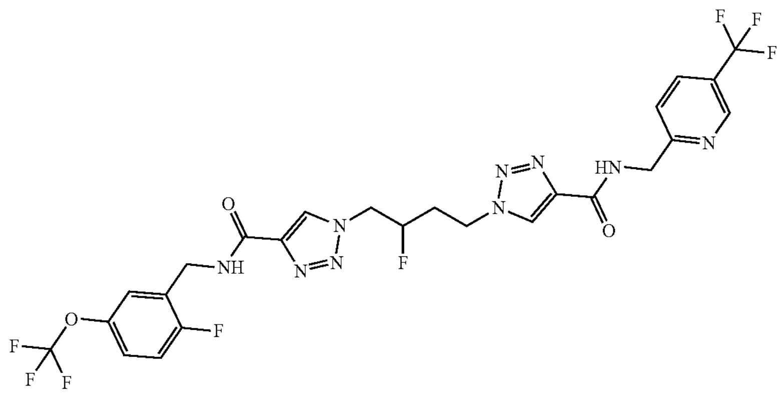 [SMILES: O=C(NCc1ccc(C(F)(F)F)cn1)c1cn(CCC(F)Cn2cc(C(=O)NCc3cc(OC(F)(F)F)ccc3F)nn2)nn1] | 1-{2-fluoro-4-[4-({[5-(trifluoromethyl)pyridin-2-yl]methyl}carbamoyl)-1H-1,2,3-triazol-1-yl]butyl}-N-{[2-fluoro-5-(trifluoromethoxy)phenyl]methyl}-1H-1,2,3-triazole-4-carboxamide |
| 442 | 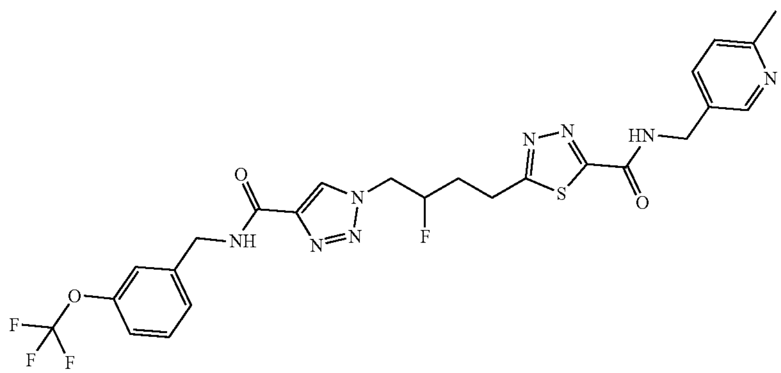 [SMILES: Cc1ccc(CNC(=O)c2nnc(CCC(F)Cn3cc(C(=O)NCc4cccc(OC(F)(F)F)c4)nn3)s2)cn1] | 5-{3-fluoro-4-[4-({[3-(trifluoromethoxy)phenyl]methyl}carbamoyl)-1H-1,2,3-triazol-1-yl]butyl}-N-[(6-methylpyridin-3-yl)methyl]-1,3,4-thiadiazole-2-carboxamide |
| 443 | 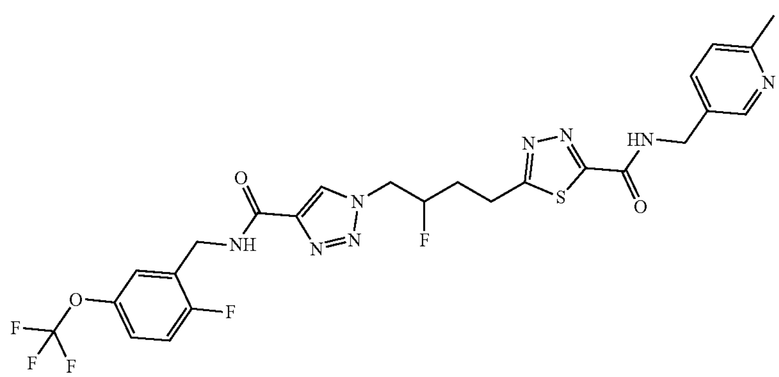 [SMILES: Cc1ccc(CNC(=O)c2nnc(CCC(F)Cn3cc(C(=O)NCc4cc(OC(F)(F)F)ccc4F)nn3)s2)cn1] | 5-{3-fluoro-4-[4-({[2-fluoro-5-(trifluoromethoxy)phenyl]methyl}carbamoyl)-1H-1,2,3-triazol-1-yl]butyl}-N-[(6-methylpyridin-3-yl)methyl]-1,3,4-thiadiazole-2-carboxamide |
| 444 | 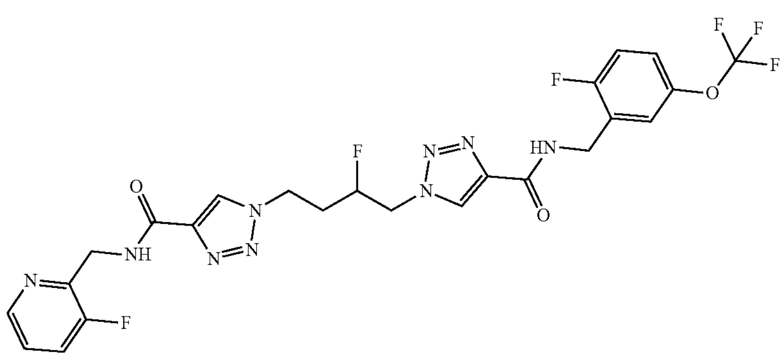 [SMILES: O=C(NCc1ncccc1F)c1cn(CCC(F)Cn2cc(C(=O)NCc3cc(OC(F)(F)F)ccc3F)nn2)nn1] | 1-{3-fluoro-4-[4-({[2-fluoro-5-(trifluoromethoxy)phenyl]methyl}carbamoyl)-1H-1,2,3-triazol-1-yl]butyl}-N-[(3-fluoropyridin-2-yl)methyl]-1H-1,2,3-triazole-4-carboxamide |

TABLE 1-continued

Synthesized Examples

| Ex. No. | Structure | Name |
|---|---|---|
| 445 | 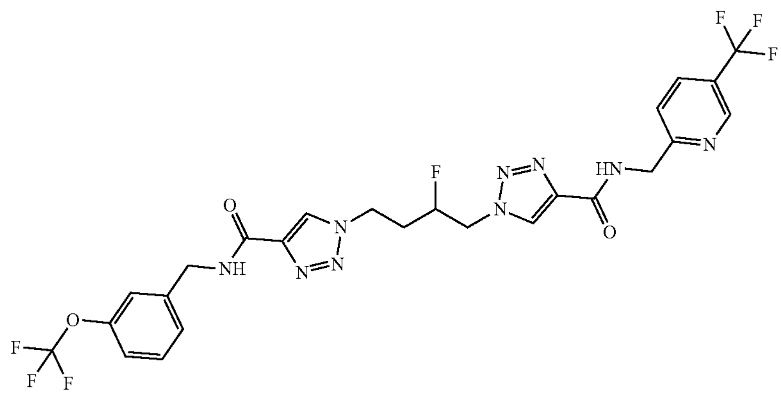 [SMILES: O=C(NCc1cccc(OC(F)(F)F)c1)c1cn(CCC(F)Cn2cc(C(=O)NCc3ccc(C(F)(F)F)cn3)nn2)nn1] | 5-{3-fluoro-4-[4-({[5-(trifluoromethyl)pyridin-2-yl]methyl}carbamoyl)-1H-1,2,3-triazol-1-yl]butyl}-N-{[3-(trifluoromethoxy)phenyl]methyl}-1,3,4-thiadiazole-2-carboxamide |
| 446 | 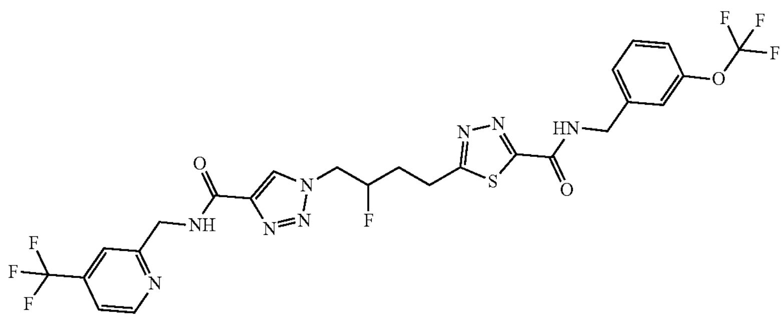 [SMILES: O=C(NCc1cc(C(F)(F)F)ccn1)c1cn(CC(F)CCc2nnc(C(=O)NCc3cccc(OC(F)(F)F)c3)s2)nn1] | 5-{3-fluoro-4-[4-({[4-(trifluoromethyl)pyridin-2-yl]methyl}carbamoyl)-1H-1,2,3-triazol-1-yl]butyl}-N-{[3-(trifluoromethoxy)phenyl]methyl}-1,3,4-thiadiazole-2-carboxamide |
| 447 | 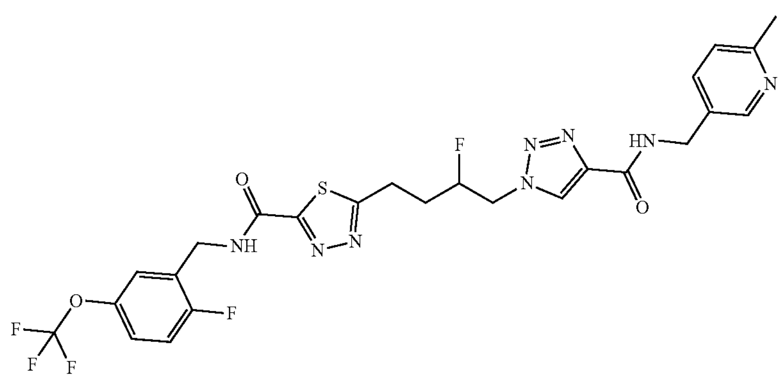 [SMILES: Cc1ccc(CNC(=O)c2cn(CC(F)CCc3nnc(C(=O)NCc4cc(OC(F)(F)F)ccc4F)s3)nn2)cn1] | 5-[3-fluoro-4-(4-{[(6-methylpyridin-3-yl)methyl]carbamoyl}-1H-1,2,3-triazol-1-yl)butyl]-N-{[2-fluoro-5-(trifluoromethoxy)phenyl]methyl}-1,3,4-thiadiazole-2-carboxamide |
| 448 | 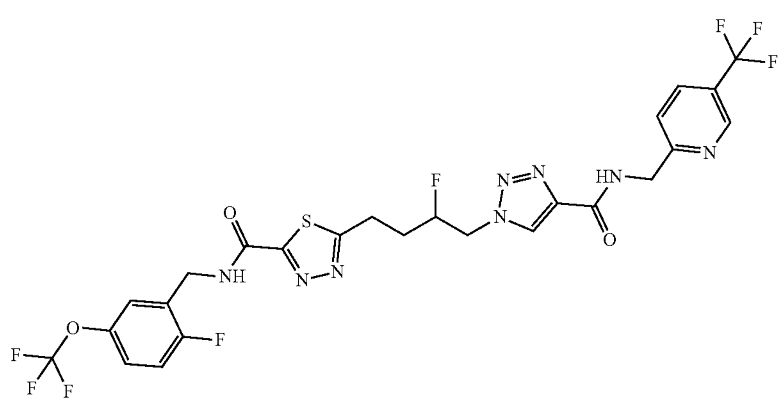 [SMILES: O=C(NCc1ccc(C(F)(F)F)cn1)c1cn(CC(F)CCc2nnc(C(=O)NCc3cc(OC(F)(F)F)ccc3F)s2)nn1] | 5-{3-fluoro-4-[4-({[5-(trifluoromethyl)pyridin-2-yl]methyl}carbamoyl)-1H-1,2,3-triazol-1-yl]butyl}-N-{[2-fluoro-5-(trifluoromethoxy)phenyl]methyl}-1,3,4-thiadiazole-2-carboxamide |

TABLE 1-continued

Synthesized Examples

| Ex. No. | Structure | Name |
|---|---|---|
| 449 | 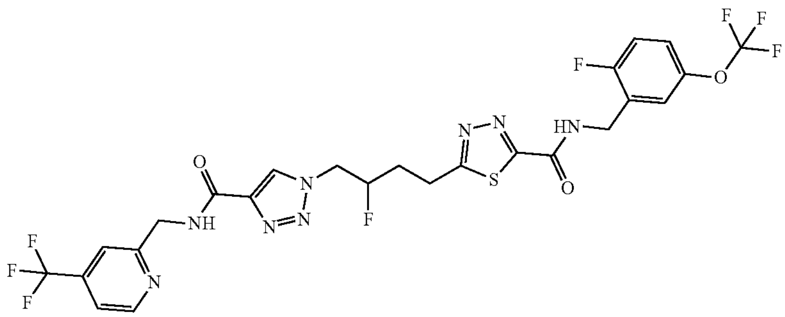 [SMILES: O=C(NCc1cc(C(F)(F)F)ccn1)c1cn(CC(F)CCc2nnc(C(=O)NCc3cc(OC(F)(F)F)ccc3F)s2)nn1] | 5-{3-fluoro-4-[4-({[4-(trifluoromethyl)pyridin-2-yl]methyl}carbamoyl)-1H-1,2,3-triazol-1-yl]butyl}-N-{[2-fluoro-5-(trifluoromethoxy)phenyl]methyl}-1,3,4-thiadiazole-2-carboxamide |
| 450 | 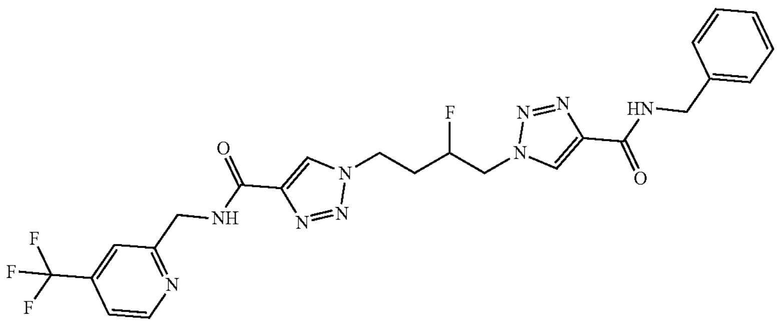 [SMILES: O=C(NCc1cc(C(F)(F)F)ccn1)c1cn(CCC(F)Cn2cc(C(=O)NCc3ccccc3)nn2)nn1] | N-benzyl-1-{2-fluoro-4-[4-({[4-(trifluoromethyl)pyridin-2-yl]methyl}carbamoyl)-1H-1,2,3-triazol-1-yl]butyl}-1H-1,2,3-triazole-4-carboxamide |
| 451 | 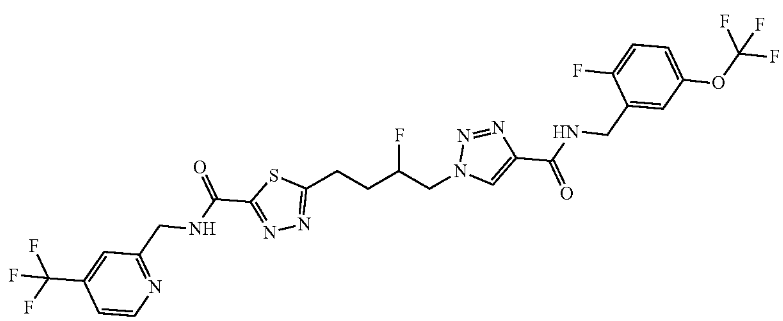 [SMILES: O=C(NCc1cc(OC(F)(F)F)ccc1F)c1cn(CC(F)CCc2nnc(C(=O)NCc3cc(C(F)(F)F)ccn3)s2)nn1] | 5-{3-fluoro-4-[4-({[2-fluoro-5-(trifluoromethoxy)phenyl]methyl}carbamoyl)-1H-1,2,3-triazol-1-yl]butyl}-N-{[4-(trifluoromethyl)pyridin-2-yl]methyl}-1,3,4-thiadiazole-2-carboxamide |
| 452 | 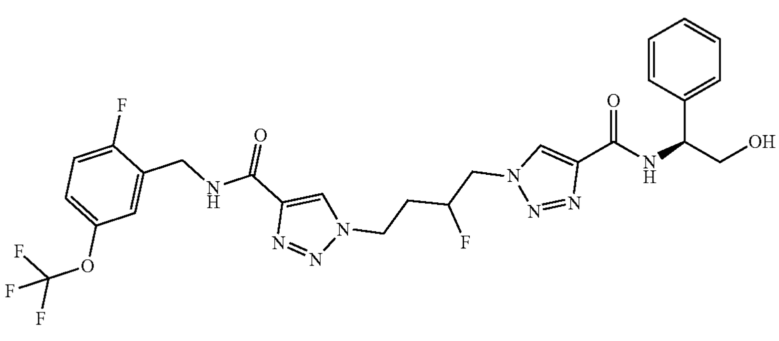 [SMILES: O=C(NCc1cc(OC(F)(F)F)ccc1F)c1cn(CCC(F)Cn2cc(C(=O)N[C@H](CO)c3ccccc3)nn2)nn1] | 1-{2-fluoro-4-[4-({[2-fluoro-5-(trifluoromethoxy)phenyl]methyl}carbamoyl)-1H-1,2,3-triazol-1-yl]butyl}-N-[(1S)-2-hydroxy-1-phenylethyl]-1H-1,2,3-triazole-4-carboxamide |

TABLE 1-continued

Synthesized Examples

| Ex. No. | Structure | Name |
|---|---|---|
| 453 | 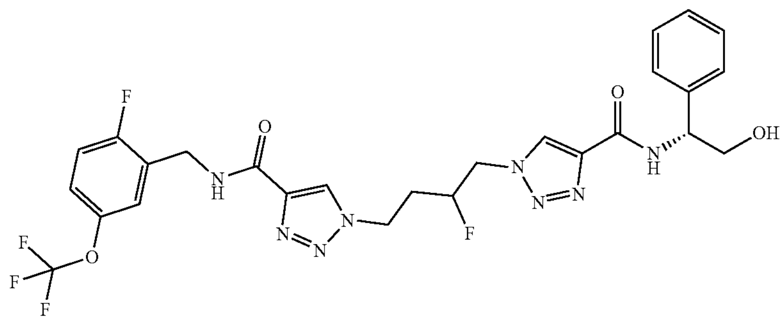 [SMILES: O=C(NCc1cc(OC(F)(F)F)ccc1F)c1cn(CCC(F)Cn2cc(C(=O)N[C@@H](CO)c3ccccc3)nn2)nn1] | 1-{2-fluoro-4-[4-({[2-fluoro-5-(trifluoromethoxy)phenyl]methyl}carbamoyl)-1H-1,2,3-triazol-1-yl]butyl}-N-[(1R)-2-hydroxy-1-phenylethyl]-1H-1,2,3-triazole-4-carboxamide |
| 454 | 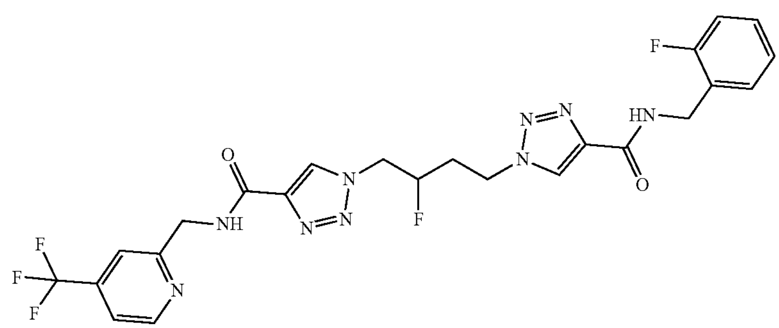 [SMILES: O=C(NCc1ccccc1F)c1cn(CCC(F)Cn2cc(C(=O)NCc3cc(C(F)(F)F)ccn3)nn2)nn1] | 1-[2-fluoro-4-(4-{[(2-fluorophenyl)methyl]carbamoyl}-1H-1,2,3-triazol-1-yl)butyl]-N-{[4-(trifluoromethyl)pyridin-2-yl]methyl}-1H-1,2,3-triazole-4-carboxamide |
| 455 | 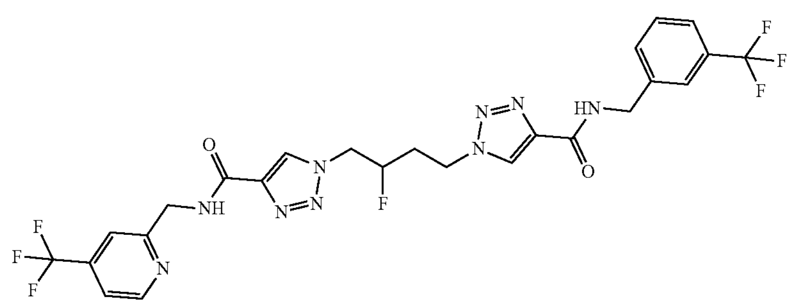 [SMILES: O=C(NCc1cccc(C(F)(F)F)c1)c1cn(CCC(F)Cn2cc(C(=O)NCc3cc(C(F)(F)F)ccn3)nn2)nn1] | 1-{2-fluoro-4-[4-({[3-(trifluoromethyl)phenyl]methyl}carbamoyl)-1H-1,2,3-triazol-1-yl]butyl}-N-{[4-(trifluoromethyl)pyridin-2-yl]methyl}-1H-1,2,3-triazole-4-carboxamide |
| 456 | 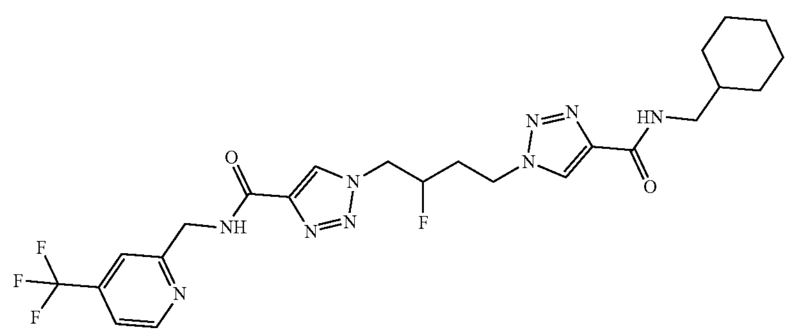 [SMILES: O=C(NCC1CCCCC1)c1cn(CCC(F)Cn2cc(C(=O)NCc3cc(C(F)(F)F)ccn3)nn2)nn1] | 1-(4-{4-[(cyclohexylmethyl)carbamoyl]-1H-1,2,3-triazol-1-yl}-2-fluorobutyl)-N-{[4-(trifluoromethyl)pyridin-2-yl]methyl}-1H-1,2,3-triazole-4-carboxamide |

TABLE 1-continued

Synthesized Examples

| Ex. No. | Structure | Name |
|---|---|---|
| 457 | 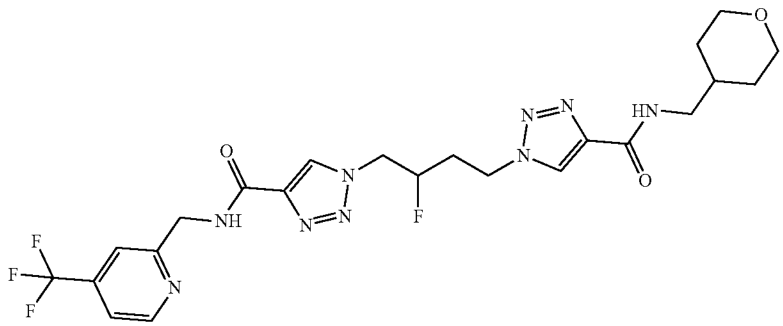 [SMILES: O=C(NCC1CCOCC1)c1cn(CCC(F)Cn2cc(C(=O)NCc3cc(C(F)(F)F)ccn3)nn2)nn1] | 1-(2-fluoro-4-{4-[(oxan-4-ylmethyl)carbamoyl]-1H-1,2,3-triazol-1-yl}butyl)-N-{[4-(trifluoromethyl)pyridin-2-yl]methyl}-1H-1,2,3-triazole-4-carboxamide |
| 458 | 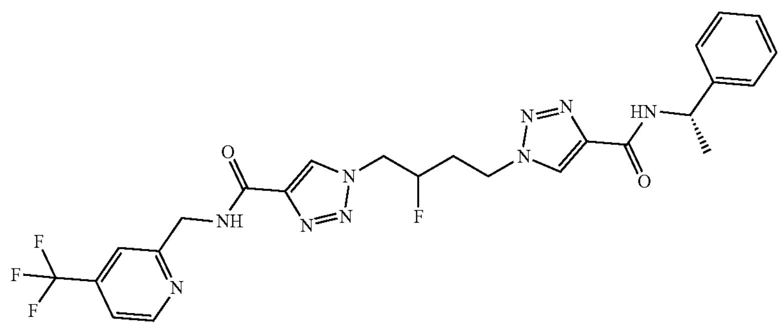 [SMILES: C[C@H](NC(=O)c1cn(CCC(F)Cn2cc(C(=O)NCc3cc(C(F)(F)F)ccn3)nn2)nn1)c1ccccc1] | 1-[2-fluoro-4-(4-{[(1S)-1-phenylethyl]carbamoyl}-1H-1,2,3-triazol-1-yl)butyl]-N-{[4-(trifluoromethyl)pyridin-2-yl]methyl}-1H-1,2,3-triazole-4-carboxamide |
| 459 | 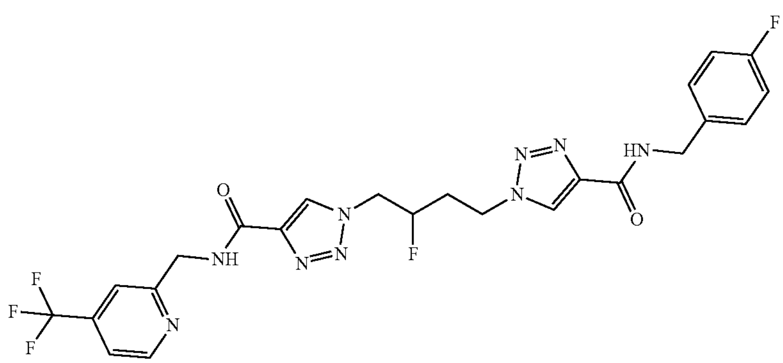 [SMILES: O=C(NCc1ccc(F)cc1)c1cn(CCC(F)Cn2cc(C(=O)NCc3cc(C(F)(F)F)ccn3)nn2)nn1] | 1-[2-fluoro-4-(4-{[(4-fluorophenyl)methyl]carbamoyl}-1H-1,2,3-triazol-1-yl)butyl]-N-{[4-(trifluoromethyl)pyridin-2-yl]methyl}-1H-1,2,3-triazole-4-carboxamide |
| 460 | 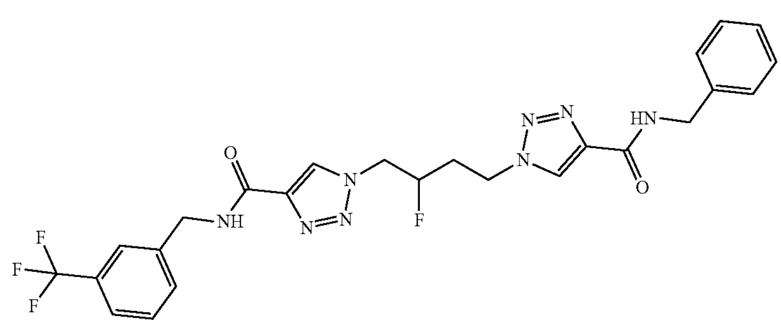 [SMILES: O=C(NCc1ccccc1)c1cn(CCC(F)Cn2cc(C(=O)NCc3cccc(C(F)(F)F)c3)nn2)nn1] | 1-{4-[4-(benzylcarbamoyl)-1H-1,2,3-triazol-1-yl]-2-fluorobutyl}-N-{[4-(trifluoromethyl)pyridin-2-yl]methyl}-1H-1,2,3-triazole-4-carboxamide |

TABLE 1-continued

Synthesized Examples

| Ex. No. | Structure | Name |
|---|---|---|
| 461 | 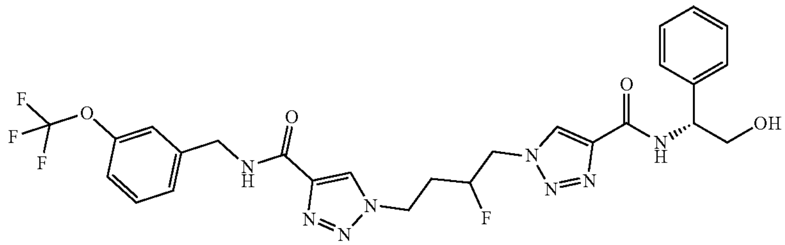 [SMILES: O=C(NCc1cccc(OC(F)(F)F)c1)c1cn(CCC(F)Cn2cc(C(=O)N[C@@H](CO)c3ccccc3)nn2)nn1] | 1-{2-fluoro-4-[4-({[3-(trifluoromethoxy)phenyl]methyl}carbamoyl)-1H-1,2,3-triazol-1-yl]butyl}-N-[(1R)-2-hydroxy-1-phenylethyl]-1H-1,2,3-triazole-4-carboxamide |
| 462 | 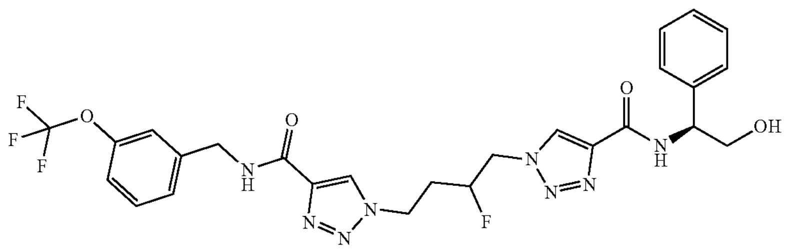 [SMILES: O=C(NCc1cccc(OC(F)(F)F)c1)c1cn(CCC(F)Cn2cc(C(=O)N[C@H](CO)c3ccccc3)nn2)nn1] | 1-{2-fluoro-4-[4-({[3-(trifluoromethoxy)phenyl]methyl}carbamoyl)-1H-1,2,3-triazol-1-yl]butyl}-N-[(1S)-2-hydroxy-1-phenylethyl]-1H-1,2,3-triazole-4-carboxamide |
| 463 | 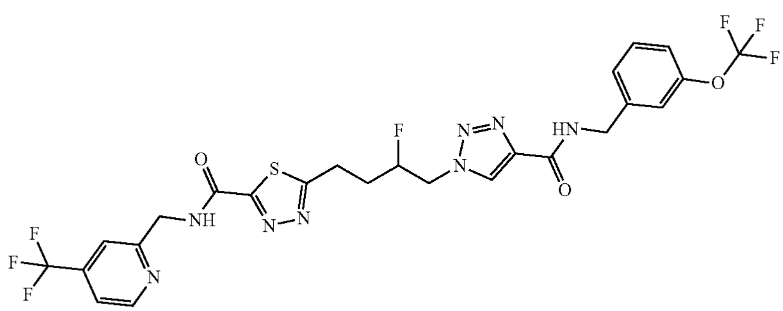 [SMILES: O=C(NCc1cccc(OC(F)(F)F)c1)c1cn(CC(F)CCc2nnc(C(=O)NCc3cc(C(F)(F)F)ccn3)s2)nn1] | 5-{3-fluoro-4-[4-({[3-(trifluoromethoxy)phenyl]methyl}carbamoyl)-1H-1,2,3-triazol-1-yl]butyl}-N-{[4-(trifluoromethyl)pyridin-2-yl]methyl}-1,3,4-thiadiazole-2-carboxamide |
| 464 | 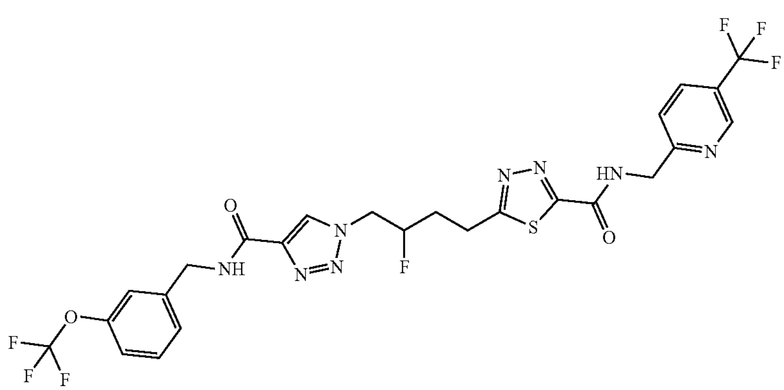 [SMILES: O=C(NCc1cccc(OC(F)(F)F)c1)c1cn(CC(F)CCc2nnc(C(=O)NCc3ccc(C(F)(F)F)cn3)s2)nn1] | 5-{3-fluoro-4-[4-({[3-(trifluoromethoxy)phenyl]methyl}carbamoyl)-1H-1,2,3-triazol-1-yl]butyl}-N-{[5-(trifluoromethyl)pyridin-2-yl]methyl}-1,3,4-thiadiazole-2-carboxamide |

TABLE 1-continued

Synthesized Examples

| Ex. No. | Structure | Name |
|---|---|---|
| 465 | 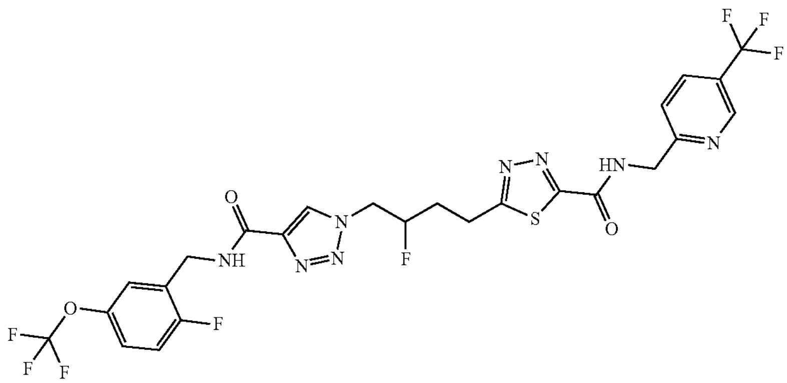 [SMILES: O=C(NCc1cc(OC(F)(F)F)ccc1F)c1cn(CC(F)CCc2nnc(C(=O)NCc3ccc(C(F)(F)F)cn3)s2)nn1] | 5-{3-fluoro-4-[4-({[2-fluoro-5-(trifluoromethoxy)phenyl]methyl}carbamoyl)-1H-1,2,3-triazol-1-yl]butyl}-N-{[5-(trifluoromethyl)pyridin-2-yl]methyl}-1,3,4-thiadiazole-2-carboxamide |
| 466 | 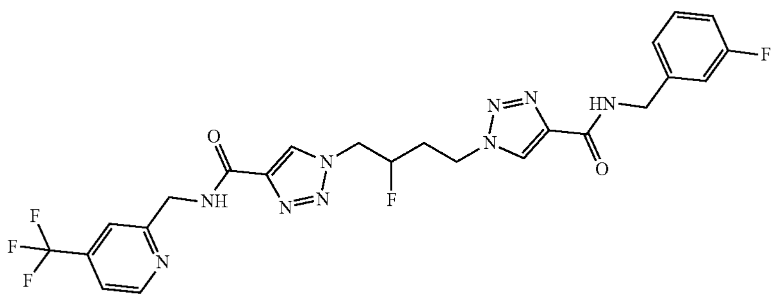 [SMILES: O=C(NCc1cccc(F)c1)c1cn(CCC(F)Cn2cc(C(=O)NCc3cc(C(F)(F)F)ccn3)nn2)nn1] | 1-[2-fluoro-4-(4-{[(3-fluorophenyl)methyl]carbamoyl}-1H-1,2,3-triazol-1-yl)butyl]-N-{[4-(trifluoromethyl)pyridin-2-yl]methyl}-1H-1,2,3-triazole-4-carboxamide |
| 467 | 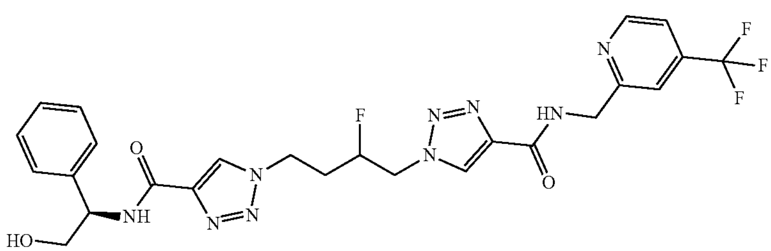 [SMILES: O=C(NCc1cc(C(F)(F)F)ccn1)c1cn(CC(F)CCn2cc(C(=O)N[C@@H](CO)c3ccccc3)nn2)nn1] | 1-[2-fluoro-4-(4-{[(1R)-2-hydroxy-1-phenylethyl]carbamoyl}-1H-1,2,3-triazol-1-yl)butyl]-N-{[4-(trifluoromethyl)pyridin-2-yl]methyl}-1H-1,2,3-triazole-4-carboxamide |
| 468 | 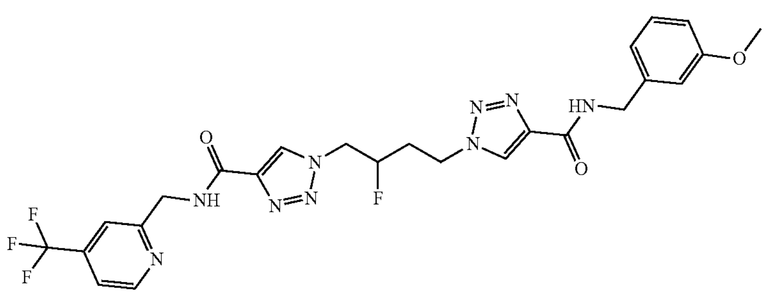 [SMILES: COc1cccc(CNC(=O)c2cn(CCC(F)Cn3cc(C(=O)NCc4cc(C(F)(F)F)ccn4)nn3)nn2)c1] | 1-[2-fluoro-4-(4-{[(3-methoxyphenyl)methyl]carbamoyl}-1H-1,2,3-triazol-1-yl)butyl]-N-{[4-(trifluoromethyl)pyridin-2-yl]methyl}-1H-1,2,3-triazole-4-carboxamide |

TABLE 1-continued

Synthesized Examples

| Ex. No. | Structure | Name |
|---|---|---|
| 469 | 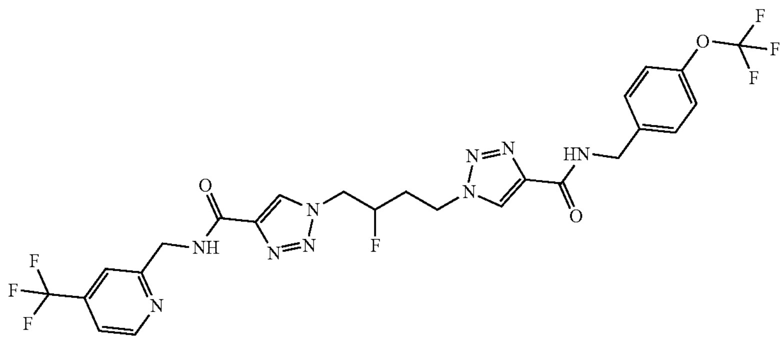 [SMILES: O=C(NCc1ccc(OC(F)(F)F)cc1)c1cn(CCC(F)Cn2cc(C(=O)NCc3cc(C(F)(F)F)ccn3)nn2)nn1] | 1-{2-fluoro-4-[4-({[4-(trifluoromethoxy)phenyl]methyl}carbamoyl)-1H-1,2,3-triazol-1-yl]butyl}-N-{[4-(trifluoromethyl)pyridin-2-yl]methyl}-1H-1,2,3-triazole-4-carboxamide |
| 470 | 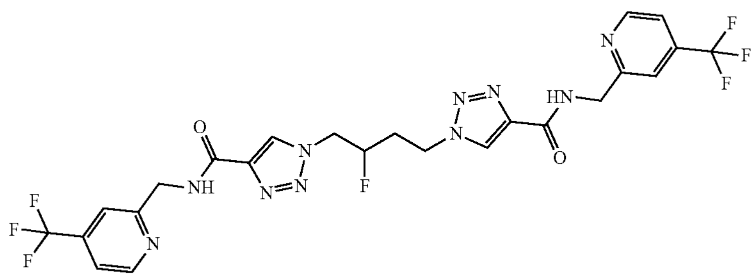 [SMILES: O=C(NCc1cc(C(F)(F)F)ccn1)c1cn(CCC(F)Cn2cc(C(=O)NCc3cc(C(F)(F)F)ccn3)nn2)nn1] | 1-{2-fluoro-4-[4-({[4-(trifluoromethyl)pyridin-2-yl]methyl}carbamoyl)-1H-1,2,3-triazol-1-yl]butyl}-N-{[4-(trifluoromethyl)pyridin-2-yl]methyl}-1H-1,2,3-triazole-4-carboxamide |
| 471 | 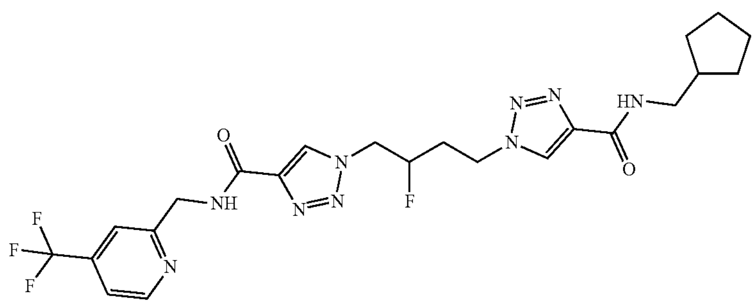 [SMILES: O=C(NCC1CCCC1)c1cn(CCC(F)Cn2cc(C(=O)NCc3cc(C(F)(F)F)ccn3)nn2)nn1] | 1-(4-{4-[(cyclopentylmethyl)carbamoyl]-1H-1,2,3-triazol-1-yl}-2-fluorobutyl)-N-{[4-(trifluoromethyl)pyridin-2-yl]methyl}-1H-1,2,3-triazole-4-carboxamide |
| 472 | 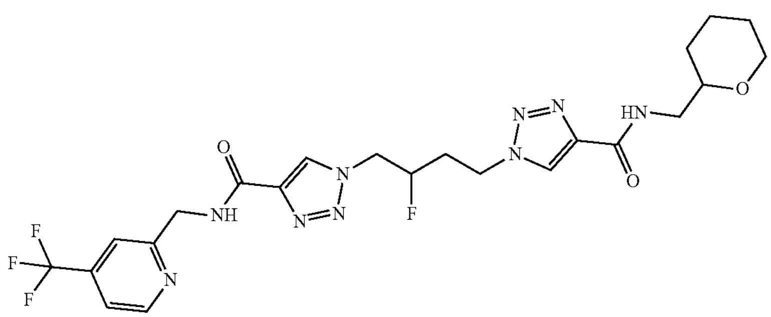 [SMILES: O=C(NCC1CCCCO1)c1cn(CCC(F)Cn2cc(C(=O)NCc3cc(C(F)(F)F)ccn3)nn2)nn1] | 1-(2-fluoro-4-{4-[(oxan-2-ylmethyl)carbamoyl]-1H-1,2,3-triazol-1-yl}butyl)-N-{[4-(trifluoromethyl)pyridin-2-yl]methyl}-1H-1,2,3-triazole-4-carboxamide |
| 473 | 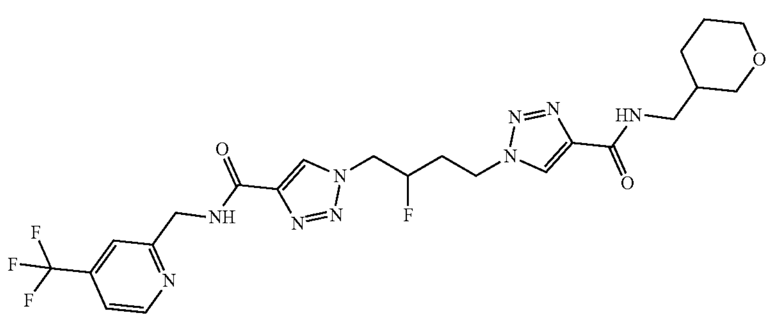 [SMILES: O=C(NCC1CCCOC1)c1cn(CCC(F)Cn2cc(C(=O)NCc3cc(C(F)(F)F)ccn3)nn2)nn1] | 1-(2-fluoro-4-{4-[(oxan-3-ylmethyl)carbamoyl]-1H-1,2,3-triazol-1-yl}butyl)-N-{[4-(trifluoromethyl)pyridin-2-yl]methyl}-1H-1,2,3-triazole-4-carboxamide |

TABLE 1-continued

Synthesized Examples

| Ex. No. | Structure | Name |
|---|---|---|
| 474 | 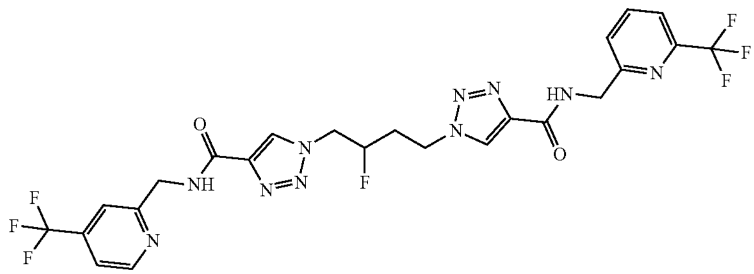 [SMILES: O=C(NCc1cccc(C(F)(F)F)n1)c1cn(CCC(F)Cn2cc(C(=O)NCc3cc(C(F)(F)F)ccn3)nn2)nn1] | 1-{2-fluoro-4-[4-({[6-(trifluoromethyl)pyridin-2-yl]methyl}carbamoyl)-1H-1,2,3-triazol-1-yl]butyl}-N-{[4-(trifluoromethyl)pyridin-2-yl]methyl}-1H-1,2,3-triazole-4-carboxamide |
| 475 | 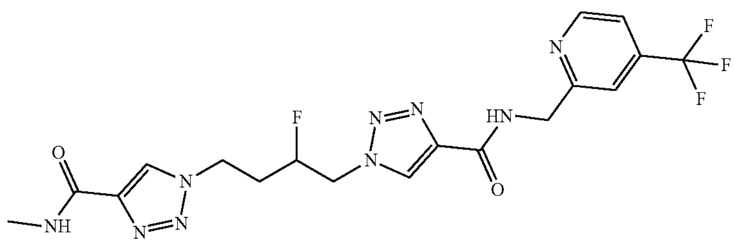 [SMILES: CNC(=O)c1cn(CCC(F)Cn2cc(C(=O)NCc3cc(C(F)(F)F)ccn3)nn2)nn1] | 1-{2-fluoro-4-[4-(methylcarbamoyl)-1H-1,2,3-triazol-1-yl]butyl}-N-{[4-(trifluoromethyl)pyridin-2-yl]methyl}-1H-1,2,3-triazole-4-carboxamide |
| 476 | 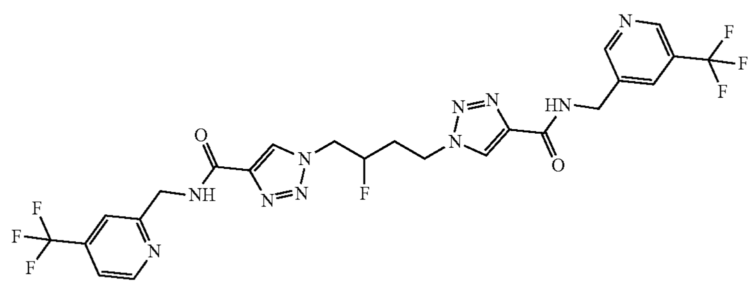 [SMILES: O=C(NCc1cncc(C(F)(F)F)c1)c1cn(CCC(F)Cn2cc(C(=O)NCc3cc(C(F)(F)F)ccn3)nn2)nn1] | 1-{2-fluoro-4-[4-({[5-(trifluoromethyl)pyridin-3-yl]methyl}carbamoyl)-1H-1,2,3-triazol-1-yl]butyl}-N-{[4-(trifluoromethyl)pyridin-2-yl]methyl}-1H-1,2,3-triazole-4-carboxamide |
| 477 | 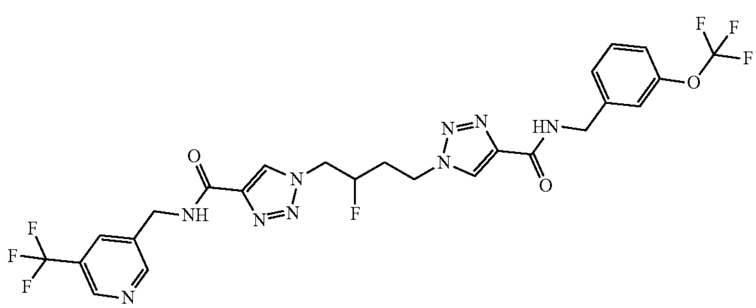 [SMILES: O=C(NCc1cccc(OC(F)(F)F)c1)c1cn(CCC(F)Cn2cc(C(=O)NCc3cncc(C(F)(F)F)c3)nn2)nn1] | 1-{2-fluoro-4-[4-({[3-(trifluoromethoxy)phenyl]methyl}carbamoyl)-1H-1,2,3-triazol-1-yl]butyl}-N-{[5-(trifluoromethyl)pyridin-3-yl]methyl}-1H-1,2,3-triazole-4-carboxamide |
| 478 | 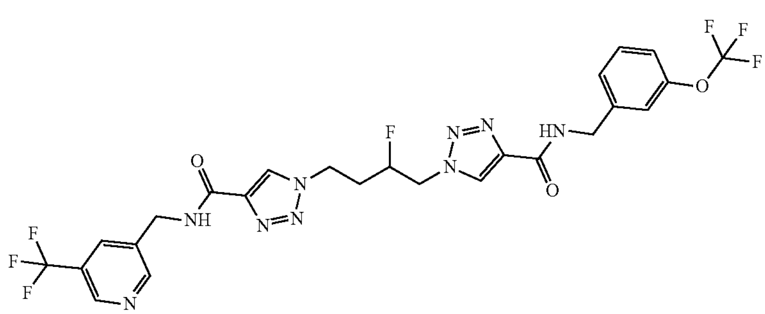 [SMILES: O=C(NCc1cncc(C(F)(F)F)c1)c1cn(CCC(F)Cn2cc(C(=O)NCc3cccc(OC(F)(F)F)c3)nn2)nn1] | 1-{3-fluoro-4-[4-({[3-(trifluoromethoxy)phenyl]methyl}carbamoyl)-1H-1,2,3-triazol-1-yl]butyl}-N-{[5-(trifluoromethyl)pyridin-3-yl]methyl}-1H-1,2,3-triazole-4-carboxamide |

TABLE 1-continued

Synthesized Examples

| Ex. No. | Structure | Name |
|---|---|---|
| 479 | 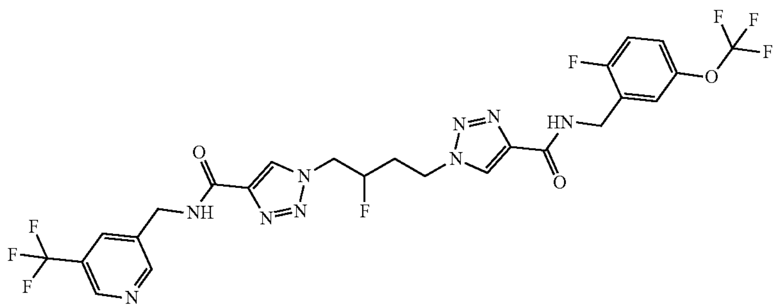 [SMILES: O=C(NCc1cc(OC(F)(F)F)ccc1F)c1cn(CCC(F)Cn2cc(C(=O)NCc3cncc(C(F)(F)F)c3)nn2)nn1] | 1-{2-fluoro-4-[4-({[2-fluoro-5-(trifluoromethoxy)phenyl]methyl}carbamoyl)-1H-1,2,3-triazol-1-yl]butyl}-N-{[5-(trifluoromethyl)pyridin-3-yl]methyl}-1H-1,2,3-triazole-4-carboxamide |
| 480 | 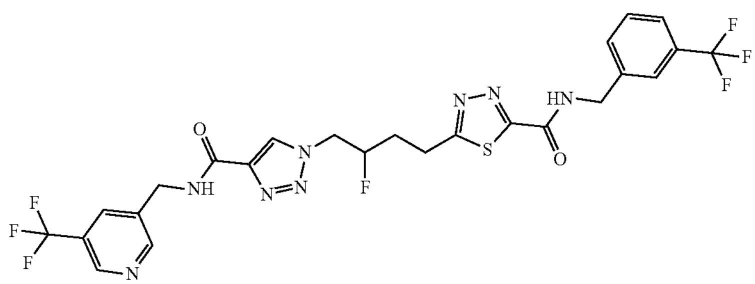 [SMILES: O=C(NCc1cncc(C(F)(F)F)c1)c1cn(CC(F)CCc2nnc(C(=O)NCc3cccc(C(F)(F)F)c3)s2)nn1] | 5-{3-fluoro-4-[4-({[5-(trifluoromethyl)pyridin-3-yl]methyl}carbamoyl)-1H-1,2,3-triazol-1-yl]butyl}-N-{[3-(trifluoromethyl)phenyl]methyl}-1,3,4-thiadiazole-2-carboxamide |
| 481 | 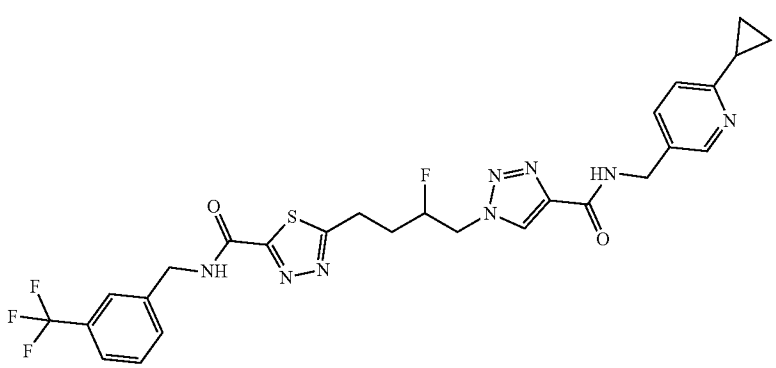 [SMILES: O=C(NCc1ccc(C2CC2)nc1)c1cn(CC(F)CCc2nnc(C(=O)NCc3cccc(C(F)(F)F)c3)s2)nn1] | 5-[4-(4-{[(6-cyclopropylpyridin-3-yl)methyl]carbamoyl}-1H-1,2,3-triazol-1-yl)-3-fluorobutyl]-N-{[3-(trifluoromethyl)phenyl]methyl}-1,3,4-thiadiazole-2-carboxamide |
| 482 | 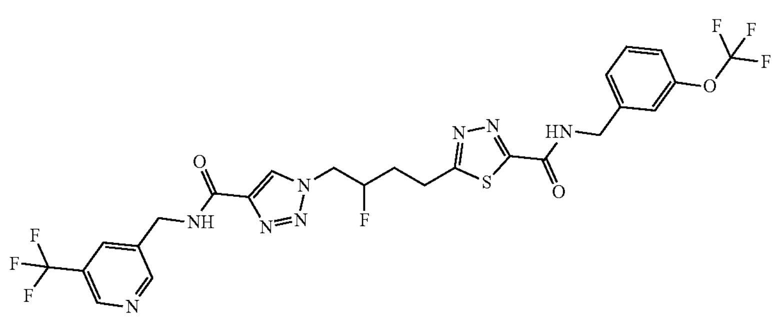 [SMILES: O=C(NCc1cncc(C(F)(F)F)c1)c1cn(CC(F)CCc2nnc(C(=O)NCc3cccc(OC(F)(F)F)c3)s2)nn1] | 5-{3-fluoro-4-[4-({[5-(trifluoromethyl)pyridin-3-yl]methyl}carbamoyl)-1H-1,2,3-triazol-1-yl]butyl}-N-{[3-(trifluoromethoxy)phenyl]methyl}-1,3,4-thiadiazole-2-carboxamide |

TABLE 1-continued

Synthesized Examples

| Ex. No. | Structure | Name |
|---|---|---|
| 483 | 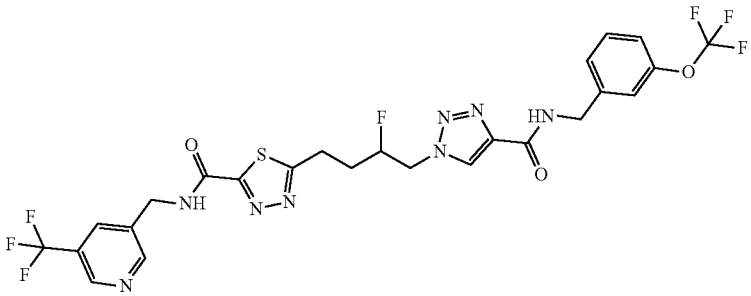 [SMILES: O=C(NCc1cccc(OC(F)(F)F)c1)c1cn(CC(F)CCc2nnc(C(=O)NCc3cncc(C(F)(F)F)c3)s2)nn1] | 5-{3-fluoro-4-[4-({[3-(trifluoromethoxy)phenyl]methyl}carbamoyl)-1H-1,2,3-triazol-1-yl]butyl}-N-{[5-(trifluoromethyl)pyridin-3-yl]methyl}-1,3,4-thiadiazole-2-carboxamide |
| 484 | 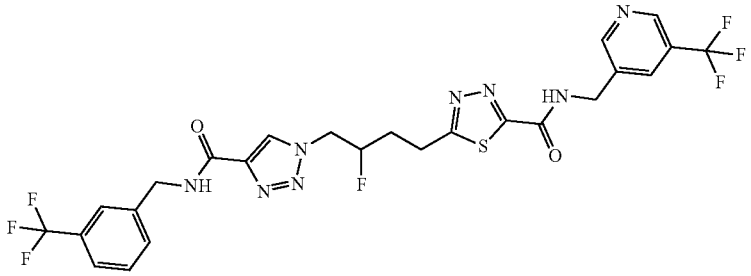 [SMILES: O=C(NCc1cccc(C(F)(F)F)c1)c1cn(CC(F)CCc2nnc(C(=O)NCc3cncc(C(F)(F)F)c3)s2)nn1] | 5-{3-fluoro-4-[4-({[3-(trifluoromethyl)phenyl]methyl}carbamoyl)-1H-1,2,3-triazol-1-yl]butyl}-N-{[5-(trifluoromethyl)pyridin-3-yl]methyl}-1,3,4-thiadiazole-2-carboxamide |
| 485 | 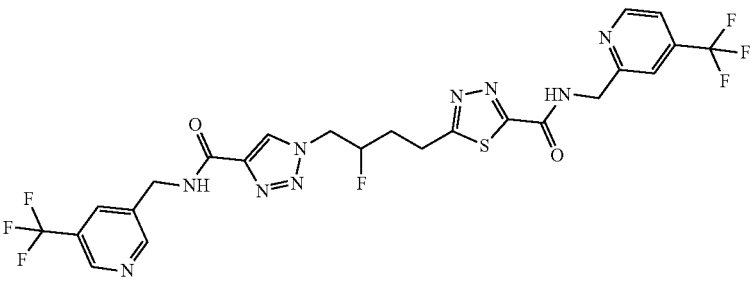 | 5-{3-fluoro-4-[4-({[5-(trifluoromethyl)pyridin-3-yl]methyl}carbamoyl)-1H-1,2,3-triazol-1-yl]butyl}-N-{[4-(trifluoromethyl)pyridin-2-yl]methyl}-1,3,4-thiadiazole-2-carboxamide |
| 486 | 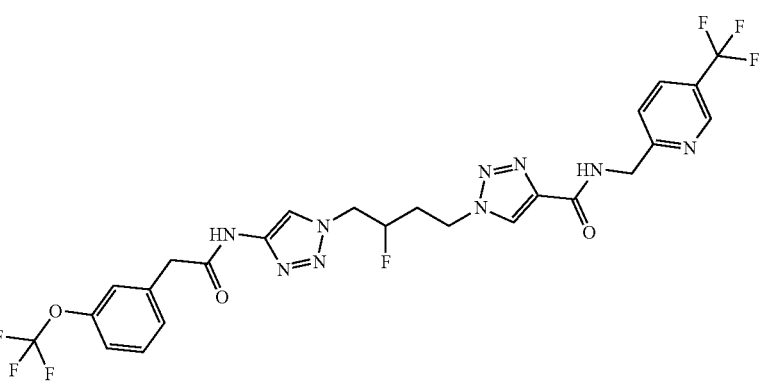 | 1-[3-fluoro-4-(4-{2-[3-(trifluoromethoxy)phenyl]acetamido}-1H-1,2,3-triazol-1-yl)butyl]-N-{[5-(trifluoromethyl)pyridin-2-yl]methyl}-1H-1,2,3-triazole-4-carboxamide |
| 487 | 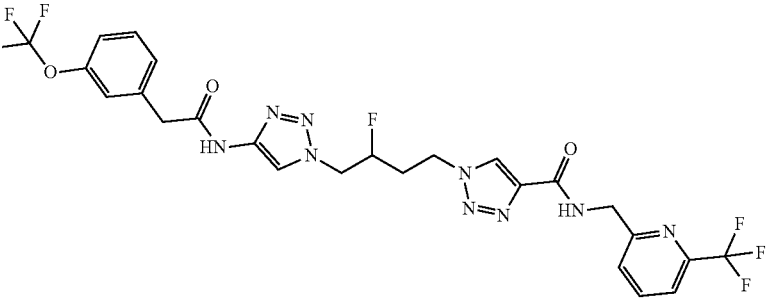 | 1-[3-fluoro-4-(4-{2-[3-(trifluoromethoxy)phenyl]acetamido}-1H-1,2,3-triazol-1-yl)butyl]-N-{[6-(trifluoromethyl)pyridin-2-yl]methyl}-1H-1,2,3-triazole-4-carboxamide |

TABLE 1-continued

Synthesized Examples

| Ex. No. | Structure | Name |
|---|---|---|
| 488 | 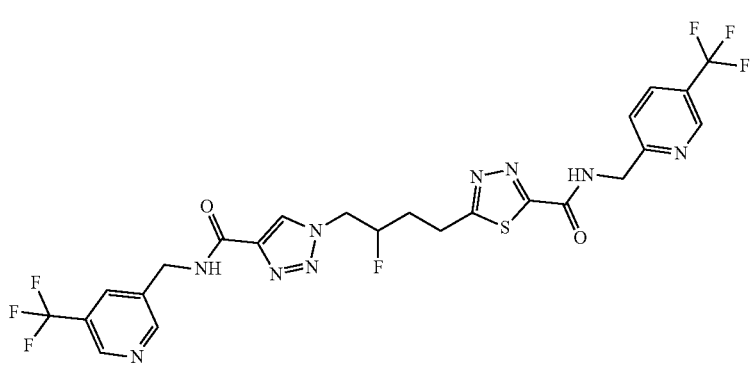 [SMILES: O=C(NCc1cncc(C(F)(F)F)c1)c1cn(CC(F)CCc2nnc(C(=O)NCc3ccc(C(F)(F)F)cn3)s2)nn1] | 5-{3-fluoro-4-[4-({[5-(trifluoromethyl)pyridin-3-yl]methyl}carbamoyl)-1H-1,2,3-triazol-1-yl]butyl}-N-{[5-(trifluoromethyl)pyridin-2-yl]methyl}-1,3,4-thiadiazole-2-carboxamide |
| 489 | 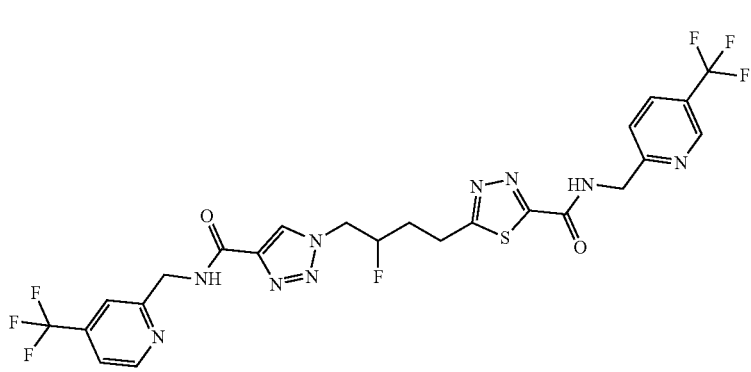 [SMILES: O=C(NCc1cc(C(F)(F)F)ccn1)c1cn(CC(F)CCc2nnc(C(=O)NCc3ccc(C(F)(F)F)cn3)s2)nn1] | 5-{3-fluoro-4-[4-({[4-(trifluoromethyl)pyridin-2-yl]methyl}carbamoyl)-1H-1,2,3-triazol-1-yl]butyl}-N-{[5-(trifluoromethyl)pyridin-2-yl]methyl}-1,3,4-thiadiazole-2-carboxamide |
| 490 | 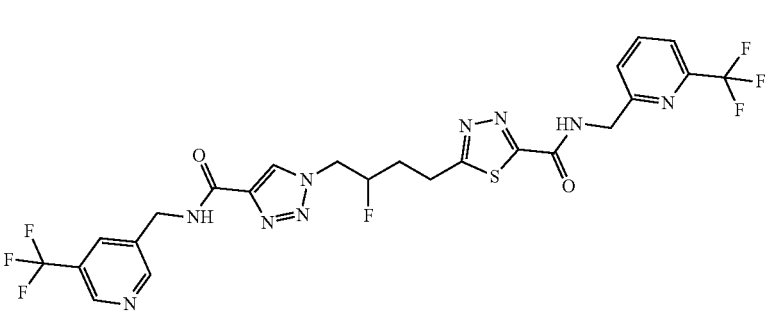 [SMILES: O=C(NCc1cncc(C(F)(F)F)c1)c1cn(CC(F)CCc2nnc(C(=O)NCc3cccc(C(F)(F)F)n3)s2)nn1] | 5-{3-fluoro-4-[4-({[5-(trifluoromethyl)pyridin-3-yl]methyl}carbamoyl)-1H-1,2,3-triazol-1-yl]butyl}-N-{[6-(trifluoromethyl)pyridin-2-yl]methyl}-1,3,4-thiadiazole-2-carboxamide |
| 491 | 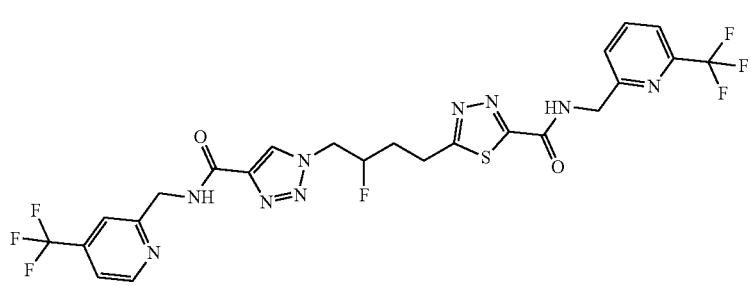 [SMILES: O=C(NCc1cc(C(F)(F)F)ccn1)c1cn(CC(F)CCc2nnc(C(=O)NCc3cccc(C(F)(F)F)n3)s2)nn1] | 5-{3-fluoro-4-[4-({[4-(trifluoromethyl)pyridin-2-yl]methyl}carbamoyl)-1H-1,2,3-triazol-1-yl]butyl}-N-{[6-(trifluoromethyl)pyridin-2-yl]methyl}-1,3,4-thiadiazole-2-carboxamide |

TABLE 1-continued

Synthesized Examples

| Ex. No. | Structure | Name |
|---|---|---|
| 492 | 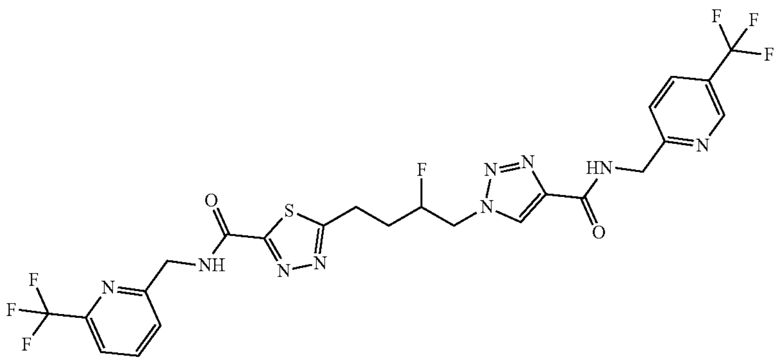 [SMILES: O=C(NCc1ccc(C(F)(F)F)cn1)c1cn(CC(F)CCc2nnc(C(=O)NCc3cccc(C(F)(F)F)n3)s2)nn1] | 5-{3-fluoro-4-[4-({[5-(trifluoromethyl)pyridin-2-yl]methyl}carbamoyl)-1H-1,2,3-triazol-1-yl]butyl}-N-{[6-(trifluoromethyl)pyridin-2-yl]methyl}-1,3,4-thiadiazole-2-carboxamide |
| 493 | 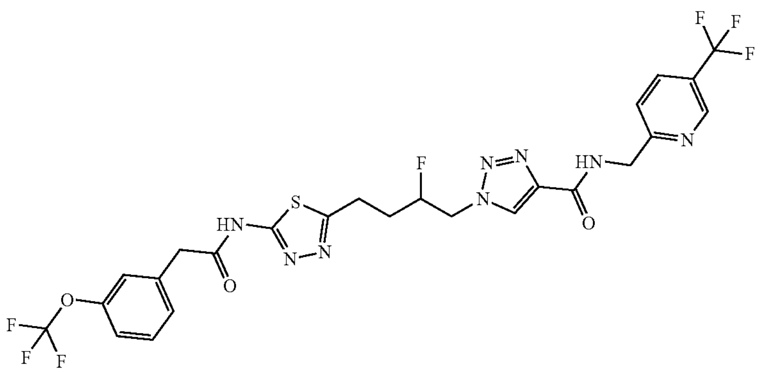 [SMILES: O=C(Cc1cccc(OC(F)(F)F)c1)Nc1nnc(CCC(F)Cn2cc(C(=O)NCc3ccc(C(F)(F)F)cn3)nn2)s1] | 1-[2-fluoro-4-(5-{2-[3-(trifluoromethoxy)phenyl]acetamido}-1,3,4-thiadiazol-2-yl)butyl]-N-{[5-(trifluoromethyl)pyridin-2-yl]methyl}-1H-1,2,3-triazole-4-carboxamide |
| 494 | 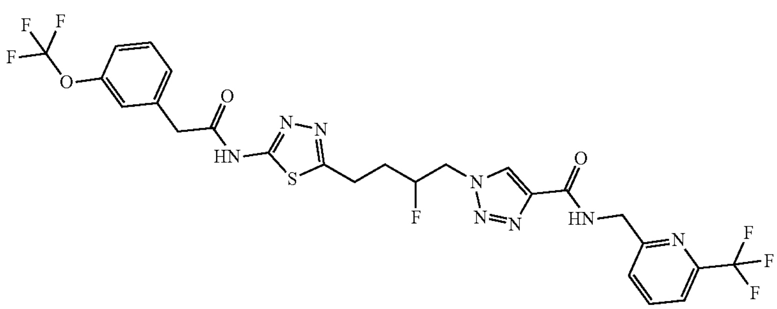 [SMILES: O=C(Cc1cccc(OC(F)(F)F)c1)Nc1nnc(CCC(F)Cn2cc(C(=O)NCc3cccc(C(F)(F)F)n3)nn2)s1] | 1-[2-fluoro-4-(5-{2-[3-(trifluoromethoxy)phenyl]acetamido}-1,3,4-thiadiazol-2-yl)butyl]-N-{[6-(trifluoromethyl)pyridin-2-yl]methyl}-1H-1,2,3-triazole-4-carboxamide |
| 495 | 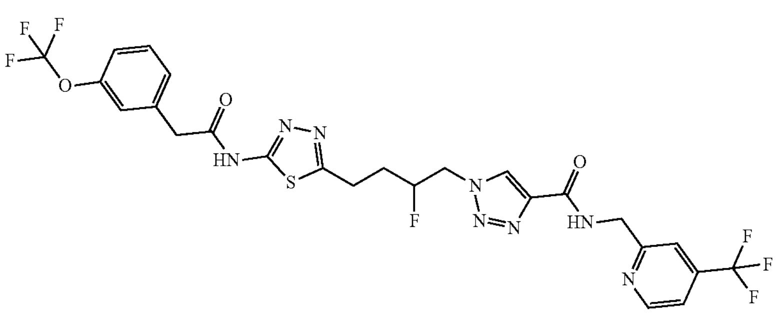 [SMILES: O=C(Cc1cccc(OC(F)(F)F)c1)Nc1nnc(CCC(F)Cn2cc(C(=O)NCc3cc(C(F)(F)F)ccn3)nn2)s1] | 1-[2-fluoro-4-(5-{2-[3-(trifluoromethoxy)phenyl]acetamido}-1,3,4-thiadiazol-2-yl)butyl]-N-{[4-(trifluoromethyl)pyridin-2-yl]methyl}-1H-1,2,3-triazole-4-carboxamide |

TABLE 1-continued

Synthesized Examples

| Ex. No. | Name |
|---|---|
| 496 | 1-[2-fluoro-4-(5-{2-[3-(trifluoromethoxy)phenyl]acetamido}-1,3,4-thiadiazol-2-yl)butyl]-N-{[5-(trifluoromethyl)pyridin-3-yl]methyl}-1H-1,2,3-triazole-4-carboxamide |
| 497 | 1-(2-fluoro-4-(5-(2-(3-(trifluoromethoxy)phenyl)acetamido)-1,3,4-thiadiazol-2-yl)butyl)-N-methyl-1H-1,2,3-triazole-4-carboxamide |
| 498 | 1-[2-fluoro-4-(5-{2-[3-(trifluoromethoxy)phenyl]acetamido}-1,3,4-thiadiazol-2-yl)butyl]-N-{[6-(trifluoromethyl)pyridin-3-yl]methyl}-1H-1,2,3-triazole-4-carboxamide |
| 499 | 5-{3-fluoro-4-[4-({[4-(trifluoromethyl)pyridin-2-yl]methyl}carbamoyl)-1H-1,2,3-triazol-1-yl]butyl}-N-(2,2,2-trifluoroethyl)-1,3,4-thiadiazole-2-carboxamide |
| 500 | 5-{3-fluoro-4-[4-({[5-(trifluoromethyl)pyridin-3-yl]methyl}carbamoyl)-1H-1,2,3-triazol-1-yl]butyl}-N-(2,2,2-trifluoroethyl)-1,3,4-thiadiazole-2-carboxamide |

TABLE 1-continued

Synthesized Examples

| Ex. No. | Structure | Name |
|---|---|---|
| 501 | 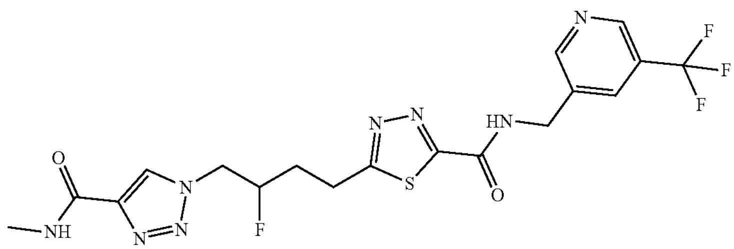 [SMILES: CNC(=O)c1cn(CC(F)CCc2nnc(C(=O)NCc3cncc(C(F)(F)F)c3)s2)nn1] | 5-{3-fluoro-4-[4-(methylcarbamoyl)-1H-1,2,3-triazol-1-yl]butyl}-N-{[5-(trifluoromethyl)pyridin-3-yl]methyl}-1,3,4-thiadiazole-2-carboxamide |
| 502 | 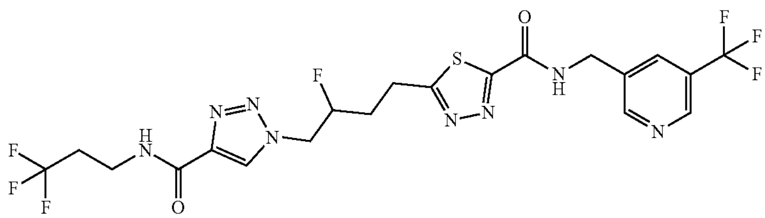 [SMILES: O=C(NCCC(F)(F)F)c1cn(CC(F)CCc2nnc(C(=O)NCc3cncc(C(F)(F)F)c3)s2)nn1] | 5-(3-fluoro-4-{4-[(3,3,3-trifluoropropyl)carbamoyl]-1H-1,2,3-triazol-1-yl}butyl)-N-{[5-(trifluoromethyl)pyridin-3-yl]methyl}-1,3,4-thiadiazole-2-carboxamide |
| 503 | 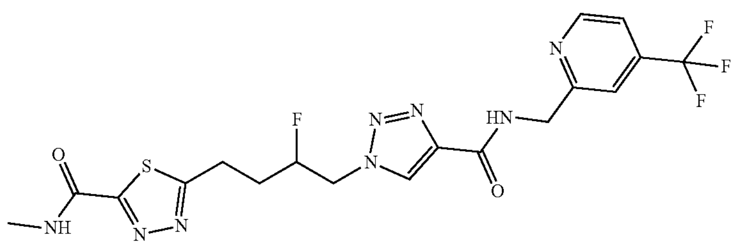 [SMILES: CNC(=O)c1nnc(CCC(F)Cn2cc(C(=O)NCc3cc(C(F)(F)F)ccn3)nn2)s1] | 5-{3-fluoro-4-[4-({[4-(trifluoromethyl)pyridin-2-yl]methyl}carbamoyl)-1H-1,2,3-triazol-1-yl]butyl}-N-methyl-1,3,4-thiadiazole-2-carboxamide |
| 504 | 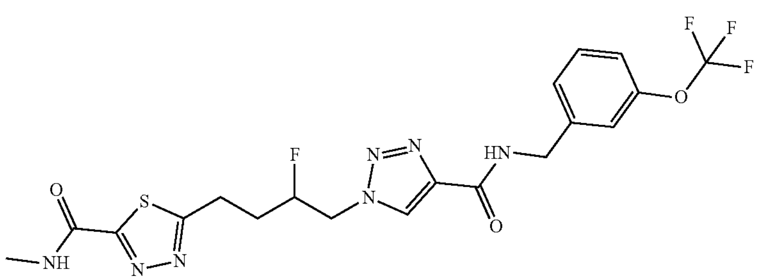 [SMILES: CNC(=O)c1nnc(CCC(F)Cn2cc(C(=O)NCc3cccc(OC(F)(F)F)c3)nn2)s1] | 5-{3-fluoro-4-[4-({[3-(trifluoromethoxy)phenyl]methyl}carbamoyl)-1H-1,2,3-triazol-1-yl]butyl}-N-methyl-1,3,4-thiadiazole-2-carboxamide |
| 505 | 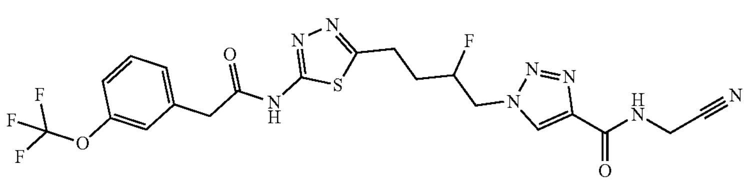 [SMILES: N#CCNC(=O)c1cn(CC(F)CCc2nnc(NC(=O)Cc3cccc(OC(F)(F)F)c3)s2)nn1] | N-(cyanomethyl)-1-[2-fluoro-4-(5-{2-[3-(trifluoromethoxy)phenyl]acetamido}-1,3,4-thiadiazol-2-yl)butyl]-1H-1,2,3-triazole-4-carboxamide |
| 506 | | 5-(3-fluoro-4-{4-[(2,2,2-trifluoroethyl)carbamoyl]-1H-1,2,3-triazol-1-yl}butyl)-N-{[5-(trifluoromethyl)pyridin-3-yl]methyl}-1,3,4-thiadiazole-2-carboxamide | ns
TABLE 1-continued

Synthesized Examples

| Ex. No. | Structure | Name |
|---|---|---|
| 507 | 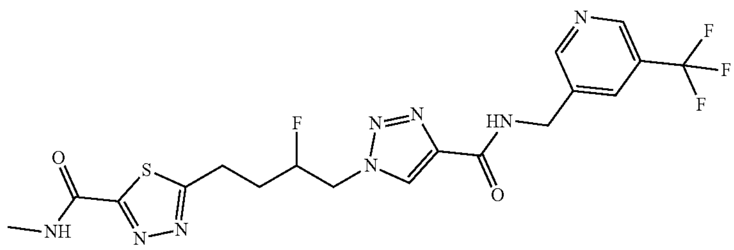 [SMILES: CNC(=O)c1nnc(CCC(F)Cn2cc(C(=O)NCc3cncc(C(F)(F)F)c3)nn2)s1] | 5-{3-fluoro-4-[4-({[5-(trifluoromethyl)pyridin-3-yl]methyl}carbamoyl)-1H-1,2,3-triazol-1-yl]butyl}-N-methyl-1,3,4-thiadiazole-2-carboxamide |
| 508 | 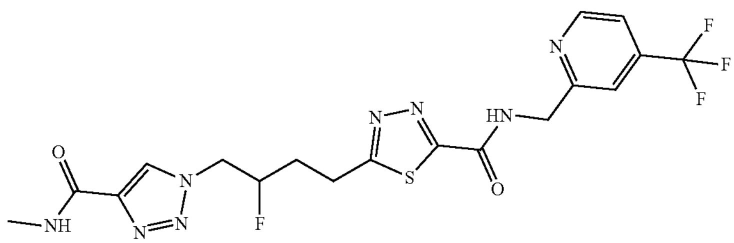 [SMILES: CNC(=O)c1cn(CC(F)CCc2nnc(C(=O)NCc3cc(C(F)(F)F)ccn3)s2)nn1] | 5-{3-fluoro-4-[4-(methylcarbamoyl)-1H-1,2,3-triazol-1-yl]butyl}-N-{[4-(trifluoromethyl)pyridin-2-yl]methyl}-1,3,4-thiadiazole-2-carboxamide |
| 509 | 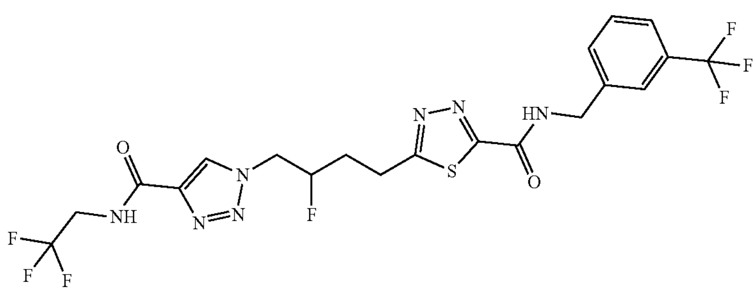 [SMILES: O=C(NCC(F)(F)F)c1cn(CC(F)CCc2nnc(C(=O)NCc3cccc(C(F)(F)F)c3)s2)nn1] | 5-(3-fluoro-4-{4-[(2,2,2-trifluoroethyl)carbamoyl]-1H-1,2,3-triazol-1-yl}butyl)-N-{[4-(trifluoromethyl)pyridin-2-yl]methyl}-1,3,4-thiadiazole-2-carboxamide |
| 510 | 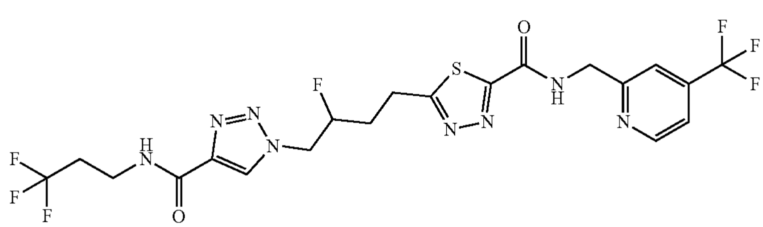 [SMILES: O=C(NCCC(F)(F)F)c1cn(CC(F)CCc2nnc(C(=O)NCc3cc(C(F)(F)F)ccn3)s2)nn1] | 5-(3-fluoro-4-{4-[(3,3,3-trifluoropropyl)carbamoyl]-1H-1,2,3-triazol-1-yl}butyl)-N-{[4-(trifluoromethyl)pyridin-2-yl]methyl}-1,3,4-thiadiazole-2-carboxamide |
| 511 | 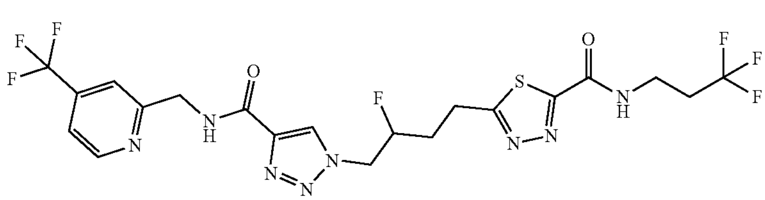 [SMILES: O=C(NCc1cc(C(F)(F)F)ccn1)c1cn(CC(F)CCc2nnc(C(=O)NCCC(F)(F)F)s2)nn1] | 5-{3-fluoro-4-[4-({[4-(trifluoromethyl)pyridin-2-yl]methyl}carbamooyl)-1H-1,2,3-triazol-1-yl]butyl}-N-(3,3,3-trifluoropropyl)-1,3,4-thiadiazole-2-carboxamide |
| 512 | 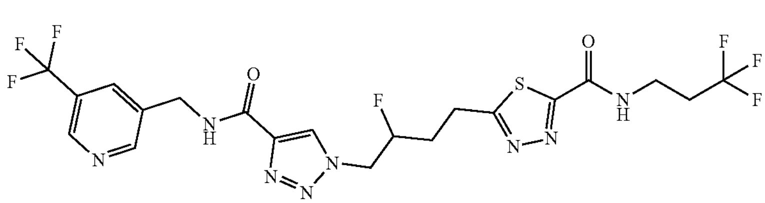 [SMILES: O=C(NCc1cncc(C(F)(F)F)c1)c1cn(CC(F)CCc2nnc(C(=O)NCCC(F)(F)F)s2)nn1] | 5-{3-fluoro-4-[4-({[5-(trifluoromethyl)pyridin-3-yl]methyl}carbamoyl)-1H-1,2,3-triazol-1-yl]butyl}-N-(3,3,3-trifluoropropyl)-1,3,4-thiadiazole-2-carboxamide |

TABLE 1-continued

Synthesized Examples

| Ex. No. | Structure | Name |
|---|---|---|
| 513 | 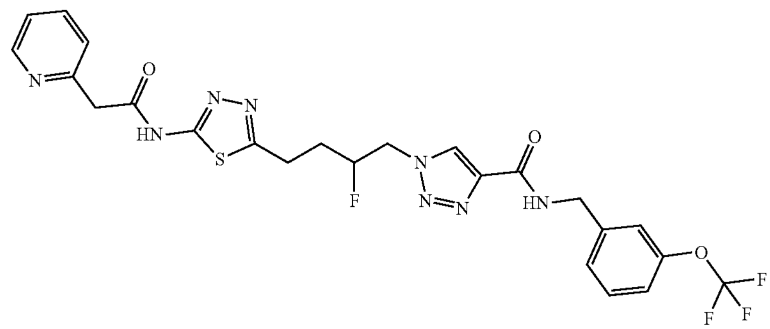 [SMILES: O=C(Cc1ccccn1)Nc1nnc(CCC(F)Cn2cc(C(=O)NCc3cccc(OC(F)(F)F)c3)nn2)s1] | 1-(2-fluoro-4-{5-[2-(pyridin-2-yl)acetamido]-1,3,4-thiadiazol-2-yl}butyl)-N-{[3-(trifluoromethoxy)phenyl]methyl}-1H-1,2,3-triazole-4-carboxamide |
| 514 | 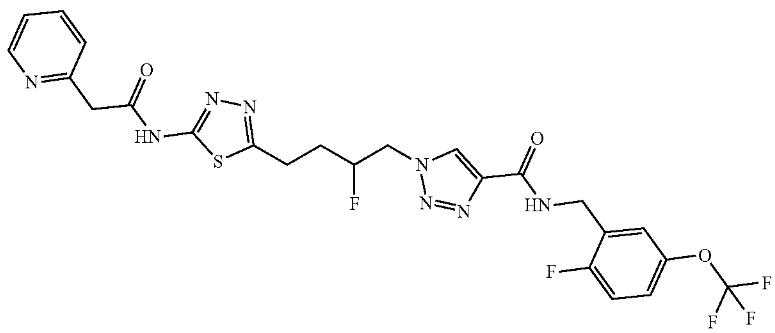 [SMILES: O=C(Cc1ccccn1)Nc1nnc(CCC(F)Cn2cc(C(=O)NCc3cc(OC(F)(F)F)ccc3F)nn2)s1] | 1-(2-fluoro-4-{4-[2-(pyridin-2-yl)acetamido]-1,3,4-thiadiazol-2-yl}butyl)-N-{[2-fluoro-5-(trifluoromethoxy)phenyl]methyl}-1H-1,2,3-triazole-4-carboxamide |
| 515 | 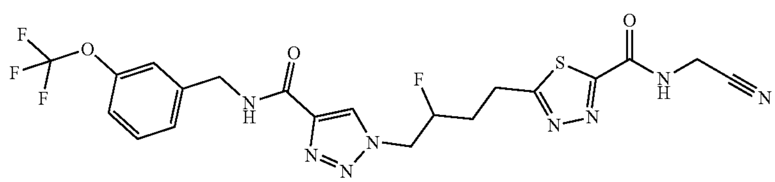 [SMILES: N#CCNC(=O)c1nnc(CCC(F)Cn2cc(C(=O)NCc3cccc(OC(F)(F)F)c3)nn2)s1] | N-(cyanomethyl)-5-{3-fluoro-4-[4-({[3-(trifluoromethoxy)phenyl]methyl}carbamoyl)-1H-1,2,3-triazol-1-yl]butyl}-1,3,4-thiadiazole-2-carboxamide |
| 516 | 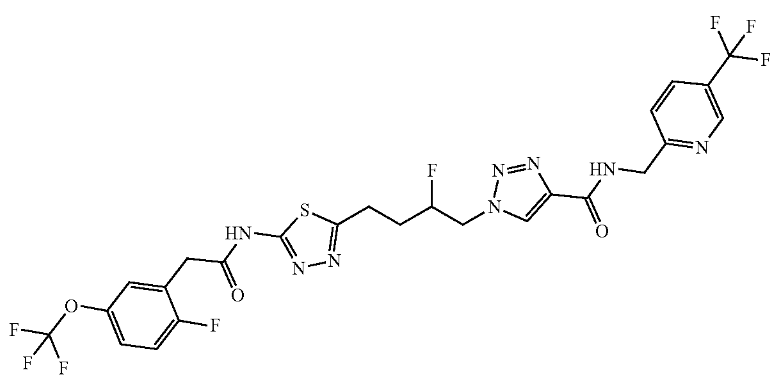 [SMILES: O=C(Cc1cc(OC(F)(F)F)ccc1F)Nc1nnc(CCC(F)Cn2cc(C(=O)NCc3ccc(C(F)(F)F)cn3)nn2)s1] | 1-[2-fluoro-4-(5-{2-[2-fluoro-5-(trifluoromethoxy)phenyl]acetamido}-1,3,4-thiadiazol-2-yl)butyl]-N-{[5-(trifluoromethyl)pyridin-2-yl]methyl}-1H-1,2,3-triazole-4-carboxamide |
| 517 | 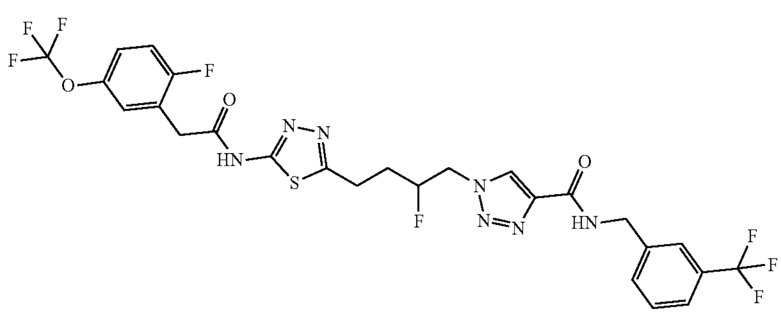 [SMILES: O=C(Cc1cc(OC(F)(F)F)ccc1F)Nc1nnc(CCC(F)Cn2cc(C(=O)NCc3cccc(C(F)(F)F)c3)nn2)s1] | 1-[2-fluoro-4-(5-{2-[2-fluoro-5-(trifluoromethoxy)phenyl]acetamido}-1,3,4-thiadiazol-2-yl)butyl]-N-{[4-(trifluoromethyl)pyridin-2-yl]methyl}-1H-1,2,3-triazole-4-carboxamide |

TABLE 1-continued

Synthesized Examples

| Ex. No. | Structure | Name |
|---|---|---|
| 518 | 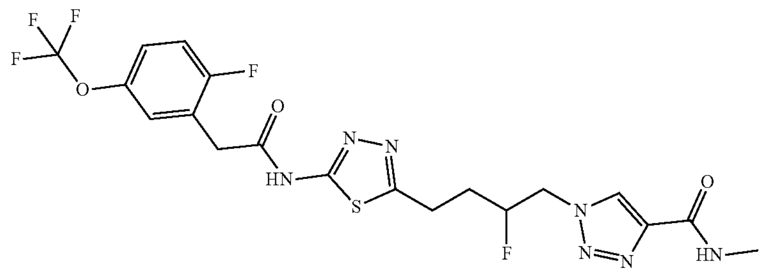 [SMILES: CNC(=O)c1cn(CC(F)CCc2nnc(NC(=O)Cc3cc(OC(F)(F)F)ccc3F)s2)nn1] | 1-[2-fluoro-4-(5-{2-[2-fluoro-5-(trifluoromethoxy)phenyl]acetamido}-1,3,4-thiadiazol-2-yl)butyl]-N-methyl-1H-1,2,3-triazole-4-carboxamide |
| 519 | 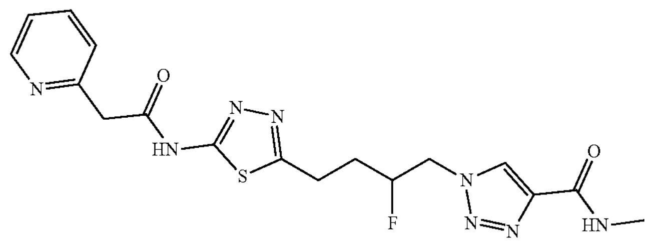 [SMILES: CNC(=O)c1cn(CC(F)CCc2nnc(NC(=O)Cc3ccccn3)s2)nn1] | 1-(2-fluoro-4-{5-[2-(pyridin-2-yl)acetamido]-1,3,4-thiadiazol-2-yl}butyl)-N-methyl-1H-1,2,3-triazole-4-carboxamide |
| 520 | 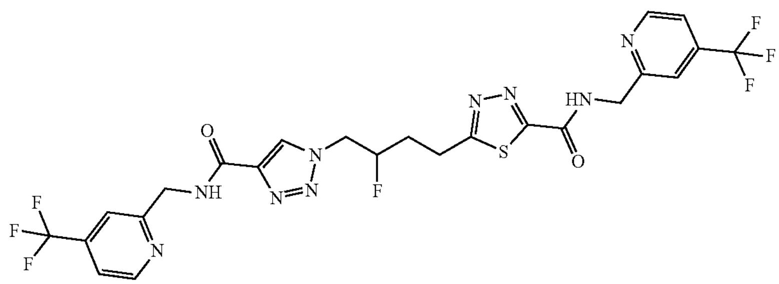 [SMILES: O=C(NCc1cc(C(F)(F)F)ccn1)c1cn(CC(F)CCc2nnc(C(=O)NCc3cc(C(F)(F)F)ccn3)s2)nn1] | 5-{3-fluoro-4-[4-({[4-(trifluoromethyl)pyridin-2-yl]methyl}carbamoyl)-1H-1,2,3-triazol-1-yl]butyl}-N-{[4-(trifluoromethyl)pyridin-2-yl]methyl}-1,3,4-thiadiazole-2-carboxamide |
| 521 | 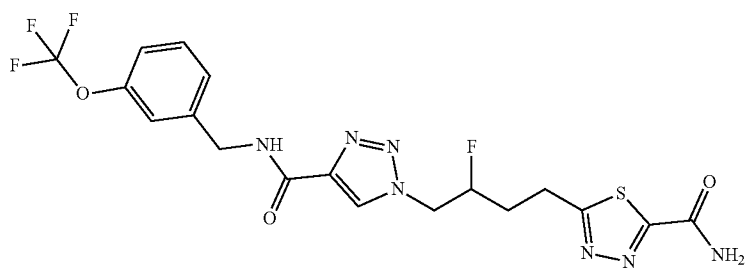 [SMILES: NC(=O)c1nnc(CCC(F)Cn2cc(C(=O)NCc3cccc(OC(F)(F)F)c3)nn2)s1] | 5-{3-fluoro-4-[4-({[3-(trifluoromethoxy)phenyl]methyl}carbamoyl)-1H-1,2,3-triazol-1-yl]butyl}-1,3,4-thiadiazole-2-carboxamide |
| 522 | 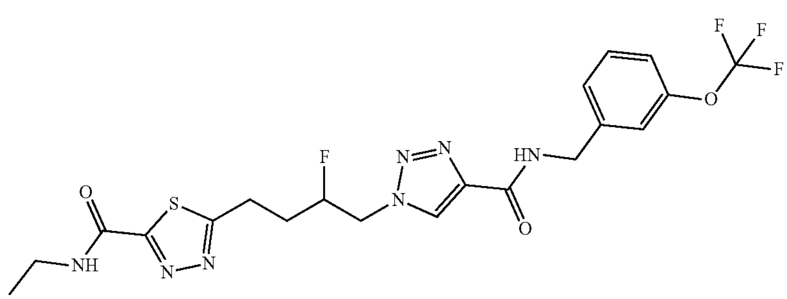 [SMILES: CCNC(=O)c1nnc(CCC(F)Cn2cc(C(=O)NCc3cccc(OC(F)(F)F)c3)nn2)s1] | N-ethyl-5-{3-fluoro-4-[4-({[3-(trifluoromethoxy)phenyl]methyl}carbamoyl)-1H-1,2,3-triazol-1-yl]butyl}-1,3,4-thiadiazole-2-carboxamide |
| 523 | 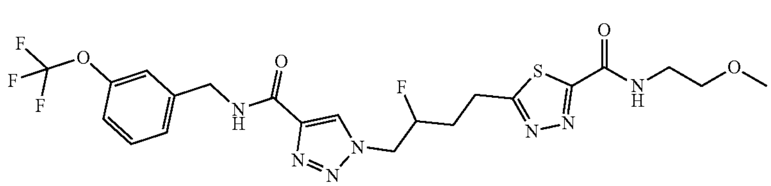 [SMILES: COCCNC(=O)c1nnc(CCC(F)Cn2cc(C(=O)NCc3cccc(OC(F)(F)F)c3)nn2)s1] | 5-{3-fluoro-4-[4-({[3-(trifluoromethoxy)phenyl]methyl}carbamoyl)-1H-1,2,3-triazol-1-yl]butyl}-N-(2-methoxyethyl)-1,3,4-thiadiazole-2-carboxamide |

TABLE 1-continued

Synthesized Examples

| Ex. No. | Name |
|---|---|
| 524 | 1-[3-fluoro-4-(4-{2-[3-(trifluoromethoxy)phenyl]acetamido}-1H-1,2,3-triazol-1-yl)butyl]-N-methyl-1H-1,2,3-triazole-4-carboxamide |
| 525 | 1-[3-fluoro-4-(4-{2-[2-fluoro-5-(trifluoromethoxy)phenyl]acetamido}-1H-1,2,3-triazol-1-yl)butyl]-N-methyl-1H-1,2,3-triazole-4-carboxamide |
| 526 | N-(propan-2-yl)-1-[4-(6-{2-[3-(trifluoromethoxy)phenyl]acetamido}pyridazin-3-yl)butyl]-1H-1,2,3-triazole-4-carboxamide |
| 527 | N-(cyanomethyl)-1-[4-(6-{2-[3-(trifluoromethoxy)phenyl]acetamido}pyridazin-3-yl)butyl]-1H-1,2,3-triazole-4-carboxamide |
| 528 | N-(2-hydroxyethyl)-1-[4-(6-{2-[3-(trifluoromethoxy)phenyl]acetamido}pyridazin-3-yl)butyl]-1H-1,2,3-triazole-4-carboxamide |

TABLE 1-continued

Synthesized Examples

| Ex. No. | Structure | Name |
|---|---|---|
| 529 | 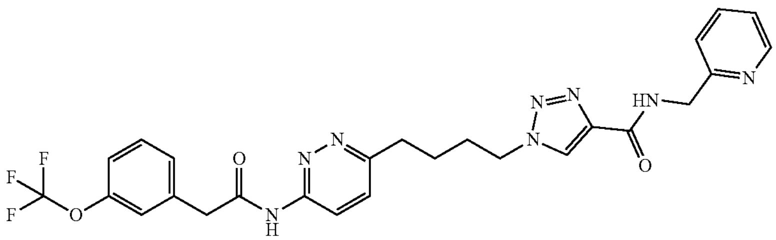 [SMILES: O=C(Cc1cccc(OC(F)(F)F)c1)Nc1ccc(CCCCn2cc(C(=O)NCc3ccccn3)nn2)nn1] | N-(pyridin-2-ylmethyl)-1-[4-(6-{2-[3-(trifluoromethoxy)phenyl]acetamido}pyridazin-3-yl)butyl]-1H-1,2,3-triazole-4-carboxamide |
| 530 | 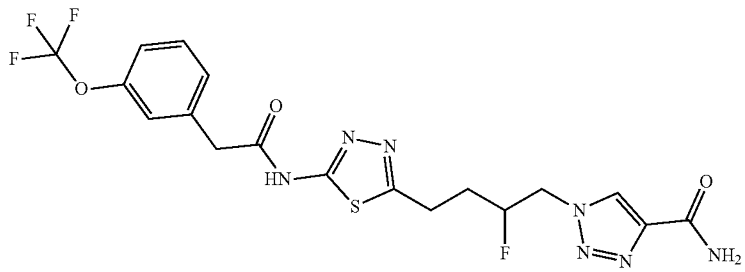 [SMILES: NC(=O)c1cn(CC(F)CCc2nnc(NC(=O)Cc3cccc(OC(F)(F)F)c3)s2)nn1] | 1-[2-fluoro-4-(5-{2-[3-(trifluoromethoxy)phenyl]acetamido}-1,3,4-thiadiazol-2-yl)butyl]-1H-1,2,3-triazole-4-carboxamide |
| 531 | 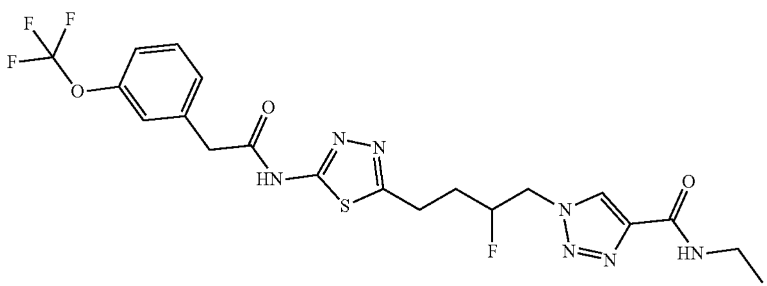 [SMILES: CCNC(=O)c1cn(CC(F)CCc2nnc(NC(=O)Cc3cccc(OC(F)(F)F)c3)s2)nn1] | N-ethyl-1-[2-fluoro-4-(5-{2-[3-(trifluoromethoxy)phenyl]acetamido}-1,3,4-thiadiazol-2-yl)butyl]-1H-1,2,3-triazole-4-carboxamide |
| 532 | 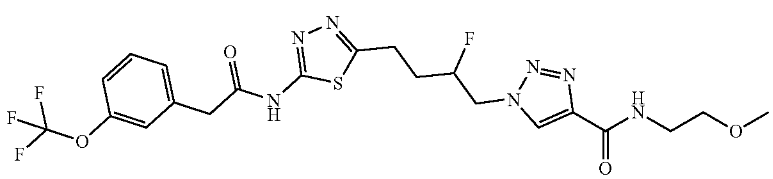 [SMILES: COCCNC(=O)c1cn(CC(F)CCc2nnc(NC(=O)Cc3cccc(OC(F)(F)F)c3)s2)nn1] | 1-[2-fluoro-4-(5-{2-[3-(trifluoromethoxy)phenyl]acetamido}-1,3,4-thiadiazol-2-yl)butyl]-N-(2-methoxyethyl)-1H-1,2,3-triazole-4-carboxamide |
| 533 | 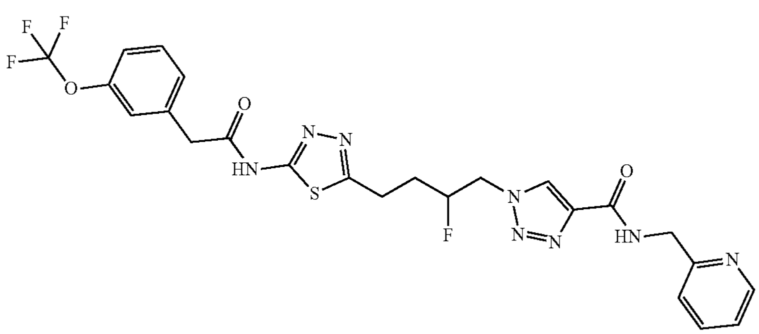 [SMILES: O=C(Cc1cccc(OC(F)(F)F)c1)Nc1nnc(CCC(F)Cn2cc(C(=O)NCc3ccccn3)nn2)s1] | 1-[2-fluoro-4-(5-{2-[3-(trifluoromethoxy)phenyl]acetamido}-1,3,4-thiadiazol-2-yl)butyl]-N-(pyridin-2-ylmethyl)-1H-1,2,3-triazole-4-carboxamide |

TABLE 1-continued

Synthesized Examples

| Ex. No. | Structure | Name |
|---|---|---|
| 534 | 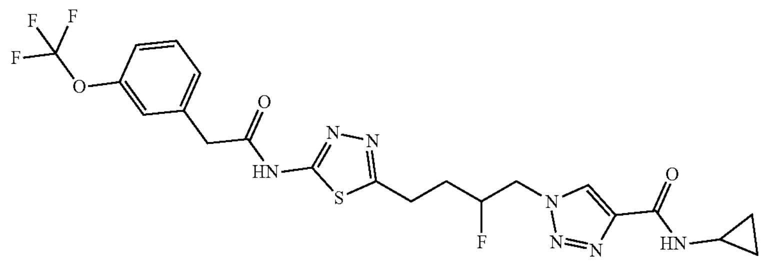 [SMILES: O=C(Cc1cccc(OC(F)(F)F)c1)Nc1nnc(CCC(F)Cn2cc(C(=O)NC3CC3)nn2)s1] | N-cyclopropyl-1-[2-fluoro-4-(5-{2-[3-(trifluoromethoxy)phenyl]acetamido}-1,3,4-thiadiazol-2-yl)butyl]-1H-1,2,3-triazole-4-carboxamide |
| 535 | 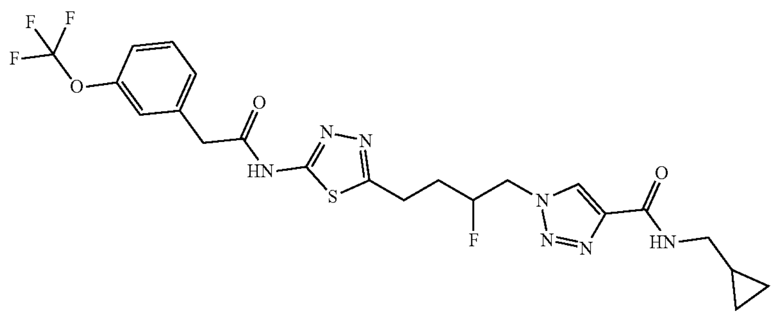 [SMILES: O=C(Cc1cccc(OC(F)(F)F)c1)Nc1nnc(CCC(F)Cn2cc(C(=O)NCC3CC3)nn2)s1] | N-(cyclopropylmethyl)-1-[2-fluoro-4-(5-{2-[3-(trifluoromethoxy)phenyl]acetamido}-1,3,4-thiadiazol-2-yl)butyl]-1H-1,2,3-triazole-4-carboxamide |
| 536 | 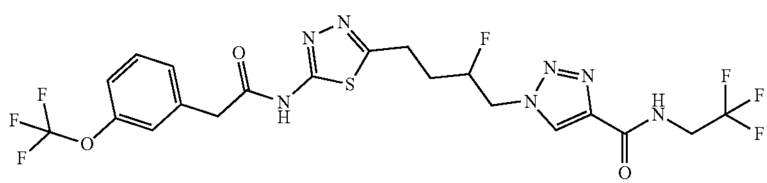 [SMILES: O=C(Cc1cccc(OC(F)(F)F)c1)Nc1nnc(CCC(F)Cn2cc(C(=O)NCC(F)(F)F)nn2)s1] | 1-[2-fluoro-4-(5-{2-[3-(trifluoromethoxy)phenyl]acetamido}-1,3,4-thiadiazol-2-yl)butyl]-N-(2,2,2-trifluoroethyl)-1H-1,2,3-triazole-4-carboxamide |
| 537 | 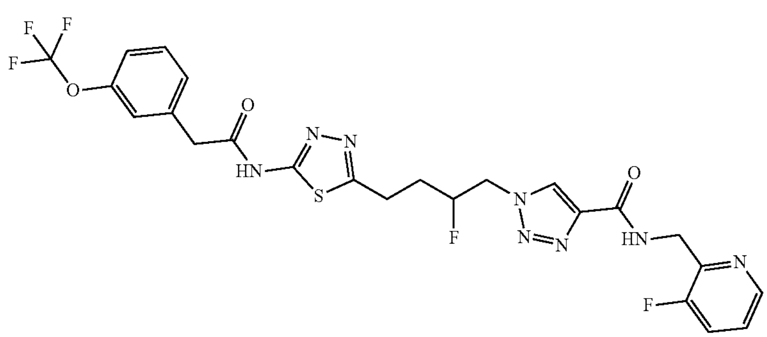 [SMILES: O=C(Cc1cccc(OC(F)(F)F)c1)Nc1nnc(CCC(F)Cn2cc(C(=O)NCc3ncccc3F)nn2)s1] | 1-[2-fluoro-4-(5-{2-[3-(trifluoromethoxy)phenyl]acetamido}-1,3,4-thiadiazol-2-yl)butyl]-N-[(3-fluoropyridin-2-yl)methyl]-1H-1,2,3-triazole-4-carboxamide |
| 538 | 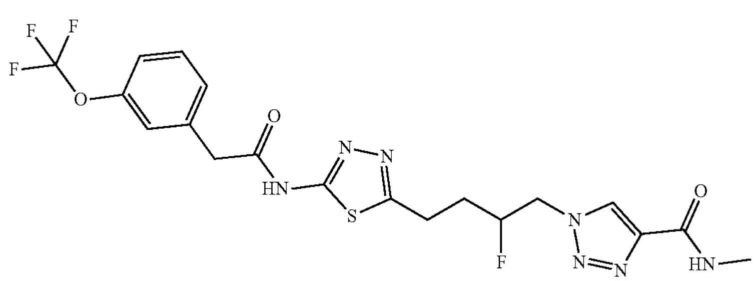 [SMILES: CNC(=O)c1cn(CC(F)CCc2nnc(NC(=O)Cc3cccc(OC(F)(F)F)c3)s2)nn1] | 1-[2-fluoro-4-(4-{2-[3-(trifluoromethoxy)phenyl]acetamido}-1H-1,2,3-triazol-1-yl)butyl]-N-methyl-1H-1,2,3-triazole-4-carboxamide |

TABLE 1-continued

Synthesized Examples

| Ex. No. | Structure | Name |
|---|---|---|
| 539 | 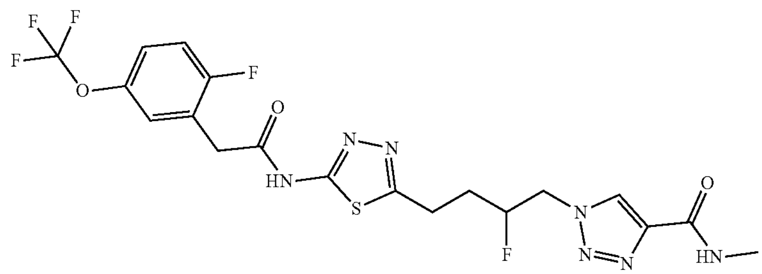 [SMILES: CNC(=O)c1cn(CC(F)CCc2nnc(NC(=O)Cc3cc(OC(F)(F)F)ccc3F)s2)nn1] | 1-[2-fluoro-4-(4-{2-[2-fluoro-5-(trifluoromethoxy)phenyl]acetamido}-1H-1,2,3-triazol-1-yl)butyl]-N-methyl-1H-1,2,3-triazole-4-carboxamide |
| 540 | 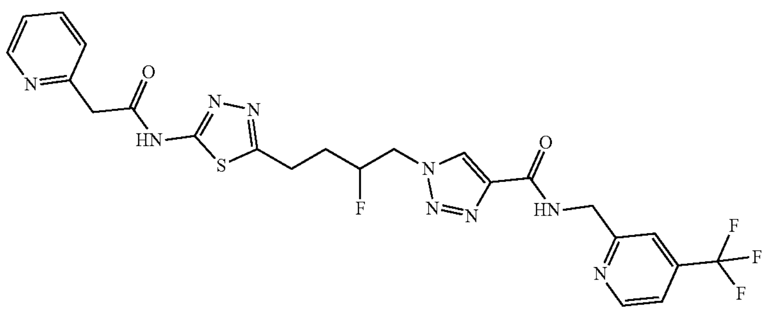 [SMILES: O=C(Cc1ccccn1)Nc1nnc(CCC(F)Cn2cc(C(=O)NCc3cc(C(F)(F)F)ccn3)nn2)s1] | 1-(2-fluoro-4-(5-(2-(pyridin-2-yl)acetamido)-1,3,4-thiadiazol-2-yl)butyl)-N-((4-(trifluoromethyl)pyridin-2-yl)methyl)-1H-1,2,3-triazole-4-carboxamide |
| 541 | 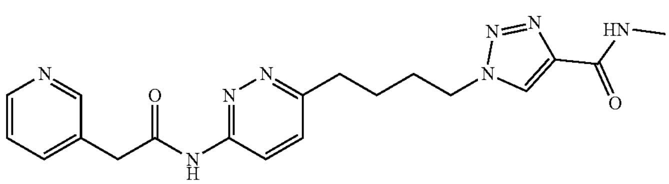 [SMILES: CNC(=O)c1cn(CCCCc2ccc(NC(=O)Cc3cccnc3)nn2)nn1] | N-methyl-1-(5-{6-[2-(pyridin-3-yl)acetamido]pyridazin-3-yl}butyl)-1H-1,2,3-triazole-4-carboxamide |
| 542 | 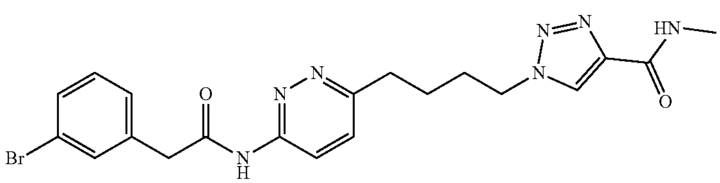 [SMILES: CNC(=O)c1cn(CCCCc2ccc(NC(=O)Cc3cccc(Br)c3)nn2)nn1] | 1-(4-{6-[2-(3-bromophenyl)acetamido]pyridazin-3-yl}butyl)-N-methyl-1H-1,2,3-triazole-4-carboxamide |
| 543 | 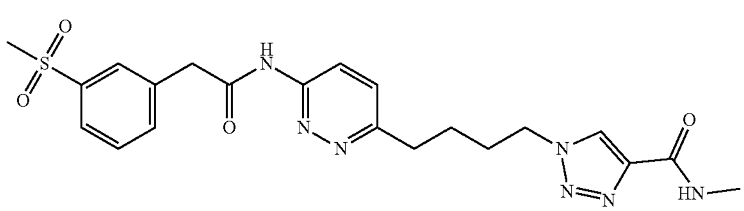 | 1-(4-{6-[2-(3-methanesulfonylphenyl)acetamido]pyridazin-3-yl}butyl)-N-methyl-1H-1,2,3-triazole-4-carboxamide |
| 544 | 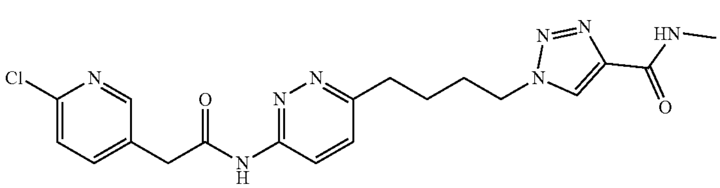 [SMILES: CNC(=O)c1cn(CCCCc2ccc(NC(=O)Cc3ccc(Cl)nc3)nn2)nn1] | 1-(4-{6-[2-(6-chloropyridin-3-yl)acetamido]pyridazin-3-yl}butyl)-N-methyl-1H-1,2,3-triazole-4-carboxamide |

TABLE 1-continued

Synthesized Examples

| Ex. No. | Structure | Name |
|---|---|---|
| 545 | 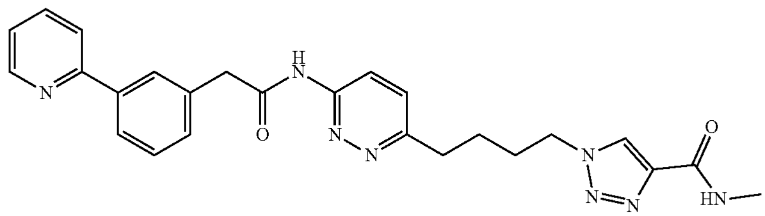 [SMILES: CNC(=O)c1cn(CCCCc2ccc(NC(=O)Cc3cccc(-c4ccccn4)c3)nn2)nn1] | N-methyl-1-[4-(6-{2-[3-(pyridin-2-yl)phenyl]acetamido}pyridazin-3-yl)butyl]-1H-1,2,3-triazole-4-carboxamide |
| 546 | 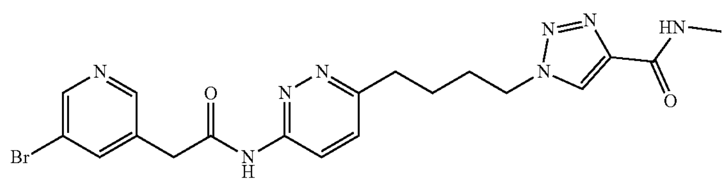 [SMILES: CNC(=O)c1cn(CCCCc2ccc(NC(=O)Cc3cncc(Br)c3)nn2)nn1] | 1-(4-{6-[2-(5-bromopyridin-3-yl)acetamido]pyridazin-3-yl}butyl)-N-methyl-1H-triazole-4-carboxamide |
| 547 | 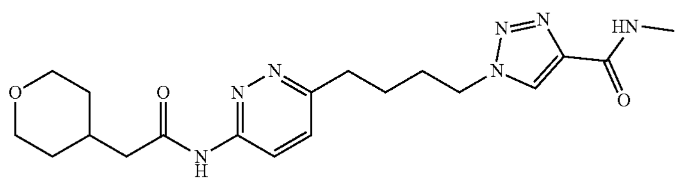 [SMILES: CNC(=O)c1cn(CCCCc2ccc(NC(=O)CC3CCOCC3)nn2)nn1] | N-methyl-1-(4-{6-[2-(oxan-4-yl)acetamido]pyridazin-3-yl}butyl)-1H-1,2,3-triazole-4-carboxamide |
| 548 | 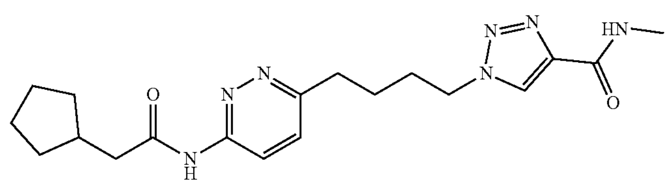 [SMILES: CNC(=O)c1cn(CCCCc2ccc(NC(=O)CC3CCCC3)nn2)nn1] | 1-{4-[6-(2-cyclopentylacetamido)pyridazin-3-yl]butyl}-N-methyl-1H-1,2,3-triazole-4-carboxamide |
| 549 | 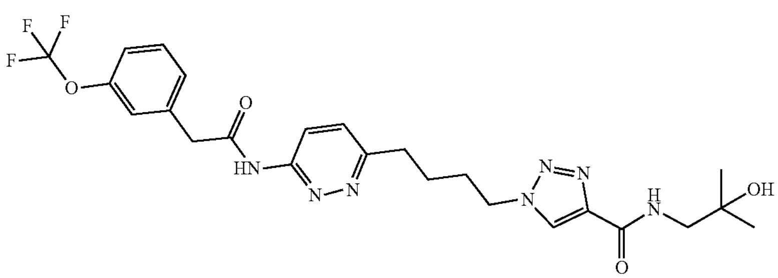 [SMILES: CC(C)(O)CNC(=O)c1cn(CCCCc2ccc(NC(=O)Cc3cccc(OC(F)(F)F)c3)nn2)nn1] | N-(2-hydroxy-2-methylpropyl)-1-[4-(6-{2-[3-(trifluoromethoxy)phenyl]acetamido}pyridazin-3-yl)butyl]-1H-1,2,3-triazole-4-carboxamide |
| 550 | 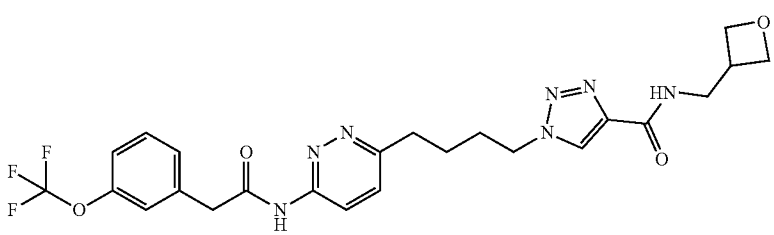 [SMILES: O=C(Cc1cccc(OC(F)(F)F)c1)Nc1ccc(CCCCn2cc(C(=O)NCC3COC3)nn2)nn1] | N-(oxetan-3-ylmethyl)-1-[4-(6-{2-[3-(trifluoromethoxy)phenyl]acetamido}pyridazin-3-yl)butyl]-1H-1,2,3-triazole-4-carboxamide |
| 551 | 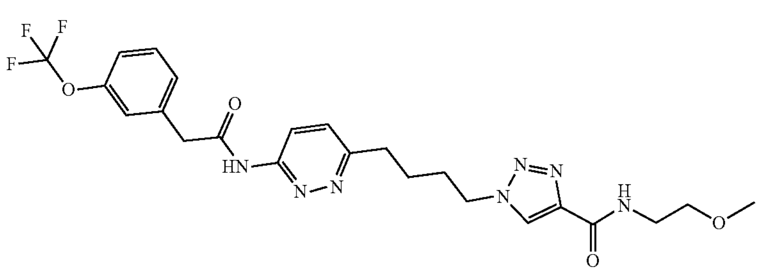 [SMILES: COCCNC(=O)c1cn(CCCCc2ccc(NC(=O)Cc3cccc(OC(F)(F)F)c3)nn2)nn1] | N-(2-methoxyethyl)-1-[4-(6-{2-[3-(trifluoromethoxy)phenyl]acetamido}pyridazin-3-yl)butyl]-1H-1,2,3-triazole-4-carboxamide |

TABLE 1-continued

Synthesized Examples

| Ex. No. | Structure | Name |
|---|---|---|
| 552 | 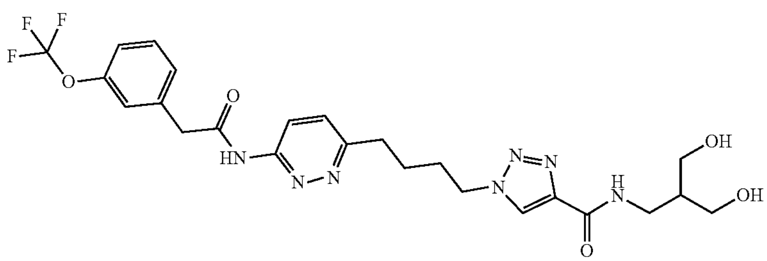 [SMILES: O=C(Cc1cccc(OC(F)(F)F)c1)Nc1ccc(CCCCn2cc(C(=O)NCC(CO)CO)nn2)nn1] | N-[3-hydroxy-2-(hydroxymethyl)propyl]-1-[4-(6-{2-[3-(trifluoromethoxy)phenyl]acetamido}-pyridazin-3-yl)butyl]-1H-1,2,3-triazole-4-carboxamide |
| 553 | 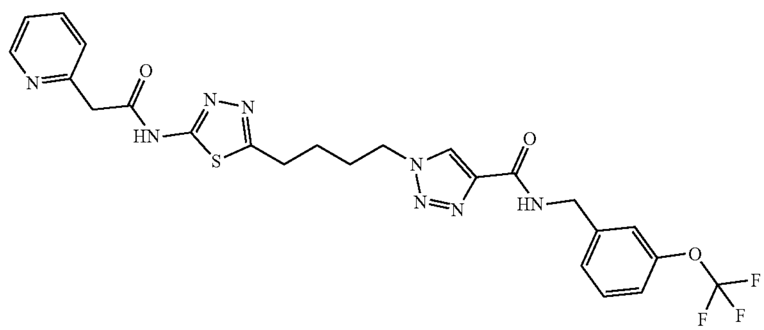 [SMILES: O=C(Cc1ccccn1)Nc1nnc(CCCCn2cc(C(=O)NCc3cccc(OC(F)(F)F)c3)nn2)s1] | 1-(4-{5-[2-(pyridin-2-yl)acetamido]-1,3,4-thiadiazol-2-yl}butyl)-N-{[3-(trifluoromethoxy)phenyl]methyl}-1H-1,2,3-triazole-4-carboxamide |
| 554 | 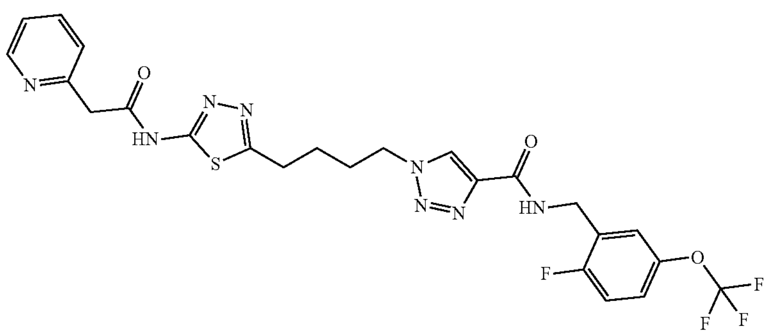 [SMILES: O=C(Cc1ccccn1)Nc1nnc(CCCCn2cc(C(=O)NCc3cc(OC(F)(F)F)ccc3F)nn2)s1] | N-{[2-fluoro-5-(trifluoromethoxy)phenyl]methyl}-1-(4-{5-[2-(pyridin-2-yl)acetamido]-1,3,4-thiadiazol-2-yl}butyl)-1H-1,2,3-triazole-4-carboxamide |
| 555 | 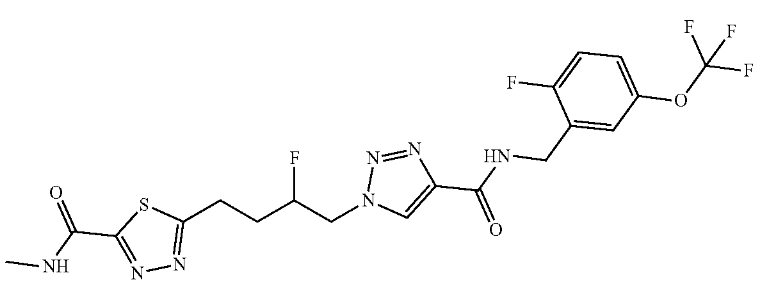 [SMILES: CNC(=O)c1nnc(CCC(F)Cn2cc(C(=O)NCc3cc(OC(F)(F)F)ccc3F)nn2)s1] | N-{3-fluoro-4-[4-({[2-fluoro-5-(trifluoromethoxy)phenyl]methyl}carbamoyl)-1H-1,2,3-triazol-1-yl]butyl}-N-methyl-1,3,4-thiadiazole-2-carboxamide |
| 556 | 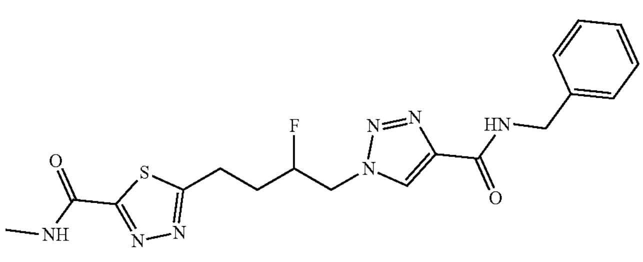 | 5-{4-[4-(benzylcarbamoyl)-1H-1,2,3-triazol-1-yl]-3-fluorobutyl}-N-methyl-1,3,4-thiadiazole-2-carboxamide |

TABLE 1-continued

Synthesized Examples

| Ex. No. | Structure | Name |
|---|---|---|
| 557 | 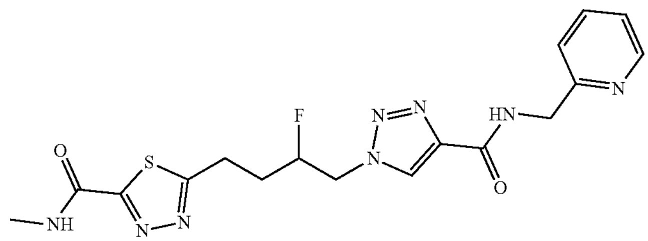 [SMILES: CNC(=O)c1nnc(CCC(F)Cn2cc(C(=O)NCc3ccccn3)nn2)s1] | 5-(3-fluoro-4-{4-[(pyridin-2-ylmethyl)carbamoyl]-1H-1,2,3-triazol-1-yl}butyl)-N-methyl-1,3,4-thiadiazole-2-carboxamide |
| 558 | 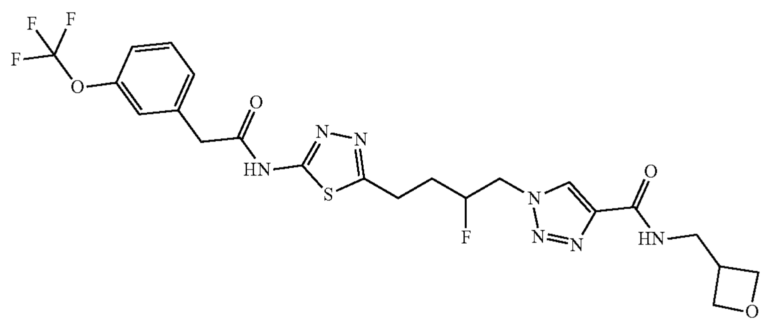 [SMILES: O=C(Cc1cccc(OC(F)(F)F)c1)Nc1nnc(CCC(F)Cn2cc(C(=O)NCC3COC3)nn2)s1] | 1-[2-fluoro-4-(5-{2-[3-(trifluoromethoxy)phenyl]acetamido}-1,3,4-thiadiazol-2-yl)butyl]-N-(oxetan-3-ylmethyl)-1H-1,2,3-triazole-4-carboxamide |
| 559 | 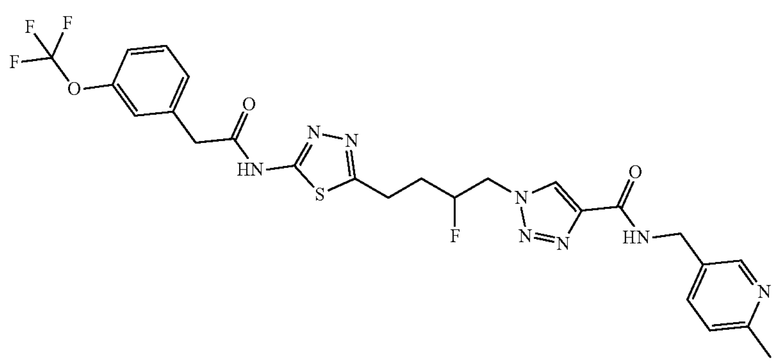 [SMILES: Cc1ccc(CNC(=O)c2cn(CC(F)CCc3nnc(NC(=O)Cc4cccc(OC(F)(F)F)c4)s3)nn2)cn1] | 1-[2-fluoro-4-(5-{2-[3-(trifluoromethoxy)phenyl]acetamido}-1,3,4-thiadiazol-2-yl)butyl]-N-[(6-methylpyridin-3-yl)methyl]-1H-1,2,3-triazole-4-carboxamide |
| 560 | 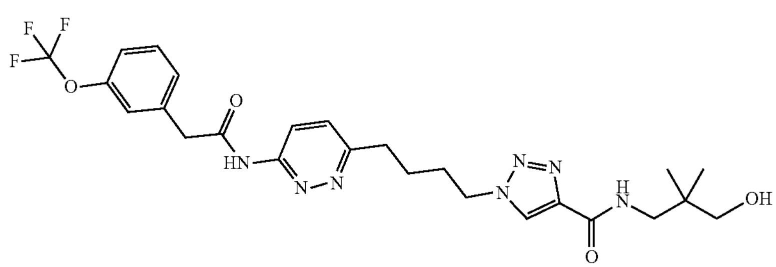 [SMILES: CC(C)(CO)CNC(=O)c1cn(CCCCc2ccc(NC(=O)Cc3cccc(OC(F)(F)F)c3)nn2)nn1] | N-(3-hydroxy-2,3-dimethylpropyl)-1-[4-(6-{2-[3-(trifluoromethoxy)phenyl]acetamido}pyridazin-3-yl)butyl]-1H-1,2,3-triazole-4-carboxamide |
| 561 | 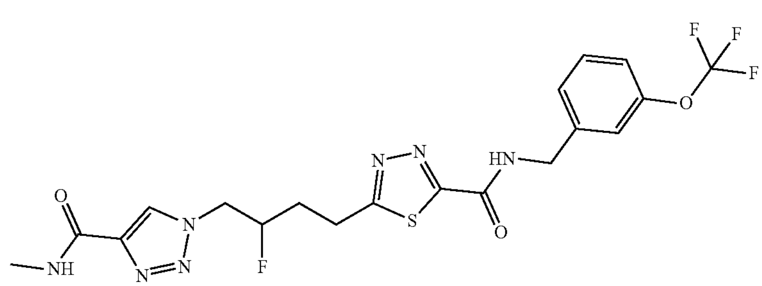 [SMILES: CNC(=O)c1cn(CC(F)CCc2nnc(C(=O)NCc3cccc(OC(F)(F)F)c3)s2)nn1] | 5-{3-fluoro-4-[4-(methylcarbamoyl)-1H-1,2,3-triazol-1-yl]butyl}-N-{[3-(trifluoromethoxy)phenyl]methyl}-1,3,4-thiadiazole-2-carboxamide |

TABLE 1-continued

Synthesized Examples

| Ex. No. | Structure | Name |
|---|---|---|
| 562 | 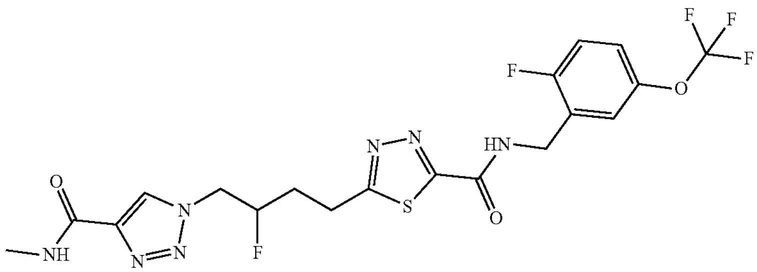 [SMILES: CNC(=O)c1cn(CC(F)CCc2nnc(C(=O)NCc3cc(OC(F)(F)F)ccc3F)s2)nn1] | 5-{3-fluoro-4-[4-(methylcarbamoyl)-1H-1,2,3-triazol-1-yl]butyl}-N-{[2-fluoro-5-(trifluoromethoxy)phenyl]methyl}-1,3,4-thiadiazole-2-carboxamide |
| 563 | 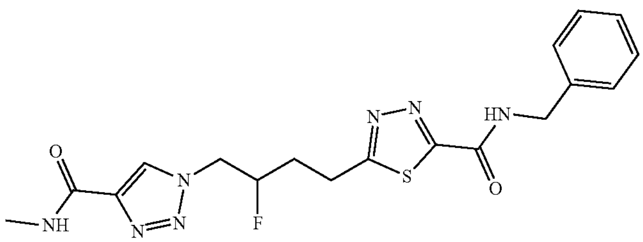 [SMILES: CNC(=O)c1cn(CC(F)CCc2nnc(C(=O)NCc3ccccc3)s2)nn1] | N-benzyl-5-{3-fluoro-4-[4-(methylcarbamoyl)-1H-1,2,3-triazol-1-yl]butyl}-1,3,4-thiadiazole-2-carboxamide |
| 564 | 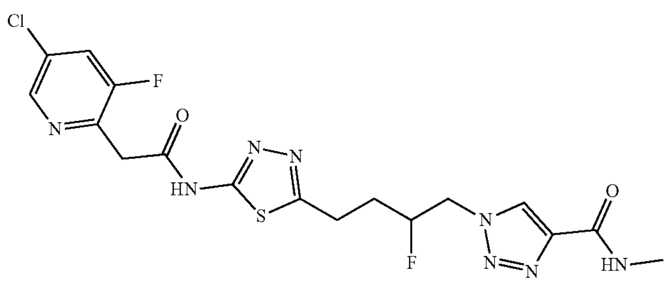 [SMILES: CNC(=O)c1cn(CC(F)CCc2nnc(NC(=O)Cc3ncc(Cl)cc3F)s2)nn1] | 1-(4-{5-[2-(5-chloro-3-fluoropyridin-2-yl)acetamido]-1,3,4-thiadiazol-2-yl}-2-fluorobutyl)-N-methyl-1H-1,2,3-triazole-4-carboxamide |
| 565 | 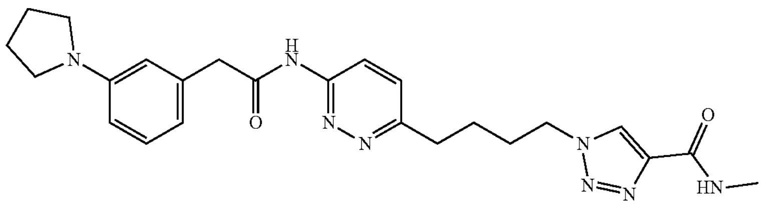 [SMILES: CNC(=O)c1cn(CCCCc2ccc(NC(=O)Cc3cccc(N4CCCC4)c3)nn2)nn1] | N-methyl-1-(4-(6-(2-(3-(pyrrolidin-1-yl)phenyl)acetamido)pyridazin-3-yl)butyl)-1H-1,2,3-triazole-4-carboxamide |
| 566 | 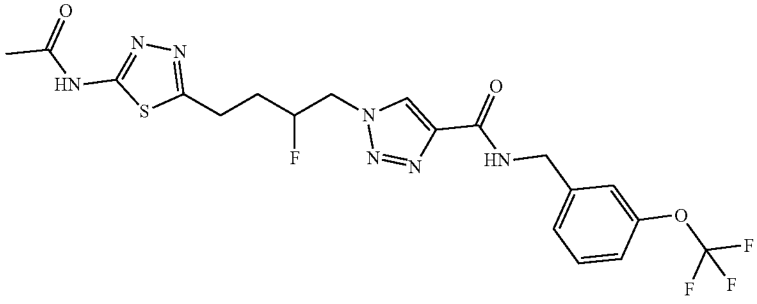 [SMILES: CC(=O)Nc1nnc(CCC(F)Cn2cc(C(=O)NCc3cccc(OC(F)(F)F)c3)nn2)s1] | 1-(4-(5-acetamido-1,3,4-thiadiazol-2-yl)-2-fluorobutyl)-N-(3-(trifluoromethoxy)benzyl)-1H-1,2,3-triazole-4-carboxamide |

TABLE 1-continued

Synthesized Examples

| Ex. No. | Structure | Name |
|---|---|---|
| 567 | 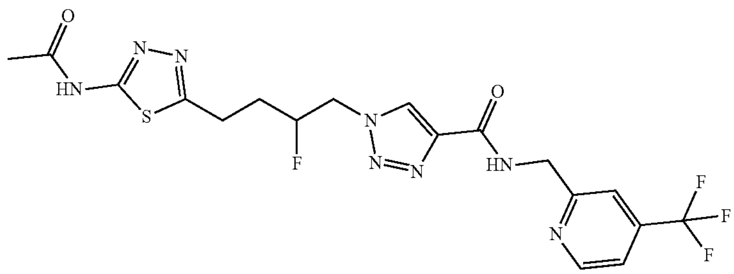 [SMILES: CC(=O)Nc1nnc(CCC(F)Cn2cc(C(=O)NCc3cc(C(F)(F)F)ccn3)nn2)s1] | 1-(4-(5-acetamido-1,3,4-thiadiazol-2-yl)-2-fluorobutyl)-N-((4-(trifluoromethyl)pyridin-2-yl)methyl)-1H-1,2,3-triazole-4-carboxamide |
| 568 | 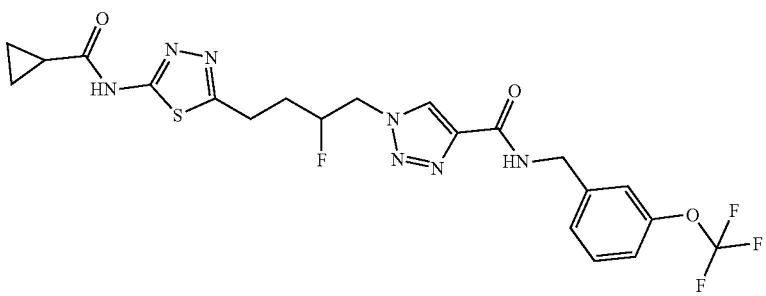 [SMILES: O=C(NCc1cccc(OC(F)(F)F)c1)c1cn(CC(F)CCc2nnc(NC(=O)C3CC3)s2)nn1] | 1-(4-(5-(cyclopropanecarboxamido)-1,3,4-thiadiazol-2-yl)-2-fluorobutyl)-N-(3-(trifluoromethoxy)benzyl)-1H-1,2,3-triazole-4-carboxamide |
| 569 | 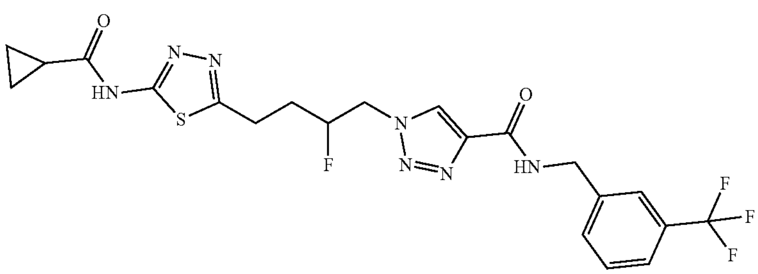 [SMILES: O=C(NCc1cccc(C(F)(F)F)c1)c1cn(CC(F)CCc2nnc(NC(=O)C3CC3)s2)nn1] | 1-(4-(5-(cyclopropanecarboxamido)-1,3,4-thiadiazol-2-yl)-2-fluorobutyl)-N-((4-(trifluoromethyl)pyridin-2-yl)methyl)-1H-1,2,3-triazole-4-carboxamide |
| 570 | 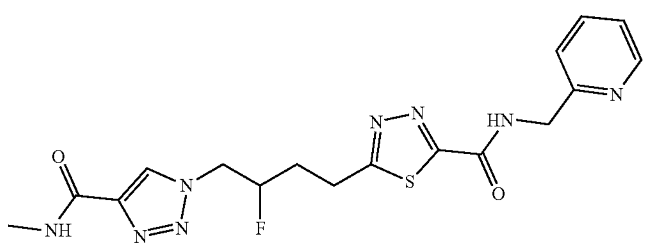 [SMILES: CNC(=O)c1cn(CC(F)CCc2nnc(C(=O)NCc3ccccn3)s2)nn1] | 5-(3-fluoro-4-(4-(methylcarbamoyl)-1H-1,2,3-triazol-1-yl)butyl)-N-(pyridin-2-ylmethyl)-1,3,4-thiadiazole-2-carboxamide |
| 571 | 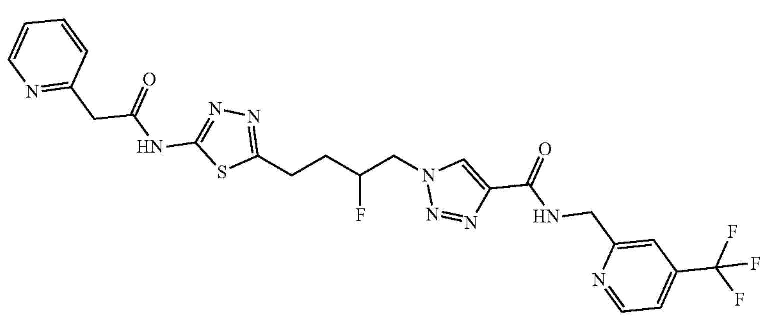 [SMILES: O=C(Cc1ccccn1)Nc1nnc(CCC(F)Cn2cc(C(=O)NCc3cc(C(F)(F)F)ccn3)nn2)s1] | 1-(2-fluoro-4-(5-(2-(pyridin-2-yl)acetamido)-1,3,4-thiadiazol-2-yl)butyl)-N-((5-(trifluoromethyl)pyridin-3-yl)methyl)-1H-1,2,3-triazole-4-carboxamide |

TABLE 1-continued

Synthesized Examples

| Ex. No. | Structure | Name |
|---|---|---|
| 572 | 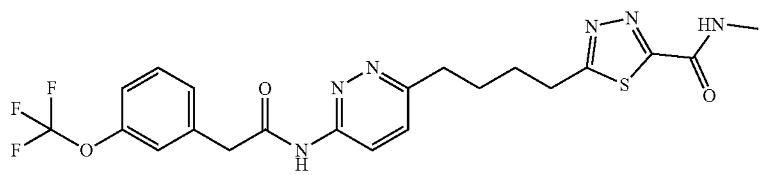 [SMILES: CNC(=O)c1nnc(CCCCc2ccc(NC(=O)Cc3cccc(OC(F)(F)F)c3)nn2)s1] | N-methyl-5-(4-(6-(2-(3-(trifluoromethoxy)phenyl)acetamido)pyridazin-3-yl)butyl)-1,3,4-thiadiazole-2-carboxamide |
| 573 | 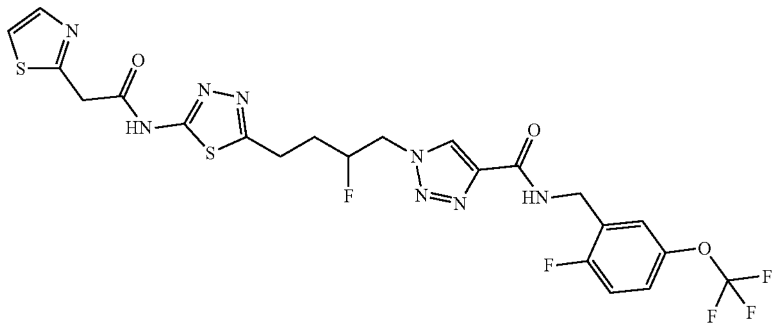 [SMILES: O=C(Cc1nccs1)Nc1nnc(CCC(F)Cn2cc(C(=O)NCc3cc(OC(F)(F)F)ccc3F)nn2)s1] | 1-(2-fluoro-4-(5-(2-(thiazol-2-yl)acetamido)-1,3,4-thiadiazol-2-yl)butyl)-N-(2-fluoro-5-(trifluoromethoxy)benzyl)-1H-1,2,3-triazole-4-carboxamide |
| 574 | 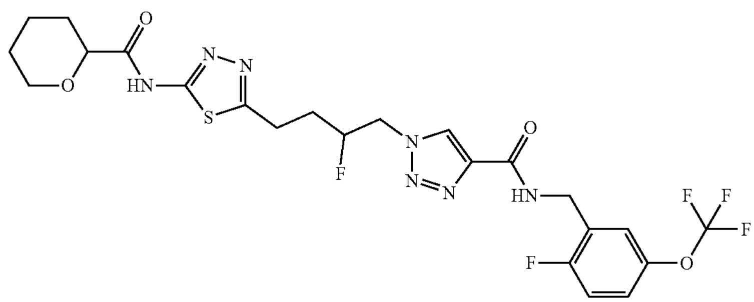 [SMILES: O=C(NCc1cc(OC(F)(F)F)ccc1F)c1cn(CC(F)CCc2nnc(NC(=O)C3CCCCO3)s2)nn1] | 1-(2-fluoro-4-(5-(tetrahydro-2H-pyran-2-carboxamido)-1,3,4-thiadiazol-2-yl)butyl)-N-(2-fluoro-5-(trifluoromethoxy)benzyl)-1H-1,2,3-triazole-4-carboxamide |
| 575 | 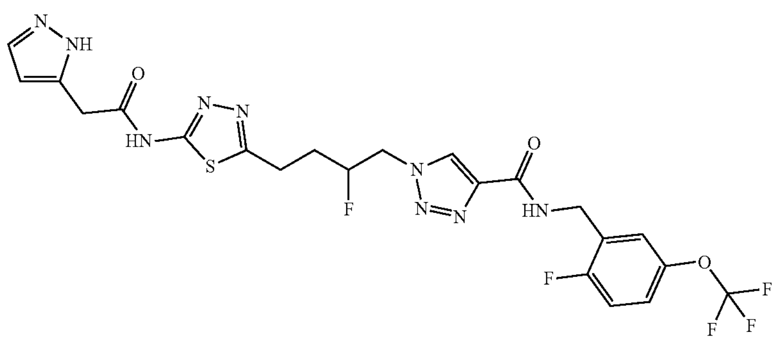 [SMILES: O=C(Cc1ccn[nH]1)Nc1nnc(CCC(F)Cn2cc(C(=O)NCc3cc(OC(F)(F)F)ccc3F)nn2)s1] | 1-(4-(5-(2-(1H-pyrazol-5-yl)acetamido)-1,3,4-thiadiazol-2-yl)-2-fluorobutyl)-N-(2-fluoro-5-(trifluoromethoxy)benzyl)-1H-1,2,3-triazole-4-carboxamide |
| 576 | 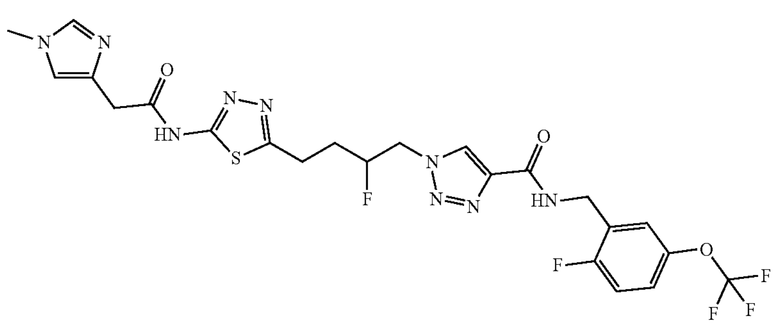 [SMILES: Cn1cnc(CC(=O)Nc2nnc(CCC(F)Cn3cc(C(=O)NCc4cc(OC(F)(F)F)ccc4F)nn3)s2)c1] | 1-(2-fluoro-4-(5-(2-(1-methyl-1H-imidazol-4-yl)acetamido)-1,3,4-thiadiazol-2-yl)butyl)-N-(2-fluoro-5-(trifluoromethoxy)benzyl)-1H-1,2,3-triazole-4-carboxamide |

TABLE 1-continued

Synthesized Examples

| Ex. No. | Structure | Name |
|---|---|---|
| 577 | 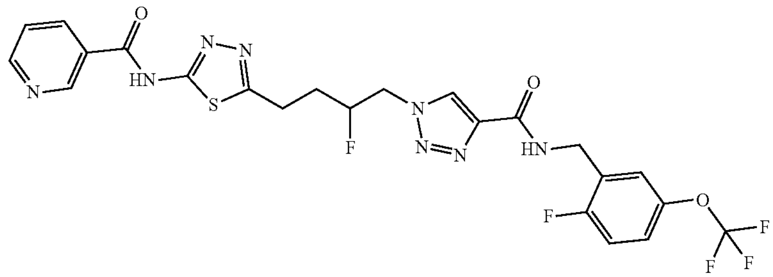 [SMILES: O=C(Nc1nnc(CCC(F)Cn2cc(C(=O)NCc3cc(OC(F)(F)F)ccc3F)nn2)s1)c1cccnc1] | N-(5-(3-fluoro-4-(4-((2-fluoro-5-(trifluoromethoxy)benzyl)carbamoyl)-1H-1,2,3-triazol-1-yl)butyl)-1,3,4-thiadiazol-2-yl)nicotinamide |
| 578 | 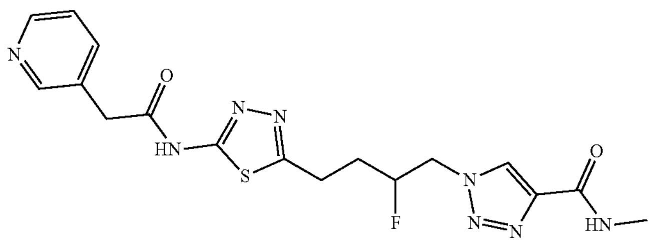 [SMILES: CNC(=O)c1cn(CC(F)CCc2nnc(NC(=O)Cc3cccnc3)s2)nn1] | 1-(2-fluoro-4-(5-(2-(pyridin-3-yl)acetamido)-1,3,4-thiadiazol-2-yl)butyl)-N-methyl-1H-1,2,3-triazole-4-carboxamide |
| 579 | 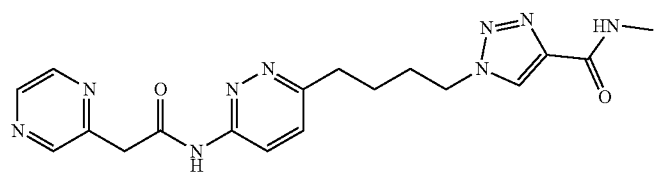 [SMILES: CNC(=O)c1cn(CCCCc2ccc(NC(=O)Cc3cnccn3)nn2)nn1] | N-methyl-1-(4-(6-(2-(pyrazin-2-yl)acetamido)pyridazin-3-yl)butyl)-1H-1,2,3-triazole-4-carboxamide |
| 580 | 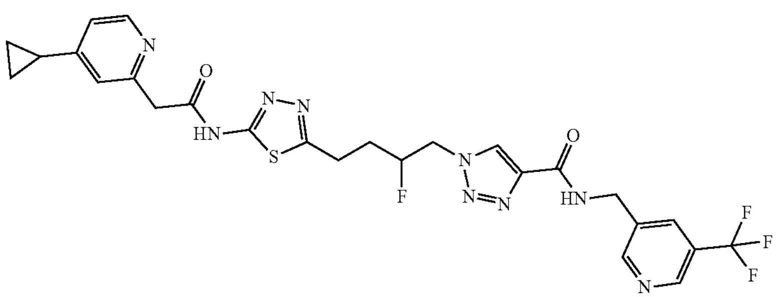 [SMILES: O=C(Cc1cc(C2CC2)ccn1)Nc1nnc(CCC(F)Cn2cc(C(=O)NCc3cncc(C(F)(F)F)c3)nn2)s1] | 1-(4-(5-(2-(4-cyclopropylpyridin-2-yl)acetamido)-1,3,4-thiadiazol-2-yl)-2-fluorobutyl)-N-((5-(trifluoromethyl)pyridin-3-yl)methyl)-1H-1,2,3-triazole-4-carboxamide |
| 581 | 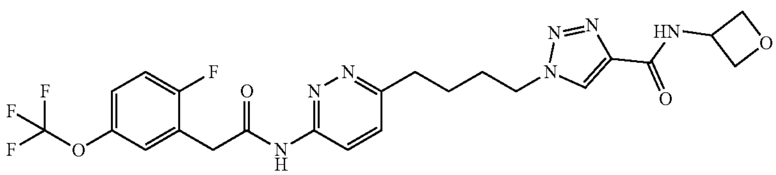 [SMILES: O=C(Cc1cc(OC(F)(F)F)ccc1F)Nc1ccc(CCCCn2cc(C(=O)NC3COC3)nn2)nn1] | 1-(4-(6-(2-(2-fluoro-5-(trifluoromethoxy)phenyl)acetamido)pyridazin-3-yl)butyl)-N-(oxetan-3-yl)-1H-1,2,3-triazole-4-carboxamide |
| 582 | 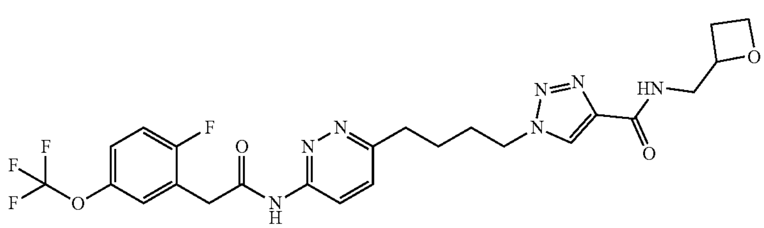 [SMILES: O=C(Cc1cc(OC(F)(F)F)ccc1F)Nc1ccc(CCCCn2cc(C(=O)NCC3CCO3)nn2)nn1] | 1-(4-(6-(2-(2-fluoro-5-(trifluoromethoxy)phenyl)acetamido)pyridazin-3-yl)butyl)-N-(oxetan-2-ylmethyl)-1H-1,2,3-triazole-4-carboxamide |

TABLE 1-continued

Synthesized Examples

| Ex. No. | Structure | Name |
|---|---|---|
| 583 | 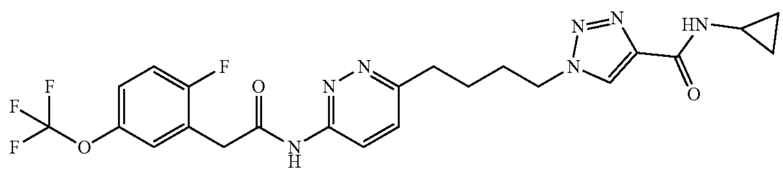 [SMILES: O=C(Cc1cc(OC(F)(F)F)ccc1F)Nc1ccc(CCCCn2cc(C(=O)NC3CC3)nn2)nn1] | N-cyclopropyl-1-(4-(6-(2-(2-fluoro-5-(trifluoromethoxy)phenyl)acetamido)pyridazin-3-yl)butyl)-1H-1,2,3-triazole-4-carboxamide |
| 584 | 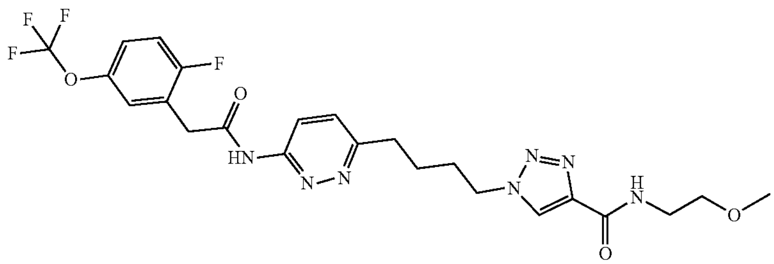 [SMILES: COCCNC(=O)c1cn(CCCCc2ccc(NC(=O)Cc3cc(OC(F)(F)F)ccc3F)nn2)nn1] | 1-(4-(6-(2-(2-fluoro-5-(trifluoromethoxy)phenyl)acetamido)pyridazin-3-yl)butyl)-N-(2-methoxyethyl)-1H-1,2,3-triazole-4-carboxamide |
| 585 | 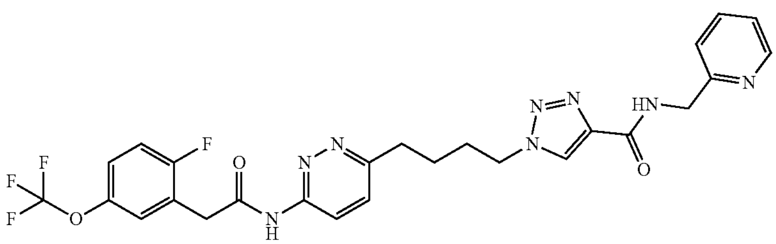 [SMILES: O=C(Cc1cc(OC(F)(F)F)ccc1F)Nc1ccc(CCCCn2cc(C(=O)NCc3ccccn3)nn2)nn1] | 1-(4-(6-(2-(2-fluoro-5-(trifluoromethoxy)phenyl)acetamido)pyridazin-3-yl)butyl)-N-(pyridin-2-ylmethyl)-1H-1,2,3-triazole-4-carboxamide |
| 586 | 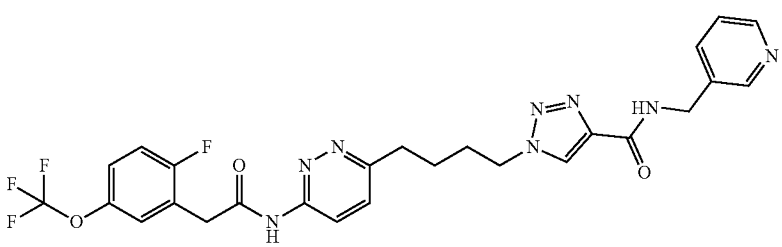 [SMILES: O=C(Cc1cc(OC(F)(F)F)ccc1F)Nc1ccc(CCCCn2cc(C(=O)NCc3cccnc3)nn2)nn1] | 1-(4-(6-(2-(2-fluoro-5-(trifluoromethoxy)phenyl)acetamido)pyridazin-3-yl)butyl)-N-(pyridin-3-ylmethyl)-1H-1,2,3-triazole-4-carboxamide |
| 587 | 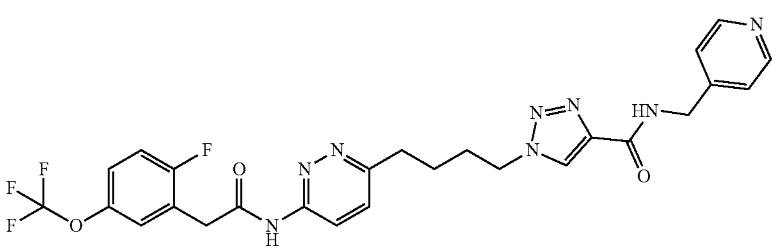 [SMILES: O=C(Cc1cc(OC(F)(F)F)ccc1F)Nc1ccc(CCCCn2cc(C(=O)NCc3ccncc3)nn2)nn1] | 1-(4-(6-(2-(2-fluoro-5-(trifluoromethoxy)phenyl)acetamido)pyridazin-3-yl)butyl)-N-(pyridin-4-ylmethyl)-1H-1,2,3-triazole-4-carboxamide |
| 588 | 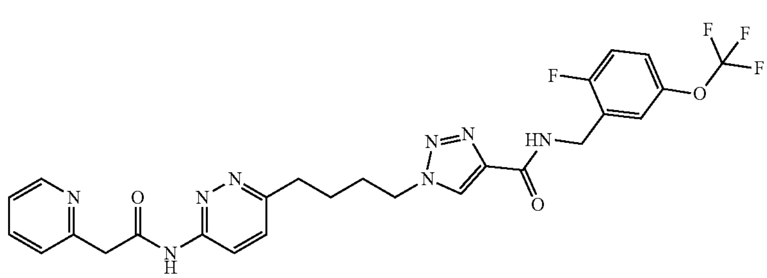 [SMILES: O=C(Cc1ccccn1)Nc1ccc(CCCCn2cc(C(=O)NCc3cc(OC(F)(F)F)ccc3F)nn2)nn1] | N-(2-fluoro-5-(trifluoromethoxy)benzyl)-1-(4-(6-(2-(pyridin-2-yl)acetamido)pyridazin-3-yl)butyl)-1H-1,2,3-triazole-4-carboxamide |

TABLE 1-continued

Synthesized Examples

| Ex. No. | Structure | Name |
|---|---|---|
| 589 | 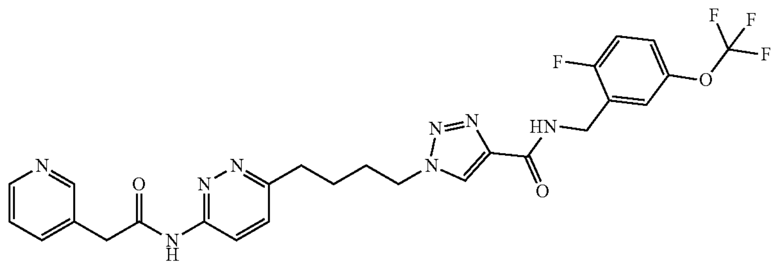 [SMILES: O=C(Cc1cccnc1)Nc1ccc(CCCCn2cc(C(=O)NCc3cc(OC(F)(F)F)ccc3F)nn2)nn1] | N-(2-fluoro-5-(trifluoromethoxy)benzyl)-1-(4-(6-(2-(pyridin-3-yl)acetamido)pyridazin-3-yl)butyl)-1H-1,2,3-triazole-4-carboxamide |
| 590 | 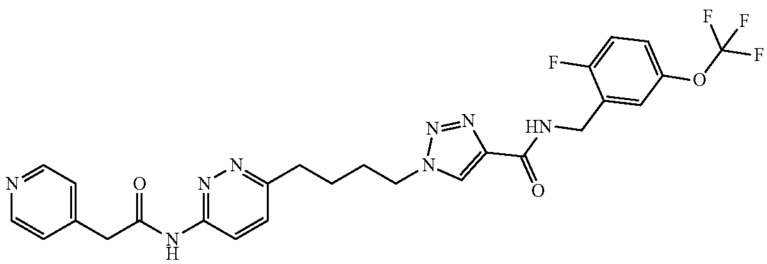 [SMILES: O=C(Cc1ccncc1)Nc1ccc(CCCCn2cc(C(=O)NCc3cc(OC(F)(F)F)ccc3F)nn2)nn1] | N-(2-fluoro-5-(trifluoromethoxy)benzyl)-1-(4-(6-(2-(pyridin-4-yl)acetamido)pyridazin-3-yl)butyl)-1H-1,2,3-triazole-4-carboxamide |
| 591 | 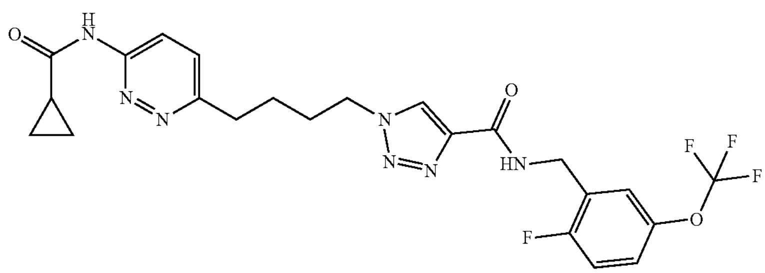 [SMILES: O=C(NCc1cc(OC(F)(F)F)ccc1F)c1cn(CCCCc2ccc(NC(=O)C3CC3)nn2)nn1] | 1-(4-(6-(cyclopropanecarboxamido)pyridazin-3-yl)butyl)-N-(2-fluoro-5-(trifluoromethoxy)benzyl)-1H-1,2,3-triazole-4-carboxamide |
| 592 | 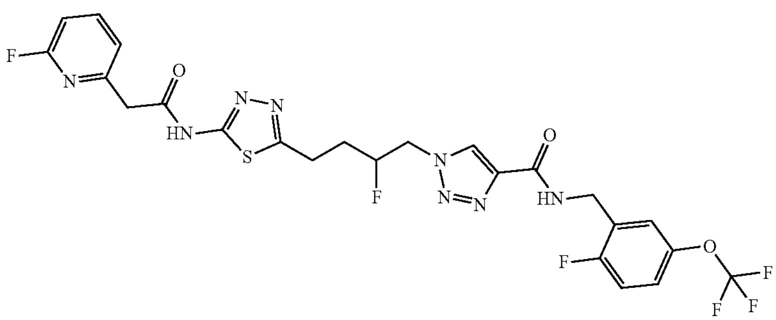 [SMILES: O=C(Cc1cccc(F)n1)Nc1nnc(CCC(F)Cn2cc(C(=O)NCc3cc(OC(F)(F)F)ccc3F)nn2)s1] | 1-(2-fluoro-4-(5-(2-(6-fluoropyridin-2-yl)acetamido)-1,3,4-thiadiazol-2-yl)butyl)-N-(2-fluoro-5-(trifluoromethoxy)benzyl)-1H-1,2,3-triazole-4-carboxamide |
| 593 | 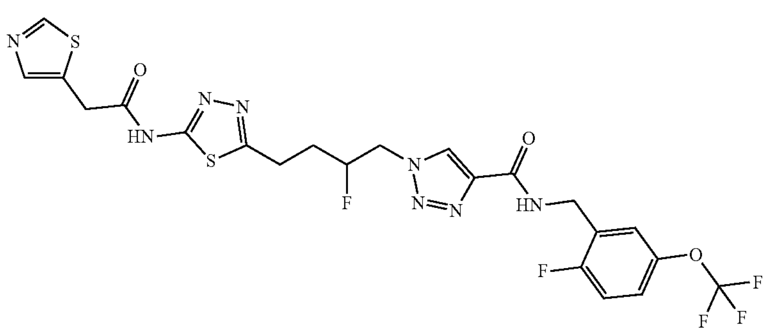 [SMILES: O=C(Cc1cncs1)Nc1nnc(CCC(F)Cn2cc(C(=O)NCc3cc(OC(F)(F)F)ccc3F)nn2)s1] | 1-(2-fluoro-4-(5-(2-(thiazol-5-yl)acetamido)-1,3,4-thiadiazol-2-yl)butyl)-N-(2-fluoro-5-(trifluoromethoxy)benzyl)-1H-1,2,3-triazole-4-carboxamide |

TABLE 1-continued

Synthesized Examples

| Ex. No. | Structure | Name |
|---|---|---|
| 594 | 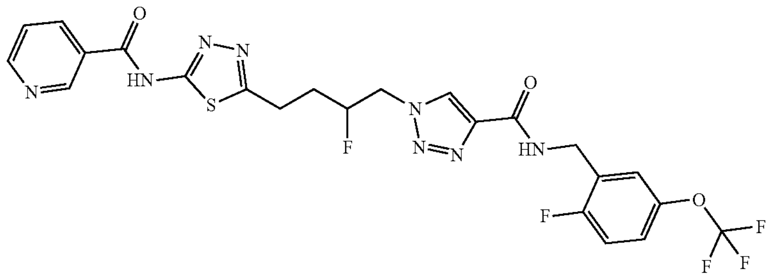 [SMILES: O=C(Nc1nnc(CCC(F)Cn2cc(C(=O)NCc3cc(OC(F)(F)F)ccc3F)nn2)s1)c1cccnc1] | N-(5-(3-fluoro-4-(4-((2-fluoro-5-(trifluoromethoxy)benzyl)carbamoyl)-1H-1,2,3-triazol-1-yl)butyl)-1,3,4-thiadiazol-2-yl)isonicotinamide |
| 595 | 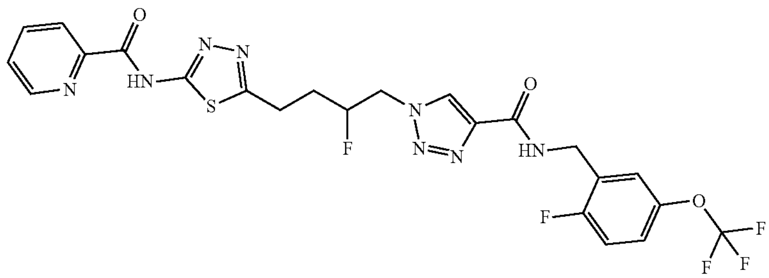 [SMILES: O=C(NCc1cc(OC(F)(F)F)ccc1F)c1cn(CC(F)CCc2nnc(NC(=O)c3ccccn3)s2)nn1] | N-(5-(3-fluoro-4-(4-((2-fluoro-5-(trifluoromethoxy)benzyl)carbamoyl)-1H-1,2,3-triazol-1-yl)butyl)-1,3,4-thiadiazol-2-yl)picolinamide |
| 596 | 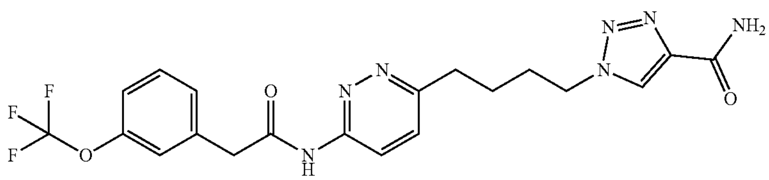 [SMILES: NC(=O)c1cn(CCCCc2ccc(NC(=O)Cc3cccc(OC(F)(F)F)c3)nn2)nn1] | 1-(4-(6-(2-(3-(trifluoromethoxy)phenyl)acetamido)pyridazin-3-yl)butyl)-1H-1,2,3-triazole-4-carboxamide |
| 597 | 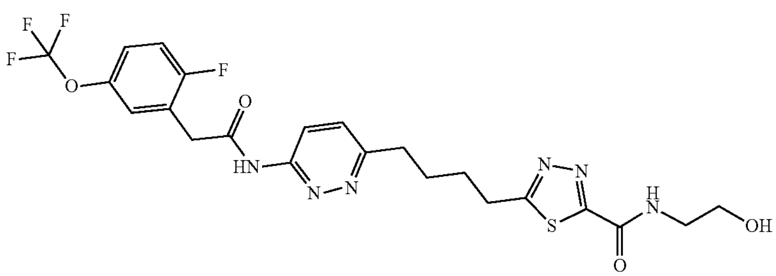 [SMILES: O=C(Cc1cc(OC(F)(F)F)ccc1F)Nc1ccc(CCCCc2nnc(C(=O)NCCO)s2)nn1] | 5-(4-(6-(2-(2-fluoro-5-(trifluoromethoxy)phenyl)acetamido)pyridazin-3-yl)butyl)-N-(2-hydroxyethyl)-1,3,4-thiadiazole-2-carboxamide |
| 598 | 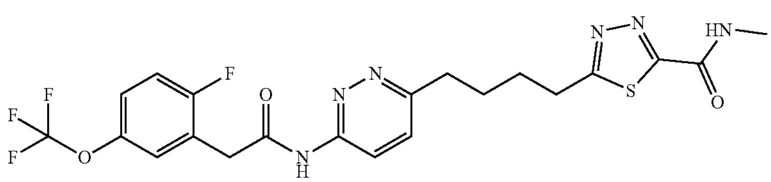 [SMILES: CNC(=O)c1nnc(CCCCc2ccc(NC(=O)Cc3cc(OC(F)(F)F)ccc3F)nn2)s1] | 5-(4-(6-(2-(2-fluoro-5-(trifluoromethoxy)phenyl)acetamido)pyridazin-3-yl)butyl)-N-methyl-1,3,4-thiadiazole-2-carboxamide |
| 599 | 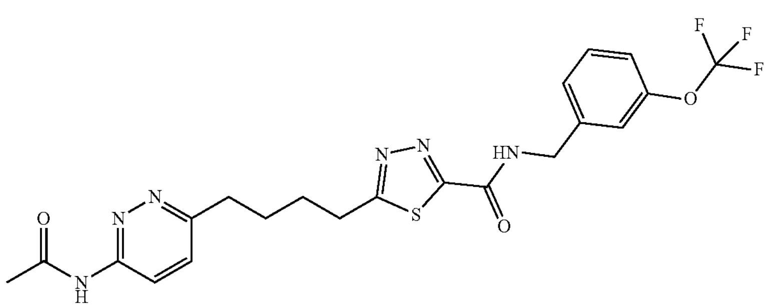 [SMILES: CC(=O)Nc1ccc(CCCCc2nnc(C(=O)NCc3cccc(OC(F)(F)F)c3)s2)nn1] | 5-(4-(6-acetamidopyridazin-3-yl)butyl)-N-(3-(trifluoromethoxy)benzyl)-1,3,4-thiadiazole-2-carboxamide |

TABLE 1-continued

Synthesized Examples

| Ex. No. | Structure | Name |
|---|---|---|
| 600 | 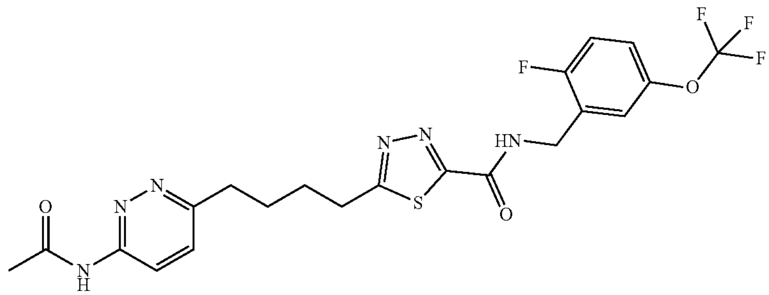 [SMILES: CC(=O)Nc1ccc(CCCCc2nnc(C(=O)NCc3cc(OC(F)(F)F)ccc3F)s2)nn1] | 5-(4-(6-acetamidopyridazin-3-yl)butyl)-N-(2-fluoro-5-(trifluoromethoxy)benzyl)-1,3,4-thiadiazole-2-carboxamide |
| 601 | 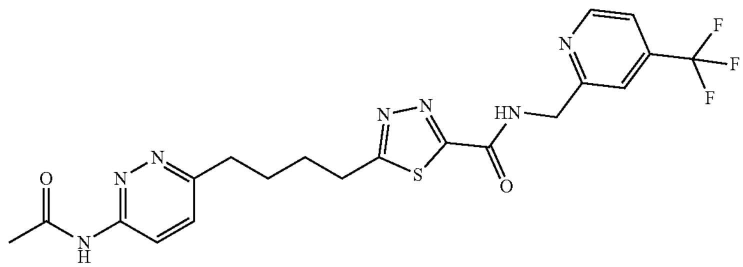 [SMILES: CC(=O)Nc1ccc(CCCCc2nnc(C(=O)NCc3cc(C(F)(F)F)ccn3)s2)nn1] | 5-(4-(6-acetamidopyridazin-3-yl)butyl)-N-((4-(trifluoromethyl)pyridin-2-yl)methyl)-1,3,4-thiadiazole-2-carboxamide |
| 602 | 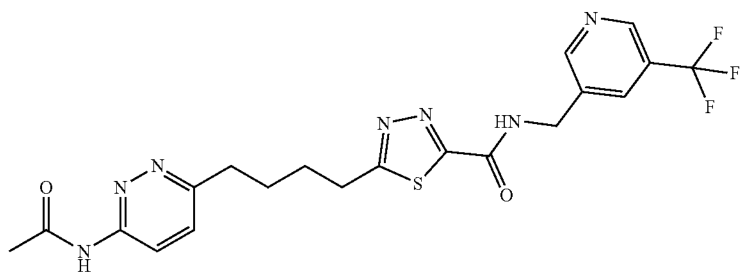 [SMILES: CC(=O)Nc1ccc(CCCCc2nnc(C(=O)NCc3cncc(C(F)(F)F)c3)s2)nn1] | 5-(4-(6-acetamidopyridazin-3-yl)butyl)-N-((5-(trifluoromethyl)pyridin-3-yl)methyl)-1,3,4-thiadiazole-2-carboxamide |
| 603 | 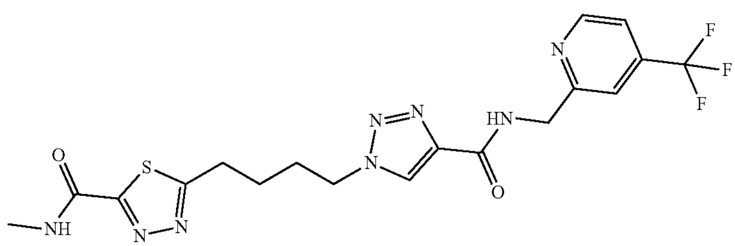 [SMILES: CNC(=O)c1nnc(CCCCn2cc(C(=O)NCc3cc(C(F)(F)F)ccn3)nn2)s1] | N-methyl-5-(4-(4-(((4-(trifluoromethyl)pyridin-2-yl)methyl)carbamoyl)-1H-1,2,3-triazol-1-yl)butyl)-1,3,4-thiadiazole-2-carboxamide |
| 604 | 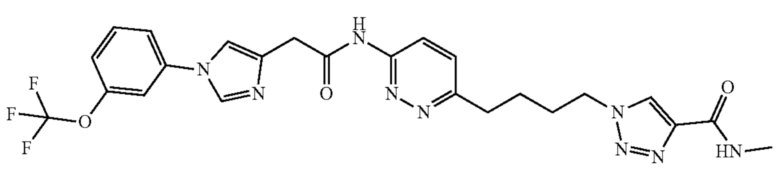 [SMILES: CNC(=O)c1cn(CCCCc2ccc(NC(=O)Cc3cn(-c4cccc(OC(F)(F)F)c4)cn3)nn2)nn1] | N-methyl-1-(4-(6-(2-(1-(3-(trifluoromethoxy)phenyl)-1H-imidazol-4-yl)acetamido)pyridazin-3-yl)butyl)-1H-1,2,3-triazole-4-carboxamide |
| 605 | 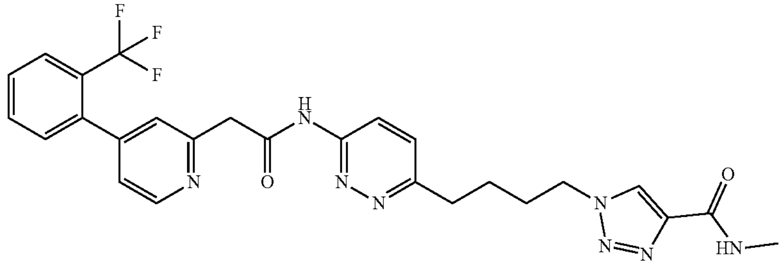 [SMILES: CNC(=O)c1cn(CCCCc2ccc(NC(=O)Cc3cc(-c4ccccc4C(F)(F)F)ccn3)nn2)nn1] | N-methyl-1-(4-(6-(2-(4-(2-(trifluoromethyl)phenyl)pyridin-2-yl)acetamido)pyridazin-3-yl)butyl)-1H-1,2,3-triazole-4-carboxamide |

TABLE 1-continued

Synthesized Examples

| Ex. No. | Structure | Name |
|---|---|---|
| 606 | 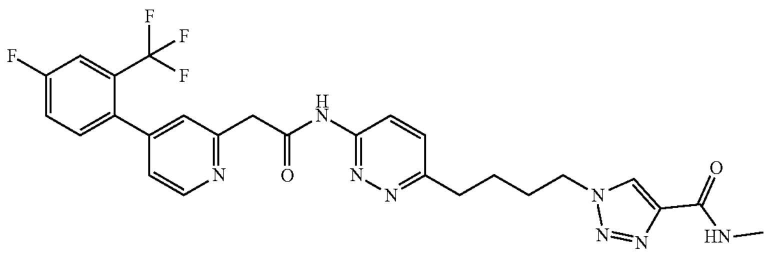 [SMILES: CNC(=O)c1cn(CCCCc2ccc(NC(=O)Cc3cc(-c4ccc(F)cc4C(F)(F)F)ccn3)nn2)nn1] | 1-(4-(6-(2-(4-(4-fluoro-2-(trifluoromethyl)phenyl)pyridin-2-yl)acetamido)pyridazin-3-yl)butyl)-N-methyl-1H-1,2,3-triazole-4-carboxamide |
| 607 | 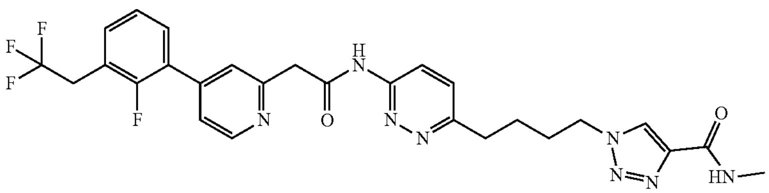 [SMILES: CNC(=O)c1cn(CCCCc2ccc(NC(=O)Cc3cc(-c4cccc(CC(F)(F)F)c4F)ccn3)nn2)nn1] | 1-(4-(6-(2-(4-(2-fluoro-3-(trifluoromethoxy)phenyl)pyridin-2-yl)acetamido)pyridazin-3-yl)butyl)-N-methyl-1H-1,2,3-triazole-4-carboxamide |
| 608 | 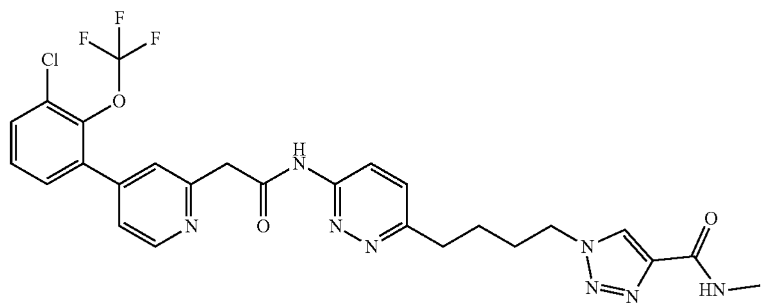 [SMILES: CNC(=O)c1cn(CCCCc2ccc(NC(=O)Cc3cc(-c4cccc(Cl)c4OC(F)(F)F)ccn3)nn2)nn1] | 1-(4-(6-(2-(4-(3-chloro-2-(trifluoromethoxy)phenyl)pyridin-2-yl)acetamido)pyridazin-3-yl)butyl)-N-methyl-1H-1,2,3-triazole-4-carboxamide |
| 609 | 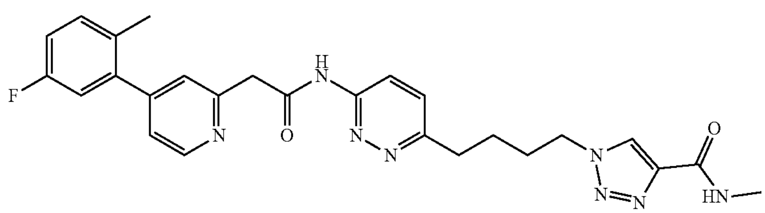 [SMILES: CNC(=O)c1cn(CCCCc2ccc(NC(=O)Cc3cc(-c4cc(F)ccc4C)ccn3)nn2)nn1] | 1-(4-(6-(2-(4-(5-fluoro-2-methylphenyl)pyridin-2-yl)acetamido)pyridazin-3-yl)butyl)-N-methyl-1H-1,2,3-triazole-4-carboxamide |

Table 2 below reports the calculated observed molecular weight of each Example, as well as the method by which each compound may be made by reference to each Example whose synthesis is substantially similar that one skilled in the art could produce the compound using, if necessary, variations know in the art.

TABLE 2

Observed Molecular Weight and Synthesis for Examples

| Ex. No. | Calc. Mass | Obs Mass | Method as in Ex. |
|---|---|---|---|
| 10 | 511 | 512 | 1 |
| 11 | 523 | 524 | 1 |
| 12 | 553 | 554 | 1 |
| 13 | 489 | 490 | 1 |
| 14 | 512 | 513 | 1 |
| 15 | 475 | 476 | 1 |
| 16 | 559 | 560 | 1 |
| 17 | 513 | 514 | 1 |
| 18 | 587 | 588 | 1 |
| 19 | 560 | 561 | 1 |
| 20 | 643 | 644 | 1 |
| 21 | 589 | 590 | 1 |
| 22 | 619 | 620 | 1 |
| 23 | 589 | 590 | 1 |
| 24 | 435 | 435 | 5 |
| 25 | 516 | 517 | 6 |
| 26 | 500 | 501 | 6 |
| 27 | 501 | 502 | 6 |
| 28 | 486 | 487 | 6 |
| 29 | 502 | 503 | 6 |
| 30 | 487 | 488 | 6 |
| 31 | 536 | 537 | 6 |
| 32 | 571 | 572 | 6 |
| 33 | 550 | 551 | 6 |
| 34 | 552 | 553 | 6 |
| 34 | 577 | 578 | 6 |
| 36 | 570 | 571 | 6 |

TABLE 2-continued

Observed Molecular Weight and Synthesis for Examples

| Ex. No. | Calc. Mass | Obs Mass | Method as in Ex. |
|---|---|---|---|
| 37 | 524 | 525 | 6 |
| 38 | 427 | 428 | 7 |
| 39 | 559 | 560 | 7 |
| 40 | 476 | 477 | 7 |
| 41 | 429 | 430 | 7 |
| 42 | 441 | 442 | 7 |
| 43 | 511 | 512 | 7 |
| 44 | 525 | 526 | 7 |
| 45 | 513 | 514 | 7 |
| 46 | 643 | 644 | 7 |
| 47 | 560 | 561 | 7 |
| 48 | 541 | 542 | 7 |
| 49 | 566 | 567 | 7 |
| 50 | 539 | 540 | 7 |
| 51 | 525 | 526 | 7 |
| 52 | 443 | 444 | 7 |
| 53 | 606 | 607 | 8 |
| 54 | 510 | 511 | 9 |
| 55 | 522 | 523 | 9 |
| 56 | 538 | 539 | 9 |
| 57 | 508 | 509 | 9 |
| 58 | 494 | 495 | 9 |
| 59 | 523 | 524 | 7 |
| 60 | 574 | 575 | 7 |
| 61 | 574 | 575 | 7 |
| 62 | 491 | 492 | 7 |
| 63 | 454 | 455 | 7 |
| 64 | 505 | 506 | 7 |
| 65 | 560 | 561.5 | 7 |
| 66 | 477 | 478 | 7 |
| 67 | 491 | 491 | 7 |
| 68 | 440 | 441 | 7 |
| 69 | 440 | 441 | 7 |
| 70 | 454 | 455 | 7 |
| 71 | 460 | 461 | 80 |
| 72 | 557 | 558 | 80 |
| 73 | 638 | 639 | 7 |
| 74 | 569 | 570 | 7 |
| 75 | 628 | 629 | 7 |
| 76 | 628 | 629 | 7 |
| 77 | 628 | 629 | 7 |
| 78 | 628 | 629 | 7 |
| 79 | 621 | 622 | 80 |
| 80 | 611 | 612 | 80 |
| 81 | 611 | 612 | 80 |
| 82 | 611 | 612 | 80 |
| 83 | 611 | 612 | 80 |
| 84 | 519 | 520 | 80 |
| 85 | 505 | 506 | 80 |
| 86 | 521 | 522 | 80 |
| 87 | 507 | 508 | 80 |
| 88 | 451 | 452 | 80 |
| 89 | 491 | 492 | 80 |
| 90 | 533 | 534 | 80 |
| 91 | 507 | 508 | 80 |
| 92 | 521 | 522 | 80 |
| 93 | 505 | 506 | 80 |
| 94 | 550 | 551 | 80 |
| 95 | 466 | 467 | 80 |
| 96 | 527 | 528 | 80 |
| 97 | 595 | 596 | 80 |
| 98 | 541 | 542 | 80 |
| 99 | 541 | 542 | 80 |
| 100 | 557 | 558 | 80 |
| 101 | 557 | 558 | 80 |
| 102 | 547 | 548 | 80 |
| 103 | 547 | 548 | 80 |
| 104 | 505 | 506 | 80 |
| 105 | 567 | 568 | 80 |
| 106 | 583 | 584 | 80 |
| 107 | 579 | 580 | 80 |
| 108 | 557 | 558 | 80 |
| 109 | 625 | 626 | 80 |
| 110 | 656 | 657 | 80 |
| 111 | 561 | 562 | 80 |
| 112 | 545 | 546 | 80 |
| 113 | 557 | 558 | 80 |
| 114 | 535 | 536 | 80 |
| 115 | 562 | 563 | 80 |
| 116 | 562 | 563 | 80 |
| 117 | 550 | 551 | 80 |
| 118 | 550 | 551 | 80 |
| 119 | 534 | 535 | 80 |
| 120 | 534 | 535 | 80 |
| 121 | 534 | 535 | 80 |
| 122 | 611 | 612 | 80 |
| 123 | 557 | 558 | 80 |
| 124 | 596 | 597 | 80 |
| 125 | 601 | 602 | 80 |
| 126 | 544 | 545 | 80 |
| 127 | 544 | 545 | 80 |
| 128 | 539 | 540 | 80 |
| 129 | 557 | 558 | 475 |
| 130 | 575 | 576 | 475 |
| 131 | 559 | 560 | 475 |
| 132 | 593 | 594 | 80 |
| 133 | 567 | 568 | 80 |
| 134 | 557 | 558 | 475 |
| 135 | 568 | 569 | 80 |
| 136 | 599 | 600 | 80 |
| 137 | 599 | 600 | 80 |
| 138 | 572 | 573 | 80 |
| 139 | 572 | 573 | 80 |
| 140 | 596 | 597 | 80 |
| 141 | 596 | 597 | 80 |
| 142 | 596 | 597 | 80 |
| 143 | 596 | 597 | 80 |
| 144 | 596 | 597 | 80 |
| 145 | 614 | 615 | 475 |
| 146 | 634 | 635 | 80 |
| 147 | 601 | 602 | 475 |
| 148 | 601 | 602 | 475 |
| 149 | 469 | 470 | 475 |
| 150 | 502 | 503 | 475 |
| 151 | 469 | 470 | 475 |
| 152 | 586 | 587 | 475 |
| 153 | 502 | 503 | 475 |
| 154 | 483 | 484 | 475 |
| 155 | 591 | 592 | 475 |
| 156 | 614 | 615 | 475 |
| 157 | 477 | 478 | 157 |
| 158 | 596 | 597 | 80 |
| 159 | 560 | 561 | 475 |
| 160 | 495 | 496 | 157 |
| 161 | 393 | 394 | 157 |
| 162 | 484 | 485 | 475 |
| 163 | 401 | 402 | 475 |
| 164 | 441 | 442 | 475 |
| 165 | 400 | 401 | 475 |
| 166 | 529 | 530 | 475 |
| 167 | 394 | 395 | 157 |
| 168 | 527 | 528 | 475 |
| 169 | 554 | 555 | 157 |
| 170 | 451 | 452 | 475 |
| 171 | 451 | 452 | 475 |
| 172 | 522 | 523 | 157 |
| 173 | 467 | 468 | 157 |
| 174 | 477 | 478 | 157 |
| 175 | 462 | 463 | 157 |
| 176 | 503 | 504 | 157 |
| 177 | 488 | 489 | 157 |
| 178 | 478 | 479 | 157 |
| 179 | 407 | 408 | 157 |
| 180 | 445 | 446 | 157 |
| 181 | 466 | 467 | 475 |
| 182 | 425 | 426 | 475 |
| 183 | 478 | 479 | 475 |
| 184 | 469 | 470 | 475 |
| 185 | 458 | 459 | 475 |
| 186 | 469 | 470 | 475 |
| 187 | 415 | 416 | 475 |
| 188 | 554 | 555 | 188 |

TABLE 2-continued

Observed Molecular Weight and Synthesis for Examples

| Ex. No. | Calc. Mass | Obs Mass | Method as in Ex. |
| --- | --- | --- | --- |
| 189 | 486 | 487 | 508 |
| 190 | 434 | 435 | 192 |
| 191 | 428 | 429 | 192 |
| 192 | 554 | 555 | 192 |
| 193 | 501 | 502 | 250 |
| 194 | 501 | 502 | 250 |
| 195 | 578 | 579 | 195 |
| 196 | 524 | 525 | 540 |
| 197 | 596 | 597 | 250 |
| 198 | 596 | 597 | 250 |
| 199 | 475 | 476 | 192 |
| 200 | 472 | 473/475 | 192 |
| 201 | 563 | 564 | 250 |
| 202 | 500 | 501 | 192 |
| 203 | 539 | 540 | 157 |
| 204 | 596 | 597 | 540 |
| 205 | 626 | 627 | 540 |
| 206 | 626 | 627 | 540 |
| 207 | 554 | 555 | 192 |
| 208 | 478 | 479 | 192 |
| 209 | 500 | 501 | 540 |
| 210 | 462 | 463 | 192 |
| 211 | 557 | 558 | 211 |
| 212 | 574 | 575 | 192 |
| 213 | 576 | 577 | 192 |
| 214 | 414 | 415 | 192 |
| 215 | 476 | 477 | 192 |
| 216 | 571 | 572 | 229 |
| 217 | 477 | 478 | 192 |
| 218 | 596 | 597 | 540 |
| 219 | 626 | 627 | 540 |
| 220 | 486 | 487 | 508 + separation |
| 221 | 486 | 487 | 508 + separation |
| 222 | 626 | 627 | 540 |
| 223 | 626 | 627 | 540 |
| 224 | 478 | 479 | 157 |
| 225 | 492 | 493 | 192 |
| 226 | 486 | 487 | 540 |
| 227 | 575 | 576 | 211 |
| 228 | 561 | 562 | 228 |
| 229 | 479 | 480 | 229 |
| 230 | 645 | 646 | 157 |
| 231 | 577 | 578 | 157 |
| 232 | 561 | 562 | 228 |
| 233 | 464 | 465 | 233 |
| 234 | 563 | 564 | 508 |
| 235 | 563 | 564 | 508 |
| 236 | 480 | 481 | 259 |
| 237 | 436 | 437 | 192 |
| 238 | 563 | 564 | 250 |
| 239 | 501 | 502 | 250 |
| 240 | 501 | 502 | 250 |
| 241 | 593 | 594 | 259 |
| 242 | 572 | 573 | 242 |
| 243 | 401 | 402 | 243 |
| 244 | 411 | 412 | 259 |
| 245 | 518 | 519 | 259 |
| 246 | 584 | 585 | 157 |
| 247 | 589 | 612 (M + Na+) | 211 |
| 248 | 480 | 481 | 259 |
| 249 | 575 | 576 | 211 |
| 250 | 563 | 564 | 250 |
| 251 | 482 | 483 | 251 |
| 252 | 518 | 519 | 272 |
| 253 | 496 | 497 | 253 |
| 254 | 412 | 413 | 259 |
| 255 | 572 | 573 | 242 |
| 256 | 412 | 413 | 259 |
| 257 | 572 | 573 | 242 |
| 258 | 490 | 491 | 258 |
| 259 | 480 | 481 | 259 |
| 260 | 480 | 481 | 259 |
| 261 | 500 | 501 | 261 |
| 262 | 510 | 511 | 262 |
| 263 | 520 | 521 | 268 |
| 264 | 494 | 495 | 268 |
| 265 | 502 | 503 | 540 |
| 266 | 524 | 525 | 262 |
| 267 | 502 | 503 | 267 |
| 268 | 494 | 495 | 268 |
| 269 | 580 | 581 | 269 |
| 270 | 561 | 562 | 270 |
| 271 | 512 | 513 | 271 |
| 272 | 518 | 519 | 272 |
| 273 | 411 | 412 | 259 |
| 274 | 478 | 479 | 274 |
| 275 | 452 | 453 | 275 |
| 276 | 506 | 507 | 297 |
| 277 | 451 | 452 | 297 |
| 278 | 423 | 424 | 297 |
| 279 | 543 | 544 | 297 |
| 280 | 465 | 466 | 297 |
| 281 | 428 | 429 | 297 |
| 282 | 456 | 457 | 297 |
| 283 | 470 | 471 | 297 |
| 284 | 465 | 466 | 297 |
| 285 | 465 | 466 | 297 |
| 286 | 548 | 549 | 297 |
| 287 | 414 | 415 | 297 |
| 288 | 442 | 443 | 297 |
| 289 | 456 | 457 | 297 |
| 290 | 451 | 452 | 297 |
| 291 | 451 | 452 | 297 |
| 292 | 534 | 535 | 297 |
| 293 | 543 | 544 | 297 |
| 294 | 543 | 544 | 297 |
| 295 | 534 | 535 | 297 |
| 296 | 548 | 549 | 297 |
| 297 | 460 | 461 | 297 |
| 298 | 460 | 461 | 297 |
| 299 | 557 | 558 | 297 |
| 300 | 437 | 438 | 297 |
| 301 | 506 | 507 | 297 |
| 302 | 423 | 424 | 297 |
| 303 | 423 | 424 | 297 |
| 304 | 414 | 415 | 297 |
| 305 | 428 | 429 | 297 |
| 306 | 474 | 475 | 297 |
| 307 | 543 | 544 | 297 |
| 308 | 423 | 424 | 297 |
| 309 | 451 | 452 | 297 |
| 310 | 465 | 466 | 297 |
| 311 | 465 | 466 | 297 |
| 312 | 479 | 480 | 297 |
| 313 | 557 | 558 | 297 |
| 314 | 474 | 475 | 297 |
| 315 | 474 | 475 | 297 |
| 316 | 488 | 489 | 297 |
| 317 | 465 | 466 | 297 |
| 318 | 479 | 480 | 297 |
| 319 | 437 | 438 | 297 |
| 320 | 460 | 461 | 297 |
| 321 | 460 | 461 | 297 |
| 322 | 474 | 475 | 297 |
| 323 | 474 | 475 | 332 |
| 324 | 456 | 457 | 332 |
| 325 | 488 | 489 | 332 |
| 326 | 502 | 503 | 332 |
| 327 | 561 | 562 | 347 |
| 328 | 575 | 576 | 347 |
| 329 | 539 | 540 | 332 |
| 330 | 557 | 558 | 332 |
| 331 | 571 | 572 | 332 |
| 332 | 585 | 586 | 332 |
| 333 | 644 | 645 | 297 |
| 334 | 594 | 595 | 297 |
| 335 | 575 | 576 | 297 |
| 336 | 525 | 526 | 297 |
| 337 | 561 | 562 | 297 |

TABLE 2-continued

Observed Molecular Weight and Synthesis for Examples

| Ex. No. | Calc. Mass | Obs Mass | Method as in Ex. |
|---|---|---|---|
| 338 | 511 | 512 | 297 |
| 339 | 644 | 645 | 347 |
| 340 | 662 | 663 | 347 |
| 341 | 579 | 580 | 347 |
| 342 | 575 | 576 | 347 |
| 343 | 593 | 594 | 347 |
| 344 | 492 | 493 | 347 |
| 345 | 510 | 511 | 347 |
| 346 | 506 | 507 | 347 |
| 347 | 561 | 562 | 347 |
| 348 | 470 | 471 | 332 |
| 349 | 507 | 508 | 332 |
| 350 | 557 | 558 | 332 |
| 351 | 488 | 489 | 332 |
| 352 | 525 | 526 | 332 |
| 353 | 575 | 576 | 332 |
| 354 | 502 | 503 | 332 |
| 355 | 539 | 540 | 332 |
| 356 | 589 | 590 | 332 |
| 357 | 506 | 507 | 332 |
| 358 | 516 | 517 | 332 |
| 359 | 553 | 554 | 332 |
| 360 | 603 | 604 | 332 |
| 361 | 520 | 521 | 332 |
| 362 | 478 | 479 | 347 |
| 363 | 579 | 580 | 347 |
| 364 | 492 | 493 | 347 |
| 365 | 496 | 497 | 347 |
| 366 | 511 | 512 | 347 |
| 367 | 561 | 562 | 347 |
| 368 | 593 | 594 | 475 |
| 369 | 579 | 580 | 475 |
| 370 | 593 | 594 | 475 |
| 371 | 557 | 558 | 372 |
| 372 | 575 | 576 | 372 |
| 373 | 579 | 580 | 347 |
| 374 | 488 | 489 | 372 |
| 375 | 579 | 580 | 347 |
| 376 | 593 | 594 | 347 |
| 377 | 680 | 681 | 347 |
| 378 | 597 | 598 | 347 |
| 379 | 662 | 663 | 347 |
| 380 | 644 | 645 | 297 |
| 381 | 662 | 663 | 297 |
| 382 | 579 | 580 | 297 |
| 383 | 575 | 576 | 297 |
| 384 | 612 | 613 | 297 |
| 385 | 594 | 595 | 297 |
| 386 | 612 | 613 | 297 |
| 387 | 529 | 530 | 297 |
| 388 | 525 | 526 | 297 |
| 389 | 474 | 475 | 372 |
| 390 | 593 | 594 | 372 |
| 391 | 575 | 576 | 372 |
| 392 | 492 | 493 | 372 |
| 393 | 506 | 507 | 372 |
| 394 | 629 | 630 | 347 |
| 395 | 647 | 648 | 347 |
| 396 | 575 | 576 | 347 |
| 397 | 578 | 579 | t397 |
| 398 | 579 | 580 | 347 |
| 399 | 546 | 547 | 347 |
| 400 | 560 | 561 | 347 |
| 401 | 542 | 543 | 372 |
| 402 | 560 | 561 | 372 |
| 403 | 561 | 562 | 372 |
| 404 | 680 | 681 | 347 |
| 405 | 593 | 594 | 347 |
| 406 | 579 | 580 | 347 |
| 407 | 629 | 630 | 347 |
| 408 | 644 | 645 | 347 |
| 409 | 492 | 493 | 372 |
| 410 | 510 | 511 | 372 |
| 411 | 629 | 630 | 347 |
| 412 | 647 | 648 | 347 |
| 413 | 629 | 630 | 297 |
| 414 | 611 | 612 | 297 |
| 415 | 562 | 563 | 297 |
| 416 | 662 | 663 | 347 |
| 417 | 597 | 598 | 347 |
| 418 | 647 | 648 | 347 |
| 419 | 579 | 580 | 347 |
| 420 | 592 | 593 | 508 |
| 421 | 647 | 648 | 475 |
| 422 | 647 | 648 | 475 |
| 423 | 647 | 648 | 475 |
| 424 | 647 | 648 | 475 |
| 425 | 647 | 648 | 475 |
| 426 | 647 | 648 | 475 |
| 427 | 597 | 598 | 475 |
| 428 | 629 | 630 | 475 |
| 429 | 579 | 580 | 475 |
| 430 | 575 | 576 | |
| 431 | 629 | 630 | 475 |
| 432 | 647 | 648 | 475 |
| 433 | 629 | 630 | 475 |
| 434 | 575 | 576 | 475 |
| 435 | 629 | 630 | 475 |
| 436 | 629 | 630 | 475 |
| 437 | 629 | 630 | 475 |
| 438 | 629 | 630 | 475 |
| 439 | 629 | 630 | 475 |
| 440 | 579 | 580 | 475 |
| 441 | 647 | 648 | 475 |
| 442 | 592 | 593 | 508 |
| 443 | 610 | 611 | 508 |
| 444 | 597 | 598 | 475 |
| 445 | 646 | 647 | 508 |
| 446 | 646 | 647 | 508 |
| 447 | 610 | 611 | 508 |
| 448 | 664 | 665 | 508 |
| 449 | 664 | 665 | 508 |
| 450 | 545 | 546 | 475 |
| 451 | 664 | 665 | 508 |
| 452 | 608 | 609 | 475 |
| 453 | 608 | 609 | 475 |
| 454 | 563 | 564 | 475 |
| 455 | 613 | 614 | 475 |
| 456 | 551 | 552 | 475 |
| 457 | 553 | 554 | 475 |
| 458 | 559 | 560 | 475 |
| 459 | 563 | 564 | 475 |
| 460 | 545 | 546 | 475 |
| 461 | 590 | 591 | 475 |
| 462 | 590 | 591 | 475 |
| 463 | 646 | 647 | 508 |
| 464 | 646 | 647 | 508 |
| 465 | 664 | 665 | 508 |
| 466 | 563 | 564 | 475 |
| 467 | 575 | 576 | 475 |
| 468 | 575 | 576 | 475 |
| 469 | 629 | 630 | 475 |
| 470 | 614 | 615 | 475 |
| 471 | 537 | 538 | 475 |
| 472 | 553 | 554 | 475 |
| 473 | 553 | 554 | 475 |
| 474 | 614 | 615 | 475 |
| 475 | 469 | 470 | 475 |
| 476 | 614 | 615 | 475 |
| 477 | 629 | 630 | 475 |
| 478 | 629 | 630 | 475 |
| 479 | 647 | 648 | 475 |
| 480 | 630 | 631 | 508 |
| 481 | 602 | 603 | 508 |
| 482 | 646 | 647 | 508 |
| 483 | 646 | 647 | 508 |
| 484 | 630 | 631 | 508 |
| 485 | 631 | 632 | 508 |
| 486 | 629 | 630 | 347 |
| 487 | 629 | 630 | 347 |
| 488 | 631 | 632 | 508 |
| 489 | 631 | 632 | 508 |

TABLE 2-continued

Observed Molecular Weight and Synthesis for Examples

| Ex. No. | Calc. Mass | Obs Mass | Method as in Ex. |
|---|---|---|---|
| 490 | 631 | 632 | 508 |
| 491 | 631 | 632 | 508 |
| 492 | 631 | 632 | 508 |
| 493 | 646 | 647 | 540 |
| 494 | 646 | 647 | 540 |
| 495 | 646 | 647 | 540 |
| 496 | 646 | 647 | 540 |
| 497 | 501 | 502 | 540 |
| 498 | 646 | 647 | 540 |
| 499 | 554 | 555 | 508 |
| 500 | 554 | 555 | 508 |
| 501 | 486 | 487 | 508 |
| 502 | 568 | 569 | 508 |
| 503 | 486 | 487 | 508 |
| 504 | 501 | 502 | 508 |
| 505 | 526 | 527 | 508 |
| 506 | 554 | 555 | 508 |
| 507 | 486 | 487 | 508 |
| 508 | 486 | 487 | 508 |
| 509 | 554 | 555 | 508 |
| 510 | 568 | 569 | 508 |
| 511 | 568 | 569 | 508 |
| 512 | 568 | 569 | 508 |
| 513 | 578 | 579 | 540 |
| 514 | 596 | 597 | 540 |
| 515 | 526 | 527 | 540 |
| 516 | 664 | 665 | 540 |
| 517 | 664 | 665 | 540 |
| 518 | 519 | 520 | 540 |
| 519 | 418 | 419 | 540 |
| 520 | 631 | 632 | 508 |
| 521 | 487 | 488 | 508 |
| 522 | 515 | 516 | 508 |
| 523 | 545 | 546 | 508 |
| 524 | 484 | 485 | 347 |
| 525 | 502 | 503 | 347 |
| 526 | 505 | 506 | 157 |
| 527 | 502 | 503 | 157 |
| 528 | 507 | 508 | 157 |
| 529 | 554 | 555 | 157 |
| 530 | 487 | 488 | 540 |
| 531 | 515 | 516 | 540 |
| 532 | 545 | 546 | 540 |
| 533 | 578 | 579 | 540 |
| 534 | 527 | 528 | 540 |
| 535 | 541 | 542 | 540 |
| 536 | 569 | 570 | 540 |
| 537 | 596 | 597 | 540 |
| 538 | 484 | 485 | 347 |
| 539 | 502 | 503 | 347 |
| 540 | 563 | 564 | 540 |
| 541 | 394 | 395 | 192 |
| 542 | 471 | 472 | 192 |
| 543 | 471 | 472 | 192 |
| 544 | 428 | 429 | 192 |
| 545 | 470 | 471 | 192 |
| 546 | 472 | 473 | 192 |
| 547 | 401 | 402 | 192 |
| 548 | 385 | 386 | 192 |
| 549 | 535 | 536 | 157 |
| 550 | 533 | 534 | 157 |
| 551 | 521 | 522 | 157 |
| 552 | 551 | 552 | 157 |
| 553 | 560 | 561 | 540 |
| 554 | 578 | 579 | 540 |
| 555 | 519 | 520 | 508 |
| 556 | 417 | 418 | 508 |
| 557 | 418 | 419 | 508 |
| 558 | 557 | 558 | 540 |
| 559 | 592 | 593 | 540 |
| 560 | 549 | 550 | 157 |
| 561 | 501 | 502 | 508 |
| 562 | 519 | 520 | 508 |
| 563 | 417 | 418 | 508 |
| 564 | 470 | 471 | 540 |
| 565 | 462 | 463 | 192 |
| 566 | 501 | 502 | 540 |
| 567 | 486 | 487 | 540 |
| 568 | 527 | 528 | 540 |
| 569 | 512 | 513 | 540 |
| 570 | 418 | 419 | 508 |
| 571 | 563 | 564 | 540 |
| 572 | 494 | 495 | 6 |
| 573 | 602 | 603 | 540 |
| 574 | 589 | 590 | 540 |
| 575 | 585 | 586 | 540 |
| 576 | 599 | 600 | 540 |
| 577 | 582 | 583 | 540 |
| 578 | 418 | 419 | 540 |
| 579 | 395 | 396 | 192 |
| 580 | 603 | 604 | 540 |
| 581 | 537 | 538 | 157 |
| 582 | 551 | 552 | 157 |
| 583 | 521 | 522 | 157 |
| 584 | 539 | 540 | 157 |
| 585 | 572 | 573.1907 | 157 |
| 586 | 572 | 573 | 157 |
| 587 | 572 | 573 | 157 |
| 588 | 572 | 573 | 192 |
| 589 | 572 | 573 | 192 |
| 590 | 572 | 573 | 192 |
| 591 | 521 | 522 | 192 |
| 592 | 614 | 615 | 540 |
| 593 | 602 | 603 | 540 |
| 594 | 582 | 583 | 540 |
| 595 | 582 | 583 | 540 |
| 596 | 463 | 464 | 157 |
| 597 | 542 | 543 | 6 |
| 598 | 512 | 513 | 6 |
| 599 | 494 | 495 | 229 |
| 600 | 512 | 513 | 229 |
| 601 | 479 | 480 | 229 |
| 602 | 479 | 480 | 229 |
| 603 | 468 | 469 | 7 |
| 604 | 543 | 544 | 192 |
| 605 | 538 | 539 | 605 |
| 606 | 556 | 557 | 605 |
| 607 | 572 | 573 | 605 |
| 608 | 588 | 589 | 605 |
| 609 | 502 | 503 | 605 |

PROPHETIC EXAMPLES

The prophetic examples shown below further illustrate the scope of this disclosure. Non-limiting prophetic examples include the following compounds and pharmaceutically acceptable salts thereof:

Example 610: (R)-1-(4-(6-(2-(4-(3,3-difluorocyclobutoxy)-6-methylpyridin-2-yl)acetamido)pyridazin-3-yl)-2-fluorobutyl)-N-methyl-1H-1,2,3-triazole-4-carboxamide

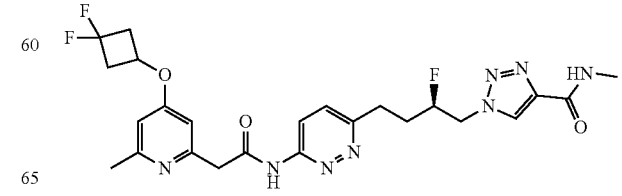

Example 611: (R)-1-(4-(6-(2-(4-cyclopropyl-6-methylpyridin-2-yl)acetamido)pyridazin-3-yl)-2-fluorobutyl)-N-methyl-1H-1,2,3-triazole-4-carboxamide
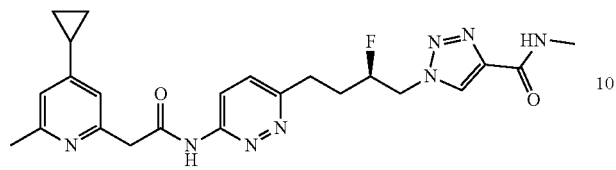
It is believed that a person of skill in the art would know how to synthesize the claimed compounds based, in part, on the provided Schemes 6 and 7.
SCHEME 6
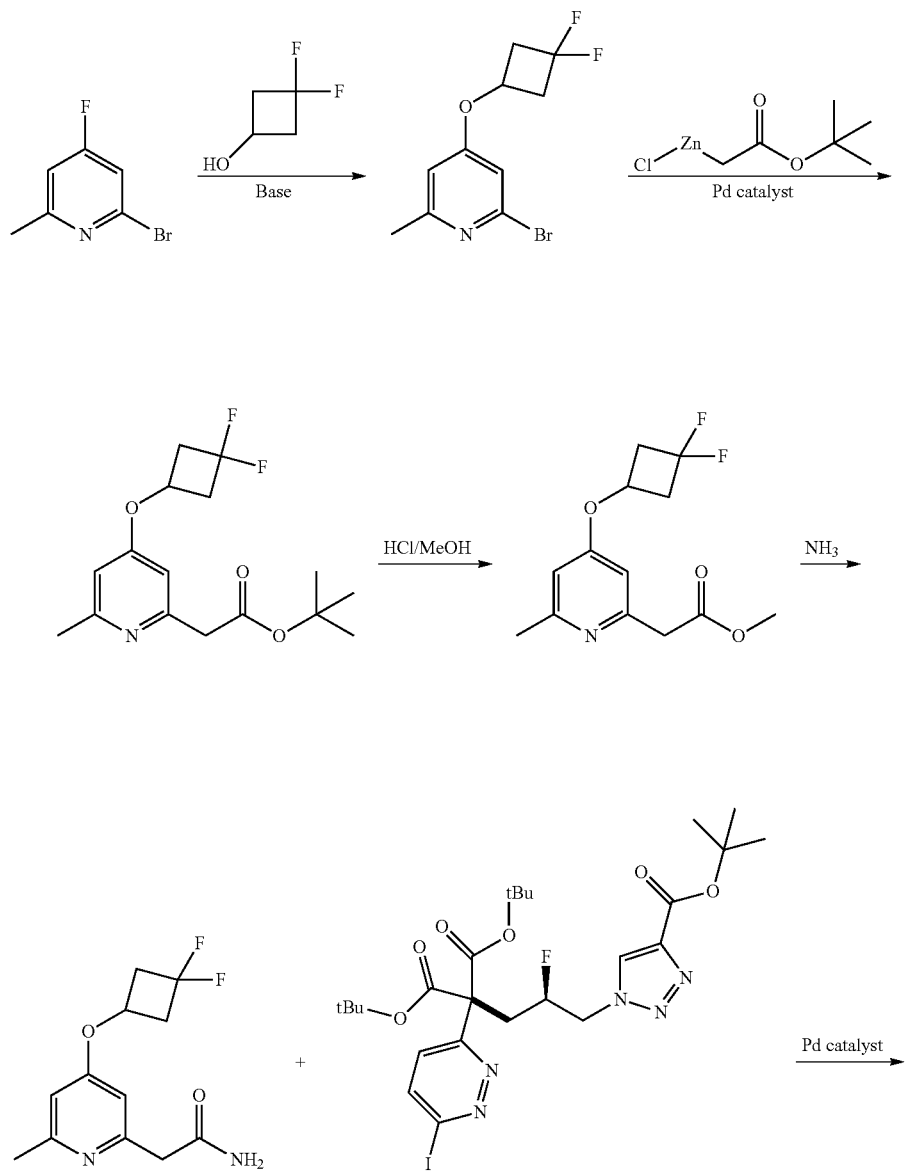

437 438
-continued
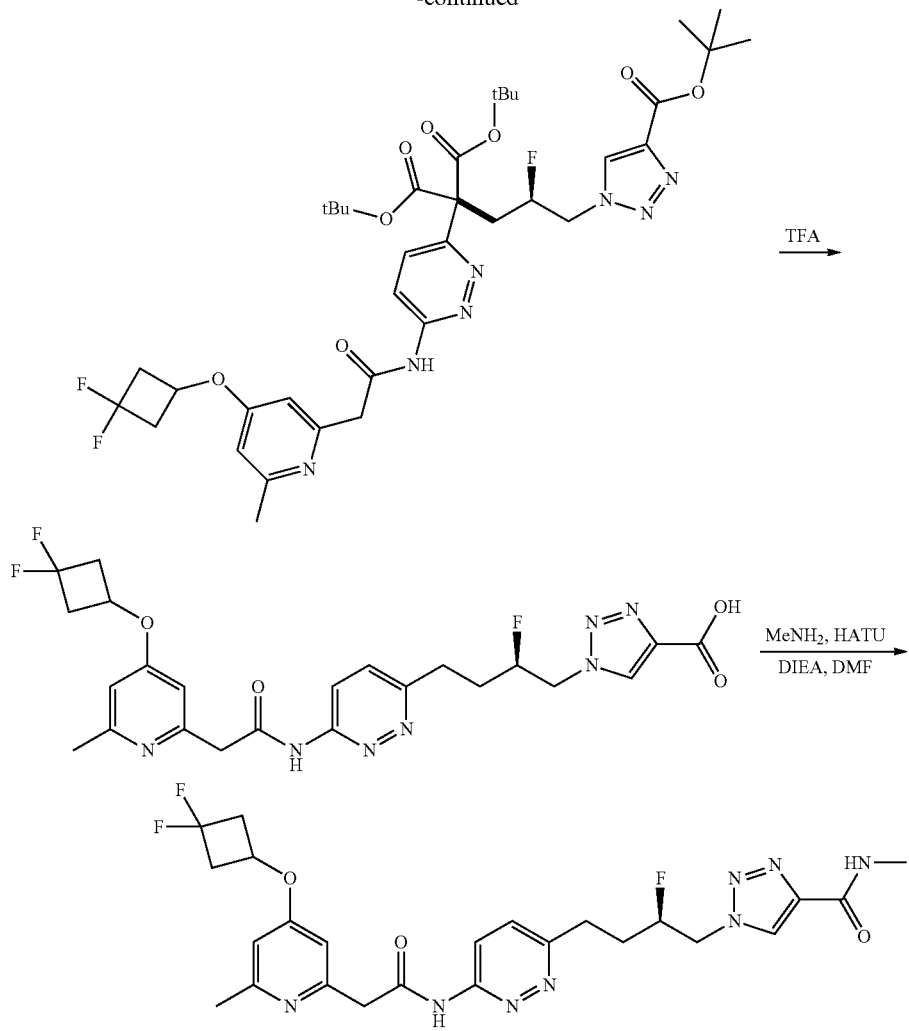
SCHEME 7
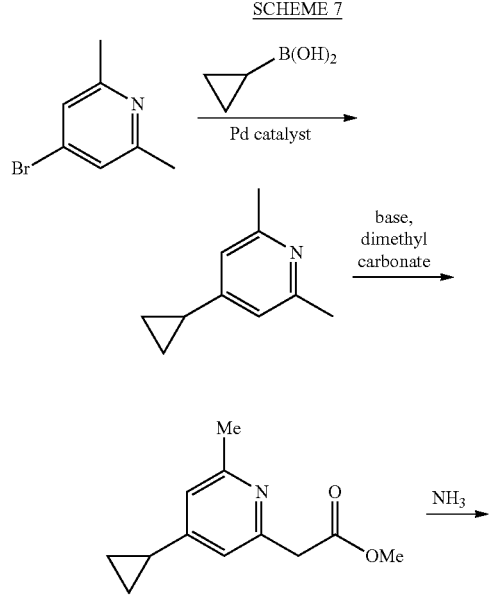
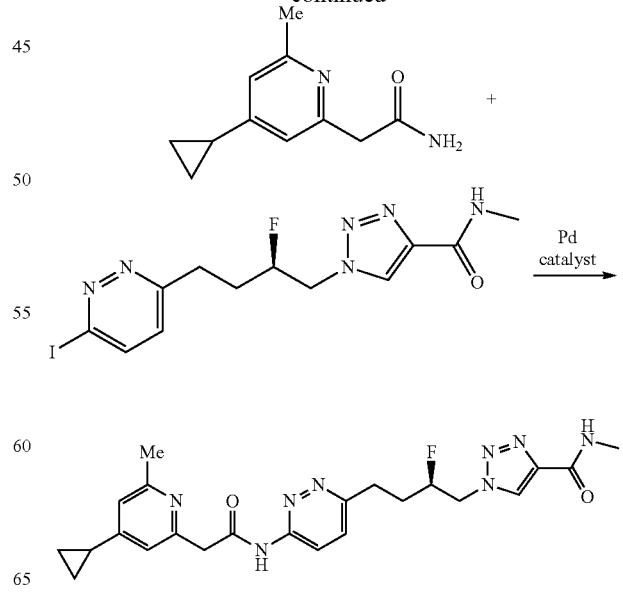

Biological Activity Assays

The following are assays that may be used to evaluate the biological efficacy of compounds of Formula (I).

GLS1 Enzymatic Activity Assay

The inhibition of purified recombinant human GAC by varying concentrations of inhibitors is assessed via a dual-coupled enzymatic assay. The glutamate produced by the glutaminase reaction is used by glutamate oxidase to produce α-ketoglutarate, ammonia, and hydrogen peroxide, with this hydrogen peroxide subsequently being used by horseradish peroxidase to produce resorufin in the presence of Amplex UltraRed. The assay buffer consisted of 50 mM Hepes (pH 7.4), 0.25 mM EDTA and 0.1 mM Triton X-100. GAC was incubated with potassium phosphate (10 minutes at room temperature) prior to incubation with inhibitor (10 minutes at room temperature). The final reaction conditions were as follows: 2 nM GAC, 50 mM potassium phosphate, 100 mU/mL glutamate oxidase (Sigma), 1 mM glutamine (Sigma), 100 mU/mL horseradish peroxidase (Sigma), 75 μM Amplex UltraRed (Life Technologies), and 1% (v/v) DMSO. The production of resorufin was monitored on a Perkin Elmer Envision plate reader (excitation 530 nm, emission 590 nm) either in a kinetics or endpoint mode (at 20 minutes). IC50 values were calculated using a four-parameter logistic curve fit.

Proliferation Assay

A549 cells were routinely maintained in RPMI 1640 media (Gibco catalog number 11875-093) supplemented with 10% dialyzed fetal bovine serum using a humidified incubator (37° C., 5% $CO_2$ and ambient $O_2$). In preparation for the viability assay, cells were inoculated into 384-well black CulturPlates (Perkin Elmer) at a density of 1000 cells/well in a volume of 40 uL. Following a 24-hour incubation at 37° C., 5% CO2 and ambient O2, cells were treated with compound (10 uL) in a final DMSO concentration of 0.5% (v/v). The microplates were then incubated for 72 hours (37° C., 5% CO2 and ambient O2). Cell Titer Fluor (Promega) was subsequently added (10 uL of 6× reagent) and mixed for 15 minutes at room temperature. The plates were then incubated for 30 minutes (37° C., 5% CO2 and ambient O2) and fluorescence was subsequently read on the Perkin Elmer Envision plate reader. IC50 values were calculated using a four-parameter logistic curve fit.

Non-limiting examples include the following compounds and pharmaceutically acceptable salts thereof. Table 3 below reports the $IC_{50}$ against GLS1 and the $EC_{50}$ against A549 cell proliferation, both in nanomolar, and both wherein A<100 nM, B=100-500 nM, C>500-5000 nM, and D>5000 nM. "ND" indicates no data. Compounds disclosed herein and not yet tested are expected to demonstrate activity in these assays as well.

TABLE 3

| Biological Data | | |
|---|---|---|
| Ex. No. | GLS1 $IC_{50}$ | A549 $EC_{50}$ |
| 1 | A | A |
| 2 | A | A |
| 3 | B | B |
| 4 | B | B |
| 5 | A | A |
| 6 | A | A |
| 7 | B | B |
| 8 | B | N.D. |
| 9 | C | N.D. |
| 10 | B | N.D. |
| 11 | A | B |

TABLE 3-continued

| Biological Data | | |
|---|---|---|
| Ex. No. | GLS1 $IC_{50}$ | A549 $EC_{50}$ |
| 12 | A | A |
| 13 | A | C |
| 14 | C | N.D. |
| 15 | A | B |
| 16 | A | A |
| 17 | B | B |
| 18 | B | B |
| 19 | A | A |
| 20 | A | A |
| 21 | A | B |
| 22 | A | B |
| 23 | A | B |
| 24 | A | A |
| 25 | A | B |
| 26 | A | A |
| 27 | A | A |
| 28 | A | B |
| 29 | A | A |
| 30 | A | A |
| 31 | A | A |
| 32 | A | A |
| 33 | A | A |
| 34 | A | B |
| 34 | B | B |
| 36 | A | A |
| 37 | A | A |
| 38 | C | N.D. |
| 39 | N.D. | B |
| 40 | B | N.D. |
| 41 | C | C |
| 42 | N.D. | N.D. |
| 43 | N.D. | B |
| 44 | N.D. | B |
| 45 | B | C |
| 46 | A | A |
| 47 | A | B |
| 48 | C | C |
| 49 | C | D |
| 50 | B | C |
| 51 | B | C |
| 52 | C | D |
| 53 | C | N.D. |
| 54 | B | BN.D. |
| 55 | B | C |
| 56 | A | A |
| 57 | C | N.D. |
| 58 | C | N.D. |
| 59 | B | C |
| 60 | A | A |
| 61 | A | A |
| 62 | B | C |
| 63 | B | C |
| 64 | A | C |
| 65 | A | B |
| 66 | C | N.D. |
| 67 | B | N.D. |
| 68 | C | N.D. |
| 69 | C | N.D. |
| 70 | C | N.D. |
| 71 | C | N.D. |
| 72 | A | A |
| 73 | A | A |
| 74 | B | N.D. |
| 75 | A | A |
| 76 | A | A |
| 77 | A | A |
| 78 | A | A |
| 79 | A | A |
| 80 | A | A |
| 81 | A | A |
| 82 | A | A |
| 83 | A | A |
| 84 | B | B |
| 85 | C | C |
| 86 | C | D |
| 87 | C | D |

TABLE 3-continued

Biological Data

| Ex. No. | GLS1 IC$_{50}$ | A549 EC$_{50}$ |
|---|---|---|
| 88 | C | C |
| 89 | C | C |
| 90 | B | B |
| 91 | C | D |
| 92 | C | C |
| 93 | B | C |
| 94 | B | B |
| 95 | B | B |
| 96 | B | B |
| 97 | A | A |
| 98 | C | C |
| 99 | C | C |
| 100 | C | D |
| 101 | C | C |
| 102 | C | C |
| 103 | B | C |
| 104 | C | C |
| 105 | A | A |
| 106 | A | A |
| 107 | A | A |
| 108 | A | B |
| 109 | A | B |
| 110 | A | A |
| 111 | A | A |
| 112 | B | B |
| 113 | A | C |
| 114 | C | C |
| 115 | C | C |
| 116 | A | B |
| 117 | B | B |
| 118 | B | B |
| 119 | B | B |
| 120 | B | C |
| 121 | B | B |
| 122 | A | A |
| 123 | A | B |
| 124 | A | A |
| 125 | A | B |
| 126 | B | B |
| 127 | B | C |
| 128 | A | A |
| 129 | A | A |
| 130 | B | B |
| 131 | B | B |
| 132 | A | A |
| 133 | A | A |
| 134 | A | A |
| 135 | A | A |
| 136 | A | A |
| 137 | A | A |
| 138 | B | B |
| 139 | B | B |
| 140 | A | A |
| 141 | A | A |
| 142 | A | A |
| 143 | A | A |
| 144 | A | A |
| 145 | A | A |
| 146 | A | A |
| 147 | A | A |
| 148 | A | A |
| 149 | B | C |
| 150 | B | B |
| 151 | B | C |
| 152 | A | A |
| 153 | A | B |
| 154 | C | C |
| 155 | A | C |
| 156 | A | A |
| 157 | A | B |
| 158 | A | A |
| 159 | A | B |
| 160 | A | A |
| 161 | A | A |
| 162 | B | B |
| 163 | C | C |
| 164 | A | B |
| 165 | B | C |
| 166 | A | B |
| 167 | A | B |
| 168 | A | B |
| 169 | A | A |
| 170 | B | C |
| 171 | B | C |
| 172 | A | A |
| 173 | B | B |
| 174 | A | B |
| 175 | A | B |
| 176 | A | B |
| 177 | A | B |
| 178 | A | B |
| 179 | A | C |
| 180 | A | B |
| 181 | B | C |
| 182 | B | D |
| 183 | B | D |
| 184 | C | D |
| 185 | B | C |
| 186 | B | C |
| 187 | B | D |
| 188 | A | A |
| 189 | C | D |
| 190 | A | B |
| 191 | A | B |
| 192 | A | A |
| 193 | A | C |
| 194 | A | A |
| 195 | A | A |
| 196 | C | C |
| 197 | A | A |
| 198 | A | A |
| 199 | A | B |
| 200 | A | B |
| 201 | A | B |
| 202 | A | B |
| 203 | A | A |
| 204 | A | A |
| 205 | A | A |
| 206 | A | A |
| 207 | A | A |
| 208 | A | B |
| 209 | B | B |
| 210 | A | B |
| 211 | A | A |
| 212 | A | A |
| 213 | A | A |
| 214 | B | D |
| 215 | B | C |
| 216 | A | A |
| 217 | A | B |
| 218 | A | A |
| 219 | A | A |
| 220 | B | C |
| 221 | B | B |
| 222 | A | A |
| 223 | A | A |
| 224 | B | B |
| 225 | A | B |
| 226 | A | A |
| 227 | A | A |
| 228 | A | A |
| 229 | A | A |
| 230 | A | A |
| 231 | A | A |
| 232 | A | A |
| 233 | A | A |
| 234 | A | B |
| 235 | A | B |
| 236 | A | A |
| 237 | A | B |
| 238 | A | B |
| 239 | A | B |

TABLE 3-continued

| Ex. No. | GLS1 IC$_{50}$ | A549 EC$_{50}$ |
|---|---|---|
| 240 | A | A |
| 241 | A | A |
| 242 | A | A |
| 243 | B | B |
| 244 | A | A |
| 245 | A | A |
| 246 | A | A |
| 247 | A | A |
| 248 | A | A |
| 249 | A | A |
| 250 | A | A |
| 251 | A | A |
| 252 | A | A |
| 253 | A | A |
| 254 | A | B |
| 255 | A | A |
| 256 | A | B |
| 257 | A | A |
| 258 | A | A |
| 259 | A | A |
| 260 | A | A |
| 261 | A | A |
| 262 | A | A |
| 263 | A | A |
| 264 | A | A |
| 265 | A | A |
| 266 | A | A |
| 267 | A | A |
| 268 | A | A |
| 269 | A | A |
| 270 | A | A |
| 271 | A | A |
| 272 | A | A |
| 273 | A | A |
| 274 | A | A |
| 275 | A | A |
| 276 | B | B |
| 277 | B | C |
| 278 | C | N.D. |
| 279 | A | B |
| 280 | B | C |
| 281 | C | N.D. |
| 282 | C | N.D. |
| 283 | C | N.D. |
| 284 | B | C |
| 285 | C | C |
| 286 | A | B |
| 287 | C | N.D. |
| 288 | B | C |
| 289 | C | N.D. |
| 290 | C | N.D. |
| 291 | C | N.D. |
| 292 | B | C |
| 293 | A | B |
| 294 | A | B |
| 295 | A | A |
| 296 | A | A |
| 297 | C | N.D. |
| 298 | C | N.D. |
| 299 | A | A |
| 300 | C | D |
| 301 | B | C |
| 302 | C | N.D. |
| 303 | C | N.D. |
| 304 | C | N.D. |
| 305 | C | C |
| 306 | B | C |
| 307 | A | B |
| 308 | C | N.D. |
| 309 | B | B |
| 310 | A | B |
| 311 | B | C |
| 312 | B | C |
| 313 | A | A |
| 314 | B | C |
| 315 | B | C |
| 316 | A | C |
| 317 | B | B |
| 318 | A | A |
| 319 | C | D |
| 320 | B | C |
| 321 | C | C |
| 322 | B | C |
| 323 | C | N.D. |
| 324 | C | N.D. |
| 325 | C | N.D. |
| 326 | C | N.D. |
| 327 | A | A |
| 328 | A | A |
| 329 | B | C |
| 330 | A | B |
| 331 | A | B |
| 332 | A | B |
| 333 | C | N.D. |
| 334 | A | A |
| 335 | A | A |
| 336 | A | B |
| 337 | A | A |
| 338 | A | B |
| 339 | A | A |
| 340 | A | A |
| 341 | A | B |
| 342 | A | A |
| 343 | A | A |
| 344 | B | D |
| 345 | B | D |
| 346 | A | C |
| 347 | A | A |
| 348 | C | N.D. |
| 349 | B | N.D. |
| 350 | B | B |
| 351 | C | N.D. |
| 352 | B | C |
| 353 | A | B |
| 354 | C | N.D. |
| 355 | B | B |
| 356 | A | A |
| 357 | C | N.D. |
| 358 | C | N.D. |
| 359 | B | B |
| 360 | A | A |
| 361 | C | N.D. |
| 362 | C | N.D. |
| 363 | A | A |
| 364 | B | C |
| 365 | C | N.D. |
| 366 | B | C |
| 367 | A | B |
| 368 | A | A |
| 369 | A | A |
| 370 | A | A |
| 371 | A | B |
| 372 | A | B |
| 373 | A | A |
| 374 | B | N.D. |
| 375 | A | A |
| 376 | A | A |
| 377 | A | A |
| 378 | A | A |
| 379 | A | A |
| 380 | A | A |
| 381 | A | A |
| 382 | A | B |
| 383 | A | A |
| 384 | A | A |
| 385 | A | A |
| 386 | A | A |
| 387 | B | C |
| 388 | A | B |
| 389 | C | D |
| 390 | A | A |
| 391 | A | B |

TABLE 3-continued

Biological Data

| Ex. No. | GLS1 IC$_{50}$ | A549 EC$_{50}$ |
|---|---|---|
| 392 | C | D |
| 393 | C | C |
| 394 | A | A |
| 395 | A | A |
| 396 | A | A |
| 397 | A | A |
| 398 | A | A |
| 399 | A | B |
| 400 | A | B |
| 401 | B | C |
| 402 | B | C |
| 403 | A | A |
| 404 | A | A |
| 405 | A | A |
| 406 | A | A |
| 407 | A | A |
| 408 | A | A |
| 409 | C | D |
| 410 | C | C |
| 411 | A | A |
| 412 | A | A |
| 413 | A | A |
| 414 | A | A |
| 415 | A | A |
| 416 | A | A |
| 417 | A | A |
| 418 | A | A |
| 419 | A | A |
| 420 | A | B |
| 421 | A | A |
| 422 | A | A |
| 423 | A | A |
| 424 | A | A |
| 425 | A | A |
| 426 | A | A |
| 427 | A | A |
| 428 | A | A |
| 429 | A | B |
| 430 | A | A |
| 431 | A | A |
| 432 | A | A |
| 433 | A | A |
| 434 | A | A |
| 435 | A | A |
| 436 | A | A |
| 437 | A | A |
| 438 | A | A |
| 439 | A | A |
| 440 | A | B |
| 441 | A | A |
| 442 | A | A |
| 443 | A | A |
| 444 | A | A |
| 445 | A | A |
| 446 | A | A |
| 447 | A | A |
| 448 | A | A |
| 449 | A | A |
| 450 | A | B |
| 451 | A | A |
| 452 | A | B |
| 453 | A | B |
| 454 | A | B |
| 455 | A | A |
| 456 | A | A |
| 457 | C | C |
| 458 | B | B |
| 459 | A | B |
| 460 | B | B |
| 461 | B | C |
| 462 | A | B |
| 463 | A | A |
| 464 | A | A |
| 465 | A | A |
| 466 | A | A |
| 467 | B | B |
| 468 | A | A |
| 469 | A | A |
| 470 | A | A |
| 471 | A | B |
| 472 | B | B |
| 473 | B | B |
| 474 | A | A |
| 475 | B | B |
| 476 | A | A |
| 477 | A | A |
| 478 | A | A |
| 479 | A | A |
| 480 | A | A |
| 481 | A | A |
| 482 | A | A |
| 483 | A | A |
| 484 | A | A |
| 485 | A | A |
| 486 | A | A |
| 487 | A | A |
| 488 | A | A |
| 489 | A | A |
| 490 | A | A |
| 491 | A | A |
| 492 | A | B |
| 493 | A | A |
| 494 | A | A |
| 495 | A | A |
| 496 | A | A |
| 497 | A | B |
| 498 | A | A |
| 499 | B | B |
| 500 | B | B |
| 501 | B | B |
| 502 | B | B |
| 503 | B | C |
| 504 | A | B |
| 505 | A | B |
| 506 | B | B |
| 507 | B | B |
| 508 | B | B |
| 509 | B | B |
| 510 | B | C |
| 511 | B | C |
| 512 | B | B |
| 513 | A | A |
| 514 | A | A |
| 515 | A | B |
| 516 | A | A |
| 517 | A | A |
| 518 | A | A |
| 519 | B | C |
| 520 | A | A |
| 521 | B | B |
| 522 | A | B |
| 523 | B | C |
| 524 | A | B |
| 525 | A | B |
| 526 | B | C |
| 527 | A | A |
| 528 | A | C |
| 529 | A | A |
| 530 | A | C |
| 531 | A | B |
| 532 | A | B |
| 533 | A | A |
| 534 | A | B |
| 535 | A | B |
| 536 | A | B |
| 537 | A | B |
| 538 | A | B |
| 539 | A | B |
| 540 | A | A |
| 541 | A | C |
| 542 | A | B |
| 543 | A | C |

TABLE 3-continued

Biological Data

| Ex. No. | GLS1 IC$_{50}$ | A549 EC$_{50}$ |
|---|---|---|
| 544 | A | B |
| 545 | A | B |
| 546 | A | B |
| 547 | B | C |
| 548 | B | C |
| 549 | B | C |
| 550 | A | B |
| 551 | A | B |
| 552 | C | D |
| 553 | A | A |
| 554 | A | A |
| 555 | A | B |
| 556 | B | C |
| 557 | C | C |
| 558 | A | C |
| 559 | A | B |
| 560 | A | B |
| 561 | A | B |
| 562 | A | B |
| 563 | C | C |
| 564 | A | C |
| 565 | A | B |
| 566 | A | B |
| 567 | A | B |
| 568 | A | B |
| 569 | A | B |
| 570 | B | C |
| 571 | A | A |
| 572 | A | B |
| 573 | A | A |
| 574 | A | A |
| 575 | A | B |
| 576 | A | A |
| 577 | A | C |
| 578 | A | C |
| 579 | B | C |
| 580 | A | A |
| 581 | A | B |
| 582 | A | B |
| 583 | A | A |
| 584 | A | B |
| 585 | A | A |
| 586 | A | A |
| 587 | A | A |
| 588 | A | A |
| 589 | A | A |
| 590 | A | A |
| 591 | A | B |
| 592 | A | A |
| 593 | A | A |
| 594 | A | C |
| 595 | A | A |
| 596 | A | B |
| 597 | A | B |
| 598 | A | A |
| 599 | A | A |
| 600 | A | A |
| 601 | A | A |
| 602 | A | A |
| 603 | C | D |
| 604 | A | A |
| 605 | A | A |
| 606 | A | A |
| 607 | A | A |
| 608 | A | A |
| 609 | A | A |

Other Embodiments

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

The invention claimed is:

1. A compound of structural Formula VIIa or VIIb:

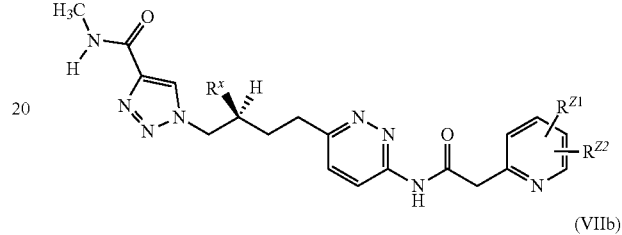

or a pharmaceutically acceptable salt thereof, wherein: $R^X$ is chosen from fluoro and H;

and each of $R^{Z1}$ and $R^{Z2}$ is independently H or chosen from alkyl, cycloalkyl, and cycloalkyl-alkyl, each of which is optionally substituted with halo and wherein alkyl is $C_{1-6}$ alkyl and cycloalkyl is cyclopropyl, cyclobutyl, cyclopentyl, or cyclohexyl.

2. The compound as recited in claim 1, or a pharmaceutically acceptable salt thereof, wherein each of $R^{Z1}$ and $R^{Z2}$ is independently chosen from H,

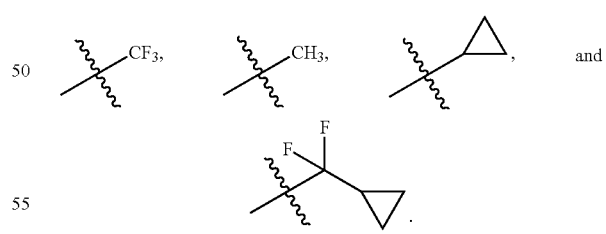

3. A compound chosen from:

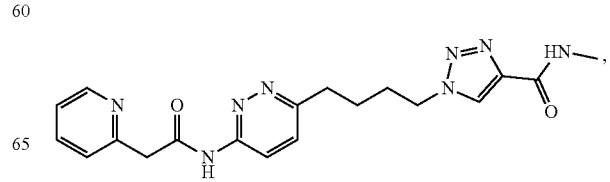

449                                                             450

-continued                                                      -continued

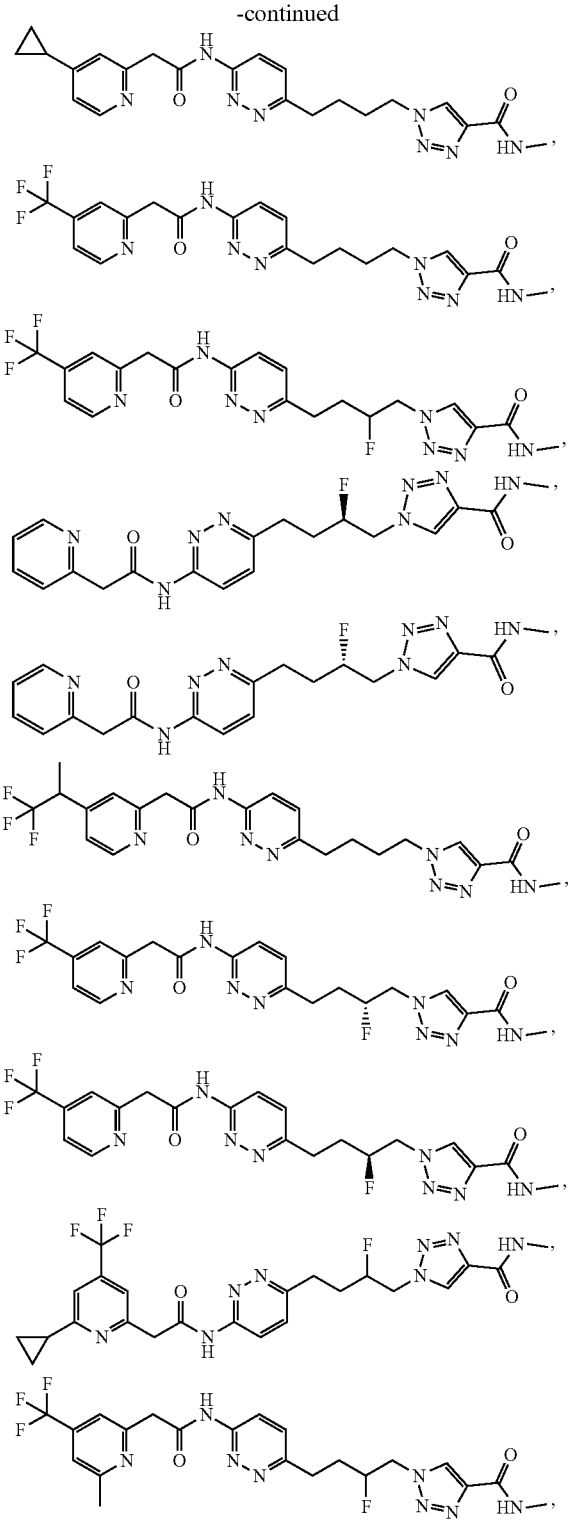
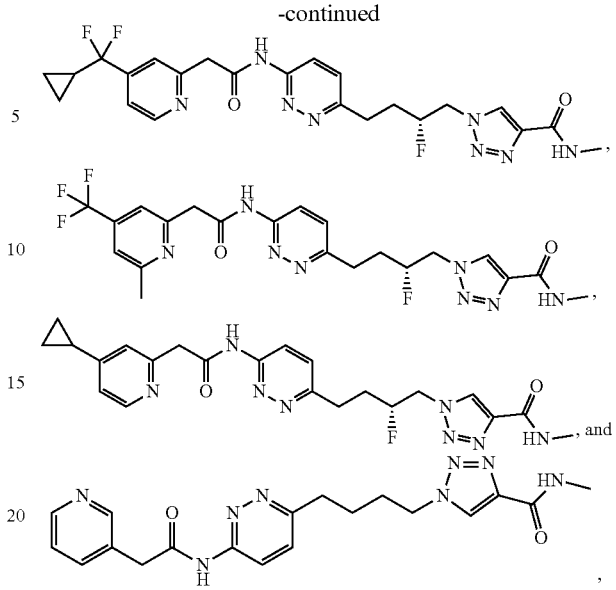

or a pharmaceutically acceptable salt thereof.

4. A composition comprising a compound as recited in claim 1, or a pharmaceutically acceptable salt thereof, and a pharmaceutically acceptable carrier, adjuvant, or vehicle.

5. A method of inhibiting GLS1 activity in a biological sample comprising contacting the biological sample with a compound as recited in claim 1, or a pharmaceutically acceptable salt thereof.

6. A method of ameliorating the symptoms of a GLS1-mediated disorder in a subject having said disorder, comprising the step of administering to the subject a compound as recited in claim 1, or a pharmaceutically acceptable salt thereof.

7. The method according to claim 6, wherein the subject is a human.

8. The method according to claim 6, wherein the GLS1-mediated disorder is chosen from cancer, immunological disorders, and neurological disorders.

9. A method of ameliorating the symptoms of a GLS1-mediated disorder in a subject in need thereof, comprising the sequential or co-administration of a compound as recited in claim 1, or a pharmaceutically acceptable salt thereof, and another therapeutic agent.

10. The method as recited in claim 9, wherein the method further comprises administering non-chemical methods of cancer treatment.

11. The method as recited in claim 9, wherein the method further comprises administering radiation therapy.

12. The method as recited in claim 9, wherein the method further comprises administering surgery, thermoablation, focused ultrasound therapy, cryotherapy, or any combination thereof.

* * * * *